United States Patent
Yuan et al.

(10) Patent No.: US 10,869,863 B2
(45) Date of Patent: Dec. 22, 2020

(54) MULTI-ARM POLYMERIC TARGETING ANTI-CANCER CONJUGATE

(71) Applicant: BrightGene Bio-Medical Technology Co., Ltd., Jiangsu (CN)

(72) Inventors: Jiandong Yuan, Jiangsu (CN); Yangqing Huang, Jiangsu (CN); Yunsong Song, Jiangsu (CN); Fang Yuan, Jiangsu (CN)

(73) Assignee: BrightGene Bio-Medical Technology Co., Ltd., Suzhou (CN)

( * ) Notice: Subject to any disclaimer, the term of this patent is extended or adjusted under 35 U.S.C. 154(b) by 43 days.

(21) Appl. No.: 16/300,428

(22) PCT Filed: May 15, 2017

(86) PCT No.: PCT/CN2017/084328
§ 371 (c)(1),
(2) Date: Nov. 9, 2018

(87) PCT Pub. No.: WO2017/198124
PCT Pub. Date: Nov. 23, 2017

(65) Prior Publication Data
US 2020/0000797 A1    Jan. 2, 2020

(30) Foreign Application Priority Data

May 16, 2016   (CN) .......................... 2016 1 0318195

(51) Int. Cl.
| | | |
|---|---|---|
| C07D 491/22 | (2006.01) | |
| A61K 31/4745 | (2006.01) | |
| A61K 47/58 | (2017.01) | |
| A61K 47/54 | (2017.01) | |
| A61K 47/64 | (2017.01) | |
| A61K 47/60 | (2017.01) | |
| A61P 35/00 | (2006.01) | |

(52) U.S. Cl.
CPC ........ *A61K 31/4745* (2013.01); *A61K 47/545* (2017.08); *A61K 47/58* (2017.08); *A61K 47/60* (2017.08); *A61K 47/64* (2017.08); *A61P 35/00* (2018.01)

(58) Field of Classification Search
CPC .... C07D 491/22; A61K 31/4745; A61P 35/00
USPC ............................................. 546/48; 514/283
See application file for complete search history.

(56) References Cited

U.S. PATENT DOCUMENTS 8,263,062 B2 *   9/2012   Zhao ...................... C08L 71/02
424/78.17

FOREIGN PATENT DOCUMENTS

| CN | 104784699 | | 7/2015 |
|---|---|---|---|
| CN | 105396141 | | 3/2016 |
| JP | 2007/505928 | | 3/2007 |
| JP | 2010/503708 | | 2/2010 |
| JP | 2013/511539 | | 4/2013 |
| WO | 2005/028539 | | 3/2005 |
| WO | 2011/063156 | | 5/2011 |
| WO | 2015051307 | A1 | 4/2015 |
| WO | 2015/187540 | | 12/2015 |
| WO | 2018192550 | A1 | 10/2018 |

OTHER PUBLICATIONS

ISA/CN, International Search Report for PCT/CN2017 /084328 (dated Aug. 9, 2017) (English translation).
Supplementary European Search Report which dated May 21, 2019 in corresponding application No. EP 17 79 8687.
Zhang et al., "Tuning Multiple Arms for Camptothecin and Folate Conjugations on Star-Shaped Copolymers to Enhance Glutathione-Mediated Intracellular Drug Delivery," the Royal Society of Chemistry, Polym. Chem., 2015, 6:2192-2203.
Zhao et al., "Novel Prodrugs of SN38 Using Multiarm Poly(ethylene glycol) Linkers," American Chemical Society, Bioconjugate Chem., 2008, 19:4.

* cited by examiner

*Primary Examiner* — Charanjit Aulakh
(74) *Attorney, Agent, or Firm* — Fish & Richardson P.C.

(57) ABSTRACT

Disclosed is a multi-arm targeting drug conjugate modified by a water-soluble polymer; the drug conjugate has the structural formula of (III). In formula (III), R is an organic core, POLY is a polymer, L is a multivalent linker, T is a targeting molecule, D is a camptothecin-based drug, and q is any integer between 3 and 8. The drug conjugate may improve the poor water solubility, high toxicity and low bioavailability of camptothecin-based drugs.

17 Claims, No Drawings

MULTI-ARM POLYMERIC TARGETING ANTI-CANCER CONJUGATE

TECHNICAL FIELD

The present disclosure generally relates to a multi-arm, water-soluble polymer, and the corresponding drug conjugate thereof. Specifically, the present disclosure relates to a targeting anticancer conjugate modified by a multi-arm PEG; more specifically, the present disclosure relates to attaching a targeting molecule to an anticancer drug via the multi-arm PEG to obtain a conjugate.

BACKGROUND

Over the years, numerous methods for improving the stability and delivery of biologically active agents have been proposed. Challenges associated with the formulation and delivery of a pharmaceutical agent may include poor water solubility, toxicity, low bioavailability, instability, and rapid in vivo degradation of the pharmaceutical agent. Although many approaches have been designed to improve the delivery of the pharmaceutical agent, there is no single approach without its disadvantages. For example, commonly adopted drug delivery methods aim at solving or at least improving one or more problems including drug encapsulation in a liposome, polymer matrix, or monomolecular micelle; covalent attachment to a water-soluble polymer such as polyethylene glycol; use of a gene-targeting agent; structures of salts, and the like.

WO2005028539, WO2010019233, WO2011063156, and WO2011063158 disclose a drug in phase III clinical trials, nktr 102. The drug is mainly used for metastatic breast cancer, and is developed by Nektar Therapeutics. The drug is a water-soluble multi-branched polymeric prodrug aiming at increasing drug loading, and its structure is as follows:

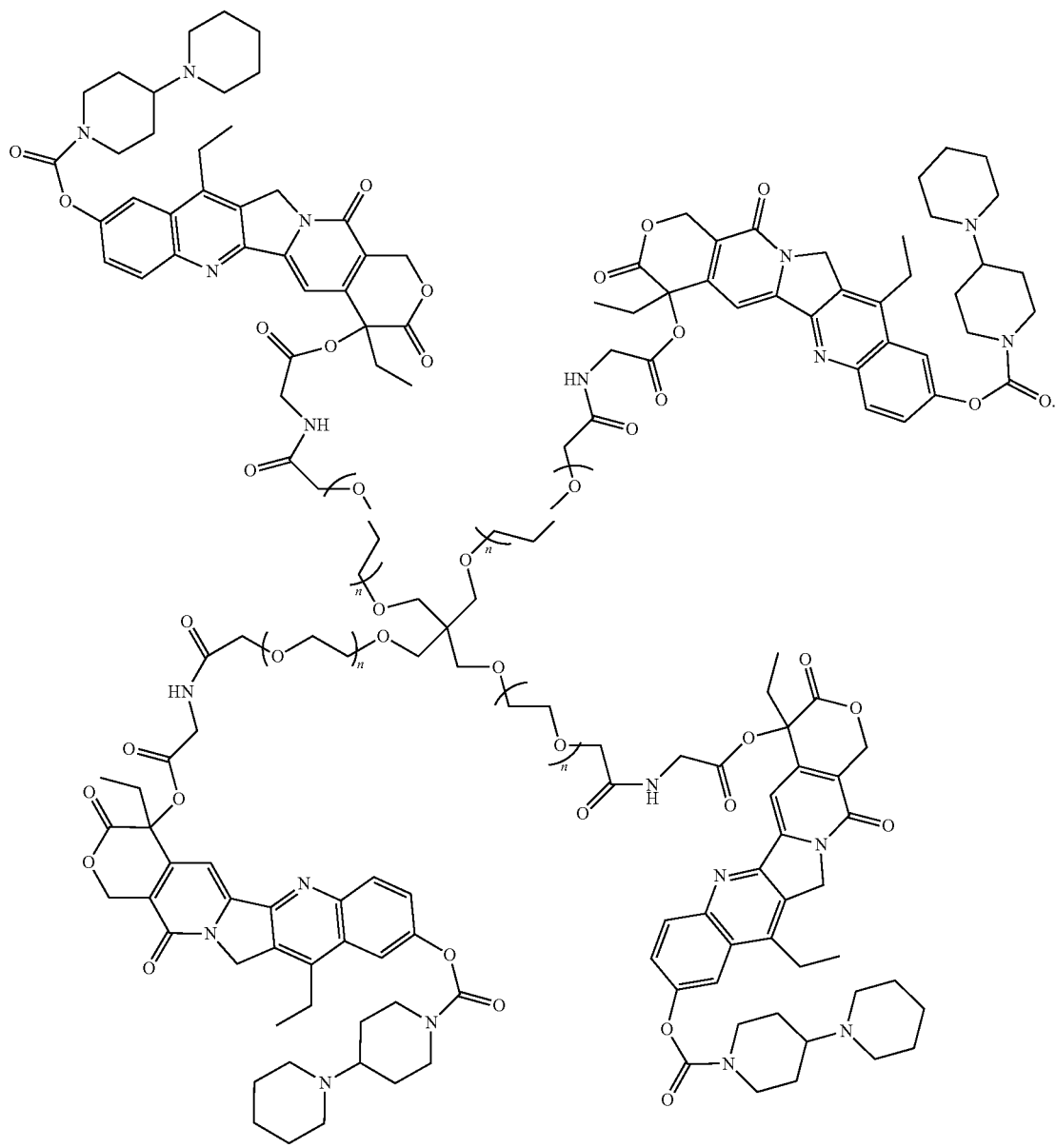

This compound is attached to irinotecan using a multi-arm PEG, so as to improve water solubility, increase drug loading, and reduce side effects without changing anticancer effects. However, this drug still has disadvantages, for example, poor targeting property, inability to act on specific cancer cells, and affecting the functions of normal cells while killing cancer cells, thus making the incidence of adverse reactions still high.

Integrins are a class of cell adhesion receptor molecules that are widely expressed on the surfaces of karyocytes. Among the integrins, integrin $\alpha_v\beta_3$ is highly expressed on the surfaces of a variety of tumor cells of tumors such as glioma, melanoma and ovarian cancer and tumor-related endothelial cells. Integrin $\alpha_v\beta_3$ is closely related to tumor angiogenesis, tumor metastasis and resistance to radiotherapy of tumors. Therefore, integrin $\alpha_v\beta_3$ is often used as a specific target for tumor targeting. Previous researches have shown that the tripeptide sequence of arginine-glycine-aspartic acid (Arg-Gly-Asp, RGD) is capable of specifically recognizing the integrin family containing $\alpha_v$ subunit(s), and has high affinity.

Traditional drugs for tumor treatment generally have disadvantages such as poor selectivity to tumor tissues and significant toxic and side effects, and how to design a good drug delivery system has become a research focus in recent years. With the proposal of "the theory that the tumor growth depends on the tumor vasculature", drugs targeting the receptors of tumor neovasculature have become a novel and rather potential approach to enhance the therapeutic effects for tumors. Integrin $\alpha_v\beta_3$ is an ideal target for tumor-targeting therapy, and its ligand RGD peptide may carry an effector molecule and specifically bind thereto, thereby inhibiting the tumor growth and neovascularization.

Taking advantage of the specific binding of the RGD peptide to integrin $\alpha_v\beta_3$, a therapeutical effector molecule may be introduced into a tumor site targetedly, and the damage to the cells of normal tissues in a tumor therapy is effectively reduced.

Although linear RGD peptides are widely present in the body, the peptide has a short half-life during in vivo circulation, has low affinity for an $\alpha_v\beta_3$ receptor, and is easy to be degraded by proteases. However, a cyclic RGD peptide has strong stability and high affinity for the receptor, and exhibits the characteristics of a tumor-penetrating peptide, thus having obvious advantages in assisting the targeting penetration of anticancer drugs and reducing the toxic and side effects of drugs on normal cells.

iRGD is disclosed in patent WO2009126349, and its specific structure is as follows:

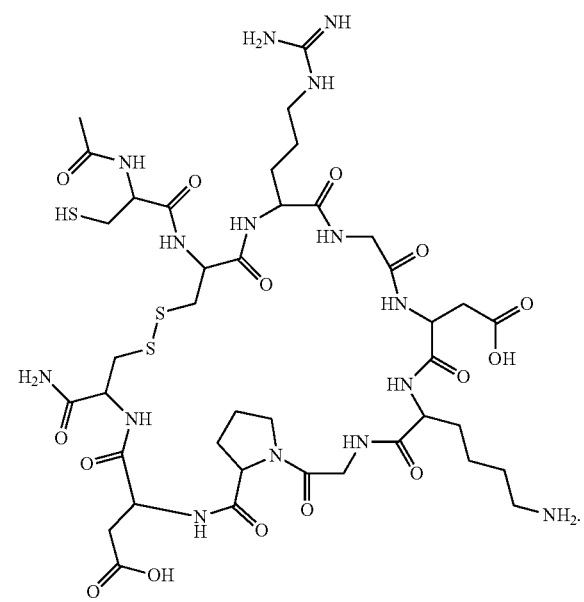 [SMILES: CC(=O)NC(CS)C(=O)NC1CSSCC(C(N)=O)NC(=O)C(CC(=O)O)NC(=O)C2CCCN2C(=O)CNC(=O)C(CCCCN)NC(=O)C(CC(=O)O)NC(=O)CNC(=O)C(CCCNC(=N)N)NC1=O]

SUMMARY

The present disclosure discloses a novel targeting multi-branched drug conjugate, the conjugate has three or more branches, and the conjugate may be represented as the following formula:

R is an organic core, POLY is a polymer, and POLY and X constitute a polymeric branch together.

Each branch and the other branches of the multi-branched drug conjugate are independent from each other. That is to say, each branch may be constituted by different POLY and X. The typical case is that a general structure corresponds to:

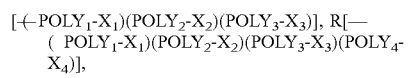

etc., and so forth. Each branch emanates from the organic core "R". However, in general, each branch of the conjugate is the same.

Each variable portion in structural formula (I) will now be described in detail.

Organic core, "R"

In structural formula (I), "R" is an organic core radical of 1 to 100 atoms. Preferably, R comprises 3 to 50 atoms, and more preferably, R comprises about 3 to 30 atoms. R may be a core in which all the atoms are carbon atoms, and may also optionally contain one or more heteroatoms such as O, S, N and P, depending on the particular central molecule used. R may be linear, branched or cyclic, and emanate at least 3 independent polymeric branches. In structural formula (I), "q" corresponds to the number of polymeric branches emanating from "R".

The organic core "R" is derived from a molecule. The molecule provides many sites for the attachment of polymers, and the number of sites is approximately equal to the number of the polymeric branches. More preferably, the main central formula of the multi-branched polymer structure at least carries a residue of a polyhydroxy compound, a polysulfide compound or a polyamine compound with 3 or more hydroxy groups, thiol groups or amino groups, and the residue is suitable as the polymeric branch. A "polyhydroxy compound" is a molecule composed of multiple (more than 2) available hydroxy groups. A "polysulfide compound" is a molecule composed of multiple (more than 2) available thiol groups. A "polyamine compound" is a molecule composed of multiple (more than 2) available amine groups. Depending on the number of polymeric branches, the parent polyhydroxy compound, polyamine compound or polysulfide compound (prior to the covalent binding of POLY) comprises typically 3 to 25 hydroxy groups, thiol groups or amino groups, preferably 3 to 10 hydroxy groups, thiol groups or amino groups, and most preferably from 3 to about 8 (for example 3, 4, 5, 6, 7, or 8) hydroxy groups, thiol groups or amino groups that are suitable for the covalent binding to POLY.

The parent of the polyhydroxy compound or polyamine compound core typically has a structural formula of R—(OH)$_p$ or R—(NH$_2$)$_p$ prior to the interaction with polymers. In structural formula (I), the p value corresponds to the q value. This is because if the position of each of the functional groups (typically, —OH and —NH$_2$) in a parent organic molecule is susceptible or liable to reaction, the functional groups may be covalently bound to POLY of the polymeric branches. In structural formula (I), after being attached to POLY, each hydroxy group of the parent polyhydroxy compound of R has been converted to one polymeric branch, and R described herein is the residue after the attachment. For example, if the molecule of the organic core is derived from pentaerythritol, the parent polyhydroxy compound has a structural formula of C(CH$_2$OH)$_4$, and the organic core radical R is represented as:

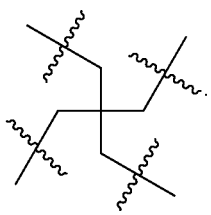 [SMILES: *CC(C*)(C*)C*]

Illustrative polyhydroxy compounds which are preferred as the cores of the polymers include aliphatic polyhydroxy compounds comprising 1 to 10 carbon atoms and 1 to 10 hydroxy groups such as ethylene glycol, alkanediol, hydrocarbyl glycol, alkylene hydrocarbyl glycol, hydrocarbyl cycloalkyl glycol, 1,5-decalindiol, 4,8-di(hydroxymethyl) tricyclodecane, cycloalkylene glycol, dihydroxyalkane, trihydroxyalkane and tetrahydroxyalkane. Cycloaliphatic polyhydroxy compounds include linear or closed-ring saccharides and sugar alcohols such as mannitol, sorbitol, inositol, xylitol, quebrachitol, threitol, arabitol, erythritol, hexanehexol, ribose, arabinose, xylose, lyxose, rhamnose, galactose, glucose, fructose, sorbose, mannose, pyranose, altrose, talose, tagatose, pyranoside, sucrose, lactose and maltose. Aromatic polyhydroxy compounds such as pyrocatechol, hydrocarbyl pyrocatechol, pyrogaelol, fluoroglycine phenol, 1,2,4-benzenetriol, resorcinol, hydrocarbyl resorcinol, dihydrocarbyl resorcinol, orcinol monohydrate, olivetol, hydroquinone, hydrocarbyl hydroquinone and phenyl hydroquinone may also be adopted. Other polyhydroxy compound cores that may be adopted include crown ethers, cyclodextrins, dextrins or other carbohydrates.

In structural formula (I), q corresponds to the number of polymeric branches attached to "R", and the specific number may be 3 to 20. Typically, the specific number of "q" is 3, 4, 5, 6, 7, or 8. Specifically, 3, 4, 5, 6, 7, or 8 polymeric branches emanate from "R" which is the core.

In certain specific embodiments, "R" has 3 polymeric branches, and "R" is preferably

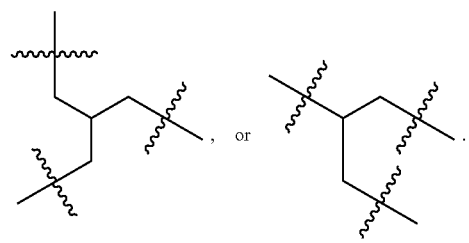 [SMILES: *CC(C*)C* ; *CC(*)C*]

In certain specific embodiments, "R" has 4 polymeric branches, and "R" is preferably

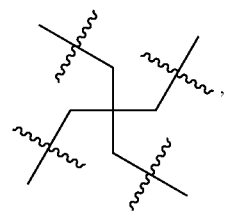

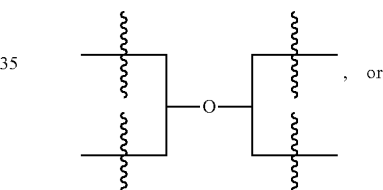

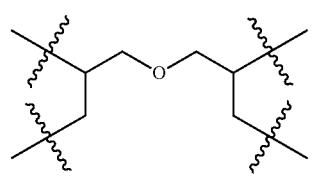

In certain specific embodiments, "R" has 6 polymeric branches, and "R" is preferably

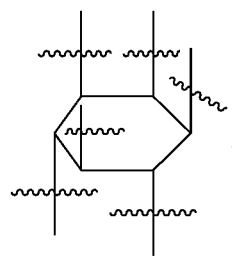

In certain specific embodiments, "R" has 8 polymeric branches, and "R" is preferably

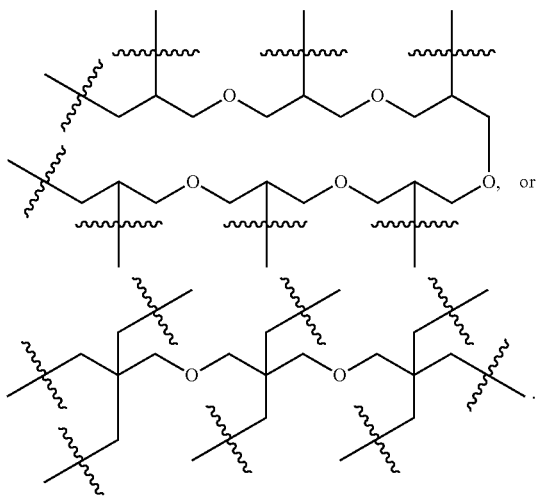

Polymer, "POLY"

In structural formula (I), "POLY" is a polymer and constitutes the polymeric branch with X together. POLY in each polymeric branch is selected independently, preferably each polymer is the same polymer, and more preferably each polymeric branch in structural formula (I) is the same. A preferred polymer is water-soluble, any water-soluble polymer may be used to form the conjugates of the present disclosure, and the polymers referred to in the present disclosure may be in any geometric configuration or form. Representative polymers include but are not limited to: polyethylene glycol, polypropylene glycol, poly(vinyl pyrrolidone), poly(hydroxyalkyl methyl acrylamide), poly(hydroxyalkyl methacrylate), poly(saccharide), poly(α-hydroxy acid), poly(acrylic acid), poly(vinyl acetate), polyphosphazine, polyoxazoline, poly(N-acryloyl morpholine), and the like.

In a typical compound, "POLY" is polyethylene glycol, and may be in any geometric configuration or form, including linear, branched, forked chains, and the like. Preferably, "POLY" is a linear polyethylene glycol, and its typical structure is

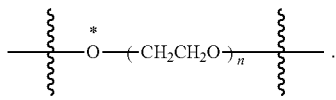

represents the attachment point of the atoms, and the oxygen atom marked with an asterisk is the atom attached to the organic core "R", wherein n ranges from about 5 to 500, preferably 50 to 200, more preferably 113. The average molecular weight is approximately 1 kDa to 60 kDa.

It should be understood by those skilled in the art that in the field of polymers, n represents the degree of polymerization of the polymer, that is, the mean value of the number of the repeating units contained in the macromolecular chain of the polymer, and it depends on the molecule weight of said polymer. For example, when n is 113, it means that the mean value is 113.

The structure of said polyethylene glycol usually further comprises part of a terminal portion residue, which is similar to the terminal group of POLY, and may be ended with H, $NH_2$, OH, $CO_2H$, $C_{1-6}$ alkyl (for example, methyl, ethyl, or propyl), $C_{1-6}$ alkoxy (for example, methoxy or ethoxy), acyl, or aryl. For example, POLY may be:

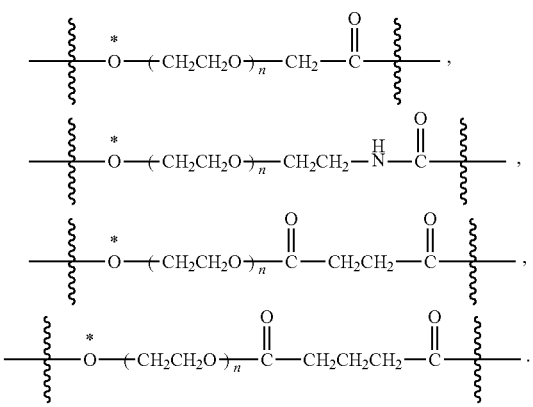

Generally, commercially available multi-arm polyethylene glycols may all carry these terminal portions. When POLY and X are linked to form the polymeric branch, the terminal portion group such as hydroxy group is reacted, and the presented form is the above-mentioned terminal portion residue.

Said polymer may also be a highly branched polymer, and the typical structure is a dendrimer. This kind of polymer refers to a spherical, size monodisperse polymer. All the bonds of the polymer emanate from a central focus or core, the branches of polymer are regular in shape and have repeating units, and each unit contributes one branch point, respectively. The dendrimer exhibits certain dendritic properties, such as encapsulation of the core, which enables it to have unique characteristics that are not possessed by other kinds of polymers.

POLY may be a dendritic polyethylene glycol linking arm, and its typical structure is as follows:

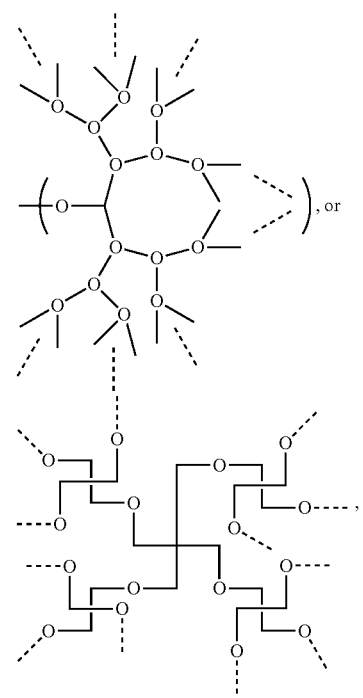

wherein " ⸜ " represents dendritic spread in the same manner.

The constituent parts of the polymeric branch, X

In structural formula (I), "X" and "POLY" constitute the polymeric branch together. X can be in 4 forms as follows:

① X is a group which comprises a relatively unreactive or unreacted group at it terminal. In this case, "X" does not comprise any active agent, and is a group which is not liable to react. In general, it is an alkoxy (—OQ), wherein Q is an organic group generally comprising a lower alkyl with 1 to 20 carbon atoms, and most preferably a $C_{1-6}$ lower alkyl, or a phenyl. "X" may be saturated or unsaturated, and it includes aryl, heteroaryl, cyclic compounds, heterocyclic compounds, and the substituendums of any one of them.

② X can be represented as $(L)-(T)_{n'}$. L represents a multivalent linker, T represents a targeting molecule, and n' is an integer greater than or equal to 1. The linker L may comprise a variety of linkers covalently attached to each other. For example, the multivalent linker L may comprise one or more spacer linkers Ls and/or inseparable linkers Ln, each of which is attached to each other, wherein the inseparable linker(s) Ln is/are attached to T. These different linkers may be selected and arranged in any order to construct the multivalent linker L. For example, the multivalent linker L may be constructed from one or more of the following divalent linkers:

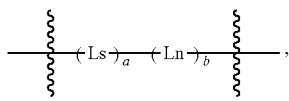

wherein a and b are integers, for example, integers in a range from 0 to 5. Several Ls may be attached in a mode of a straight chain, a branched chain, a terminal branch, and the like. Ls may also be absent, and POLY is directly attached to T via Ln.

It should be understood that the multivalent linker may be attached to POLY and T in a variety of structural configurations, including but not limited to the following exemplary general formulae:

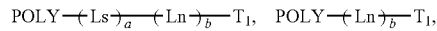
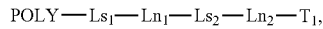
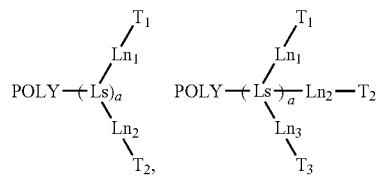
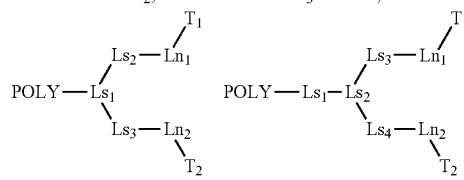
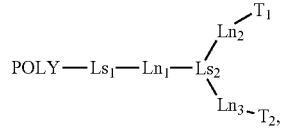

-continued

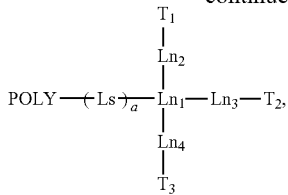

wherein, each of $Ls_1$, $Ls_2$, $Ls_3$, and $Ls_4$ is the spacer linker, and may be the same or different; each of $Ln_1$, $Ln_2$, $Ln_3$, and $Ln_4$ is the inseparable linker, and may be the same or different; and each of $T_1$, $T_2$, and $T_3$ is the targeting molecule, and may be the same or different, preferably, $T_1$, $T_2$, and $T_3$ are the same targeting molecule.

③ X can be represented as $(L)-(D)_{n'}$. L represents a multivalent linker, D represents an active agent, and n' is an integer greater than or equal to 1. The multivalent linker L may comprise a variety of linkers covalently attached to each other. For example, the multivalent linker L may comprise one or more spacer linkers Ls and/or separable linkers Lr, each of which is attached to each other, wherein the separable linker(s) Lr is/are attached to D. These different linkers may be selected and arranged in any order to construct the multivalent linker L. For example, the multivalent linker L may be constructed from one or more of the following divalent linkers:

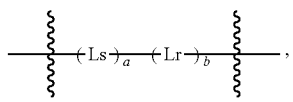

wherein a and b are integers, for example, integers in a range from 0 to 5. Several Ls may be attached in a mode of a straight chain, a branched chain, a terminal branch, and the like. Ls may also be absent, and POLY is attached to D by Lr.

It should be understood that the multivalent linker may be attached to POLY and D in a variety of structural configurations, including but not limited to the following exemplary general formulae:

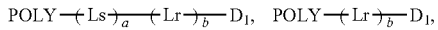
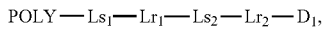
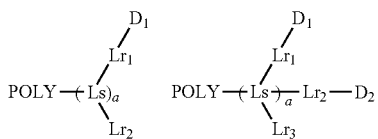
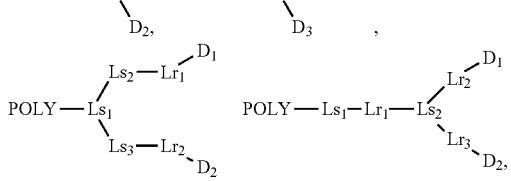
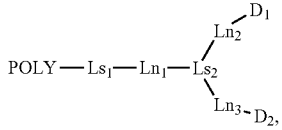

-continued

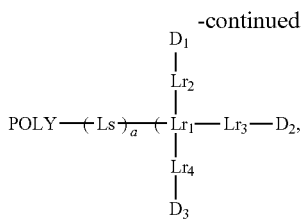

wherein each of $Ls_1$, $Ls_2$, $Ls_3$, and $Ls_4$ is the spacer linker, and may be the same or different; each of $Lr_1$, $Lr_2$, $Lr_3$, and $Lr_4$ is the separable linker, and may be the same or different; and each of $D_1$, $D_2$, and $D_3$ is the active agent, and may be the same or different, preferably, $D_1$, $D_2$, and $D_3$ are the same active agent.

④ X is composed of a multivalent linker L, targeting molecule(s) T and active agent(s) D, and this mode is the best mode of the present disclosure.

In this case, X may be represented as $(T)_{n'}$-(L)-$(D)_{n'}$. L represents the multivalent linker, D represents the active agent, and n' is an integer greater than or equal to 1. The multivalent linker L may comprise a variety of linkers covalently attached to each other. For example, the multivalent linker L may comprise one or more spacer linkers Ls, inseparable linkers Ln, and separable linkers Lr, each of which is attached to each other, wherein the inseparable linker Ln is/are attached to T, and the separable linker(s) Lr is/are attached to D. These different linkers may be selected and arranged in any order. Several Ls may be attached in a mode of a straight chain, a branched chain, a terminal branch, and the like. Ls may also be absent, and POLY is attached to T and D directly via Ln or Lr.

It should be understood that the multivalent linker may be attached to POLY, T and D in a variety of structural configurations, including but not limited to the following exemplary general formulae:

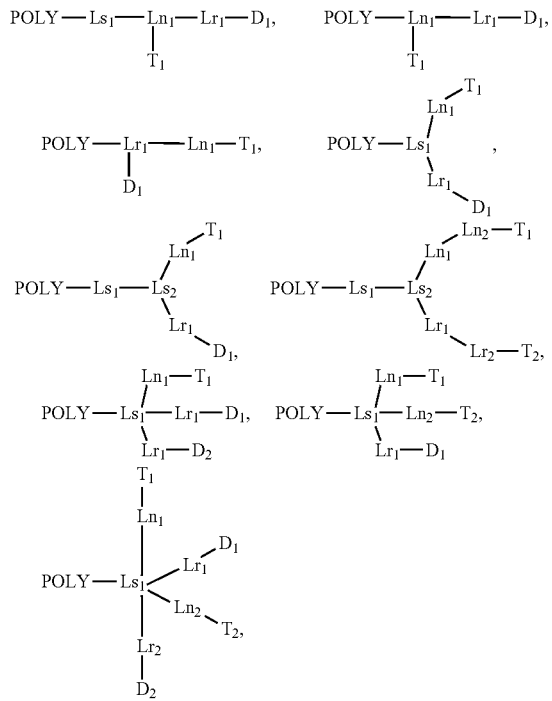

wherein, each of $Ls_1$ and $Ls_2$ is the spacer linker, and may be the same or different; each of $Lr_1$ and $Lr_2$ is the separable linker, and may be the same or different; each of $D_1$ and $D_2$ is the active agent, and may be the same or different, preferably, $D_1$ and $D_2$ are the same active agent; and each of $T_1$ and $T_2$ is the targeting molecule, and may be the same or different, preferably, $T_1$ and $T_2$ are the same targeting molecule. X may comprise 1 to 30 targeting molecules T, more preferably 1 to 5 targeting molecules T. In addition, X may comprise 1 to 30 active agents D, more preferably 1 to 5 active agents D. The ratio of the number of T to the number of D may be 1-5:5-1, for example, 1:1, 1:2, 1:3, 2:1, 3:1, or the like. Preferably, the ratio of the number of T to the number of D is 1:1.

Among the above linking modes for the attachment of the multivalent linker to POLY, T and D, the most preferred embodiment is:

In this embodiment, the ratio of the number of T to the number of D is 1:1.

That is, the most preferred drug conjugate of the present disclosure may be represented as the following formula:

The drug conjugate of the present disclosure will now be described in detail by taking the most preferred scheme (formula (III)) as an example.

In formula (III), Ls, Ln, and Lr are attached together to form the multivalent linker L, such as polyvalent 3-thiolarylalkoxycarbonyl or 3-dithioarylalkoxycarbonyl, 3-thiolarylalkylaminocarbonyl or 3-dithioarylalkylaminocarbonyl, polyvalent 3-thiolalkoxycarbonyl or 3-dithioalkoxycarbonyl, or polyvalent 3-thiolalkylaminocarbonyl or 3-dithioalkylaminocarbonyl, wherein L and D form a cleavable bond, and L and T form a chemical bond that is more stable to hydrolysis.

The following are typical multivalent linkers L:

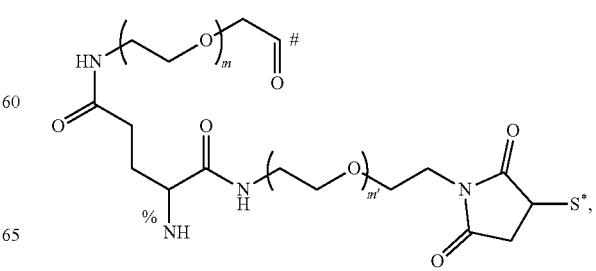

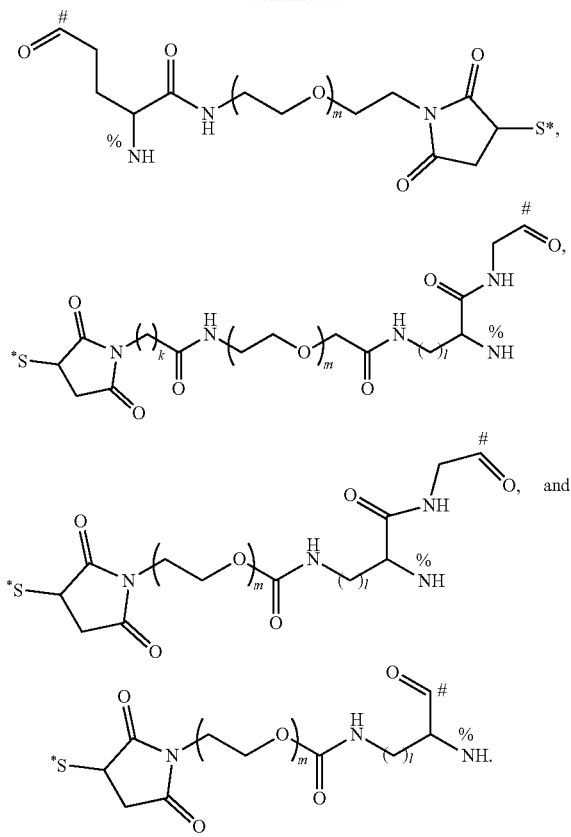

Here, symbol "*" represents an attachment point of the multivalent linker L and the targeting molecule T, "#" represents an attachment point of the multivalent linker L and the active agent D, and "%" represents an attachment point of the multivalent linker L and POLY, wherein m and m' are any integer between 1 and 20 respectively, and l and k are any integer between 1 and 10 respectively.

It should be pointed out that the S—C bond (which is more difficult to be hydrolyzed) of the "inseparable linker" in the above-mentioned typical multivalent linkers is formed by a reaction of forming a covalent bond between the targeting molecule T and the inseparable linker. In a typical compound, the atom S is brought by the targeting molecule T.

The above examples are merely the typical examples of the "inseparable linker", and do not limit the selection of the inseparable linker for the compound of the present disclosure.

The above examples are merely as the typical examples of "L", and do not limit the selection of "L" for the compounds of the present disclosure. In some specific preferred embodiments, "L" is:

The spacer linker Ls referred to in the present disclosure refers to a series of atoms connected to each other, which are used to link the separable linker Lr and the inseparable linker Ln, and are used to link POLY.

In one embodiment, the multivalent linker L comprises at least one peptide spacer linker formed by amino acids, said amino acids are independently selected from natural amino acids and non-natural α-amino acids. In another embodiment, said multivalent linker L comprises peptide spacer linker(s) formed by 1 to 40 amino acids, and said amino acids are preferably natural amino acids. Further, said multivalent linker L comprises a peptide spacer linker formed by 1 to 20 amino acids. Still further, said L preferably comprises a peptide spacer linker formed by 10 to 15 amino acids. Still further, L comprises at least one amino acid selected from the following group: aspartic acid, arginine, glycine, ornithine, cysteine, lysine, asparagine, arginine, threonine, glutamic acid, serine, citrulline, valine and glutamine.

Still further, said L preferably comprises one or more spacer linkers of dipeptide, tripeptide, tetrapeptide, pentapeptide, hexapeptide, heptapeptide, octapeptide, decapeptide, undecapeptides, and dodecapeptides formed by amino acids selected from aspartic acid, arginine, glycine, ornithine, cysteine, citrulline, valine, lysine, and combinations thereof.

The "separable linker" referred to in the present disclosure is also referred to as a cleavable linker, which refers to a linker comprising at least one bond capable of being cleaved under physiological conditions (for example, a pH-labile, acid-labile, oxidatively-labile, or enzyme-labile bond). Such physiological conditions which lead to the cleavage of a bond include, for example, standard chemical hydrolysis reactions occurring at physiological pH. Or, due to the compartmentalization into organelles such as endosomes with a lower pH than that of cytoplasm, the bond is hydrolyzed by in vivo proteolytic enzymes, lipases, cholinesterases, phosphomonoesterases, nucleases, sulfatases, and the like.

It should be understood that the cleavable bond described herein does not singly present in the separable linker; on the contrary, after the separable linker is covalently attached to the active agent D, the linking moiety is the cleavable bond. The adjacent atoms of the separable linker and the active agent D are linked by the cleavable bond, and the separable linker breaks into two or more fragments after the bond is cleaved. After the cleavable bond is cleaved, the active agent D is released and separated from the parent to exert physiological activity.

It should be understood that the active agent D referred to herein comprises an active agent moiety which is suitable for covalently binding to the separable linker to form a cleavable bond. In this way, when the cleavable bond is cleaved, the active agent D is released in an unmodified form, that is, a form in which no covalent bond is formed. The selection of D and the formation of the cleavable bond

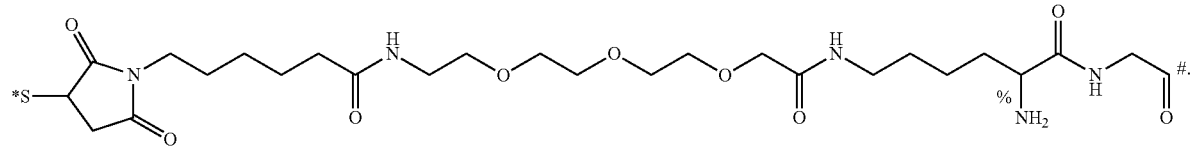

with the separable linker in the conjugate will be described in detail in the following content.

The cleavable bond refers to a relatively weak bond, and it is able to react with water (i.e., be hydrolyzed) under physiological conditions. The tendency of a bond to be hydrolyzed in water depends not only on the type of the attachment of the two central atoms, but also on the substituents attached to these central atoms. Typical hydrolysis-labile linking groups include carboxylates, phosphates, anhydrides, acetal, ketals, acyloxyalkyl esters, imines, orthoesters, peptides, oligonucleotides, and the like.

The active agent referred to in the present disclosure, the active agent "D", refers to a part of an unmodified parent active agent, or a residue of the unmodified parent active agent prior to the formation of a covalent chain (or its activated or chemically modified form) by the covalent attachment of a drug to the multivalent linker of the present disclosure. When the linking group between the active agent moiety and the multivalent linker is hydrolyzed or digested, the active agent itself is released.

According to the purpose of the present disclosure, the term "residue" should be understood as a part of the compound, and it refers to the remainder after undergoing a substitution reaction with another compound.

The active agent "D" referred to in the present disclosure is a camptothecin-based anticancer agent. Camptothecin-based drugs are topoisomerase I inhibitors for clinical use. While having high activity, camptothecin-based drugs have disadvantages such as poor water solubility and great toxic and side effects on normal body tissues, which greatly limit the clinical application of the camptothecin-based anticancer agents.

D may be the camptothecin-based drug represented by the following formula:

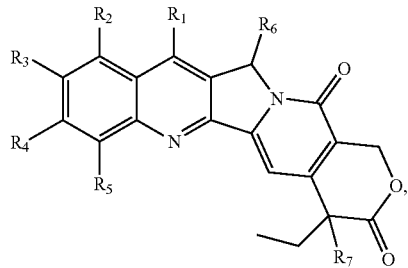

wherein $R_1$ to $R_5$ are selected from the following groups independently from each other: hydrogen, halogen, acyl, alkyl, substituted alkyl, alkoxy, substituted alkoxy, alkenyl, alkynyl, cycloalkyl, hydroxyl, cyano, nitro, azido, amido, hydrazine, amine group, substituted amine group, hydroxycarbonyl, alkoxycarbonyl, alkoxycarbonyloxy, carbamoyloxy, arylsulfonyloxy, alkylsulfonyloxy, and the like. $R_6$ is H or $OR_8$, $R_8$ is alkyl, alkenyl, cycloalkyl, halogenated alkyl or hydroxyalkyl. $R_7$ is a position where the separable linker is covalently bonded thereto, and is preferably a hydroxy group.

The only limitation for the camptothecin-based anticancer agents suitable for the content herein is that the compound has at least one functional group available for chemical reactions (i.e., covalent attachment to the multivalent linker), such as amino group, hydroxy group, or thiol group, which is attached to structural formula (I), and the compound coupled to structural formula (I) described herein has no significant loss of biological activity.

Among them, the active agent "D" is a camptothecin-based anticancer agent, and is preferably irinotecan, SN-38, 10-hydroxycamptothecin, or rubitecan.

Among them, the structure of irinotecan is as follows:

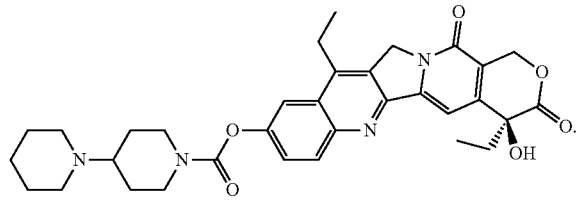 [SMILES: CCc1c2c(nc3ccc(OC(=O)N4CCC(N5CCCCC5)CC4)cc13)-c1cc3c(c(=O)n1C2)COC(=O)[C@]3(O)CC]

The structure of SN-38 is as follows:

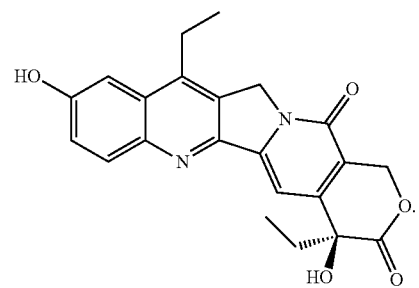 [SMILES: CCc1c2c(nc3ccc(O)cc13)-c1cc3c(c(=O)n1C2)COC(=O)[C@]3(O)CC]

The structure of 10-hydroxycamptothecin is as follows:

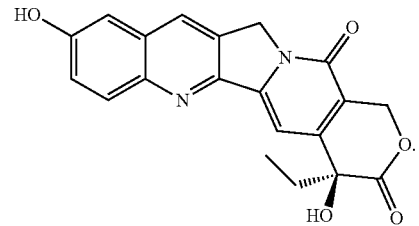 [SMILES: CC[C@@]1(O)C(=O)OCc2c1cc1n(c2=O)Cc2cc3cc(O)ccc3nc2-1]

The structure of rubitecan is as follows:

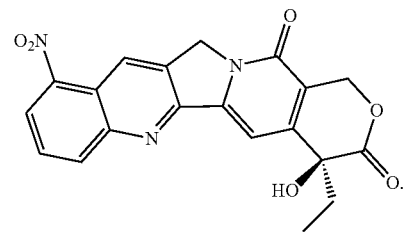 [SMILES: CC[C@@]1(O)C(=O)OCc2c1cc1n(c2=O)Cc2cc3c([N+](=O)[O-])cccc3nc2-1]

The hydroxy group may form a cleavable ester bond with the separable linker.

The "inseparable linker" referred to in the present disclosure means it comprises at least one chemical bond that is more stable to hydrolysis under physiological conditions, particularly, a covalent bond. That is to say, no significant hydrolysis will occur under physiological conditions in the long term. Examples of a linking group which is stable to hydrolysis include but are not limited to the following cases: a carbon-carbon bond (for example, in an aliphatic chain), a carbon-sulfur bond, a disulfide bond, an ester bond, an amide bond, polyurethanes, and analogs thereof, etc. In general, a bond which is stable to hydrolysis has a hydrolysis rate less than about 1% to 2% under physiological conditions.

In the present disclosure, "T" is a targeting molecule with or without pharmaceutical effect. The effect of this targeting molecule is to increase the targeting property, such that the concentration of the conjugate in a target tissue is higher and the physiological activity or pharmaceutical effect is enhanced. "T" may be a monofunctional targeting molecule, and may also be a multifunctional targeting molecule. In some alternative embodiments, "T" may also be a targeting moiety composed of two or more targeting molecules. In certain specific embodiments, "T" may be an RGD peptide containing a sequence of "arginine-glycine-aspartic acid", and the RGD peptide is the recognition site of the interaction between integrin and its ligand protein. A preferred RGD peptide includes iRGD, cRGD, and the like.

The structure of iRGD is as follows:

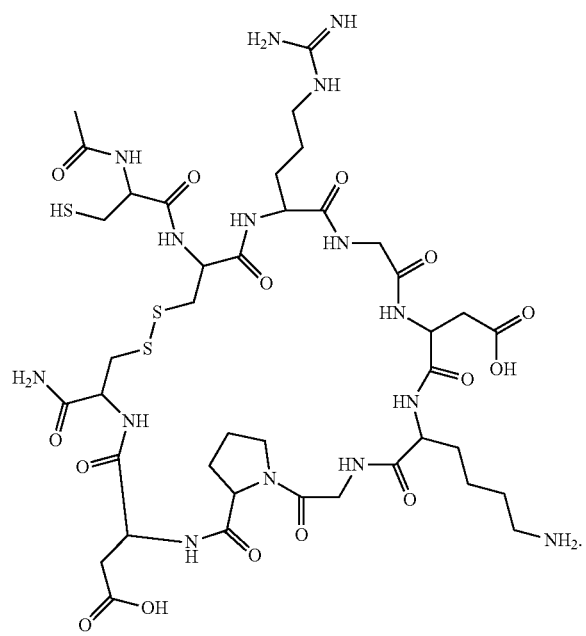 [SMILES: CC(=O)NC(CS)C(=O)NC1CSSCC(C(N)=O)NC(=O)C(CC(=O)O)NC(=O)C2CCCN2C(=O)CNC(=O)C(CCCCN)NC(=O)C(CC(=O)O)NC(=O)CNC(=O)C(CCCNC(=N)N)NC1=O]

cRGD is a series of compounds, and the typical compounds include:

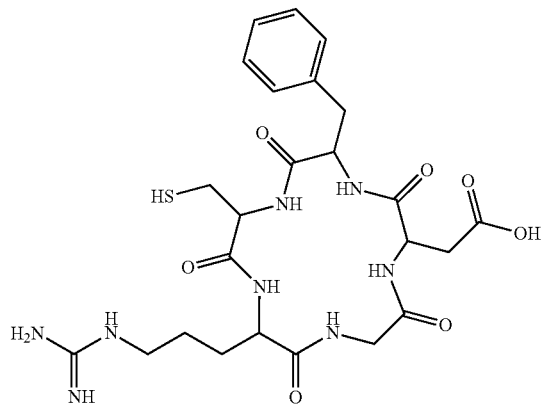

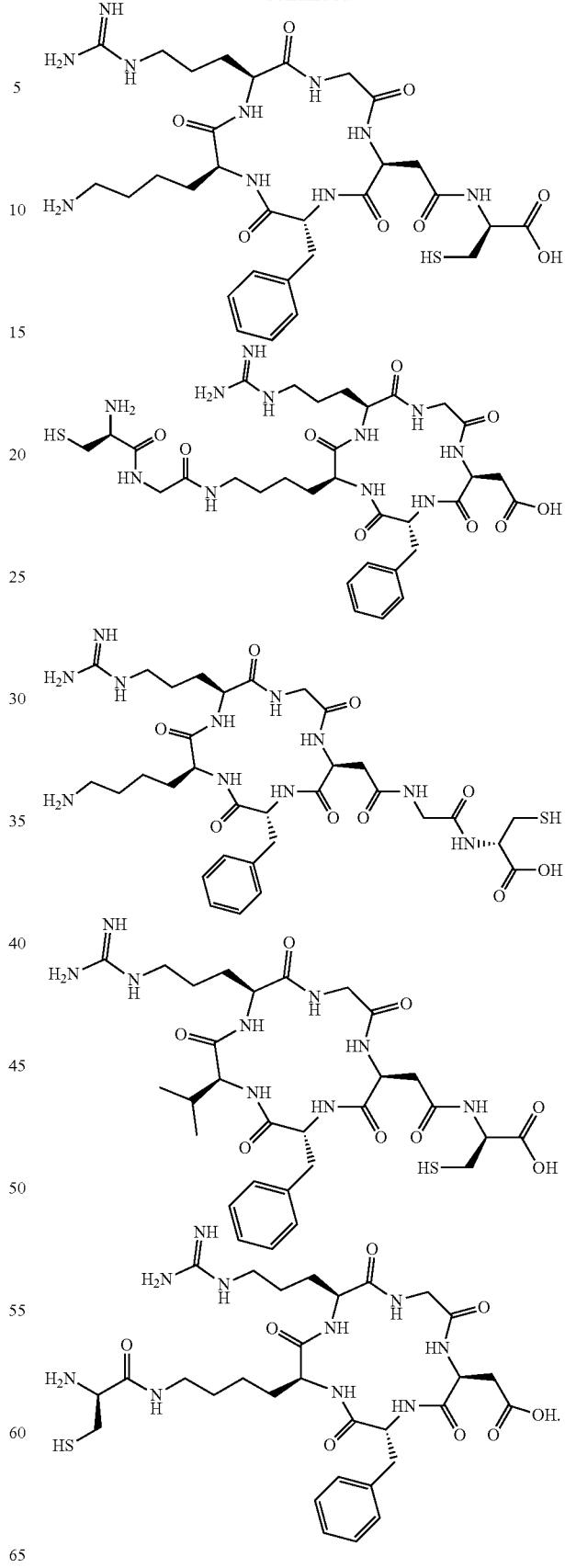

Other preferred targeting molecules include tLyp-1, Lyp-1, RPARPAR, Angiopep2, GE11, or folic acid.

The structure of tLyp-1 is as follows:

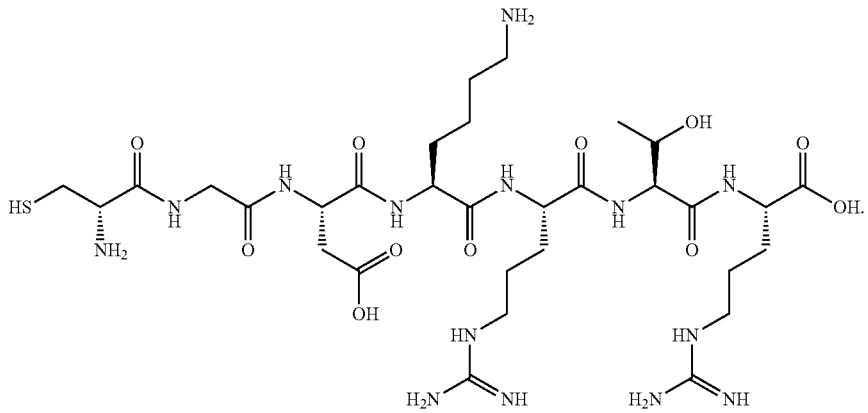 [SMILES: CC(O)[C@H](NC(=O)[C@H](CCCNC(=N)N)NC(=O)[C@H](CCCCN)NC(=O)[C@H](CC(=O)O)NC(=O)CNC(=O)[C@H](N)CS)C(=O)N[C@@H](CCCNC(=N)N)C(=O)O]

The structure of Lyp-1 is as follows:

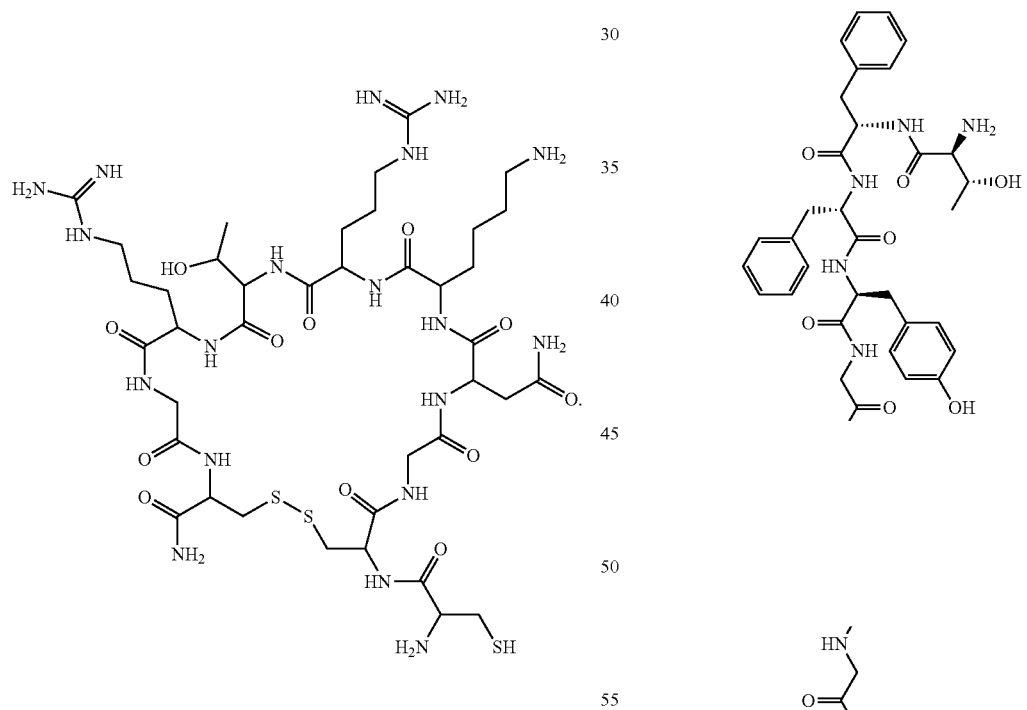

The polypeptide sequence of RPARPAR is arginine-proline-alanine-arginine-proline-alanine-arginine. Here, it should be specified that since RPARPAR needs to be attached to the multivalent linker L, it is required to attach RPARPAR to L with cysteine in the preparation. Therefore, in a specific compound, RPARPAR appears as CRPARPAR.

The polypeptide sequence of Angiopep2 is TFFYGGSRGKRNNFKTEEY, and its structure is as follows:

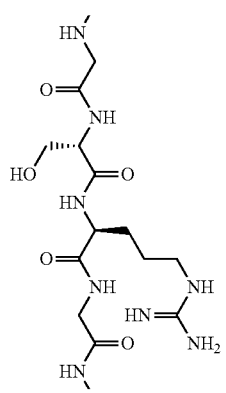

-continued
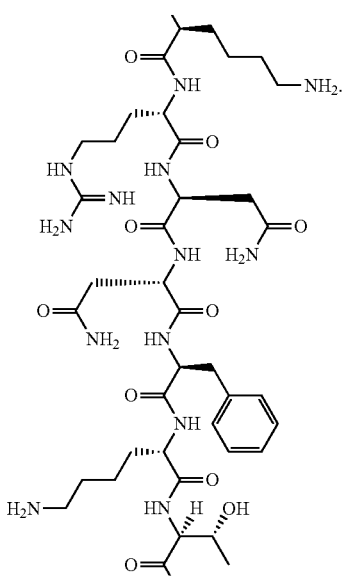
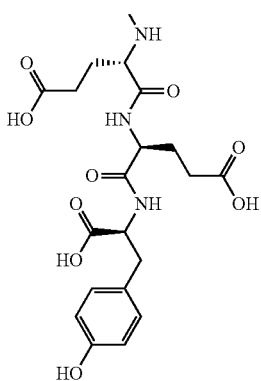
The polypeptide sequence of GE11 is YHWYGYTPQNVI, and its structure is:
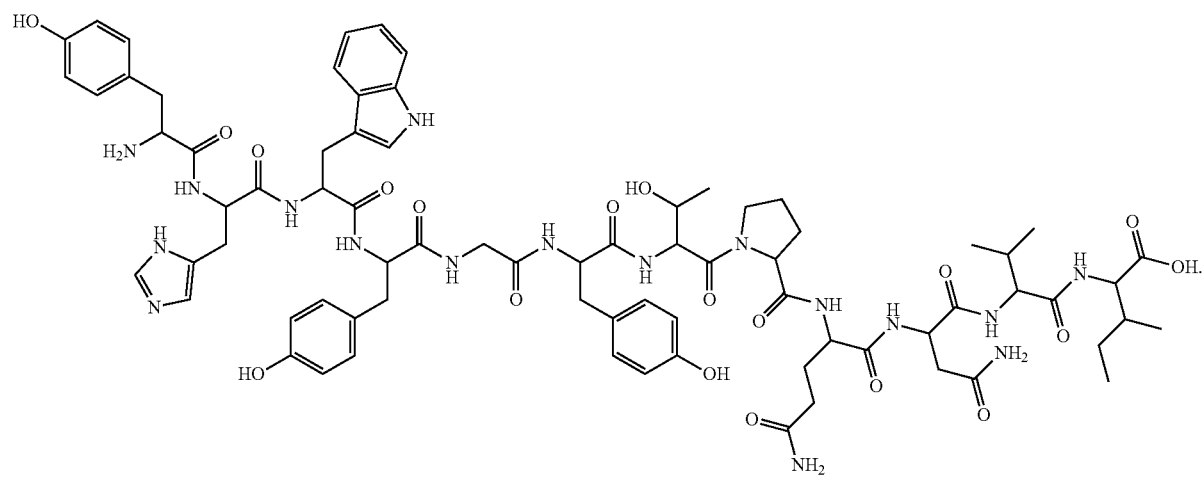 [SMILES: CCC(C)C(NC(=O)C(NC(=O)C(CC(N)=O)NC(=O)C(CCC(N)=O)NC(=O)C1CCCN1C(=O)C(NC(=O)C(Cc1ccc(O)cc1)NC(=O)CNC(=O)C(Cc1ccc(O)cc1)NC(=O)C(Cc1c[nH]c2ccccc12)NC(=O)C(Cc1cnc[nH]1)NC(=O)C(N)Cc1ccc(O)cc1)C(C)O)C(C)C)C(=O)O]
The structure of folic acid is as follows:
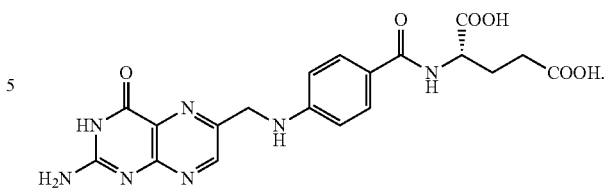
In preferred embodiments of the present disclosure, "POLY" is a linear polyethylene glycol linking arm, that is, the conjugate of the present disclosure includes the following types of compounds:
three-arm:
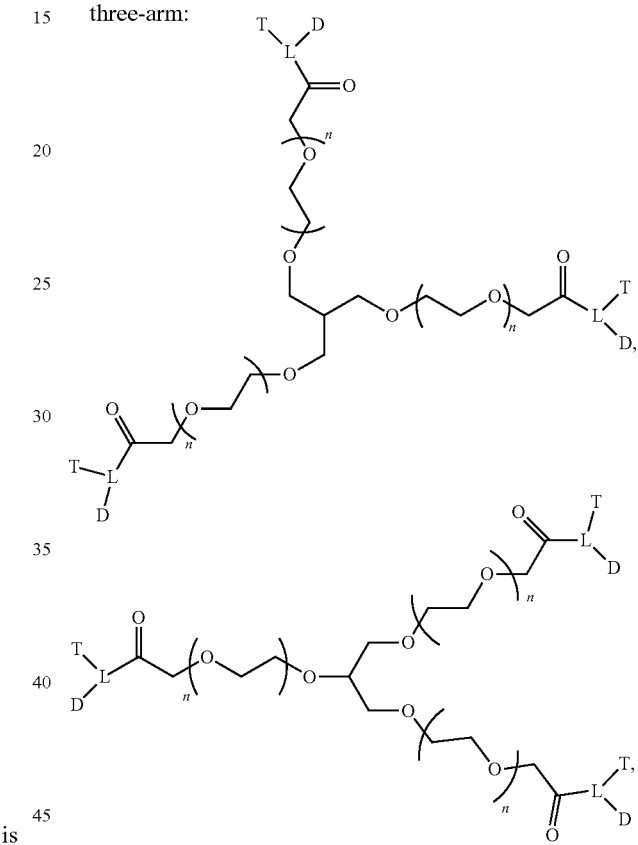

four-arm:
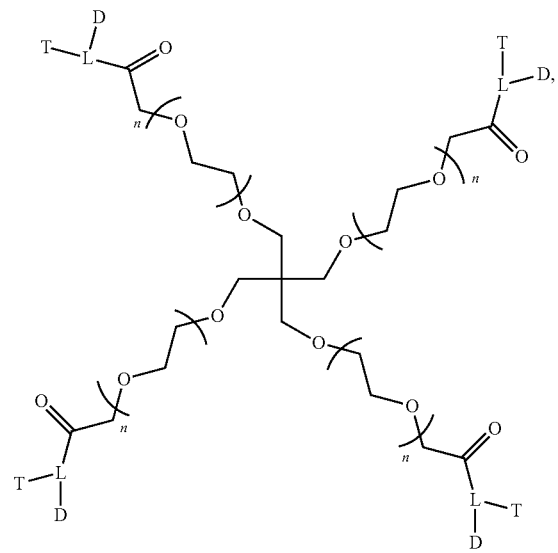
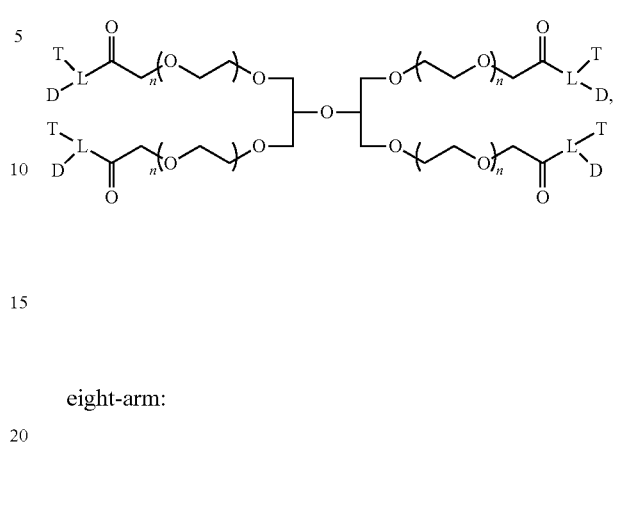
eight-arm:
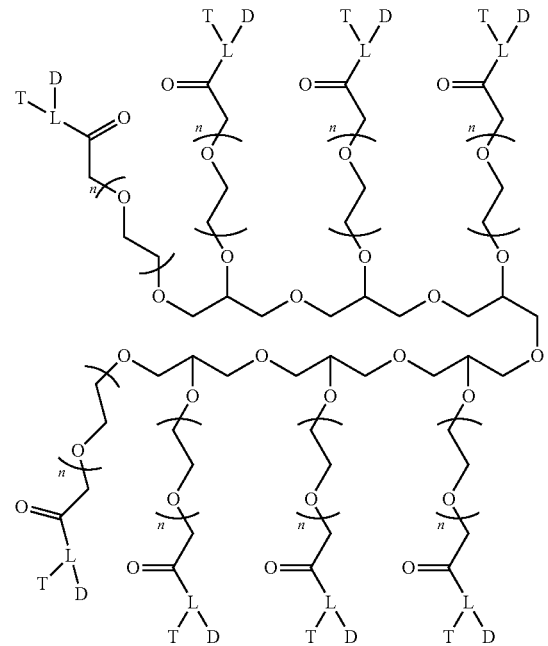

-continued

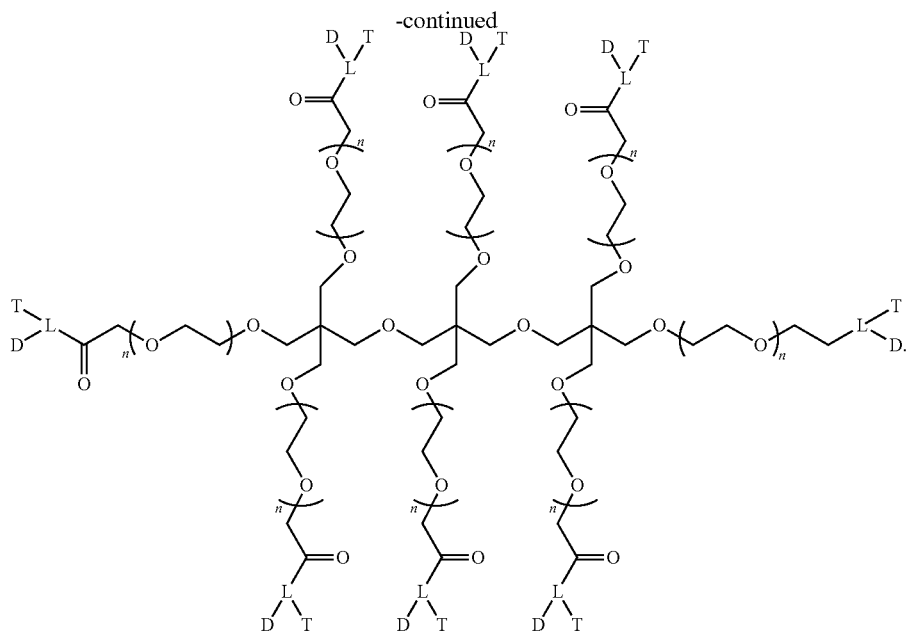

It should be specified that, in the above preferred embodiments, the linear polyethylene glycol is:

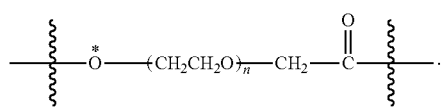

However, this linear polyethylene glycol is not the limitation of the present disclosure, and may be replaced with other linear polyethylene glycols, for example:

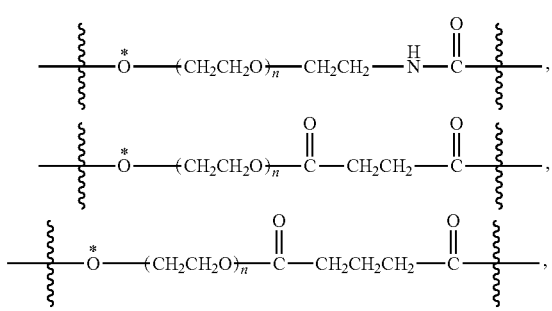

and the like.

In a preferred embodiment of the present disclosure, R is

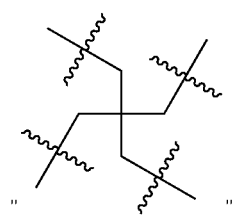

with 5 carbon atoms, that is, the conjugate of the present disclosure is:

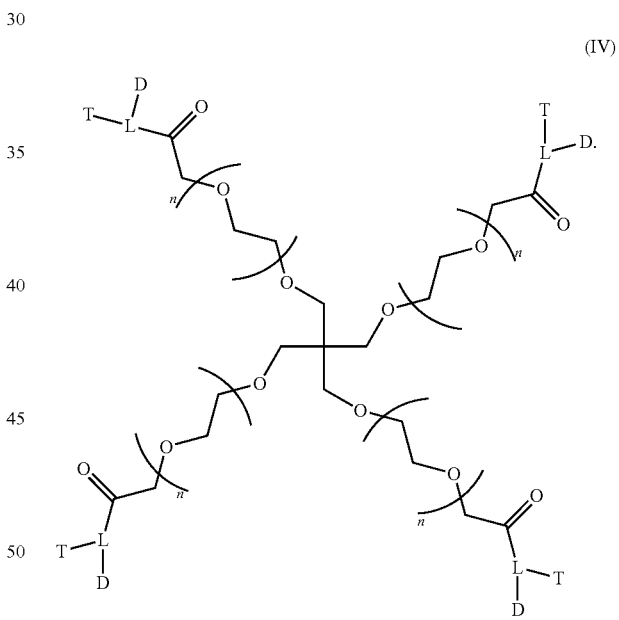

(IV)

On the basis of formula (IV), n is 5 to 500, preferably 50 to 200, and most preferably 113. In a more preferred embodiment, the targeting moiety "T" of the conjugate of the present disclosure is one selected from iRGD, tLyp-1, Lyp-1, RPARPAR, cRGD, Angiopep2, GE11, or folic acid, and the active agent "D" is one selected from irinotecan, SN-38, 10-hydroxycamptothecin, and rubitecan.

Any shape of the conjugate of the present disclosure should be included in the present disclosure, and these shapes are determined by the mode of attachment of the active agent, the targeting molecule and various multivalent linkers in the present disclosure. In one aspect, the overall three-dimensional shape of the conjugate of the present disclosure is linear. In another aspect, the conjugate described herein preferably have a three-dimensional shape which is an "X" shape or a cruciform.

In another preferred embodiment of the present disclosure, R is

with 4 carbon atoms, that is, the conjugate of the present disclosure is:

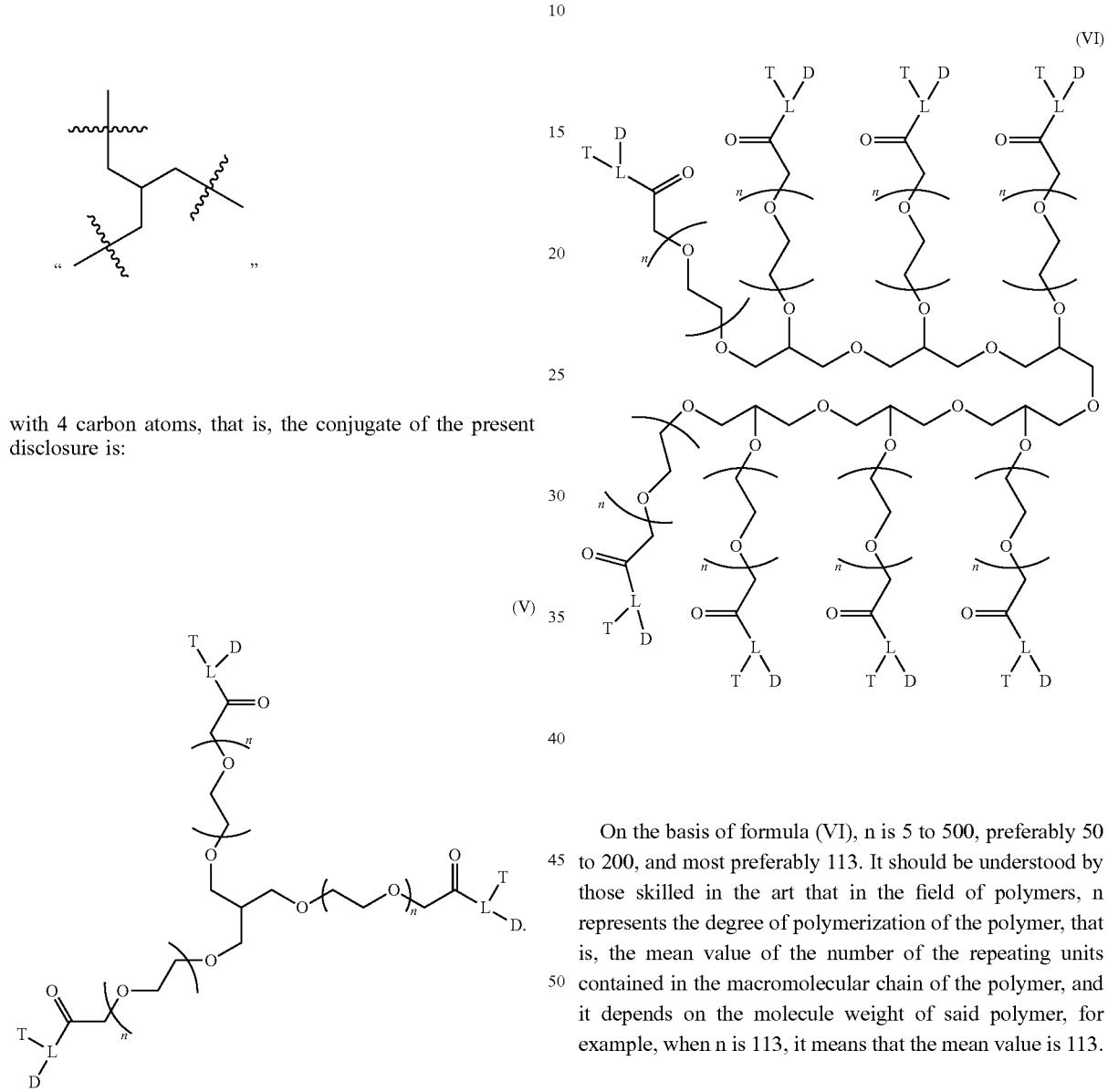

On the basis of the formular (V), n is 5 to 500, preferably 50 to 200, and most preferably 113. In a more preferred embodiment, the targeting moiety "T" of the conjugate of the present disclosure is one selected from iRGD, tLyp-1, Lyp-1, RPARPAR, cRGD, Angiopep2, GE11, or folic acid, and the active agent "D" is one selected from irinotecan, SN-38, 10-hydroxycamptothecin, and rubitecan.

In a third preferred embodiment of the present disclosure, the conjugate of the present disclosure is:

On the basis of formula (VI), n is 5 to 500, preferably 50 to 200, and most preferably 113. It should be understood by those skilled in the art that in the field of polymers, n represents the degree of polymerization of the polymer, that is, the mean value of the number of the repeating units contained in the macromolecular chain of the polymer, and it depends on the molecule weight of said polymer, for example, when n is 113, it means that the mean value is 113.

In a more preferred embodiment, the targeting moiety "T" of the conjugate of the present disclosure is one selected from iRGD, tLyp-1, Lyp-1, RPARPAR, cRGD, Angiopep2, GE11, or folic acid, and the active agent "D" is one selected from irinotecan, SN-38, 10-hydroxycamptothecin, and rubitecan.

Based on the formulae (IV), (V) and (VI), in certain specific embodiments, the compound of the present disclosure is as follows:

Compound 1
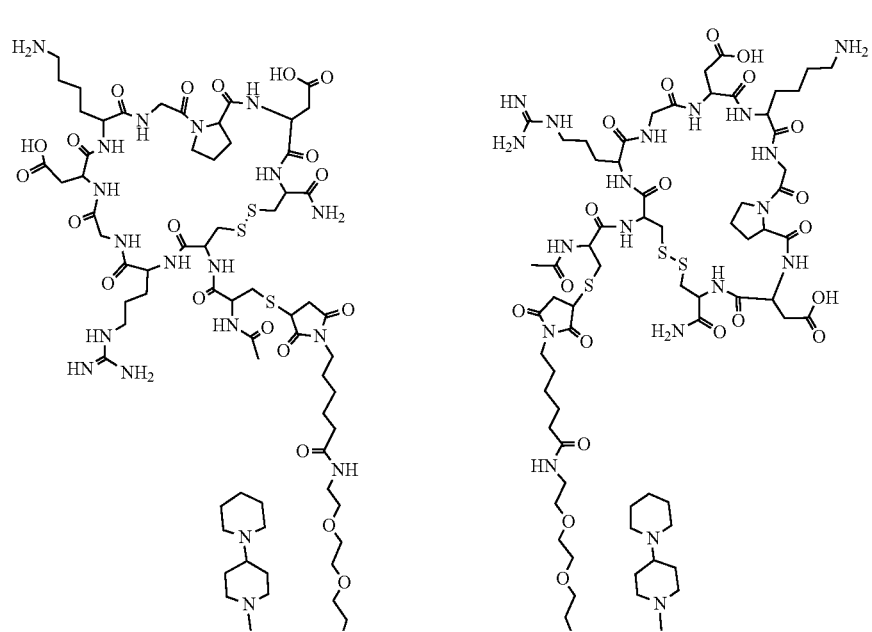
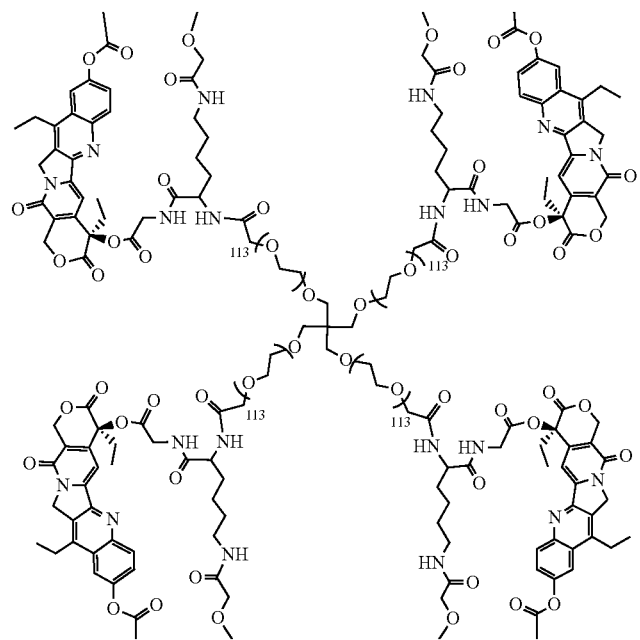

-continued
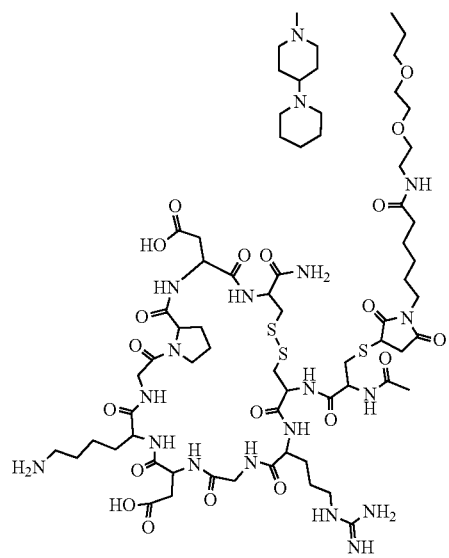
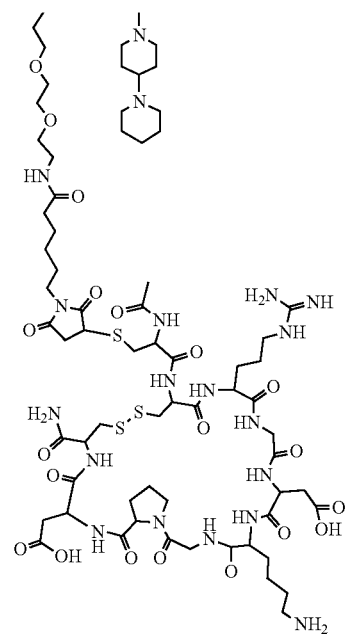
D is irinotecan, and T is iRGD.
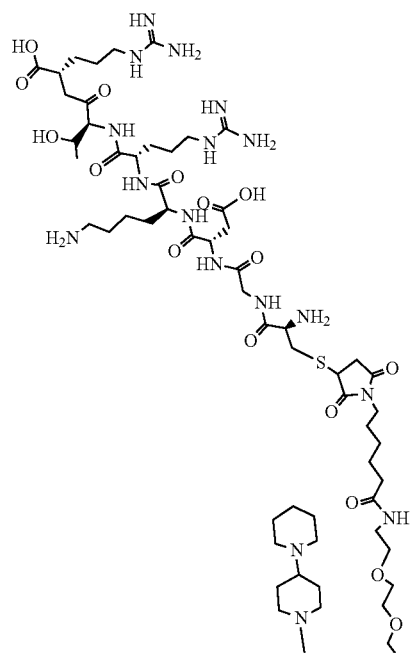
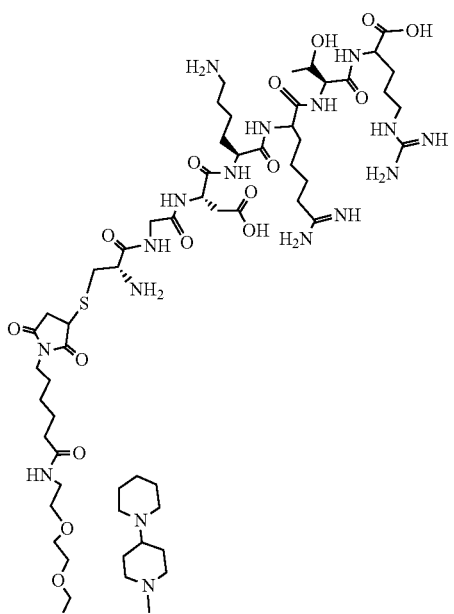
Compound 2

-continued
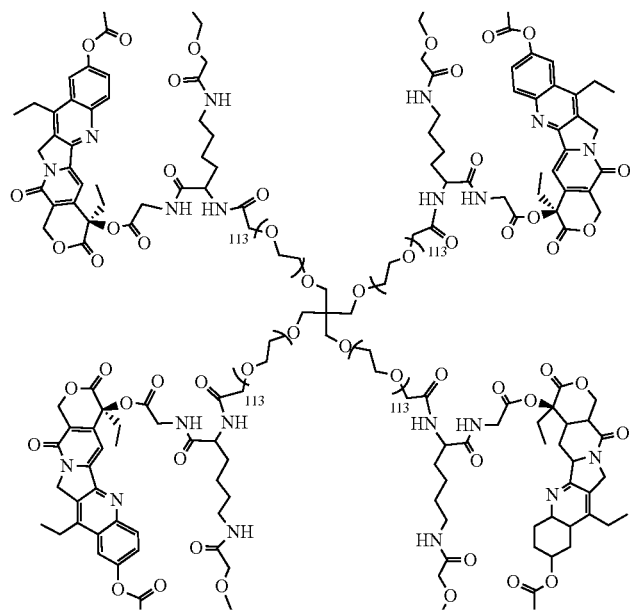
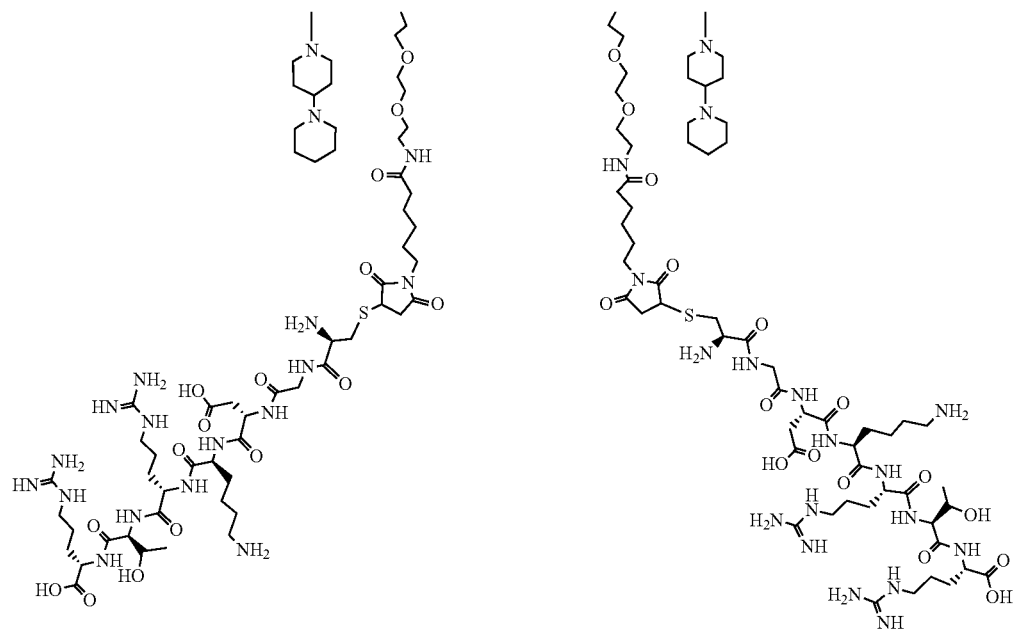
D is irinotecan, and T is tLyp-1.

-continued
Compound 3
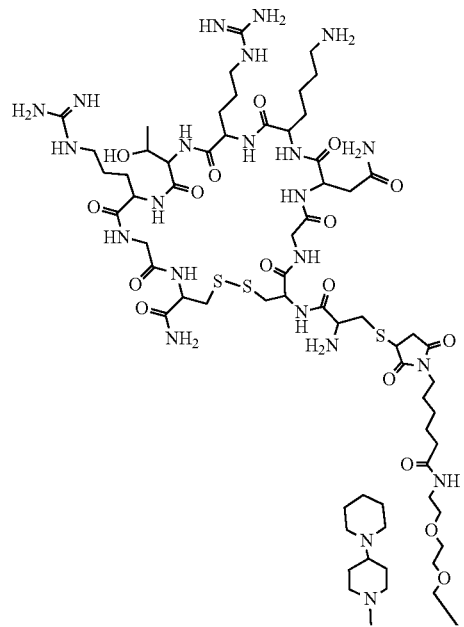
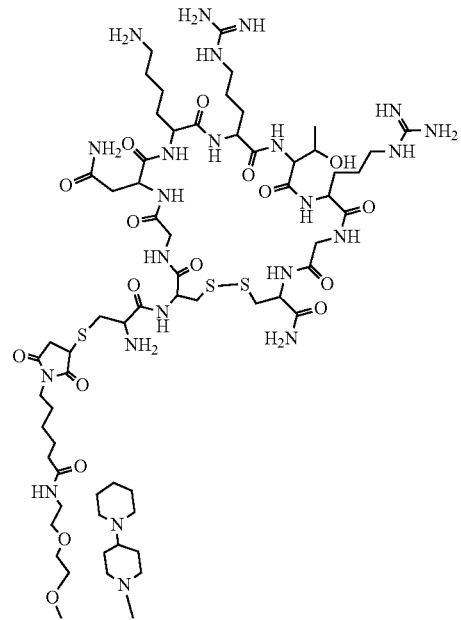
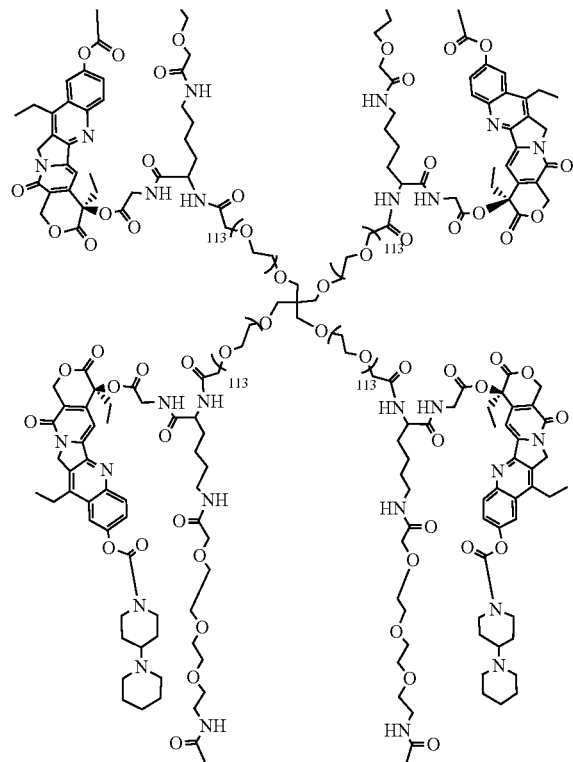

37
38
-continued
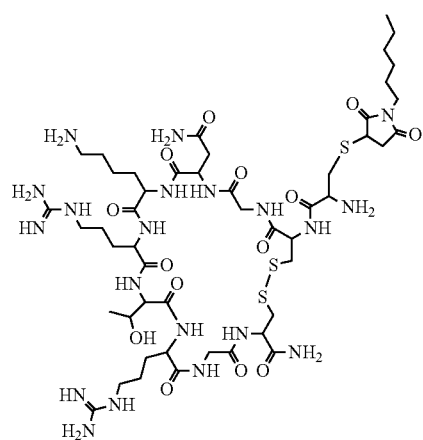
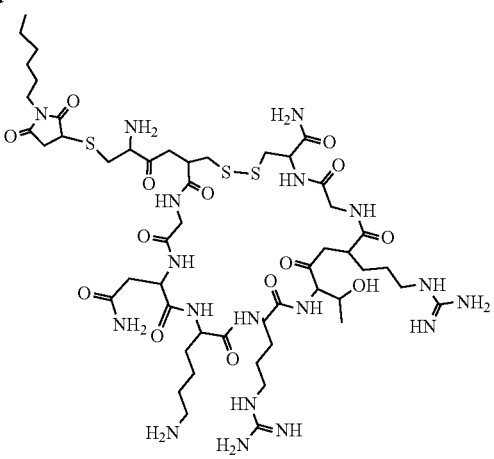
Compound 4
D is irinotecan, and T is Lyp-1.
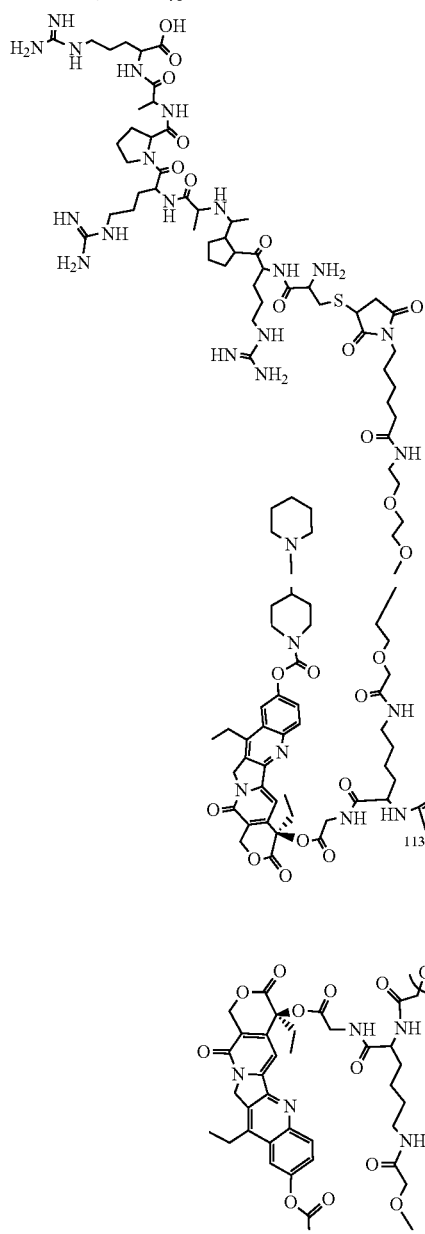
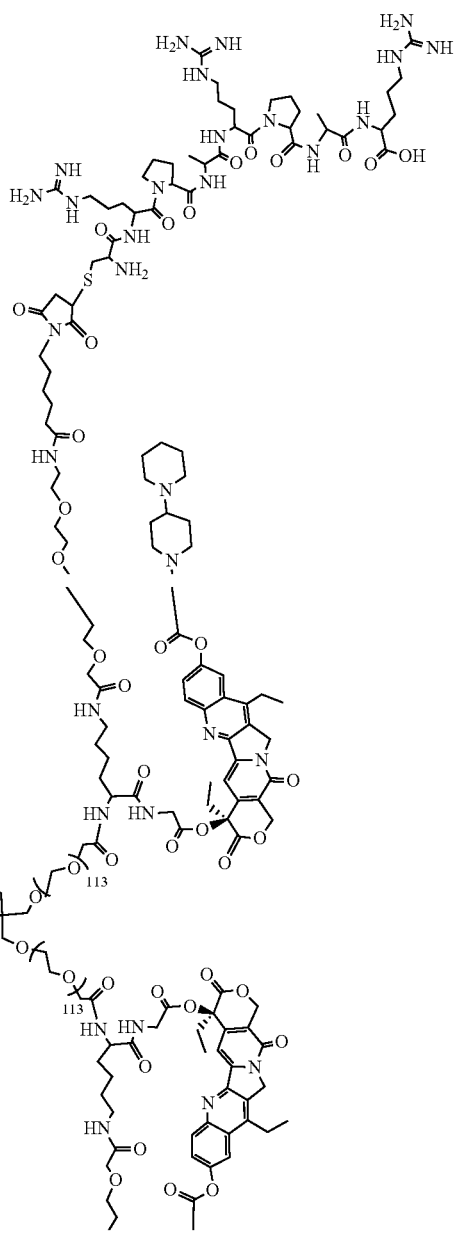

-continued
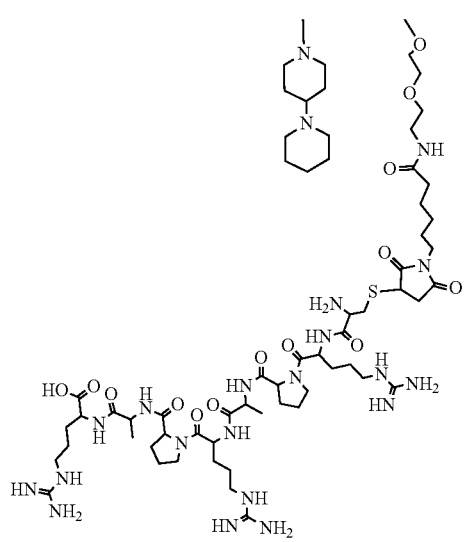
D is irinotecan, and T is RPARPAR.
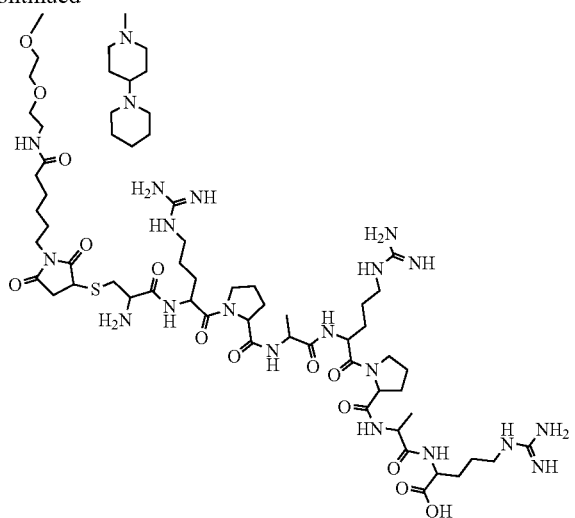
Compound 5
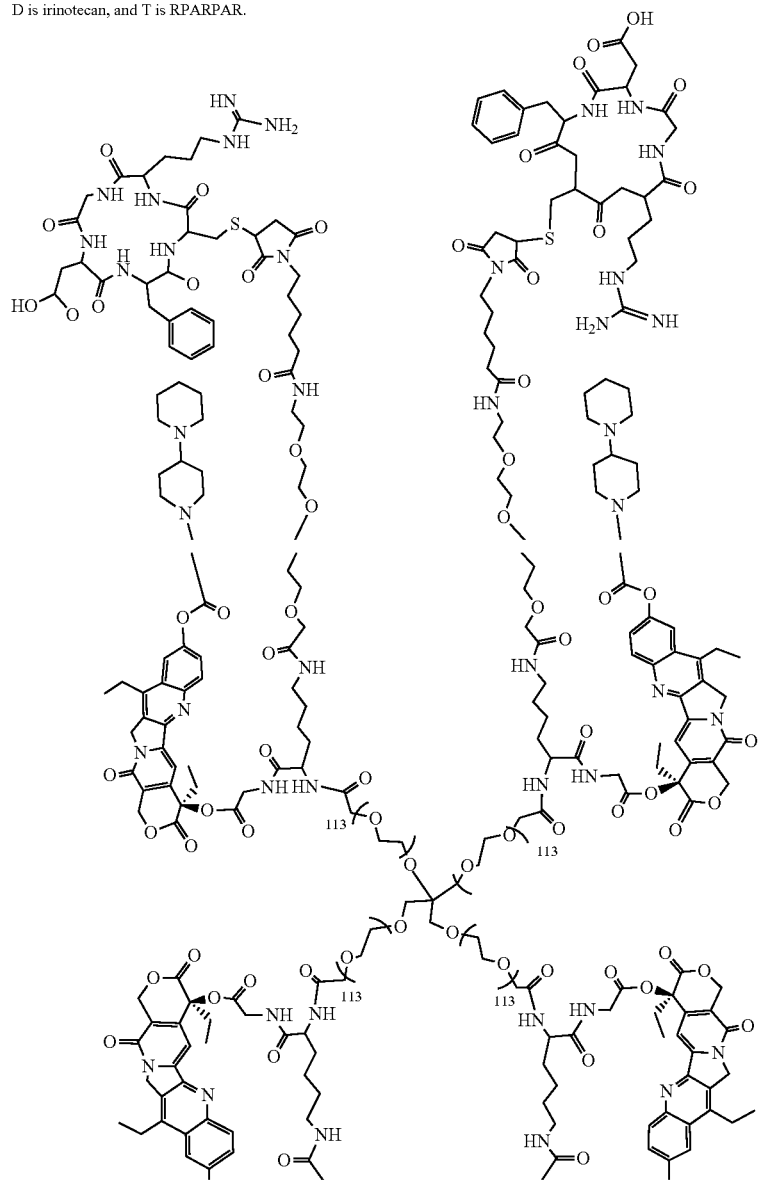

-continued
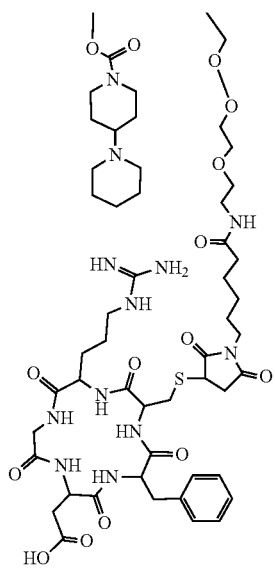 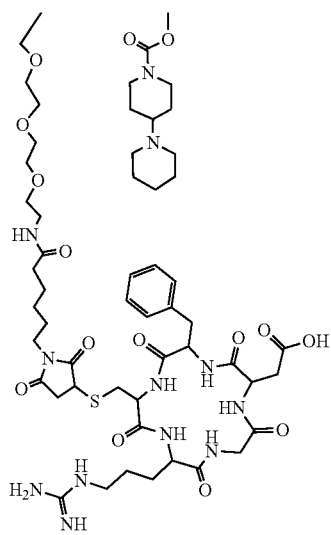
D is irinotecan, and T is cRGD.
Compound 6
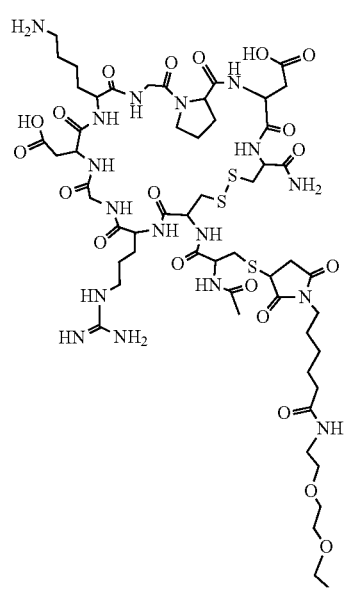 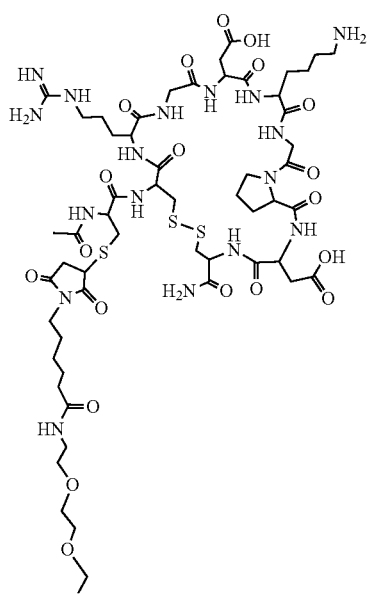

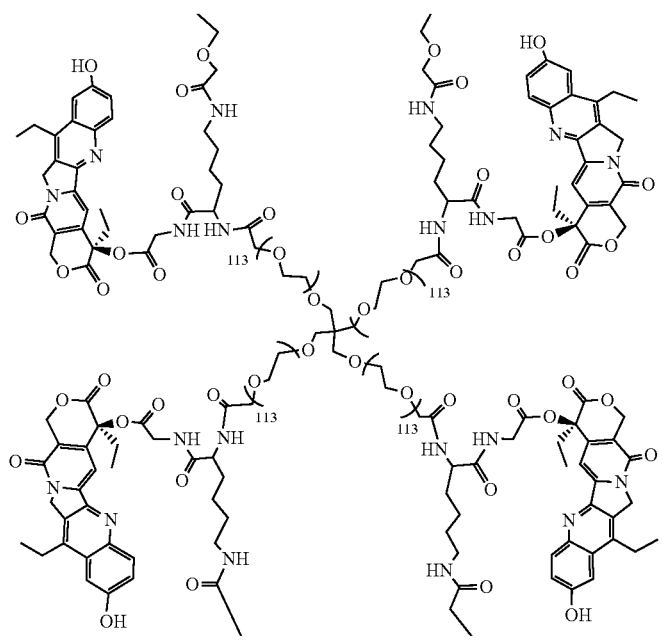
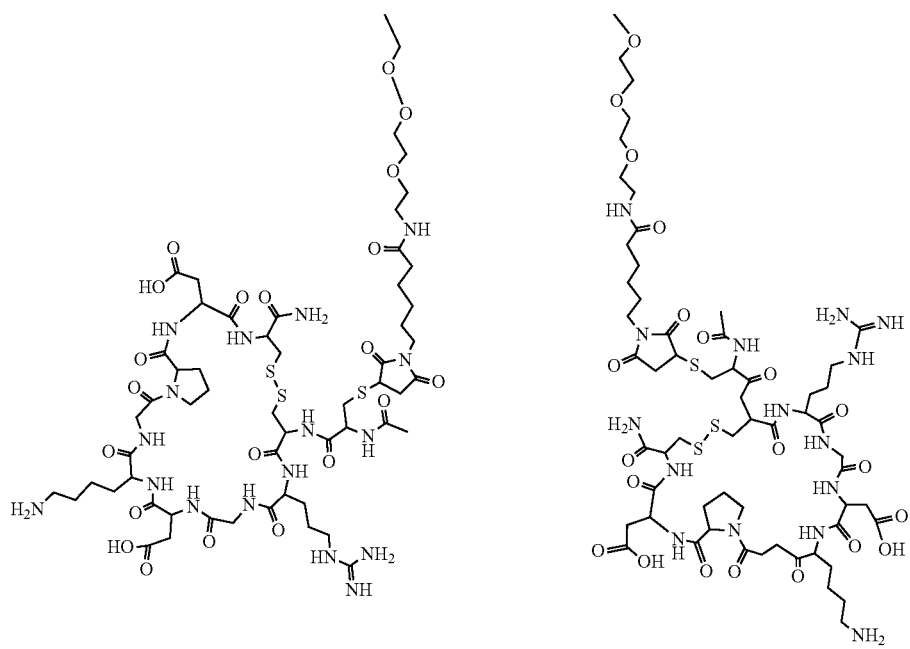
D is SN-38, and T is iRGD.

-continued
Compound 7
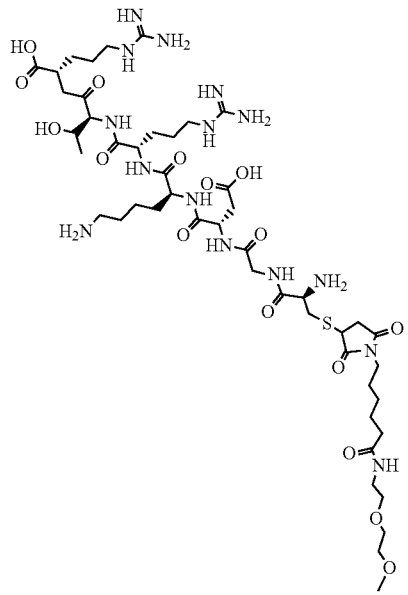
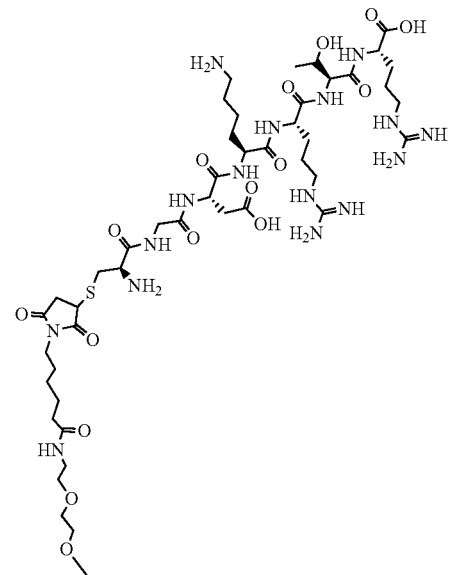
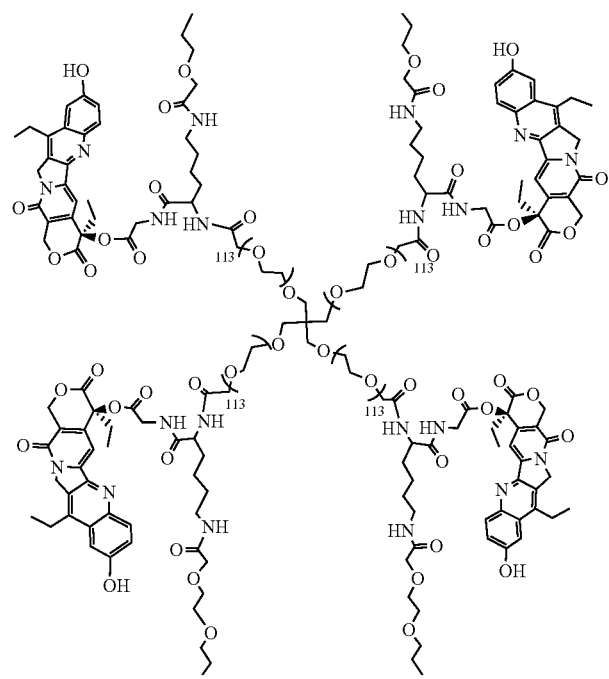

-continued
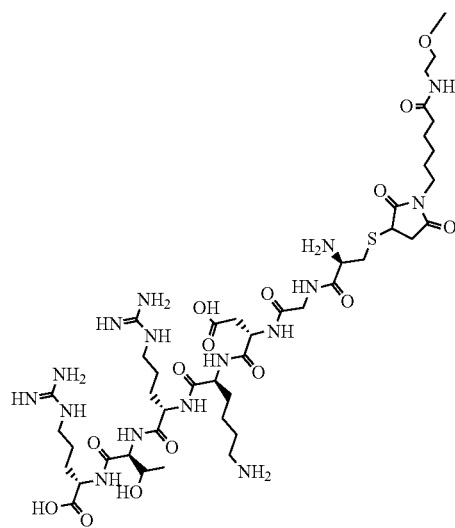
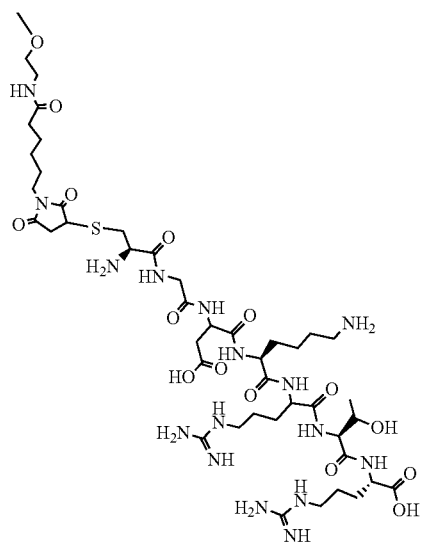
D is SN-38, and T is tLyp-1.
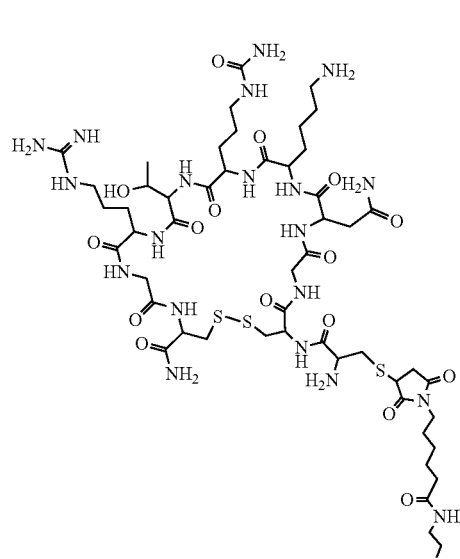
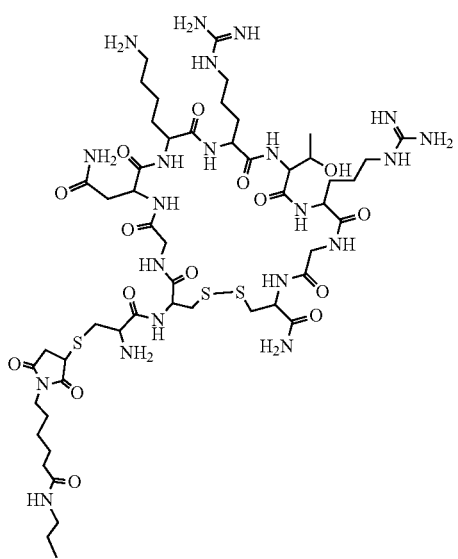
Compound 8

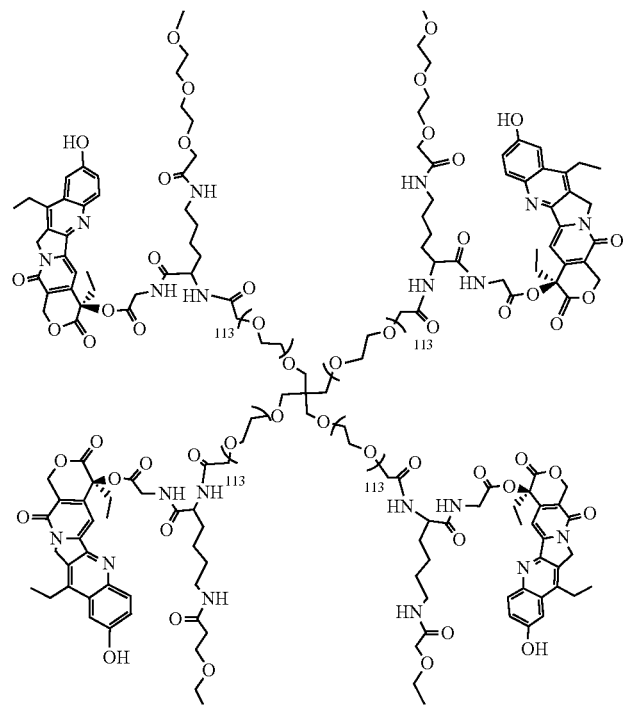
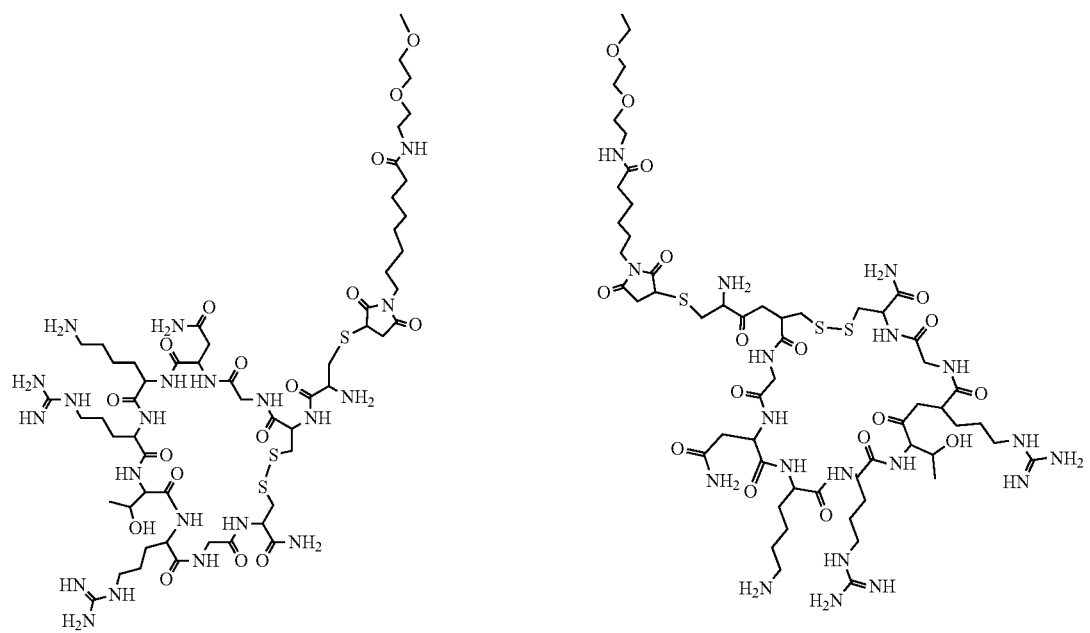
D is SN-38, and T is Lyp-1.

Compound 9
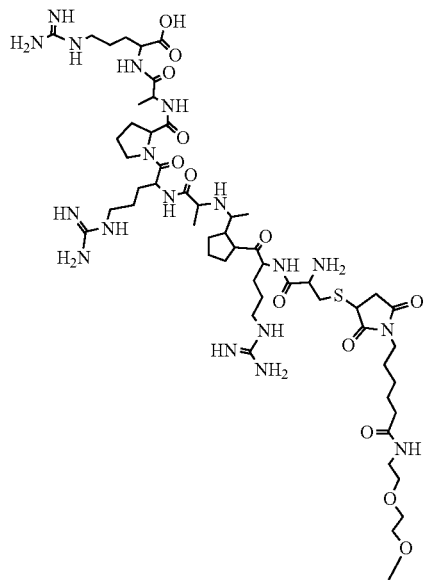
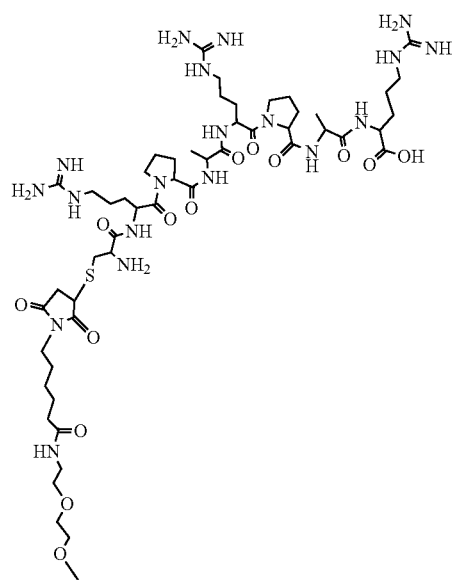
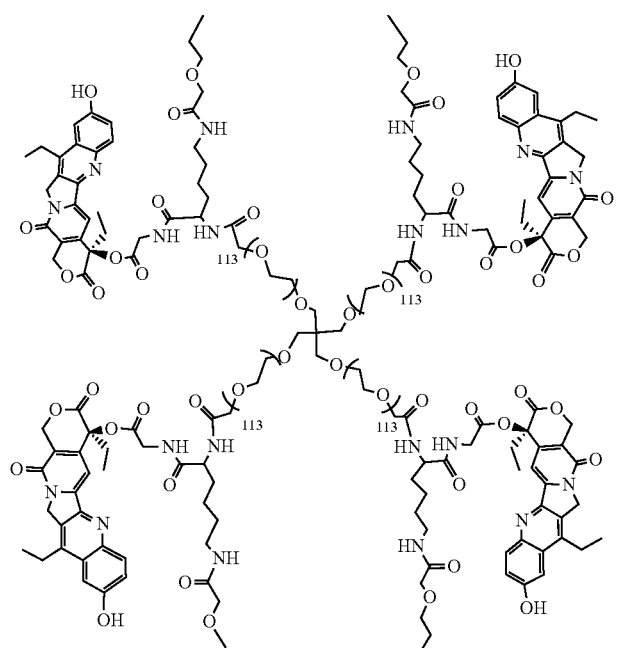

-continued
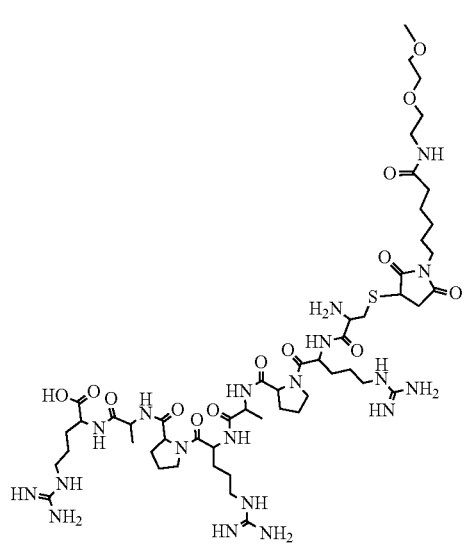
D is SN-38, and T is RPARPAR.
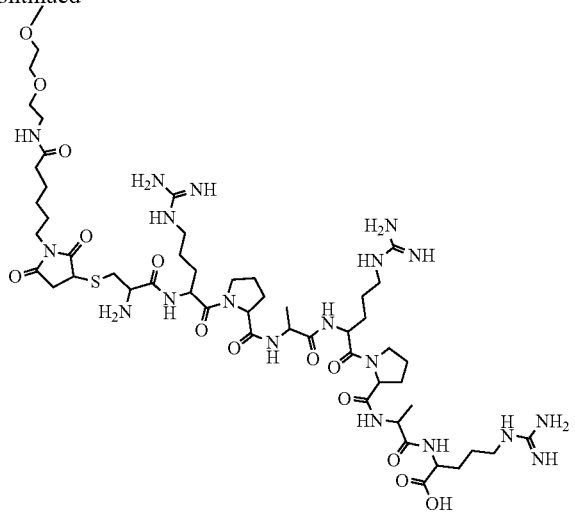
Compound 10
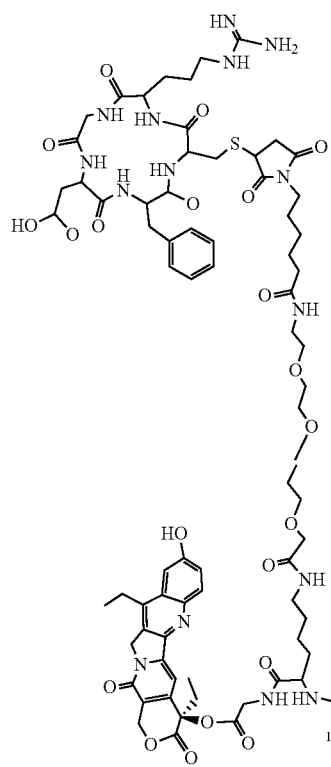
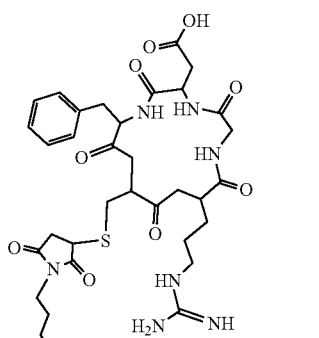
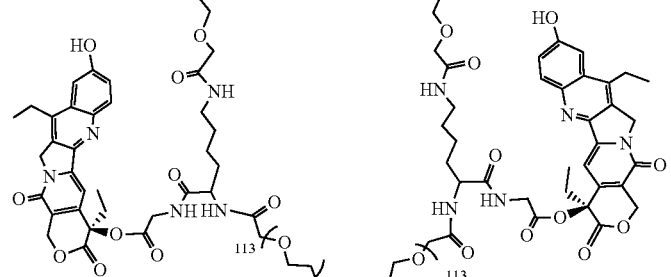
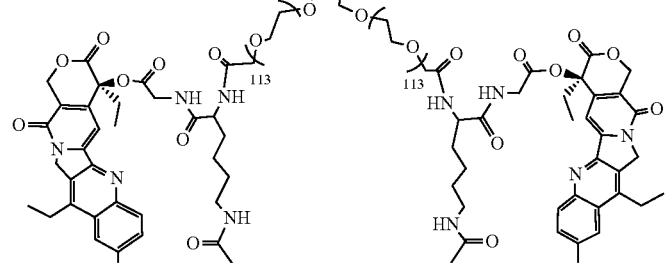

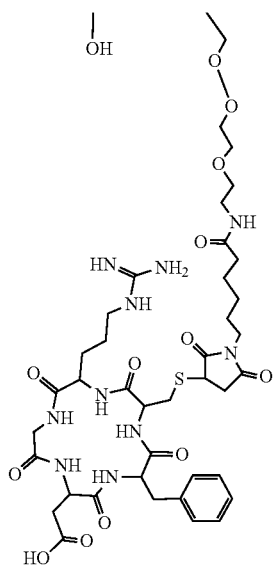
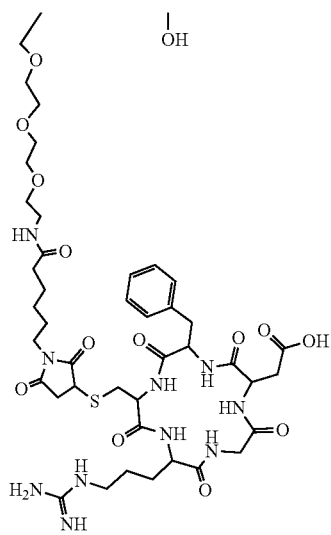
D is SN-38, and T is cRGD.
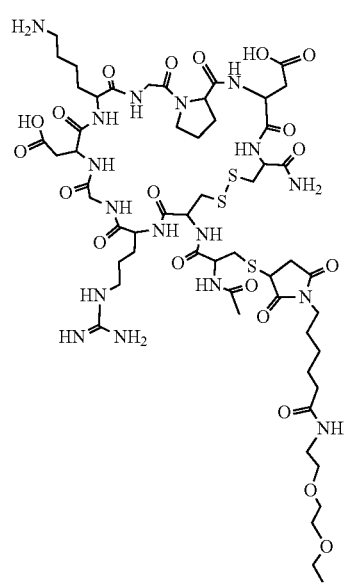
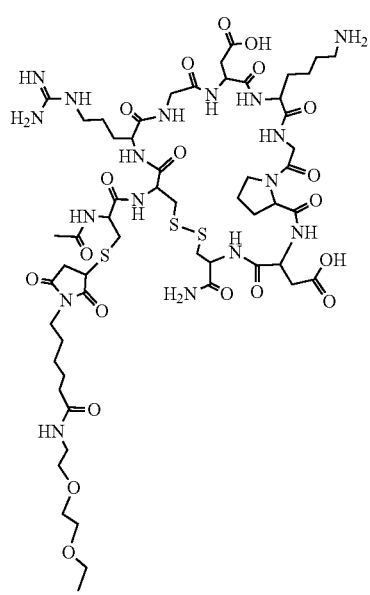
Compound 11

-continued
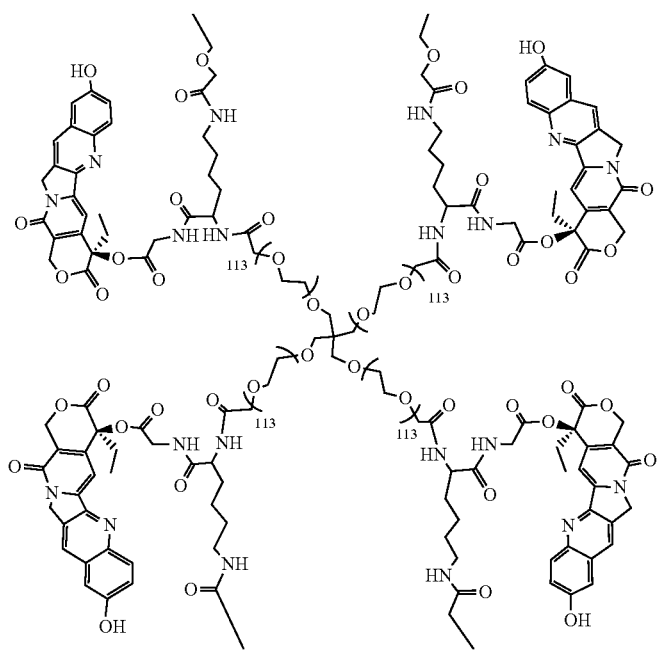
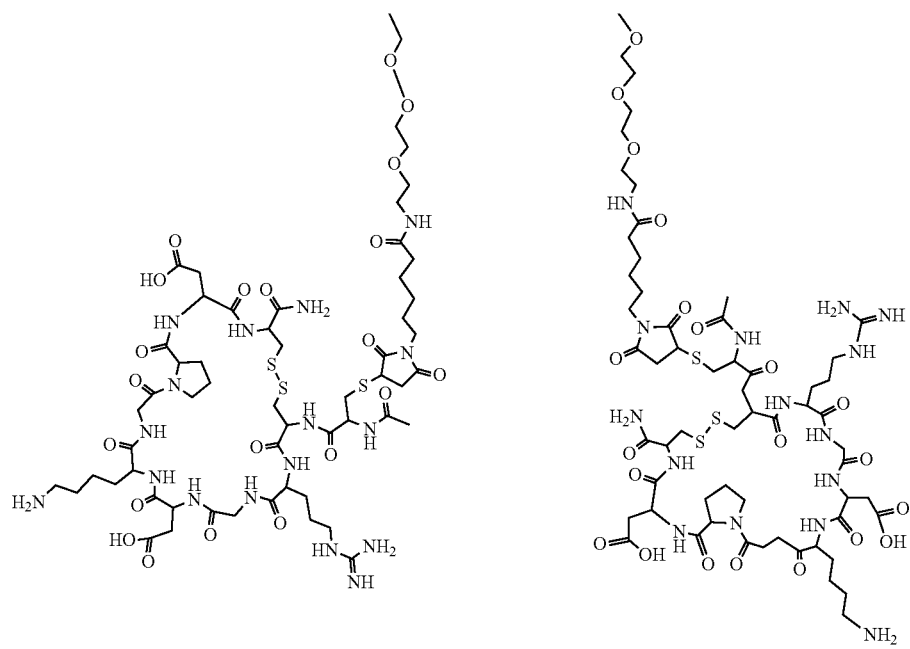
D is 10-hydroxycamptothecin, and T is iRGD.

Compound 12
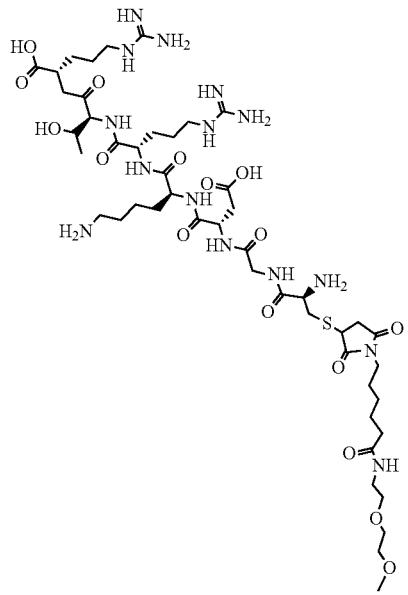
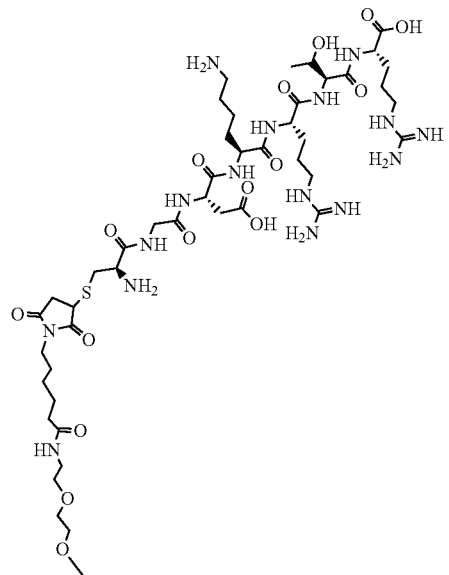
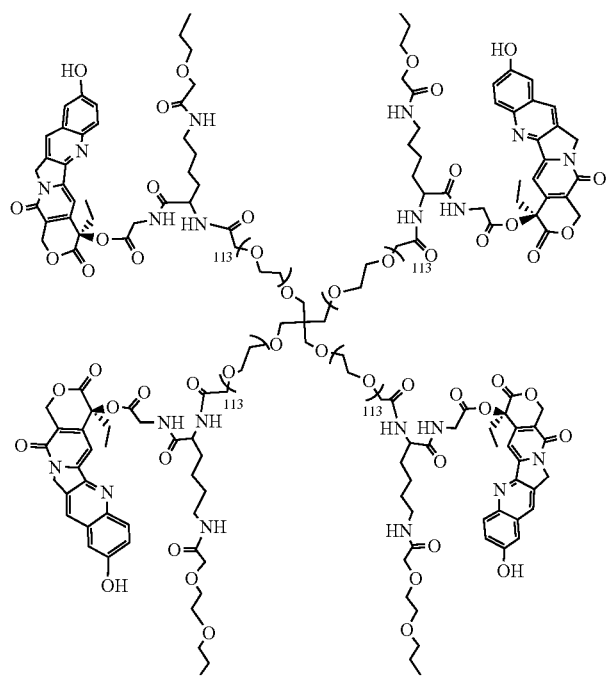

-continued
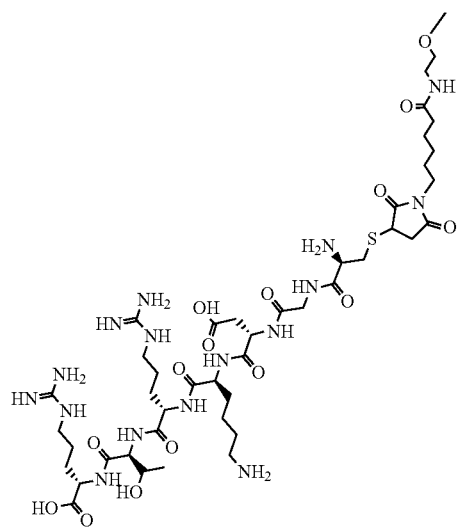 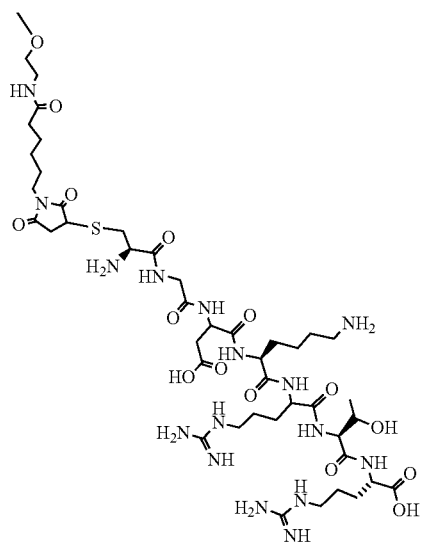
D is 10-hydroxycamptohecin, and T is tLyp-1.
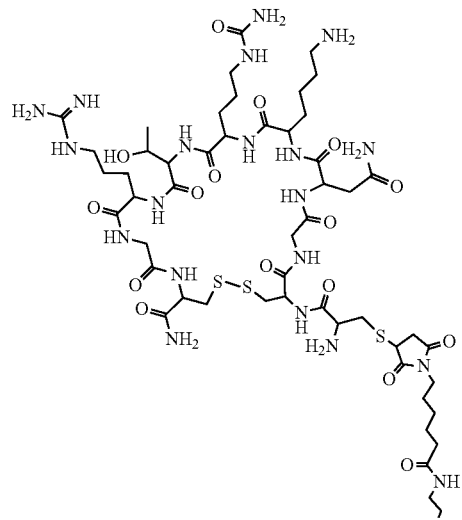 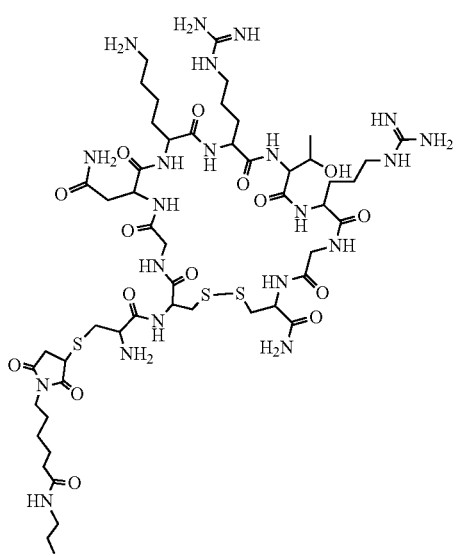
Compound 13

-continued
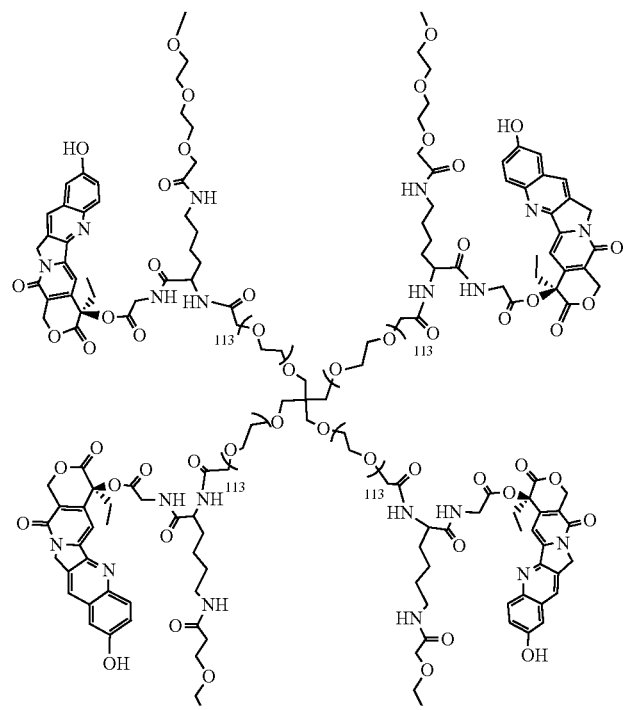
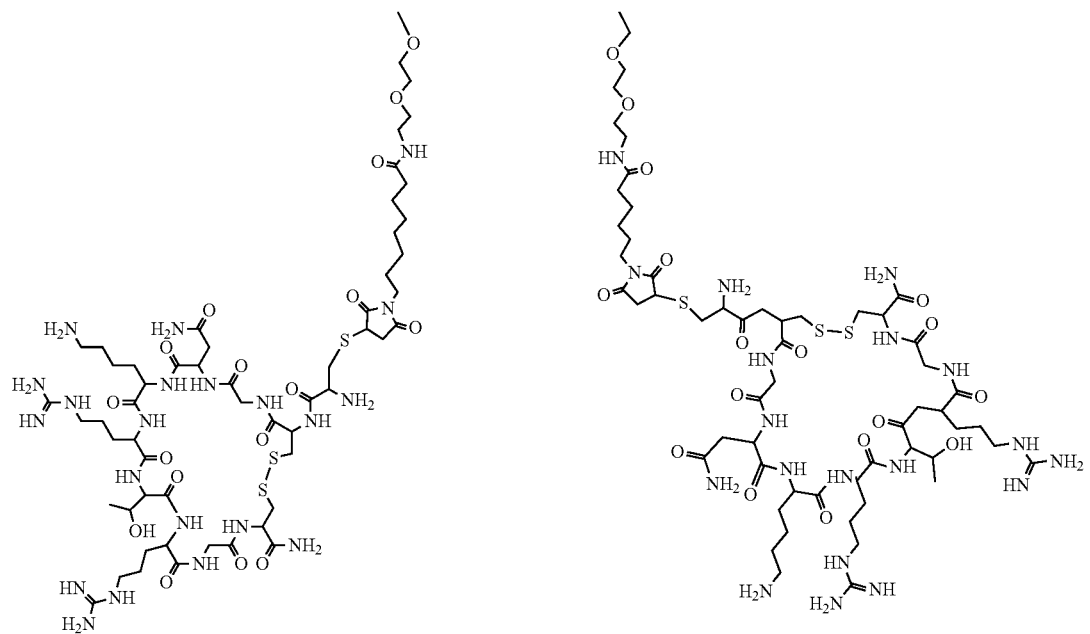
D is 10-hydroxycamptothecin, and T is Lyp-1.

Compound 14
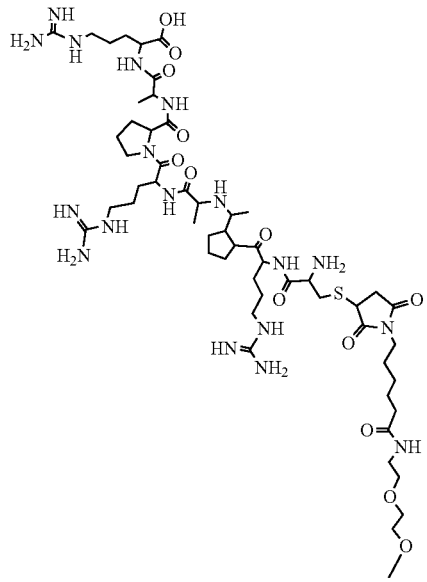
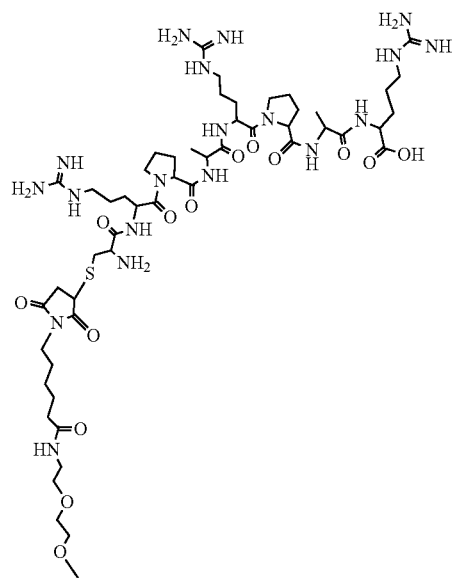
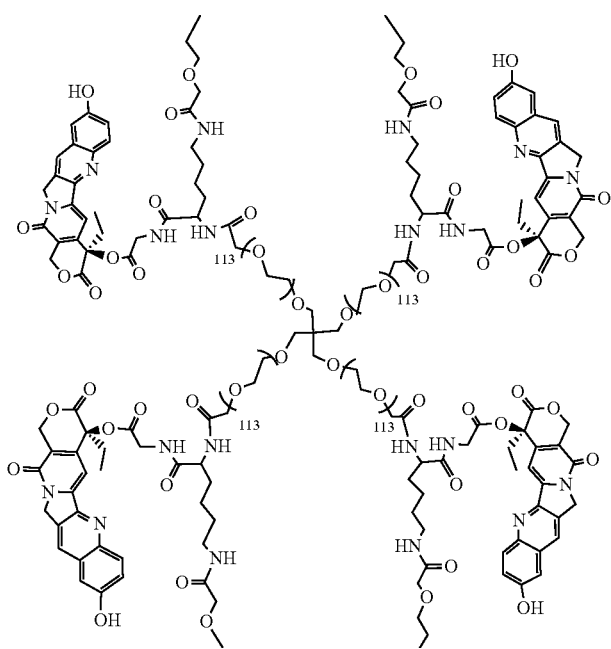

-continued
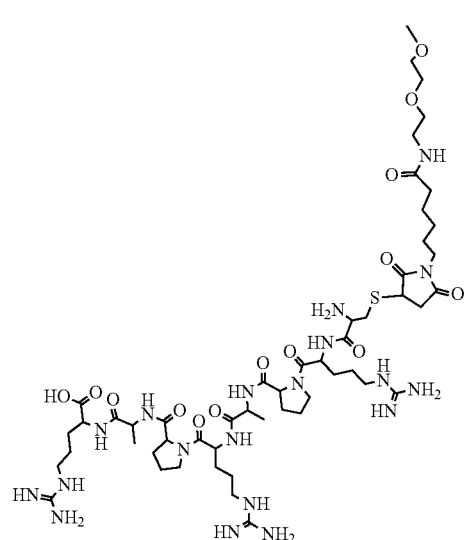
D is 10-hydroxycamptothecin, and T is RPARPAR.
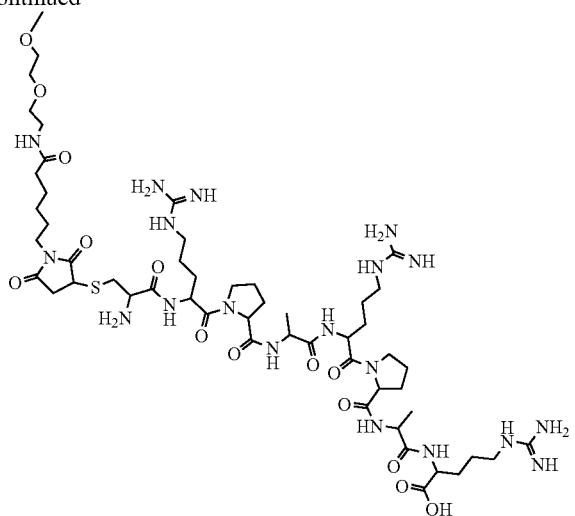
Compound 15
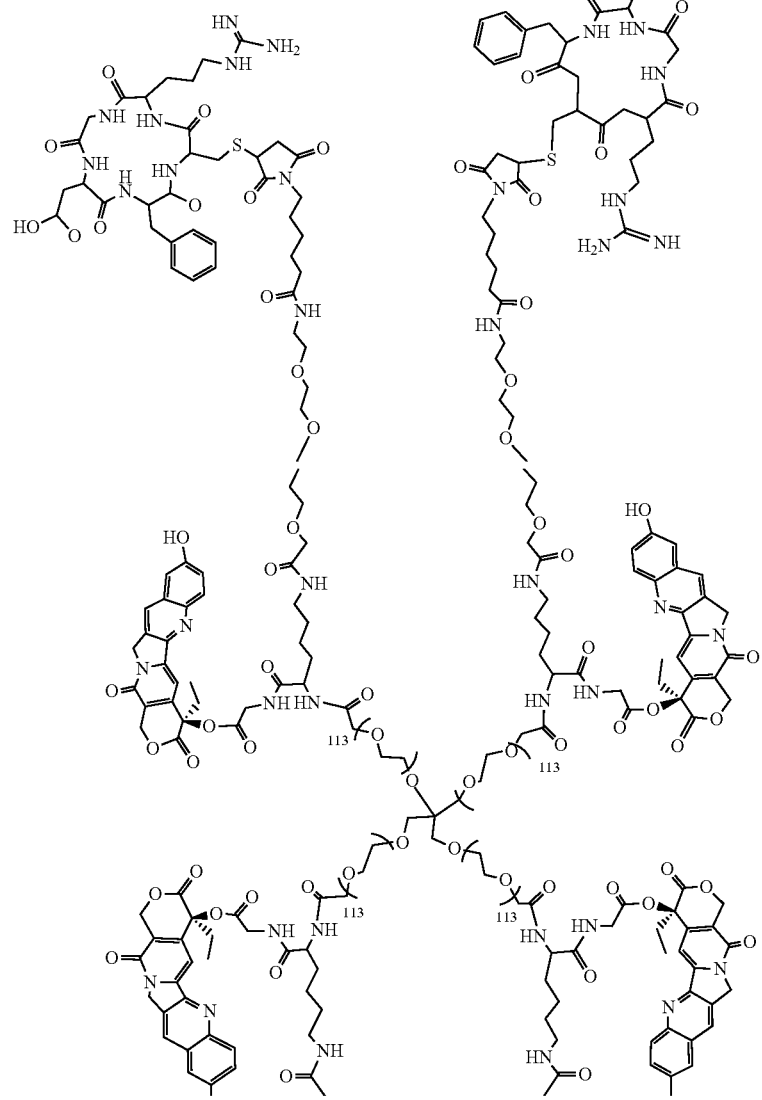

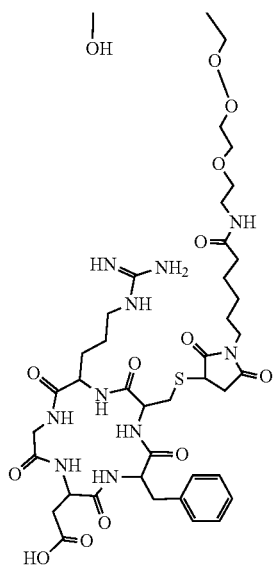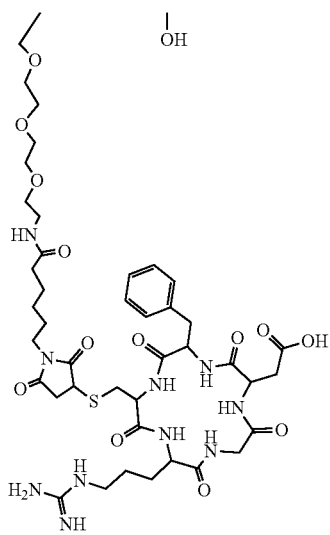
D is 10-hydroxycamptothecin, and T is cRGD.
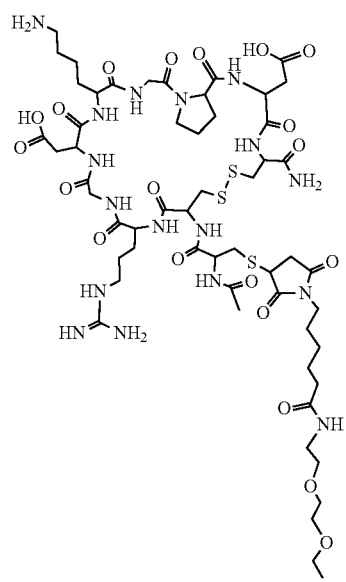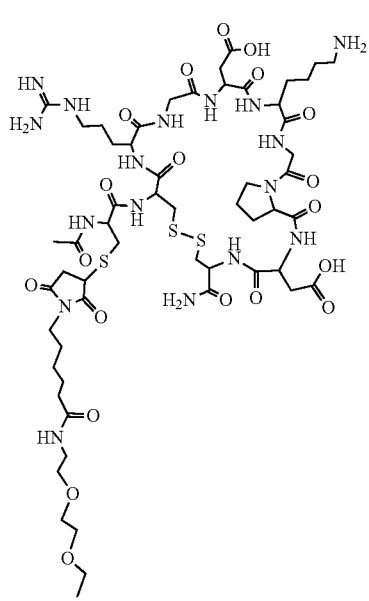
Compound 16

-continued
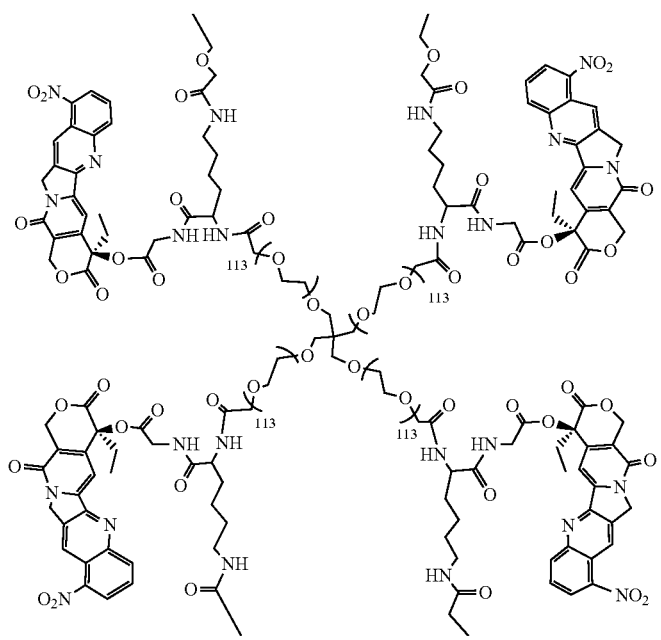
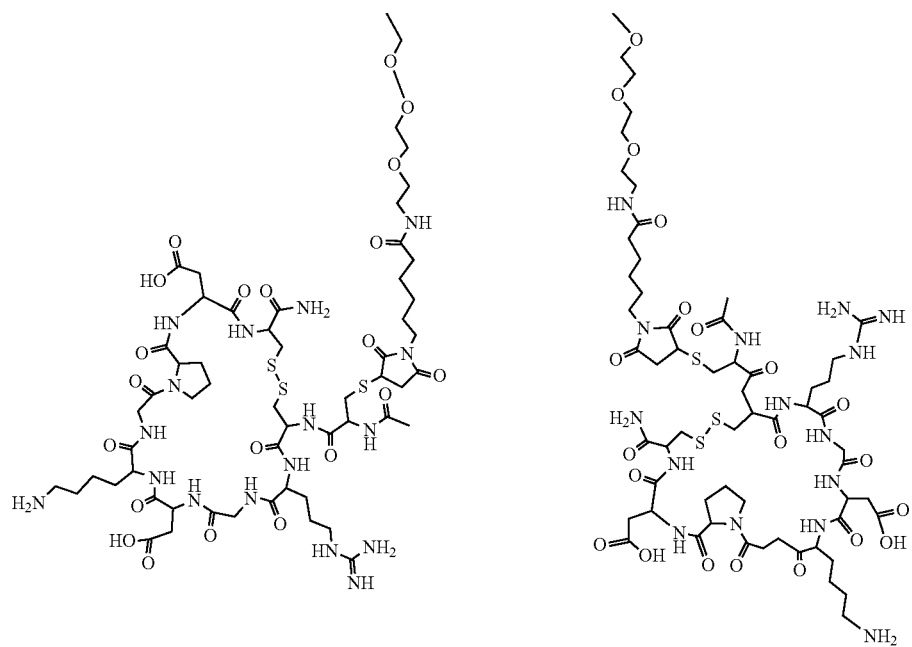
D is rubitecan, and T is iRGD.

-continued
Compound 17
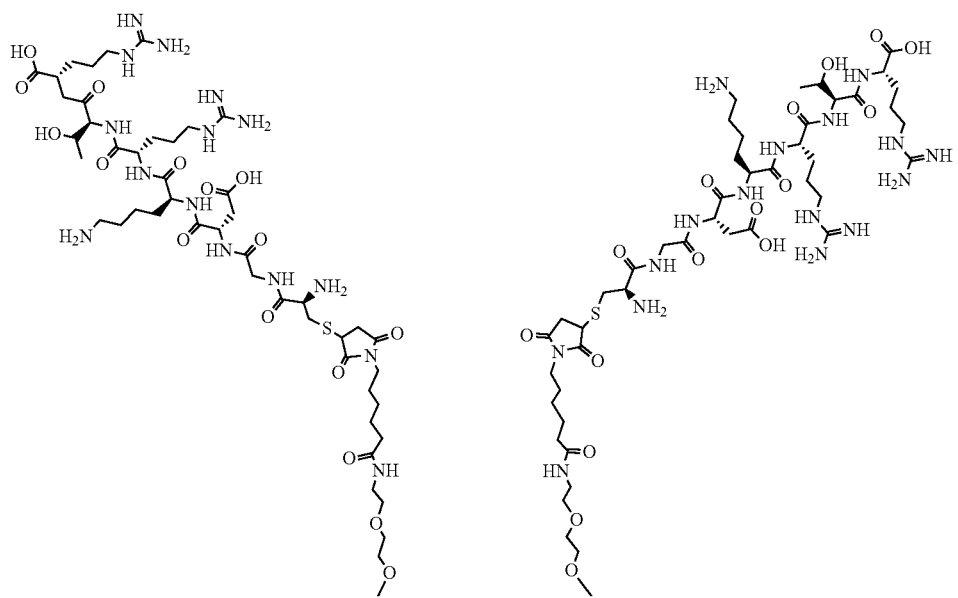
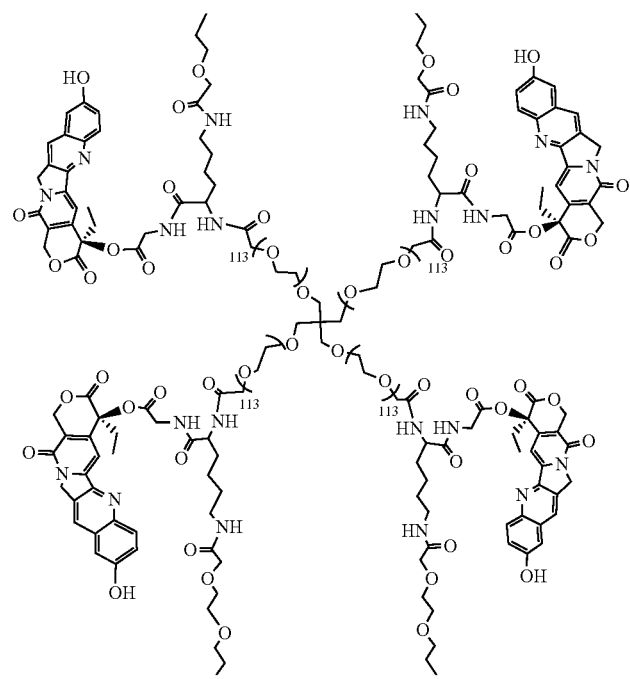

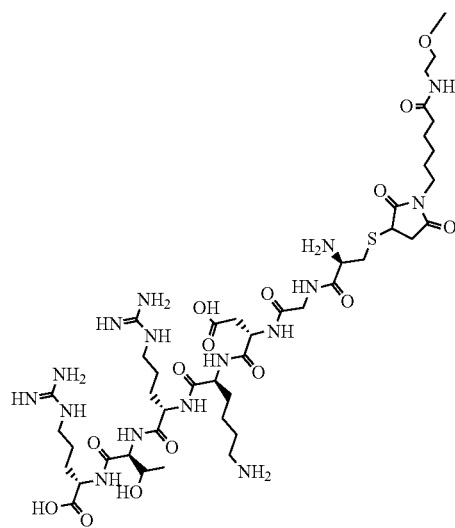
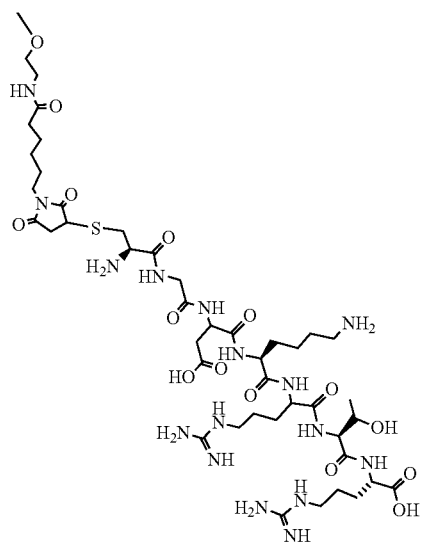
D is rubitecan, and T is tLyp-1.
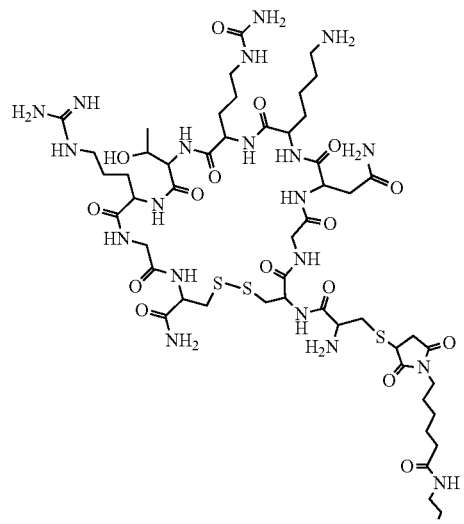
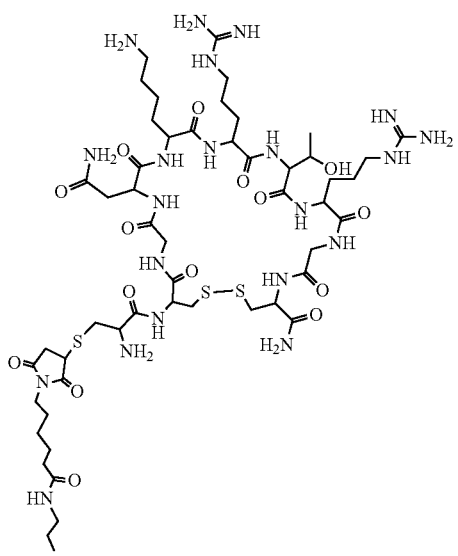
Compound 18

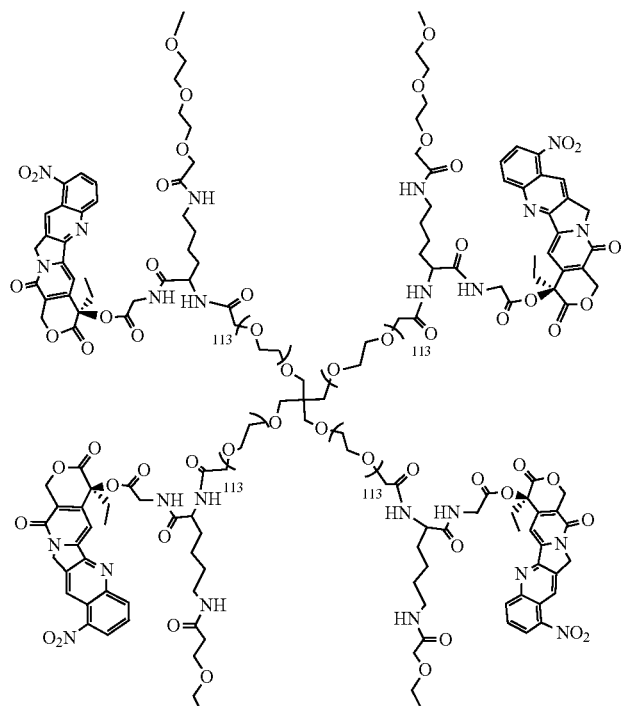
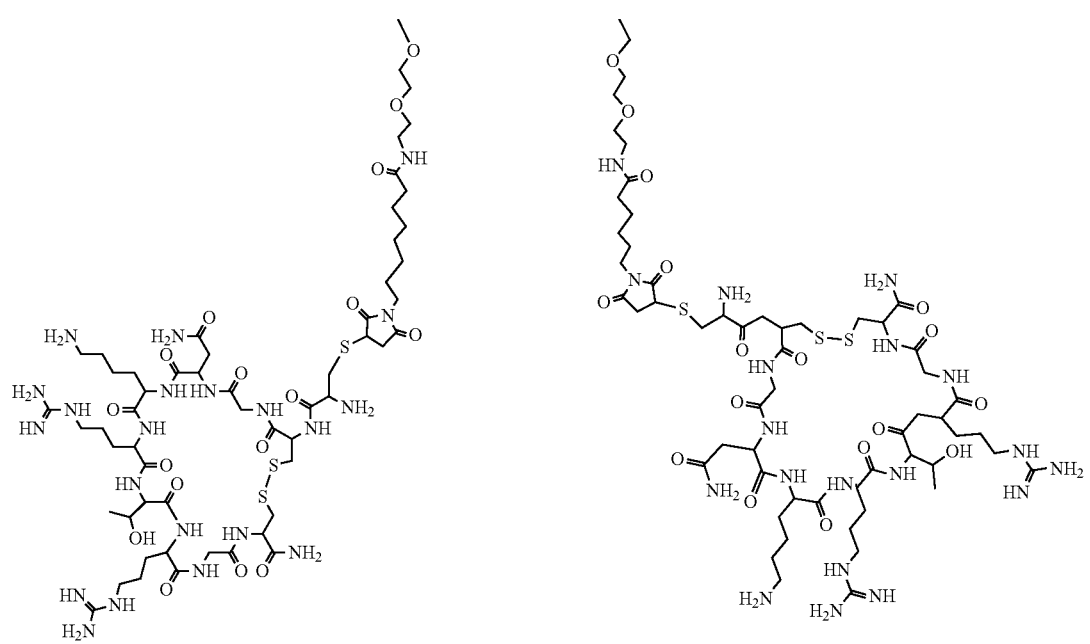
D is rubitecan, and T is Lyp-1.

Compound 19
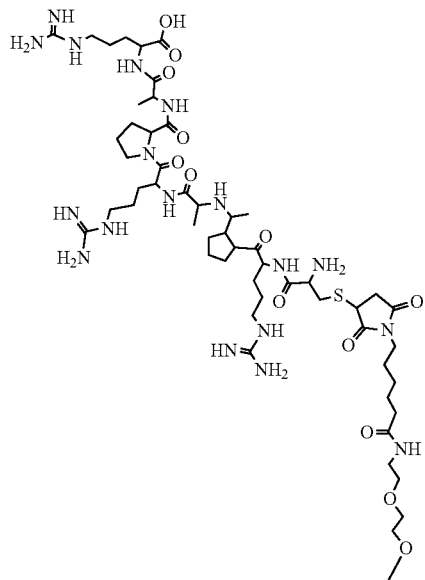
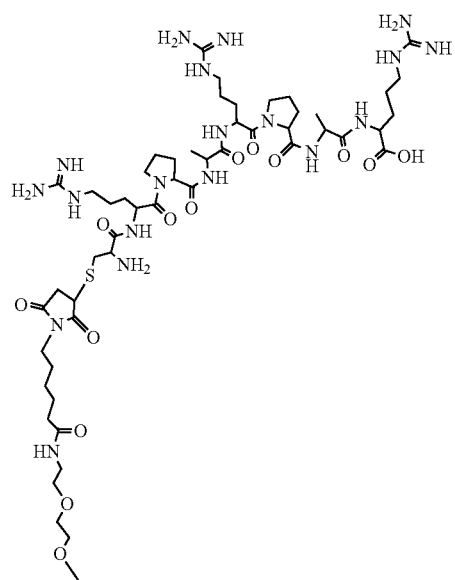
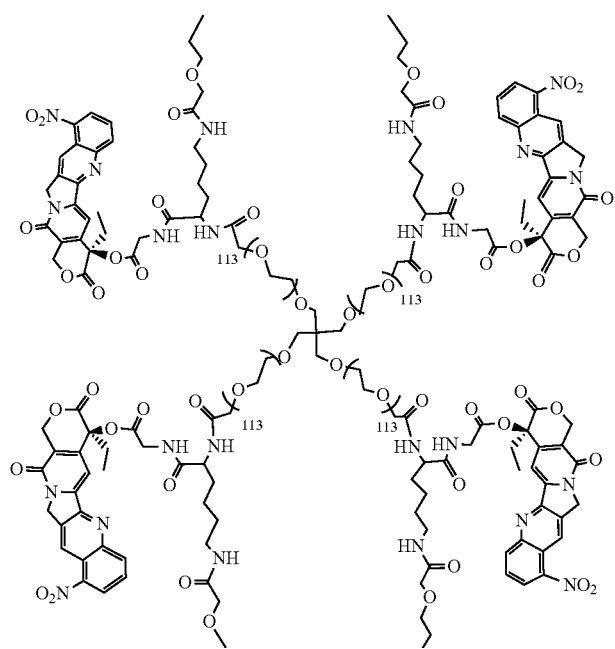

-continued
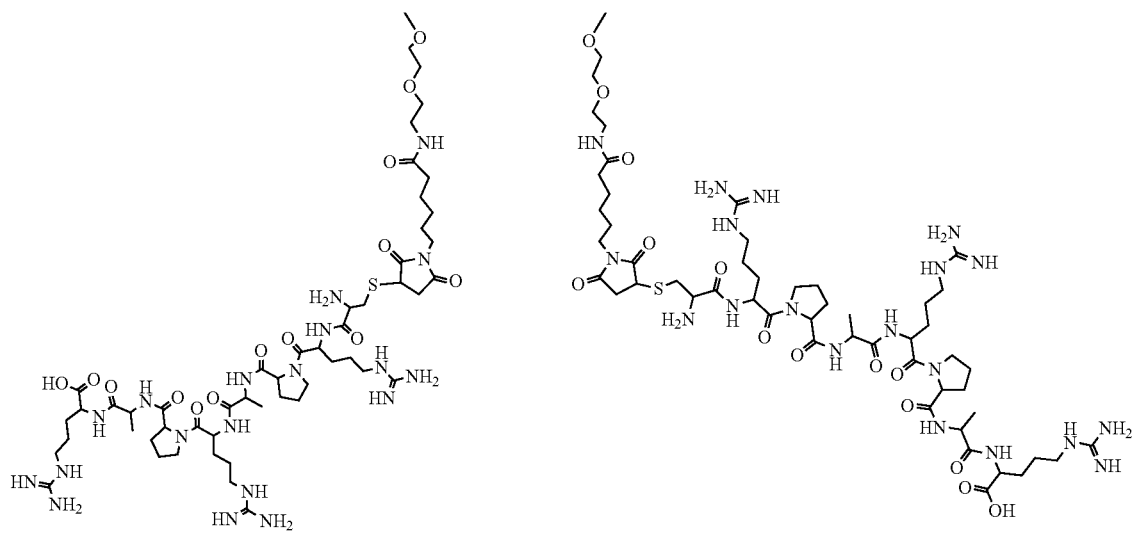
D is rubitecan, and T is RPARPAR.
Compound 20
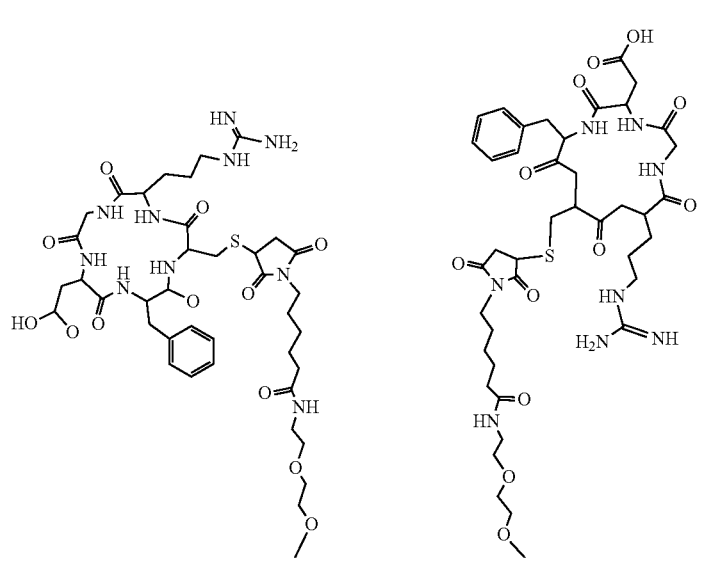

-continued
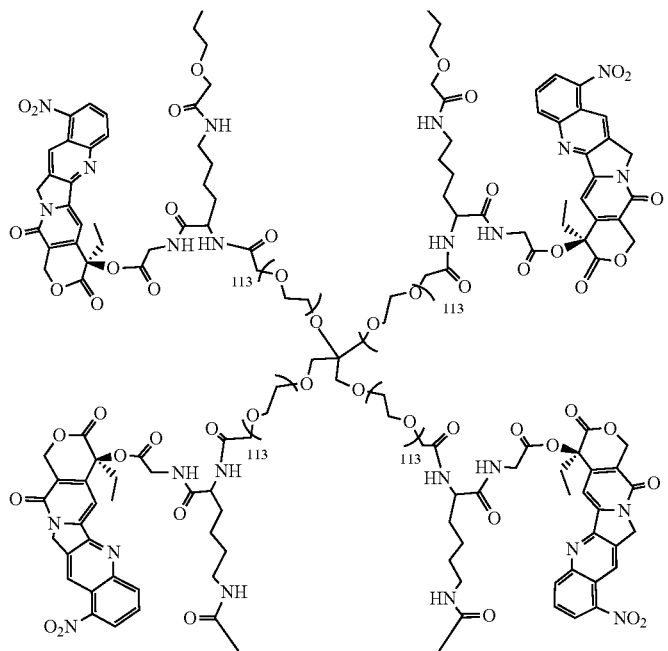
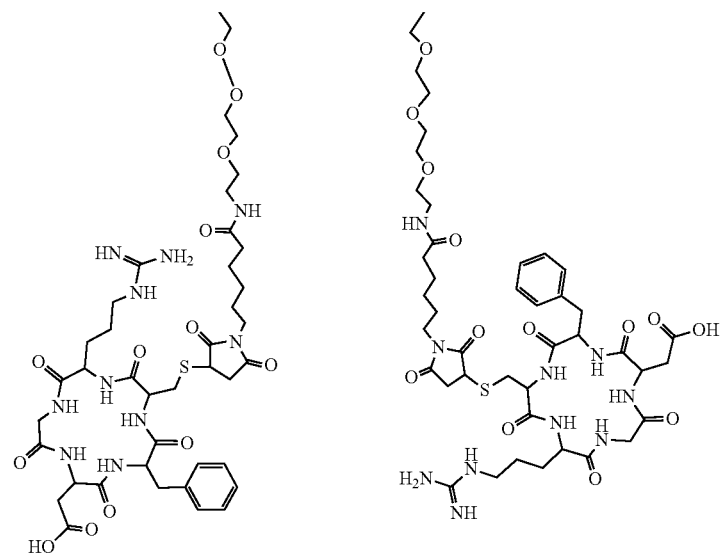
D is rubitecan, and T is cRGD.

Compound 21
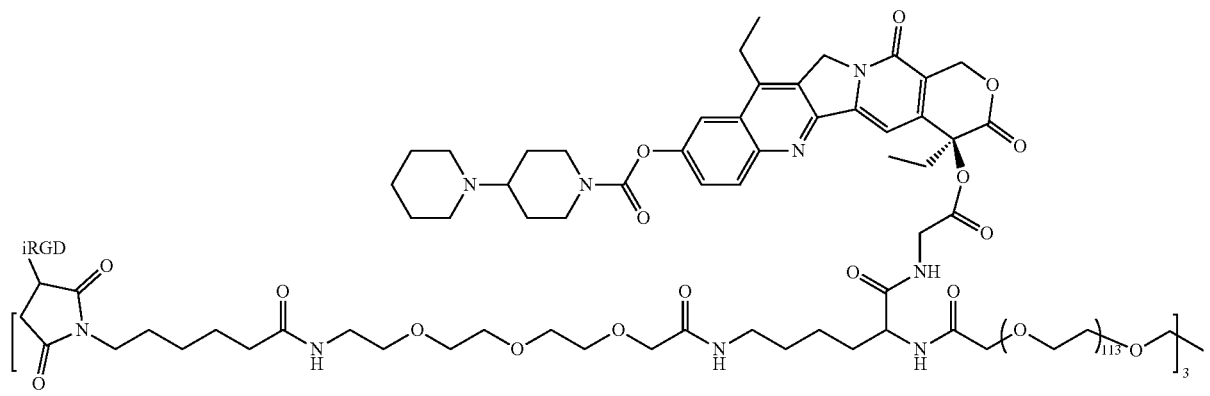
Compound 22
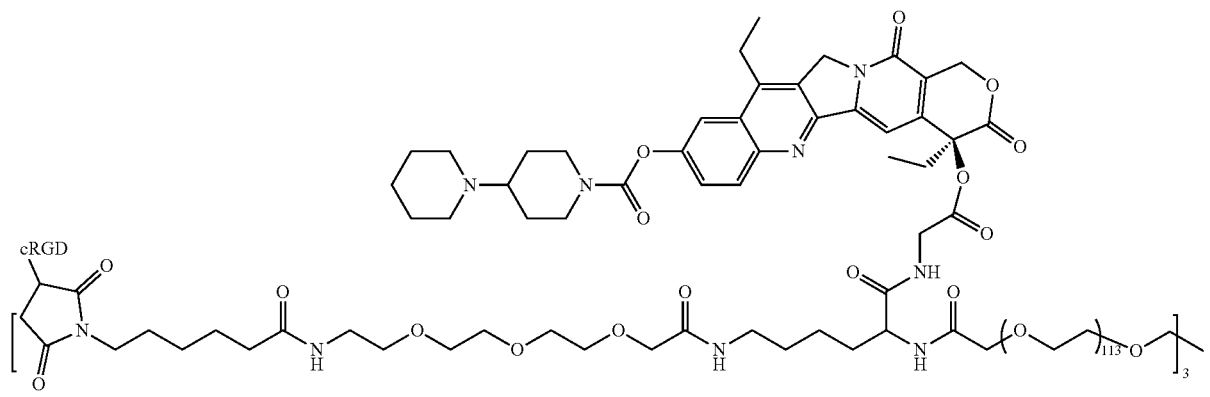
Compound 23
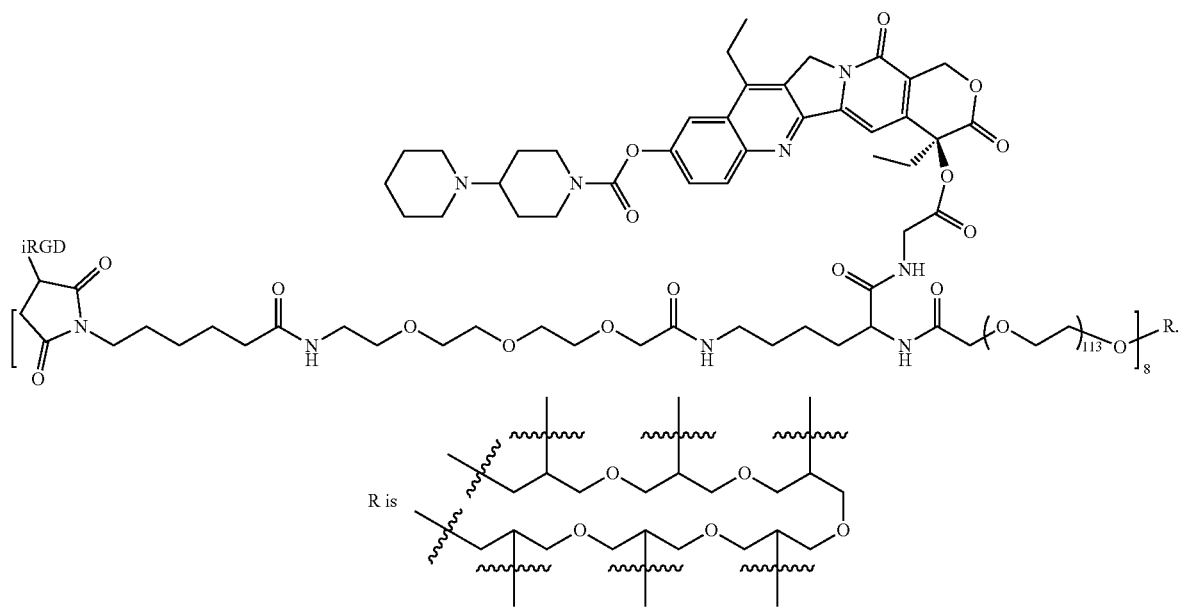

Compound 24
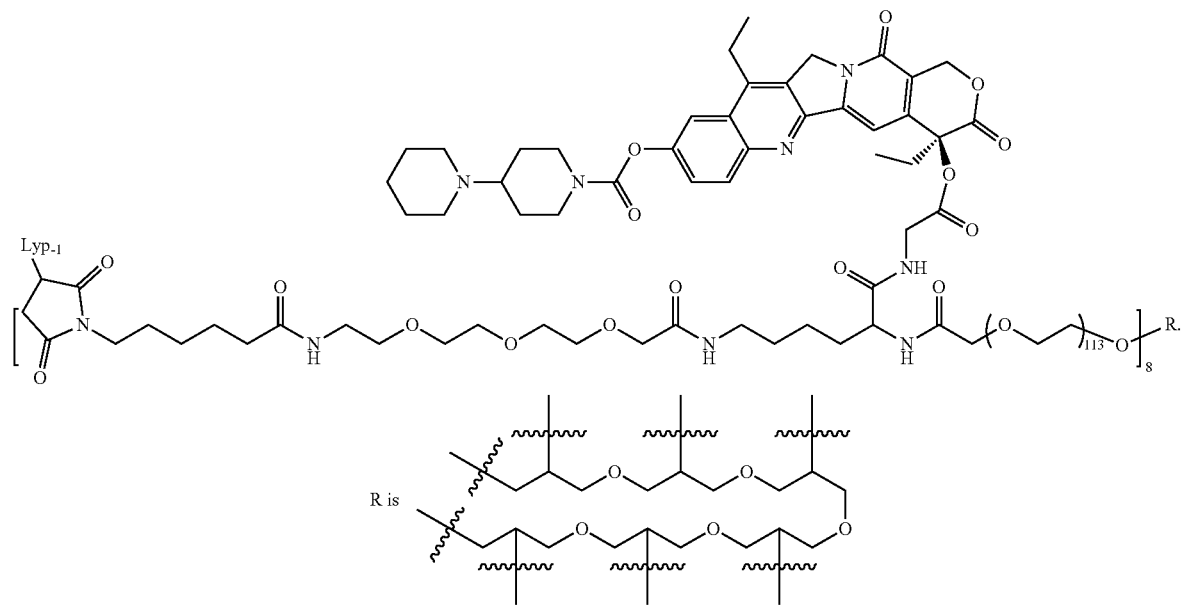
Compound 25
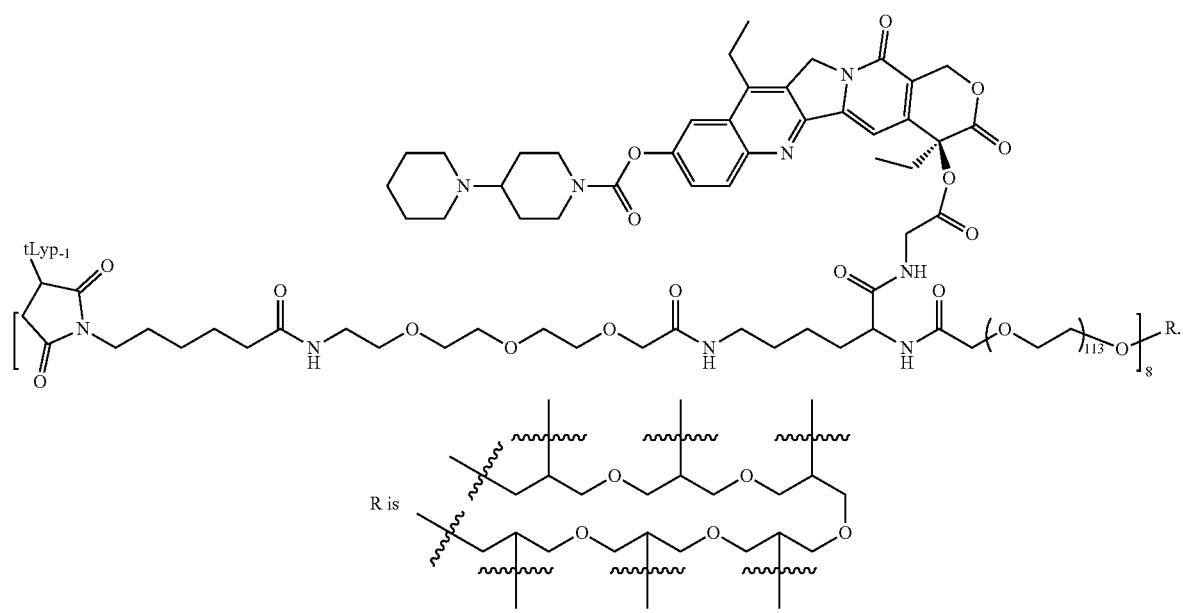

-continued
Compound 26
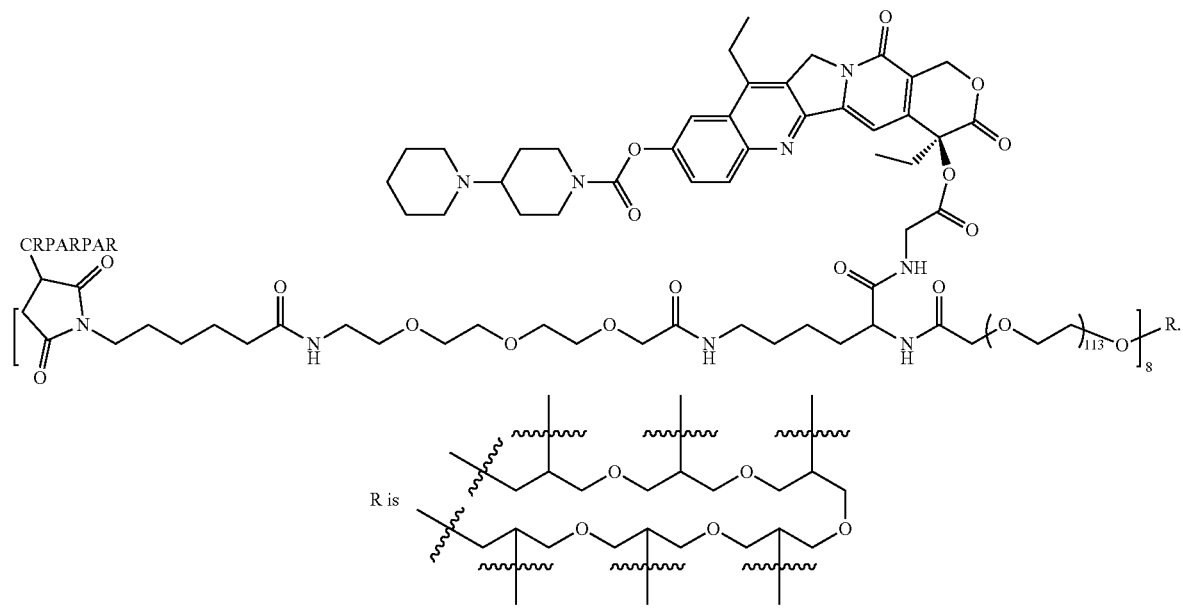
Compound 27
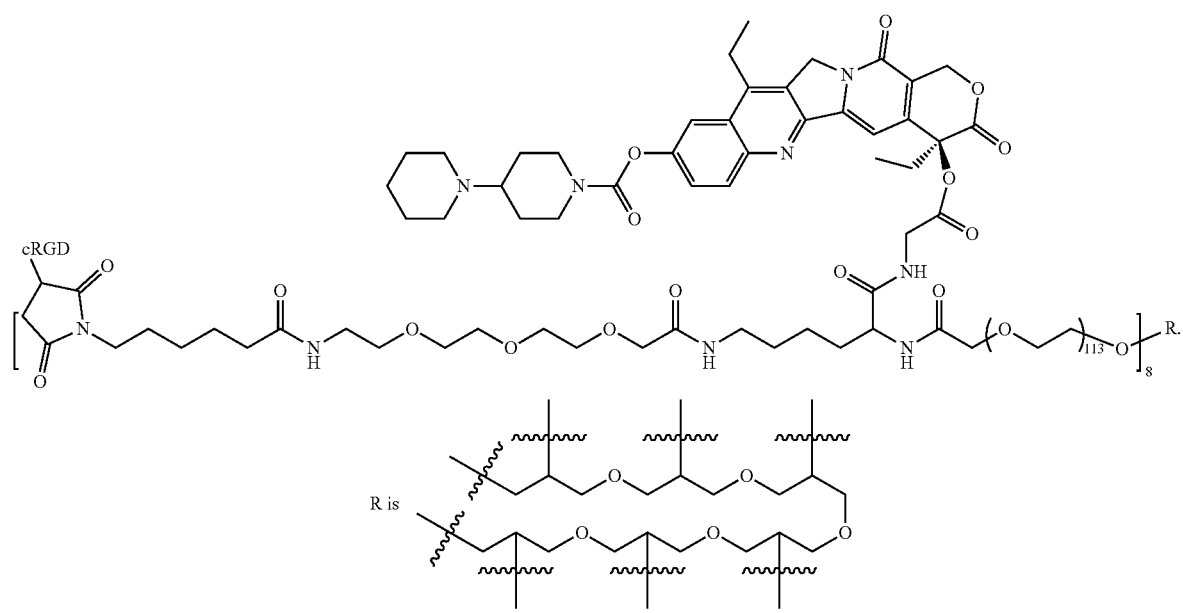

Compound 28
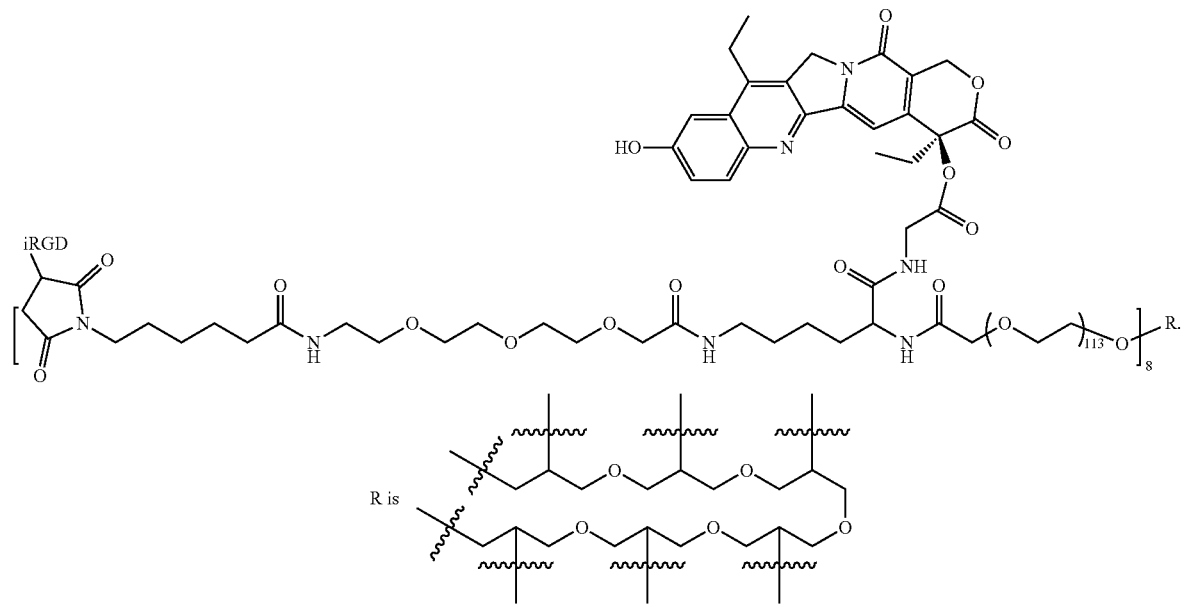
Compound 29
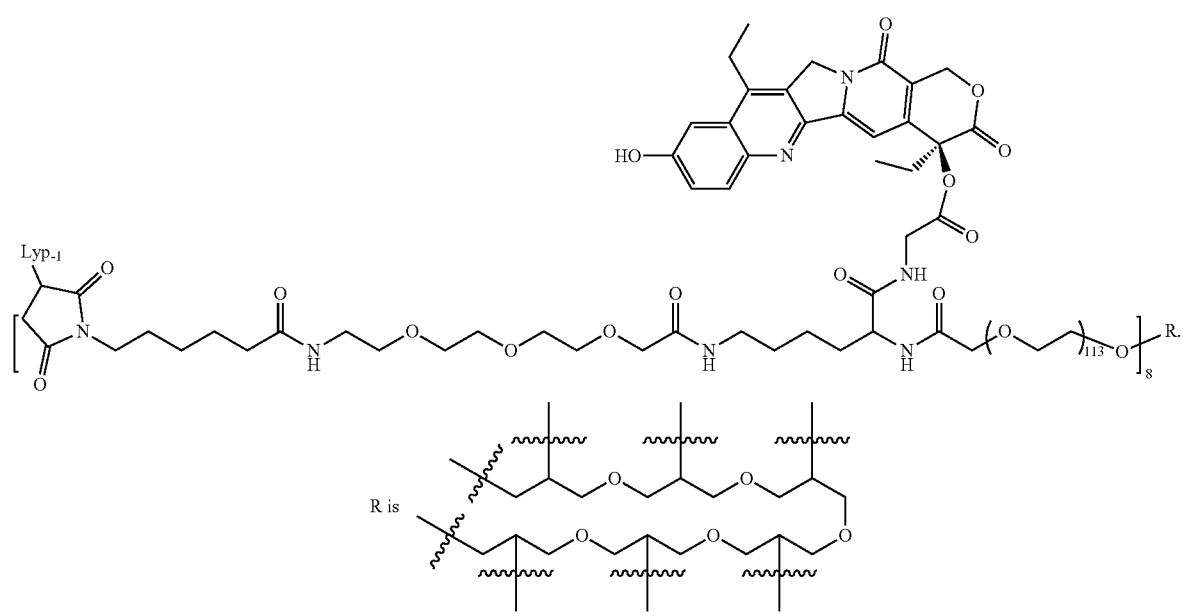

Compound 30
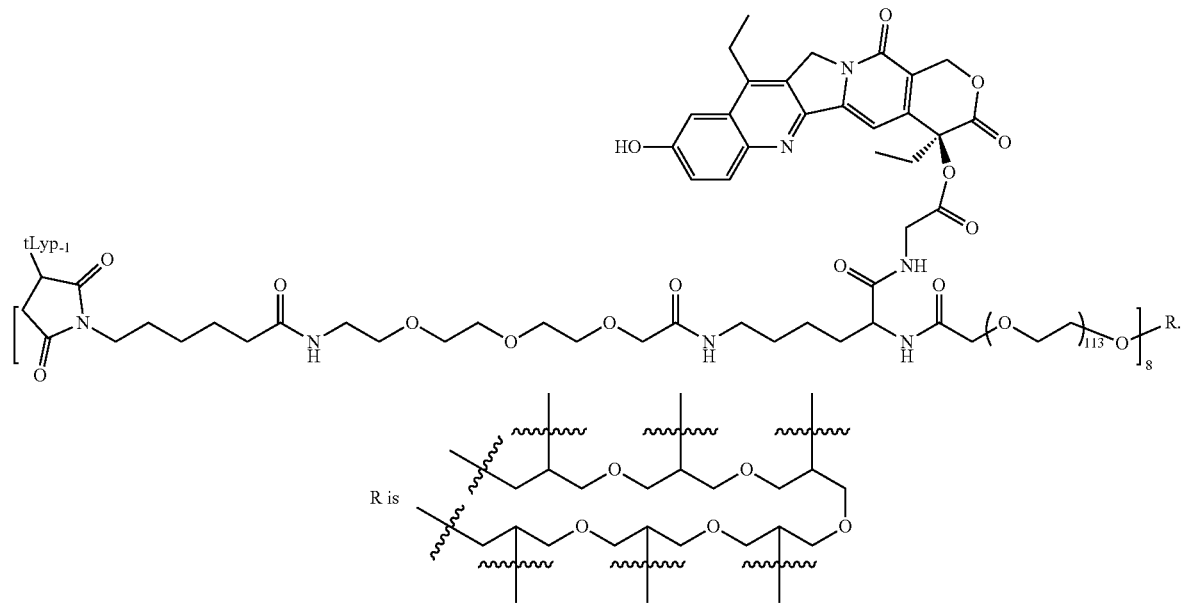
Compound 31
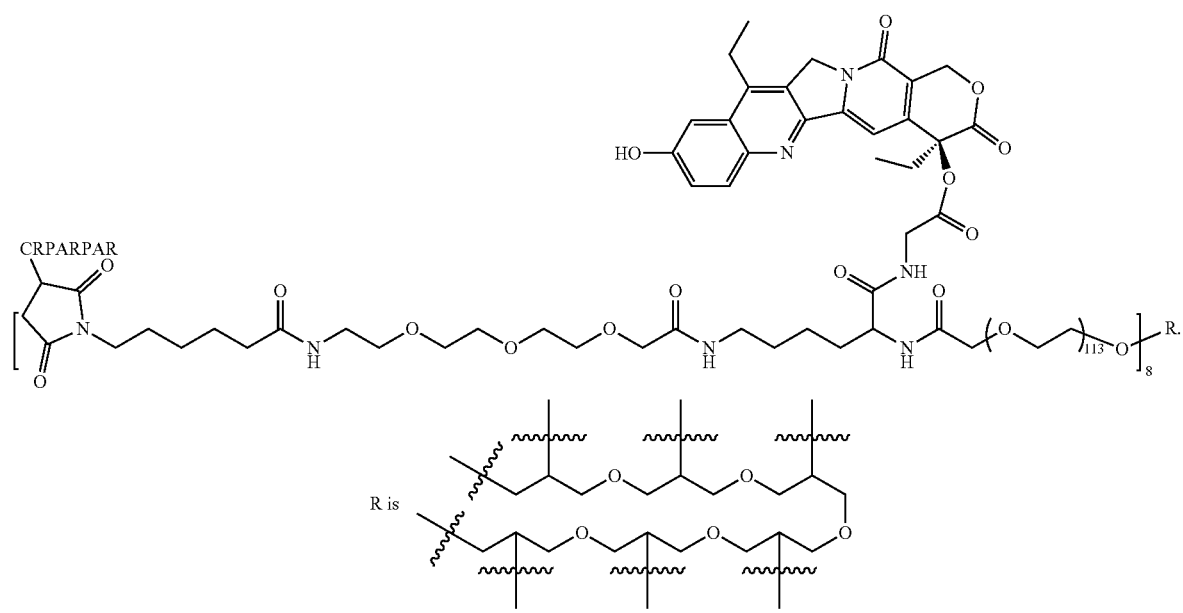

Compound 32
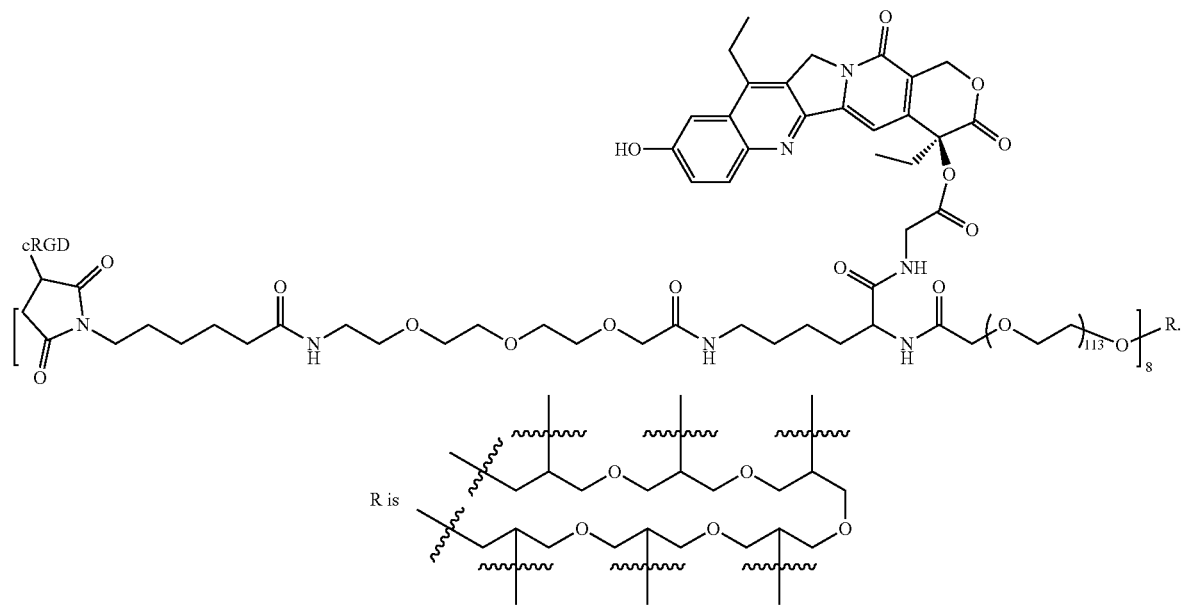
Compound 33
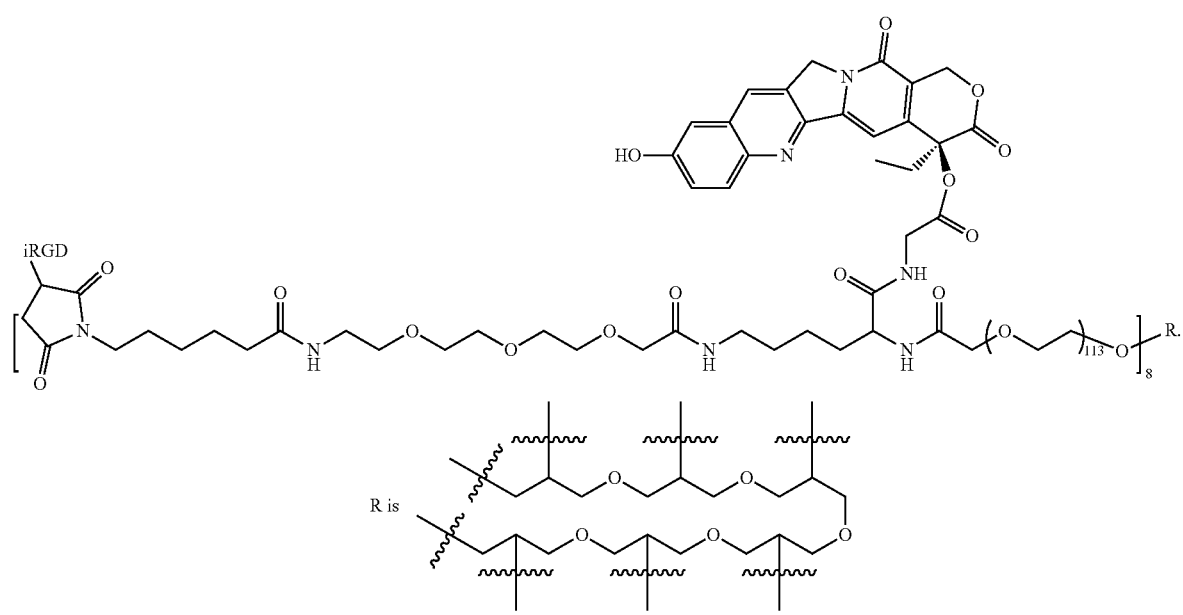

Compound 34
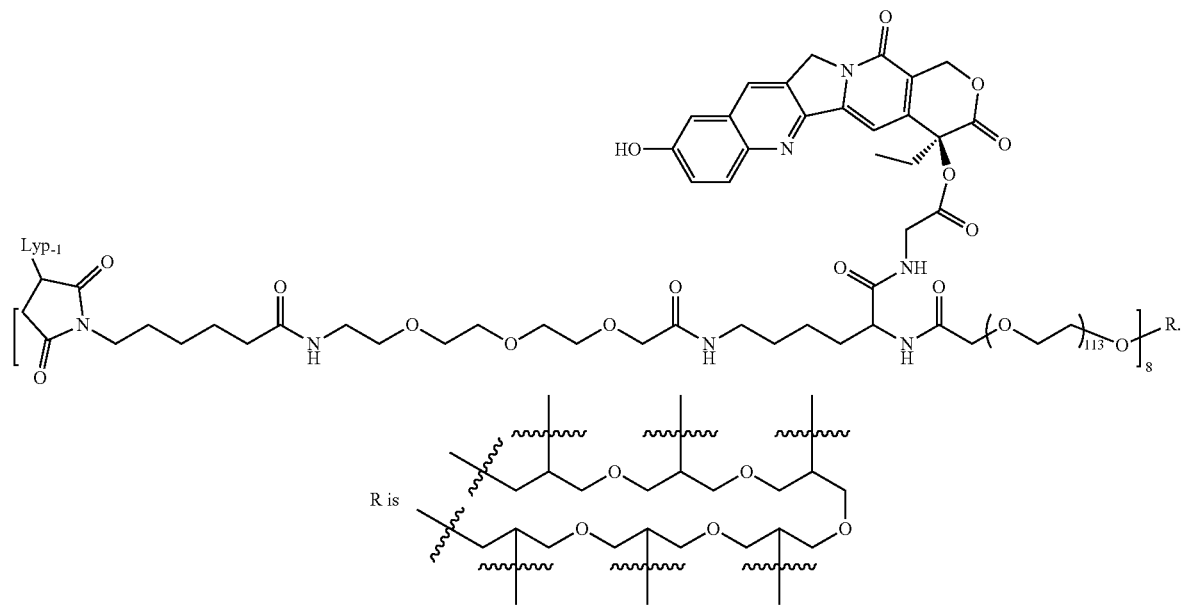
Compound 35
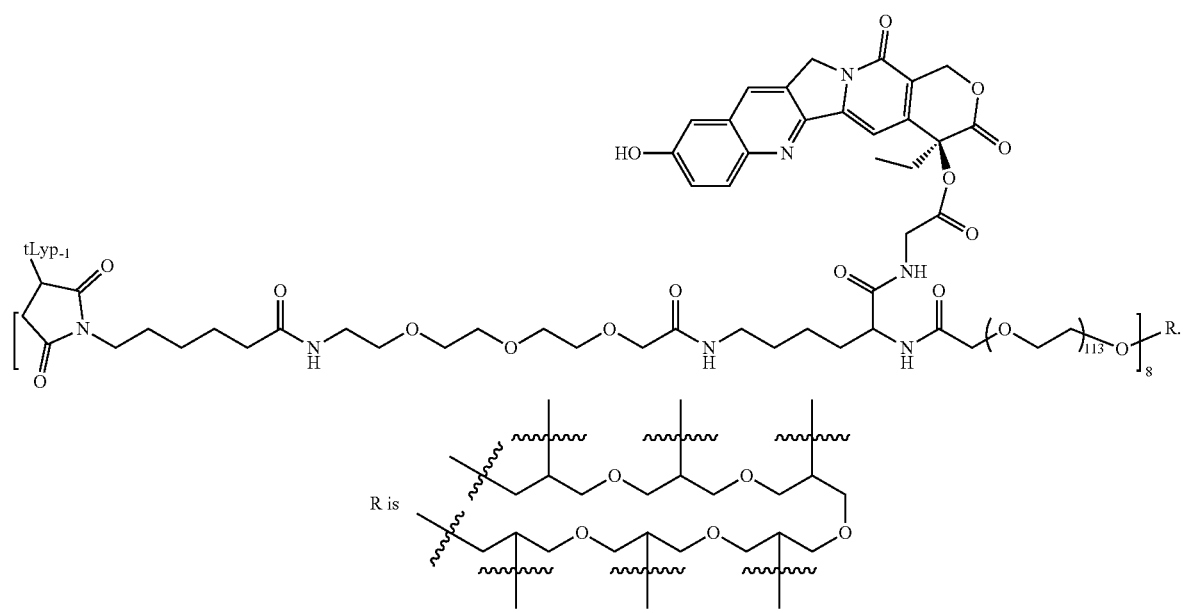

Compound 36
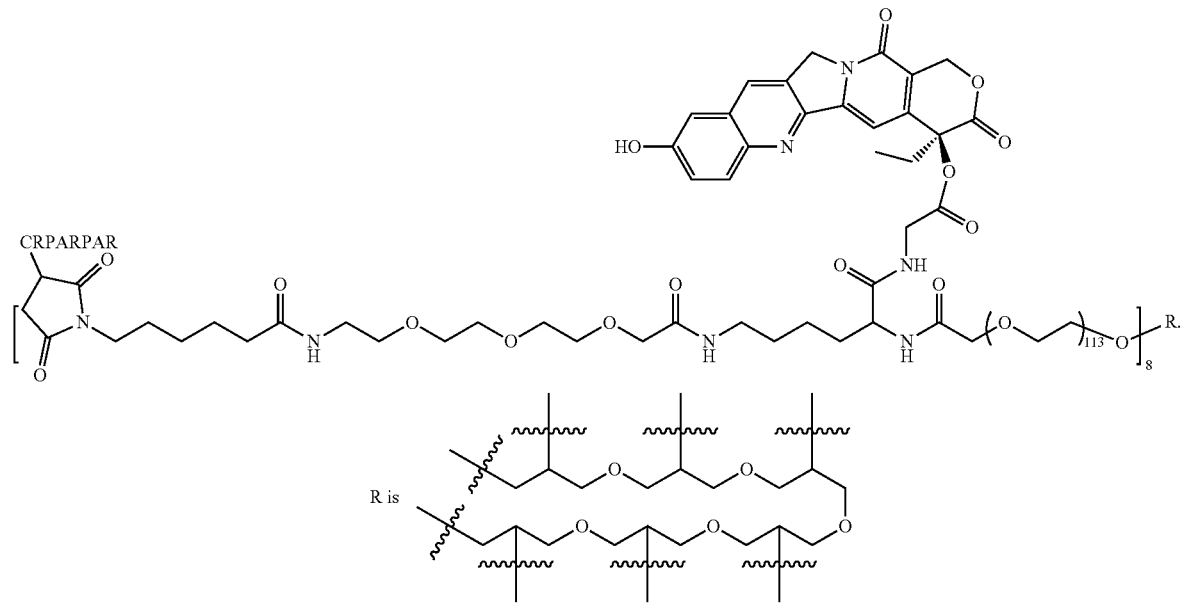
Compound 37
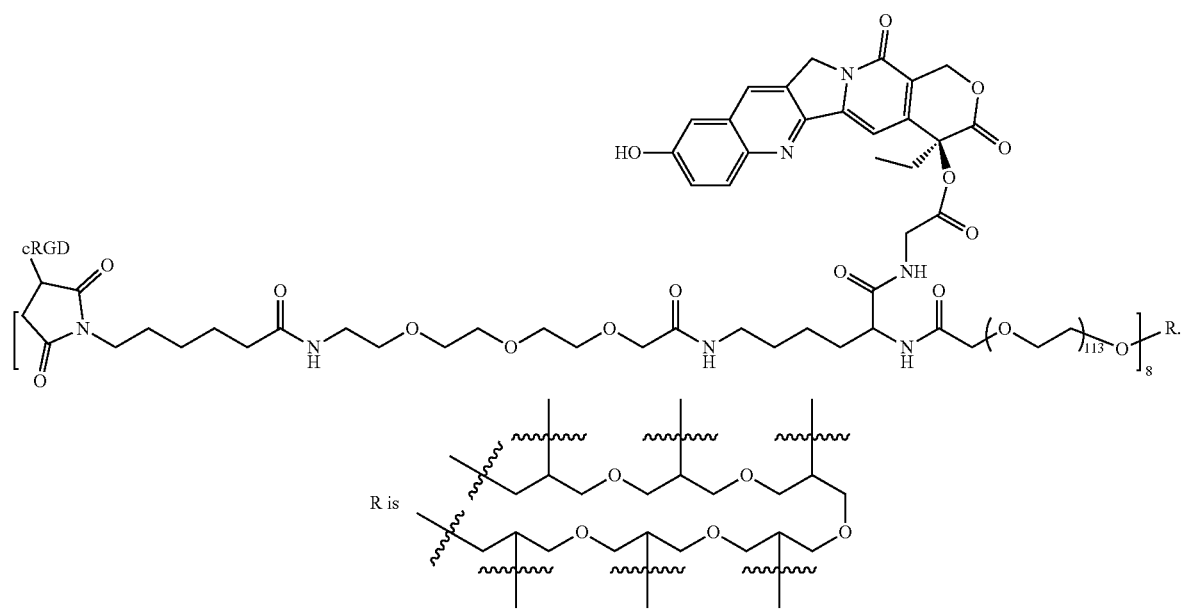

Compound 38
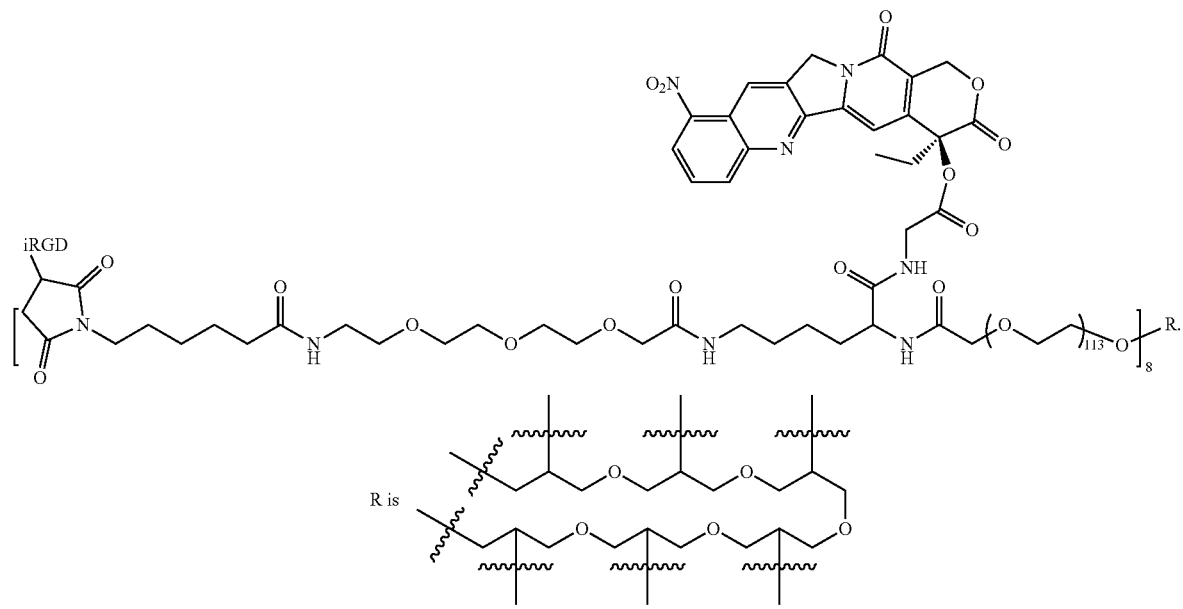
Compound 39
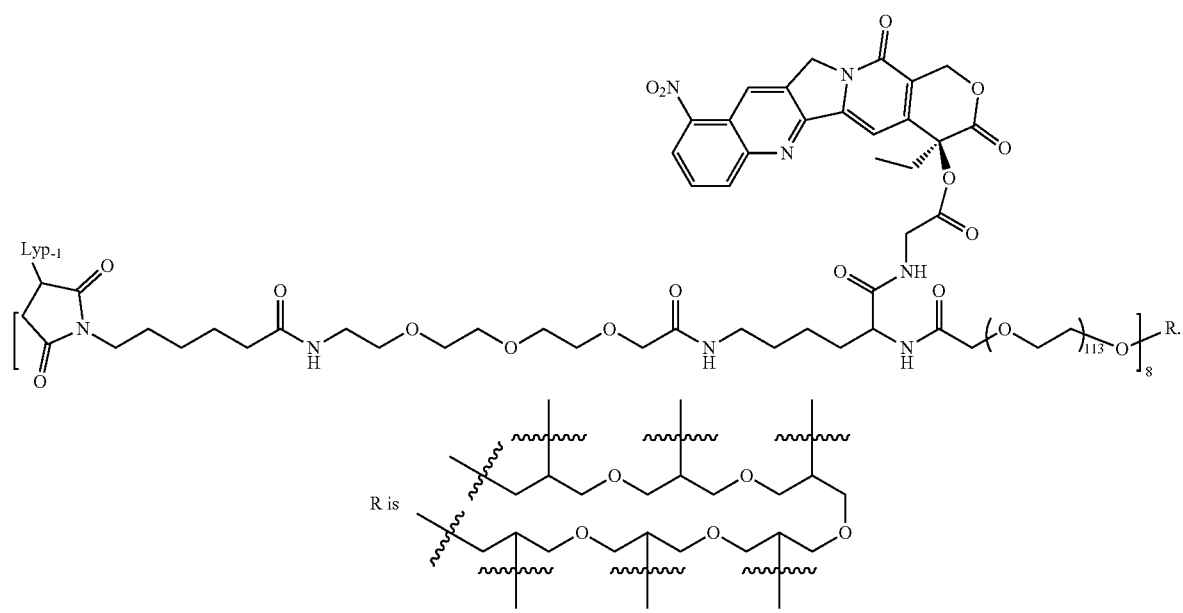

-continued
Compound 40
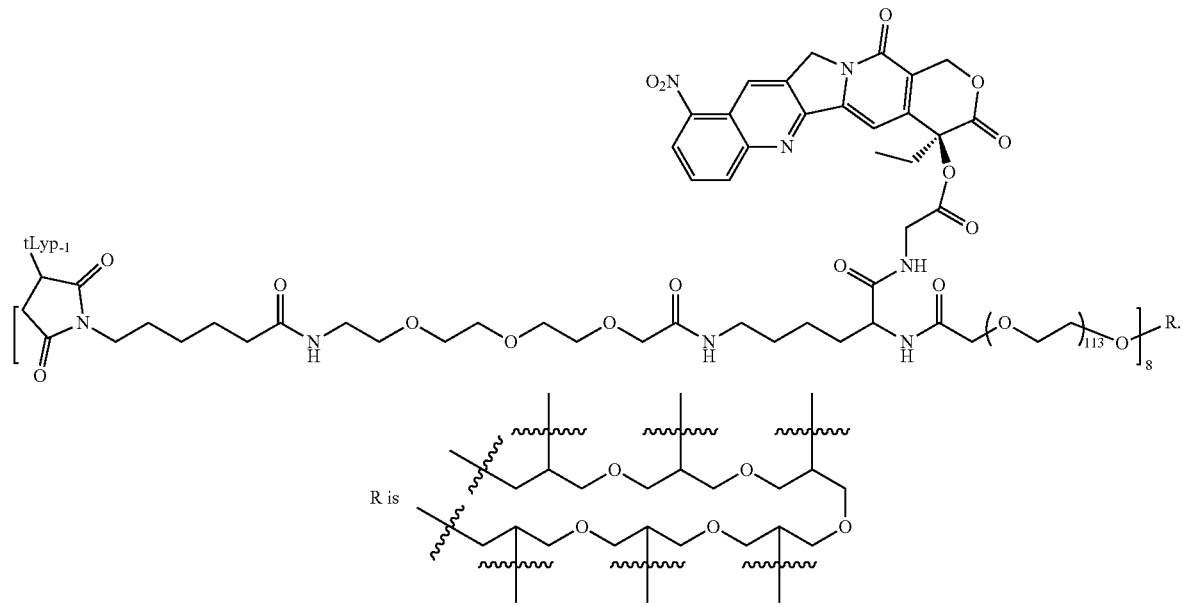
Compound 41
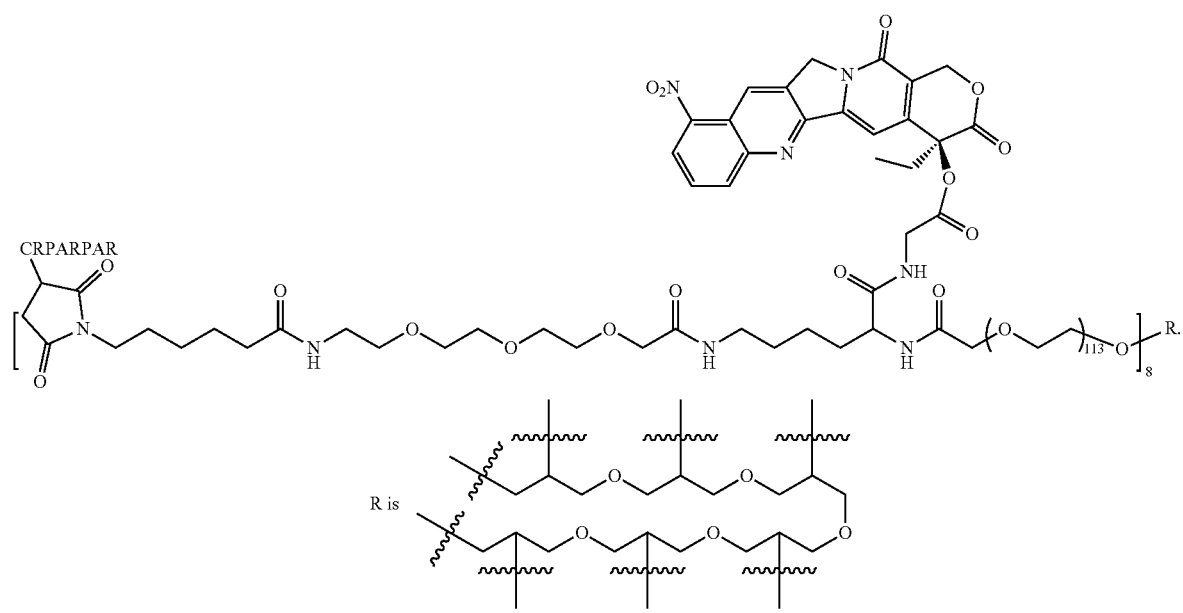

-continued
Compound 42
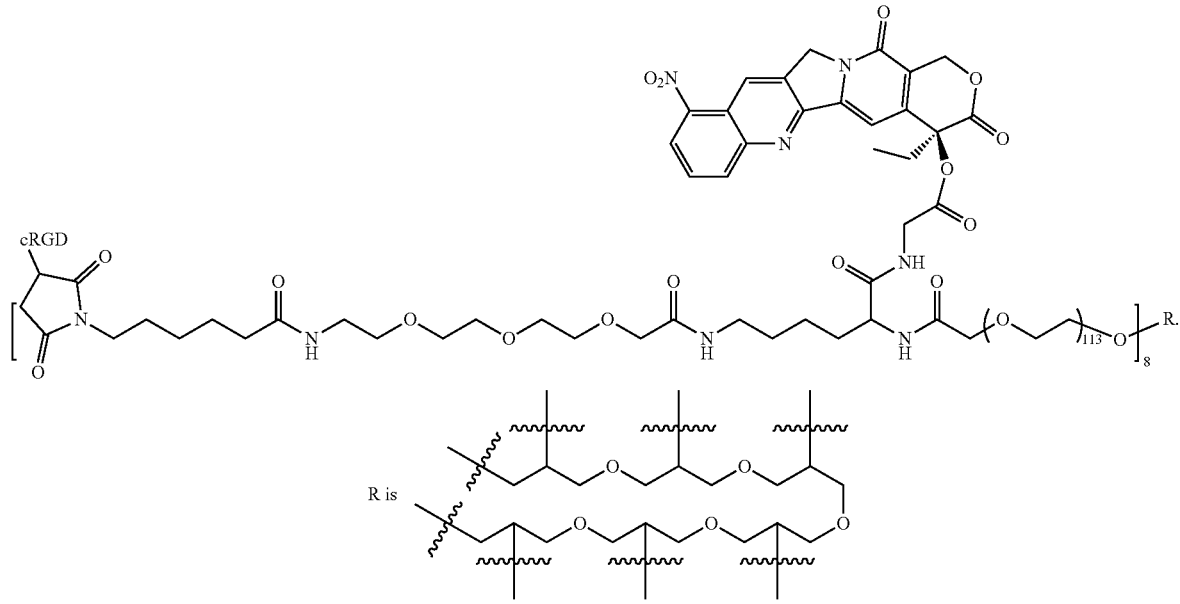
The present disclosure is further explained by taking Compound 1 as an example.
In Compound 1, R is
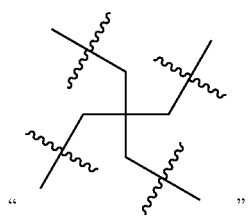
with 5 carbon atoms, POLY is
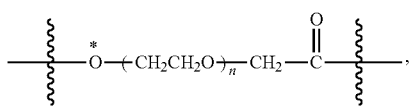
and POLY and R constitute the carrier of the active agent together:
After the multivalent linker L is attached to T and D, the structure is:

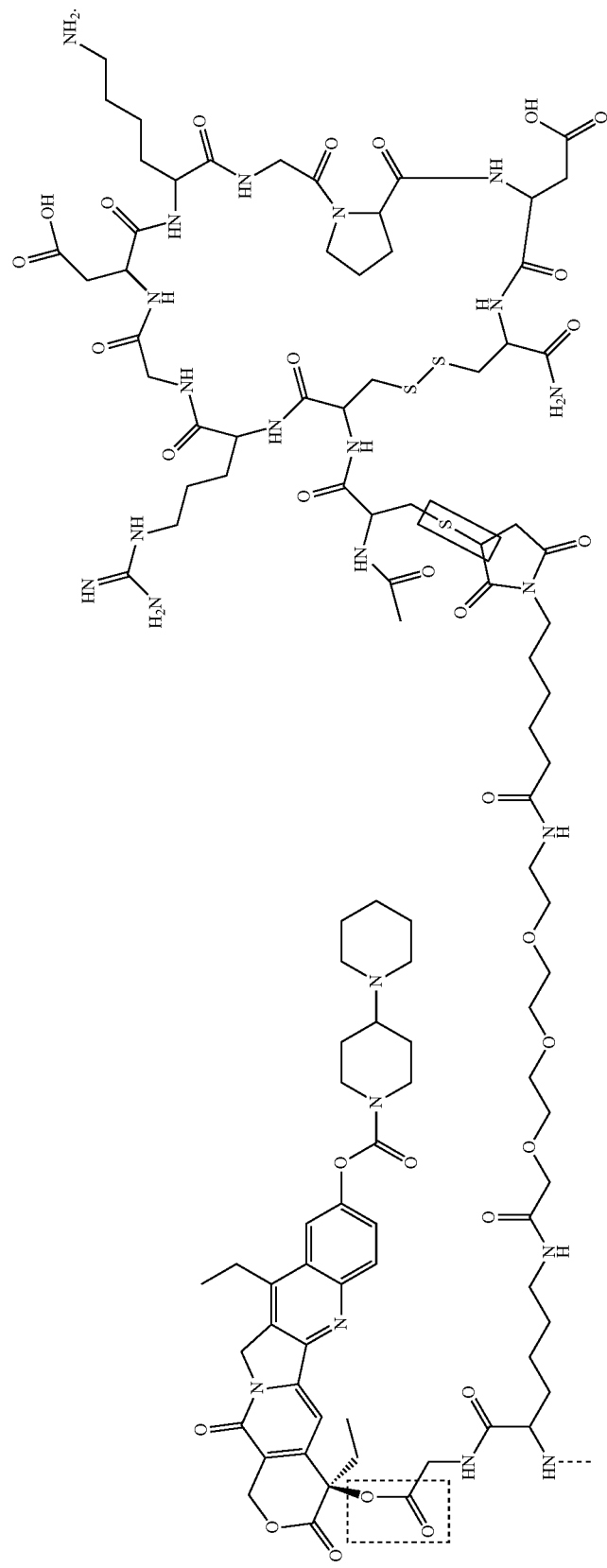

The ester bond in

"[- - - - -]"

is a cleavable bond formed by the covalent binding of the above-mentioned separable linker of the present disclosure with the active agent D. When the conjugate of the present disclosure reaches a target cell, the conjugate releases the active agent irinotecan after the cleavable bond is hydrolyzed or digested under physiological conditions, and irinotecan exerts anticancer effect on the target cell The carbon-sulfur bond in

"[ ]"

is a chemical bond formed by the above-mentioned inseparable linker of the present disclosure and the targeting molecule T, and the chemical bond is more stable to hydrolysis under physiological conditions, wherein the atom S is brought by iRGD. Due to the targeting property of the targeting molecule, the conjugate of the present disclosure is allowed to reach a particular target cell while the targeting molecule and the parent are not liable to separate.

"—" represents the attachment to POLY.

In another aspect, the present disclosure provides a preparation method of said conjugate. In this method, a hydroxy group-containing active agent D is first reacted with an amino acid or a peptide formed by amino acids to form a separable linker, and the hydroxy group of the active agent D forms a cleavable bond (ester bond) with the carboxyl group of the amino acid. An inseparable linker and a spacer linker form the remainder of a multivalent linker together. This remainder comprises a reactive carboxyl group, which reacts with the amino group of the separable linker to form a D-L portion.

Preparation of an active agent carrier composed of POLY and an organic core R: POLY and the organic core R actually constitute a multi-arm polymer, i.e., R$-$(POLY)$_q$. In one preferred example of the present disclosure, the multi-arm polymer is multi-arm polyethylene glycol, which may be obtained from commercially available raw materials. For example, various types of four-arm and eight-arm polyethylene glycol derivatives are commercially available from Beijing Jenkem Technology Co., Ltd. These commercially available multi-arm PEGs may react with the above-mentioned D-L portion directly.

For example, in the preparation of the conjugate of formula (IV), a usable four-arm polyethylene glycol is as follows:

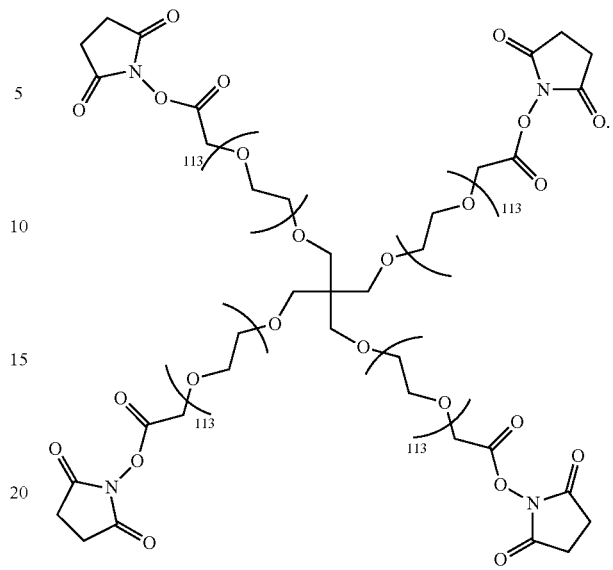

This preferred four-arm polyethylene glycol is referred to as 4armPEG20K-SCM, and its molecule weight is approximately 20 kDa.

In the preparation of the conjugate of formula (V), a usable three-arm polyethylene glycol is as follows:

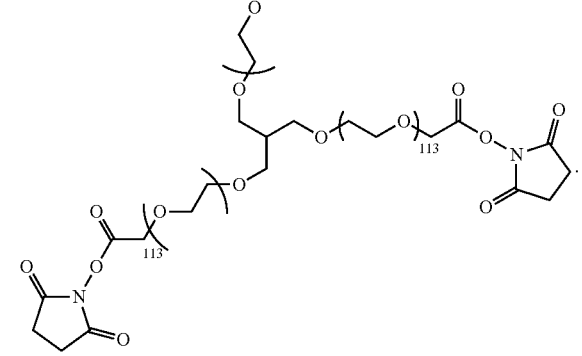

This preferred three-arm polyethylene glycol is referred to as 3armPEG20K-SCM.

In the preparation of the conjugate of formula (VI), a usable eight-arm polyethylene glycol is as follows:

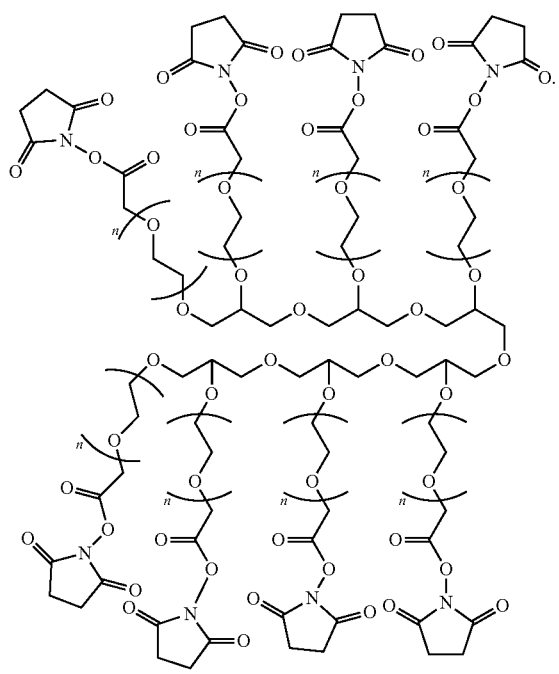

wherein $R_1$ to $R_5$ are selected from the following groups independently from each other: hydrogen, halogen, acyl, alkyl, substituted alkyl, alkoxy, substituted alkoxy, alkenyl, alkynyl, cycloalkyl, hydroxyl, cyano, nitro, azido, amido, hydrazine, amine group, substituted amine group, hydroxycarbonyl, alkoxycarbonyl, alkoxycarbonyloxy, carbamoyloxy, arylsulfonyloxy, and alkylsulfonyloxy; $R_6$ is H or $OR_8$; $R_8$ is alkyl, alkenyl, cycloalkyl, halogenated alkyl, or hydroxy alkyl; and R7 is hydroxyl;

(1) the active agent D is attached to the multivalent linker L to obtain a D-L portion;

(2) the D-L portion is attached to a multi-arm polymer R─(POLY)$_q$ to obtain R─(POLY-L-D)$_q$;

(3) R─(POLY-L-D)$_q$ obtained in the previous step is attached to the targeting molecule T.

According to the above-mentioned preparation method, D is preferably irinotecan, SN-38, 10-hydroxycamptothecin, or rubitecan;

the multi-arm polymer R─(POLY)$_q$ is 3armPEG20K-SCM, 4armPEG20K-SCM, or 8armPEG20K-SCM;

L is

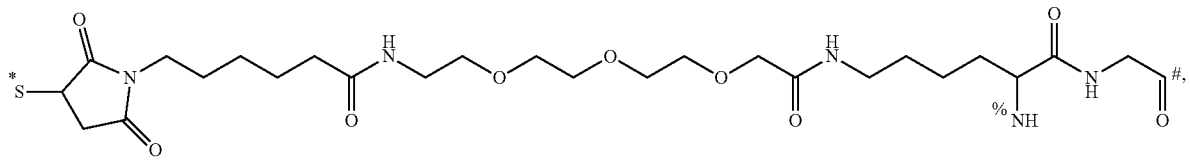

This preferred eight-arm polyethylene glycol is referred to as 8armPEG20K-SCM, and n is 113.

For example, a preparation method of a multi-branched drug conjugate or a pharmaceutically acceptable salt thereof comprises:

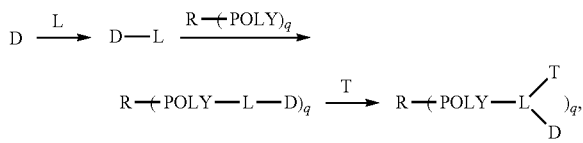

wherein R is an organic core, POLY is a polymer, L is a multivalent linker, T is a targeting molecule, D is an active agent, q is any integer between 3 and 8, and D is a camptothecin-based drug represented by the following formula:

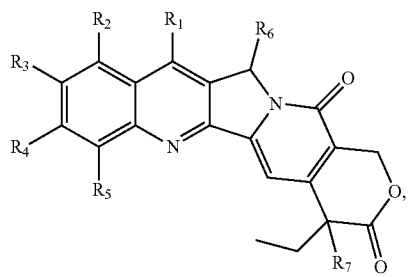

wherein symbol "*" represents an attachment point of the multivalent linker L and the targeting molecule T, "#" represents an attachment point of the multivalent linker L and the active agent D, and "%" represents an attachment point of the multivalent linker L and POLY; and T is iRGD, cRGD, tLyp-1, Lyp-1, RPARPAR, Angiopep2, GE11, or folic acid.

Alternatively, the multi-arm polyethylene glycol of the present disclosure may be prepared by synthesis. For example, a certain amount of any suitable polyol core material may be commercially available from chemical suppliers. The terminal hydroxy groups on the polyol are first converted to their anionic form, for example, an appropriate position suitable for the activation of a polymerization reaction is provided by a strong alkali. A single molecule (e.g., ethylene oxide) is then polymerized on the core directly. The establishment of the chain will continue until each branch reaches the desired length. Next, the reaction is terminated, for example, by quenching.

In another alternative method, the multi-arm polyethylene glycol of the present disclosure may be synthesized and prepared by the following method. First, a necessary polyol core material is provided. Next, the polyol is subjected to mesylation reaction with heteroatomic bifunctional PEG having a suitable length under a suitable condition, wherein the unmesylated PEG is selectively protected to avoid reacting with the polyol.

The multi-arm polyethylene glycol provided by the the present disclosure, which is suitable as an active agent carrier, particularly comprises one terminal functional group, for example, N-succinimidyl carbonate (see U.S. Pat. Nos. 5,281,698 and 5,468,478), succinimidyl propionate and succinimidyl butyrate (see U.S. Pat. No. 5,672,662), succinimidyl succinate, succinimidyl ester (see U.S. Pat. No. 5,650,234), and the like.

As described above, the conjugate carrier (composed of R and POLY) of the present disclosure is attached to at least one targeting molecule and one active agent. In a more typical and preferred compound, the conjugate carrier of the present disclosure is attached to at least 3 targeting molecules and 3 active agents, perferably to at least 4 targeting molecules and 4 active agents, so as to ensure high loading capacity.

The conjugate of the present disclosure is a typical prodrug. By hydrolysis or enzymolysis, the active agent D is released and separated from the parent, and exerts physiological activity.

The conjugate of the present disclosure shows high loading capacity, so that the total dosage may be lowered to treat a particular disease such as cancer. That is to say, the conjugate active agent carrier of the present disclosure is capable of covalently binding to a variety of active agent molecules effectively, allowing a greater amount of therapeutic agent (i.e., the active agent moiety) to be administered per certain amount of the conjugate. The conjugate of the present disclosure is modified by a water-soluble polymer, and the conjugate is also hydrophilic in nature. The bioavailability of the conjugate is enhanced especially when the active agent is a water-insoluble drug.

As compared with an unconjugated drug, the conjugate of the present disclosure is capable of exhibiting a stronger effect and are more enriched in the tissues of the body of human or other animals.

The conjugate prodrug of the present disclosure possesses many unique properties, especially in the case where the active agent is an anticancer compound. This kind of prodrug is able to inhibit the tumor growth with higher efficiency. This small molecule used herein is a small molecule known to have anticancer properties. However, by binding to the multi-branched polymer as described above, the efficacy and pharmacokinetics of the binded small molecule are greatly improved as compared with this small molecule (for example, anticancer compound itself). The types of suitable solid tumors include colon cancer, breast cancer, ovarian cancer, pancreatic cancer, gastric cancer, brain glioma, and malignant sarcoma, cancer and lymphoma of breast, ovary, colon, kidney, bile duct, lung and brain.

In summary, the present disclosure concerns a targeting anticancer conjugate modified by a multi-arm polymer, wherein the modification of a water-soluble polymer may enhance the water solubility of the conjugate so as to increase drug loading; the targeting property of the targeting molecule is increased, which enables the concentration of the conjugate to be higher in a target tissue; L is an arbitrary linker, the role of which is to first link the targeting molecule to an anticancer drug, then link the targeting molecule and the anticancer drug to the polymer arm, enabling the entire conjugate to form an organic whole.

As for compounds 1 to 42 of the present disclosure, the pharmaceutically acceptable salts thereof are preferably hydrochlorides, and the salt formation may be carried out by conventional means in the field of medicinal chemistry. The pharmaceutically acceptable salts may also be trifluoroacetates, sulfates, phosphates, acetates, and the like.

DETAILED DESCRIPTION

The present disclosure will be described in detail below. However, the present disclosure may be embodied in many different forms, and it should not be limited to the examples described herein. The purpose of providing these examples is to make the disclosed content more complete and more comprehensive. The reagents and raw materials used are all commercially available except for those with preparation method provided.

Unless otherwise defined, all technical terms in the present description have the same meaning as those commonly understood by those skilled in the art of the claimed subjected matters.

Unless otherwise specified, the terms used herein have the following meanings:
DMF: N, N-dimethylformamide
DCM: dichloromethane
Boc-Gly-OH:

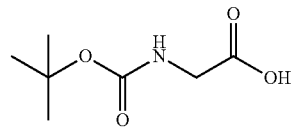

DMAP: 4-dimethylaminopyridine
DCC: dicyclohexylcarbodiimide
IPA: isopropanol
TFA: trifluoroacetic acid
TBME: tert-butyl methyl ether
EA: ethyl acetate
DME: ethylene glycol dimethyl ether
HOSU: N-succinimidyl carbonate
THF: tetrahydrofuran
Boc-Lys-OH:

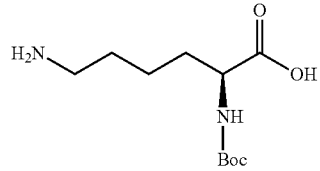 [SMILES: CC(C)(C)OC(=O)N[C@@H](CCCCN)C(=O)O]

DIEA: N,N-diisopropylethylamine
DEPC: diethyl cyanophosphonate
Phf:

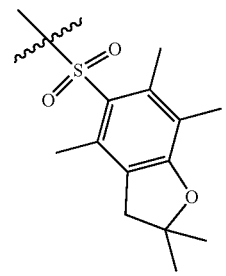 [SMILES: *S(=O)(=O)c1c(C)c(C)c2c(c1C)CC(C)(C)O2]

HOBT: 1-hydroxybenzotriazole
DIC: N,N-diisopropylcarbodiimide
MTBE: tert-butyl methyl ether
EDT: dithioglycol
PBS: phosphate buffer
EDC.HCl: 1-ethyl-(3-dimethylaminopropyl)carbodiimide hydrochloride

Example 1

Preparation of iRGD

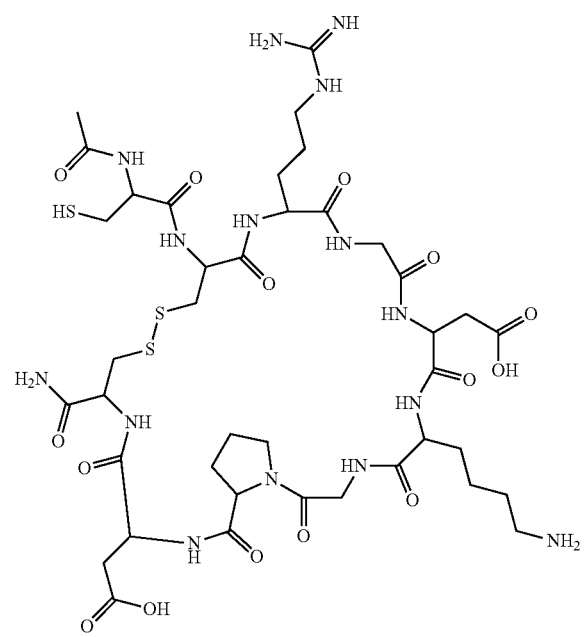 [SMILES: CC(=O)NC(CS)C(=O)NC1CSSCC(C(N)=O)NC(=O)C(CC(=O)O)NC(=O)C2CCCN2C(=O)CNC(=O)C(CCCCN)NC(=O)C(CC(=O)O)NC(=O)CNC(=O)C(CCCNC(=N)N)NC1=O]

Fmoc was removed from 10.0 g of Fmoc-Rink MBHA Amide Resin. HOBT/DIC was adopted as a coupling reagent, DMF was a reaction solvent, the reaction was monitored by ninhydrin detection method, and the following protecting amino acids were sequentially attached to the resin: Fmoc-Cys(Acm)-OH, Fmoc-Asp(OtBu)OH, Fmoc-Pro-OH, Fmoc-Gly-OH, Fmoc-Lys(Boc)-OH, Fmoc-Asp(OtBu)OH, Fmoc-Gly-OH, Fmoc-Arg(Pbf)-OH, and Fmoc-Cys(Acm)-OH. After washing the mixture with DMF, thallium trifluoroacetate (2.0 eq) was added. After being stirred for 18 h, the mixture was washed with DMF, and Fmoc was removed. Fmoc-Cys(Trt)-OH was condensed, the mixture was washed with DMF, and Fmoc was removed. Acetic anhydride and pyridine were added to react for 20 min, and the mixture was washed with DMF, DCM and methanol, followed by drying. 82.5% TFA/5% phenol/5% water/2.5% EDT/5% thioanisole was added as a cleavage reagent, ice-cold MTBE was added to precipitate, and the mixture was washed. The crude product was purified by reverse phase HPLC and lyophilized to obtain a white floc iRGD (1.56 g).

Preparation of the L Portion

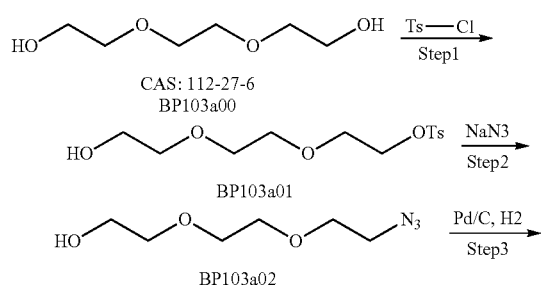

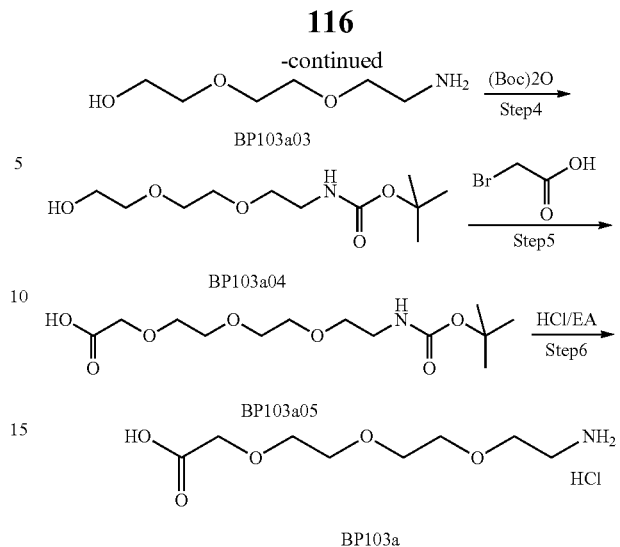

1. Preparation of BP103a01

Under nitrogen protection, to a 1000 mL three-necked flask, 200 mL of pyridine (120 g 1 (1.0 eq)) was added, stirred and cooled to 0° C. 151.8 g (1.0 eq) of TsCl was added in batch and stirred for 1 h. Then, the temperature was raised slowly to room temperature, and stirring was continued for 3 h to 4 h. After the reaction was complete, the reaction solution was poured into an ice-cold dilute hydrochloric acid solution, and EA was added for extraction. The EA layer was washed once with dilute hydrochloric acid, washed with saturated sodium bicarbonate and saturated saline, and dried over anhydrous $Na_2SO_4$. The solvent was removed by distillation under reduced pressure, and 55 g of pure BP103a01 was obtained by silica gel column chromatography.

2. Preparation of BP103a02

To a 1000 mL three-necked flask, 55 g (1.0 eq) of BP103a01 and 160 mL of DMSO were added and stirred until homogeneous, and 23.52 g (2.0 eq) of NaN3 was then added. The mixture was heated to 50° C. to react for 3 h and cooled to room temperature. The reaction solution was poured into water and EA was used for extraction. The organic phases were combined, dried over anhydrous sodium sulfate, and concentrated to obtain 29.2 g of BP103a02 as a colorless liquid.

3. Preparation of BP103a03

To a 1 L hydrogenation reaction kettle, 29 g of Compound 3, 360 mL of methanol, and 5.0 g of palladium on carbon were added, stirred and purged with nitrogen. Hydrogen was fed to react for 3 h to 4 h. After the completion of the reaction was monitored by TLC, the reaction solution was filtered, and the filtrate was concentrated to obtain 23.5 g of BP103a03 as an oil-like substance.

4. Preparation of BP103a04

To a 1 L three-necked flask, 23.5 g (1.0 eq) of Compound BP103a03, 68.6 g (2.0 eq) of (Boc)$_2$O, and 500 mL of a mixed solution of methanol:triethylamine (9:1) were added, stirred, the temperature was raised to reflux, and reacted for 1 h. After the completion of the reaction was monitored by TLC, methanol and triethylamine were removed by distillation, water was added for dissolution, and the mixture was extracted 3 times with dichloromethane. The organic layers were combined, washed once with water, and dried over anhydrous sodium sulfate. The solvent was removed by distillation, and the mixture was dried to obtain 34.8 g of BP103a04 as a solid.

5. Preparation of BP103a05

To a 1000 mL three-necked flask, 34.8 g (1.0 eq) of Compound BP103a04, toluene and THF (each 150 mL), and 58.2 g (3 eq) of bromoacetic acid were added, stirred and heated to 45° C. to 50° C. 33.5 g (6 eq) of sodium hydroxide was then added, and reacted overnight. After the completion of the reaction was monitored by TLC, the reaction solution was removed by distillation, water and EA were added for extraction, and the pH of the aqueous phase was adjusted to 3. The aqueous phase was extracted with dichloromethane, and the dichloromethane layers were combined. After being dried over anhydrous sodium sulfate, the mixture was concentrated to obtain 18 g of BP103a05 as an oily compound.

6. Preparation of BP103a

To a 250 mL three-necked flask, 18 g of Compound BP103a05 and 100 mL of EA were added, stirred and dissolved, then cooled to 0° C. 150 mL (3.5M) of EA/HCl was added, and the temperature was kept at 0° C. The completion of the reaction was monitored by TLC, the mixture was filtered, and the filter cake was washed with TBME to obtain 10.4 g of BP103a as a white solid.

completion of the reaction was monitored by TLC, the organic solvent was removed by distillation, and 5.2 g of oil-like substance M2 was obtained by column chromatography.

Preparation of M3

To a 200 mL three-necked flask, 9.00 g (1.0 eq) of Compound M2, 3.96 g (1.53 eq) of HOSU, 90 mL of DCM, and 6.60 g (1.53 eq) of EDC.HCl were added and reacted at room temperature for 2 h. After the completion of the reaction was monitored by TLC, the mixture was diluted with DCM, then washed twice with a 50 mmol/L aqueous solution of potassium dihydrogen phosphate (pH=6.0), washed with saturated saline, dried over anhydrous sodium sulfate, and concentrated to obtain 5.9 g of Compound M3 as a colorless oil-like substance.

Preparation of M4

To a 200 mL flask, 2.93 g (1.0 eq) of Compound Boc-Lys-OH, 60 mL of water and 2.00 g (2.0 eq) of NaHCO3 were added and stirred. A solution of 5.9 g (1.0 eq) of Compound M3 in 60 mL of DME (ethylene glycol dimethyl ether) was added dropwise, 60 mL of THF was further

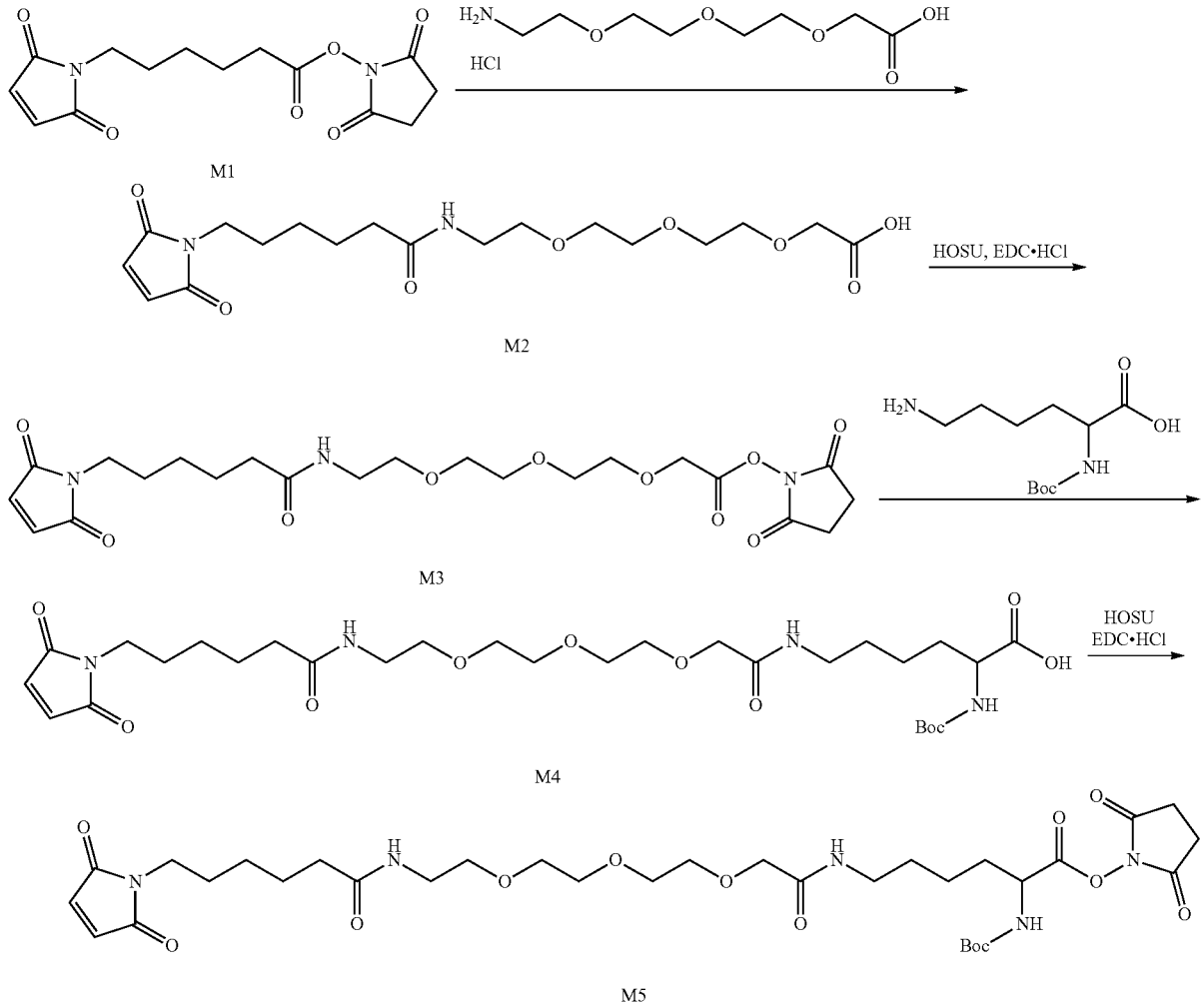

Preparation of M2

To a 100 mL flask, 3.0 g (1.0 eq) of BP103a, 4.0 g (1.0 eq) of Compound M1, 40 mL of DCM, and 4.0 mL (2.0 eq) of DIEA were added and stirred under room temperature. The added, and the mixture was stirred overnight. The completion of the reaction was monitored by TLC, the organic solvent was removed by distillation, and the pH was adjusted to 4 with acetic acid. The mixture was extracted with EA, dried over anhydrous sodium sulfate, and concentrated to obtain 4.50 g of Compound M4 as a colorless oil-like substance.

Preparation of M5

To a 100 mL flask, 3.81 g (1.0 eq) of Compound M4, 40 mL of DCM, 1.07 g of HOSU and 1.78 g of EDC.HCl were added, stirred, and reacted at room temperature for 4 h. The completion of the reaction was monitored by TLC. After being diluted with DCM, the mixture was washed twice with a 50 mM aqueous solution of potassium dihydrogen phosphate, washed once with purified water, washed once with saturated saline, dried over anhydrous sodium sulfate, and concentrated to obtain 4.1 g of Compound M5 as a colorless oil-like substance.

Preparation of the Conjugate

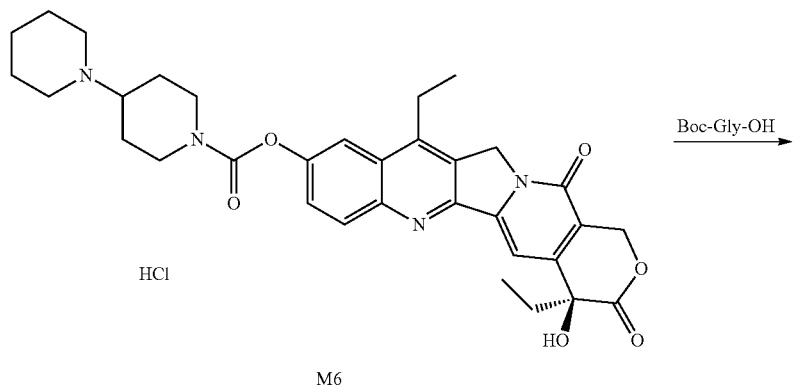

M6

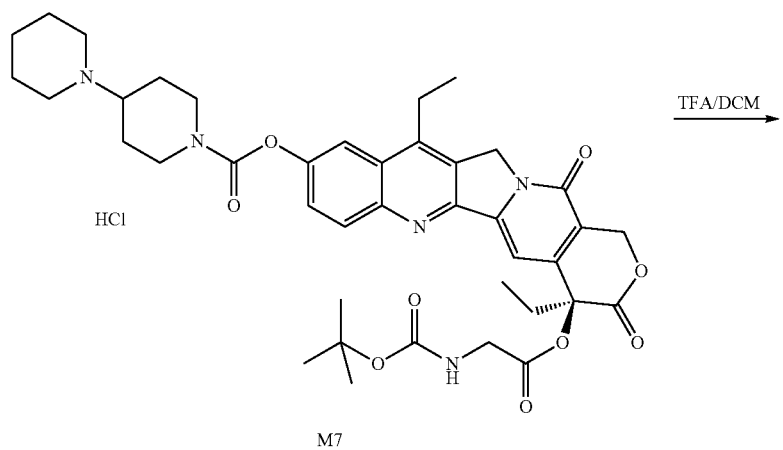

M7

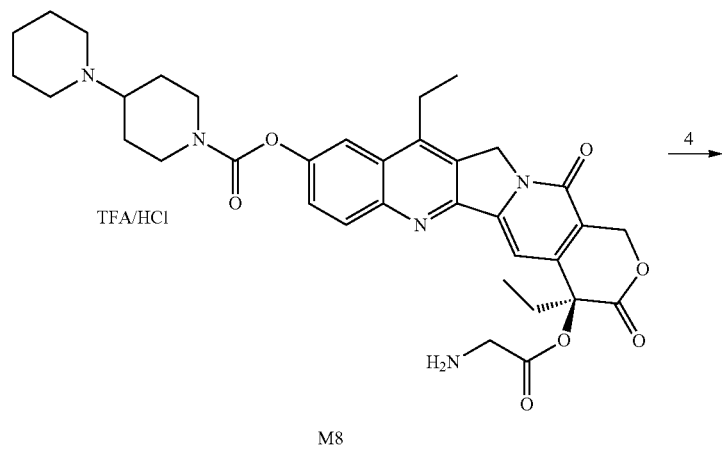

M8

-continued

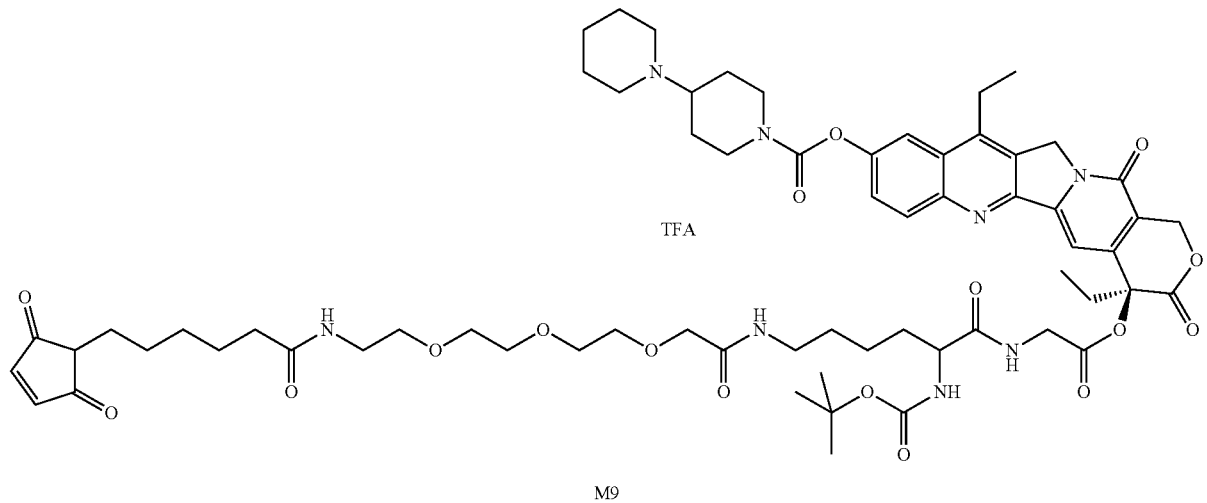

M9

Preparation of M7

To a 250 mL round bottom flask, 3.50 g (1.0 eq) of Compound M6 and 52.5 mL of DMF were added and heated to 60° C. for dissolution. After 5 to 10 min, DMF was removed by distillation under reduced pressure. 300 mL of n-heptane was added and distilled under reduced pressure, and the procedure was repeated three times. After the mixture was dried by rotary evaporation, 105 mL of DCM, 1.08 g of Boc-Gly-OH (1.2 eq) and 63 mg of DMAP (0.1 eq) were added, a solution of 1.59 g of DCC (1.5 eq) in 10 mL of DCM was added dropwise, and the mixture was reacted at 20° C. for 4 h. After the completion of the reaction was monitored by TLC, the mixture was filtered, and 120 mL of IPA was added when the mixture was concentrated to 25% of its total volume. 75% of the solvent was removed by distillation, and 150 mL of n-heptane was added. The mixture was stirred at room temperature for 1 h, filtered, washed twice with n-heptane, and dried to obtain 4.02 g of Compound M7 as a pale yellow solid.

Preparation of M8

To a 100 mL three-necked flask, 4.02 g of Compound M7 and 50 mL of DCM were added. After the mixture was stirred and dissolved, 11.6 mL of TFA was added dropwise, and the mixture was reacted at room temperature for 2 h. After the completion of the reaction was monitored by TLC, 150 mL of acetonitrile was added. After 120 mL of solvent was distilled under reduced pressure, the mixture was poured into 320 mL of TBME solution, stirred for 30 min, and filtered. The filter cake was washed with TBME to obtain a pale yellow solid M8 (4.00 g).

Preparation of M9

To a 200 mL three-necked flask, 2.95 g of Compound M8, 80 mL of DCM, 2.57 g (1.05 eq) of Compound 4, 2.16 mL of DIEA (3.0 eq) and 0.96 mL of DEPC (1.5 eq) were added and reacted at room temperature for 4 h. After the completion of the reaction was monitored by TLC, the mixture was diluted with DCM, then the mixture was washed twice with water, washed once with saturated saline, dried, concentrated, purified by HPLC, and then lyophilized to obtain a pale yellow solid M9 (1.48 g).

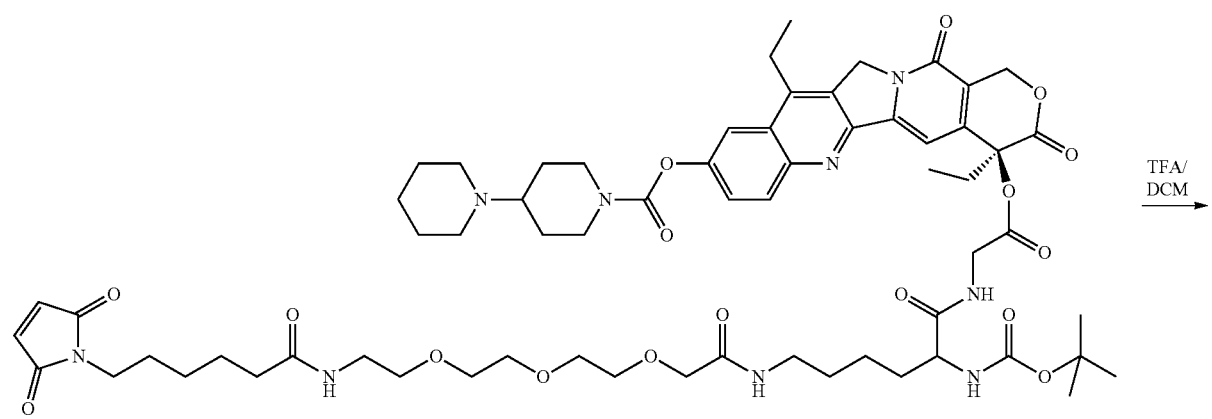

M9

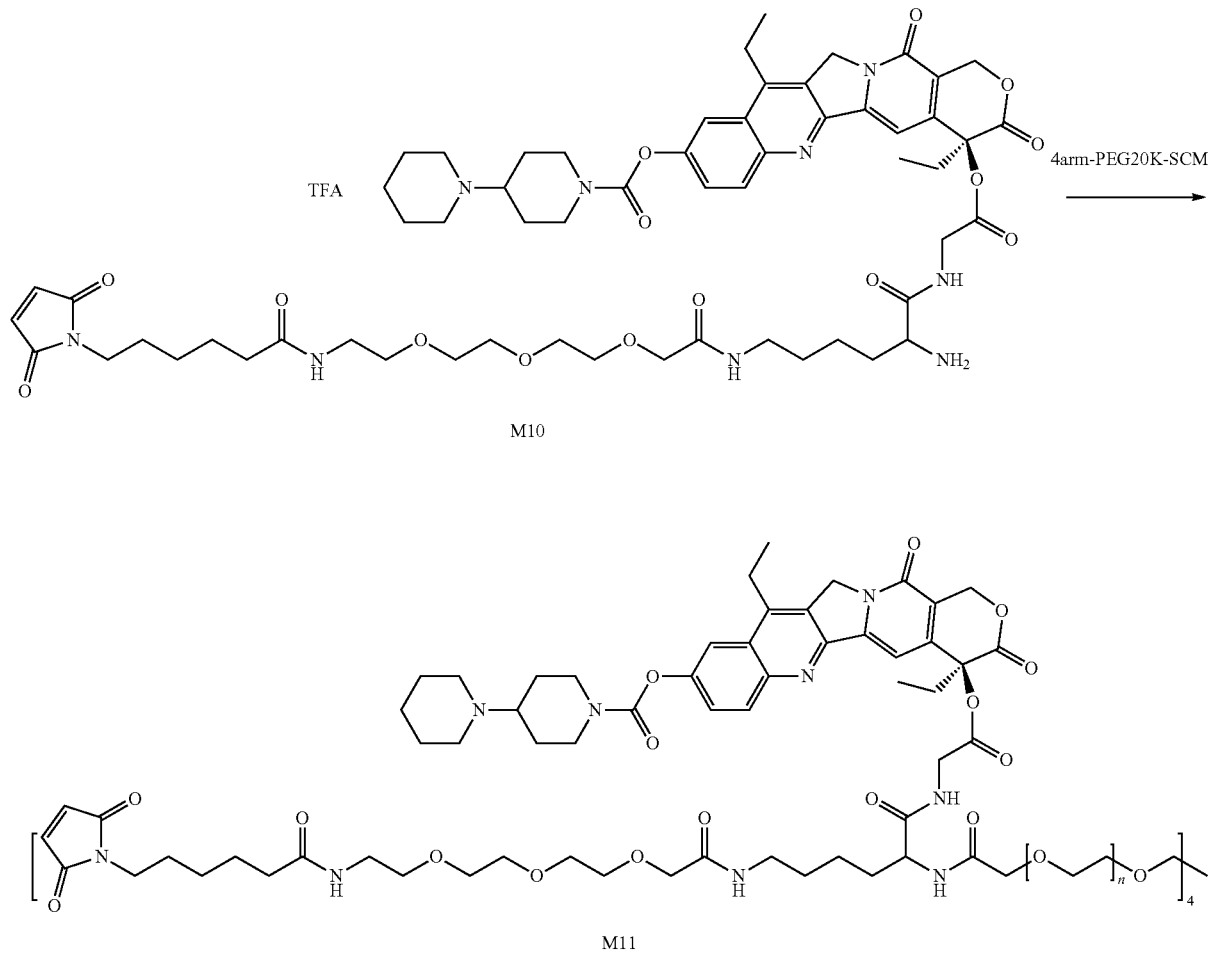

M10

M11

Preparation of M10

To a 50 mL round bottom flask, 260 mg of Compound M9 and 10 mL of 20% TFA/DCM were added and reacted at room temperature for 4 h. After the completion of the reaction was monitored by TLC, the mixture was poured into TBME, centrifuged, and dried to obtain a pale yellow solid M10 (210 mg).

Preparation of M11

To a 10 mL round bottom flask, 51 mg (4.0 eq) of Compound M10, 2 mL of DCM, 11 μL (8.0 eq) of TEA and 201 mg (1.0 eq) of 4armPEG20K-SCM were added. After reacting at room temperature overnight, the mixture was concentrated, added to TBME, centrifuged, and dried to obtain an off-white solid M11 (240 mg).

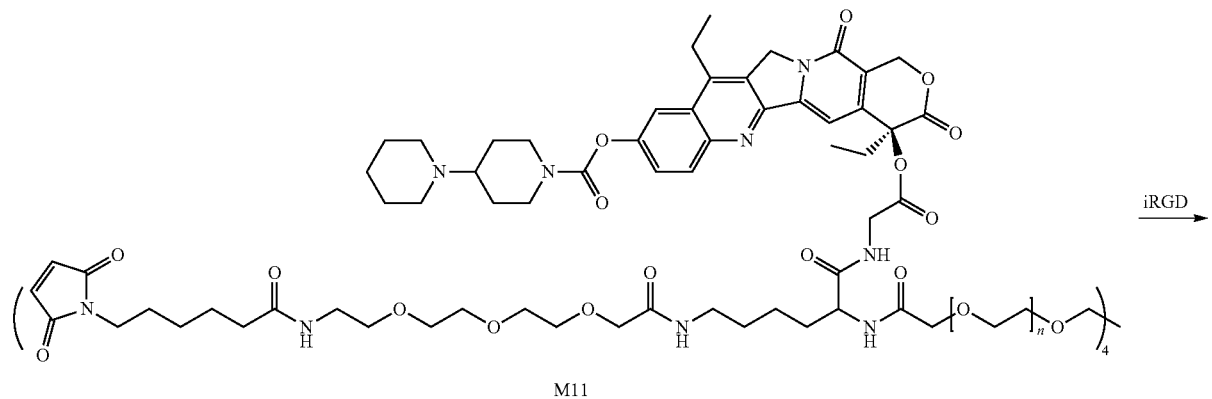

M11

-continued

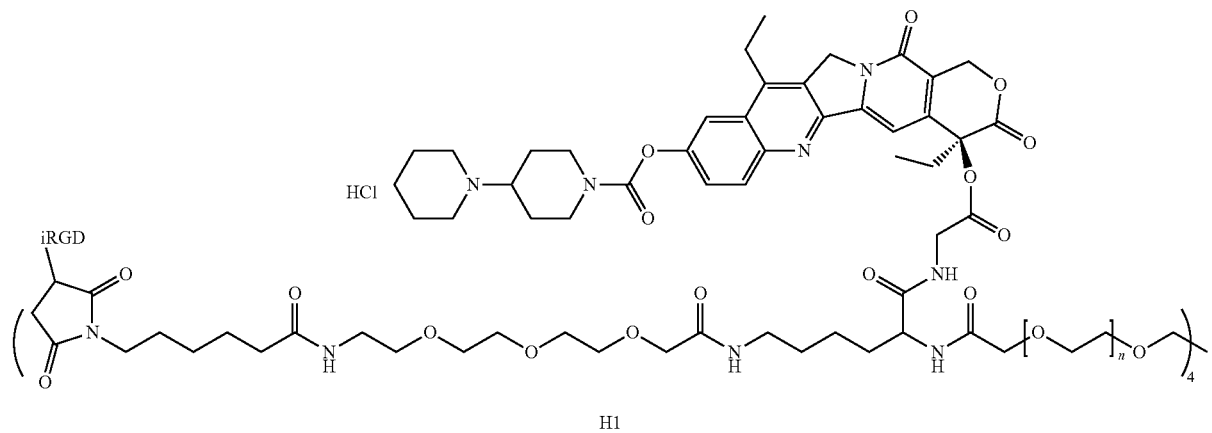

H1

Preparation of Compound 1 and H1

To a 10 mL round bottom flask, 50 mg (1.0 eq) of Compound M11 and 1.5 mL of PBS (pH=7, 0.01M) were added. After the mixture was dissolved to give a clear solution, a solution of 10.6 mg of iRGD in 1 mL of PBS (pH=7, 0.01M) was added. After reacting at room temperature for 4 h, the mixture was dialyzed and concentrated to obtain compound 1. The crude product was dissolved in methanol, and a solution of HCl/EA was added. The mixture was concentrated, added to TBME, centrifuged, and dried to obtain a yellow solid H1 (Hydrochloride of compound 1)(50 mg).

$^1$HNMR (DMSO+D$_2$O): δ0.902 (t, CH$_2$C$\underline{H}_3$), 3.5 (br m PEG), 5.328 (s, 2H), 5.480 (s, 2H), 7.0-8.5 (m N$\underline{H}$)

Example 2

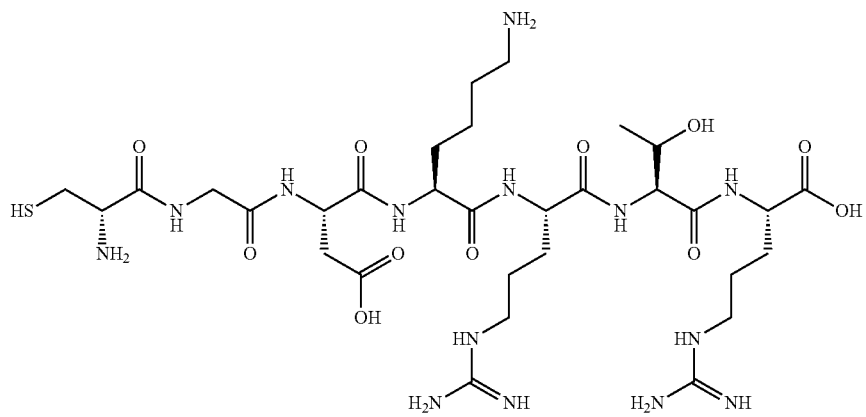 [SMILES: CC(O)[C@H](NC(=O)[C@H](CCCNC(=N)N)NC(=O)[C@H](CCCCN)NC(=O)[C@H](CC(=O)O)NC(=O)CNC(=O)[C@H](N)CS)C(=O)N[C@@H](CCCNC(=N)N)C(=O)O]

10.0 g of 2Cl-Trt Resin was used, HOBT/DIC was adopted as a coupling reagent, DMF was a reaction solvent, the reaction was monitored by ninhydrin detection method, and the following protecting amino acids were sequentially attached to the resin: Fmoc-Arg(pbf)-OH, Fmoc-Thr(tBu)-OH, Fmoc-Arg(pbf)-OH, Fmoc-Lys(Boc)-OH, Fmoc-Asn(Trt)-OH, Fmoc-Gly-OH, and Fmoc-Cys(Trt)-OH. 82.5% TFA/5% phenol/5% water/2.5% EDT/5% thioanisole was added as a cleavage reagent, ice-cold MTBE was added to precipitate, and the mixture was washed. The crude product was purified by reverse phase HPLC and lyophilized to obtain a white floc (5.5 g).

Preparation of the L Portion was the Same as Example 1

Preparation of the Conjugate

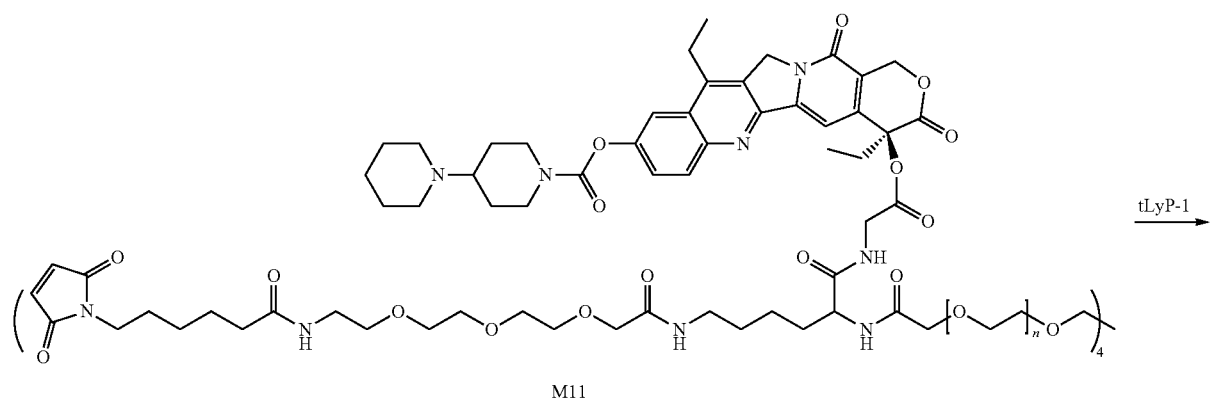

M11

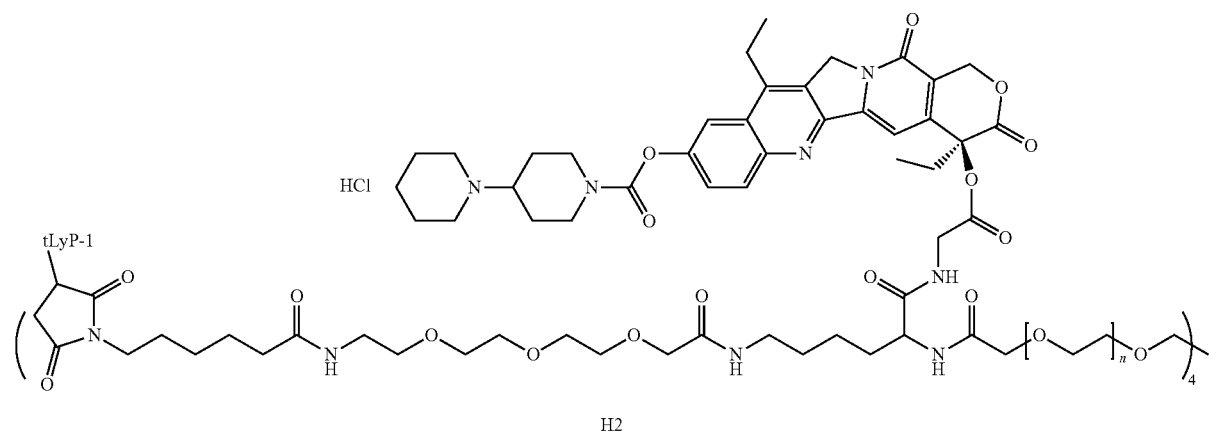

H2

Preparation of Compound 2 and H2

To a 100 mL round bottom flask, 1.0 g (1.0 eq) of Compound M11 and 20 mL of PBS (pH=7, 0.01M) were added. After the mixture was dissolved to give a clear solution, a solution of 139 mg of tLyP-1 in 10 mL of PBS (pH=7, 0.01M) was added. After reacting at room temperature for 4 h, the mixture was dialyzed and concentrated to obtain compound 2, the crude product was dissolved in methanol, and a solution of HCl/EA was added. The mixture was concentrated, added to TBME, centrifuged, and dried to obtain a yellow solid H2 (Hydrochloride of compound 2) (1.0 g).

$^1$HNMR (DMSO+D$_2$O): δ0.903 (t, CH$_2$C$\underline{H}_3$), 3.5 (br m PEG), 5.332 (s, 2H), 5.484 (s, 2H), 7.0-8.5 (m N$\underline{H}$)

Example 3

Preparation of Lyp-1

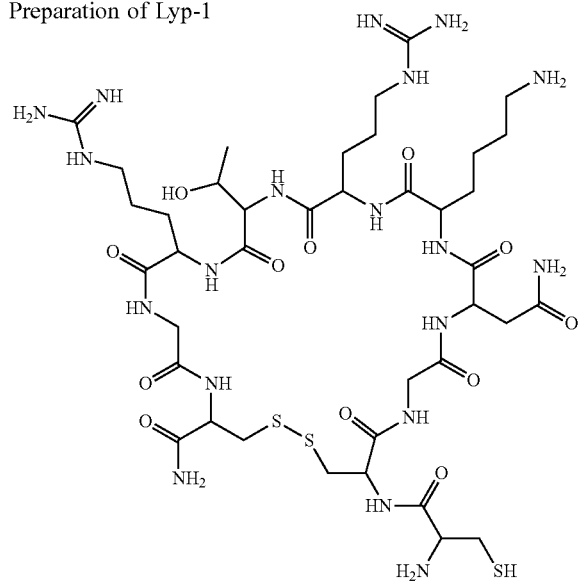

Fmoc was removed from 10.0 g of Fmoc-Rink MBHA Amide Resin. HOBT/DIC was adopted as a coupling reagent, DMF was a reaction solvent, the reaction was monitored by ninhydrin detection method, and the following protecting amino acids were sequentially attached to the resin: Fmoc-Cys(Acm)-OH, Fmoc-Gly-OH, Fmoc-Arg (Pbf)-OH, Fmoc-Thr(tBu)-OH, Fmoc-Arg(pbf-OH, Fmoc-Lys(Boc)-OH, Fmoc-Asn(Trt)-OH, Fmoc-Gly-OH, and Fmoc-Cys(Acm)-OH. After washing the mixture with DMF, thallium trifluoroacetate (2.0 eq) was added. After being stirred for 18 h, the mixture was washed with DMF, and Fmoc was removed. Fmoc-Cys(Trt)-OH was condensed, the mixture was washed with DMF, Fmoc was removed, and then the mixture was dried. 82.5% TFA/5% phenol/5% water/2.5% EDT/5% thioanisole was added as a cleavage reagent, ice-cold MTBE was added to precipitate, and the mixture was washed. The crude product was purified by reverse phase HPLC and lyophilized to obtain a white floc LyP-1 (765 mg).

Preparation of the L Portion was the Same as Example 1

Preparation of the Conjugate (pH=7, 0.01M) was added. After reacting at room temperature for 4 h, the mixutre was dialyzed and concentrated to obtain compound 3. The crude product was dissolved in methanol, and a solution of HCl/EA was added. The mixture was concentrated, added to TBME, centrifuged, and dried to obtain a yellow solid H3 (Hydrochloride of compound 3) (1.05 g).

$^1$HNMR (DMSO+D$_2$O): δ0.901 (t, CH$_2$C$\underline{H}_3$), 3.5 (br m PEG), 5.328 (s, 2H), 5.481 (s, 2H), 7.0-8.5 (m N$\underline{H}$)

Example 4

Preparation of CPARPAR 10.0 g of 2Cl-Trt Resin was used, HOBT/DIC was adopted as a coupling reagent, DMF was a reaction solvent, the reaction was monitored by ninhydrin detection method, and the following protecting amino acids were sequentially attached to the resin: Fmoc-Arg(pbf)-OH, Fmoc-Ala-OH, Fmoc-Pro-OH, Fmoc-Arg(pbf)-OH, Fmoc-Ala-OH, Fmoc-Pro-OH, Fmoc-Arg(pbf)-OH, and Fmoc-Cys(Trt)-OH.

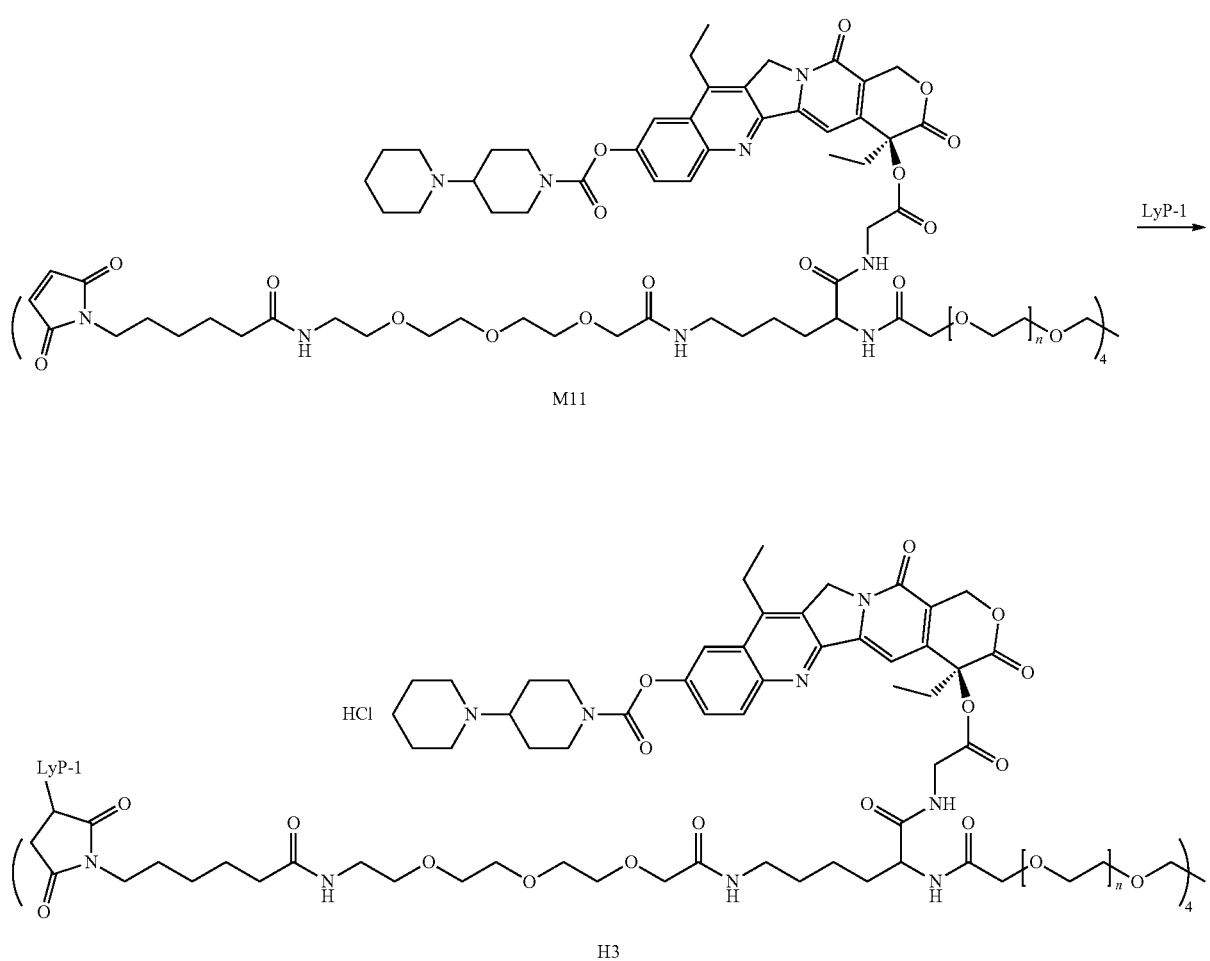

Preparation of Compound 3 and H3

To a 100 mL round bottom flask, 1.0 g (1.0 eq) of Compound M11 and 20 mL of PBS (pH=7, 0.01M) were added. After the mixture was dissolved to give a clear solution, a solution of 182 mg of LyP-1 in 10 mL of PBS 82.5% TFA/5% phenol/5% water/2.5% EDT/5% thioanisole was added as a cleavage reagent, ice-cold MTBE was added to precipitate, and the mixture was washed. The crude product was purified by reverse phase HPLC and lyophilized to obtain a white floc CRPARPAR (6.1 g).

Preparation of the L Portion was the Same as Example 1
Preparation of the Conjugate

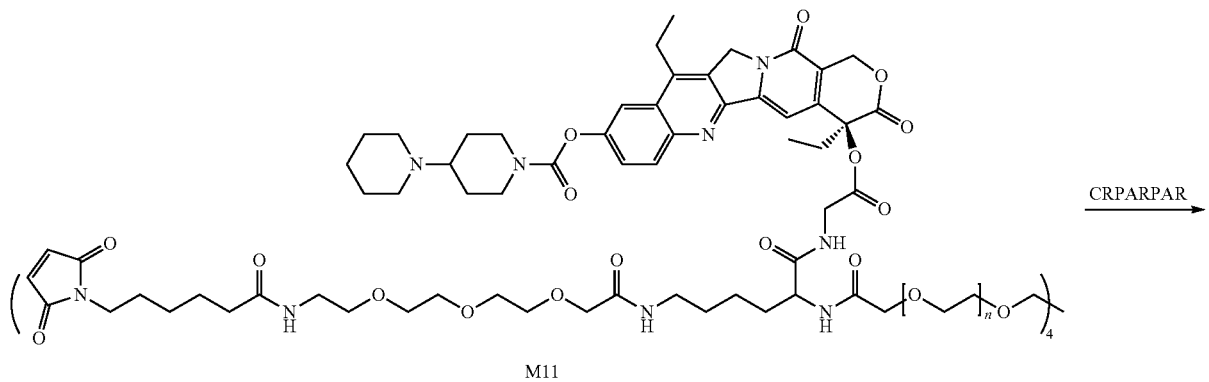

M11

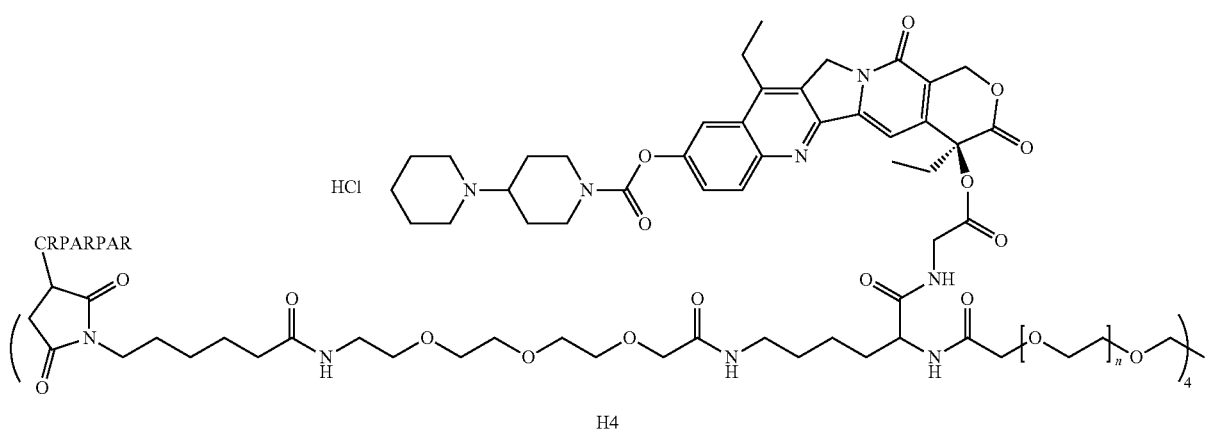

H4

Preparation of Compound 4 and H4

To a 100 mL round bottom flask, 1.0 g (1.0 eq) of Compound M11 and 20 ml of PBS (pH=7, 0.01M) were added. After the mixture was dissolved to give a clear solution, a solution of 154 mg of CRPARPAR in 10 mL of PBS (pH=7, 0.01M) was added. After reacting at room temperature for 4 h, the mixture was dialyzed and concentrated to obtain compound 4, the crude product was dissolved in methanol, and a solution of HCl/EA was added. The mixture was concentrated, added to TBME, centrifuged, and dried to obtain a yellow solid H4 (Hydrochloride of compound 4) (1.09 g).

$^1$HNMR (DMSO+D$_2$O): δ0.905 (t, CH$_2$C$\underline{H}_3$), 3.5 (br m PEG), 5.335 (s, 2H), 5.486 (s, 2H), 7.0-8.5 (m N$\underline{H}$)

Example 5

Preparation of cRGD

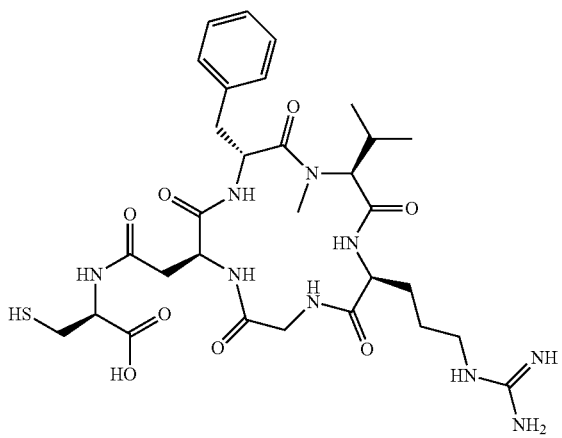 [SMILES: CC(C)[C@H]1C(=O)N[C@@H](CCCNC(=N)N)C(=O)NCC(=O)N[C@@H](CC(=O)N[C@H](CS)C(=O)O)C(=O)N[C@H](Cc2ccccc2)C(=O)N1C]

cRGD used in the present disclosure was obtained from outsourcing.

Preparation of the L Portion was the Same as Example 1

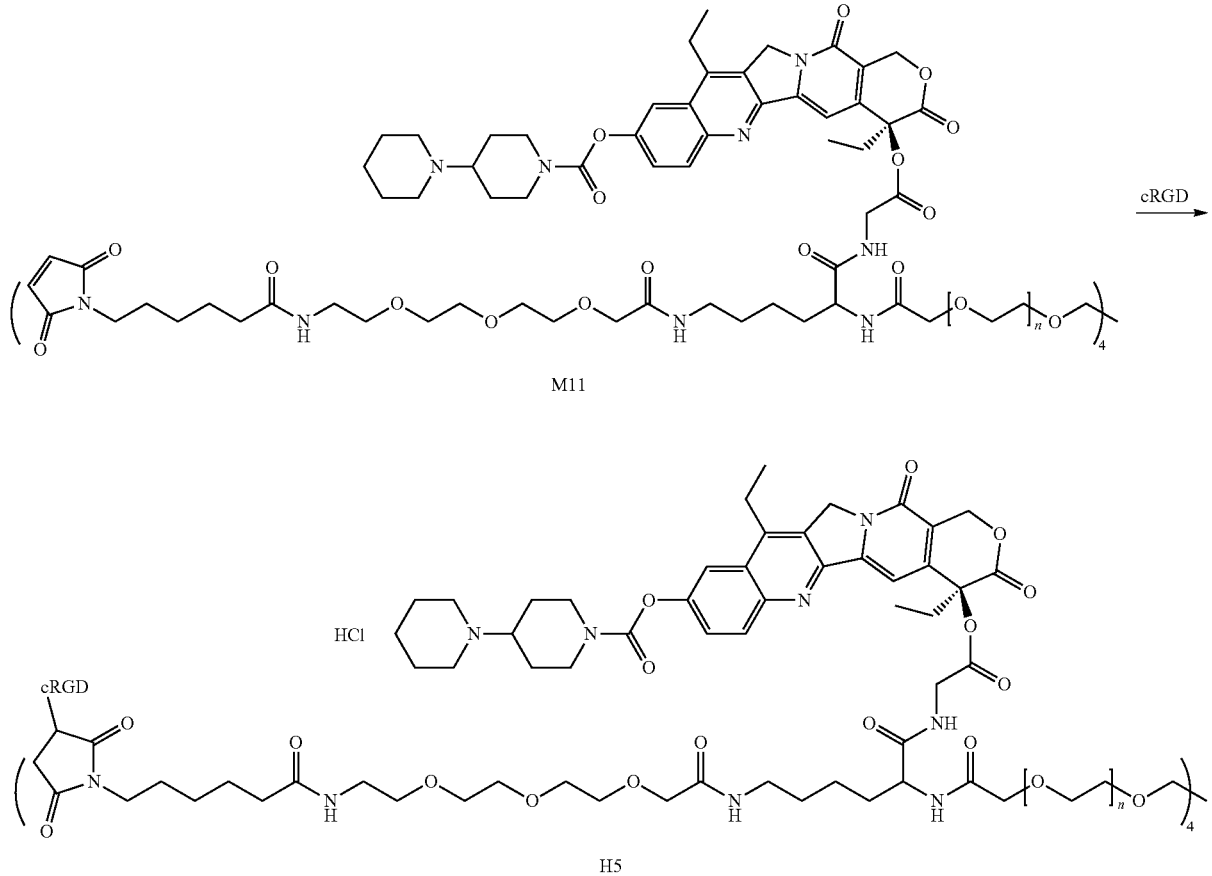

Preparation of Compound 5 and H5

To a 100 mL round bottom flask, 1.0 g (1.0 eq) of Compound M11 and 20 mL of PBS (pH=7, 0.01M) were added. After the mixture was dissolved to give a clear solution, a mixed solution of 96.4 g of cRGD in 4 mL of PBS (pH=7, 0.01M) and 6 mL of methanol was added. After reacting at room temperature for 4 h, the mixture was dialyzed and concentrated to obtain compound 5, the crude product was dissolved in methanol, and a solution of HCl/EA was added. The mixture was concentrated, added to TBME, centrifuged, and dried to obtain a yellow solid H5 (Hydrochloride of compound 5) (1.06 g).

$^1$HNMR (DMSO+D$_2$O): δ0.902 (t, CH$_2$C$\underline{H}_3$), 3.5 (br m PEG), 5.326 (s, 2H), 5.480 (s, 2H), 7.0-8.5 (m N$\underline{H}$)

Example 6

Preparation of iRGD was the Same as Example 1
Preparation of the L Portion was the Same as Example 1
Preparation of the Conjugate

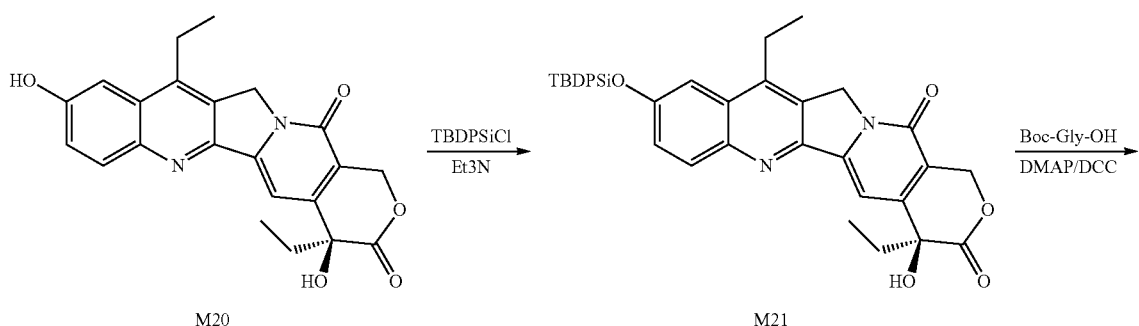

135
-continued
136
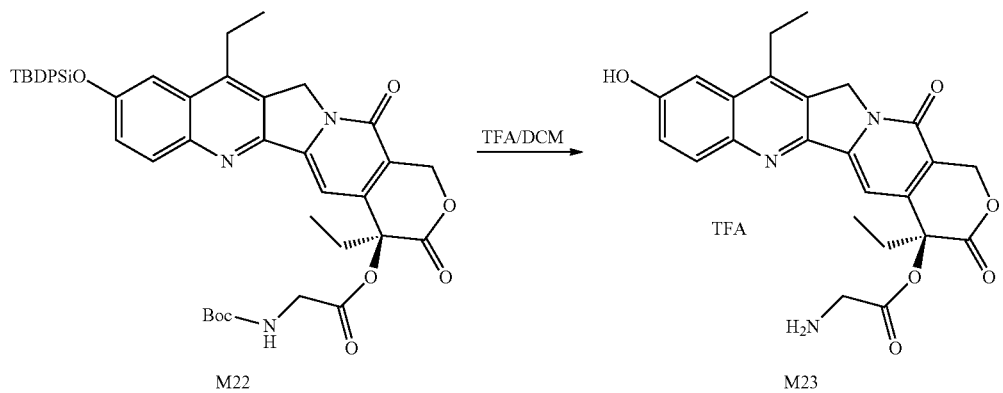
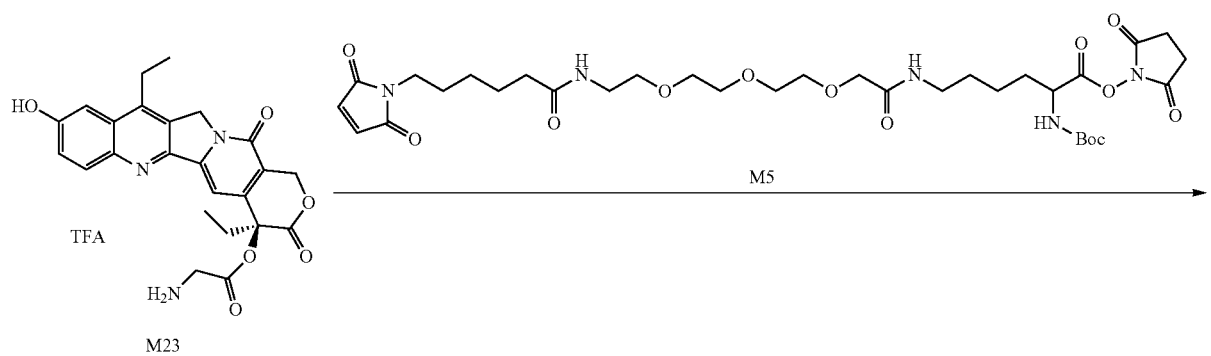
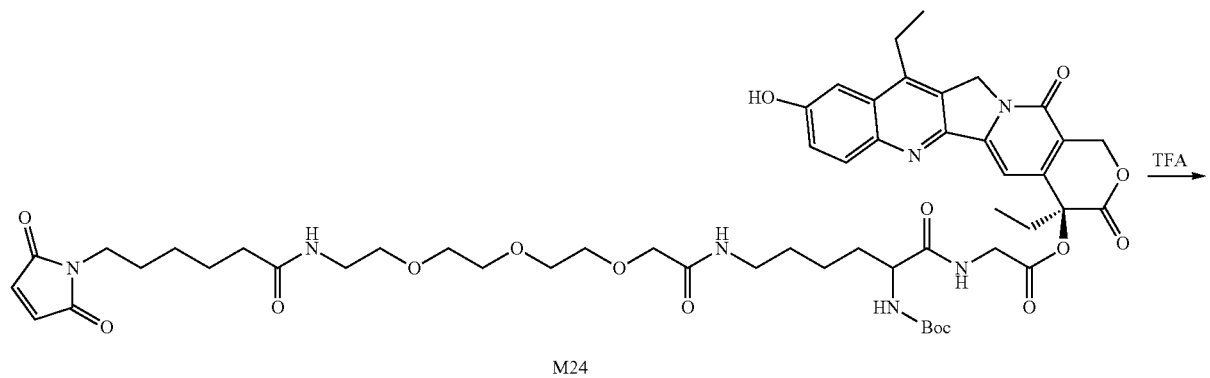
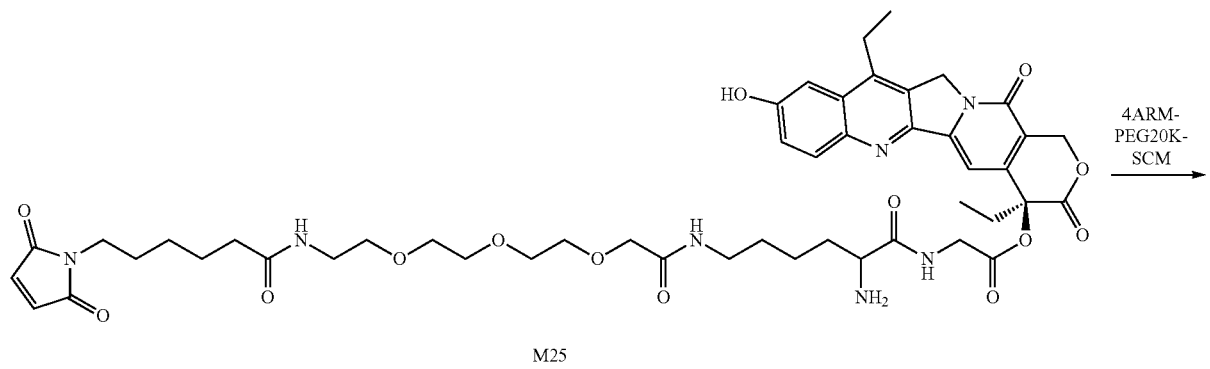

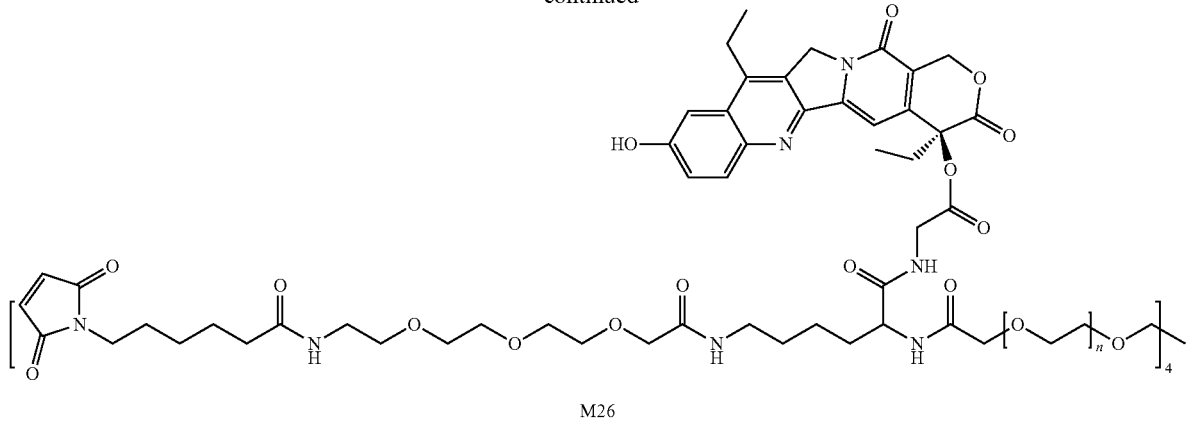

M26

1. Preparation of M21

To a 250 mL round bottom flask, 5.00 g (1.0 eq) of Compound M20, 100 mL of DCM and 3.89 g (3.0 eq) of TEA were added, and a solution of 3.50 g (1.0 eq) of TBDPS-Cl in 20 mL of DCM was added dropwise. After the completion of the reaction was monitored by TLC, the mixture was washed with water, washed with saturated saline, dried over anhydrous sodium sulfate, and then subjected to column chromatography to obtain 3.62 g of Compound M21 as a pale yellow solid.

2. Preparation of M22

To a 250 mL round bottom flask, 4.80 g (1.0 eq) of Compound M21, 145 mL of DCM, 1.64 g (1.2 eq) of Boc-Gly-OH and 95 mg (0.1 eq) of DMAP were added, a solution of 2.41 g (1.5 eq) of DCC in 10 mL of DCM was added dropwise, and the mixture was reacted at 20° C. for 4 h. After the completion of the reaction was monitored by TLC, the mixture was filtered, and 130 mL of IPA was added when the mixture was concentrated to 25% of its total volume. 75% of the solvent was removed by distillation, and 160 mL of n-heptane was added. The mixture was stirred at room temperature for 1 h, filtered, washed twice with n-heptane, and dried to obtain 4.65 g of Compound M22 as a pale yellow solid.

3. Preparation of M23

To a 100 mL three-necked flask, 4.65 g of Compound M22 and 50 mL of DCM were added. After the mixture was stirred and dissolved, 11.6 mL of TFA was added dropwise, and the mixture was reacted at room temperature for 2 h. After the completion of the reaction was monitored by TLC, 150 mL of acetonitrile was added. After 120 mL of solvent was distilled under reduced pressure, the mixture was poured into 320 mL of TBME solution, stirred for 30 min, and filtered. The filter cake was washed with TBME to obtain a pale yellow solid M23 (2.48 g).

4. Preparation of M24

To a 200 mL three-necked flask, 2.3 g of Compound M23, 45 mL of DCM, 3.196 g (1.05 eq) of Compound M5 and 1.75 mL (3.0 eq) of TEA were added and reacted at room temperature for 4 h. After the completion of the reaction was monitored by TLC, the mixture was diluted with DCM, then washed twice with water, washed once with saturated saline, dried, concentrated, purified by HPLC, and then lyophilized to obtain a pale yellow solid M24 (2.20 g).

5. Preparation of M25

To a 200 mL round bottom flask, 2.0 g of Compound M24 and 60 mL of 20% TFA/DCM were added and reacted at room temperature for 4 h. After the completion of the reaction was monitored by TLC, the mixture was poured into TBME, centrifuged, and dried to obtain a pale yellow solid M25 (1.75 g).

6. Preparation of M26

To a 500 mL round bottom flask, 1.51 g (4.0 eq) of Compound M25, 140 mL of DCM, 390 μL (8.0 eq) of TEA and 7.0 g (1.0 eq) of 4armPEG20K-SCM were added. After reacting at room temperature overnight, the mixture was concentrated, added to TBME, centrifuged, and dried to obtain an off-white solid M26 (7.9 g).

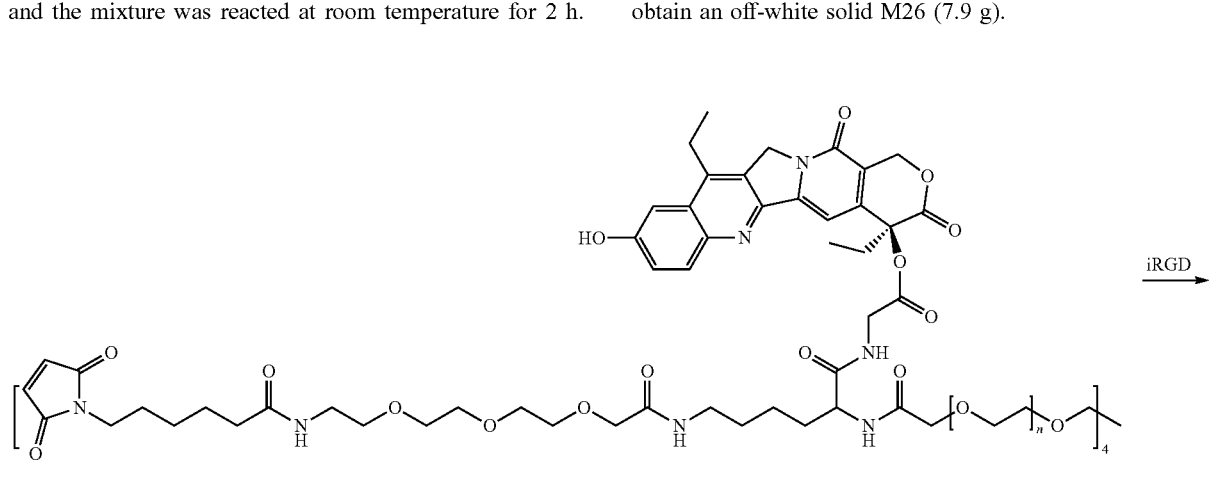

M26

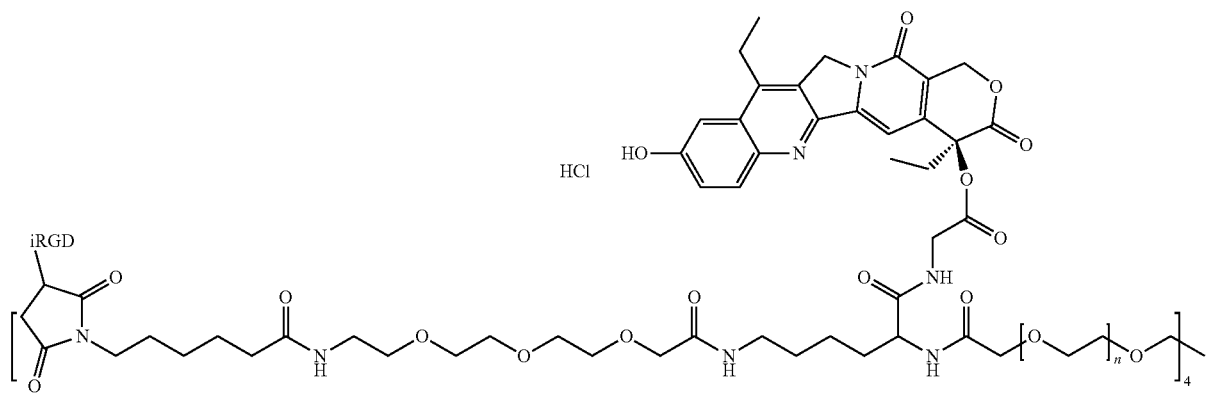

H6

Preparation of Compound 6 and H6

To a 100 mL round bottom flask, 1.0 g (1.0 eq) of Compound M26 and 20 mL of PBS (pH=7, 0.01M) were added. After the mixture was dissolved to give a clear solution, a solution of 188 mg of iRGD in 10 mL of PBS (pH=7, 0.01M) was added. After reacting at room temperature for 4 h, the mixture was dialyzed and concentrated to obtain compound 6, the crude product was dissolved in methanol, and a solution of HCl/EA was added. The mixture was concentrated, added to TBME, centrifuged, and dried to obtain a yellow solid H6 (Hydrochloride of compound 6) (980 mg).

$^1$HNMR (DMSO+D$_2$O): δ0.905 (t, CH$_2$CH$_3$), 3.5 (br m PEG), 5.333 (s, 2H), 5.487 (s, 2H), 7.0-8.5 (m NH)

Example 7

Preparation of tLyp-1 was the Same as Example 2
Preparation of the L Portion was the Same as Example 1
Preparation of the Conjugate

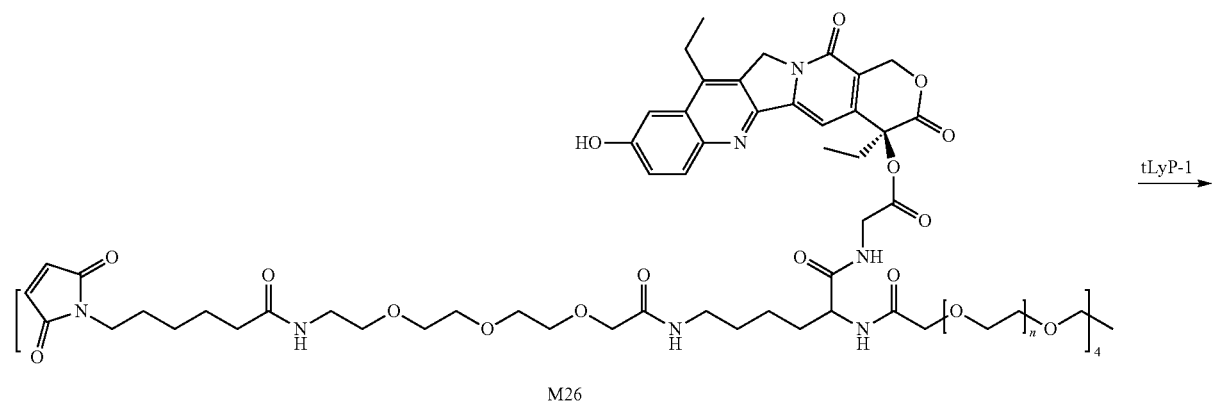

M26

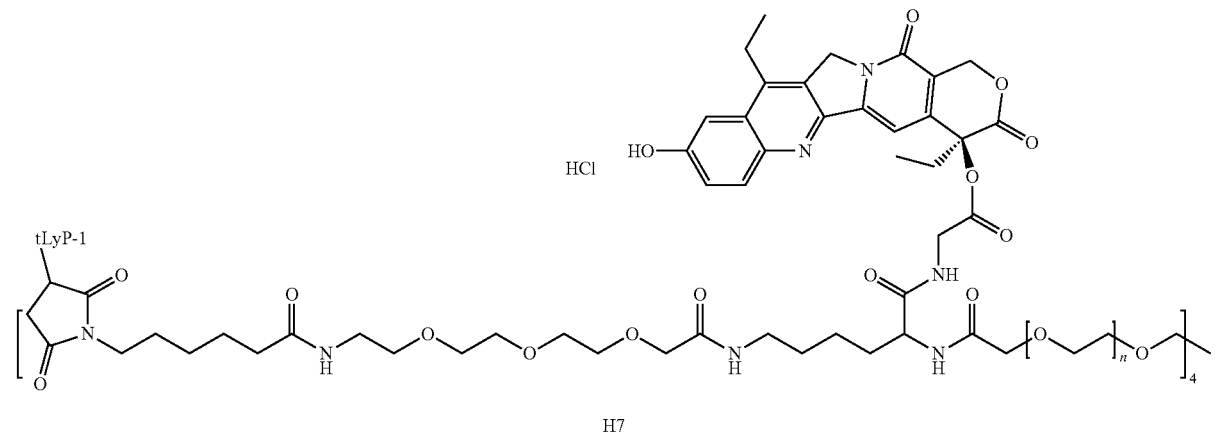

H7

Preparation of Compound 7 and H7

To a 100 mL round bottom flask, 1.0 g (1.0 eq) of Compound M26 and 20 mL of PBS (pH=7, 0.01M) were added. After the mixture was dissolved to give a clear solution, a solution of 144 mg of tLyP-1 in 10 mL of PBS (pH=7, 0.01M) was added. After reacting at room temperature for 4 h, the mixture was dialyzed and concentrated to obtain compound 7, the crude product was dissolved in methanol, and a solution of HCl/EA was added. The mixture was concentrated, added to TBME, centrifuged, and dried to obtain a yellow solid H7 (Hydrochloride of compound 7) (1.01 g).

$^1$HNMR (DMSO+D$_2$O): δ0.904 (t, CH$_2$CH$_3$), 3.5 (br m PEG), 5.335 (s, 2H), 5.488 (s, 2H), 7.0-8.5 (m NH)

Example 8

Preparation of Lyp-1 was the Same as Example 3
Preparation of the L Portion was the Same as Example 1
Preparation of the Conjugate

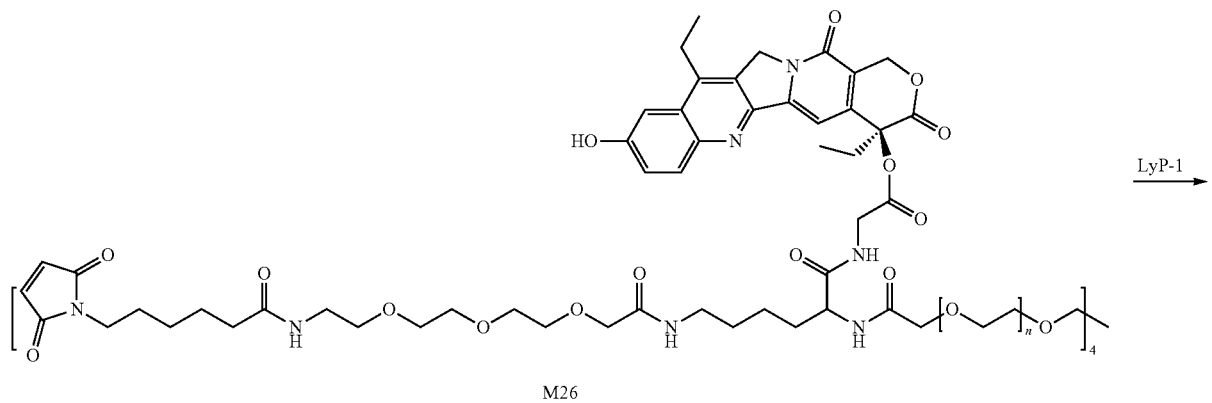

M26

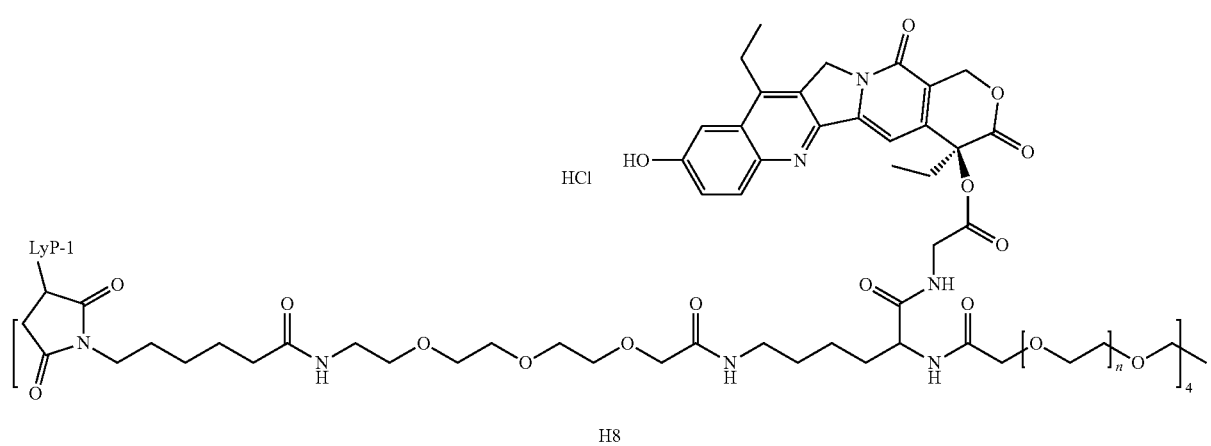

H8

Preparation of Compound 8 and H8

To a 100 mL round bottom flask, 1.0 g (1.0 eq) of Compound M26 and 20 mL of PBS (pH=7, 0.01M) were added. After the mixture was dissolved to give a clear solution, a solution of 188 mg of LyP-1 in 10 mL of PBS (pH=7, 0.01M) was added. After reacting at room temperature for 4 h, the mixture was dialyzed and concentrated to obtain compound 8, the crude product was dissolved in methanol, and a solution of HCl/EA was added. The mixture was concentrated, added to TBME, centrifuged, and dried to obtain a yellow solid H8 (Hydrochloride of compound 8) (1.04 g).

$^1$HNMR (DMSO+D$_2$O): δ0.902 (t, CH$_2$CH$_3$), 3.5 (br m PEG), 5.328 (s, 2H), 5.481 (s, 2H), 7.0-8.5 (m NH)

Example 9

Preparation of CRPARPAR was the Same as Example 4
Preparation of the L Portion was the Same as Example 1
Preparation of the Conjugate

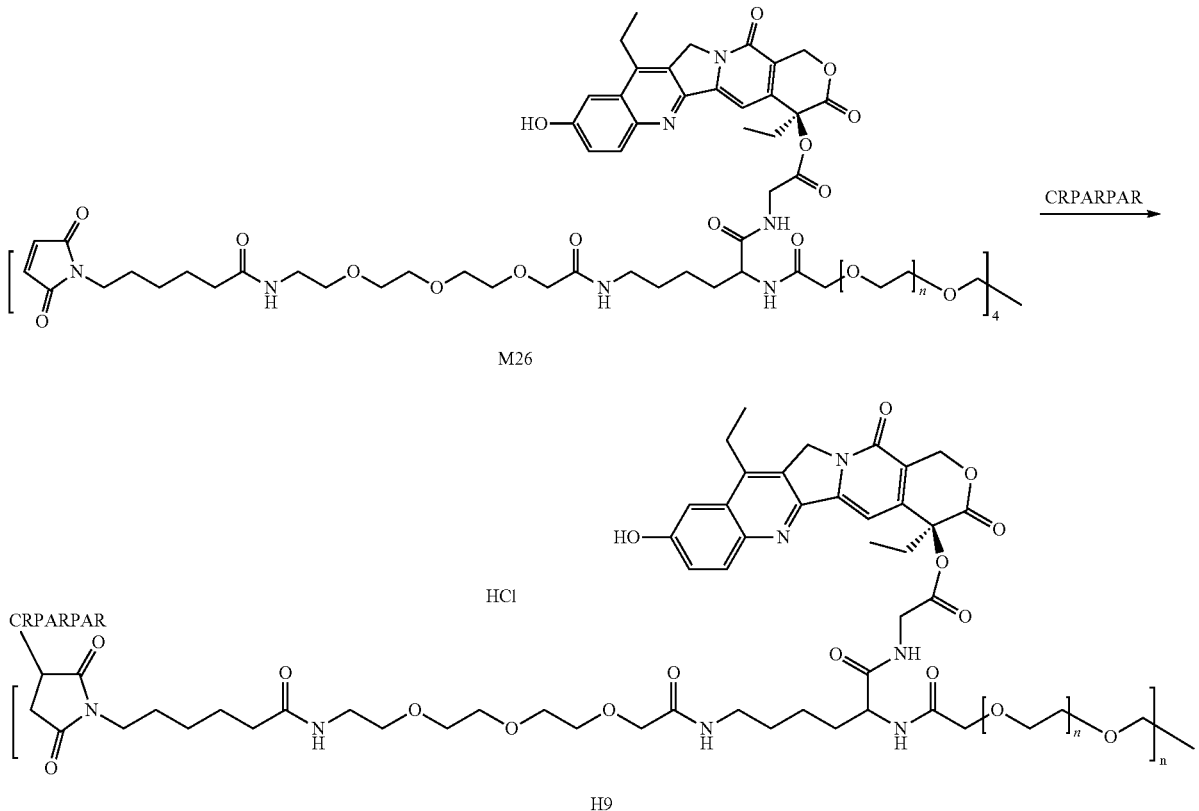

Preparation of Compound 9 and H9

To a 100 mL round bottom flask, 1.0 g (1.0 eq) of Compound M26 and 20 mL of PBS (pH=7, 0.01M) were added. After the mixture was dissolved to give a clear solution, a solution of 159 mg of CRPARPAR in 10 mL of PBS (pH=7, 0.01M) was added. After reacting at room temperature for 4 h, the mixture was dialyzed and concentrated to obtain compound 9, the crude product was dissolved in methanol, and a solution of HCl/EA was added. The mixture was concentrated, added to TBME, centrifuged, and dried to obtain a yellow solid H9 (Hydrochloride of compound 9) (1.04 g).

$^1$HNMR (DMSO+D$_2$O): δ0.910 (t, CH$_2$C$\underline{H}_3$), 3.5 (br m PEG), 5.328 (s, 2H), 5.480 (s, 2H), 7.0-8.5 (m N$\underline{H}$)

Example 10

Preparation of cRGD was the Same as Example 5
Preparation of the L Portion was the Same as Example 1
Preparation of the Conjugate

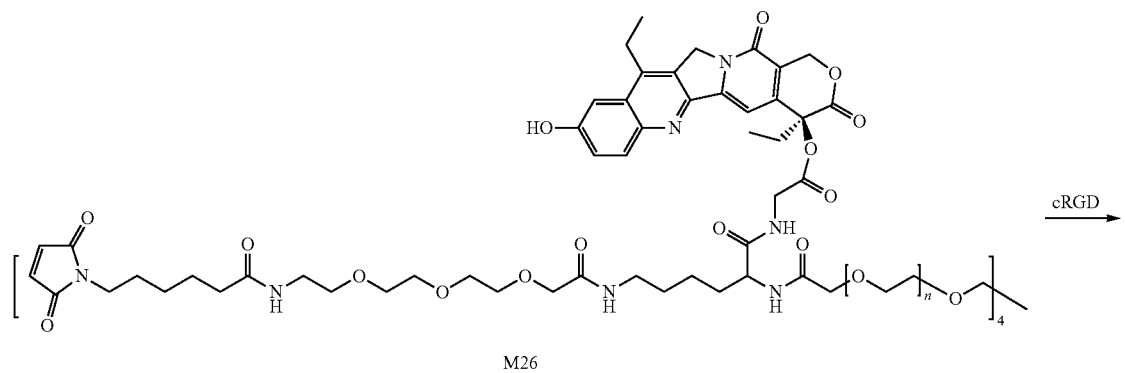

-continued

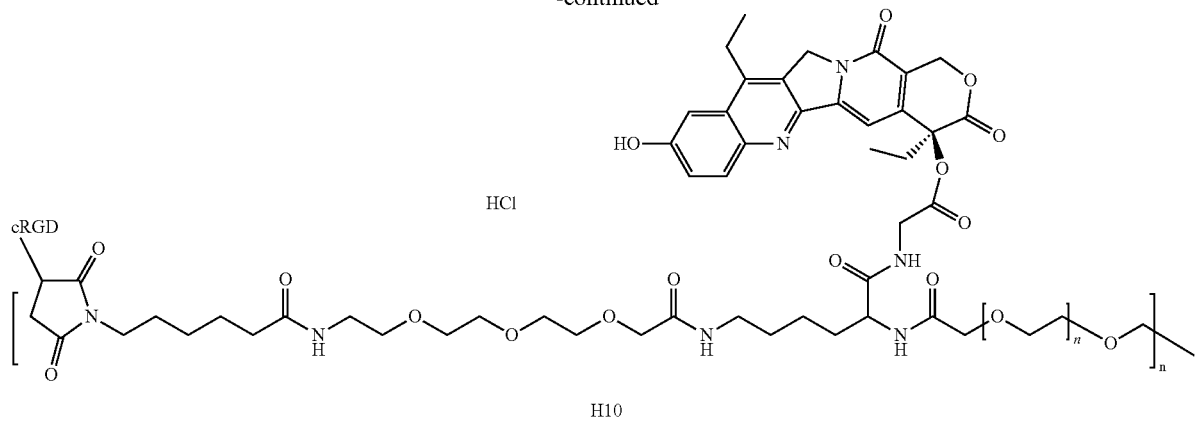

H10

Preparation of Compound 10 and H10

To a 100 mL round bottom flask, 1.0 g (1.0 eq) of Compound M26 and 20 mL of PBS (pH=7, 0.01M) were added. After the mixture was dissolved to give a clear solution, a mixed solution of 99.5 mg of cRGD in 4 mL of PBS (pH=7, 0.01M) and 6 mL of methanol was added. After reacting at room temperature for 4 h, the mixture was dialyzed and concentrated to obtain compound 10, the crude product was dissolved in methanol, and a solution of HCl/EA was added. The mixture was concentrated, added to TBME, centrifuged, and dried to obtain a yellow solid H10 (Hydrochloride of compound 10) (1.03 g).

$^1$HNMR (DMSO+D$_2$O): δ0.915 (t, CH$_2$C$\underline{H}_3$), 3.5 (br m PEG), 5.337 (s, 2H), 5.484 (s, 2H), 7.0-8.5 (m N$\underline{H}$)

Example 11

Preparation of iRGD was the Same as Example 1
Preparation of the L Portion was the Same as Example 1
Preparation of the Conjugate

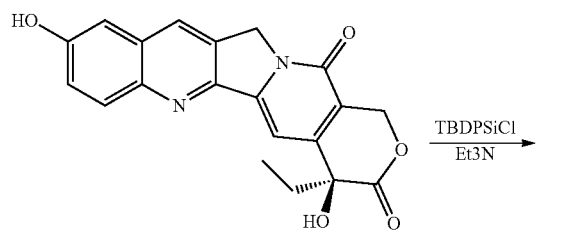

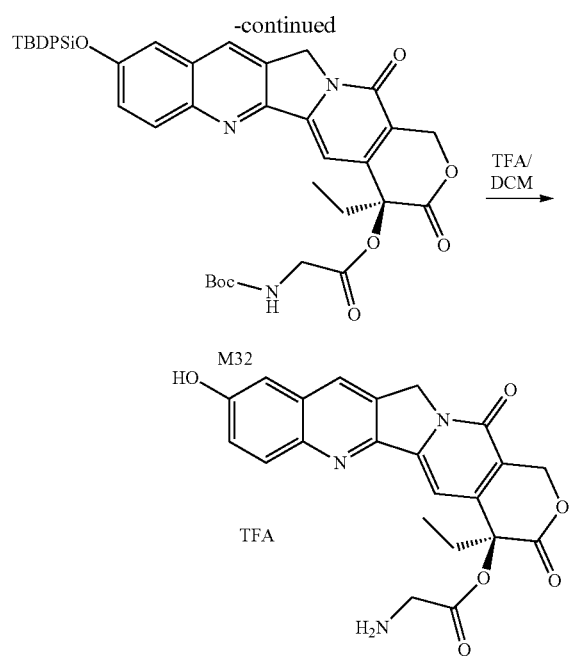

Preparation of M31

To a 250 mL round bottom flask, 6.00 g (1.0 eq) of Compound M30, 120 mL of DCM and 5.00 g (3.0 eq) of TEA were added, and a solution of 4.53 g (1.0 eq) of TBDPS-Cl in 20 mL of DCM was added dropwise. After the completion of the reaction was monitored by TLC, the mixture was washed with water and saturated saline, dried over anhydrous sodium sulfate, and then subjected to column chromatography to obtain 4.32 g of Compound M31 as a pale yellow solid.

Preparation of M32

To a 250 mL round bottom flask, 5.0 g (1.0 eq) of Compound M31, 150 mL of DCM, 1.73 g (1.2 eq) of Boc-Gly-OH and 101 mg (0.1 eq) of DMAP were added, a solution of 2.55 g (1.5 eq) of DCC in 10 mL of DCM was added dropwise, and the mixture was reacted at 20° C. for 4 h. After the completion of the reaction was monitored by TLC, the mixture was filtered, and 130 mL of IPA was added when the mixture was concentrated to 25% of its total volume. 75% of the solvent was removed by distillation, and 160 mL of n-heptane was added. The mixture was stirred at room temperature for 1 h, filtered, washed twice with n-heptane, and dried to obtain 4.52 g of Compound M32 as a pale yellow solid.

Preparation of M33

To a 100 mL three-necked flask, 4.40 g of Compound M32 and 50 mL of DCM were added. After the mixture was stirred and dissolved, 11.6 mL of TFA was added dropwise, and the mixture was reacted at room temperature for 2 h. After the completion of the reaction was monitored by TLC, 150 mL of acetonitrile was added. After 120 mL of solvent was distilled under reduced pressure, the mixture was poured into 320 mL of TBME solution, stirred for 30 min, and filtered. The filter cake was washed with TBME to obtain a pale yellow solid M33 (2.32 g).

Preparation of M34

To a 200 mL three-necked flask, 2.3 g of Compound M33, 45 mL of DCM, 2.77 g (1.05 eq) of Compound M5 and 1.1 g (3.0 eq) of TEA were added and reacted at room temperature for 4 h. After the completion of the reaction was monitored by TLC, the mixture was diluted with DCM, then washed twice with water, washed once with saturated saline, dried, concentrated, purified by HPLC, and then lyophilized to obtain a pale yellow solid M34 (2.02 g).

Preparation of M35

To a 200 mL round bottom flask, 2.0 g of Compound M34 and 60 mL of 20% TFA/DCM were added and reacted at room temperature for 4 h. After the completion of the reaction was monitored by TLC, the mixture was poured

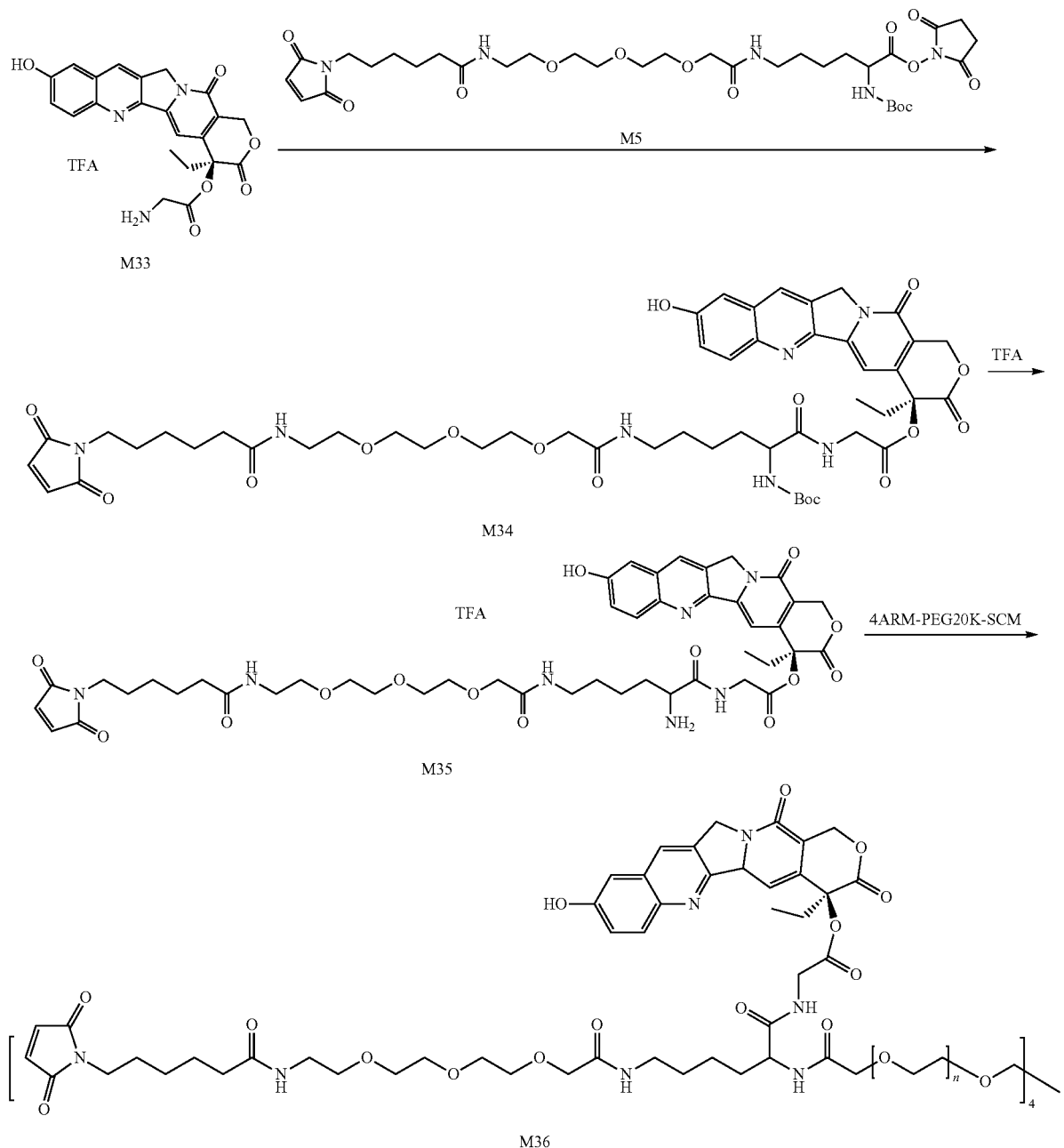

into TBME, centrifuged, and dried to obtain a pale yellow solid M35 (1.69 g).

Preparation of M36

To a 500 mL round bottom flask, 1.50 g (4.0 eq) of Compound M35, 140 mL of DCM, 390 μL (8.0 eq) of TEA and 7.0 g (1.0 eq) of 4armPEG20K-SCM were added. After reacting at room temperature overnight, the mixture was concentrated, added to TBME, centrifuged, and dried to obtain an off-white solid M36 (7.64 g).

Preparation of Compound 11 and H11

To a 100 mL round bottom flask, 1.0 g (1.0 eq) of Compound M36 and 20 mL of PBS (pH=7, 0.01M) were added. After the mixture was dissolved to give a clear solution, a solution of 189 mg of iRGD in 10 mL of PBS (pH=7, 0.01M) was added. After reacting at room tempera-ture for 4 h, the mixture was dialyzed and concentrated to obtain compound 11, the crude product was dissolved in methanol, and a solution of HCl/EA was added. The mixture was concentrated, added to TBME, centrifuged, and dried to obtain a yellow solid H11 (Hydrochloride of compound 11) (1.08 g).

$^1$HNMR (DMSO+D$_2$O): δ0.909 (t, CH$_2$CH$_3$), 3.5 (br m PEG), 5.333 (s, 2H), 5.481 (s, 2H), 7.0-8.5 (m NH)

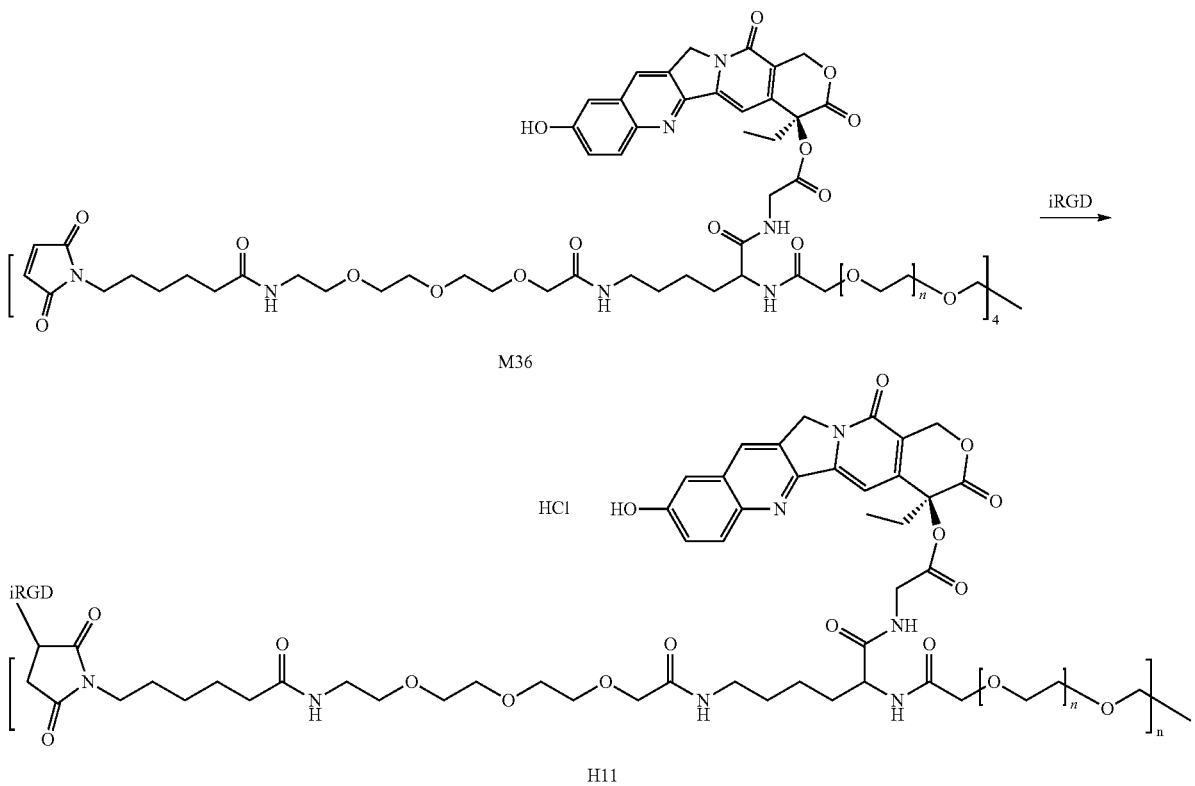

Example 12

Preparation of tLyp-1 was the Same as Example 2
Preparation of the L Portion was the Same as Example 1
Preparation of the Conjugate

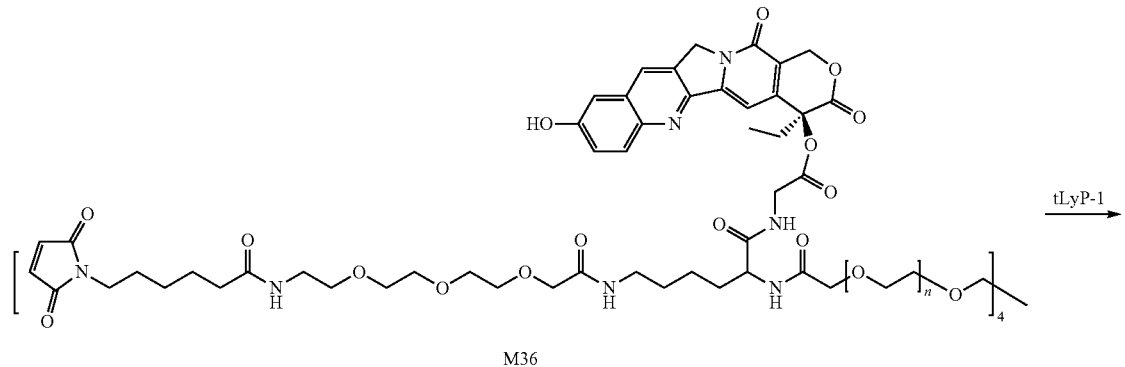

-continued

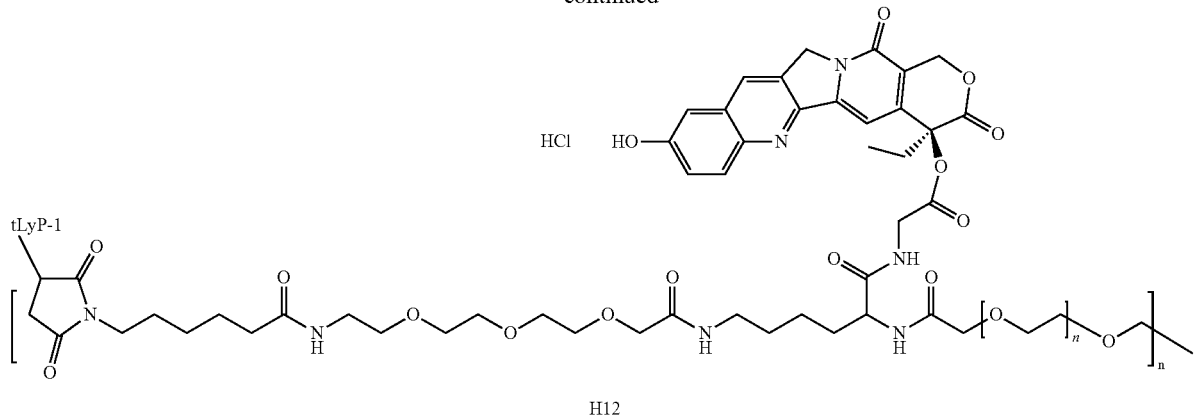

H12

Preparation of Compound 12 and H12

To a 100 mL round bottom flask, 1.0 g (1.0 eq) of Compound M36 and 20 mL of PBS (pH=7, 0.01M) were added. After the mixture was dissolved to give a clear solution, a solution of 144 mg of tLyP-1 in 10 mL of PBS (pH=7, 0.01M) was added. After reacting at room temperature for 4 h, the mixture was dialyzed and concentrated to obtain compound 12, the crude product was dissolved in methanol, and a solution of HCl/EA was added. The mixture was concentrated, added to TBME, centrifuged, and dried to obtain a yellow solid H12 (Hydrochloride of compound 12) (0.99 g).

$^1$HNMR (DMSO+D$_2$O): δ0.915 (t, CH$_2$CH$_3$), 3.5 (br m PEG), 5.340 (s, 2H), 5.487 (s, 2H), 7.0-8.5 (m NH)

Example 13

Preparation of Lyp-1 was the Same as Example 3
Preparation of the L Portion was the Same as Example 1
Preparation of the Conjugate

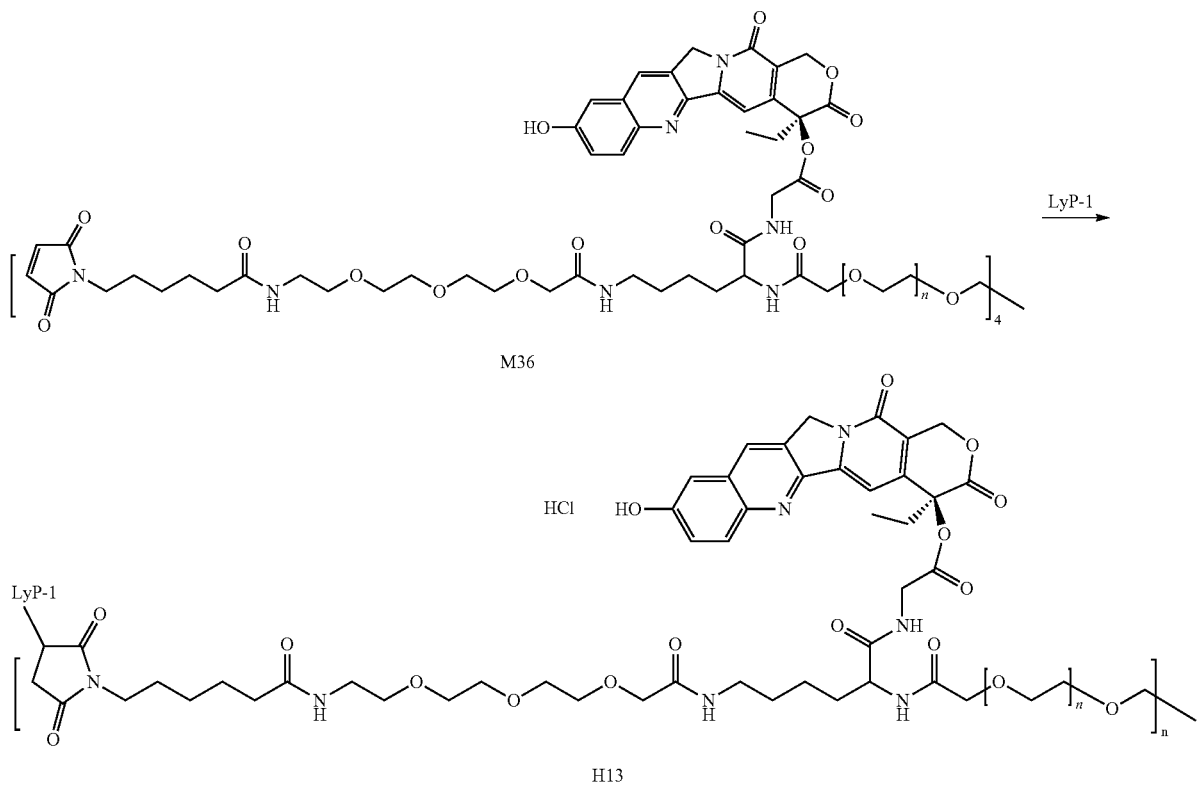

Preparation of Compound 13 and H13

To a 100 mL round bottom flask, 1.0 g (1.0 eq) of Compound M36 and 20 mL of PBS (pH=7, 0.01M) were added. After the mixture was dissolved to give a clear solution, a solution of 189 mg of LyP-1 in 10 mL of PBS (pH=7, 0.01M) was added. After reacting at room temperature for 4 h, the mixture was dialyzed and concentrated to obtain compound 13, the crude product was dissolved in methanol, and a solution of HCl/EA was added. The mixture was concentrated, added to TBME, centrifuged, and dried to obtain a yellow solid H13 (Hydrochloride of compound 13) (1.06 g).

$^1$HNMR (DMSO+D$_2$O): δ0.908 (t, CH$_2$C$\underline{H}_3$), 3.5 (br m PEG), 5.335 (s, 2H), 5.484 (s, 2H), 7.0-8.5 (m N$\underline{H}$)

Example 14

Preparation of CRPARPAR was the Same as Example 4
Preparation of the L Portion was the Same as Example 1
Preparation of the Conjugate PBS (pH=7, 0.01M) was added. After reacting at room temperature for 4 h, the mixture was dialyzed and concentrated to obtain compound 14, the crude product was dissolved in methanol, and a solution of HCl/EA was added. The mixture was concentrated, added to TBME, centrifuged, and dried to obtain a yellow solid H14 (Hydrochloride of compound 14) (1.01 g).

$^1$HNMR (DMSO+D$_2$O): δ0.910 (t, CH$_2$C$\underline{H}_3$), 3.5 (br m PEG), 5.336 (s, 2H), 5.485 (s, 2H), 7.0-8.5 (m N$\underline{H}$)

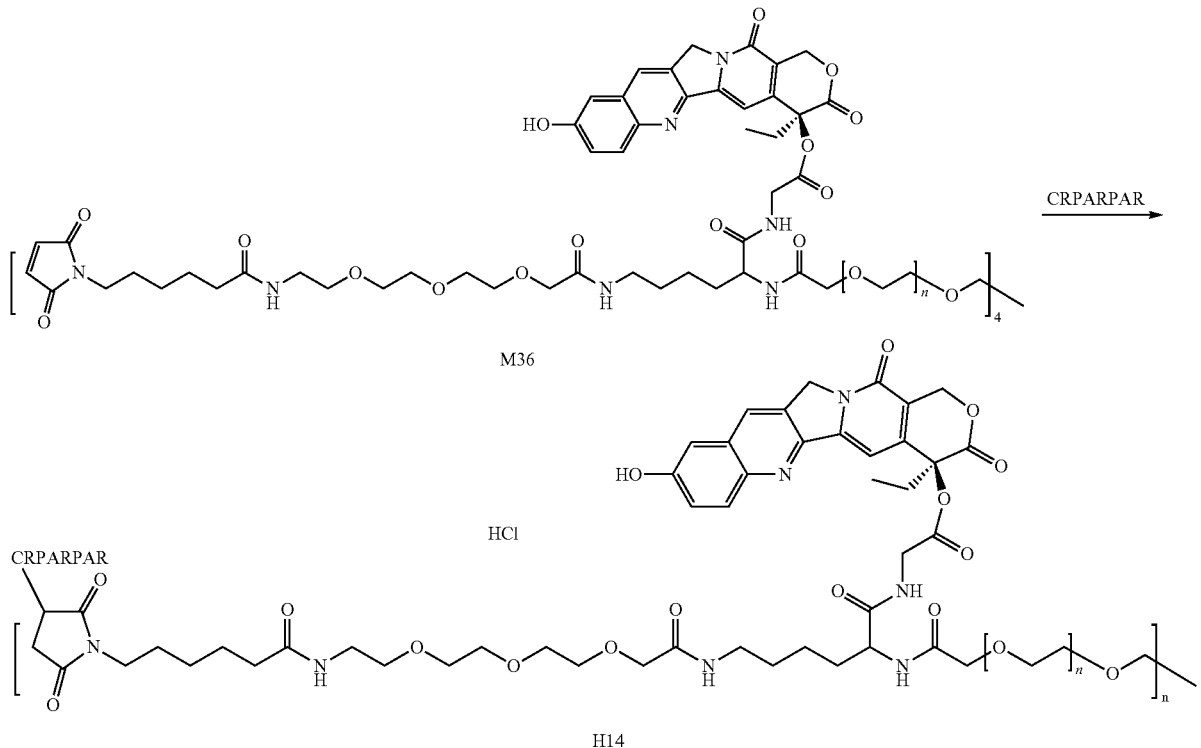

Preparation of Compound 14 and H14

To a 100 mL round bottom flask, 1.0 g (1.0 eq) of Compound M36 and 20 mL of PBS (pH=7, 0.01M) were added. After the mixture was dissolved to give a clear solution, a solution of 160 mg of CRPARPAR in 10 mL of Example 15

Preparation of cRGD was the Same as Example 5
Preparation of the L Portion was the Same as Example 1
Preparation of the Conjugate

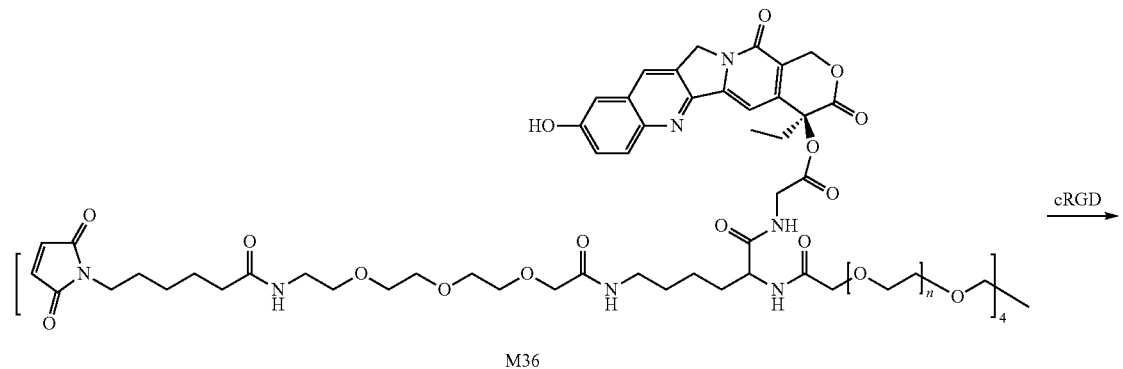

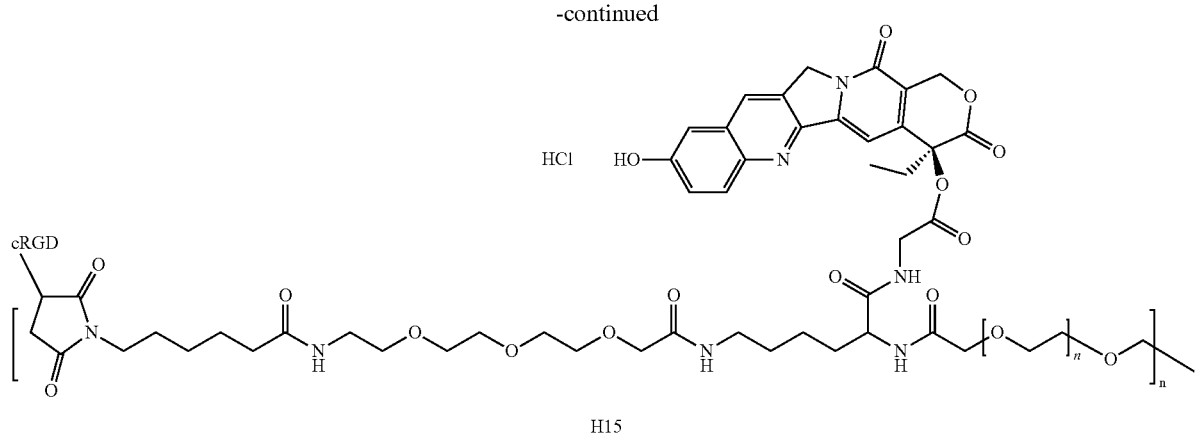

H15

Preparation of Compound 15 and H15

To a 100 mL round bottom flask, 1.0 g (1.0 eq) of Compound M36 and 20 mL of PBS (pH=7, 0.01M) were added. After the mixture was dissolved to give a clear solution, a mixed solution of 100 mg of cRGD in 4 mL of PBS (pH=7, 0.01M) and 6 mL of methanol was added. After reacting at room temperature for 4 h, the mixture was dialyzed and concentrated to obtain compound 15, the crude product was dissolved in methanol, and a solution of HCl/EA was added. The mixture was concentrated, added to TBME, centrifuged, and dried to obtain a yellow solid H15 (Hydrochloride of compound 15) (1.05 g).

$^1$HNMR (DMSO+D$_2$O): δ0.914 (t, CH$_2$C$\underline{H}_3$), 3.5 (br m PEG), 5.340 (s, 2H), 5.489 (s, 2H), 7.0-8.5 (m N$\underline{H}$)

Example 16

Preparation of iRGD was the Same as Example 1
Preparation of the L Portion was the Same as Example 1
Preparation of the Conjugate

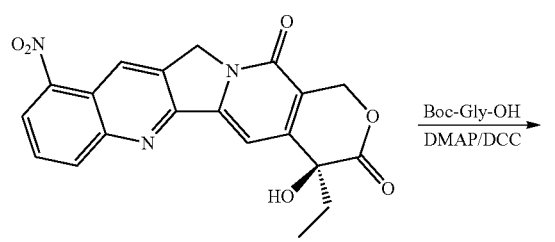

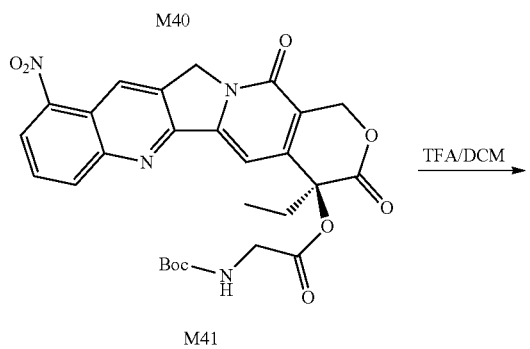

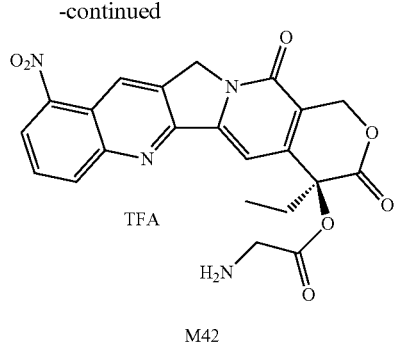

1. Preparation of M41

To a 250 mL round bottom flask, 5.0 g (1.0 eq) of Compound M40, 150 mL of DCM, 2.67 g (1.2 eq) of Boc-Gly-OH and 155 mg (0.1 eq) of DMAP were added, a solution of 3.93 g (1.5 eq) of DCC in 15 mL of DCM was added dropwise, and the mixture was reacted at 20° C. for 4 h. After the completion of the reaction was monitored by TLC, the mixture was filtered, and 130 mL of IPA was added when the mixture was concentrated to 25% of its total volume. 75% of the solvent was removed by distillation, and 160 mL of n-heptane was added. The mixture was stirred at room temperature for 1 h, filtered, washed twice with n-heptane, and dried to obtain 6.85 g of Compound M41 as a pale yellow solid.

2. Preparation of M42

To a 100 mL three-necked flask, 4.00 g of Compound M41 and 50 mL of DCM were added. After the mixture was stirred and dissolved, 11.6 mL of TFA was added dropwise, and the mixture was reacted at room temperature for 2 h. After the completion of the reaction was monitored by TLC, 150 mL of acetonitrile was added. After 120 mL of solvent was distilled under reduced pressure, the mixture was poured into 320 mL of TBME solution, stirred for 30 min, and filtered. The filter cake was washed with TBME to obtain a pale yellow solid M42 (3.54 g).

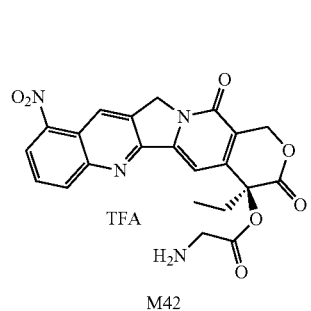
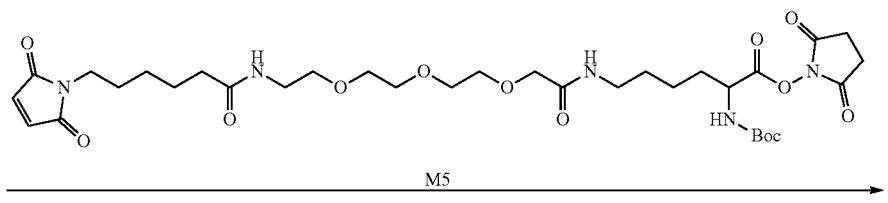
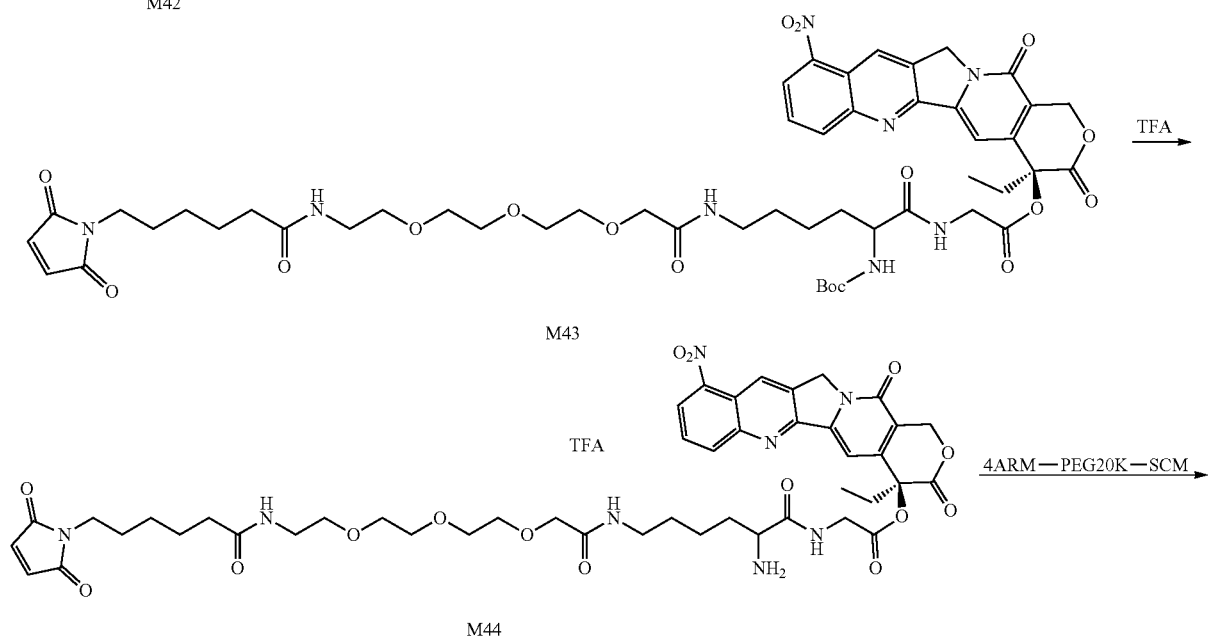
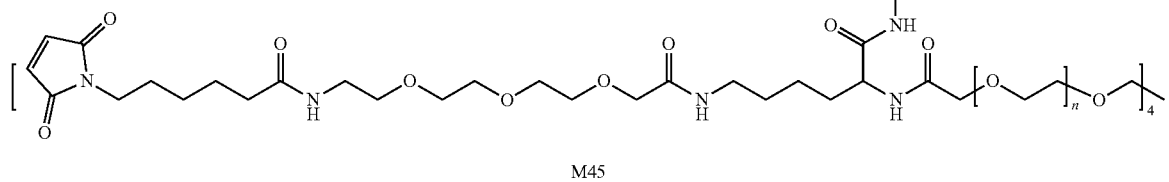

1. Preparation of M43

To a 200 mL three-necked flask, 3.00 g of Compound M42, 45 mL of DCM, 3.46 g (1.05 eq) of Compound M5 and 1.38 g (3.0 eq) of TEA were added and reacted at room temperature for 4 h. After the completion of the reaction was monitored by TLC, the mixture was diluted with DCM, then the mixture was washed twice with water, washed once with saturated saline, dried, concentrated, purified by HPLC, and then lyophilized to obtain a pale yellow solid M43 (2.68 g).

2. Preparation of M44

To a 200 mL round bottom flask, 2.0 g of Compound M43 and 60 mL of 20% TFA/DCM were added and reacted at room temperature for 4 h. After the completion of the reaction was monitored by TLC, the mixture was poured into TBME, centrifuged, dried to obtain a pale yellow solid M44 (1.61 g).

3. Preparation of M45

To a 500 mL round bottom flask, 1.50 g (4.0 eq) of Compound M44, 140 mL of DCM, 391 μL (8.0 eq) of TEA and 7.0 g (1.0 eq) of 4armPEG20K-SCM were added. After reacting at room temperature overnight, the mixture was concentrated, added to TBME, centrifuged, and dried to obtain an off-white solid M45 (7.61 g).

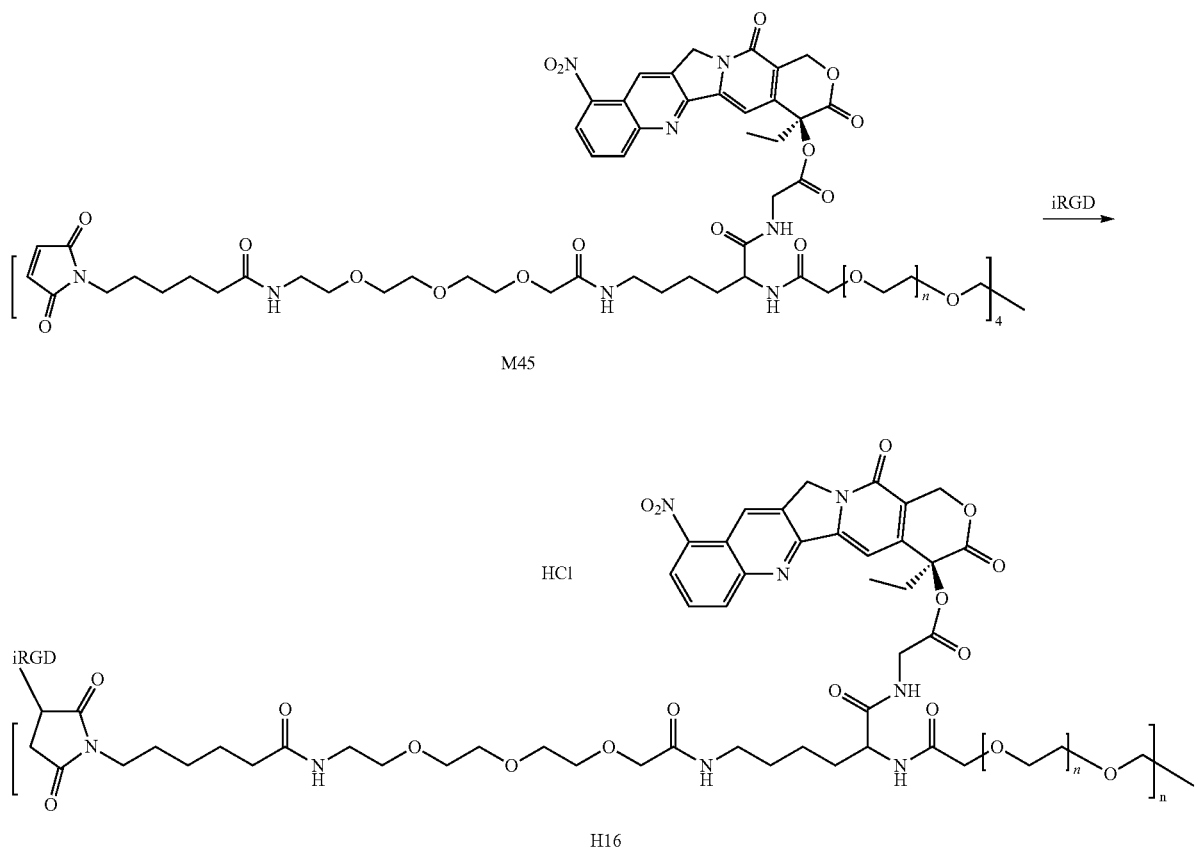

Preparation of Compound 16 and H16

To a 100 mL round bottom flask, 1.0 g (1.0 eq) of Compound M45 and 20 mL of PBS (pH=7, 0.01M) were added. After the mixture was dissolved to give a clear solution, a solution of 188 mg of iRGD in 10 mL of PBS (pH=7, 0.01M) was added. After reacting at room temperature for 4 h, the mixture was dialyzed and concentrated to obtain compound 16, the crude product was dissolved in methanol, and a solution of HCl/EA was added. The mixture was concentrated, added to TBME, centrifuged, and dried to obtain a yellow solid H16 (Hydrochloride of compound 16) (1.09 g).

$^1$HNMR (DMSO+D$_2$O): δ0.909 (t, CH$_2$CH$_3$), 3.5 (br m PEG), 5.335 (s, 2H), 5.482 (s, 2H), 7.0-8.5 (m NH)

Example 17

Preparation of tLyp-1 was the Same as Example 2
Preparation of the L Portion was the Same as Example 1
Preparation of the Conjugate

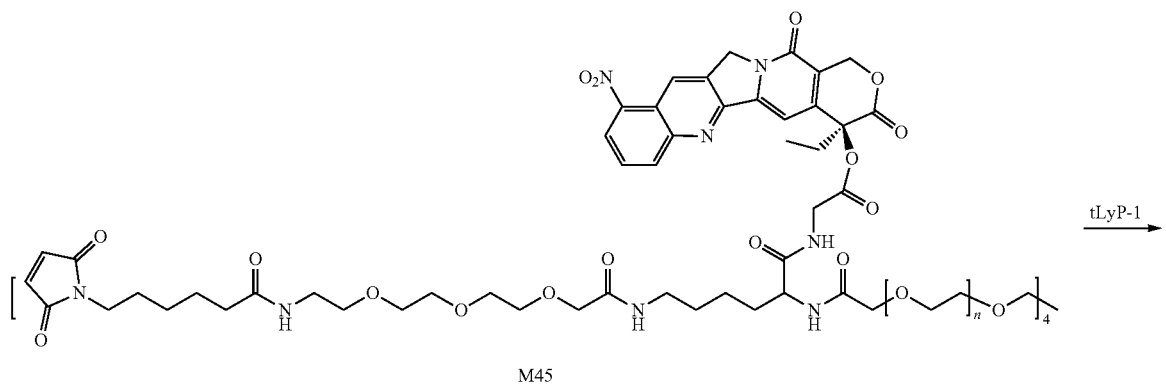

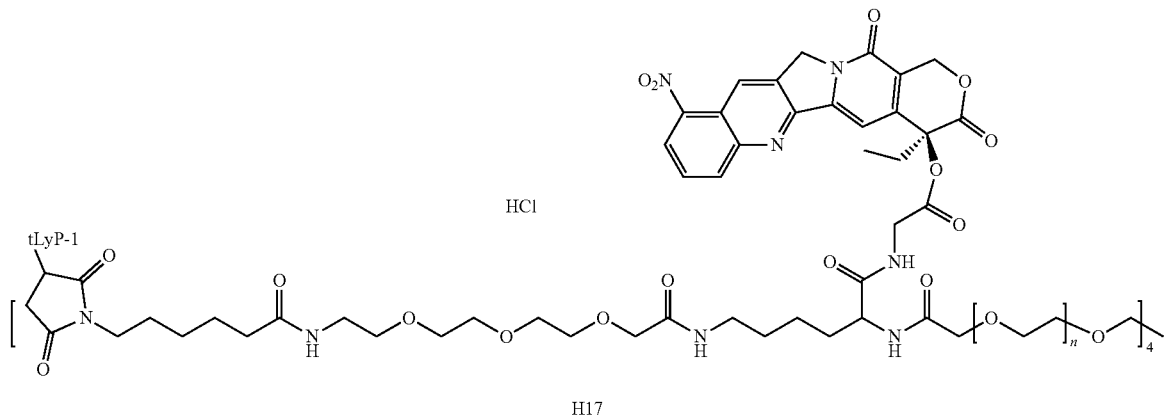

H17

Preparation of Compound 17 and H17

To a 100 mL round bottom flask, 1.0 g (1.0 eq) of Compound M45 and 20 mL of PBS (pH=7, 0.01M) were added. After the mixture was dissolved to give a clear solution, a solution of 144 mg of tLyP-1 in 10 mL of PBS (pH=7, 0.01M) was added. After reacting at room temperature for 4 h, the mixture was dialyzed and concentrated to obtain compound 17, the crude product was dissolved in methanol, and a solution of HCl/EA was added. The mixture was concentrated, added to TBME, centrifuged, and dried to obtain a yellow solid H17 (Hydrochloride of compound 17) (1.02 g).

$^1$HNMR (DMSO+D$_2$O): δ0.912 (t, CH$_2$CH$_3$), 3.5 (br m PEG), 5.336 (s, 2H), 5.485 (s, 2H), 7.0-8.5 (m N$\underline{H}$)

Example 18

Preparation of Lyp-1 was the Same as Example 3
Preparation of the L Portion was the Same as Example 1
Preparation of the Conjugate

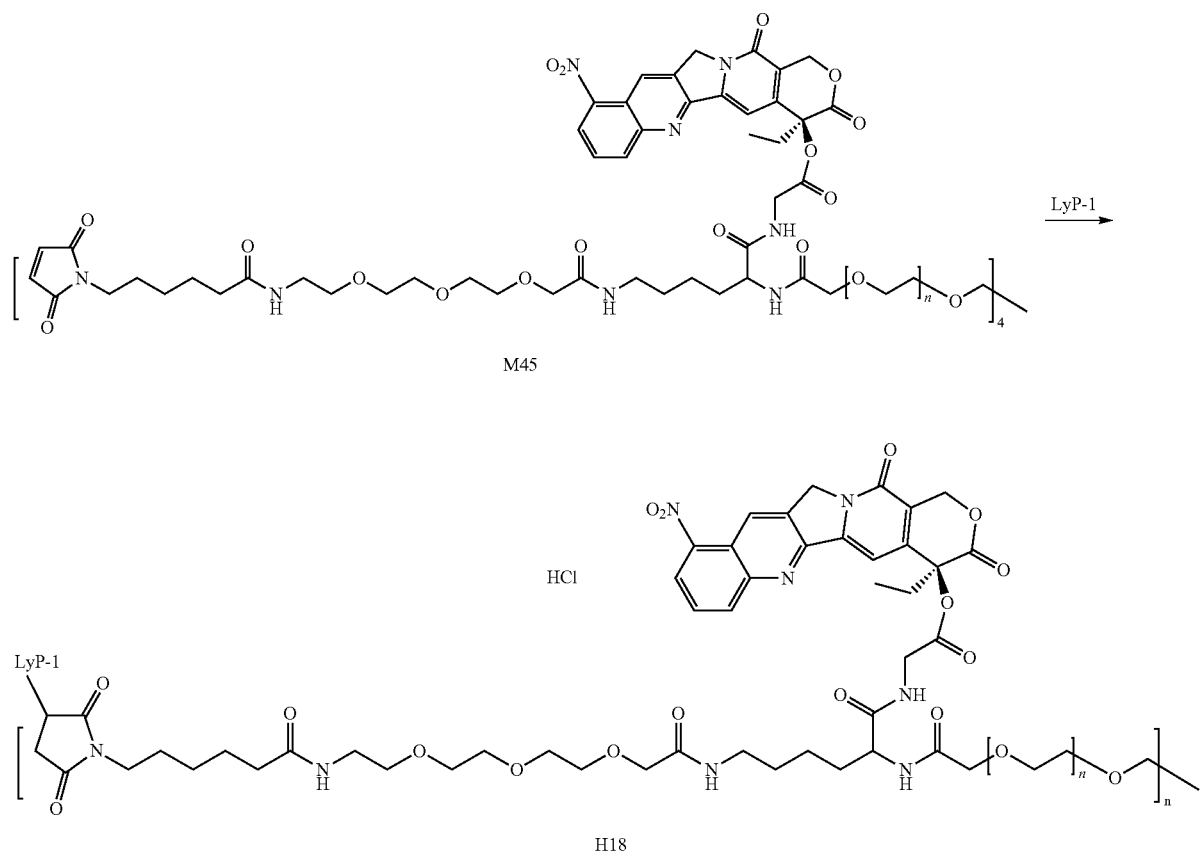

M45

H18

Preparation of Compound 18 and H18

To a 100 mL round bottom flask, 1.0 g (1.0 eq) of Compound M45 and 20 mL of PBS (pH=7, 0.01M) were added. After the mixture was dissolved to give a clear solution, a solution of 188 mg of LyP-1 in 10 mL of PBS (pH=7, 0.01M) was added. After reacting at room temperature for 4 h, the mixture was dialyzed and concentrated to obtain compound 18, the crude product was dissolved in methanol, and a solution of HCl/EA was added. The mixture was concentrated, added to TBME, centrifuged, and dried to obtain a yellow solid H18 (Hydrochloride of compound 18) (1.06 g).

$^1$HNMR (DMSO+D$_2$O): δ0.917 (t, CH$_2$C$\underline{H}_3$), 3.5 (br m PEG), 5.340 (s, 2H), 5.491 (s, 2H), 7.0-8.5 (m N$\underline{H}$)

Example 19

Preparation of CRPARPAR was the Same as Example 4
Preparation of the L Portion was the Same as Example 1
Preparation of the Conjugate Preparation of Compound 19 and H19

To a 100 mL round bottom flask, 1.0 g (1.0 eq) of Compound M45 and 20 mL of PBS (pH=7, 0.01M) were added. After the mixture was dissolved to give a clear solution, a solution of 159 mg of CRPARPAR in 10 mL of PBS (pH=7, 0.01M) was added. After reacting at room temperature for 4 h, the mixture was dialyzed and concentrated to obtain compound 19, the crude product was dissolved in methanol, and a solution of HCl/EA was added. The mixture was concentrated, added to TBME, centrifuged, and dried to obtain a yellow solid H19 (Hydrochloride of compound 19) (1.07 g).

$^1$HNMR (DMSO+D$_2$O): δ0.911 (t, CH$_2$C$\underline{H}_3$), 3.5 (br m PEG), 5.332 (s, 2H), 5.480 (s, 2H), 7.0-8.5 (m N$\underline{H}$)

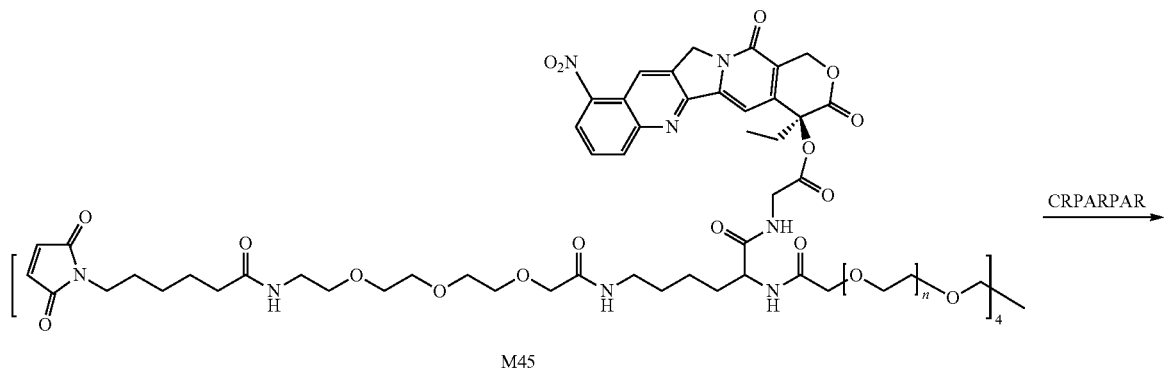

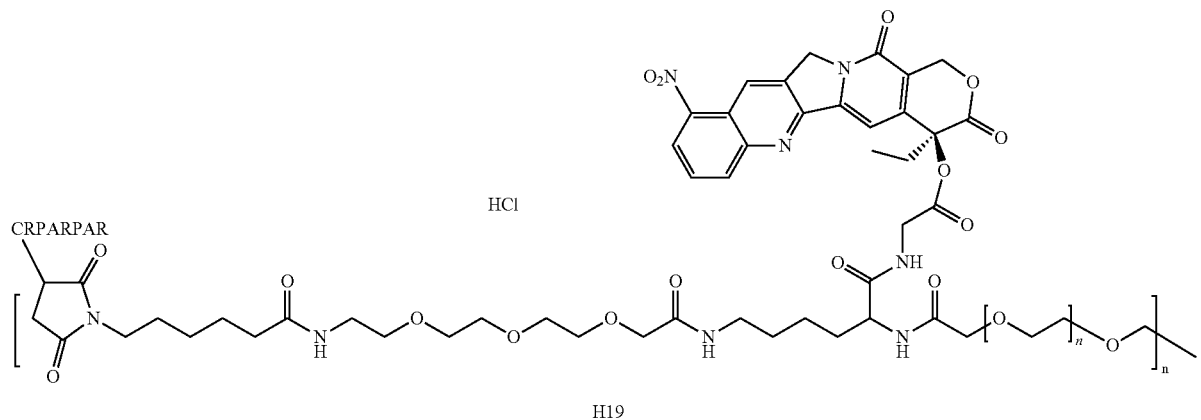

Example 20

Preparation of cRGD was the Same as Example 5
Preparation of the L Portion was the Same as Example 1
Preparation of the Conjugate

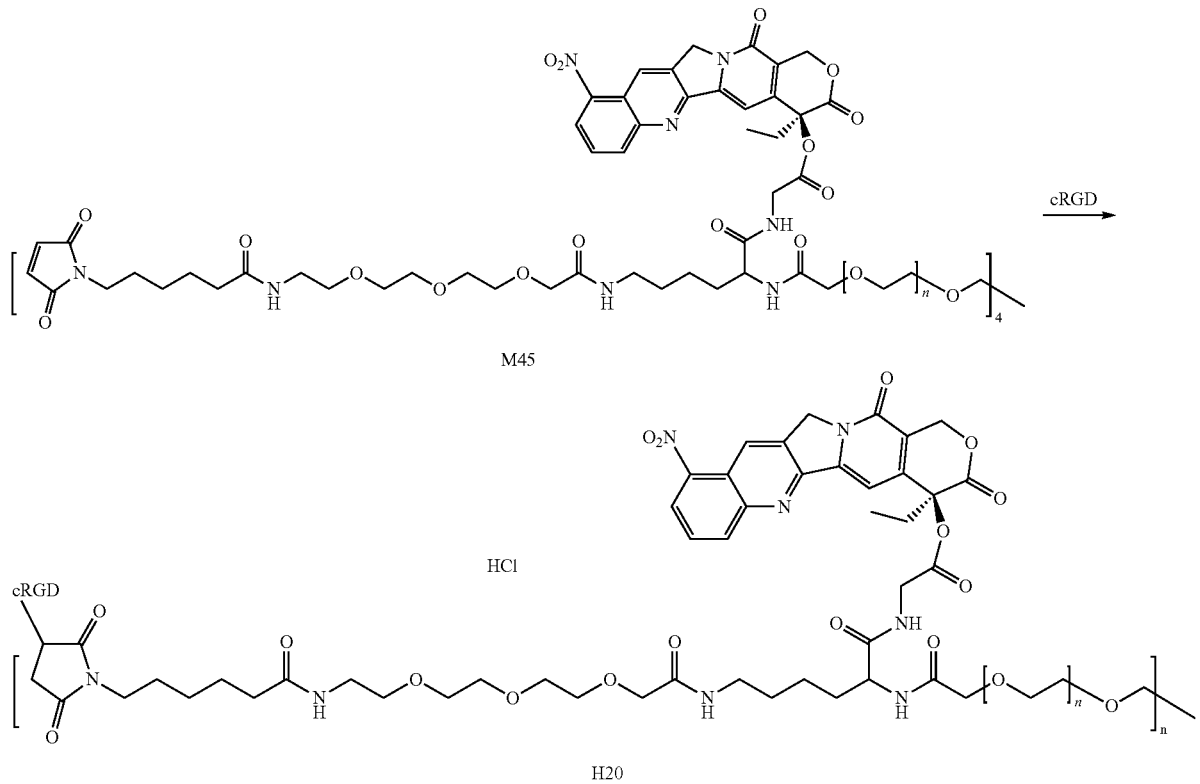

Preparation of Compound 20 and H20

To a 100 mL round bottom flask, 1.0 g (1.0 eq) of Compound M45 and 20 mL of PBS (pH=7, 0.01M) were added. After the mixture was dissolved to give a clear solution, a mixed solution of 99.5 mg of cRGD in 4 mL of PBS (pH=7, 0.01M) and 6 mL of methanol was added. After reacting at room temperature for 4 h, the mixture was dialyzed and concentrated to obtain compound 20, the crude product was dissolved in methanol, and a solution of HCl/EA was added. The mixture was concentrated, added to TBME, centrifuged, and dried to obtain a yellow solid H20 (Hydrochloride of compound 20) (1.03 g).

$^1$HNMR (DMSO+D$_2$O): δ0.909 (t, CH$_2$C$\underline{H}_3$), 3.5 (br m PEG), 5.331 (s, 2H), 5.478 (s, 2H), 7.0-8.5 (m N$\underline{H}$)

Example 21

Preparation of iRGD was the Same as Example 1
Preparation of the L Portion was the Same as Example 1

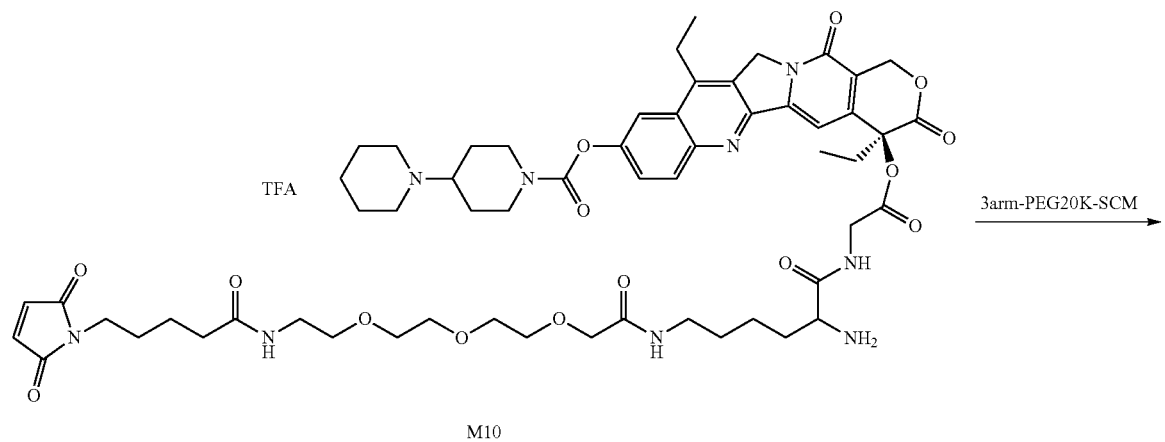

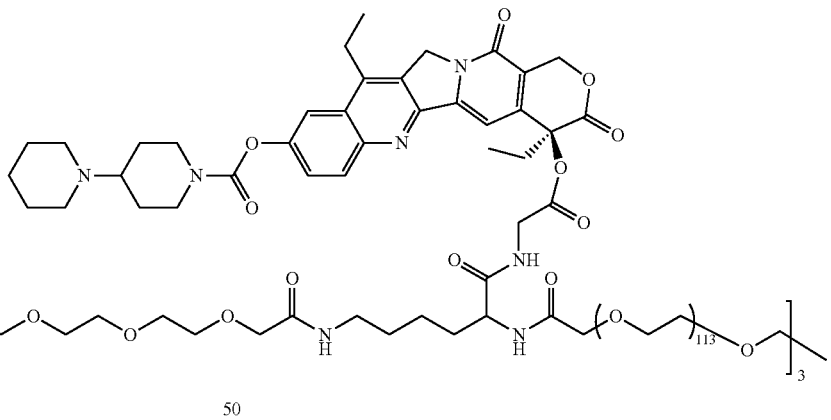

50

Preparation of 50

To a 10 mL round bottom flask, 52 mg (3.0 eq) of Compound M10, 2 mL of DCM, 11 μL (6.0 eq) of TEA and 273 mg (1.0 eq) of 3armPEG20K-SCM were added. After reacting at room temperature overnight, the mixture was concentrated, added to TBME, centrifuged, and dried to obtain an off-white solid 50 (310 mg).

Preparation of Compound 21

To a 10 mL round bottom flask, 50 mg (1.0 eq) of Compound 50 and 1.5 mL of PBS (pH=7, 0.01M) were added. After the mixture was dissolved to give a clear solution, a solution of 7.2 mg of iRGD in 1 mL of PBS (pH=7, 0.01M) was added. After reacting at room temperature for 4 h, the mixture was dialyzed and concentrated, the crude product was dissolved in methanol, and a solution of

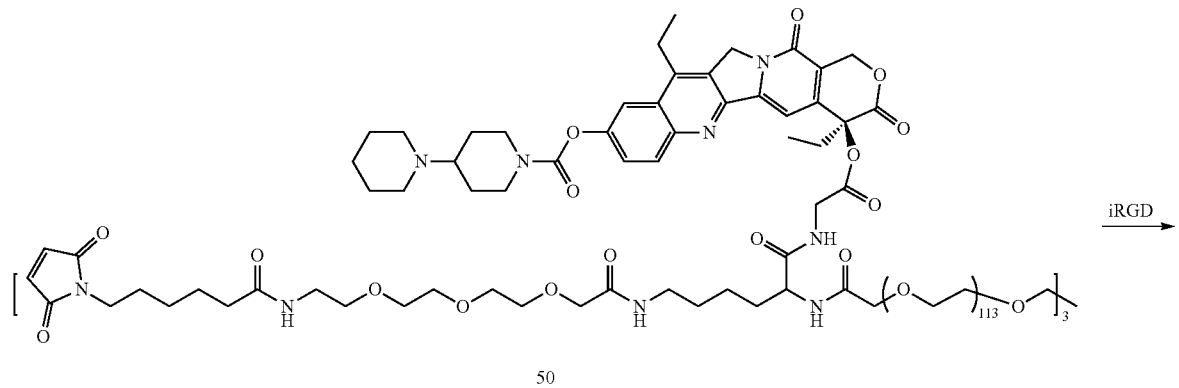

50

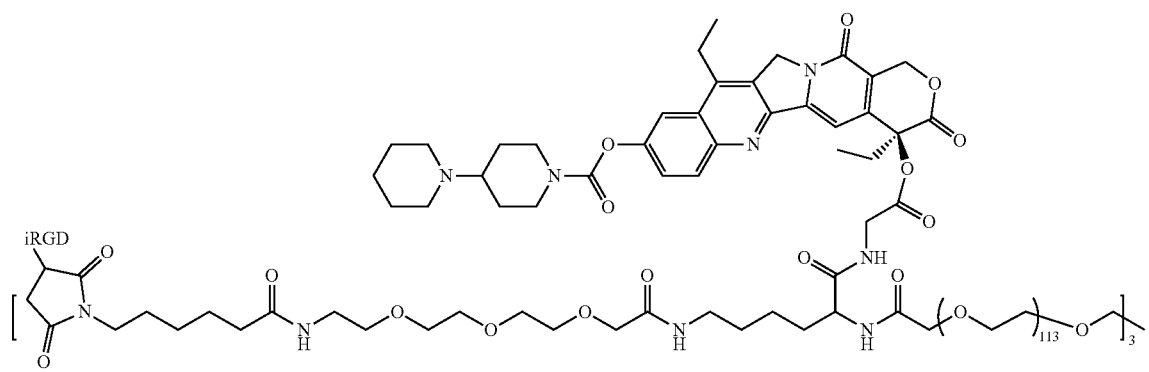

21

HCl/EA was added. The mixture was concentrated, added to TBME, centrifuged, and dried to obtain a yellow solid 21 (49 mg).

$^1$HNMR (DMSO+D$_2$O): δ0.901 (t, CH$_2$C$\underline{H}_3$), 3.5 (br m PEG), 5.328 (s, 2H), 5.480 (s, 2H), 7.0-8.5 (m N$\underline{H}$)

Example 22

Preparation of the L Portion was the Same as Example 1

After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 22 (50 mg).

$^1$HNMR (DMSO+D$_2$O): δ0.901 (t, CH$_2$C$\underline{H}_3$), 3.5 (br m PEG), 5.333 (s, 2H), 5.487 (s, 2H), 7.0-8.5 (m N$\underline{H}$)

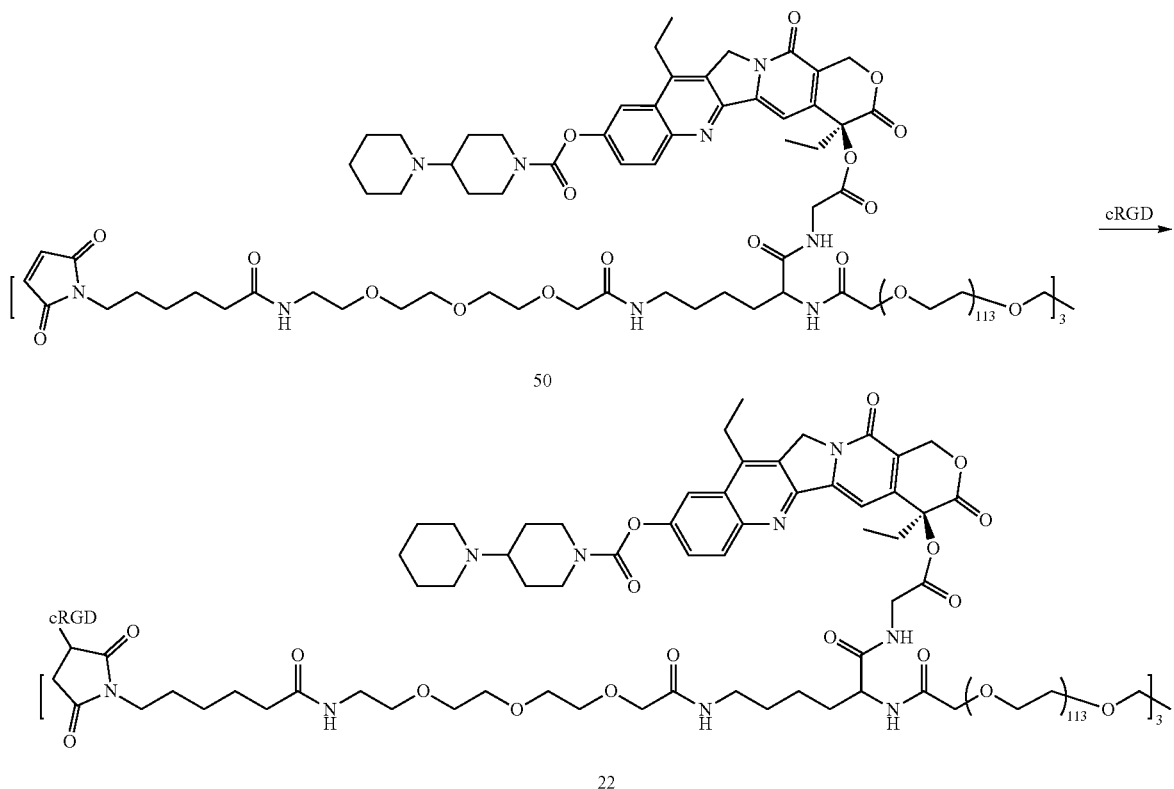

Preparation of Compound 22

To a 10 mL round bottom flask, 55 mg (1.0 eq) of Compound 50 and 1.5 mL of PBS (pH=7, 0.01M) were added. After the mixture was dissolved to give a clear solution, a mixed solution of 4.2 mg of cRGD in 1 mL of PBS (pH=7, 0.01M) and 1.5 mL of methanol was added.

Example 23

Preparation of iRGD was the Same as Example 1

Preparation of the L Portion was the Same as Example 1

Preparation of the Conjugate

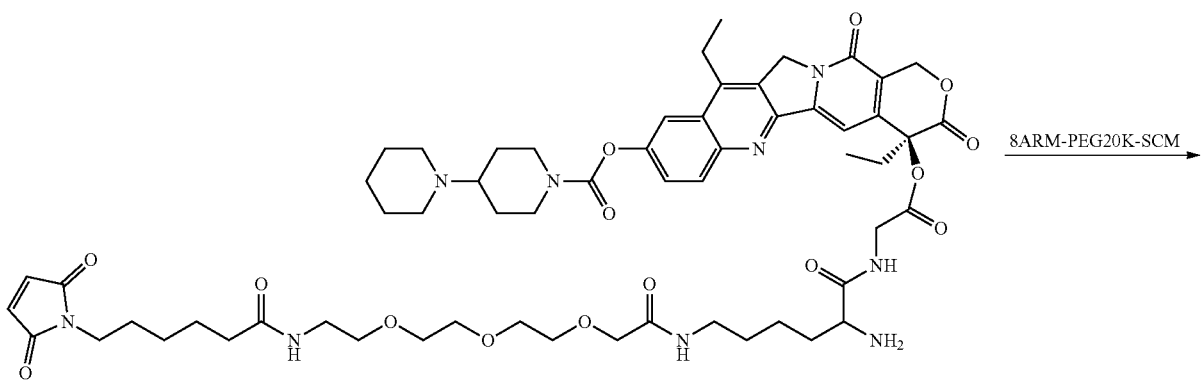

M10

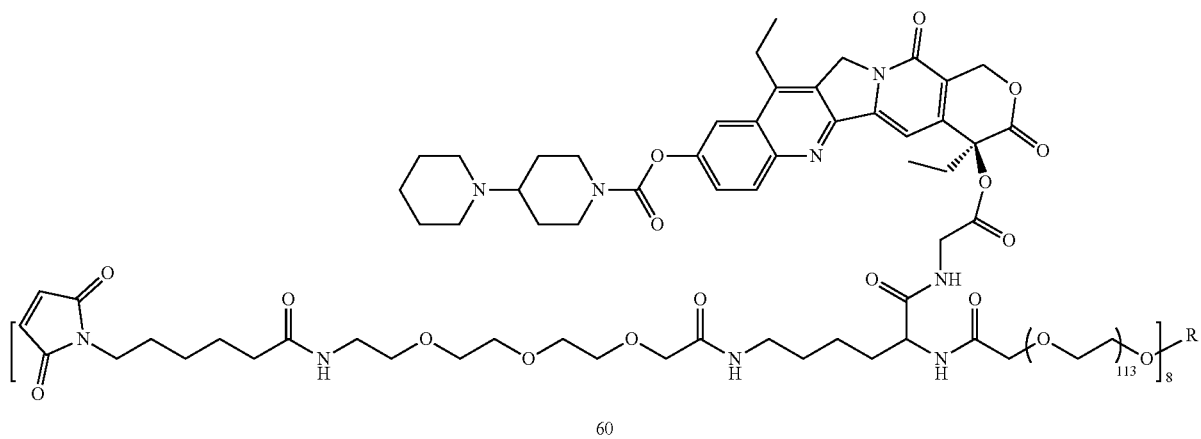

60

Preparation of 60

To a 100 mL round bottom flask, 476 mg (8.0 eq) of Compound M10, 15 mL of DCM, 105 μL (16.0 eq) of TEA, and 1.0 g (1.0 eq) of 8armPEG20K-SCM were added. After reacting at room temperature overnight, the mixture was concentrated, added to TBME, centrifuged, and dried to obtain an off-white solid 60 (1.37 g).

Preparation of Compound 23

To a 10 mL round bottom flask, 50 mg (1.0 eq) of Compound 60 and 1.5 mL of PBS (pH=7, 0.01M) were added. After the mixture was dissolved to give a clear solution, a solution of 14.5 mg of iRGD in 1 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to

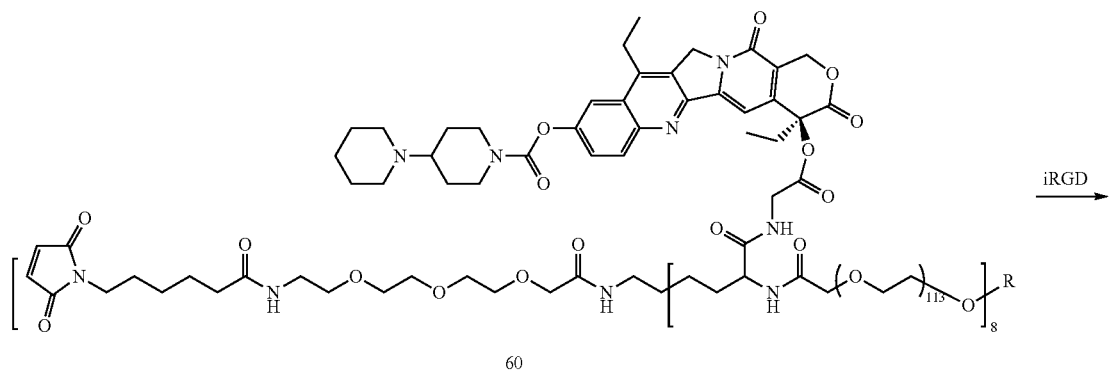

60 iRGD ⟶

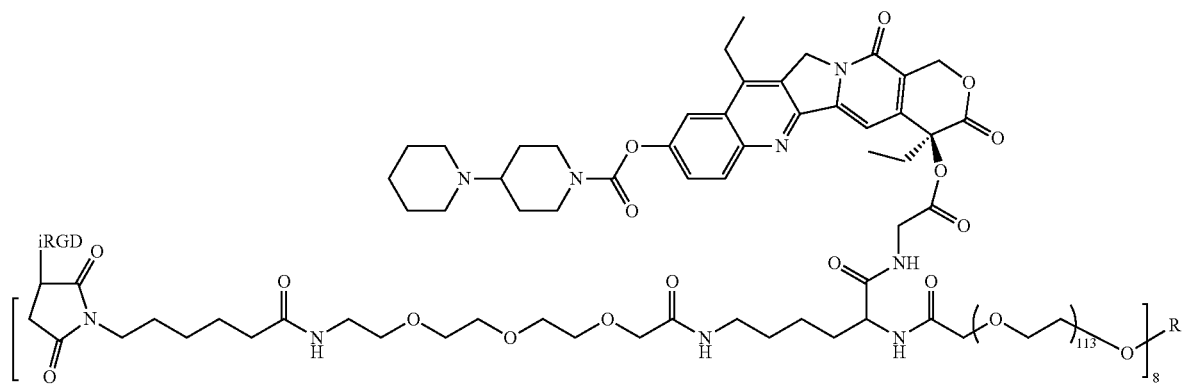

23

TBME, centrifuged, and dried to obtain a yellow solid 23 (54 mg).

$^1$HNMR (DMSO+D$_2$O): δ0.901 (t, CH$_2$C$\underline{H}_3$), 3.5 (br m PEG), 5.328 (s, 2H), 5.480 (s, 2H), 7.0-8.5 (m NH)

Example 24

Preparation of Lyp-1 was the Same as Example 3
Preparation of the L Portion was the Same as Example 1
Preparation of the Conjugate

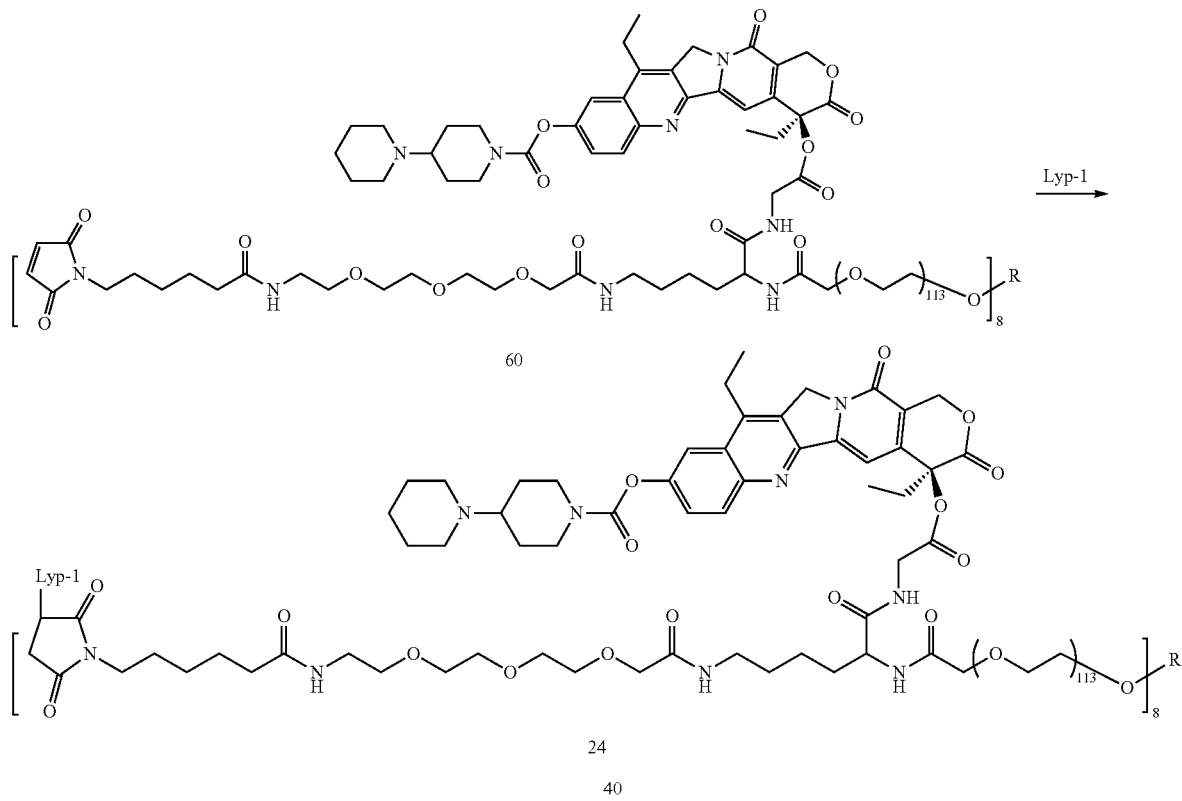

Preparation of Compound 24

To a 10 mL round bottom flask, 60 mg (1.0 eq) of Compound 60 and 1.5 mL of PBS (pH=7, 0.01M) were added. After the mixture was dissolved to give a clear solution, a solution of 17.4 mg of LyP-1 in 1 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 24 (68 mg).

$^1$HNMR (DMSO+D$_2$O): δ0.901 (t, CH$_2$C$\underline{H}_3$), 3.5 (br m PEG), 5.329 (s, 2H), 5.481 (s, 2H), 7.0-8.5 (m N$\underline{H}$)

Example 25

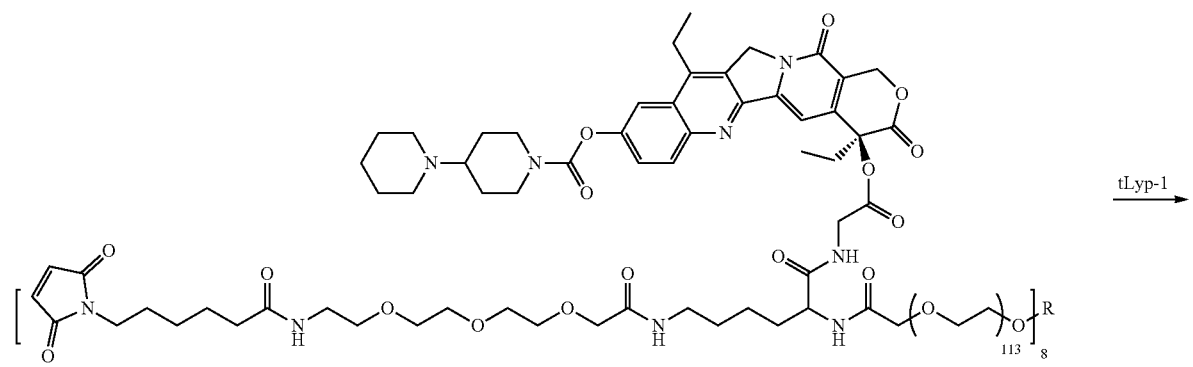

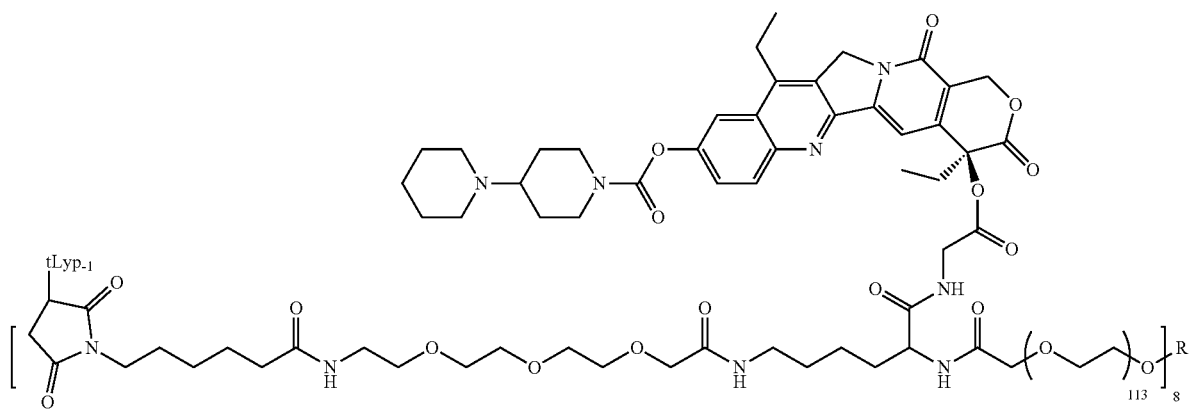

25

Preparation of Compound 25

To a 10 mL round bottom flask, 45 mg (1.0 eq) of Compound 60 and 1.5 mL of PBS (pH=7, 0.01M) were added. After the mixture was dissolved to give a clear solution, a solution of 10.0 mg of tLyP-1 in 1 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 25 (45 mg).

$^{1}$HNMR (DMSO+D$_2$O): δ0.901 (t, CH$_2$C$\underline{H}_3$), 3.5 (br m PEG), 5.330 (s, 2H), 5.482 (s, 2H), 7.0-8.5 (m N$\underline{H}$)

Example 26

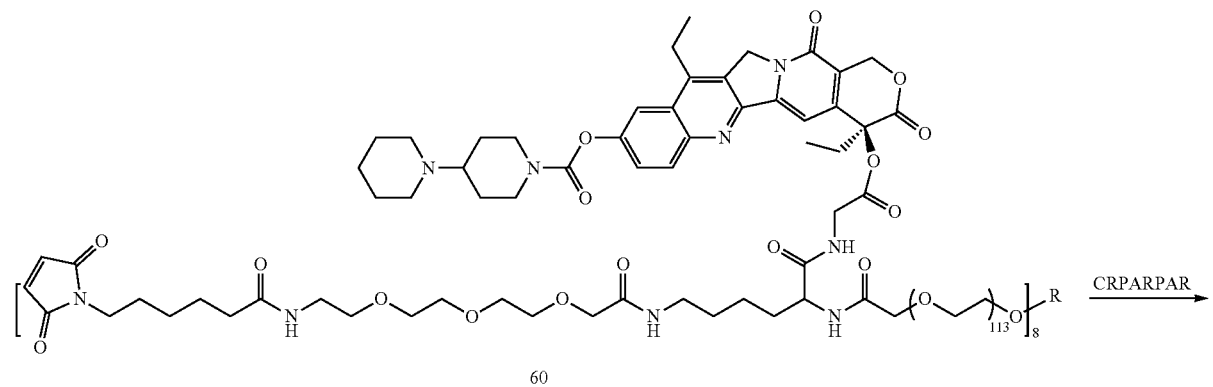

60

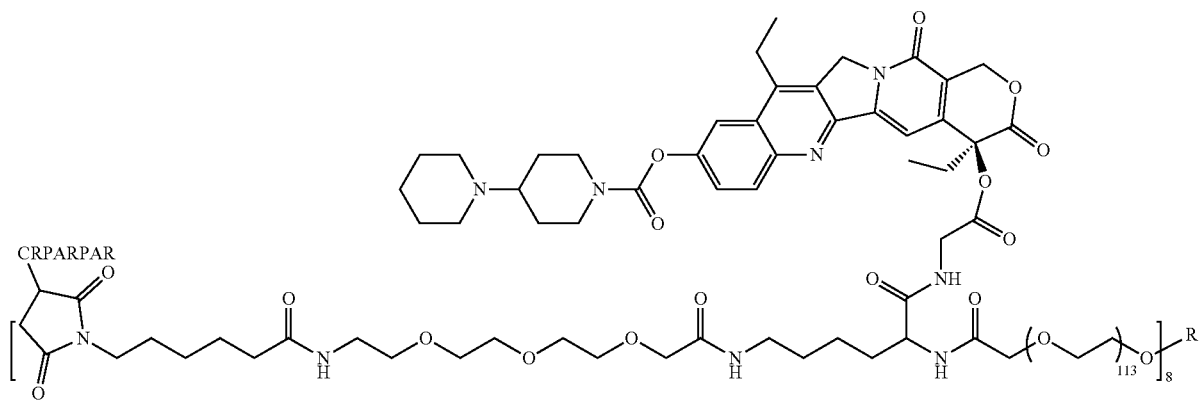

26

Preparation of Compound 26

To a 10 mL round bottom flask, 55 mg (1.0 eq) of Compound 60 and 1.5 mL of PBS (pH=7, 0.01M) were added. After the mixture was dissolved to give a clear solution, a solution of 13.5 mg of CRPARPAR in 1 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 26 (62 mg).

$^1$HNMR (DMSO+D$_2$O): δ0.901 (t, CH$_2$C$\underline{H}_3$), 3.5 (br m PEG), 5.331 (s, 2H), 5.480 (s, 2H), 7.0-8.5 (m N$\underline{H}$)

Example 27

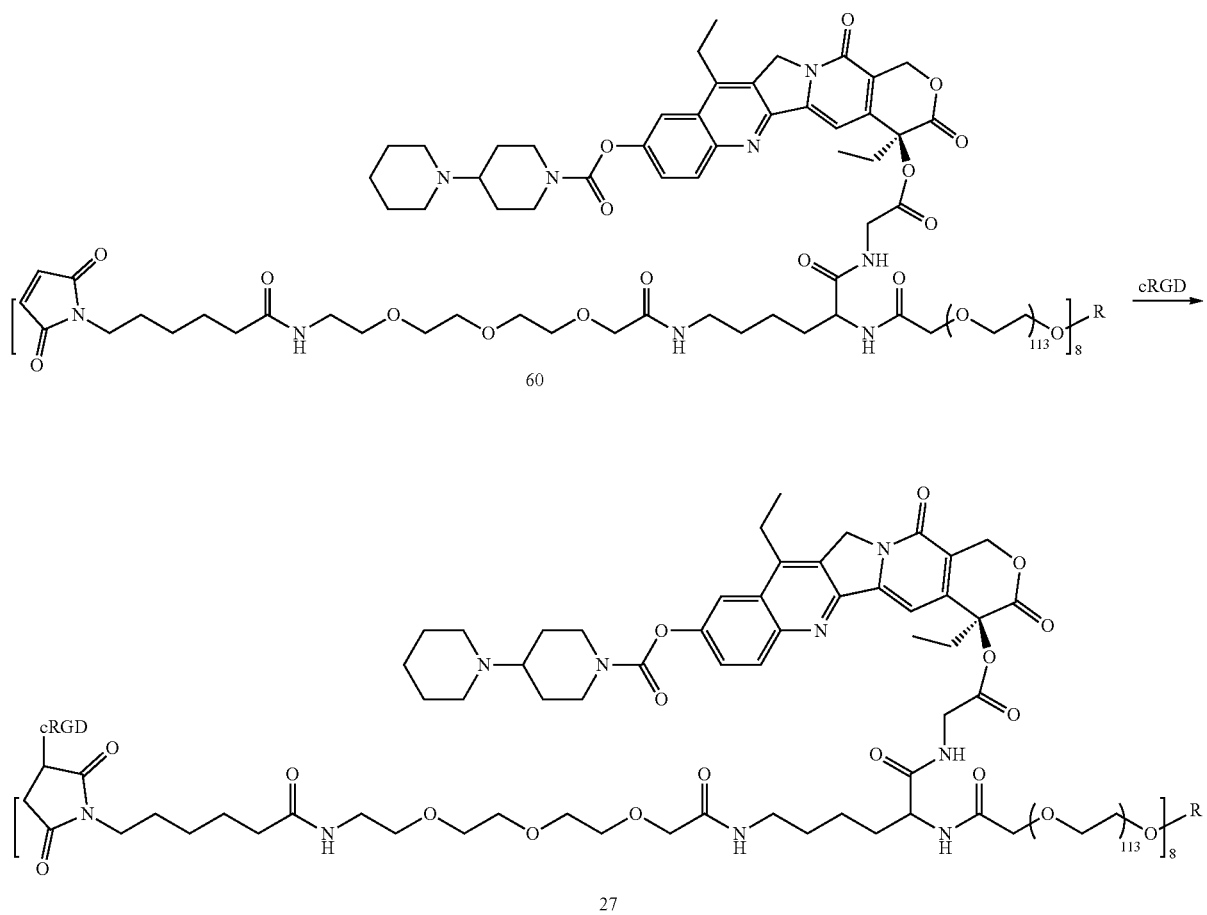

Preparation of Compound 27

To a 10 mL round bottom flask, 50 mg (1.0 eq) of Compound 60 and 1.5 mL of PBS (pH=7, 0.01M) were added. After the mixture was dissolved to give a clear solution, a mixed solution of 7.7 mg of cRGD in 1 mL of PBS (pH=7, 0.01M) and 1.5 mL of methanol was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 27 (50 mg).

$^1$HNMR (DMSO+D$_2$O): δ0.902 (t, CH$_2$C$\underline{H}_3$), 3.5 (br m PEG), 5.328 (s, 2H), 5.481 (s, 2H), 7.0-8.5 (m N$\underline{H}$)

Example 28
Preparation of iRGD was the Same as Example 1
Preparation of the L Portion was the Same as Example 1
Preparation of the Conjugate
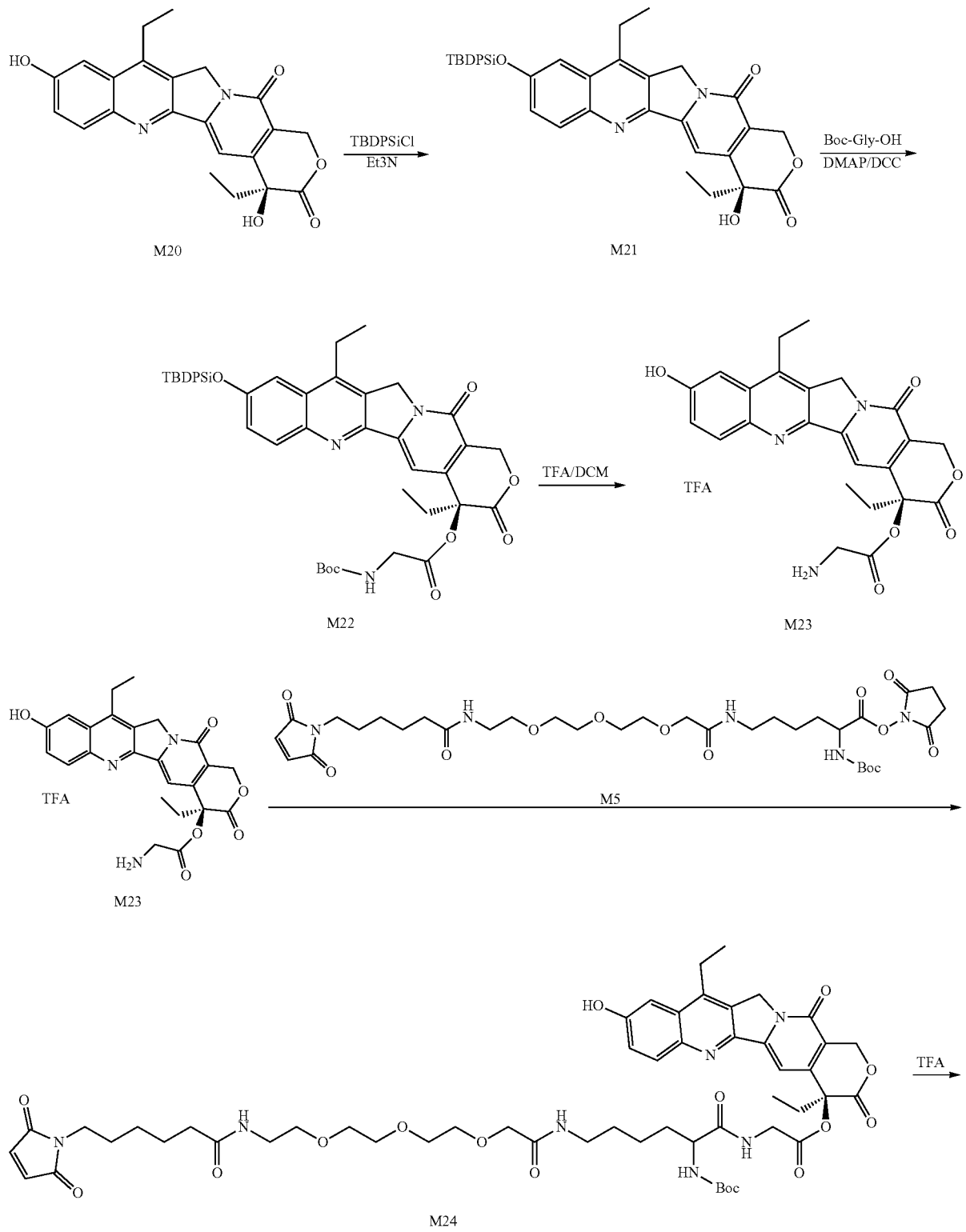

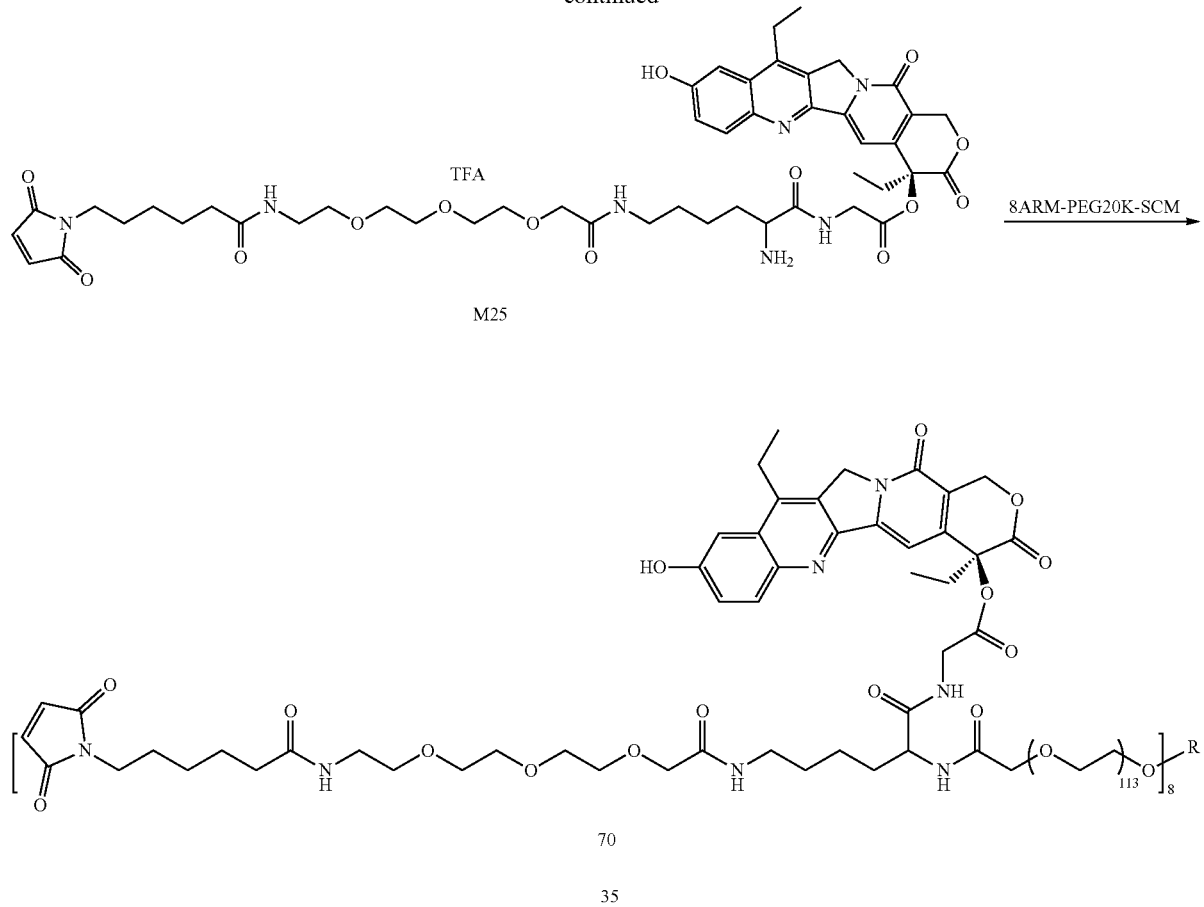

M25

70

Preparation of M21

To a 250 mL round bottom flask, 5.00 g (1.0 eq) of Compound M20, 100 mL of DCM, and 3.87 g (3.0 eq) of TEA were added, and a solution of 3.49 g (1.0 eq) of TBDPS-Cl in 20 mL of DCM was added dropwise. After the completion of the reaction was monitored by TLC, the mixture was washed with water and saturated saline, dried over anhydrous sodium sulfate, and then subjected to column chromatography to obtain 3.52 g of Compound M21 as a pale yellow solid.

Preparation of M22

To a 250 mL round bottom flask, 4.50 g (1.0 eq) of Compound M21, 135 mL of DCM, 1.5 g (1.2 eq) of Boc-Gly-OH, and 87 mg (0.1 eq) of DMAP were added, a solution of 2.21 g (1.5 eq) of DCC in 10 mL of DCM was added dropwise, and the mixture was reacted at 20° C. for 4 h. After the completion of the reaction was monitored by TLC, the mixture was filtered, and 120 mL of IPA was added when the mixture was concentrated to 25% of its total volume. 75% of the solvent was removed by distillation, and 150 mL of n-heptane was added. The mixture was stirred at room temperature for 1 h, filtered, washed twice with n-heptane, and dried to obtain 4.95 g of Compound M22 as a pale yellow solid.

Preparation of M23

To a 100 mL three-necked flask, 4.95 g of Compound M22 and 55 mL of DCM were added. After being stirred and dissolved, 13.7 mL of TFA were added dropwise, and the mixture was reacted at room temperature for 2 h. After the completion of the reaction was monitored by TLC, 150 mL of acetonitrile was added. After 120 mL of solvent was distilled under reduced pressure, the mixture was poured into 320 mL of TBME solution, stirred for 30 min, and filtered. The filter cake was washed with TBME to obtain a pale yellow solid M23 (2.5 g).

Preparation of M24

To a 200 mL three-necked flask, 2.3 g of Compound M23, 45 mL of DCM, 3.9 g (1.05 eq) of Compound 5 and 2.14 mL (3.0 eq) of TEA were added and reacted at room temperature for 4 h. After the completion of the reaction was monitored by TLC, the mixture was diluted with DCM, then washed twice with water, washed once with saturated saline, dried, concentrated, purified by HPLC, and then lyophilized to obtain a pale yellow solid M24 (2.45 g).

Preparation of M25

To a 200 mL round bottom flask, 2.2 g of Compound M24 and 65 mL of 20% TFA/DCM were added and reacted at room temperature for 4 h. After the completion of the reaction was monitored by TLC, the mixture was poured into TBME, centrifuged, and dried to obtain a pale yellow solid M25 (1.7 g).

Preparation of 70

To a 100 mL round bottom flask, 1.21 g (8.0 eq) of Compound M25, 60 mL of DCM, 314 μL (16.0 eq) of TEA and 3.0 g (1.0 eq) of 4armPEG20K-SCM were added. After reacting at room temperature overnight, the mixture was concentrated, added to TBME, centrifuged, and dried to obtain an off-white solid 70 (3.9 g).

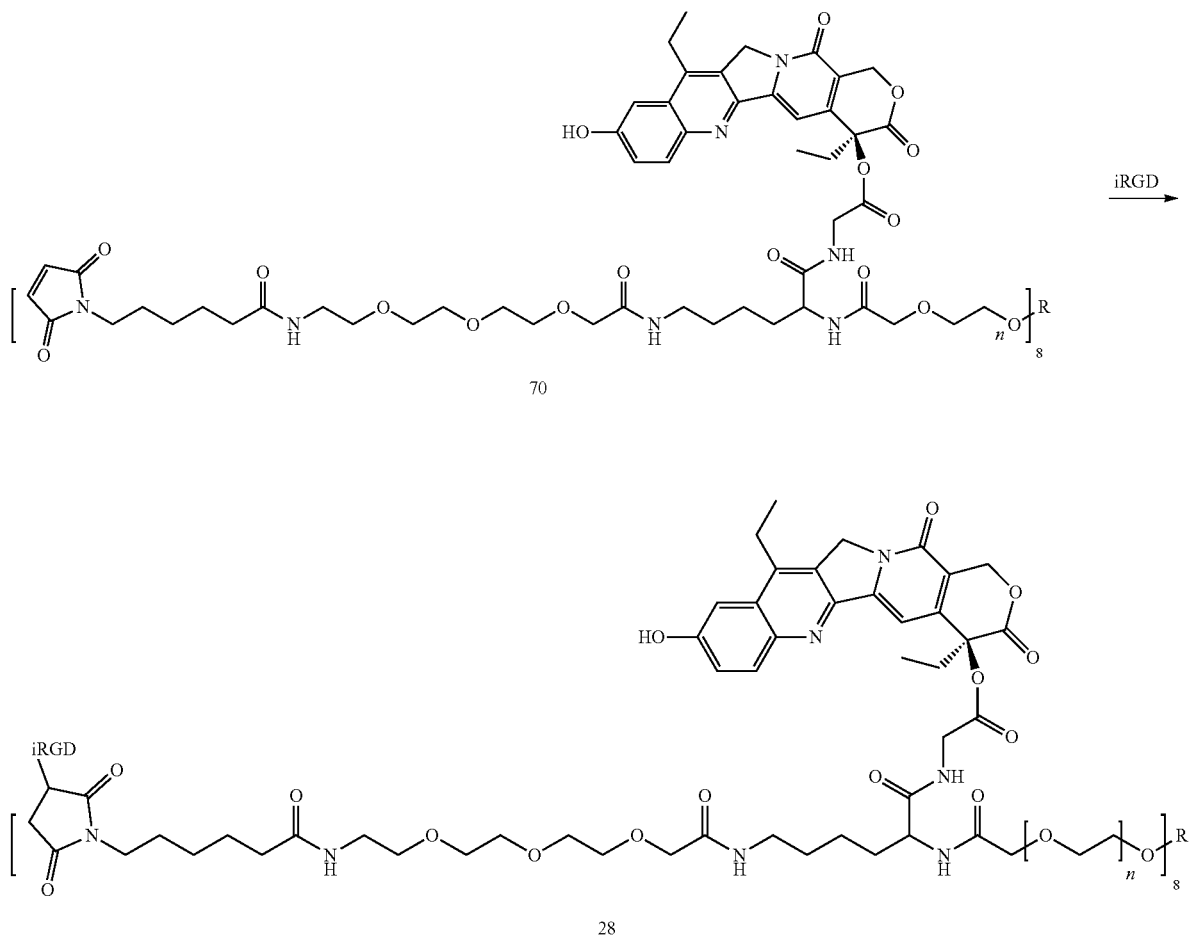

70

28

Preparation of Compound 28

To a 10 mL round bottom flask, 50 mg (1.0 eq) of Compound 70 and 1.5 mL of PBS (pH=7, 0.01M) were added. After the mixture was dissolved to give a clear solution, a solution of 15.3 mg of iRGD in 1 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 28 (55 mg).

$^1$HNMR (DMSO+D$_2$O): δ0.901 (t, CH$_2$C$\underline{H}_3$), 3.5 (br m PEG), 5.335 (s, 2H), 5.487 (s, 2H), 7.0-8.5 (m N$\underline{H}$)

Example 29

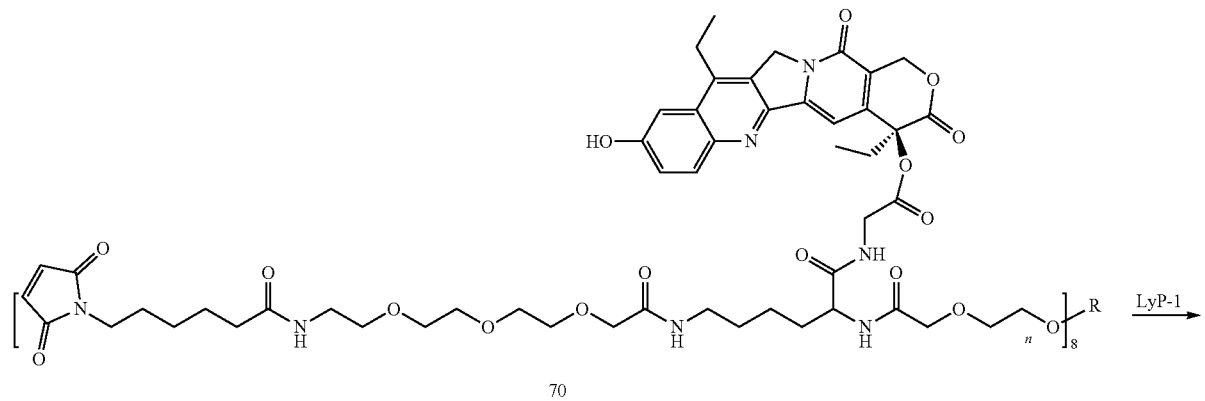

70

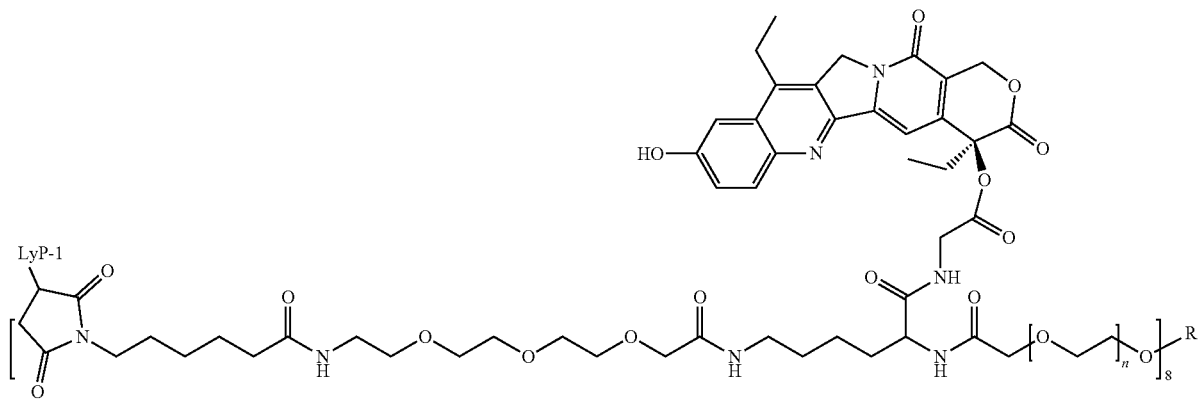

29

Preparation of Compound 29

To a 10 mL round bottom flask, 60 mg (1.0 eq) of Compound 70 and 1.5 mL of PBS (pH=7, 0.01M) were added. After the mixture was dissolved to give a clear solution, a solution of 18.3 mg of LyP-1 in 1 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 29 (68 mg).

$^1$HNMR (DMSO+D$_2$O): δ0.902 (t, CH$_2$CH$_3$), 3.5 (br m PEG), 5.333 (s, 2H), 5.486 (s, 2H), 7.0-8.5 (m NH)

Example 30

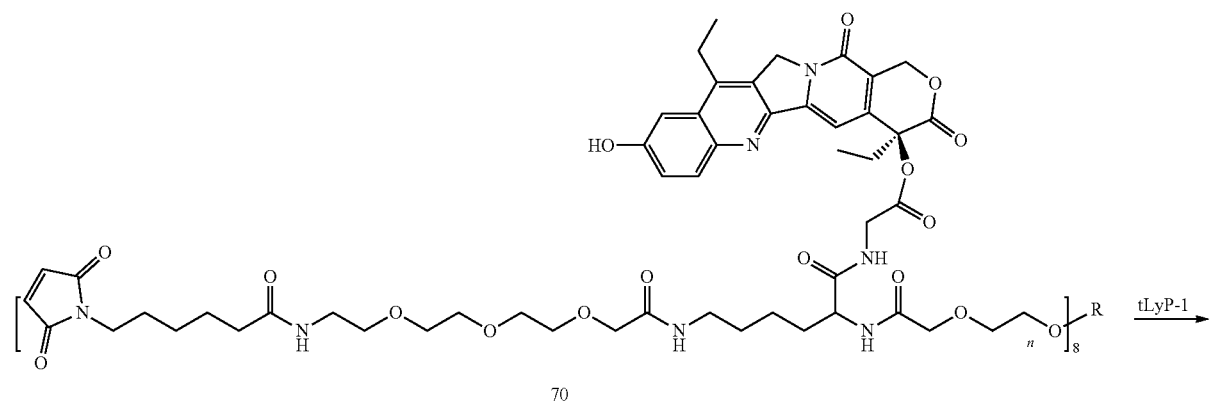

70

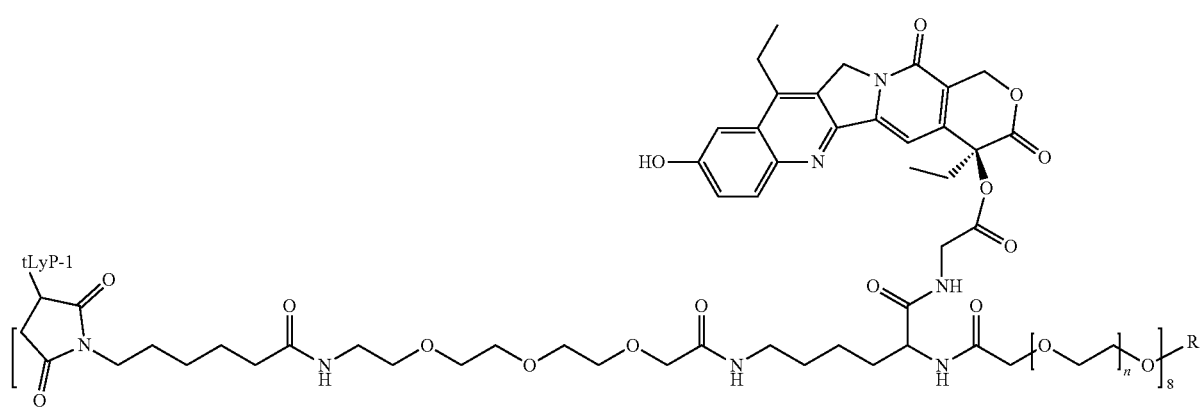

30

Preparation of Compound 30

To a 10 mL round bottom flask, 55 mg (1.0 eq) of Compound 70 and 1.5 mL of PBS (pH=7, 0.01M) were added. After the mixture was dissolved to give a clear solution, a solution of 12.8 mg of tLyP-1 in 1 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 30 (55 mg).

$^1$HNMR (DMSO+D$_2$O): δ0.901 (t, CH$_2$C$\underline{H}_3$), 3.5 (br m PEG), 5.335 (s, 2H), 5.488 (s, 2H), 7.0-8.5 (m N$\underline{H}$)

Example 31

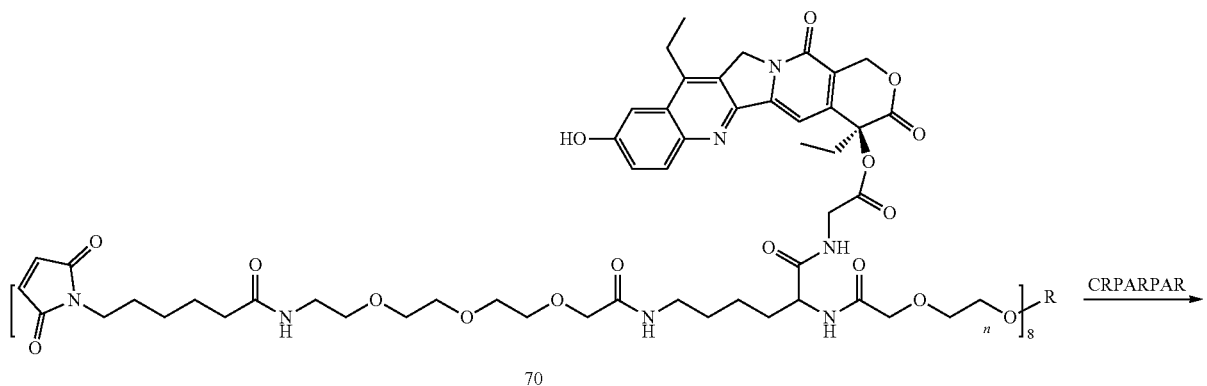

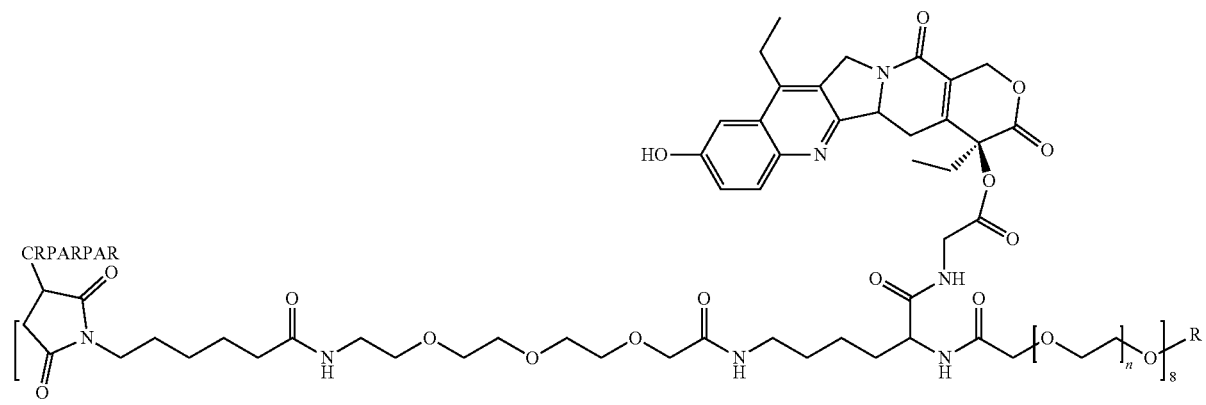

Preparation of Compound 31

To a 10 mL round bottom flask, 55 mg (1.0 eq) of Compound 70 and 1.5 mL of PBS (pH=7, 0.01M) were added. After the mixture was dissolved to give a clear solution, a solution of 14.2 mg of CRPARPAR in 1 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 31 (60 mg).

$^1$HNMR (DMSO+D$_2$O): δ0.902 (t, CH$_2$C$\underline{H}_3$), 3.5 (br m PEG), 5.332 (s, 2H), 5.487 (s, 2H), 7.0-8.5 (m N$\underline{H}$)

Example 32

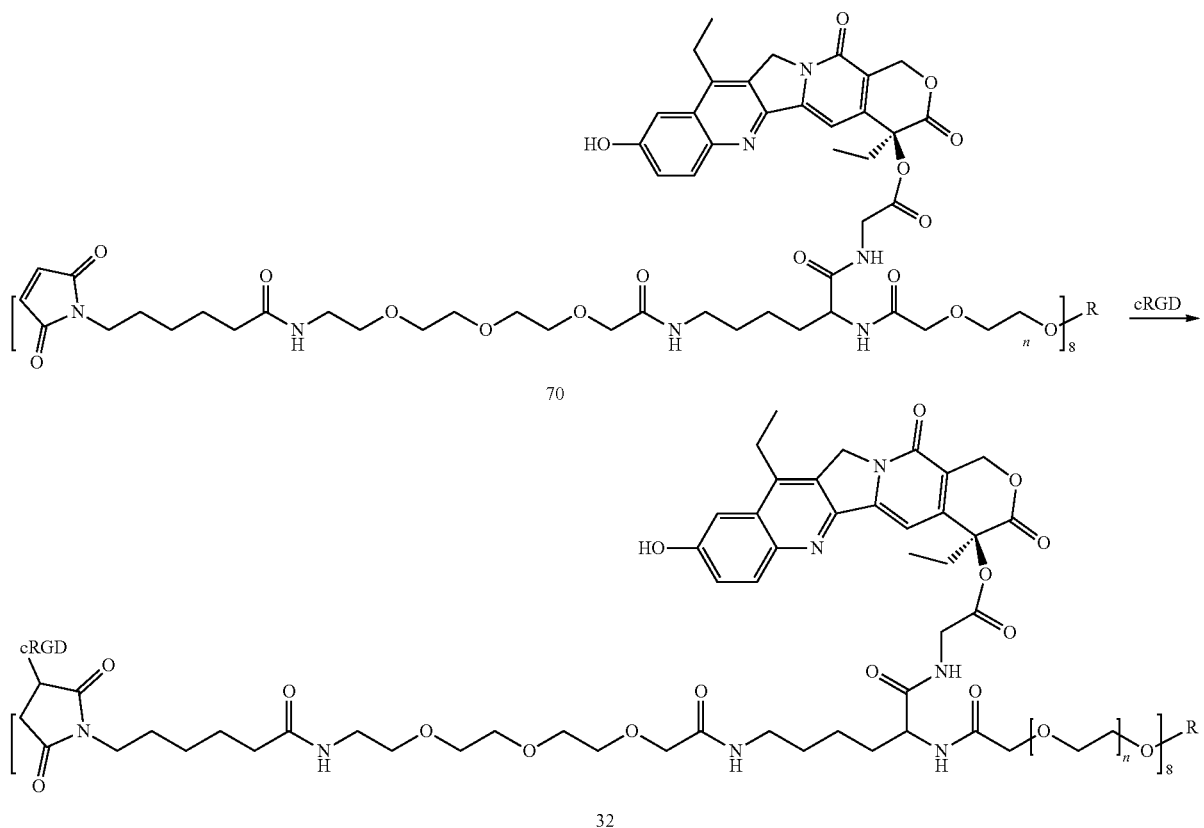

Preparation of Compound 32

To a 10 mL round bottom flask, 60 mg (1.0 eq) of Compound 70 and 1.5 mL of PBS (pH=7, 0.01M) were added. After the mixture was dissolved to give a clear solution, a mixed solution of 9.7 mg of cRGD in 1 mL of PBS (pH=7, 0.01M) and 1.5 mL of methanol was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 32 (62 mg).

$^1$HNMR (DMSO+D$_2$O): δ0.900 (t, CH$_2$CH$_3$), 3.5 (br m PEG), 5.333 (s, 2H), 5.487 (s, 2H), 7.0-8.5 (m NH)

Example 33

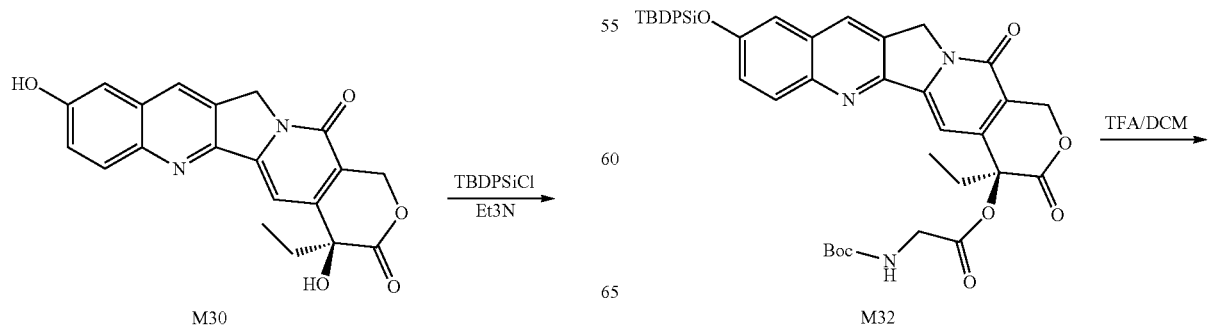

-continued

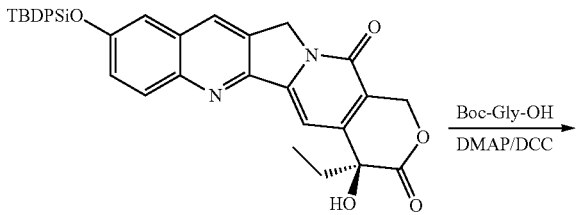

191

-continued

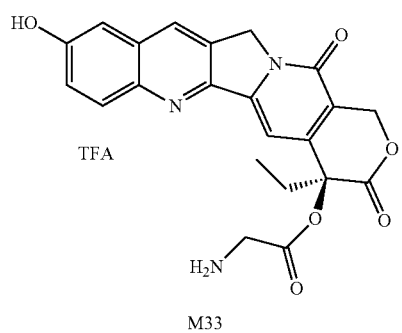

M33

Preparation of M31

To a 250 mL round bottom flask, 6.00 g (1.0 eq) of Compound M30, 120 mL of DCM and 5.00 g (3.0 eq) of TEA were added, and a solution of 4.53 g (1.0 eq) of TBDPS-Cl in 20 mL of DCM was added. After the completion of the reaction was monitored by TLC, the mixture was washed with water and saturated saline, dried over anhydrous sodium sulfate, and then subjected to column chromatography to obtain 4.32 g of Compound M31 as a pale yellow solid.

192

Preparation of M32

To a 250 mL round bottom flask, 5.0 g (1.0 eq) of Compound M31, 150 mL of DCM, 1.73 g (1.2 eq) of Boc-Gly-OH, and 101 mg (0.1 eq) of DMAP were added, a solution of 2.55 g (1.5 eq) of DCC in 10 mL of DCM was added dropwise, and the mixture was reacted at 20° C. for 4 h. After the completion of the reaction was monitored by TLC, the mixture was filtered, and 130 mL of IPA was added when the mixture was concentrated to 25% of its total volume. 75% of the solvent was removed by distillation, and 160 mL of n-heptane was added. The mixture was stirred at room temperature for 1 h, filtered, washed twice with n-heptane, and dried to obtain 4.52 g of Compound M32 as a pale yellow solid.

Preparation of M33

To a 100 mL three-necked flask, 4.40 g of Compound M32 and 50 mL of DCM were added. After the mixture was stirred and dissolved, 11.6 mL of TFA was added dropwise, and the mixture was reacted at room temperature for 2 h. After the completion of the reaction was monitored by TLC, 150 mL of acetonitrile was added. After 120 mL of solvent was distilled under reduced pressure, the mixture was poured into 320 mL of TBME solution, stirred for 30 min, and filtered. The filter cake was washed with TBME to obtain a pale yellow solid M33 (2.32 g).

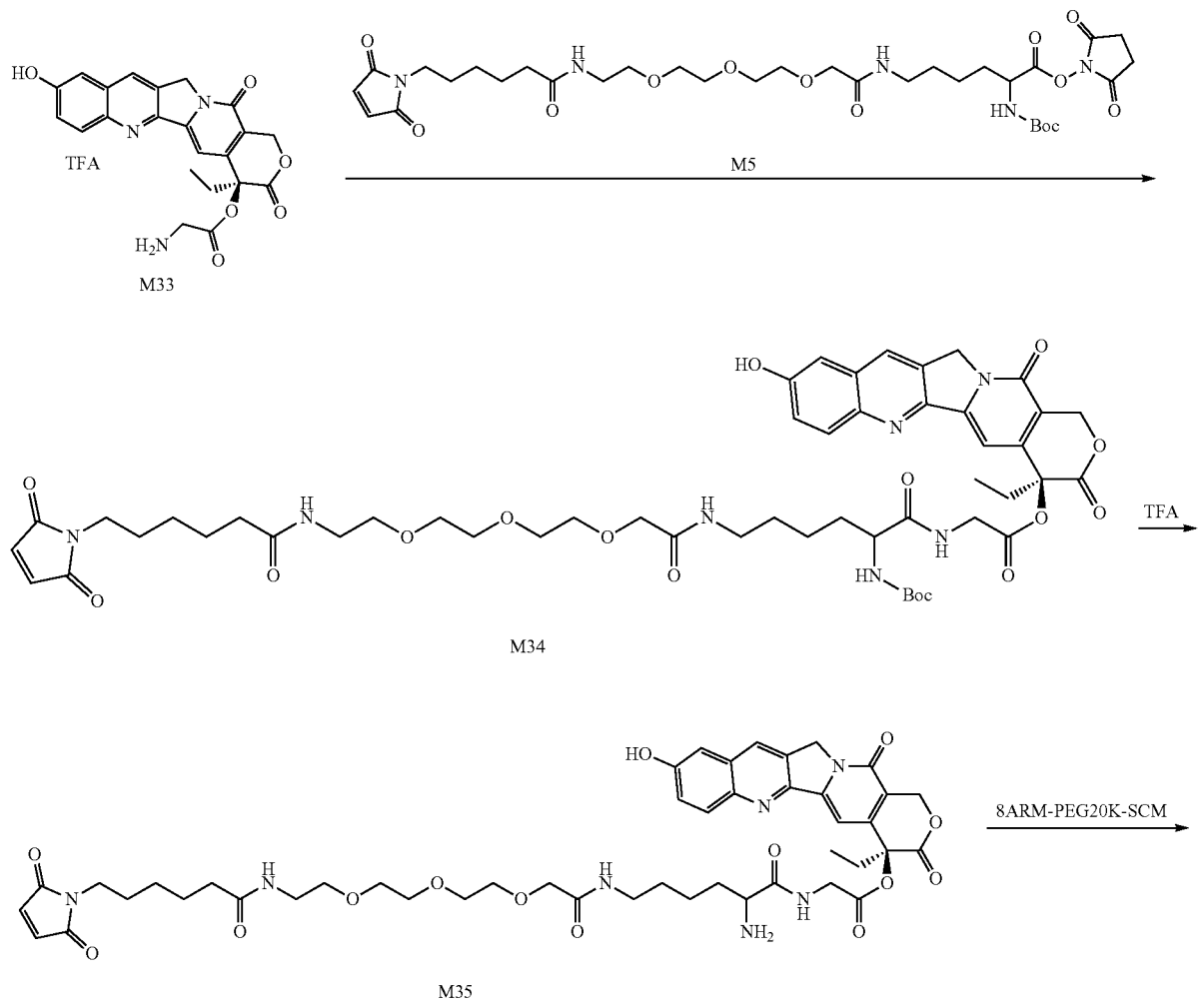

-continued

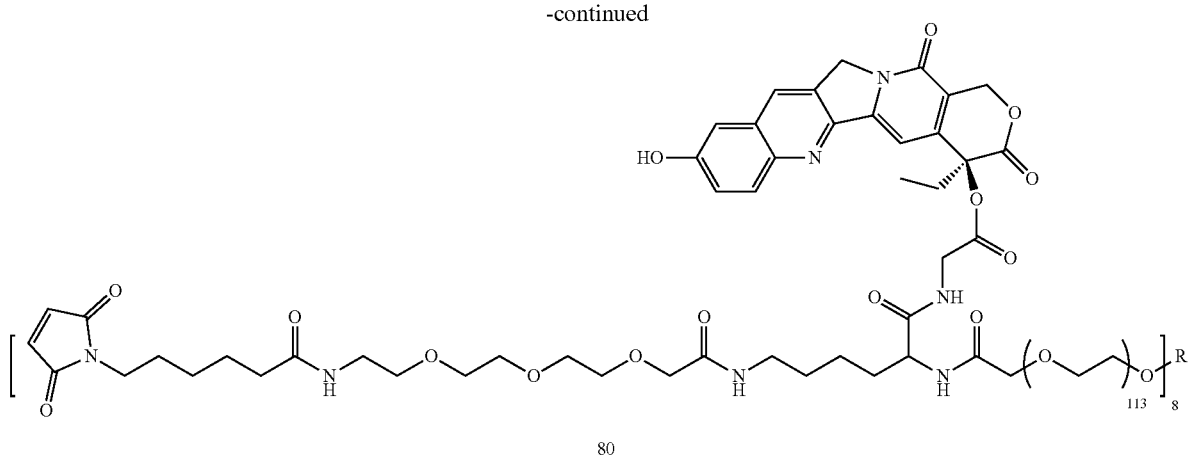

80

Preparation of M34

To a 200 mL three-necked flask, 2.3 g of Compound M33, 45 mL of DCM, 2.77 g (1.05 eq) of Compound M5, and 1.1 g (3.0 eq) of TEA were added and reacted at room temperature for 4 h. After the completion of the reaction was monitored by TLC, the mixture was diluted with DCM, then washed twice with water, washed once with saturated saline, dried, concentrated, purified by HPLC, and then lyophilized to obtain a pale yellow solid M34 (2.02 g).

Preparation of M35

To a 200 mL round bottom flask, 2.0 g of Compound M34 and 60 mL of 20% TFA/DCM were added and reacted at room temperature for 4 h. After the completion of the reaction was monitored by TLC, the mixture was poured into TBME, centrifuged, and dried to obtain a pale yellow solid M35 (1.69 g).

Preparation of 80

To a 500 mL round bottom flask, 2.75 g (8.0 eq) of Compound M35, 140 mL of DCM, 730 μL (16.0 eq) of TEA and 7.0 g (1.0 eq) of 8armPEG20K-SCM were added. After reacting at room temperature overnight, the mixture was concentrated, added to TBME, centrifuged, and dried to obtain an off-white solid 80 (8.64 g).

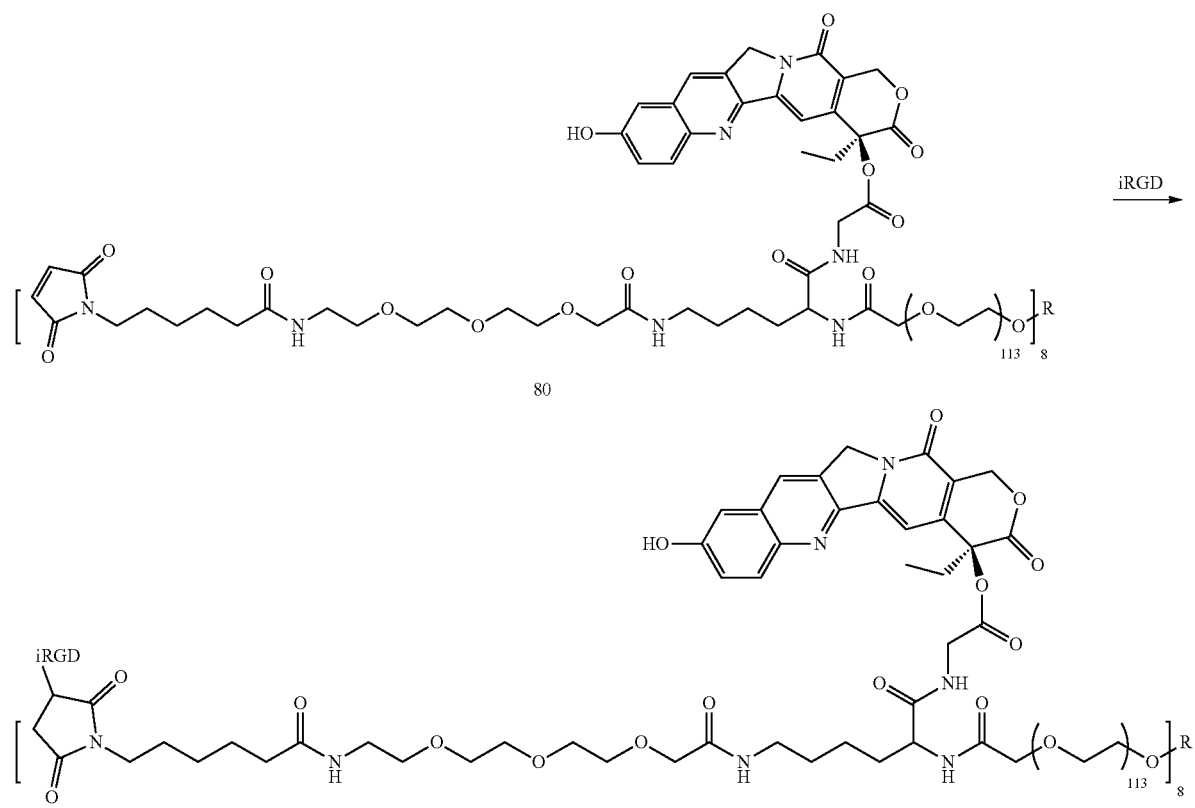

Preparation of Compound 33

To a 100 mL round bottom flask, 1.0 g (1.0 eq) of Compound 80 and 20 mL of PBS (pH=7, 0.01M) were added. After the mixture was dissolved to give a clear solution, a solution of 307 mg of iRGD in 15 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 33 (1.18 g).

$^1$HNMR (DMSO+D$_2$O): δ0.903 (t, CH$_2$C$\underline{H}_3$), 3.5 (br m PEG), 5.334 (s, 2H), 5.487 (s, 2H), 7.0-8.5 (m N$\underline{H}$)

Example 34

Preparation of Compound 34

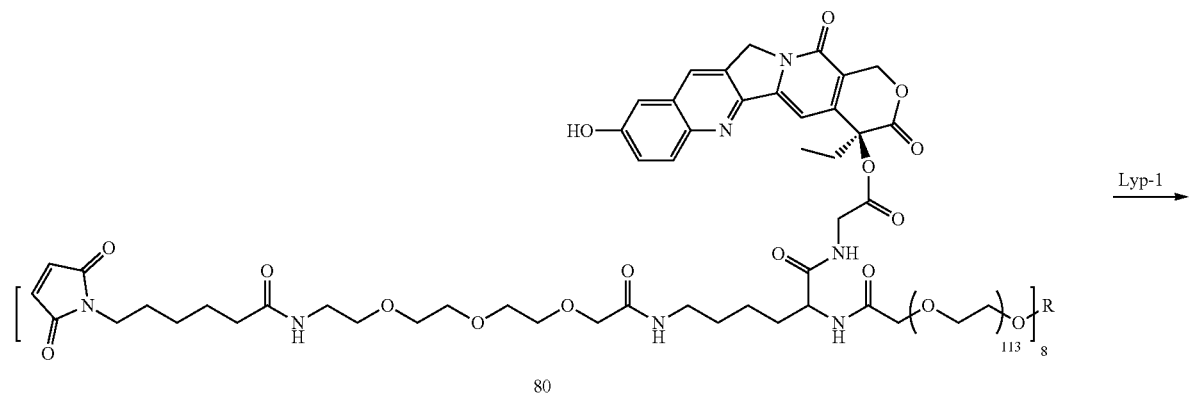

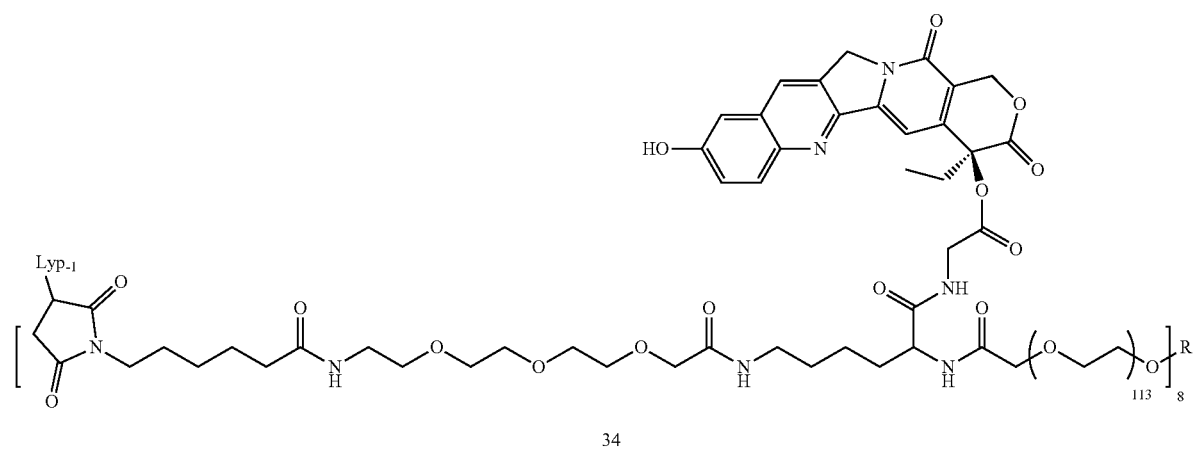

Example 35

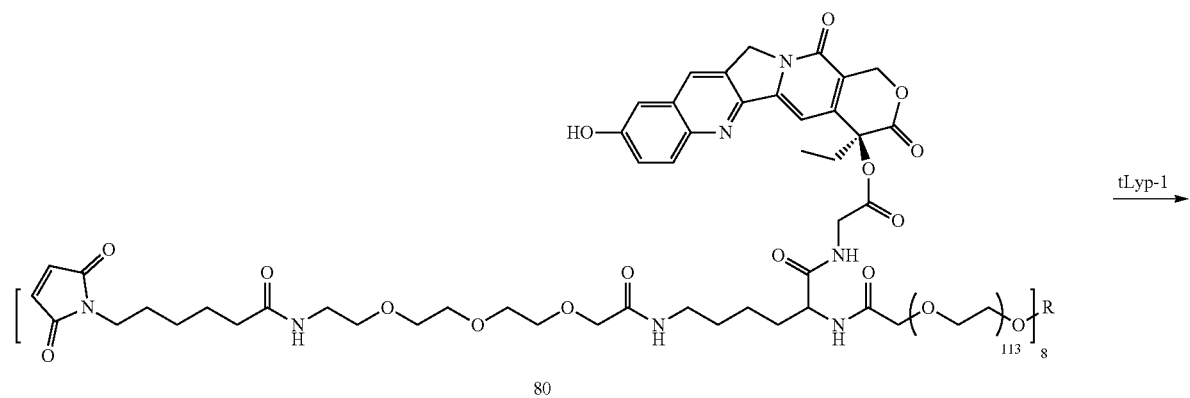

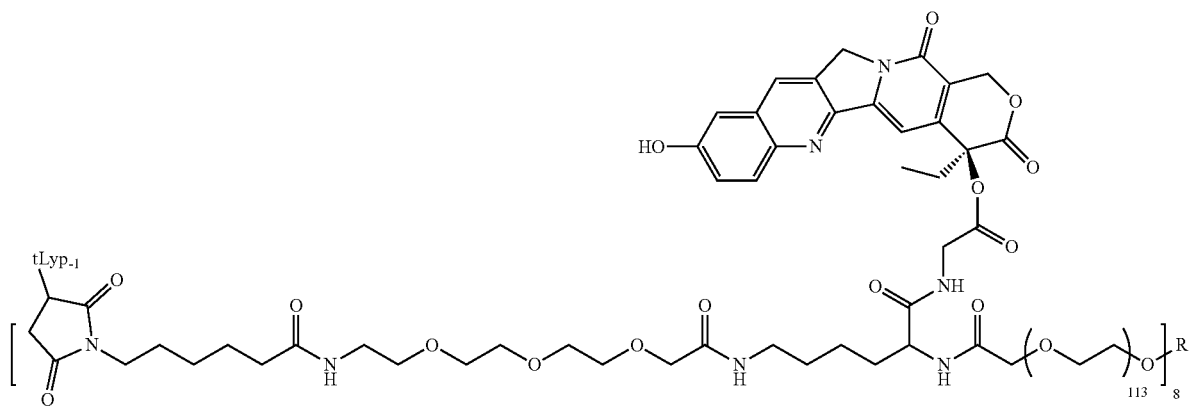

35

Preparation of Compound 35

To a 100 mL round bottom flask, 1.0 g (1.0 eq) of Compound 80 and 20 mL of PBS (pH=7, 0.01M) were added. After the mixture was dissolved to give a clear solution, a solution of 235 mg of tLyP-1 in 15 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 35 (1.05 g).

$^1$HNMR (DMSO+D$_2$O): δ0.904 (t, CH$_2$CH$_3$), 3.5 (br m PEG), 5.334 (s, 2H), 5.489 (s, 2H), 7.0-8.5 (m N$\underline{H}$)

Example 36

Preparation of Compound 36

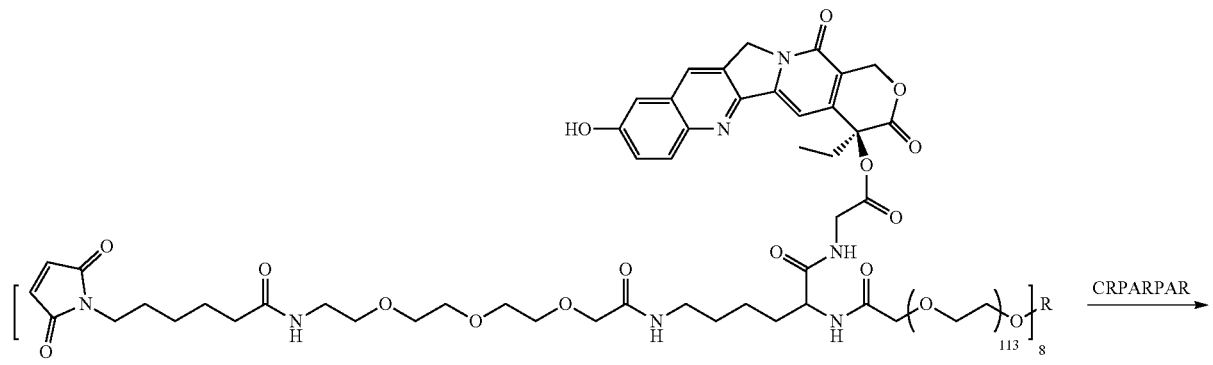

80

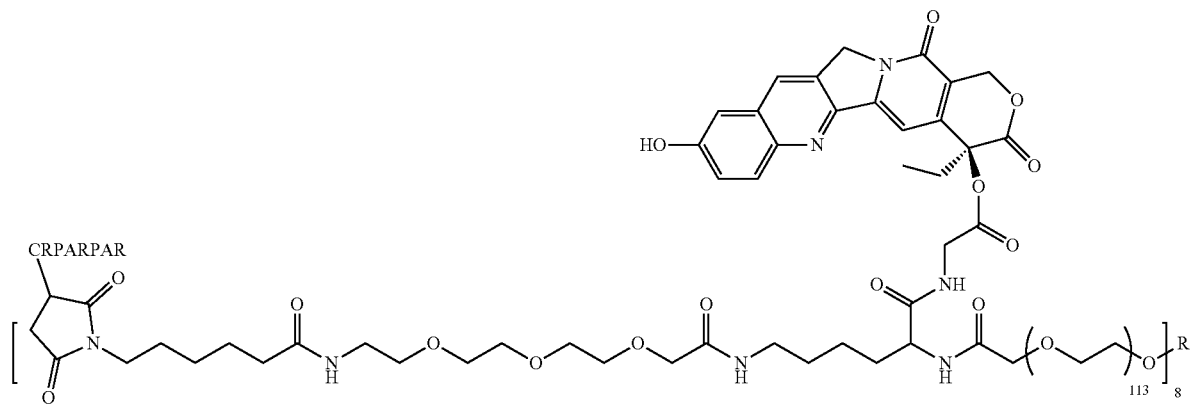

36

Example 37

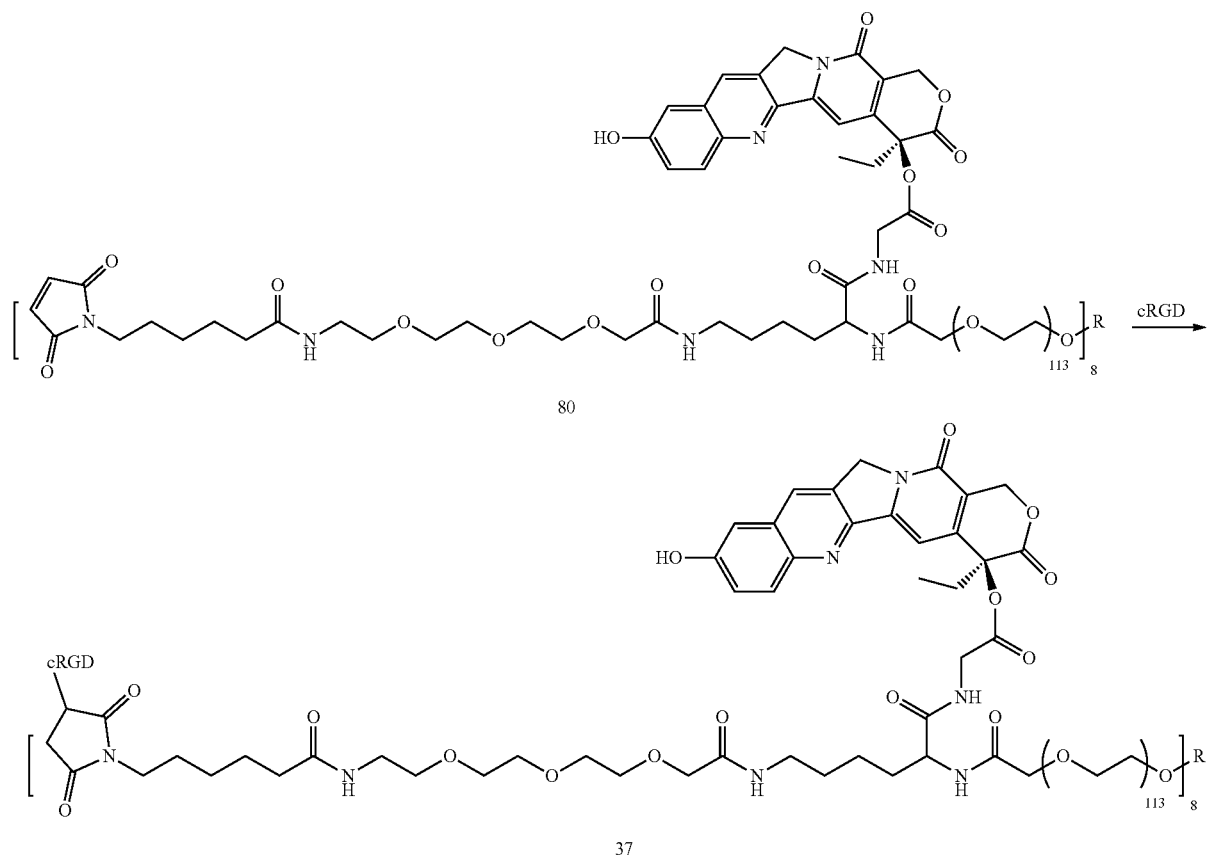

Preparation of Compound 37

To a 100 mL round bottom flask, 1.0 g (1.0 eq) of Compound 80 and 20 mL of PBS (pH=7, 0.01M) were added. After the mixture was dissolved to give a clear solution, a mixed solution of 163 mg of cRGD in 6 mL of PBS (pH=7, 0.01M) and 10 mL of methanol was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 37 (1.00 g).

$^1$HNMR (DMSO+D$_2$O): δ0.903 (t, CH$_2$C$\underline{H}_3$), 3.5 (br m PEG), 5.334 (s, 2H), 5.487 (s, 2H), 7.0-8.5 (m N$\underline{H}$)

Example 38

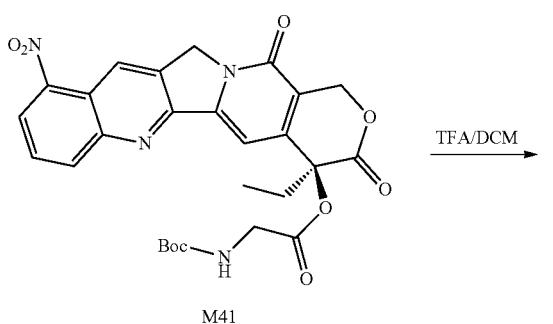

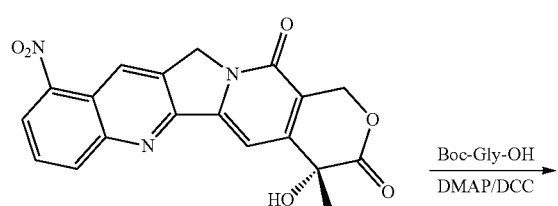

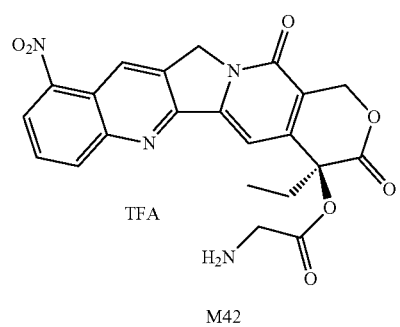

Preparation of M41

To a 250 mL round bottom flask, 5.0 g (1.0 eq) of Compound M40, 150 mL of DCM, 2.67 g (1.2 eq) of Boc-Gly-OH and 155 mg (0.1 eq) of DMAP were added, a solution of 3.93 g (1.5 eq) of DCC in 15 mL of DCM was added dropwise, and the mixture was reacted at 20° C. for 4 h. After the completion of the reaction was monitored by TLC, the mixture was filtered, and 130 mL of IPA was added when the mixture was concentrated to 25% of its total volume. 75% of the solvent was removed by distillation, and 160 mL of n-heptane was added. The mixture was stirred at room temperature for 1 h, filtered, washed twice with n-heptane, and dried to obtain 6.85 g of Compound M41 as a pale yellow solid.

Preparation of M42

To a 100 mL three-necked flask, 4.00 g of Compound M41 and 50 mL of DCM were added. After the mixture was stirred and dissolved, 11.6 mL of TFA was added dropwise, and the mixture was reacted at room temperature for 2 h. After the completion of the reaction was monitored by TLC, 150 mL of acetonitrile was added. After 120 mL of solvent was distilled under reduced pressure, the mixture was poured into 320 mL of TBME solution, stirred for 30 min, and filtered. The filter cake was washed with TBME to obtain a pale yellow solid M42 (3.54 g).

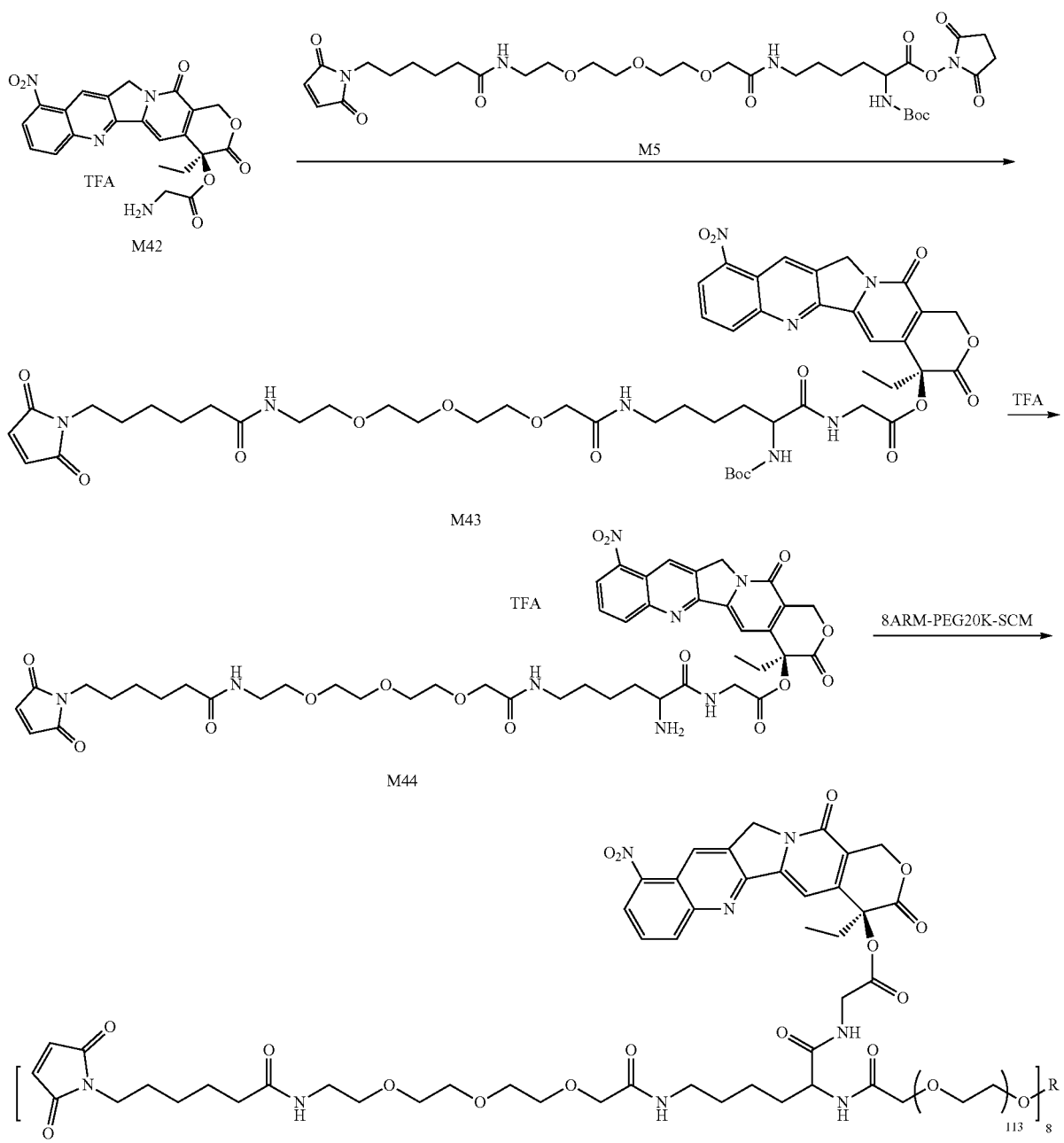

Preparation of M43

To a 200 mL three-necked flask, 3.00 g of Compound M42, 45 mL of DCM, 3.46 g (1.05 eq) of Compound M5, and 1.38 g (3.0 eq) of TEA were added and reacted at room temperature for 4 h. After the completion of the reaction was monitored by TLC, the mixture was diluted with DCM, then washed twice with water, washed once with saturated saline, dried, concentrated, purified by HPLC, and then lyophilized to obtain a pale yellow solid M43 (2.68 g).

Preparation of M44

To a 200 mL round bottom flask, 2.0 g of Compound M43 and 60 mL of 20% TFA/DCM were added and reacted at room temperature for 4 h. After the completion of the reaction was monitored by TLC, the mixture was poured into TBME, centrifuged, and dried to obtain a pale yellow solid M44 (1.61 g).

Preparation of 90

To a 250 mL round bottom flask, 1.61 g (8.0 eq) of Compound M44, 80 mL of DCM, 418 µL (16.0 eq) of TEA, and 4.0 g (1.0 eq) of 8armPEG20K-SCM were added. After reacting at room temperature overnight, the mixture was concentrated, added to TBME, centrifuged, and dried to obtain an off-white solid 90 (5.15 g).

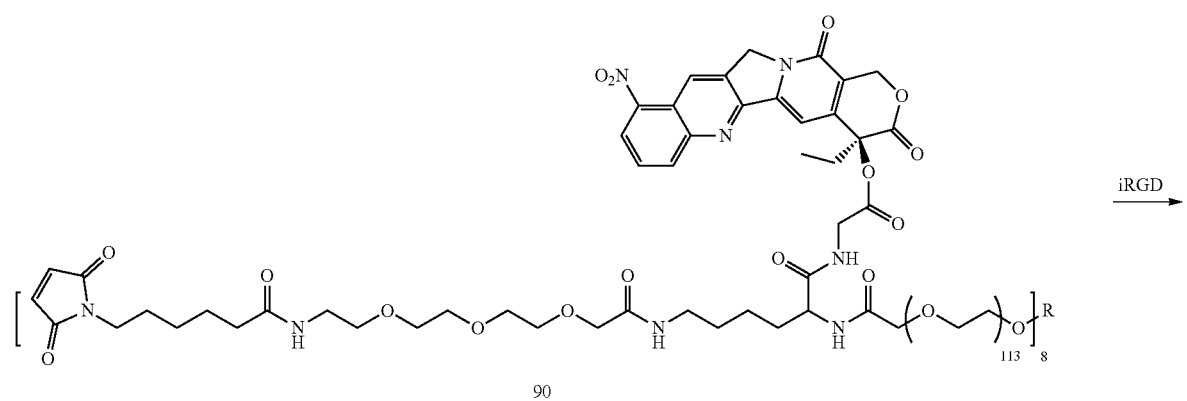

90

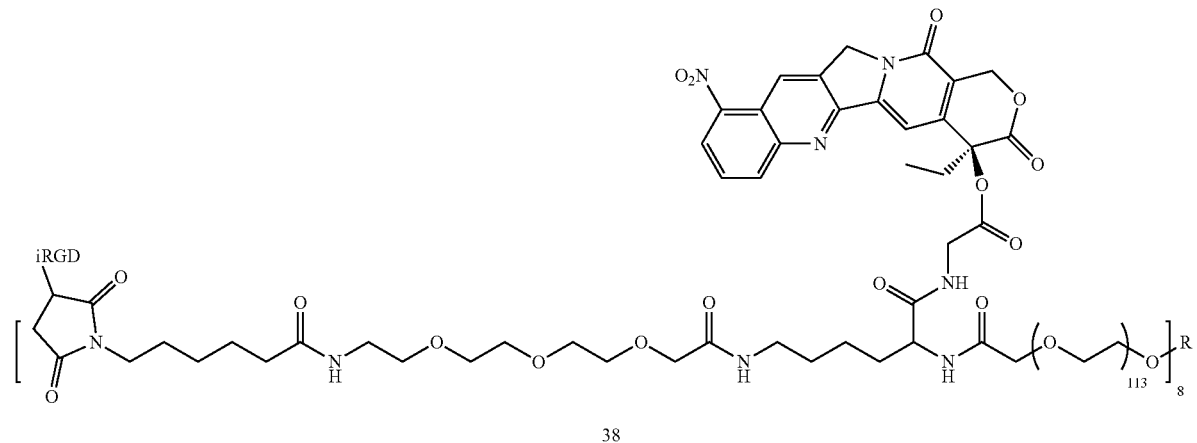

38

Preparation of Compound 38

To a 50 mL round bottom flask, 0.5 g (1.0 eq) of Compound 90 and 10 mL of PBS (pH=7, 0.01M) were added. After the mixture was dissolved to give a clear solution, a solution of 152 mg of iRGD in 5 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 38 (0.53 g).

$^1$HNMR (DMSO+D$_2$O): δ0.902 (t, CH$_2$C$\underline{H}_3$), 3.5 (br m PEG), 5.333 (s, 2H), 5.488 (s, 2H), 7.0-8.5 (m N$\underline{H}$)

Example 39

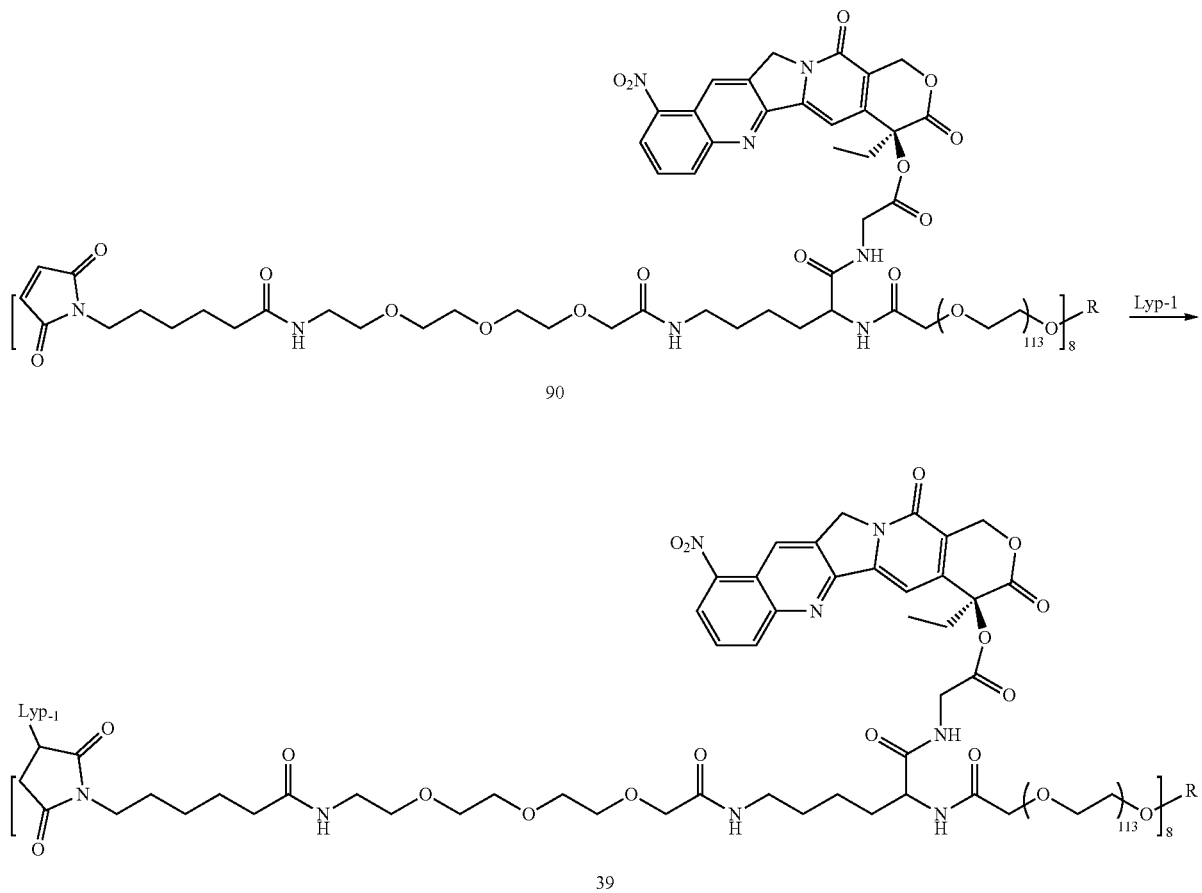

Preparation of Compound 39

To a 50 mL round bottom flask, 0.5 g (1.0 eq) of Compound 90 and 10 mL of PBS (pH=7, 0.01M) were added. After the mixture was dissolved to give a clear solution, a solution of 153 mg of LyP-1 in 5 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 39 (0.57 g).

$^1$HNMR (DMSO+D$_2$O): δ0.900 (t, CH$_2$C$\underline{H}_3$), 3.5 (br m PEG), 5.332 (s, 2H), 5.487 (s, 2H), 7.0-8.5 (m N$\underline{H}$)

Example 40

Preparation of Compound 40

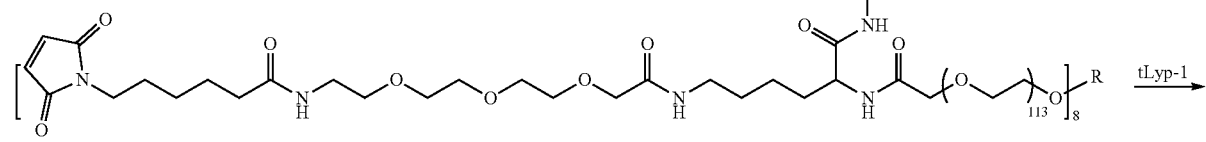

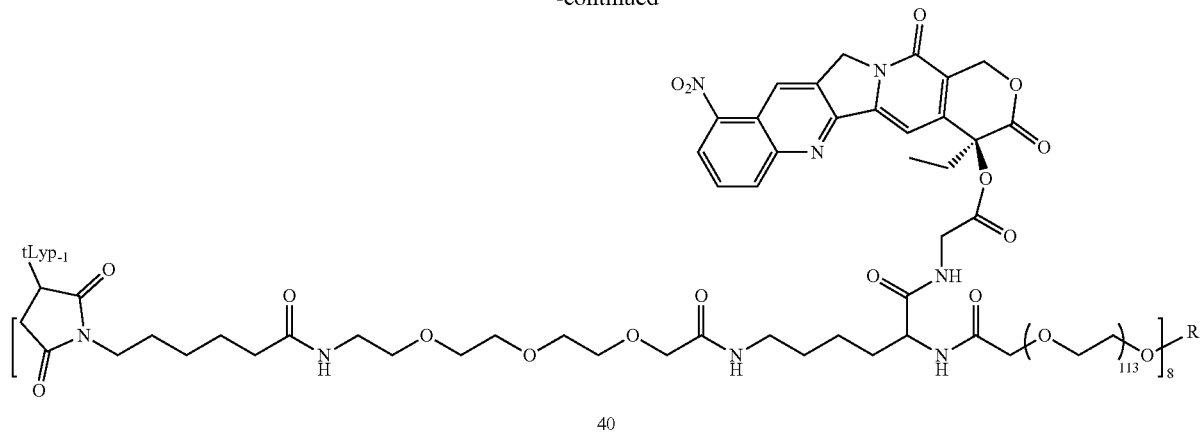

40

Example 41

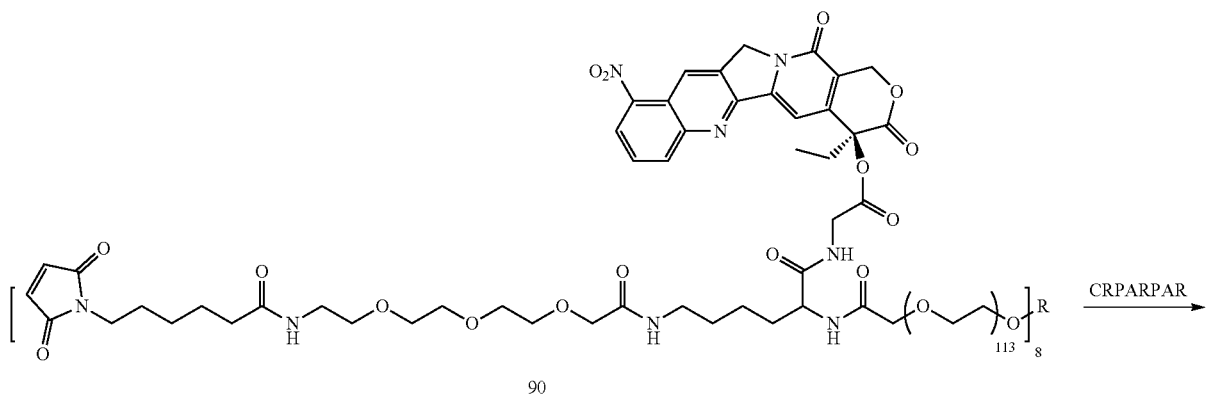

90

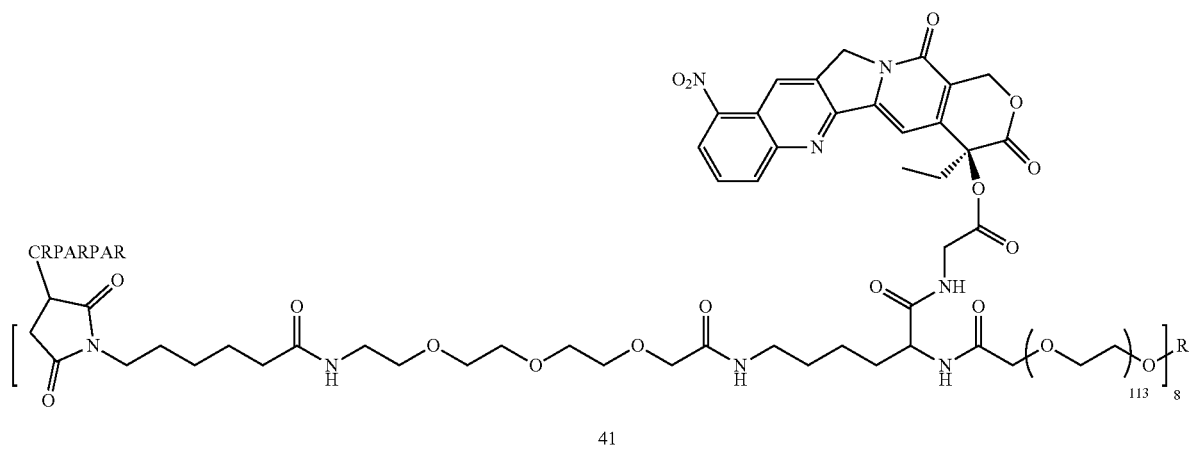

41

Preparation of Compound 41

To a 50 mL round bottom flask, 0.5 g (1.0 eq) of Compound 90 and 10 mL of PBS (pH=7, 0.01M) were added. After the mixture was dissolved to give a clear solution, a solution of 129 mg of CRPARPAR in 5 mL of PBS (pH=7, 0.01M) was added. After reacting at room temperature for 4 h, the mixture was dialyzed and concentrated, the crude product was dissolved in methanol, and a solution of HCl/EA was added. The mixture was concentrated, added to TBME, centrifuged, and dried to obtain a yellow solid 41 (0.55 g).

$^1$HNMR (DMSO+D$_2$O): δ0.901 (t, CH$_2$C$\underline{H}_3$), 3.5 (br m PEG), 5.331 (s, 2H), 5.487 (s, 2H), 7.0-8.5 (m N$\underline{H}$)

Example 42

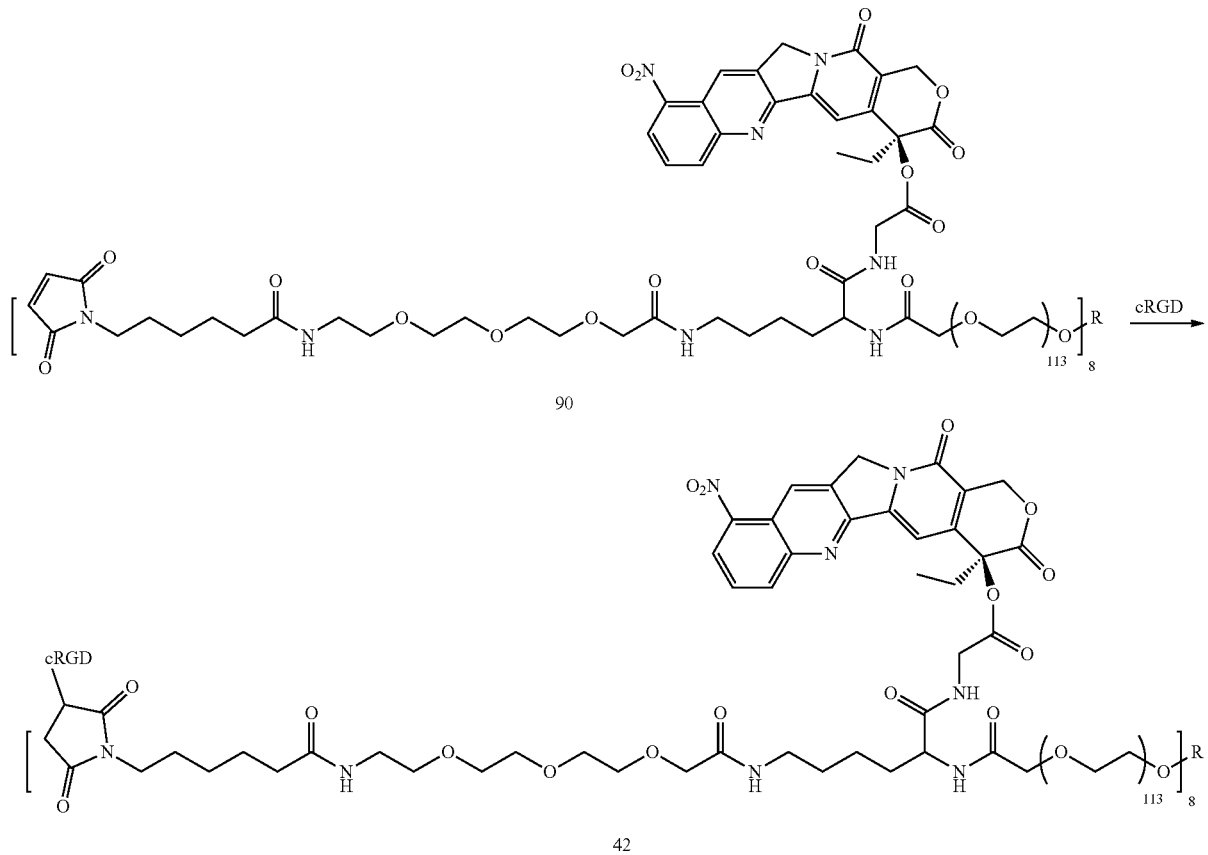

Preparation of Compound42

To a 50 mL round bottom flask, 0.5 g (1.0 eq) of Compound 90 and 10 mL of PBS (pH=7, 0.01M) were added. After the mixture was dissolved to give a clear solution, a mixed solution of 80.8 mg of cRGD in 4 mL of PBS (pH=7, 0.01M) and 6 mL of methanol was added. After reacting at room temperature for 4 h, the mixture was dialyzed and concentrated, the crude product was dissolved in methanol, and a solution of HCl/EA was added. The final mixture was concentrated, added to TBME, centrifuged, and dried to obtain a yellow solid 42 (0.50 g).

$^1$HNMR (DMSO+D$_2$O): δ0.903 (t, CH$_2$CH$_3$), 3.5 (br m PEG), 5.330 (s, 2H), 5.487 (s, 2H), 7.0-8.5 (m NH)

In the preparation of Compounds 23 to 42, R was

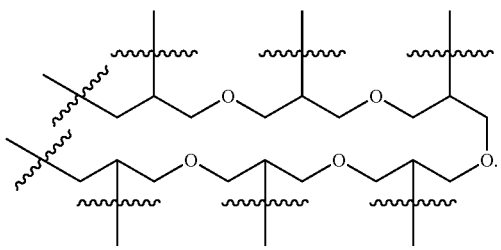 [SMILES: *CC(*)COCC(*)COCC(*)COCC(*)COCC(*)COCC(*)C*]

Example 43 Inhibitory Effect on In Vivo Tumor Growth in a Human Colon Cancer HT-29 Transplated Tumor Model in Nude Mice 1. Experimental Purpose The inhibitory effects of Compounds 1 to 42 on in vivo tumor growth in the human colon cancer HT-29 transplanted tumor model in nude mice were tested.

2. Experimental Materials 2.1 Test Articles

Irinotecan (bulk drug) and nktr-102 (bulk drug) were obtained by purchasing, and Compounds 1 to 42 were all provided by Brightgene Bio-Medical Technology Co., Ltd.

2.2 Reagents

McCoy's 5A liquid culture medium, fetal bovine serum (FBS), trypsin, penicillin-streptomycin bispecific antibody, water for injection, lactic acid, and sorbitol.

2.3 Experimental Animals

Female BALB/c nude mice (number of animals: 300, weeks of age: 5 to 7 weeks old) were purchased from Beijing Vital River Laboratory Animal Technology Co., Ltd., housed in an SPF animal room. The temperature was 20° C. to 25° C., the relative humidity was 40% to 70%, and the light and dark were respectively 12 h. The animals had free access to water and food. After about one week of normal feeding, upon a veterinary inspection, mice with good physical signsand conditions could be selected for the experiment. A marking pen was used to mark the base of the tails of the animals before the grouping, and each animal was marked by ear clipping after the grouping.

2.4 Transplantable Tumor Cell Line

Human colon cancer cell HT-29, derived from Cell Bank of Committee on Type Culture Collection of Chinese Academy of Science (CAS, stored frozen in liquid nitrogen in the laboratory).

3 Experimental Methods 3.1 Culture of HT-29 Cells

Under a culture condition of 5% $CO_2$ and 37° C., HT-29 cells were subjected to conventional cell cultivation in McCoy's 5A liquid culture medium containing 10% fetal bovine serum, digested with 0.25% trypsin, and passaged. According to the condition of cell growth, the cells were passaged 2 to 3 times every week, and were passaged in a ratio of 1:3 to 1:8.

3.2 Preparation of the Animal Model

HT-29 cells in logarithmic phase of growth were collected. The cells were resuspended in an McCoy's 5A culture medium free of serum after being counted, and the concentration of the cells was adjusted to $6 \times 10^7$ cells/mL. The cells were charged into a 50 mL centrifuge tube after being pipetted with a pipettor to make them evenly dispersed, and the centrifuge tube was placed in an ice box. Cell suspension was aspirated with a 1 mL syringe, and injected subcutaneously to the anterior right armpit of nude mice. Each animal was inoculated with 100 μL ($6 \times 10^6$ cells/animal), and the HT-29 transplated tumor model in nude mice was established. Animal status and the condition of tumor growth were observed regularly after inoculation, an electronic vernier caliper was used to measure the tumor diameters, the data was directly input to an Excel spreadsheet, and the tumor volumes were calculated. When the tumor volumes reached 100 mm³ to 300 mm³, 225 animals with good health condition and similar tumor volume were selected and divided into 45 groups using randomized block method (n=5). The tumor diameters were measured twice a week after the initiation of the experiment, the tumor volumes were calculated, and the body weights of the animals were weighed and recorded at the same time.

The calculation formula of the tumor volume (TV) was as follows:

$$TV(mm^3) = l \times w^2 / 2$$

wherein l represented the long diameter of a tumor (mm), and w represented the short diameter of a tumor (mm).

3.3 Preparation of the Solvent 0.5 g of sorbitol was weighed and charged into a 50 mL centrifuge tube, 50 mL of water for injection was added to the centrifuge tube, and the solid substance was dissolved completely by vortexing, so that an aqueous sorbitol solution (w/v) with a concentration of 1% was formulated. The solution was stored in a refrigerator at 4° C. until use.

3.4 Preparation of the Dosing Formulations 3.4.1 Preparation of the Dosing Formulation of Irinotecan 12.0 mg of irinotecan was weighed, 0.15 mL of 1% lactic acid was added, the drug was dissolved completely by vortexing, and 2.85 mL of 1% aqueous sorbitol solution was then added respectively. The mixture was mixed evenly by vortexing, and the ratio of 1% lactic acid to 1% aqueous sorbitol solution was approximately 5:95 (v/v) in the solution. The concentration of free irinotecan in the solution was 4.0 mg·mL$^{-1}$.

3.4.2 Preparation of the Dosing Formulation of nktr-102

Before each administration, 88.55 mg of nktr-102 was weighed accurately, 2.3 mL of physiological saline was added, the drug was dissolved completely by vortexing, and the concentration of free irinotecan in the solution was 4.0 mg·mL$^{-1}$.

3.4.3 Preparation of the Dosing Formulations of Compounds 1 to 5

Before each administration, 113.85 mg of Compound 1 was weighed accurately, 2.3 mL of physiological saline was added, the drug was dissolved completely by vortexing, and the concentration of free irinotecan in the solution was 4.0 mg·mL$^{-1}$.

Before each administration, 109.80 mg of Compound 2 was weighed accurately, 2.3 mL of physiological saline was added, the drug was dissolved completely by vortexing, and the concentration of free irinotecan in the solution was 4.0 mg·mL$^{-1}$.

Before each administration, 113.88 mg of Compound 3 was weighed accurately, 2.3 mL of physiological saline was added, the drug was dissolved completely by vortexing, and the concentration of free irinotecan in the solution was 4.0 mg·mL$^{-1}$.

Before each administration, 111.24 mg of Compound 4 was weighed accurately, 2.3 mL of physiological saline was added, the drug was dissolved completely by vortexing, and the concentration of free irinotecan in the solution was 4.0 mg·mL$^{-1}$.

Before each administration, 105.78 mg of Compound 5 was weighed accurately, 2.3 mL of physiological saline was added, the drug was dissolved completely by vortexing, and the concentration of free irinotecan in the solution was 4.0 mg·mL$^{-1}$.

3.4.4 Preparation of the Dosing Formulations of Compounds 6 to 10

Before each administration, 113.09 mg of Compound 6 was weighed accurately, 2.3 mL of physiological saline was added, the drug was dissolved completely by vortexing, and the concentration of free SN-38 in the solution was 4.0 mg·mL$^{-1}$.

Before each administration, 109.05 mg of Compound 7 was weighed accurately, 2.3 mL of physiological saline was added, the drug was dissolved completely by vortexing, and the concentration of free SN-38 in the solution was 4.0 mg·mL$^{-1}$.

Before each administration, 113.12 mg of Compound 8 was weighed accurately, 2.3 mL of physiological saline was added, the drug was dissolved completely by vortexing, and the concentration of free SN-38 in the solution was 4.0 mg·mL$^{-1}$.

Before each administration, 110.48 mg of Compound 9 was weighed accurately, 2.3 mL of physiological saline was added, the drug was dissolved completely by vortexing, and the concentration of free SN-38 in the solution was 4.0 mg·mL$^{-1}$.

Before each administration, 105.02 mg of Compound 10 was weighed accurately, 2.3 mL of physiological saline was added, the drug was dissolved completely by vortexing, and the concentration of free SN-38 in the solution was 4.0 mg·mL$^{-1}$.

3.4.5 Preparation of the Dosing Formulations of Compounds 11 to 15

Before each administration, 112.98 mg of Compound 11 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 108.94 mg of Compound 12 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 113.01 mg of Compound 13 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 110.37 mg of Compound 14 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 104.91 mg of Compound 15 was weighed accurately, 2.3 mL of physiological saline was added, the drug was dissolved completely by vortexing, and the concentration of free 10-hydroxycamptothecin in the solution was 4.0 mg·mL$^{-1}$.

3.4.6 Preparation of the Dosing Formulations of Compounds 16 to 20

Before each administration, 113.09 mg of Compound 11 was weighed accurately, 2.3 mL of physiological saline was added, the drug was dissolved completely by vortexing, and the concentration of free rubitecan in the solution was 4.0 mg·mL$^{-1}$.

Before each administration, 109.05 mg of Compound 12 was weighed accurately, 2.3 mL of physiological saline was added, the drug was dissolved completely by vortexing, and the concentration of free rubitecan in the solution was 4.0 mg·mL$^{-1}$.

Before each administration, 113.12 mg of Compound 13 was weighed accurately, 2.3 mL of physiological saline was added, the drug was dissolved completely by vortexing, and the concentration of free rubitecan in the solution was 4.0 mg·mL$^{-1}$.

Before each administration, 110.48 mg of Compound 14 was weighed accurately, 2.3 mL of physiological saline was added, the drug was dissolved completely by vortexing, and the concentration of free rubitecan in the solution was 4.0 mg·mL$^{-1}$.

Before each administration, 105.02 mg of Compound 15 was weighed accurately, 2.3 mL of physiological saline was added, the drug was dissolved completely by vortexing, and the concentration of free rubitecan in the solution was 4.0 mg·mL$^{-1}$.

3.4.7 Preparation of the Dosing Formulations of Compounds 21 to 42

The preparation methods were as described above, so that the concentration of the free active agent in the solution was 4.0 mg·mL$^{-1}$.

3.5 Grouping of Animals and Administration

The grouping of animals and the dosing regimens were as shown in Table 1.

Groups with irinotecan as the active agent (Groups 1 to 8). The first administration was initiated on the day of grouping, the experiment was ended after 21 days, and the volumes of administration were all 10 mL·kg$^{-1}$. Group 1 was a solvent control group, and was given blank solvent by intravenous injection via tail once every 4 days for a total of 3 times (Q4D×3). Groups 2 to 8 were given irinotecan, nktr-102, and Compounds 1 to 5 as test samples by intravenous injection via tail, respectively, and the dosages of administration were all 40 mg·kg$^{-1}$ (calculated in terms of the content of irinotecan), Q4D×3.

Groups with SN-38 as the active agent (Groups 9 to 13). The first administration was initiated on the day of grouping, the experiment was ended after 21 days, and the volumes of administration were all 10 mL·kg$^{-1}$. Groups 9 to 13 were given Compounds 6 to 10 as test samples by intravenous injection via tail, respectively, and the dosages of administration were all 40 mg·kg$^{-1}$ (calculated in terms of the content of SN-38), Q4D×3.

Groups with 10-hydroxycamptothecin as the active agent (Groups 14 to 18). The first administration was initiated on the day of grouping, the experiment was ended after 21 days, and the volumes of administration were all 10 mL·kg$^{-1}$. Groups 14 to 18 were given Compounds 11 to 15 as test samples by intravenous injection via tail, respectively, and the dosages of administration were all 40 mg·kg$^{-1}$ (calculated in terms of the content of 10-hydroxycamptothecin), Q4D×3.

Groups with rubitecan as the active agent (Groups 19 to 23). The first administration was initiated on the day of grouping, the experiment was ended after 21 days, and the volumes of administration were all 10 mL·kg$^{-1}$. Groups 19 to 23 were given Compounds 16 to 20 as test samples by intravenous injection via tail, respectively, and the dosages of administration were all 40 mg·kg$^{-1}$ (calculated in terms of the content of rubitecan), Q4D×3.

The modes of administration of Groups 24 to 25 were as described above.

TABLE 1

Dosing regimens of the pharmacodynamic experiments in transplanted tomor models in nude mice

| Group | Sample | Number of animals | Dosage (mg · kg$^{-1}$) | Volume of administration (mL · kg$^{-1}$) | Route of administration | Period of administration |
|---|---|---|---|---|---|---|
| 1 | blank solvent | 5 | — | 10 | IV | Q4D × 3 |
| 2 | irinotecan | 5 | 40 | 10 | IV | Q4D × 3 |
| 3 | nktr-102 | 5 | 40 | 10 | IV | Q4D × 3 |
| 4 | Compound 1 | 5 | 40 | 10 | IV | Q4D × 3 |
| 5 | Compound 2 | 5 | 40 | 10 | IV | Q4D × 3 |
| 6 | Compound 3 | 5 | 40 | 10 | IV | Q4D × 3 |
| 7 | Compound 4 | 5 | 40 | 10 | IV | Q4D × 3 |
| 8 | Compound 5 | 5 | 40 | 10 | IV | Q4D × 3 |
| 9 | Compound 6 | 5 | 40 | 10 | IV | Q4D × 3 |
| 10 | Compound 7 | 5 | 40 | 10 | IV | Q4D × 3 |
| 11 | Compound 8 | 5 | 40 | 10 | IV | Q4D × 3 |
| 12 | Compound 9 | 5 | 40 | 10 | IV | Q4D × 3 |
| 13 | Compound 10 | 5 | 40 | 10 | IV | Q4D × 3 |
| 14 | Compound 11 | 5 | 40 | 10 | IV | Q4D × 3 |
| 15 | Compound 12 | 5 | 40 | 10 | IV | Q4D × 3 |

TABLE 1-continued

Dosing regimens of the pharmacodynamic experiments in transplanted tumor models in nude mice

| Group | Sample | Number of animals | Dosage $(mg \cdot kg^{-1})$ | Volume of administration $(mL \cdot kg^{-1})$ | Route of administration | Period of administration |
|---|---|---|---|---|---|---|
| 16 | Compound 13 | 5 | 40 | 10 | IV | Q4D × 3 |
| 17 | Compound 14 | 5 | 40 | 10 | IV | Q4D × 3 |
| 18 | Compound 15 | 5 | 40 | 10 | IV | Q4D × 3 |
| 19 | Compound 16 | 5 | 40 | 10 | IV | Q4D × 3 |
| 20 | Compound 17 | 5 | 40 | 10 | IV | Q4D × 3 |
| 21 | Compound 18 | 5 | 40 | 10 | IV | Q4D × 3 |
| 22 | Compound 19 | 5 | 40 | 10 | IV | Q4D × 3 |
| 23 | Compound 20 | 5 | 40 | 10 | IV | Q4D × 3 |
| 24 | Compound 21 | 5 | 40 | 10 | IV | Q4D × 3 |
| 25 | Compound 22 | 5 | 40 | 10 | IV | Q4D × 3 |
| 26 | Compound 23 | 5 | 40 | 10 | IV | Q4D × 3 |
| 27 | Compound 24 | 5 | 40 | 10 | IV | Q4D × 3 |
| 28 | Compound 25 | 5 | 40 | 10 | IV | Q4D × 3 |
| 29 | Compound 26 | 5 | 40 | 10 | IV | Q4D × 3 |
| 30 | Compound 27 | 5 | 40 | 10 | IV | Q4D × 3 |
| 31 | Compound 28 | 5 | 40 | 10 | IV | Q4D × 3 |
| 32 | Compound 29 | 5 | 40 | 10 | IV | Q4D × 3 |
| 33 | Compound 30 | 5 | 40 | 10 | IV | Q4D × 3 |
| 34 | Compound 31 | 5 | 40 | 10 | IV | Q4D × 3 |
| 35 | Compound 32 | 5 | 40 | 10 | IV | Q4D × 3 |
| 36 | Compound 33 | 5 | 40 | 10 | IV | Q4D × 3 |
| 37 | Compound 34 | 5 | 40 | 10 | IV | Q4D × 3 |
| 38 | Compound 35 | 5 | 40 | 10 | IV | Q4D × 3 |
| 39 | Compound 36 | 5 | 40 | 10 | IV | Q4D × 3 |
| 40 | Compound 37 | 5 | 40 | 10 | IV | Q4D × 3 |
| 41 | Compound 38 | 5 | 40 | 10 | IV | Q4D × 3 |
| 42 | Compound 39 | 5 | 40 | 10 | IV | Q4D × 3 |
| 43 | Compound 40 | 5 | 40 | 10 | IV | Q4D × 3 |
| 44 | Compound 41 | 5 | 40 | 10 | IV | Q4D × 3 |
| 45 | Compound 42 | 5 | 40 | 10 | IV | Q4D × 3 |

3.6 End of the Experiment

On the last day of the experiment, the animals were euthanized ($CO_2$) after the body weights were weighed and the tumor diameters were measured. The tumor tissues were excised, weighed and photographed (respectively photographed according to the following combinations), and the tumor weight inhibition rates were calculated. The animals were subjected to gross anatomy, and whether there was abnormality in internal organs were observed by naked eyes.

4 Data Recording and Calculation Formulae

The calculation formula of the relative tumor volume (RTV) was:

$$RTV = TV_t / TV_{initial}$$

wherein $TV_{initial}$ was the tumor volume measured at the time of grouping and first administration, and $TV_t$ was the tumor volume at each measurement during administration.

The calculation formula of the relative tumor proliferation rate (% T/C) was:

$$\% \, T/C = 100\% \times (RTV_T / RTV_C)$$

wherein $RTV_T$ represented the RTV of a treatment group, and $RTV_C$ represented the RTV of the solvent control group.

The calculation formula of the tumor growth inhibition rate (TGI (%)) was:

$$TGI = 100\% \times [1 - (TV_{t(T)} - TV_{initial(T)}) / (TV_{t(C)} - TV_{initial(C)})]$$

wherein $TV_{t(T)}$ represented the tumor volume of a treatment group at each measurement, $TV_{initial(T)}$ represented the tumor volume of a treatment group measured at the time of grouping and first administration, $TV_{t(C)}$ represented the tumor volume of the solvent control group at each measurement, and $TV_{initial(C)}$ represented the tumor volume of the solvent control group measured at the time of grouping and first administration.

The calculation formula of the decline rate of animal body weight was:

$$\text{decline rate of animal body weight} = 100\% \times (BW_{initial} - BW_t) / BW_{initial}$$

wherein $BW_t$ represented the animal body weight at each measurement during administration, and $BW_{initial}$ represented the animal body weight at the time of grouping and first administration.

The calculation formula of the tumor weight inhibition rate (IR (%)) was:

$$IR(\%) = 100\% \times (W_C - W_T) / W_C$$

wherein $W_C$ represented the tumor weight of the control group, and $W_T$ represented the tumor weight of a treatment group.

5 Method for Statistical Analysis

The experimental data was subjected to calculation and related statistical treatments using Microsoft Office Excel 2007 Software. Unless otherwise specified, the data was represented by mean±standard error (Mean±SE), and t test was adopted for the comparison between two groups.

6 Experimental Observation

During the experiment, experimenter(s) and veterinarian(s) needed to continuously observe the physical signs and health status of the experimental animals. Any abnormal performance of the animals, such as pain, depression, and decreased activity, should be recorded in the original experiment record. If abnormal performances of the experimental animals exceeded the provisions of the IACUC-related animal welfare documents, the veterinarian(s) could judge whether to suspend the experiment and notify the person in charge of the experimental project.

7 Results

As for the human cancer xenograft models, the relative tumor proliferation rate T/C (%) was recommended to be adopted as the evaluation index of the experiment. Lower proliferation rate indicated better tumor inhibitory effect, as shown in Table 2.

TABLE 2

Relative tumor proliferation rate T/C (%)

| Group | Sample | Number of animals | Relative tumor volume (RTV) | Relative tumor proliferation rate (% T/C) |
|---|---|---|---|---|
| 1 | blank solvent | 5 | 13.78 | — |
| 2 | irinotecan | 5 | 9.52 | 69% |
| 3 | nktr-102 | 5 | 6.37 | 46% |
| 4 | Compound 1 | 5 | 2.07* | 15%# |
| 5 | Compound 2 | 5 | 2.48* | 18%# |
| 6 | Compound 3 | 5 | 2.70* | 19.5%# |
| 7 | Compound 4 | 5 | 2.65* | 19.2%# |
| 8 | Compound 5 | 5 | 2.46* | 17.9%# |
| 9 | Compound 6 | 5 | 2.27* | 16.5%# |
| 10 | Compound 7 | 5 | 2.50* | 18.1%# |
| 11 | Compound 8 | 5 | 3.18* | 23.1%# |
| 12 | Compound 9 | 5 | 2.90* | 21.1%# |
| 13 | Compound 10 | 5 | 2.16* | 15.7%# |
| 14 | Compound 11 | 5 | 2.61* | 18.9%# |
| 15 | Compound 12 | 5 | 2.53* | 18.3%# |
| 16 | Compound 13 | 5 | 2.35* | 17%# |
| 17 | Compound 14 | 5 | 2.47* | 17.9%# |
| 18 | Compound 15 | 5 | 2.20* | 16.8%# |
| 19 | Compound 16 | 5 | 2.48* | 18%# |
| 20 | Compound 17 | 5 | 2.65* | 19.2%# |
| 21 | Compound 18 | 5 | 2.78* | 20.2%# |
| 22 | Compound 19 | 5 | 2.68* | 19.4%# |
| 23 | Compound 20 | 5 | 2.33* | 16.9%# |
| 24 | Compound 21 | 5 | 2.14* | 15.5%# |
| 25 | Compound 22 | 5 | 2.31* | 16.7%# |
| 26 | Compound 23 | 5 | 2.25* | 16.3%# |
| 27 | Compound 24 | 5 | 2.47* | 17.9%# |
| 28 | Compound 25 | 5 | 2.76* | 20.0%# |
| 29 | Compound 26 | 5 | 2.69* | 19.5%# |
| 30 | Compound 27 | 5 | 2.37* | 17.2%# |
| 31 | Compound 28 | 5 | 2.93* | 21.2%# |
| 32 | Compound 29 | 5 | 2.72* | 19.7%# |
| 33 | Compound 30 | 5 | 2.54* | 18.4%# |
| 34 | Compound 31 | 5 | 2.31* | 16.7%# |
| 35 | Compound 32 | 5 | 2.57* | 18.6%# |
| 36 | Compound 33 | 5 | 3.01* | 21.8%# |
| 37 | Compound 34 | 5 | 2.67* | 19.3%# |
| 38 | Compound 35 | 5 | 2.29* | 16.6%# |
| 39 | Compound 36 | 5 | 2.46* | 17.8%# |
| 40 | Compound 37 | 5 | 2.39* | 17.3%# |
| 41 | Compound 38 | 5 | 2.84* | 20.6%# |
| 42 | Compound 39 | 5 | 2.57* | 18.6%# |
| 43 | Compound 40 | 5 | 2.48* | 18.0%# |
| 44 | Compound 41 | 5 | 2.76* | 20.0%# |
| 45 | Compound 42 | 5 | 2.64* | 19.1%# |

*P < 0.05, as compared with the RTV of the blank solvent group, irinotecan group and nktr-102 group.
P < 0.05, as compared with % T/C of the blank solvent group, irinotecan group and nktr-102 group.

The experimental results showed that the compounds of the present disclosure had good inhibitory effects on in vivo tumor growth in the human colon cancer HT-29 transplanted tumor model in nude mice, and were superior to irinotecan and nktr-102. Example 44 Inhibitory effect in a human breast cancer MDA-MB-231 xenograft model in nude mice 1. Experimental Purpose The human breast cancer MDA-MB-231 transplanted tumor model in nude mice was used in this study to evaluate the in vivo antitumor activities of Compounds 1 to 42.

2. Experimental Animals 2.1 Animal species

Mice.

2.2 Strain

BALB/c nude mice.

2.3 Sex

Female.

2.4 Number 320 animals were inoculated, and 225 animals were used for the experiment.

2.5 Age 6 to 8 week old.

2.6 Body weight 20 to 22 g±20% of the average body weight.

2.7 Animal source (supplier)

Shanghai Xipuer-Bikai Experimental Animal Co., Ltd. (BK), license number: SCXK (Shanghai) 2008-0016.

2.8 Management of Experimental Animals

All experimental animals were housed in an SPF-level laboratory. Experimenters were responsible for daily care and experimental research.

2.8.1 Identification Method of Animal Identity

Each mice cage had an identification card with information such as the experimental number, experimental group, name(s) of the experimenter(s), and the strain and sex of mice. The mice were marked with earrings.

2.8.2 Random Grouping

After the tumor volumes reached 150 mm$^3$ to 200 mm$^3$, the animals were grouped using randomized block method with 5 mice in each group, ensuring the tumor volumes and the body weights of the mice were uniform between each group. The difference between the mean value of the tumor volumes in each group and the mean value of the tumor volumes of all experimental animals was no more than ±10%.

2.8.3 Operating and Managing Practice

The operation and management of all experimental animals strictly adhered to the guideline of the use and management of animals.

2.8.4 Feeding Conditions

Living conditions: IVC system, 5 animals per cage
Temperature: 20° C. to 26° C.
Humidity: 40% to 70%
Illumination: 12 h light/dark cycle 2.8.5 Feed Irradiated feed for rat and mice, purchased from Beijing Keao Xieli Feed Co., Ltd. The animals had free access to food.

2.8.6 Drinking Water

City tap water, used for drinking after being filtered and autoclaved.

2.8.7 Beddings

Corn cobs (Shanghai Maoshengyan Biologic Science & Technology Co., Ltd.) were used after being autoclaved. Beddings were changed twice a week.

2.8.8 Acclimation Period

The mice were given at least one week of acclimation period for the environment before the experiment.

3. Experimental Materials 3.1 Test Drugs

Irinotecan (bulk drug) and nktr-102 (bulk drug) were obtained by purchasing, and Compounds 1 to 42 were all provided by Brightgene Bio-Medical Technology Co., Ltd.

3.2 Other Chemical Reagents and Materials 3.2.1 Physiological Saline

Physiological saline was purchased from Shanghai Huayuan Changfu Pharmaceutical (Group) Co., Ltd.

3.2.2 Sterile Syringe 1 mL sterile syringes were purchased from Shanghai Kindly Enterprise Development Group Co., Ltd (Shanghai, China).

3.2.3 Cell Strain

Human breast cancer MDA-MB-231 cells were purchased from Shanghai Institute of Biochemistry and Cell Biology of Chinese Academy of Sciences.

MDA-MB-231 cells were cultured in DMEM culture medium (GIBCO, USA) containing 10% fetal bovine serum FBS (GIBCO, USA), and cultured in a 37° C. incubator containing 5% $CO_2$.

3.2.4 Matrigel (BD Matrigel)

Matrigel was purchased from Becton, Dickinson and Company (BD), the USA.

3.3 Instruments

Biosafe cabinet (model: AC2-6E1), purchased from ESCO; water jacketed $CO_2$ cell incubator (model: 3111), purchased from Thermo Scientific Forma; inverted microscope (model: CKX41SF), purchased from Olympus;

electric suction apparatus (model: YX930D), purchased from Shanghai Medical Instruments (Group) Co., Ltd.;

balance (METTLER-TOLEDO AB135-S), purchased from METTLER-TOLEDO;

low speed centrifuge (model: LD5-2A), purchased from Beijing Lab Centrifuge Co., Ltd.; digimatic caliper (model: SF2000), purchased from Guilin Guanglu Measuring Instrument Co., Ltd.

4. Experimental Design

A human breast cancer MDA-MB-231 subcutaneous transplanted tumor model in nude mice was established, and each animal was inoculated with $1\times10^6$ cells.

The following dosages of administration and dosing regimens (Table 3) were designed for the experiment.

TABLE 3

Antitumor effect in the human breast cancer MDA-MB-231 transplanted tumor model in nude mice

| Group | Number of animals | Sample | Route of administration | Dosage (mg · kg$^{-1}$) | Volume of administration (mL · kg$^{-1}$) | Period of administration |
| --- | --- | --- | --- | --- | --- | --- |
| 1 | 5 | physiological saline | IV | N/A | 10 | Q4D × 3 |
| 2 | 5 | irinotecan | IV | 40 | 10 | Q4D × 3 |
| 3 | 5 | nktr-102 | IV | 40 | 10 | Q4D × 3 |
| 4 | 5 | Compound 1 | IV | 40 | 10 | Q4D × 3 |
| 5 | 5 | Compound 2 | IV | 40 | 10 | Q4D × 3 |
| 6 | 5 | Compound 3 | IV | 40 | 10 | Q4D × 3 |
| 7 | 5 | Compound 4 | IV | 40 | 10 | Q4D × 3 |
| 8 | 5 | Compound 5 | IV | 40 | 10 | Q4D × 3 |
| 9 | 5 | Compound 6 | IV | 40 | 10 | Q4D × 3 |
| 10 | 5 | Compound 7 | IV | 40 | 10 | Q4D × 3 |
| 11 | 5 | Compound 8 | IV | 40 | 10 | Q4D × 3 |
| 12 | 5 | Compound 9 | IV | 40 | 10 | Q4D × 3 |
| 13 | 5 | Compound 10 | IV | 40 | 10 | Q4D × 3 |
| 14 | 5 | Compound 11 | IV | 40 | 10 | Q4D × 3 |
| 15 | 5 | Compound 12 | IV | 40 | 10 | Q4D × 3 |
| 16 | 5 | Compound 13 | IV | 40 | 10 | Q4D × 3 |
| 17 | 5 | Compound 14 | IV | 40 | 10 | Q4D × 3 |
| 18 | 5 | Compound 15 | IV | 40 | 10 | Q4D × 3 |
| 19 | 5 | Compound 16 | IV | 40 | 10 | Q4D × 3 |
| 20 | 5 | Compound 17 | IV | 40 | 10 | Q4D × 3 |
| 21 | 5 | Compound 18 | IV | 40 | 10 | Q4D × 3 |
| 22 | 5 | Compound 19 | IV | 40 | 10 | Q4D × 3 |
| 23 | 5 | Compound 20 | IV | 40 | 10 | Q4D × 3 |
| 24 | 5 | Compound 21 | IV | N/A | 10 | Q4D × 3 |
| 25 | 5 | Compound 22 | IV | 40 | 10 | Q4D × 3 |
| 26 | 5 | Compound 23 | IV | 40 | 10 | Q4D × 3 |
| 27 | 5 | Compound 24 | IV | 40 | 10 | Q4D × 3 |
| 28 | 5 | Compound 25 | IV | 40 | 10 | Q4D × 3 |
| 29 | 5 | Compound 26 | IV | 40 | 10 | Q4D × 3 |
| 30 | 5 | Compound 27 | IV | N/A | 10 | Q4D × 3 |
| 31 | 5 | Compound 28 | IV | 40 | 10 | Q4D × 3 |
| 32 | 5 | Compound 29 | IV | 40 | 10 | Q4D × 3 |
| 33 | 5 | Compound 30 | IV | 40 | 10 | Q4D × 3 |
| 34 | 5 | Compound 31 | IV | 40 | 10 | Q4D × 3 |
| 35 | 5 | Compound 32 | IV | 40 | 10 | Q4D × 3 |
| 36 | 5 | Compound 33 | IV | N/A | 10 | Q4D × 3 |
| 37 | 5 | Compound 34 | IV | 40 | 10 | Q4D × 3 |
| 38 | 5 | Compound 35 | IV | 40 | 10 | Q4D × 3 |
| 39 | 5 | Compound 36 | IV | 40 | 10 | Q4D × 3 |
| 40 | 5 | Compound 37 | IV | 40 | 10 | Q4D × 3 |
| 41 | 5 | Compound 38 | IV | 40 | 10 | Q4D × 3 |
| 42 | 5 | Compound 39 | IV | N/A | 10 | Q4D × 3 |
| 43 | 5 | Compound 40 | IV | 40 | 10 | Q4D × 3 |
| 44 | 5 | Compound 41 | IV | 40 | 10 | Q4D × 3 |
| 45 | 5 | Compound 42 | IV | 40 | 10 | Q4D × 3 |

5. Preparation of the Dosing Formulations of the Compounds

The preparation methods were provided by Brightgene Bio-Medical Technology Co., Ltd.

Volume required for a single dose:

20 g (body weight)×10 (animals)×10 mL/kg/1000×1.5=3 mL 5.1 Preparation of the Dosing Formulation of Irinotecan 12.0 mg of irinotecan was weighed, 0.15 mL of 1% lactic acid was added, the drug was dissolved completely by vortexing, and 2.85 mL of 1% aqueous sorbitol solution was then added respectively. The mixture was mixed evenly by vortexing, and the ratio of 1% lactic acid to 1% aqueous sorbitol solution was approximately 5:95 (v/v) in the solution. The concentration of free irinotecan in the solution was 4.0 mg·mL$^{-1}$.

5.2 Preparation of the Dosing Formulation of nktr-102

Before each administration, 88.55 mg of nktr-102 was weighed accurately, 2.3 mL of physiological saline was added, the drug was dissolved completely by vortexing, and the concentration of free irinotecan in the solution was 4.0 mg·mL$^{-1}$.

5.3 Preparation of the Dosing Formulations of Compounds 1 to 5

Before each administration, 113.85 mg of Compound 1 was weighed accurately, 2.3 mL of physiological saline was added, the drug was dissolved completely by vortexing, and the concentration of free irinotecan in the solution was 4.0 mg·mL$^{-1}$.

Before each administration, 109.80 mg of Compound 2 was weighed accurately, 2.3 mL of physiological saline was added, the drug was dissolved completely by vortexing, and the concentration of free irinotecan in the solution was 4.0 mg·mL$^{-1}$.

Before each administration, 113.88 mg of Compound 3 was weighed accurately, 2.3 mL of physiological saline was added, the drug was dissolved completely by vortexing, and the concentration of free irinotecan in the solution was 4.0 mg·mL$^{-1}$.

Before each administration, 111.24 mg of Compound 4 was weighed accurately, 2.3 mL of physiological saline was added, the drug was dissolved completely by vortexing, and the concentration of free irinotecan in the solution was 4.0 mg·mL$^{-1}$.

Before each administration, 105.78 mg of Compound 5 was weighed accurately, 2.3 mL of physiological saline was added, the drug was dissolved completely by vortexing, and the concentration of free irinotecan in the solution was 4.0 mg·mL$^{-1}$.

5.4 Preparation of the Dosing Formulations of Compounds 6 to 10

Before each administration, 113.09 mg of Compound 6 was weighed accurately, 2.3 mL of physiological saline was added, the drug was dissolved completely by vortexing, and the concentration of free SN-38 in the solution was 4.0 mg·mL$^{-1}$.

Before each administration, 109.05 mg of Compound 7 was weighed accurately, 2.3 mL of physiological saline was added, the drug was dissolved completely by vortexing, and the concentration of free SN-38 in the solution was 4.0 mg·mL$^{-1}$.

Before each administration, 113.12 mg of Compound 8 was weighed accurately, 2.3 mL of physiological saline was added, the drug was dissolved completely by vortexing, and the concentration of free SN-38 in the solution was 4.0 mg·mL$^{-1}$.

Before each administration, 110.48 mg of Compound 9 was weighed accurately, 2.3 mL of physiological saline was added, the drug was dissolved completely by vortexing, and the concentration of free SN-38 in the solution was 4.0 mg·mL$^{-1}$.

Before each administration, 105.02 mg of Compound 10 was weighed accurately, 2.3 mL of physiological saline was added, the drug was dissolved completely by vortexing, and the concentration of free SN-38 in the solution was 4.0 mg·mL$^{-1}$.

5.4 Preparation of the Dosing Formulations of Compounds 11 to 15

Before each administration, 112.98 mg of Compound 11 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 108.94 mg of Compound 12 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 113.01 mg of Compound 13 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 110.37 mg of Compound 14 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 104.91 mg of Compound 15 was weighed accurately, 2.3 mL of physiological saline was added, the drug was dissolved completely by vortexing, and the concentration of free 10-hydroxycamptothecin in the solution was 4.0 mg·mL$^{-1}$.

5.5 Preparation of the Dosing Formulations of Compounds 16 to 20

Before each administration, 113.09 mg of Compound 11 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 109.05 mg of Compound 12 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 113.12 mg of Compound 13 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 110.48 mg of Compound 14 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 105.02 mg of Compound 15 was weighed accurately, 2.3 mL of physiological saline was added, the drug was dissolved completely by vortexing, and the concentration of free 10-hydroxycamptothecin in the solution was 4.0 mg·mL$^{-1}$.

5.6 Preparation of the Dosing Formulations of Compounds 21 to 42

The preparation methods were as described above, so that the concentration of the free active agent in the solution was 4.0 mg·mL$^{-1}$.

6. Experimental Methods

MDA-MB-231 cells were cultured in DMEM, which contained 10% fetal bovine serum FBS (GIBCO, USA). The cells were placed in a 37° C. incubator containing 5% $CO_2$ to cultivate.

A subcutaneous tumor xenograft model in nude mice was established by cell inoculation method: tumor cells in logarithmic phase of growth were collected, counted and then resuspended in 1×PBS, and the concentration of the cell suspension was adjusted to 1×10$^7$/mL. 1 mL syringes (4 gauge needle) were used to inoculate the tumor cells to the right back of the nude mice subcutaneously, 1×10$^6$/0.1 mL/mice.

When the tumor volumes reached 100 mm$^3$ to 200 mm$^3$, the animals were grouped randomly according to randomized block method, so that the difference of the tumor volumes between each group was less than 10% of the mean value. There were 5 animals in each group, Day 0 was the day when the animals were grouped, and the animals were administered on the same day when being grouped.

The experimental period lasted for 3 weeks, and the body weights and the tumor sizes of the animals were measured twice a week during the experiment. The clinical symptoms were observed and recorded daily. On the last day of the experiment, the animals were sacrificed, the body weights were weighed, and the tumors were excised, weighed and recorded by photographing.

The operation of all animal experiments strictly adhered to the principles of the use and management of animals. For the calculation of the tumor-related parameters, "Technical guidelines for non-clinical research on cytotoxic antitumor drugs" by Chinese CFDA was referred.

The calculation formula of the tumor volume (TV) was: TV=a×b$^2$/2, wherein a and b represented the measured length and width of the tumor, respectively. The calculation formula of the relative tumor volume (RTV) was: RTV=$V_t$/$V_0$, wherein $V_0$ was the tumor volume measured at the time of grouping and first administration, and $V_t$ was the tumor volume at the time of a measurement. The evaluation indexes of the antitumor activity were the relative tumor proliferation rate (T/C (%)) and the tumor inhibition rate (%), and the calculation formulae were T/C(%)=($T_{RTV}$/$C_{RTV}$)×100%, wherein $T_{RTV}$ was the RTV of a treatment group, and $C_{RTV}$ was the RTV of the negative control group; and tumor inhibition rate (%)=(the average tumor weight of the negative control group−the average tumor weight of a treatment group)/the average tumor weight of the negative control group×100%, respectively.

Body weight change (%) of a tumor-bearing animal was calculated as follows: (the body weight at the time of a measurement−the body weight at the time of grouping)/the body weight at the time of grouping×100.

7. Data Analysis

The experimental data was subjected to calculation and related statistical treatments using Microsoft Office Excel 2007 Software. Unless otherwise specified, the data was represented by mean±standard error (Mean±SE), and t test was adopted for the comparison between two groups.

8. Results and Reports

According to "Technical guidelines for non-clinical research on cytotoxic antitumor drugs" (November 2006) by Chinese CFDA, the treatment was considered to be effective when T/C (%) 40% and p<0.05 according to statistical analysis, as shown in Table 4.

TABLE 4

| | | | | |
|---|---|---|---|---|
| | | Relative tumor proliferation rate T/C (%) | | |
| Group | Sample | Number of animals | Relative tumor volume (RTV) | Relative tumor proliferation rate (% T/C) |
| 1 | blank solvent | 5 | 12.56 | — |
| 2 | irinotecan | 5 | 6.19 | 44.8% |
| 3 | nktr-102 | 5 | 4.46 | 32.2% |
| 4 | Compound 1 | 5 | 1.28* | 9.3%# |
| 5 | Compound 2 | 5 | 1.66* | 12.1%# |
| 6 | Compound 3 | 5 | 1.89* | 13.65%# |
| 7 | Compound 4 | 5 | 1.59* | 11.5%# |
| 8 | Compound 5 | 5 | 1.97* | 14.3%# |
| 9 | Compound 6 | 5 | 1.34* | 9.7%# |
| 10 | Compound 7 | 5 | 1.80* | 13.1%# |
| 11 | Compound 8 | 5 | 2.03* | 14.8%# |
| 12 | Compound 9 | 5 | 1.97* | 14.3%# |
| 13 | Compound 10 | 5 | 1.40* | 10.2%# |
| 14 | Compound 11 | 5 | 1.88* | 13.6%# |
| 15 | Compound 12 | 5 | 1.65* | 11.9# |
| 16 | Compound 13 | 5 | 1.60* | 11.6%# |
| 17 | Compound 14 | 5 | 1.53* | 11.10%# |
| 18 | Compound 15 | 5 | 1.40* | 10.8%# |
| 19 | Compound 16 | 5 | 1.79* | 13.0%# |
| 20 | Compound 17 | 5 | 1.59* | 11.5%# |
| 21 | Compound 18 | 5 | 1.75* | 12.7%# |
| 22 | Compound 19 | 5 | 1.77* | 12.8%# |
| 23 | Compound 20 | 5 | 1.51* | 11.0%# |
| 24 | Compound 21 | 5 | 1.38* | 10.0%# |
| 25 | Compound 22 | 5 | 1.52* | 11.0%# |
| 26 | Compound 23 | 5 | 1.29* | 9.3%# |
| 27 | Compound 24 | 5 | 1.49* | 10.8%# |
| 28 | Compound 25 | 5 | 1.73* | 12.6%# |
| 29 | Compound 26 | 5 | 1.64* | 10.3%# |
| 30 | Compound 27 | 5 | 1.67* | 12.1%# |
| 31 | Compound 28 | 5 | 1.57* | 11.4%# |
| 32 | Compound 29 | 5 | 1.72* | 12.5%# |
| 33 | Compound 30 | 5 | 1.49* | 10.8%# |
| 34 | Compound 31 | 5 | 1.52* | 11.0%# |
| 35 | Compound 32 | 5 | 1.87* | 13.6%# |
| 36 | Compound 33 | 5 | 1.63* | 11.8%# |
| 37 | Compound 34 | 5 | 1.50* | 9.7%# |
| 38 | Compound 35 | 5 | 1.46* | 10.6%# |
| 39 | Compound 36 | 5 | 1.73* | 12.6%# |
| 40 | Compound 37 | 5 | 1.41* | 10.2%# |
| 41 | Compound 38 | 5 | 1.54* | 11.2%# |
| 42 | Compound 39 | 5 | 1.73* | 12.6%# |
| 43 | Compound 40 | 5 | 1.87* | 13.6%# |
| 44 | Compound 41 | 5 | 1.69* | 12.3%# |
| 45 | Compound 42 | 5 | 1.76* | 12.8%# |

*$P < 0.05$, as compared with the RTV of the blank solvent group, irinotecan group and nktr-102 group.
$P < 0.05$, as compared with % T/C of the blank solvent group, irinotecan group and nktr-102 group.

The experimental results showed that the compounds of the present disclosure had good inhibitory effects on human breast cancer MDA-MB-231 transplanted tumor in nude mice, and were superior to irinotecan and nktr-102.

Example 45 Inhibitory Effect in a Human Pancreatic Cancer MIA Paca-2 Xenograft Model in Nude Mice 1. Experimental Purpose The human pancreatic cancer MIA Paca-2 transplanted tumor model in nude mice was used in the study to evaluate the in vivo antitumor activities of Compounds 1 to 42.

2. Experimental Animals
2.1 Animal Species
Mice.
2.2 Strain
BALB/c-nu/nu nude mice.

2.3 Sex
Female.
2.4 Number
300.
2.5. Age
6 to 8 week old.
2.6. Body weight
20 to 22 g±20% of the average body weight.
2.7. Animal Source (Supplier)
Shanghai Xipuer-Bikai Experimental Animal Co., Ltd. (BK), license number: SCXK (Shanghai) 2008-0016.
2.8. Management of the Experimental Animals
All experimental animals were housed in an SPF-level laboratory.
2.8.1 Identification Method of Animal Identity
Each mice cage had an identification card with information such as the experimental number, experimental group, name(s) of experimenter(s), and the strain and sex of mice. The mice were marked with earrings.
2.8.2 Random grouping After the tumor volumes reached 150 $mm^3$ to 200 $mm^3$, the animals were grouped using randomized block method with 5 mice in each group, ensuring the tumor volumes and the body weights of the mice were uniform between each group. The difference between the mean value of the tumor volumes in each group and the mean value of the tumor volumes of all experimental animals was no more than ±10%. 2.8.3 Operating and managing practice
The operation and management of all experimental animals strictly adhered to the guideline of the use and management of experimental animals.
2.8.4 Feeding Conditions
Living conditions: IVC system, 5 animals per cage
Temperature: 25° C.±1° C.
Humidity: 65%±10%
Illumination: 12 h light/dark cycle
2.8.5 Feed
Irradiated feed for rat and mice, purchased from Beijing Keao Xieli Feed Co., Ltd. The animals had free access to food.
2.8.6 Drinking Water
City tap water, used for drinking after being filtered and autoclaved.
2.8.7 Bedding
Corn cobs (Shanghai Maoshengyan Biologic Science & Technology Co., Ltd.) were used after being autoclaved. Beddings were changed twice a week.

2.8.8 Acclimation Period
The mice were given at least one week of acclimation period for the environment before the experiment.
3. Experimental Materials
3.1 Test Drugs
Irinotecan (bulk drug) and nktr-102 (bulk drug) were obtained by purchasing, and Compounds 1 to 42 were all provided by Brightgene Bio-Medical Technology Co., Ltd.
3.2 Other Chemical Reagents and Materials
3.2.1 Physiological Saline
Physiological saline was purchased from Shanghai Huayuan Changfu Pharmaceutical (Group) Co., Ltd. (Shanghai, China).
3.2.2 Sterile Syringe
1 mL sterile syringes were purchased from Shanghai Kindly Enterprise Development Group Co., Ltd (Shanghai, China).
3.2.3 Cell Strain
Human pancreatic cancer MIA Paca-2 cells were purchased from Shanghai Institute of Biochemistry and Cell Biology of Chinese Academy of Sciences.
MIA Paca-2 cells were cultured in DMEM culture medium (GIBCO, USA) containing 10% fetal bovine serum FBS (GIBCO, USA) and 2.5% HS, and cultured in a 37° C. incubator containing 5% $CO_2$.
3.2.4 Matrigel (BD Matrigel)
Matrigel was purchased from Becton, Dickinson and Company (BD), the USA.
3.3 Instruments
Biosafe cabinet (model: AC2-6E1), purchased from ESCO;
water jacketed $CO_2$ cell incubator (model: 3111), purchased from Thermo Scientific Forma;
inverted microscope (model: CKX41SF), purchased from Olympus;
wlectric suction apparatus (model: YX930D), purchased from Shanghai Medical Instruments (Group) Co., Ltd.;
balance (METTLER-TOLEDOAB135-S), purchased from METTLER-TOLEDO;
low speed centrifuge (model: LD5-2A), purchased from Beijing Lab Centrifuge Co., Ltd.;
digimatic caliper (model: SF2000), purchased from Guilin Guanglu Measuring Instrument Co., Ltd.
4. Experimental Design
A human pancreatic cancer MIA Paca-2 subcutaneous transplanted tumor model in nude mice was established, and each animal was inoculated with $3\times10^6$ cells.
The following dosages of administration and dosing regimen were designed for the experiment (Table 5).

TABLE 5

Antitumor effect in the human pancreatic cancer MIA Paca-2 transplanted tumor model in nude mice
Tumor cell strain: MIA Paca-2; a total of 225 animals were inoculated.

| Group | Number of animals | Sample | Route of administration | Dosage (mg · $kg^{-1}$) | Volume of administration (mL · $kg^{-1}$) | Period of administration |
|---|---|---|---|---|---|---|
| 1 | 5 | physiological saline | IV | N/A | 10 | Q4D × 3 |
| 2 | 5 | irinotecan | IV | 40 | 10 | Q4D × 3 |
| 3 | 5 | nktr-102 | IV | 40 | 10 | Q4D × 3 |
| 4 | 5 | Compound 1 | IV | 40 | 10 | Q4D × 3 |
| 5 | 5 | Compound 2 | IV | 40 | 10 | Q4D × 3 |
| 6 | 5 | Compound 3 | IV | 40 | 10 | Q4D × 3 |
| 7 | 5 | Compound 4 | IV | 40 | 10 | Q4D × 3 |
| 8 | 5 | Compound 5 | IV | 40 | 10 | Q4D × 3 |
| 9 | 5 | Compound 6 | IV | 40 | 10 | Q4D × 3 |
| 10 | 5 | Compound 7 | IV | 40 | 10 | Q4D × 3 |
| 11 | 5 | Compound 8 | IV | 40 | 10 | Q4D × 3 |

TABLE 5-continued

Antitumor effect in the human pancreatic cancer MIA Paca-2 transplanted tumor model in nude mice
Tumor cell strain: MIA Paca-2; a total of 225 animals were inoculated.

| Group | Number of animals | Sample | Route of administration | Dosage (mg·kg$^{-1}$) | Volume of administration (mL·kg$^{-1}$) | Period of administration |
|---|---|---|---|---|---|---|
| 12 | 5 | Compound 9 | IV | 40 | 10 | Q4D × 3 |
| 13 | 5 | Compound 10 | IV | 40 | 10 | Q4D × 3 |
| 14 | 5 | Compound 11 | IV | 40 | 10 | Q4D × 3 |
| 15 | 5 | Compound 12 | IV | 40 | 10 | Q4D × 3 |
| 16 | 5 | Compound 13 | IV | 40 | 10 | Q4D × 3 |
| 17 | 5 | Compound 14 | IV | 40 | 10 | Q4D × 3 |
| 18 | 5 | Compound 15 | IV | 40 | 10 | Q4D × 3 |
| 19 | 5 | Compound 16 | IV | 40 | 10 | Q4D × 3 |
| 20 | 5 | Compound 17 | IV | 40 | 10 | Q4D × 3 |
| 21 | 5 | Compound 18 | IV | 40 | 10 | Q4D × 3 |
| 22 | 5 | Compound 19 | IV | 40 | 10 | Q4D × 3 |
| 23 | 5 | Compound 20 | IV | 40 | 10 | Q4D × 3 |
| 24 | 5 | Compound 21 | IV | N/A | 10 | Q4D × 3 |
| 25 | 5 | Compound 22 | IV | 40 | 10 | Q4D × 3 |
| 26 | 5 | Compound 23 | IV | 40 | 10 | Q4D × 3 |
| 27 | 5 | Compound 24 | IV | 40 | 10 | Q4D × 3 |
| 28 | 5 | Compound 25 | IV | 40 | 10 | Q4D × 3 |
| 29 | 5 | Compound 26 | IV | 40 | 10 | Q4D × 3 |
| 30 | 5 | Compound 27 | IV | N/A | 10 | Q4D × 3 |
| 31 | 5 | Compound 28 | IV | 40 | 10 | Q4D × 3 |
| 32 | 5 | Compound 29 | IV | 40 | 10 | Q4D × 3 |
| 33 | 5 | Compound 30 | IV | 40 | 10 | Q4D × 3 |
| 34 | 5 | Compound 31 | IV | 40 | 10 | Q4D × 3 |
| 35 | 5 | Compound 32 | IV | 40 | 10 | Q4D × 3 |
| 36 | 5 | Compound 33 | IV | N/A | 10 | Q4D × 3 |
| 37 | 5 | Compound 34 | IV | 40 | 10 | Q4D × 3 |
| 38 | 5 | Compound 35 | IV | 40 | 10 | Q4D × 3 |
| 39 | 5 | Compound 36 | IV | 40 | 10 | Q4D × 3 |
| 40 | 5 | Compound 37 | IV | 40 | 10 | Q4D × 3 |
| 41 | 5 | Compound 38 | IV | 40 | 10 | Q4D × 3 |
| 42 | 5 | Compound 39 | IV | N/A | 10 | Q4D × 3 |
| 43 | 5 | Compound 40 | IV | 40 | 10 | Q4D × 3 |
| 44 | 5 | Compound 41 | IV | 40 | 10 | Q4D × 3 |
| 45 | 5 | Compound 42 | IV | 40 | 10 | Q4D × 3 |

5. Preparation of the Dosing Formulations of the Compounds

The preparation methods were provided by Brightgene Bio-Medical Technology Co., Ltd.

Volume required for a single dose:

20 g (body weight)×10 (animals)×10 mL/kg/1000×1.5=3 mL 5.1 Preparation of the Dosing Formulation of Irinotecan 12.0 mg of irinotecan was weighed, 0.15 mL of 1% lactic acid was added, the drug was dissolved completely by vortexing, and 2.85 mL of 1% aqueous sorbitol solution was then added respectively. The mixture was mixed evenly by vortexing, and the ratio of 1% lactic acid to 1% aqueous sorbitol solution was approximately 5:95 (v/v) in the solution. The concentration of free irinotecan in the solution was 4.0 mg·mL$^{-1}$.

5.2 Preparation of the Dosing Formulation of nktr-102

Before each administration, 88.55 mg of nktr-102 was weighed accurately, 2.3 mL of physiological saline was added, the drug was dissolved completely by vortexing, and the concentration of free irinotecan in the solution was 4.0 mg·mL$^{-1}$.

5.3 Preparation of the Dosing Formulations of Compounds 1 to 5

Before each administration, 113.85 mg of Compound 1 was weighed accurately, 2.3 mL of physiological saline was added, the drug was dissolved completely by vortexing, and the concentration of free irinotecan in the solution was 4.0 mg·mL$^{-1}$.

Before each administration, 109.80 mg of Compound 2 was weighed accurately, 2.3 mL of physiological saline was added, the drug was dissolved completely by vortexing, and the concentration of free irinotecan in the solution was 4.0 mg·mL$^{-1}$.

Before each administration, 113.88 mg of Compound 3 was weighed accurately, 2.3 mL of physiological saline was added, the drug was dissolved completely by vortexing, and the concentration of free irinotecan in the solution was 4.0 mg·mL$^{-1}$.

Before each administration, 111.24 mg of Compound 4 was weighed accurately, 2.3 mL of physiological saline was added, the drug was dissolved completely by vortexing, and the concentration of free irinotecan in the solution was 4.0 mg·mL$^{-1}$.

Before each administration, 105.78 mg of Compound 5 was weighed accurately, 2.3 mL of physiological saline was added, the drug was dissolved completely by vortexing, and the concentration of free irinotecan in the solution was 4.0 mg·mL$^{-1}$.

5.4 Preparation of the Dosing Formulations of Compounds 6 to 10

Before each administration, 113.09 mg of Compound 6 was weighed accurately 2.3 mL of physiological saline was added, the drug was dissolved completely by vortexing, and the concentration of free SN-38 in the solution was 4.0 mg·mL$^{-1}$.

Before each administration, 109.05 mg of Compound 7 was weighed accurately, 2.3 mL of physiological saline was added, the drug was dissolved completely by vortexing, and the concentration of free SN-38 in the solution was 4.0 mg·mL$^{-1}$.

Before each administration, 113.12 mg of Compound 8 was weighed accurately, 2.3 mL of physiological saline was added, the drug was dissolved completely by vortexing, and the concentration of free SN-38 in the solution was 4.0 mg·mL$^{-1}$.

Before each administration, 110.48 mg of Compound 9 was weighed accurately, 2.3 mL of physiological saline was added, the drug was dissolved completely by vortexing, and the concentration of free SN-38 in the solution was 4.0 mg·mL$^{-1}$.

Before each administration, 105.02 mg of Compound 10 was weighed accurately, 2.3 mL of physiological saline was added, the drug was dissolved completely by vortexing, and the concentration of free SN-38 in the solution was 4.0 mg·mL$^{-1}$.

5.5 Preparation of the Dosing Formulations of Compounds 11 to 15

Before each administration, 112.98 mg of Compound 11 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 108.94 mg of Compound 12 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 113.01 mg of Compound 13 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 110.37 mg of Compound 14 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 104.91 mg of Compound 15 was weighed accurately, 2.3 mL of physiological saline was added, the drug was dissolved completely by vortexing, and the concentration of free 10-hydroxycamptothecin in the solution was 4.0 mg·mL$^{-1}$.

5.6 Preparation of the Dosing Formulations of Compounds 16 to 20

Before each administration, 113.09 mg of Compound 11 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 109.05 mg of Compound 12 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 113.12 mg of Compound 13 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 110.48 mg of Compound 14 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 105.02 mg of Compound 15 was weighed accurately, 2.3 mL of physiological saline was added, the drug was dissolved completely by vortexing, and the concentration of free 10-hydroxycamptothecin in the solution was 4.0 mg·mL$^{-1}$.

5.7 Preparation of the Dosing Formulations of Compounds 21 to 42

The preparation methods were as described above, so that the concentration of the free active agent in the solution was 4.0 mg·mL$^{-1}$.

6. Experimental Methods

MIA Paca-2 cells were cultured in DMEM, which contained 10% fetal bovine serum FBS (GIBCO, USA) and 2.5% HS. The cells were placed in a 37° C. incubator containing 5% $CO_2$ to cultivate.

A subcutaneous tumor xenograft model in nude mice was established by cell inoculation method: tumor cells in logarithmic phase of growth were collected, counted and then resuspended in 1×PBS, and the concentration of the cell suspension was adjusted to $3\times10^7$/mL. 1 mL syringes (4 gauge needle) were used to inoculate the tumor cells to the right back of the nude mice subcutaneously, $3\times10^6$/0.1 mL/mice.

When the tumor volumes reached 100 mm$^3$ to 200 mm$^3$, the animals were grouped randomly according to randomized block method, so that the difference of the tumor volumes between each group was less than 10% of the mean value. There were 5 animals in each group, Day 0 was the day when the animals were grouped, and the animals were administered on the same day when being grouped.

The experimental period lasted for 3 weeks, and the body weights and the tumor sizes of the animals were measured twice a week during the experiment. The clinical symptoms were observed and recorded daily. On the last day of the experiment, the animals were sacrificed, the body weights were weighed, and the tumors were excised, weighed and recorded by photographing.

The operation of all animal experiments strictly adhered to the principles of the use and management of animals. For the calculation of the tumor-related parameters, "Technical guidelines for non-clinical research on cytotoxic antitumor drugs" by Chinese SFDA was referred.

The calculation formula of the tumor volume (TV) was: TV=a×b$^2$/2, wherein a and b represented the measured length and width of the tumor, respectively. The calculation formula of the relative tumor volume (RTV) was: RTV=V$_t$/V$_0$, wherein V$_0$ was the tumor volume measured at the time of grouping and first administration, and V$_t$ was the tumor volume at the time of a measurement. The evaluation indexes of the antitumor activity were the relative tumor proliferation rate (T/C (%)) and the tumor inhibition rate (%), the calculation formulae were T/C (%)=(T$_{RTV}$/C$_{RTV}$)× 100%, wherein T$_{RTV}$ was the RTV of a treatment group, and C$_{RTV}$ was the RTV of the negative control group; and tumor inhibition rate (%)=(the average tumor weight of the negative control group−the average tumor weight of a treatment group)/the average tumor weight of the negative control group×100%, respectively.

Body weight change (%) of a tumor-bearing animal was calculated as follows: (the body weight at the time of a measurement−the body weight at the time of grouping)/the body weight at the time of grouping×100.

According to "Technical guidelines for non-clinical research on cytotoxic antitumor drugs" (November 2016) by Chinese SFDA, the treatment was considered to be effective when T/C (%) 40% and P<0.05 according to statistical analysis.

7. Data Analysis

The experimental data was subjected to calculation and related statistical treatments using Microsoft Office Excel 2007 Software. Unless otherwise specified, the data was represented by mean±standard error (Mean±SE), t test was adopted for the comparison between groups, and P<0.05 was considered as a significant difference.

8. Results and Reports

According to "Technical guidelines for non-clinical research on cytotoxic antitumor drugs" (November 2006) by Chinese CFDA, the treatment was considered to be effective when T/C (%) 40% and P<0.05 according to statistical analysis, as shown in Table 6.

TABLE 6

Relative tumor proliferation rate T/C (%)

| Group | Sample | Number of animals | Relative tumor volume (RTV) | Relative tumor proliferation rate (% T/C) |
|---|---|---|---|---|
| 1 | blank solvent | 5 | 11.95 | — |
| 2 | irinotecan | 5 | 7.79 | 59.4% |
| 3 | nktr-102 | 5 | 5.42 | 37.5% |
| 4 | Compound 1 | 5 | 2.21* | 12.1%[#] |
| 5 | Compound 2 | 5 | 2.65* | 14.5%[#] |
| 6 | Compound 3 | 5 | 2.57* | 13.3%[#] |
| 7 | Compound 4 | 5 | 2.06* | 10.6%[#] |
| 8 | Compound 5 | 5 | 2.68* | 13.8%[#] |
| 9 | Compound 6 | 5 | 3.21* | 16.6%[#] |
| 10 | Compound 7 | 5 | 2.25* | 11.6%[#] |
| 11 | Compound 8 | 5 | 2.48* | 12.8%[#] |
| 12 | Compound 9 | 5 | 2.98* | 15.3%[#] |
| 13 | Compound 10 | 5 | 2.68* | 13.8%[#] |
| 14 | Compound 11 | 5 | 2.36* | 12.1%[#] |
| 15 | Compound 12 | 5 | 2.48* | 12.71[#] |
| 16 | Compound 13 | 5 | 2.73* | 14.0%[#] |
| 17 | Compound 14 | 5 | 2.24* | 11.5%[#] |
| 18 | Compound 15 | 5 | 2.69* | 13.8%[#] |
| 19 | Compound 16 | 5 | 3.23* | 16.6%[#] |
| 20 | Compound 17 | 5 | 2.75* | 14.1%[#] |
| 21 | Compound 18 | 5 | 2.48* | 12.7%[#] |
| 22 | Compound 19 | 5 | 2.78* | 14.2%[#] |
| 23 | Compound 20 | 5 | 2.67* | 13.6%[#] |
| 24 | Compound 21 | 5 | 2.49* | 12.1%[#] |
| 25 | Compound 22 | 5 | 2.73* | 14.9%[#] |
| 26 | Compound 23 | 5 | 2.39* | 13.1%[#] |
| 27 | Compound 24 | 5 | 2.84* | 15.5%[#] |
| 28 | Compound 25 | 5 | 3.07* | 16.8%[#] |
| 29 | Compound 26 | 5 | 2.92* | 16.0%[#] |
| 30 | Compound 27 | 5 | 2.59* | 14.2%[#] |
| 31 | Compound 28 | 5 | 2.67* | 14.6%[#] |
| 32 | Compound 29 | 5 | 2.74* | 15.0%[#] |
| 33 | Compound 30 | 5 | 2.68* | 14.7%[#] |
| 34 | Compound 31 | 5 | 2.43* | 13.3%[#] |
| 35 | Compound 32 | 5 | 2.79* | 15.3%[#] |
| 36 | Compound 33 | 5 | 3.13* | 17.1%[#] |
| 37 | Compound 34 | 5 | 2.74* | 15.0%[#] |
| 38 | Compound 35 | 5 | 2.57* | 14.1%[#] |
| 39 | Compound 36 | 5 | 2.65* | 14.5%[#] |
| 40 | Compound 37 | 5 | 2.76* | 15.1%[#] |
| 41 | Compound 38 | 5 | 2.91* | 15.9%[#] |
| 42 | Compound 39 | 5 | 2.73* | 14.9%[#] |
| 43 | Compound 40 | 5 | 2.93* | 16.0%[#] |
| 44 | Compound 41 | 5 | 2.84* | 15.5%[#] |
| 45 | Compound 42 | 5 | 2.91* | 15.9%[#] |

*P < 0.05, as compared with the RTV of the blank solvent group, irinotecan group and nktr-102 group.
[#]P < 0.05, as compared with % T/C of the blank solvent group, irinotecan group and nktr-102 group.

The experimental results showed that the compounds of the present disclosure had good inhibitory effects on the human pancreatic cancer MIA Paca-2 transplanted tumor in nude mice, and were superior to irinotecan and nktr-102.

Example 46 Inhibitory Effect on In Vivo Tumor Growth in a Human Gastric Cancer NCI-N87 Cell Strain Transplanted Model in Nude Mice 1. Experimental Purpose The inhibitory effects of the test compounds 1 to 42 on in vivo tumor growth in the human gastric cancer NCI-N87 cell strain transplanted tumor model in nude mice were evaluated.

2. Experimental Materials 2.1 Test Articles

Irinotecan (bulk drug), SN-38, 10-hydroxycamptothecin, rubitecan, and nktr-102 were obtained by purchasing, and Compounds 1 to 42 were all provided by Brightgene Bio-Medical Technology Co., Ltd.

2.2 Reagents

RPMI-1640 liquid culture medium, fetal bovine serum (FBS), trypsin, penicillin-streptomycin, and physiological saline.

2.3 Experimental Animals

Female BALB/c nude mice (number of animals: 150, weeks of age: 6 to 8 weeks) were purchased from Beijing Vital River Laboratory Animal Technology Co., Ltd., housed in an SPF animal room in Suzhou Shengsu New Drug Development Co., Ltd., the temperature was 20° C. to 25° C., the relative humidity was 40% to 70%, and the light and dark were respectively 12 h. The animals had free access to water and food. After about one week of normal feeding, upon a veterinary inspection, mice with good physical signs and conditions could be selected for the experiment. A marking pen was used to mark the base of the tails of the animals before the grouping, and each animal was marked by ear clipping after the grouping.

2.4 Transplantable Tumor Cell Strain

Human gastric cancer cell NCI-N87, derived from Cell Bank of Committee on Type Culture Collection of Chinese Academy of Science (CAS, stored frozen in liquid nitrogen in the laboratory).

3 Experimental Methods 3.1 Culture of NCI-N87 Cells

Under a culture condition of 5% $CO_2$ and 37° C., NCI-N87 cells were subjected to conventional cell cultivation in RPMI-1640 liquid culture medium containing 10% fetal bovine serum, digested with 0.25% trypsin, and passaged. According to the condition of cell growth, the cells were passaged once or twice every week, and were passaged in a ratio of 1:2 to 1:6.

3.2 Preparation of the Animal Model

NCI-N87 cells in logarithmic phase of growth were collected. The cells were resuspended in RPMI-1640 culture medium free of serum after being counted, and the concentration of the cells was adjusted to $5 \times 10^7$ cells/mL. The cells were charged into a 50 mL centrifuge tube after being pipetted with a pipettor to make them evenly dispersed, and the centrifuge tube was placed in an ice box. Cell suspension was aspirated with a 1 mL syringe, and injected subcutaneously to the anterior right armpit of the nude mice. Each animal was inoculated with 100 µL ($5 \times 10^6$ cells/animal), and the NCI-N87 transplanted tumor model in nude mice was established. Animal status and the condition of tumor growth were observed regularly after inoculation, an electronic vernier caliper was used to measure the tumor diameters, the data was directly input to an Excel spreadsheet, and the tumor volumes were calculated. When the tumor volumes reached 100 mm$^3$ to 300 mm$^3$, 225 animals with good health condition and similar tumor volume were selected and divided into 45 groups using randomized block method (n=5). The tumor diameters were measured twice a week after the initiation of the experiment, the tumor volumes were calculated, and the body weights of the animals were weighed and recorded at the same time.

The calculation formula of the tumor volume (TV) was as follows:

$$TV(mm^3) = l \times w^2 / 2$$

wherein l represented the long diameter of a tumor (mm), and w represented the short diameter of a tumor (mm).

3.3 Preparation of the Solvent 0.5 g of sorbitol was weighed and charged into a 50 mL centrifuge tube, 50 mL of water for injection was added to the centrifuge tube, and the solid substance was dissolved completely by vortexing, so that an aqueous sorbitol solution (w/v) with a concentration of 1% was formulated. The solution was stored in a refrigerator at 4° C. until use.

3.4 Preparation of the Dosing Formulations 3.4.1 Preparation of the Dosing Formulation of Irinotecan 12.0 mg of irinotecan was weighed, 0.15 mL of 1% lactic acid was added, the drug was dissolved completely by vortexing, and 2.85 mL of 1% aqueous sorbitol solution was then added respectively. The mixture was mixed evenly by vortexing, and the ratio of 1% lactic acid to 1% aqueous sorbitol solution was approximately 5:95 (v/v) in the solution. The concentration of free irinotecan in the solution was 4.0 mg·mL$^{-1}$.

3.4.2 Preparation of the Dosing Formulation of nktr-102

Before each administration, 88.55 mg of nktr-102 was weighed accurately, 2.3 mL of physiological saline was added, the drug was dissolved completely by vortexing, and the concentration of free irinotecan in the solution was 4.0 mg·mL$^{-1}$.

3.4.3 Preparation of the Dosing Formulations of Compounds 1 to 5

Before each administration, 113.85 mg of Compound 1 was weighed accurately, 2.3 mL of physiological saline was added, the drug was dissolved completely by vortexing, and the concentration of free irinotecan in the solution was 4.0 mg·mL$^{-1}$.

Before each administration, 109.80 mg of Compound 2 was weighed accurately, 2.3 mL of physiological saline was added, the drug was dissolved completely by vortexing, and the concentration of free irinotecan in the solution was 4.0 mg·mL$^{-1}$.

Before each administration, 113.88 mg of Compound 3 was weighed accurately, 2.3 mL of physiological saline was added, the drug was dissolved completely by vortexing, and the concentration of free irinotecan in the solution was 4.0 mg·mL$^{-1}$.

Before each administration, 111.24 mg of Compound 4 was weighed accurately, 2.3 mL of physiological saline was added, the drug was dissolved completely by vortexing, and the concentration of free irinotecan in the solution was 4.0 mg·mL$^{-1}$.

Before each administration, 105.78 mg of Compound 5 was weighed accurately, 2.3 mL of physiological saline was added, the drug was dissolved completely by vortexing, and the concentration of free irinotecan in the solution was 4.0 mg·mL$^{-1}$.

3.4.4 Preparation of the Dosing Formulations of Compounds 6 to 10

Before each administration, 113.09 mg of Compound 6 was weighed accurately, 2.3 mL of physiological saline was added, the drug was dissolved completely by vortexing, and the concentration of free SN-38 in the solution was 4.0 mg·mL$^{-1}$.

Before each administration, 109.05 mg of Compound 7 was weighed accurately, 2.3 mL of physiological saline was added, the drug was dissolved completely by vortexing, and the concentration of free SN-38 in the solution was 4.0 mg·mL$^{-1}$.

Before each administration, 113.12 mg of Compound 8 was weighed accurately, 2.3 mL of physiological saline was added, the drug was dissolved completely by vortexing, and the concentration of free SN-38 in the solution was 4.0 mg·mL$^{-1}$.

Before each administration, 110.48 mg of Compound 9 was weighed accurately, 2.3 mL of physiological saline was added, the drug was dissolved completely by vortexing, and the concentration of free SN-38 in the solution was 4.0 mg·mL$^{-1}$.

Before each administration, 105.02 mg of Compound 10 was weighed accurately, 2.3 mL of physiological saline was added, the drug was dissolved completely by vortexing, and the concentration of free SN-38 in the solution was 4.0 mg·mL$^{-1}$.

3.4.5 Preparation of the Dosing Formulations of Compounds 11 to 15

Before each administration, 112.98 mg of Compound 11 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 108.94 mg of Compound 12 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 113.01 mg of Compound 13 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 110.37 mg of Compound 14 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 104.91 mg of Compound 15 was weighed accurately, 2.3 mL of physiological saline was added, the drug was dissolved completely by vortexing, and the concentration of free 10-hydroxycamptothecin in the solution was 4.0 mg·mL$^{-1}$.

3.4.6 Preparation of the Dosing Formulations of Compounds 16 to 20

Before each administration, 113.09 mg of Compound 11 was weighed accurately, 2.3 mL of physiological saline was added, the drug was dissolved completely by vortexing, and the concentration of free rubitecan in the solution was 4.0 mg·mL$^{-1}$.

Before each administration, 109.05 mg of Compound 12 was weighed accurately, 2.3 mL of physiological saline was added, the drug was dissolved completely by vortexing, and the concentration of free rubitecan in the solution was 4.0 mg·mL$^{-1}$.

Before each administration, 113.12 mg of Compound 13 was weighed accurately, 2.3 mL of physiological saline was added, the drug was dissolved completely by vortexing, and the concentration of free rubitecan in the solution was 4.0 mg·mL$^{-1}$.

Before each administration, 110.48 mg of Compound 14 was weighed accurately, 2.3 mL of physiological saline was added, the drug was dissolved completely by vortexing, and the concentration of free rubitecan in the solution was 4.0 mg·mL$^{-1}$.

Before each administration, 105.02 mg of Compound 15 was weighed accurately, 2.3 mL of physiological saline was added, the drug was dissolved completely by vortexing, and the concentration of free rubitecan in the solution was 4.0 mg·mL$^{-1}$.

3.4.7 Preparation of the Dosing Formulations of Compounds 21 to 42

The preparation methods were as described above, so that the concentration of the free active agent in the solution was 4.0 mg·mL$^{-1}$.

3.5 Grouping of Animals and Administration

The grouping of animals and the dosing regimens were as shown in Table 7.

Groups with irinotecan as the active agent (Groups 1 to 8). The first administration was initiated on the day of grouping, the experiment was ended after 21 days, and the volumes of administration were all 10 mL·kg$^{-1}$. Group 1 was a solvent control group, and was given blank solvent by intravenous injection via tail once every 4 days for a total of 3 times (Q4D×3). Groups 2 to 8 were given irinotecan, nktr-102 and Compounds 1 to 5 as test samples by intravenous injection via tail, respectively, and the dosages of administration were all 40 mg·kg$^{-1}$ (calculated in terms of the content of irinotecan), Q4D×3.

Groups with SN-38 as the active agent (Groups 9 to 13). The first administration was initiated on the day of grouping, the experiment was ended after 21 days, and the volumes of administration were all 10 mL·kg$^{-1}$. Groups 9 to 13 were given Compounds 6 to 10 as test samples by intravenous injection via tail, respectively, and the dosages of administration were all 40 mg·kg$^{-1}$ (calculated in terms of the content of SN-38), Q4D×3.

Groups with 10-hydroxycamptothecin as the active agent (Groups 14 to 18). The first administration was initiated on the day of grouping, the experiment was ended after 21 days, and the volumes of administration were all 10 mL·kg$^{-1}$. Groups 14 to 18 were given Compounds 11 to 15 as test samples by intravenous injection via tail, respectively, and the dosages of administration were all 40 mg·kg$^{-1}$ (calculated in terms of the content of 10-hydroxycamptothecin), Q4D×3.

Groups with rubitecan as the active agent (Groups 19 to 23). The first administration was initiated on the day of grouping, the experiment was ended after 21 days, and the volumes of administration were all 10 mL·kg$^{-1}$. Groups 19 to 23 were given Compounds 16 to 20 as test samples by intravenous injection via tail, respectively, and the dosages of administration were all 40 mg·kg$^{-1}$ (calculated in terms of the content of rubitecan), Q4D×3.

The modes of administration of Groups 24 to 25 were as described above.

TABLE 7

Dosing regimens of the pharmacodynamic experiments in transplanted tumor model in nude mice

| Group | Sample | Number of animals | Dosage (mg · kg$^{-1}$) | Volume of administration (mL · kg$^{-1}$) | Route of administration | Period of administration |
|---|---|---|---|---|---|---|
| 1 | blank solvent | 5 | — | 10 | IV | Q4D × 3 |
| 2 | irinotecan | 5 | 40 | 10 | IV | Q4D × 3 |
| 3 | nktr-102 | 5 | 40 | 10 | IV | Q4D × 3 |
| 4 | Compound 1 | 5 | 40 | 10 | IV | Q4D × 3 |
| 5 | Compound 2 | 5 | 40 | 10 | IV | Q4D × 3 |
| 6 | Compound 3 | 5 | 40 | 10 | IV | Q4D × 3 |
| 7 | Compound 4 | 5 | 40 | 10 | IV | Q4D × 3 |
| 8 | Compound 5 | 5 | 40 | 10 | IV | Q4D × 3 |
| 9 | Compound 6 | 5 | 40 | 10 | IV | Q4D × 3 |
| 10 | Compound 7 | 5 | 40 | 10 | IV | Q4D × 3 |
| 11 | Compound 8 | 5 | 40 | 10 | IV | Q4D × 3 |
| 12 | Compound 9 | 5 | 40 | 10 | IV | Q4D × 3 |
| 13 | Compound 10 | 5 | 40 | 10 | IV | Q4D × 3 |
| 14 | Compound 11 | 5 | 40 | 10 | IV | Q4D × 3 |
| 15 | Compound 12 | 5 | 40 | 10 | IV | Q4D × 3 |
| 16 | Compound 13 | 5 | 40 | 10 | IV | Q4D × 3 |
| 17 | Compound 14 | 5 | 40 | 10 | IV | Q4D × 3 |
| 18 | Compound 15 | 5 | 40 | 10 | IV | Q4D × 3 |
| 19 | Compound 16 | 5 | 40 | 10 | IV | Q4D × 3 |
| 20 | Compound 17 | 5 | 40 | 10 | IV | Q4D × 3 |
| 21 | Compound 18 | 5 | 40 | 10 | IV | Q4D × 3 |
| 22 | Compound 19 | 5 | 40 | 10 | IV | Q4D × 3 |
| 23 | Compound 20 | 5 | 40 | 10 | IV | Q4D × 3 |
| 24 | Compound 21 | 5 | 40 | 10 | IV | Q4D × 3 |
| 25 | Compound 22 | 5 | 40 | 10 | IV | Q4D × 3 |
| 26 | Compound 23 | 5 | 40 | 10 | IV | Q4D × 3 |
| 27 | Compound 24 | 5 | 40 | 10 | IV | Q4D × 3 |
| 28 | Compound 25 | 5 | 40 | 10 | IV | Q4D × 3 |
| 29 | Compound 26 | 5 | 40 | 10 | IV | Q4D × 3 |
| 30 | Compound 27 | 5 | 40 | 10 | IV | Q4D × 3 |
| 31 | Compound 28 | 5 | 40 | 10 | IV | Q4D × 3 |
| 32 | Compound 29 | 5 | 40 | 10 | IV | Q4D × 3 |
| 33 | Compound 30 | 5 | 40 | 10 | IV | Q4D × 3 |
| 34 | Compound 31 | 5 | 40 | 10 | IV | Q4D × 3 |
| 35 | Compound 32 | 5 | 40 | 10 | IV | Q4D × 3 |
| 36 | Compound 33 | 5 | 40 | 10 | IV | Q4D × 3 |
| 37 | Compound 34 | 5 | 40 | 10 | IV | Q4D × 3 |
| 38 | Compound 35 | 5 | 40 | 10 | IV | Q4D × 3 |

TABLE 7-continued

Dosing regimens of the pharmacodynamic experiments in transplanted tumor model in nude mice

| Group | Sample | Number of animals | Dosage (mg · kg$^{-1}$) | Volume of administration (mL · kg$^{-1}$) | Route of administration | Period of administration |
|---|---|---|---|---|---|---|
| 39 | Compound 36 | 5 | 40 | 10 | IV | Q4D × 3 |
| 40 | Compound 37 | 5 | 40 | 10 | IV | Q4D × 3 |
| 41 | Compound 38 | 5 | 40 | 10 | IV | Q4D × 3 |
| 42 | Compound 39 | 5 | 40 | 10 | IV | Q4D × 3 |
| 43 | Compound 40 | 5 | 40 | 10 | IV | Q4D × 3 |
| 44 | Compound 41 | 5 | 40 | 10 | IV | Q4D × 3 |
| 45 | Compound 42 | 5 | 40 | 10 | IV | Q4D × 3 |

3.6 End of the Experiment

After the experiment was ended, the animals were euthanized ($CO_2$) after the body weights were weighed and the tumor diameters were measured. The tumor tissues were excised and weighed, and the tumor weight inhibition rates were calculated. After being weighed, the tumor tissues were transferred to a refrigerator below −70° C. for subsequent analysis.

4. Data Recording and Calculation Formulas

The calculation formula of the relative tumor volume (RTV) was:

$$RTV = TV_t / TV_{initial}$$

wherein $TV_{initial}$ was the tumor volume measured at the time of grouping and first administration, and $TV_t$ was the tumor volume at each measurement during administration.

The calculation formula of the relative tumor proliferation rate (% T/C) was:

$$\% T/C = 100\% \times (RTV_T / RTV_C)$$

wherein $RTV_T$ represented the RTV of a treatment group, and $RTV_C$ represented the RTV of the solvent control group.

The calculation formula of the tumor growth inhibition rate (TGI (%)) was:

$$TGI = 100\% \times [1 - (TV_{t(T)} - TV_{initial(T)}) / (TV_{t(C)} - TV_{initial(C)})]$$

wherein $TV_{t(T)}$ represented the tumor volume of a treatment group at each measurement, $TV_{initial(T)}$ represented the tumor volume of a treatment group measured at the time of grouping and first administration, $TV_{t(C)}$ represented the tumor volume of the solvent control group at each measurement, and $TV_{initial(C)}$ represented the tumor volume of the solvent control group measured at the time of grouping and first administration.

The calculation formula of the decline rate of animal body weight was:

$$\text{decline rate of animal body weight} = 100\% \times (BW_{initial} - BW_t) / BW_{initial}$$

wherein $BW_t$ represented the animal body weight at each measurement during administration, and $BW_{initial}$ represented the animal body weight at the time of grouping and first administration.

The calculation formula of the tumor weight inhibition rate (IR (%)) was:

$$IR(\%) = 100\% \times (W_C - W_T) / W_C$$

wherein $W_C$ represented the tumor weight of the control group, and $W_T$ represented the tumor weight of a treatment group.

5. Method for Statistical Analysis

The experimental data was subjected to calculation and related statistical treatments using Microsoft Office Excel 2007 Software. Unless otherwise specified, the data was represented by mean±standard error (Mean±SE), and t test was adopted for the comparison between two groups.

6. Experimental Observation

During the experiment, experimenter(s) and veterinarian(s) needed to continuously observe the physical signs and health status of the experimental animals. Any abnormal performance of the animals, such as pain, depression, and decreased activity, should be recorded in the original record of the experiment. If the abnormal performance of the experimental animals exceeded the provisions of the IACUC-related animal welfare documents, the veterinarian(s) could judge whether to suspend the experiment, and notify the person in charge of the experimental project.

7. Results

As for the transplanted tumor models of human cancer, the relative tumor proliferation rate T/C (%) was recommended to be adopted as the evaluation index of the experiment. Lower proliferation rate indicated better tumor inhibitory effect, as shown in Table 8.

TABLE 8

Relative tumor proliferation rate T/C (%)

| Group | Sample | Number of animals | Relative tumor volume (RTV, mm$^3$) | Average relative tumor proliferation rate (% T/C) |
|---|---|---|---|---|
| 1 | Blank solvent | 5 | 2.98 | — |
| 2 | irinotecan | 5 | 7.78 | 63.2% |
| 3 | nktr-102 | 5 | 6.03 | 50.0% |
| 4 | Compound 1 | 5 | 3.62 | 30.1% |
| 5 | Compound 2 | 5 | 3.08* | 25.6%[#] |
| 6 | Compound 3 | 5 | 3.39* | 28.2%[#] |
| 7 | Compound 4 | 5 | 2.92* | 24.3%[#] |
| 8 | Compound 5 | 5 | 3.80* | 31.6%[#] |
| 9 | Compound 6 | 5 | 3.61* | 30.0%[#] |
| 10 | Compound 7 | 5 | 3.18* | 26.4%[#] |
| 11 | Compound 8 | 5 | 3.63* | 30.1%[#] |
| 12 | Compound 9 | 5 | 3.20* | 27.1%[#] |
| 13 | Compound 10 | 5 | 2.98* | 25.2%[#] |
| 14 | Compound 11 | 5 | 3.28* | 27.7%[#] |
| 15 | Compound 12 | 5 | 3.94* | 33.2[#] |
| 16 | Compound 13 | 5 | 2.76* | 23.2%[#] |
| 17 | Compound 14 | 5 | 3.31* | 27.8%[#] |
| 18 | Compound 15 | 5 | 3.48* | 29.2%[#] |
| 19 | Compound 16 | 5 | 3.06* | 25.7%[#] |
| 20 | Compound 17 | 5 | 3.37* | 28.3%[#] |
| 21 | Compound 18 | 5 | 3.23* | 27.2%[#] |
| 22 | Compound 19 | 5 | 3.72* | 31.3%[#] |
| 23 | Compound 20 | 5 | 3.46* | 29.1%[#] |
| 24 | Compound 21 | 5 | 3.14 | 26.1% |
| 25 | Compound 22 | 5 | 3.39 | 28.2% |
| 26 | Compound 23 | 5 | 3.29 | 27.4% |

TABLE 8-continued

Relative tumor proliferation rate T/C (%)

| Group | Sample | Number of animals | Relative tumor volume (RTV, mm³) | Average relative tumor proliferation rate (% T/C) |
|---|---|---|---|---|
| 27 | Compound 24 | 5 | 2.94 | 24.4% |
| 28 | Compound 25 | 5 | 3.07 | 25.5% |
| 29 | Compound 26 | 5 | 3.36 | 27.9% |
| 30 | Compound 27 | 5 | 3.63 | 30.1% |
| 31 | Compound 28 | 5 | 2.97 | 24.7% |
| 32 | Compound 29 | 5 | 3.15 | 26.2% |
| 33 | Compound 30 | 5 | 3.38 | 28.1% |
| 34 | Compound 31 | 5 | 3.27 | 27.2% |
| 35 | Compound 32 | 5 | 3.21 | 26.7% |
| 36 | Compound 33 | 5 | 3.08 | 25.6% |
| 37 | Compound 34 | 5 | 3.57 | 29.7% |
| 38 | Compound 35 | 5 | 3.18 | 26.4% |
| 39 | Compound 36 | 5 | 3.21 | 26.7% |
| 40 | Compound 37 | 5 | 3.03 | 25.2% |
| 41 | Compound 38 | 5 | 3.12 | 25.9% |
| 42 | Compound 39 | 5 | 3.42 | 28.4% |
| 43 | Compound 40 | 5 | 3.74 | 31.1% |
| 44 | Compound 41 | 5 | 3.56 | 29.6% |
| 45 | Compound 42 | 5 | 3.33 | 27.7% |

*$P < 0.05$, as compared with the RTV of the blank solvent group, irinotecan group and nktr-102 group.
$P < 0.05$, as compared with % T/C of the blank solvent group, irinotecan group and nktr-102 group.

The experimental results showed that the compounds of the present disclosure had good inhibitory effects on tumor growth in the human gastric cancer NCI-N87 cell strain transplanted tumor model in nude mice, and were superior to irinotecan and nktr-102.

Example 47 Effect on the Survival Rate of an Orthotopic U87MG Brain Glioma Model in Nude Mice 1. Experimental Purpose The effects of the test compounds 1 to 42 on the survival rate of the orthotopic U87MG brain glioma model in nude mice were evaluated.

2. Experimental Materials 2.1 Test Articles

Irinotecan (bulk drug) and nktr-102 (bulk drug) were obtained by purchasing, and Compounds 1 to 42 were all provided by Brightgene Bio-Medical Technology Co., Ltd.

2.2 Reagents

RPMI-1640 liquid culture medium, trypsin, penicillin-streptomycin, and physiological saline.

2.3 Experimental Animals

Female BALB/c nude mice (number of animals: 300, weeks of age: 6 to 8 weeks) were purchased from Beijing Vital River Laboratory Animal Technology Co., Ltd., housed in an SPF animal room, the temperature was 20° C. to 25° C., the relative humidity was 40% to 70%, and the light and dark were respectively 12 h. The animals had free access to water and food. After about one week of normal feeding, upon a veterinary inspection, mice with good physical signs and conditions could be selected for the experiment. A marking pen was used to mark the base of the tails of the animals before the grouping, and each animal was marked by ear clipping after the grouping.

2.4 Transplantable Tumor Cell Line

Brain glioma cell U87MG, derived from Cell Bank of Committee on Type Culture Collection of Chinese Academy of Science (CAS, stored frozen in liquid nitrogen in the laboratory).

3. Experimental Methods

Culture of U87MG Cells

Under a culture condition of 5% $CO_2$ and 37° C., U87MG cells were subjected to conventional cell cultivation in RPMI-1640 liquid culture medium, digested with 0.25% trypsin, and passaged. According to the condition of cell growth, the cells were passaged once or twice every week, and were passaged in a ratio of 1:2 to 1:6.

3.1 Preparation of the Animal Model

U87MG cells in logarithmic phase of growth were collected. The cells were resuspended in RPMI-1640 culture medium free of serum after being counted, and the concentration of the cells was adjusted to $1 \times 10^8$ cells/mL. The cells were charged into a 50 mL centrifuge tube after being pipetted with a pipettor to make them evenly dispersed, and the centrifuge tube was placed in an ice box. Cell suspension was aspirated with a 1 mL syringe, 1 µL of human brain glioma cell (U87MG cells) cultured in vitro was inoculated ($1 \times 10^5$ cells/animal) using microinjection method via the guidance of a stereotactic apparatus for animals, the orthotopic U87MG brain glioma model was established, and animal status was observed periodically after inoculation. On the 12th day after inoculation, 225 animals were selected and divided into 45 groups using randomized block method (n=5).

3.2 Preparation of the Dosing Formulations 3.2.1 Preparation of the Dosing Formulation of Irinotecan 12.0 mg of irinotecan was weighed, 0.15 mL of 1% lactic acid was added, the drug was dissolved completely by vortexing, and 2.85 mL of 1% aqueous sorbitol solution was then added respectively. The mixture was mixed evenly by vortexing, and the ratio of 1% lactic acid to 1% aqueous sorbitol solution was approximately 5:95 (v/v) in the solution. The concentration of free irinotecan in the solution was 4.0 mg·mL$^{-1}$.

3.2.2 Preparation of the Dosing Formulation of nktr-102

Before each administration, 88.55 mg of nktr-102 was weighed accurately, 2.3 mL of physiological saline was added, the drug was dissolved completely by vortexing, and the concentration of free irinotecan in the solution was 4.0 mg·mL$^{-1}$.

3.2.3 Preparation of the Dosing Formulations of Compounds 1 to 5

Before each administration, 113.85 mg of Compound 1 was weighed accurately, 2.3 mL of physiological saline was added, the drug was dissolved completely by vortexing, and the concentration of free irinotecan in the solution was 4.0 mg·mL$^{-1}$.

Before each administration, 109.80 mg of Compound 2 was weighed accurately, 2.3 mL of physiological saline was added, the drug was dissolved completely by vortexing, and the concentration of free irinotecan in the solution was 4.0 mg·mL$^{-1}$.

Before each administration, 113.88 mg of Compound 3 was weighed accurately, 2.3 mL of physiological saline was added, the drug was dissolved completely by vortexing, and the concentration of free irinotecan in the solution was 4.0 mg·mL$^{-1}$.

Before each administration, 111.24 mg of Compound 4 was weighed accurately, 2.3 mL of physiological saline was added, the drug was dissolved completely by vortexing, and the concentration of free irinotecan in the solution was 4.0 mg·mL$^{-1}$.

Before each administration, 105.78 mg of Compound 5 was weighed accurately, 2.3 mL of physiological saline was added, the drug was dissolved completely by vortexing, and the concentration of free irinotecan in the solution was 4.0 mg·mL$^{-1}$.

3.2.4 Preparation of the Dosing Formulations of Compounds 6 to 10

Before each administration, 113.09 mg of Compound 6 was weighed accurately, 2.3 mL of physiological saline was added, the drug was dissolved completely by vortexing, and the concentration of free SN-38 in the solution was 4.0 mg·mL$^{-1}$.

Before each administration, 109.05 mg of Compound 7 was weighed accurately, 2.3 mL of physiological saline was added, the drug was dissolved completely by vortexing, and the concentration of free SN-38 in the solution was 4.0 mg·mL$^{-1}$.

Before each administration, 113.12 mg of Compound 8 was weighed accurately, 2.3 mL of physiological saline was added, the drug was dissolved completely by vortexing, and the concentration of free SN-38 in the solution was 4.0 mg·mL$^{-1}$.

Before each administration, 110.48 mg of Compound 9 was weighed accurately, 2.3 mL of physiological saline was added, the drug was dissolved completely by vortexing, and the concentration of free SN-38 in the solution was 4.0 mg·mL$^{-1}$.

Before each administration, 105.02 mg of Compound 10 was weighed accurately, 2.3 mL of physiological saline was added, the drug was dissolved completely by vortexing, and the concentration of free SN-38 in the solution was 4.0 mg·mL$^{-1}$.

3.2.5 Preparation of the Dosing Formulations of Compounds 11 to 15

Before each administration, 112.98 mg of Compound 11 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 108.94 mg of Compound 12 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 113.01 mg of Compound 13 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 110.37 mg of Compound 14 was weighed accurately, 2.3 mL of physiological saline was added, the drug was dissolved completely by vortexing, and the concentration of free 10-hydroxycamptothecin in the solution was 4.0 mg·mL$^{-1}$.

Before each administration, 104.91 mg of Compound 15 was weighed accurately, 2.3 mL of physiological saline was added, the drug was dissolved completely by vortexing, and the concentration of free 10-hydroxycamptothecin in the solution was 4.0 mg·mL$^{-1}$.

3.2.6 Preparation of the Dosing Formulations of Compounds 16 to 20

Before each administration, 113.09 mg of Compound 11 was weighed accurately, 2.3 mL of physiological saline was added, the drug was dissolved completely by vortexing, and the concentration of free rubitecan in the solution was 4.0 mg·mL$^{-1}$.

Before each administration, 109.05 mg of Compound 12 was weighed accurately, 2.3 mL of physiological saline was added, the drug was dissolved completely by vortexing, and the concentration of free rubitecan in the solution was 4.0 mg·mL$^{-1}$.

Before each administration, 113.12 mg of Compound 13 was weighed accurately, 2.3 mL of physiological saline was added, the drug was dissolved completely by vortexing, and the concentration of free rubitecan in the solution was 4.0 mg·mL$^{-1}$.

Before each administration, 110.48 mg of Compound 14 was weighed accurately, 2.3 mL of physiological saline was added, the drug was dissolved completely by vortexing, and the concentration of free rubitecan in the solution was 4.0 mg·mL$^{-1}$.

Before each administration, 105.02 mg of Compound 15 was weighed accurately, 2.3 mL of physiological saline was added, the drug was dissolved completely by vortexing, and the concentration of free rubitecan in the solution was 4.0 mg·mL$^{-1}$.

3.2.7 Preparation of the Dosing Formulations of Compounds 21 to 42

The preparation methods were as described above, so that the concentration of the free active agent in the solution was 4.0 mg·mL$^{-1}$.

3.3 Grouping of Animals and Administration

The grouping of animals and the dosing regimens were as shown in Table 9.

Groups with irinotecan as the active agent (Group 1-8). The first administration was initiated on the day of grouping, the experiment was ended after 21 days, and the volumes of administration were all 10 mL·kg$^{-1}$. Group 1 was a solvent control group, and was given blank solvent by intravenous injection via tail once every 4 days for a total of 3 times (Q4D×3). Groups 2 to 8 were given irinotecan, nktr-102 and Compounds 1 to 5 as test samples by intravenous injection via tail, respectively, and the dosages of administration were all 40 mg·kg$^{-1}$ (calculated in terms of the content of irinotecan), Q4D×3.

Groups with SN-38 as the active agent (Groups 9 to 13). The first administration was initiated on the day of grouping, the experiment was ended after 21 days, and the volumes of administration were all 10 mL·kg$^{-1}$. Groups 9 to 13 were given Compounds 6 to 10 as test samples by intravenous injection via tail, respectively, and the dosages of administration were all 40 mg·kg$^{-1}$ (calculated in terms of the content of SN-38), Q4D×3.

Groups with 10-hydroxycamptothecin as the active agent (Groups 14 to 18). The first administration was initiated on the day of grouping, the experiment was ended after 21 days, and the volumes of administration were all 10 mL·kg$^{-1}$. Groups 14 to 18 were given Compounds 11 to 15 as test samples by intravenous injection via tail, respectively, and the dosages of administration were all 40 mg·kg$^{-1}$ (calculated in terms of the content of 10-hy droxy camptothecin), Q4D×3.

Groups with rubitecan as the active agent (Groups 19 to 23). The first administration was initiated on the day of grouping, the experiment was ended after 21 days, and the volumes of administration were all 10 mL·kg$^{-1}$. Groups 19 to 23 were given Compounds 16 to 20 as test samples by intravenous injection via tail, respectively, and the dosages of administration were all 40 mg·kg$^{-1}$ (calculated in terms of the content of rubitecan), Q4D×3.

The modes of administration of Groups 24 to 25 were as described above.

TABLE 9

Dosing regimens of the pharmacodynamic experiments in transplanted tumor model in nude mice

| Group | Sample | Number of animals | Dosage (mg · kg$^{-1}$) | Volume of administration (mL · kg$^{-1}$) | Route of administration | Period of administration |
|---|---|---|---|---|---|---|
| 1 | blank solvent | 5 | — | 10 | IV | Q4D × 3 |
| 2 | irinotecan | 5 | 40 | 10 | IV | Q4D × 3 |
| 3 | nktr-102 | 5 | 40 | 10 | IV | Q4D × 3 |
| 4 | Compound 1 | 5 | 40 | 10 | IV | Q4D × 3 |
| 5 | Compound 2 | 5 | 40 | 10 | IV | Q4D × 3 |
| 6 | Compound 3 | 5 | 40 | 10 | IV | Q4D × 3 |
| 7 | Compound 4 | 5 | 40 | 10 | IV | Q4D × 3 |
| 8 | Compound 5 | 5 | 40 | 10 | IV | Q4D × 3 |
| 9 | Compound 6 | 5 | 40 | 10 | IV | Q4D × 3 |
| 10 | Compound 7 | 5 | 40 | 10 | IV | Q4D × 3 |
| 11 | Compound 8 | 5 | 40 | 10 | IV | Q4D × 3 |
| 12 | Compound 9 | 5 | 40 | 10 | IV | Q4D × 3 |
| 13 | Compound 10 | 5 | 40 | 10 | IV | Q4D × 3 |
| 14 | Compound 11 | 5 | 40 | 10 | IV | Q4D × 3 |
| 15 | Compound 12 | 5 | 40 | 10 | IV | Q4D × 3 |
| 16 | Compound 13 | 5 | 40 | 10 | IV | Q4D × 3 |
| 17 | Compound 14 | 5 | 40 | 10 | IV | Q4D × 3 |
| 18 | Compound 15 | 5 | 40 | 10 | IV | Q4D × 3 |
| 19 | Compound 16 | 5 | 40 | 10 | IV | Q4D × 3 |
| 20 | Compound 17 | 5 | 40 | 10 | IV | Q4D × 3 |
| 21 | Compound 18 | 5 | 40 | 10 | IV | Q4D × 3 |
| 22 | Compound 19 | 5 | 40 | 10 | IV | Q4D × 3 |
| 23 | Compound 20 | 5 | 40 | 10 | IV | Q4D × 3 |
| 24 | Compound 21 | 5 | 40 | 10 | IV | Q4D × 3 |
| 25 | Compound 22 | 5 | 40 | 10 | IV | Q4D × 3 |
| 26 | Compound 23 | 5 | 40 | 10 | IV | Q4D × 3 |
| 27 | Compound 24 | 5 | 40 | 10 | IV | Q4D × 3 |
| 28 | Compound 25 | 5 | 40 | 10 | IV | Q4D × 3 |
| 29 | Compound 26 | 5 | 40 | 10 | IV | Q4D × 3 |
| 30 | Compound 27 | 5 | 40 | 10 | IV | Q4D × 3 |
| 31 | Compound 28 | 5 | 40 | 10 | IV | Q4D × 3 |
| 32 | Compound 29 | 5 | 40 | 10 | IV | Q4D × 3 |
| 33 | Compound 30 | 5 | 40 | 10 | IV | Q4D × 3 |
| 34 | Compound 31 | 5 | 40 | 10 | IV | Q4D × 3 |
| 35 | Compound 32 | 5 | 40 | 10 | IV | Q4D × 3 |
| 36 | Compound 33 | 5 | 40 | 10 | IV | Q4D × 3 |
| 37 | Compound 34 | 5 | 40 | 10 | IV | Q4D × 3 |
| 38 | Compound 35 | 5 | 40 | 10 | IV | Q4D × 3 |
| 39 | Compound 36 | 5 | 40 | 10 | IV | Q4D × 3 |
| 40 | Compound 37 | 5 | 40 | 10 | IV | Q4D × 3 |
| 41 | Compound 38 | 5 | 40 | 10 | IV | Q4D × 3 |
| 42 | Compound 39 | 5 | 40 | 10 | IV | Q4D × 3 |
| 43 | Compound 40 | 5 | 40 | 10 | IV | Q4D × 3 |
| 44 | Compound 41 | 5 | 40 | 10 | IV | Q4D × 3 |
| 45 | Compound 42 | 5 | 40 | 10 | IV | Q4D × 3 |

4. Data recording and Calculation Formulae
The survival time of the animals were recorded.
5. Method for Statistical Analysis
The experimental data was subjected to calculation and related statistical treatments using Microsoft Office Excel 2007 Software. t test was adopted for the comparison between two groups.
6. Results
See Table 10

TABLE 10

Survival time of the animals (day)

| Group | Sample | Number of animals | Survival time | Median survival time |
|---|---|---|---|---|
| 1 | blank solvent | 5 | 16 to 22 | 20 |
| 2 | irinotecan | 5 | 22 to 32 | 27 |
| 3 | nktr-102 | 5 | 25 to 37 | 31 |
| 4 | Compound 1 | 5 | 34 to 46 | 40* |
| 5 | Compound 2 | 5 | 34 to 43 | 38* |
| 6 | Compound 3 | 5 | 33 to 44 | 36* |
| 7 | Compound 4 | 5 | 34 to 45 | 38* |
| 8 | Compound 5 | 5 | 30 to 39 | 35* |
| 9 | Compound 6 | 5 | 34 to 43 | 41* |
| 10 | Compound 7 | 5 | 33 to 44 | 39* |
| 11 | Compound 8 | 5 | 32 to 45 | 40* |
| 12 | Compound 9 | 5 | 33 to 42 | 38* |
| 13 | Compound 10 | 5 | 29 to 39 | 35* |
| 14 | Compound 11 | 5 | 28 to 42 | 37* |
| 15 | Compound 12 | 5 | 35 to 45 | 42* |
| 16 | Compound 13 | 5 | 34 to 41 | 38* |
| 17 | Compound 14 | 5 | 34 to 44 | 40* |
| 18 | Compound 15 | 5 | 35 to 44 | 41* |
| 19 | Compound 16 | 5 | 30 to 42 | 37* |
| 20 | Compound 17 | 5 | 32 to 43 | 38* |
| 21 | Compound 18 | 5 | 31 to 40 | 36* |
| 22 | Compound 19 | 5 | 35 to 46 | 40* |
| 23 | Compound 20 | 5 | 33 to 43 | 39* |
| 24 | Compound 21 | 5 | 34 to 43 | 41* |

TABLE 10-continued

Survival time of the animals (day)

| Group | Sample | Number of animals | Survival time | Median survival time |
|---|---|---|---|---|
| 25 | Compound 22 | 5 | 34 to 46 | 40* |
| 26 | Compound 23 | 5 | 34 to 41 | 38* |
| 27 | Compound 24 | 5 | 34 to 46 | 40* |
| 28 | Compound 25 | 5 | 34 to 44 | 40* |
| 29 | Compound 26 | 5 | 30 to 42 | 37* |
| 30 | Compound 27 | 5 | 30 to 39 | 35* |
| 31 | Compound 28 | 5 | 29 to 39 | 35* |
| 32 | Compound 29 | 5 | 33 to 44 | 36* |
| 33 | Compound 30 | 5 | 35 to 46 | 40* |
| 34 | Compound 31 | 5 | 35 to 44 | 41* |
| 35 | Compound 32 | 5 | 33 to 44 | 39* |
| 36 | Compound 33 | 5 | 33 to 44 | 39* |
| 37 | Compound 34 | 5 | 34 to 46 | 40* |
| 38 | Compound 35 | 5 | 34 to 43 | 38* |
| 39 | Compound 36 | 5 | 30 to 42 | 37* |
| 40 | Compound 37 | 5 | 33 to 45 | 40* |
| 41 | Compound 38 | 5 | 29 to 39 | 35* |
| 42 | Compound 39 | 5 | 34 to 46 | 40* |
| 43 | Compound 40 | 5 | 33 to 40 | 36* |
| 44 | Compound 41 | 5 | 33 to 44 | 39* |
| 45 | Compound 42 | 5 | 30 to 42 | 38* |

*$P < 0.05$, as compared with the median survival time of blank solvent group, irinotecan group and nktr-102 group.

The experimental results showed that the compounds of the present disclosure had good inhibitory effects on brain glioma, and were superior to irinotecan and nktr-102.

What is claimed is:

1. A multi-branched drug conjugate having the following structural formula (III) or a pharmaceutically acceptable salt thereof:

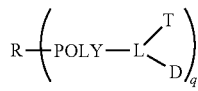

(III)

wherein R is an organic core, POLY is polyethylene glycol, L is a multivalent linker, T is a targeting molecule, D is an active agent, and q is any integer between 3 and 8, wherein D is a camptothecin-based drug represented by the following formula:

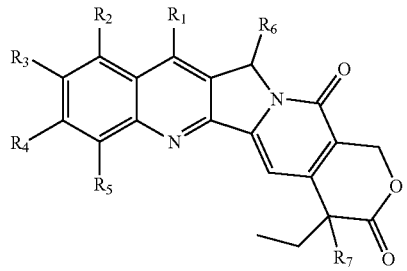

wherein $R_1$ to $R_5$ are selected from the following groups independently from each other:
hydrogen, halogen, acyl, alkyl, substituted alkyl, alkoxy, substituted alkoxy, alkenyl, alkynyl, cycloalkyl, hydroxyl, cyano, nitro, azido, amido, hydrazine, amine group, substituted amine group, hydroxycarbonyl, alkoxycarbonyl, alkoxycarbonyloxy, carbamoyloxy, arylsulfonyloxy, and alkylsulfonyloxy; $R_6$ is H or $OR_8$; $R_8$ is alkyl, alkenyl, cycloalkyl, halogenated alkyl, or hydroxyalkyl; and $R_7$ is hydroxyl;

the multivalent linker L is:

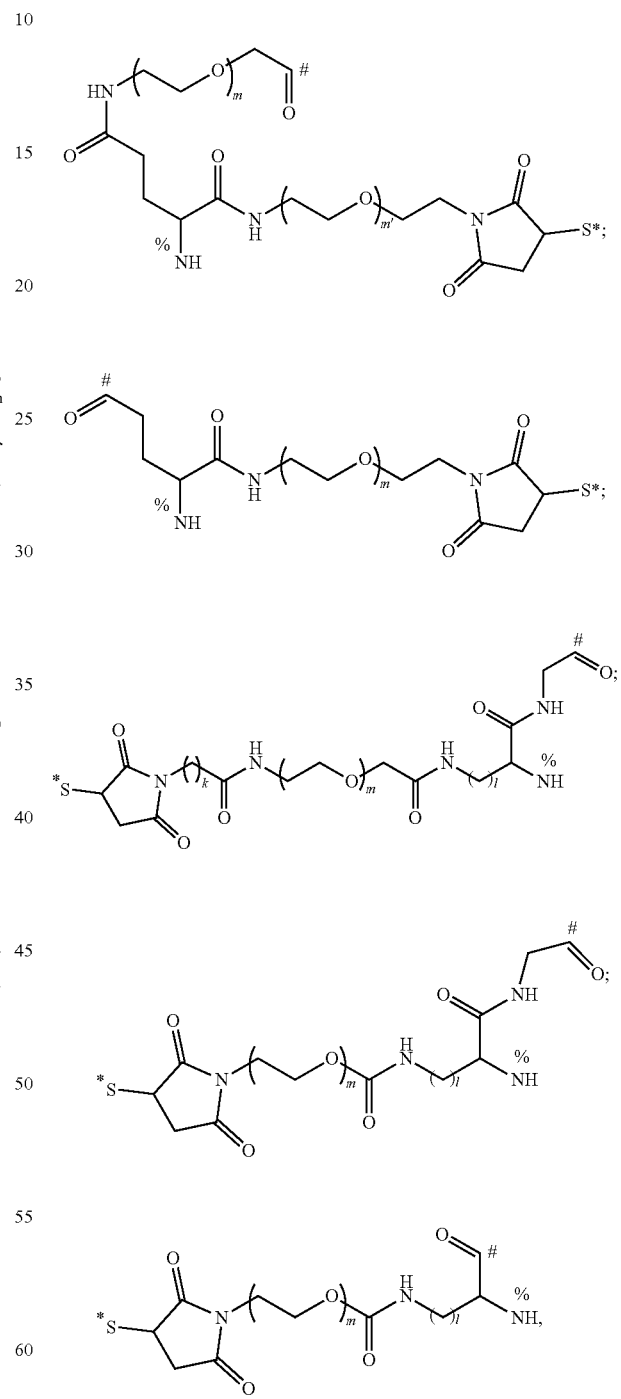

symbol "*" represents an attachment point of the multivalent linker L and the targeting molecule T, "#" represents an attachment point of the multivalent linker L and the active agent D, "%" represents an attachment point of the multivalent linker L and POLY, wherein m and m' are any integer between 1 and 20 respectively, and l and k are any integer between 1 and 10 respectively;

T is an "arginine-glycine-aspartic acid" sequence-containing RGD peptide, tLyp-1, Lyp-1, RPARPAR, Angiopep2, GE11, or folic acid.

2. The multi-branched drug conjugate or a pharmaceutically acceptable salt thereof according to claim 1, wherein D is irinotecan, SN-38, 10-hydroxycamptothecin, or rubitecan.

3. The multi-branched drug conjugate or a pharmaceutically acceptable salt thereof according to claim 1, wherein POLY is:

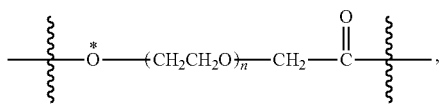

n is 5 to 500.

4. The multi-branched drug conjugate or a pharmaceutically acceptable salt thereof according to claim 1, wherein the multivalent linker L is:

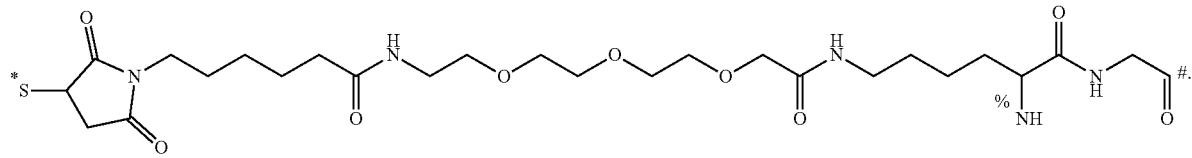 [SMILES: NC(CCCCNC(=O)COCCOCCOCCNC(=O)CCCCCN1C(=O)CC(S)C1=O)C(=O)NCC=O]

5. The multi-branched drug conjugate or a pharmaceutically acceptable salt thereof according to claim 1, wherein T is iRGD or cRGD.

6. The multi-branched drug conjugate or a pharmaceutically acceptable salt thereof according to claim 1, wherein said multi-branched drug conjugate has a structure represented by structural formula (IV), (V), or (VI):

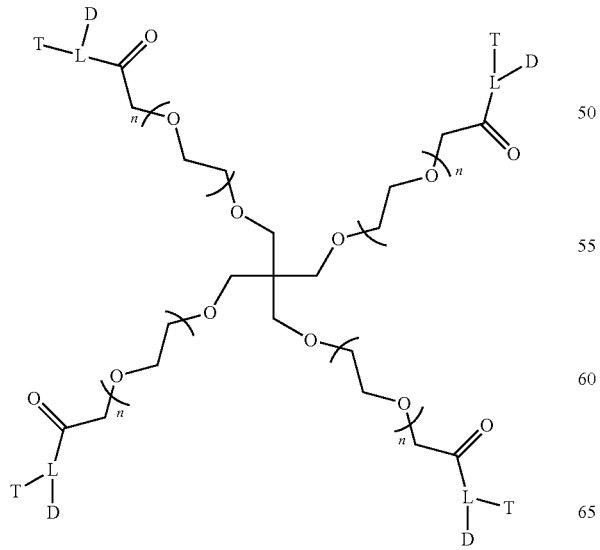

(IV)

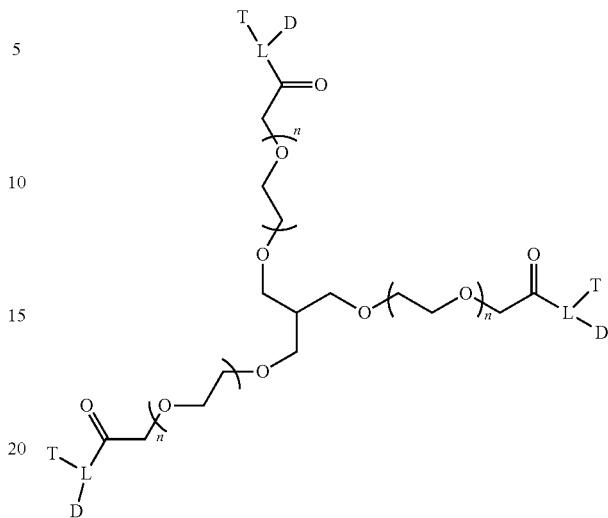

(V)

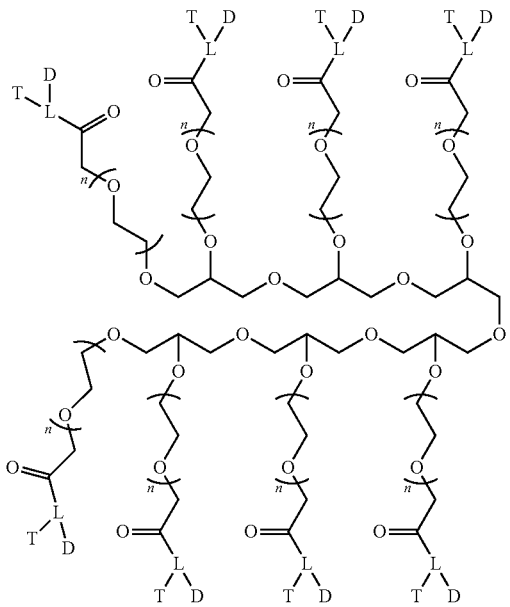

(VI)

wherein n is 5 to 500.

7. A multi-branched drug conjugate having the following structure or a pharmaceutically acceptable salt thereof:

Compound 1
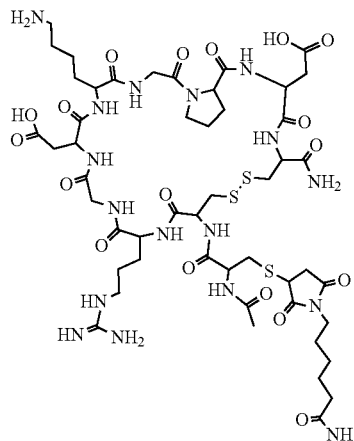
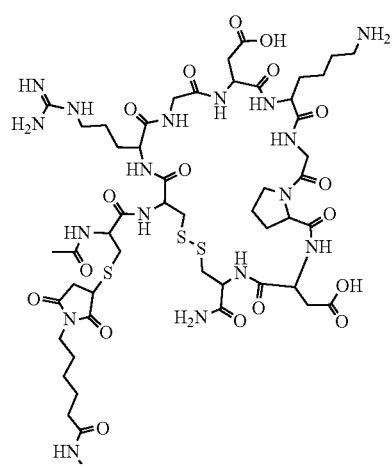
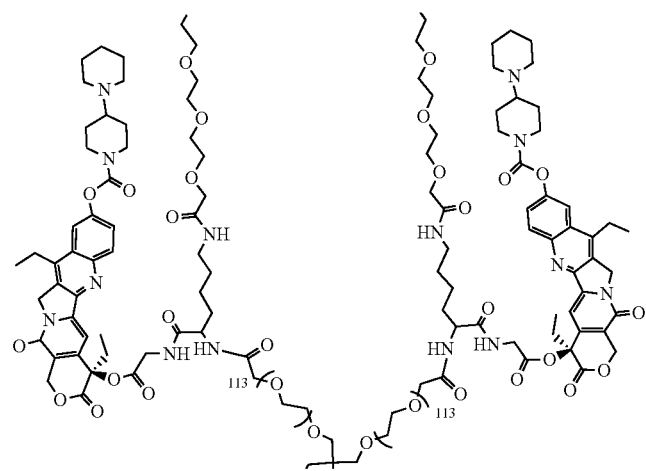
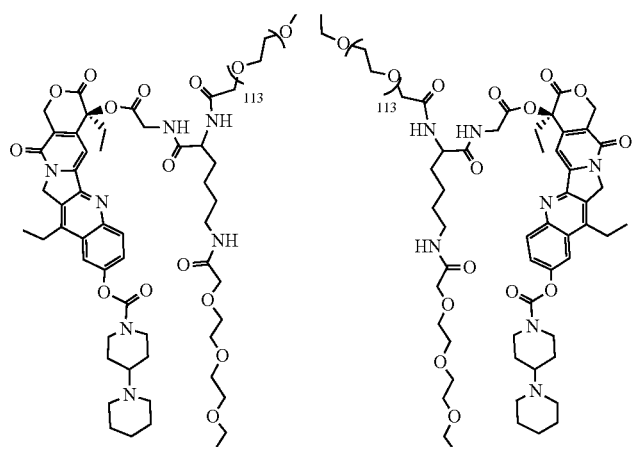

-continued
251
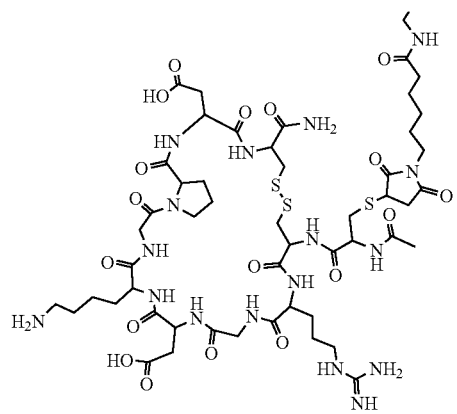
252
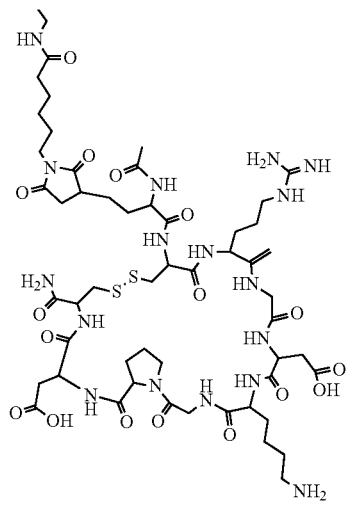
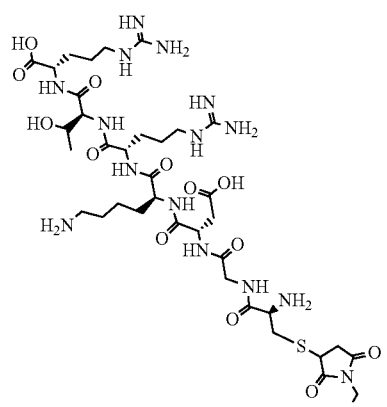
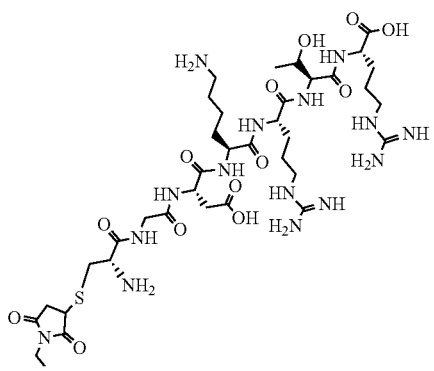
Compound 2
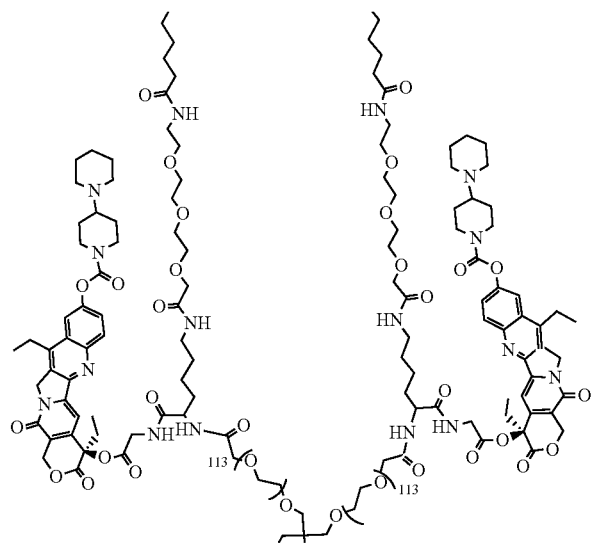

253 254
-continued
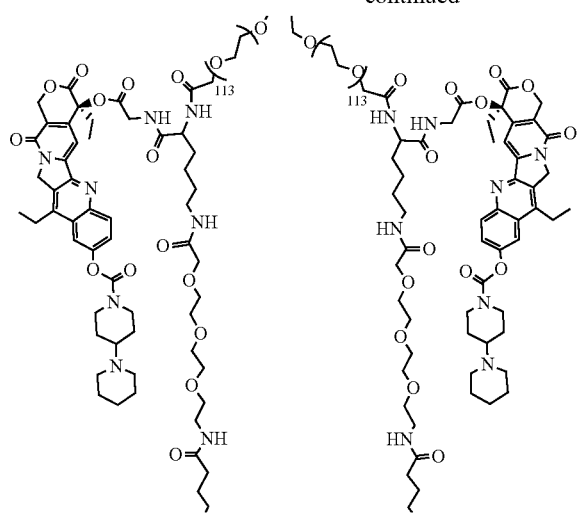
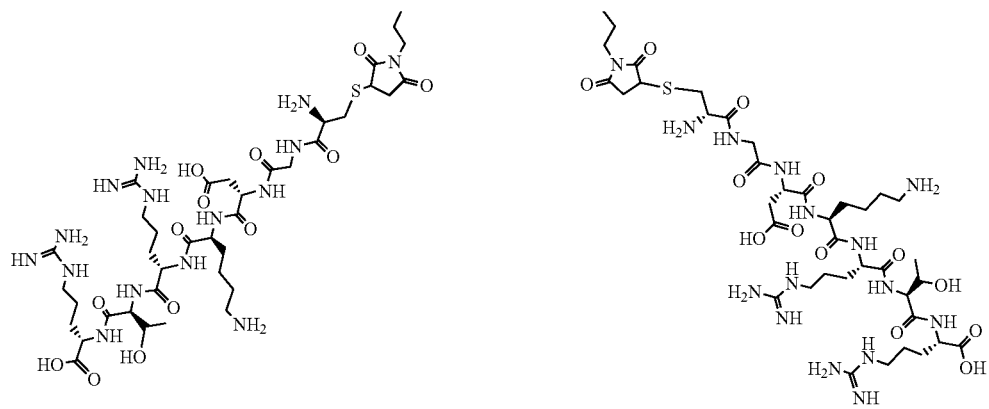
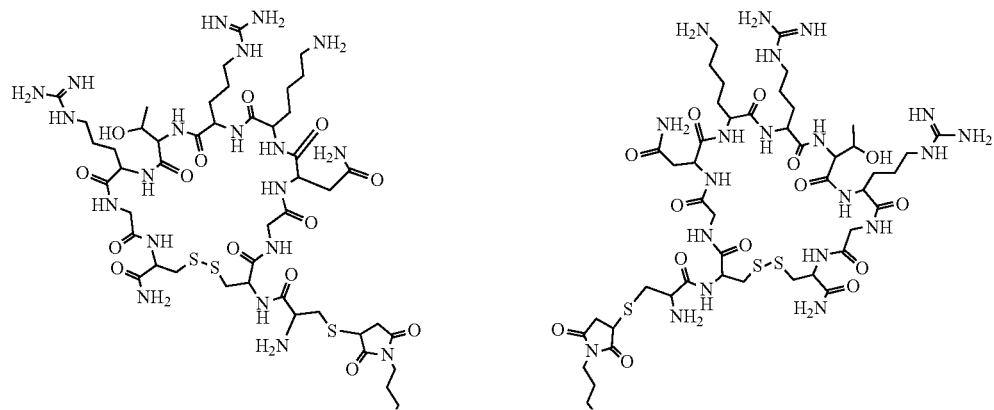
Compound 3

-continued
255
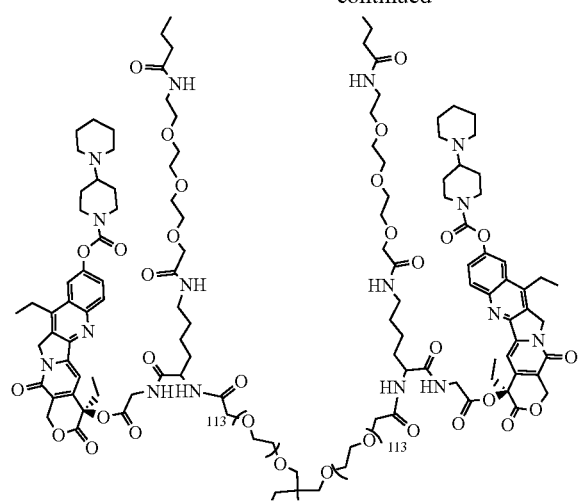
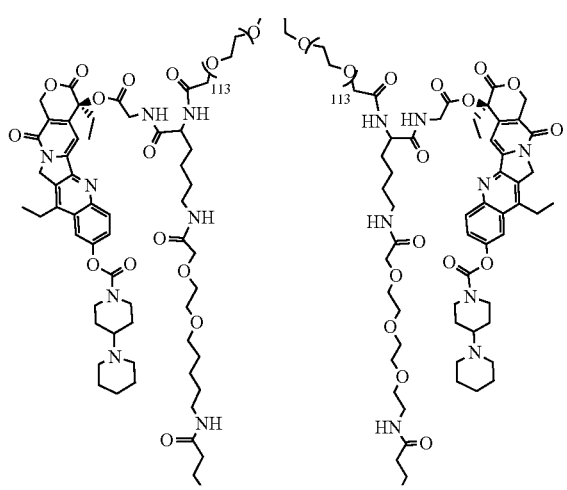
256
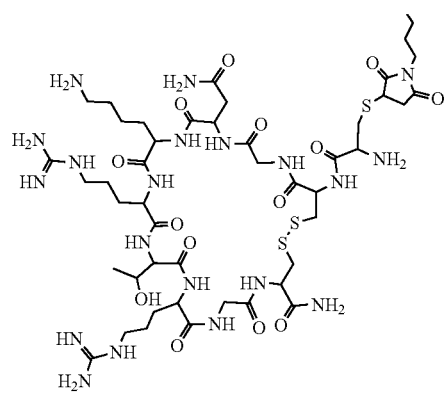
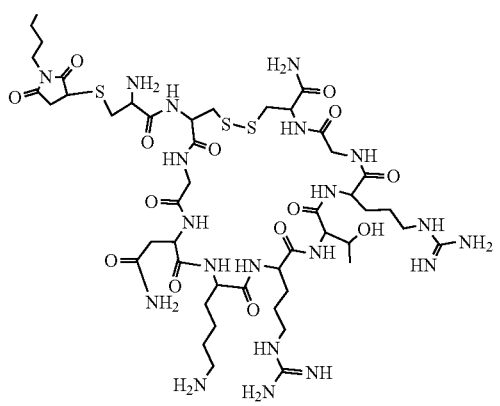

Compound 4
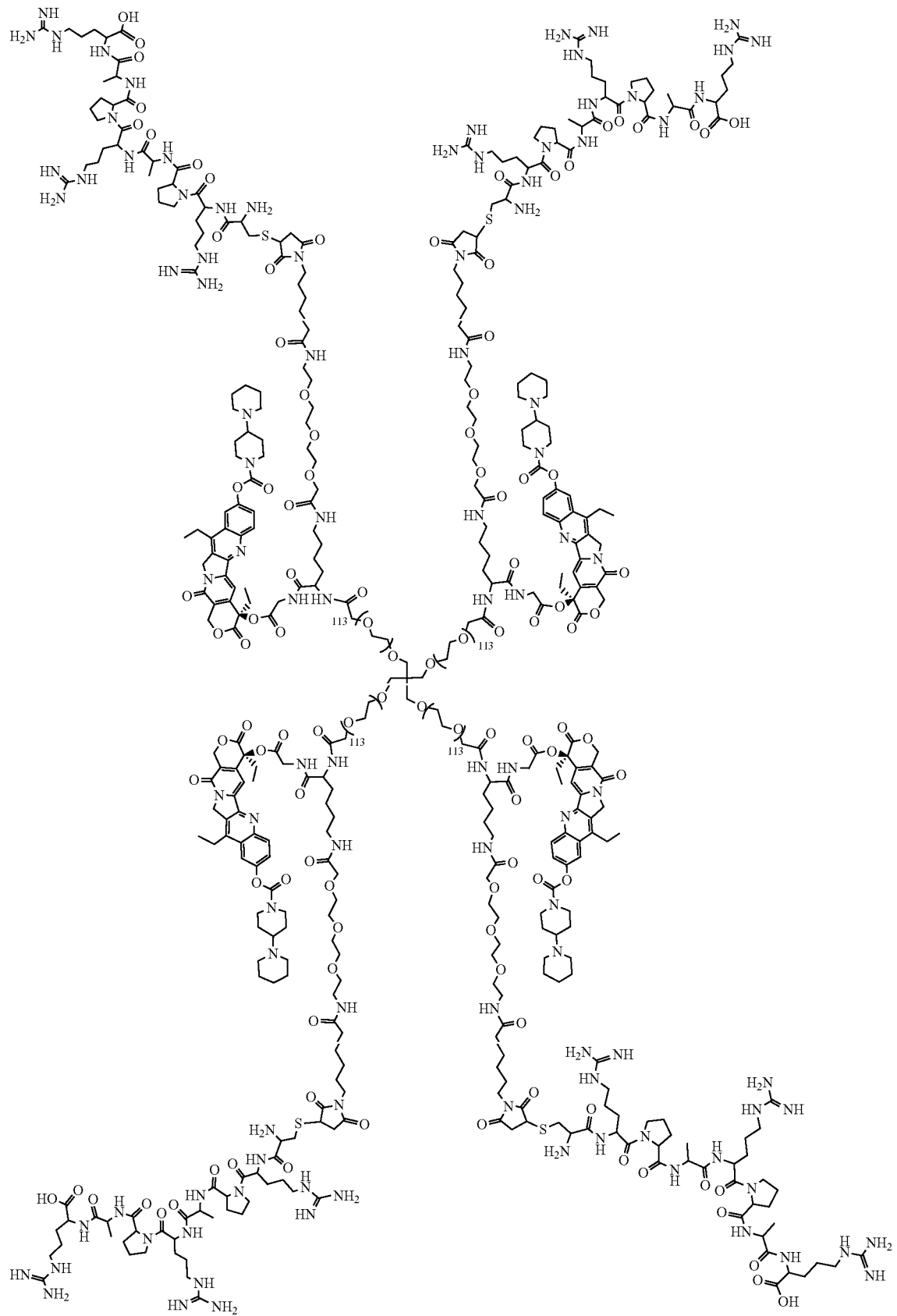

-continued
Compound 5
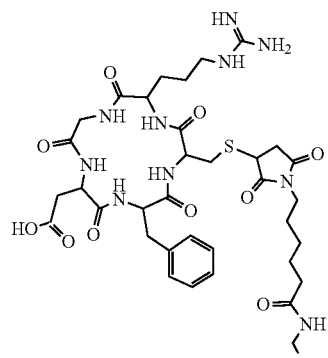
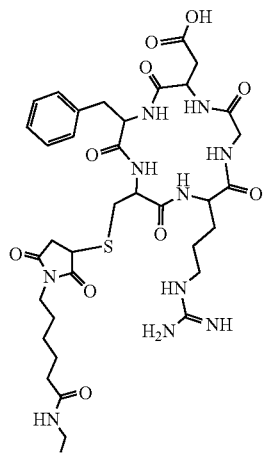
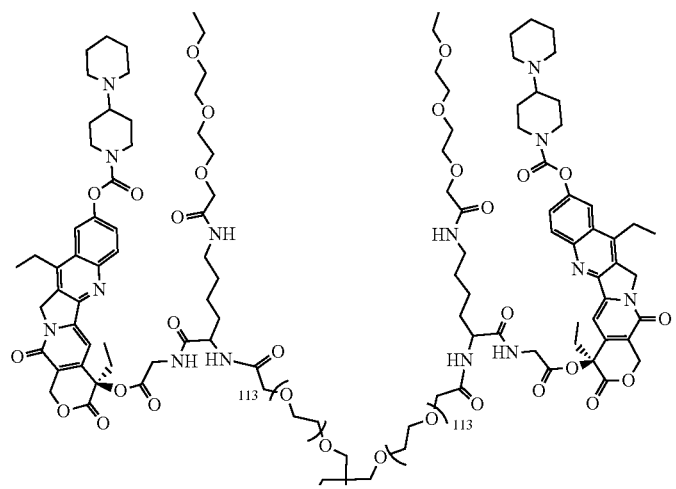
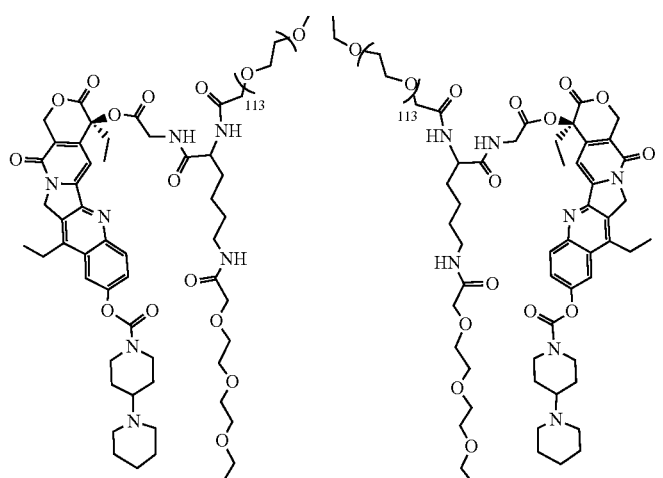

-continued
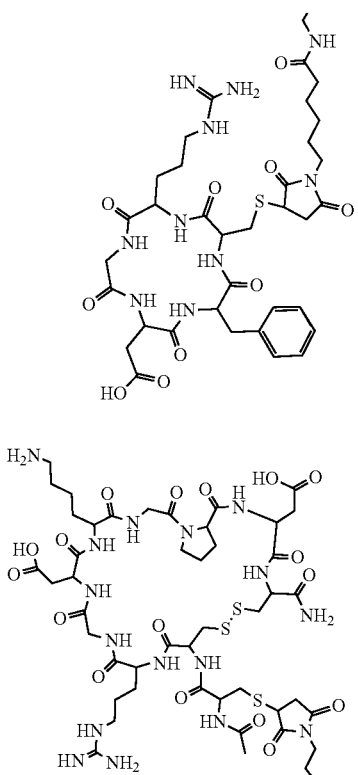
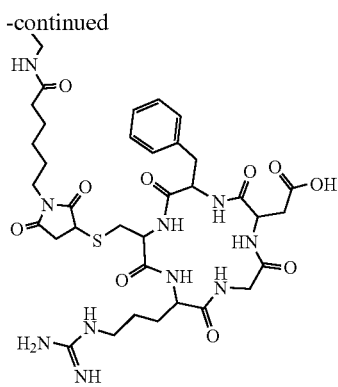
Compound 6
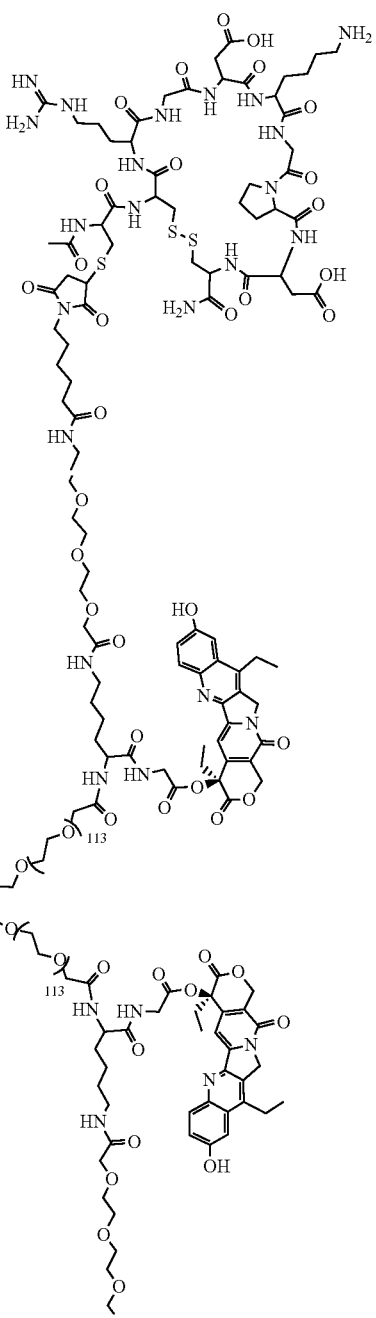

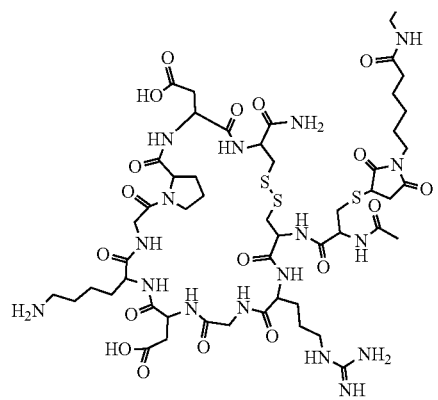
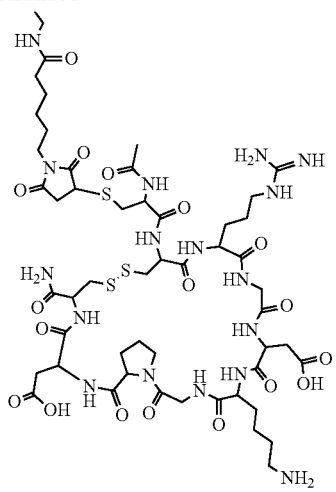
Compound 7
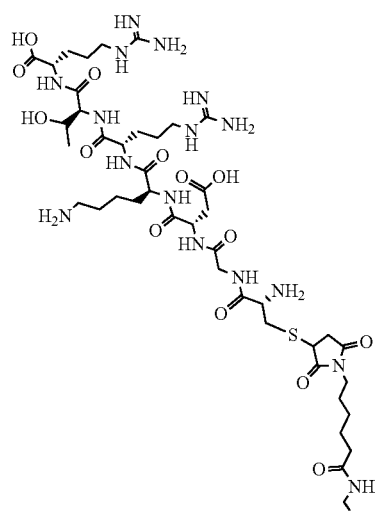
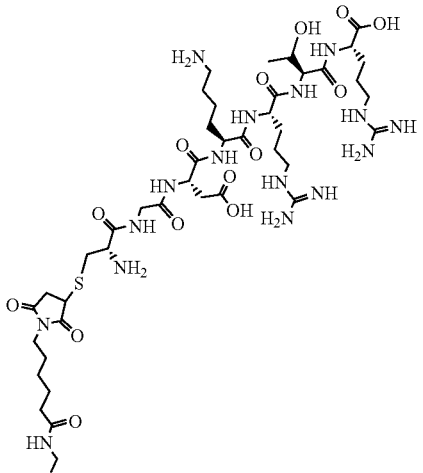
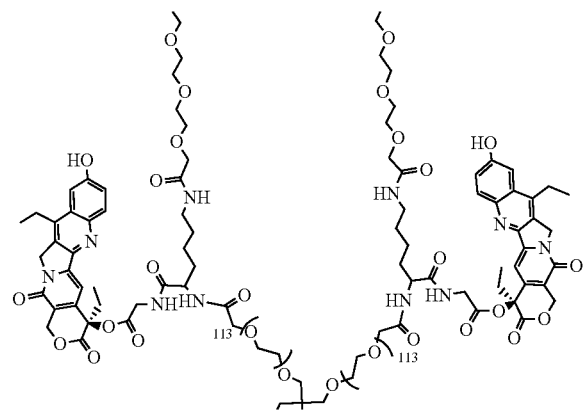

-continued
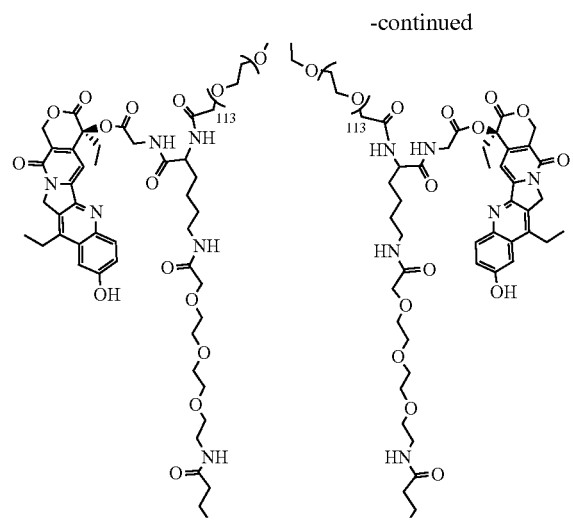
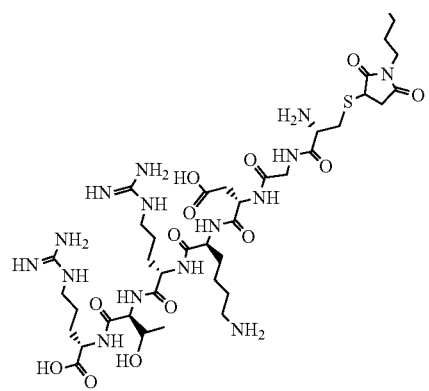
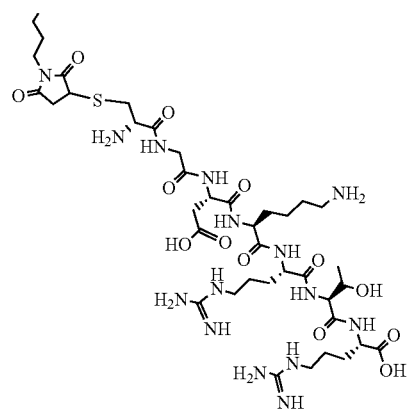
Compound 8
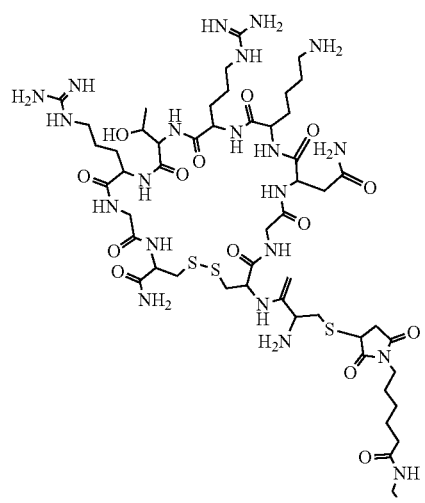
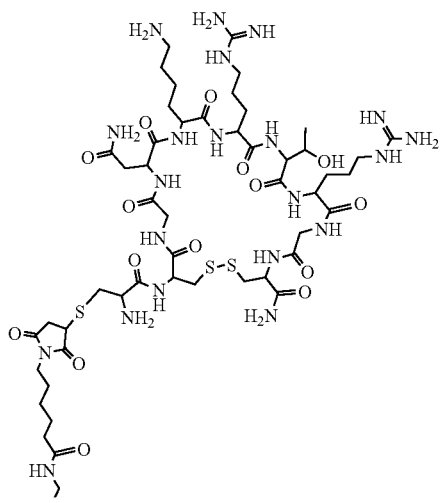

-continued
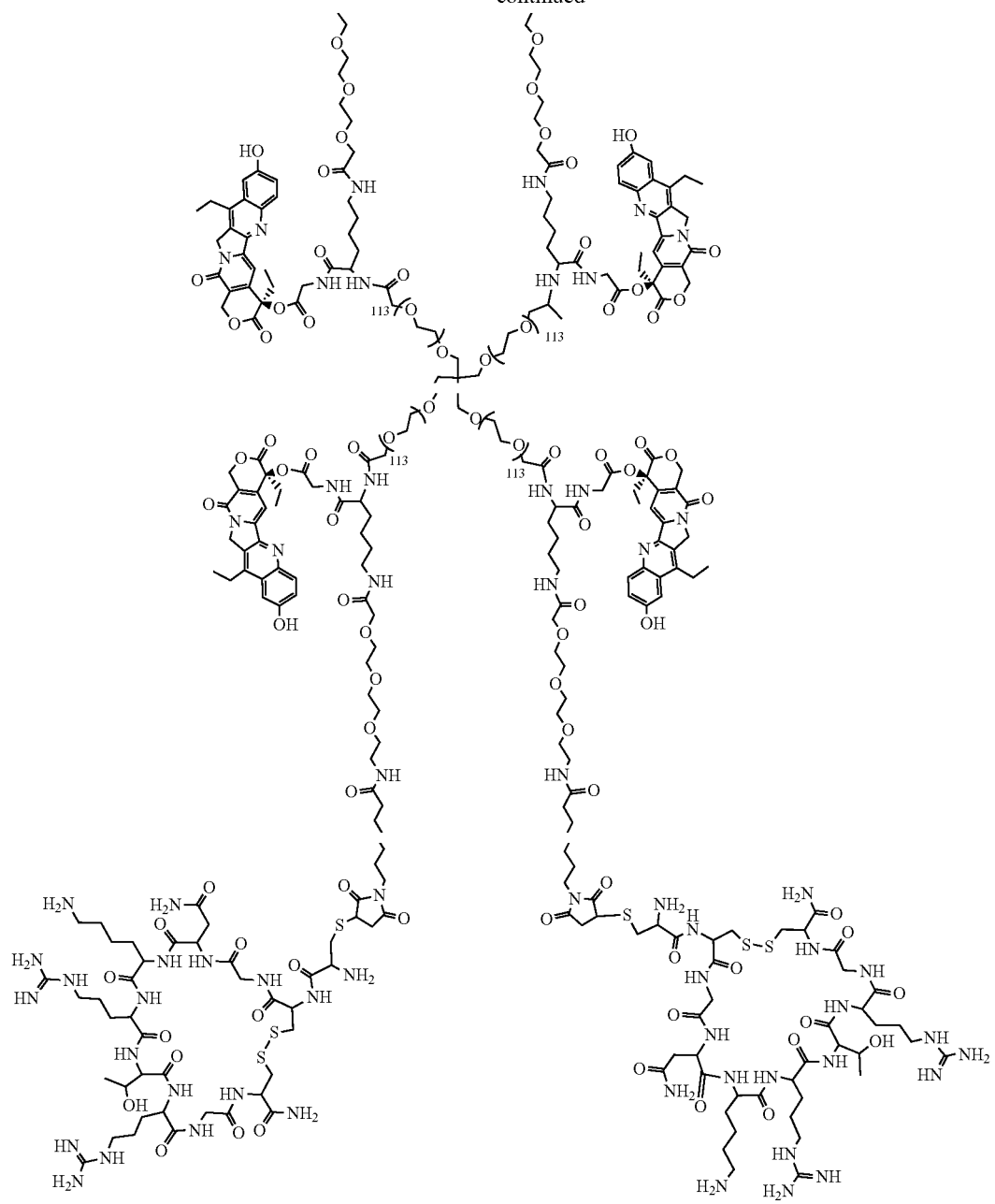
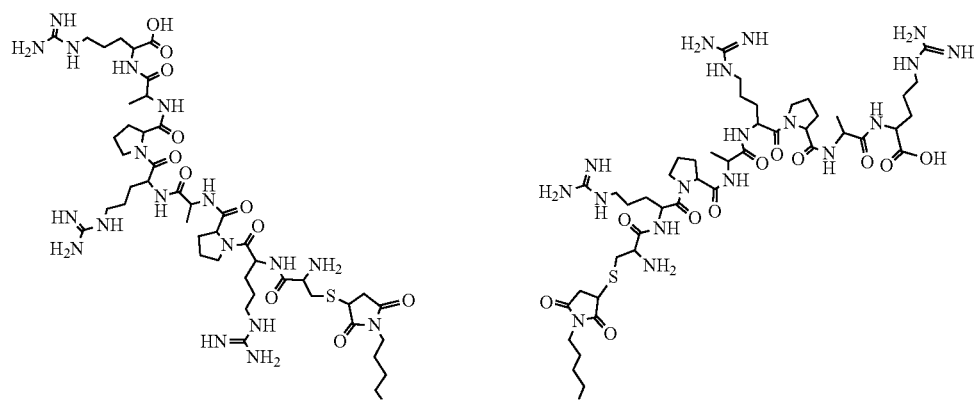
Compound 9

-continued
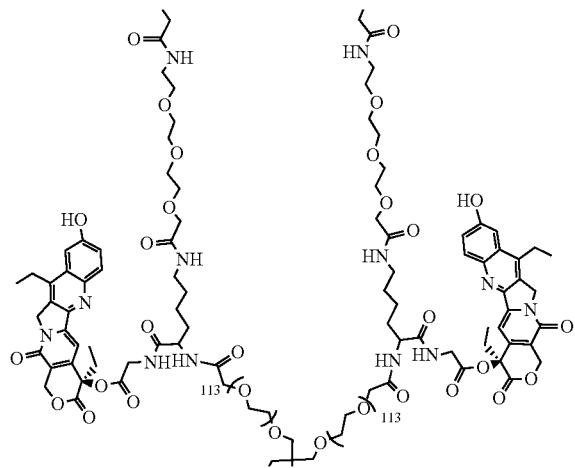
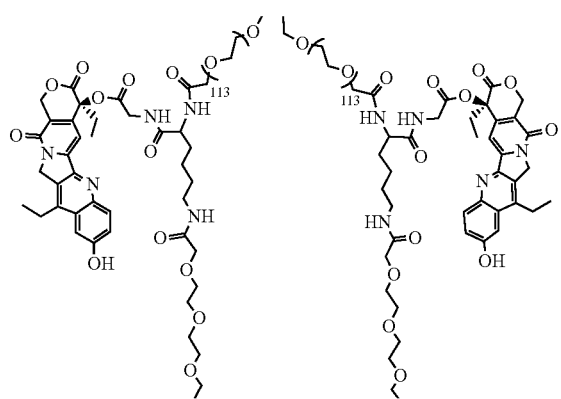
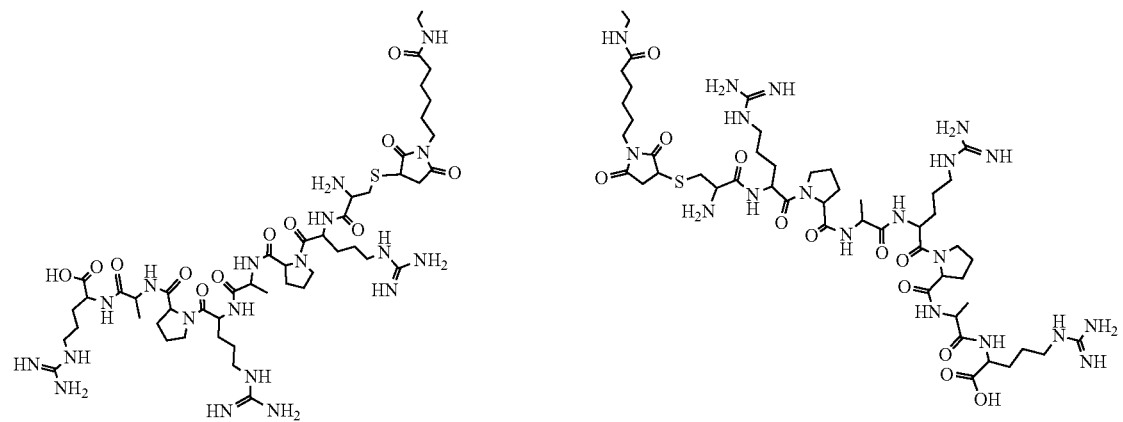

271 272
-continued
Compound 10
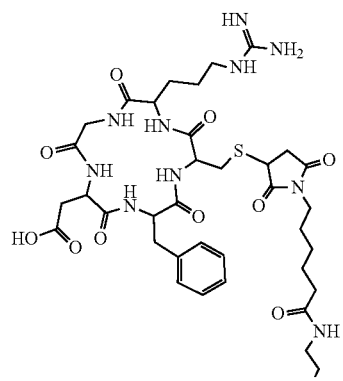
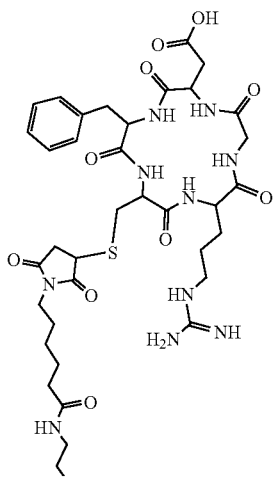
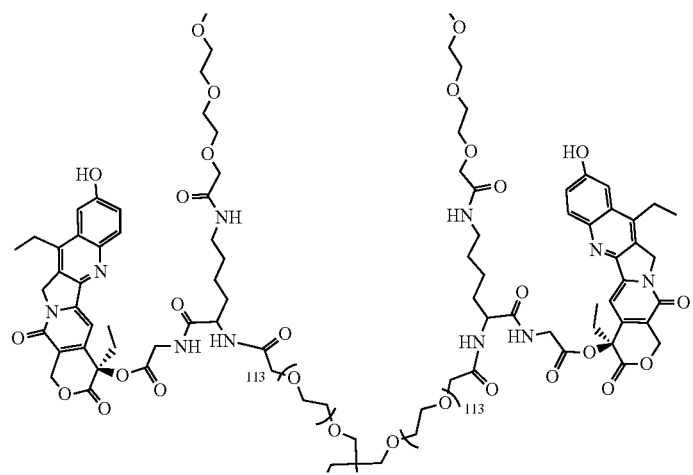
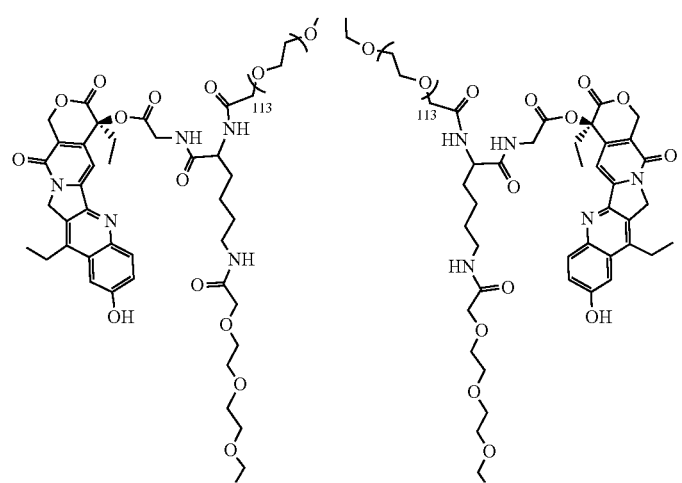

-continued
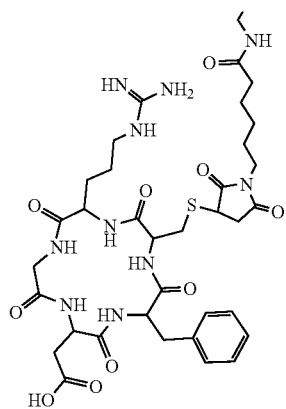
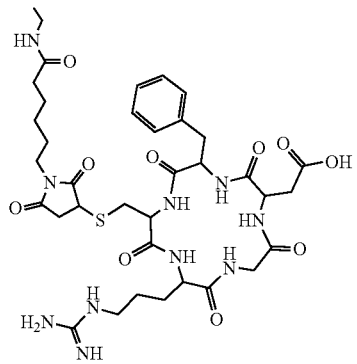
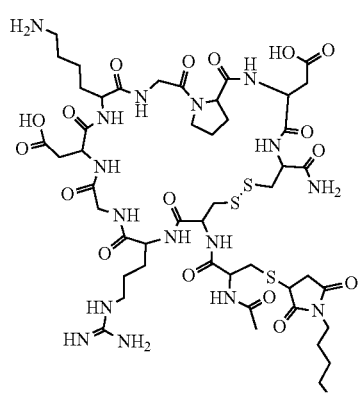
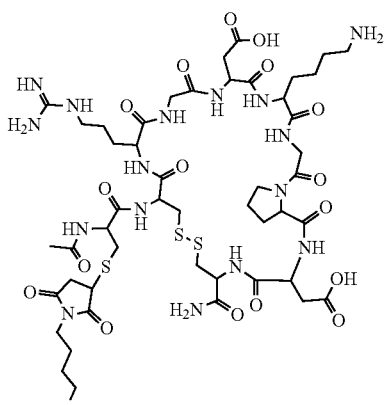
Compound 11
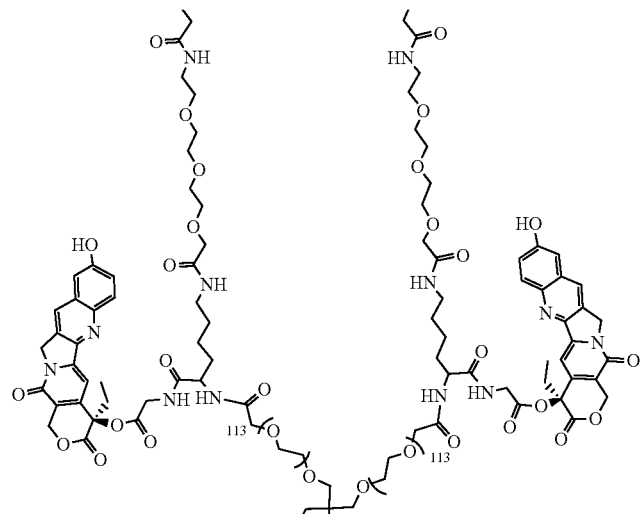

-continued
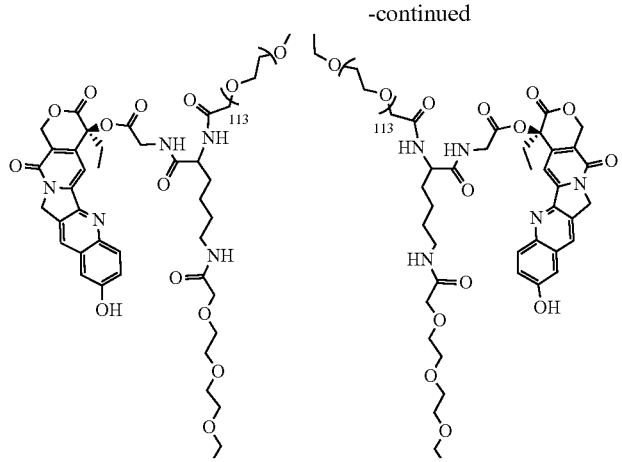
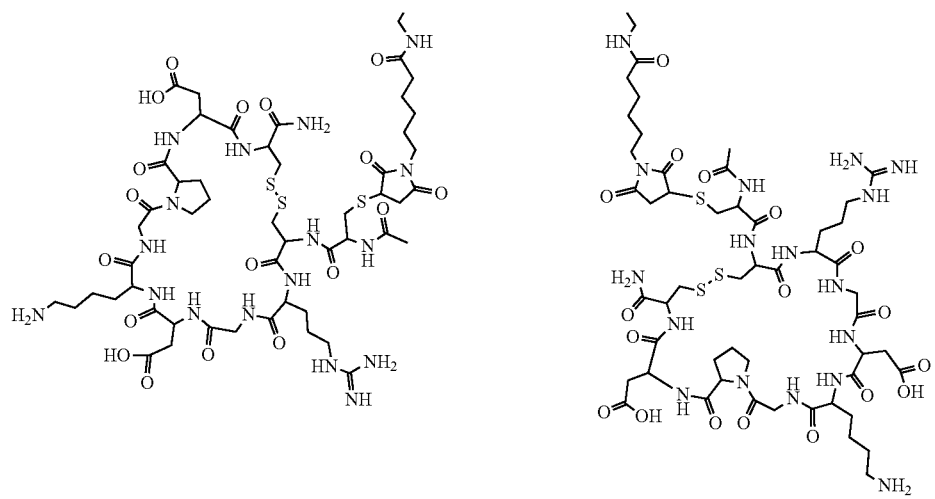
Compound 12
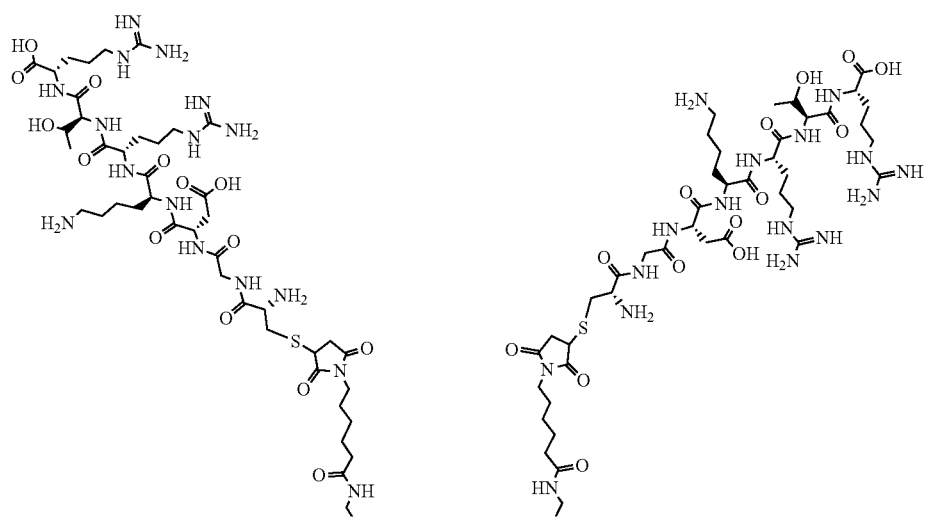

277 278
-continued
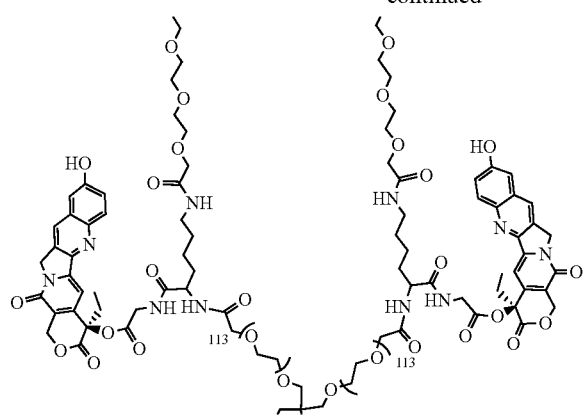
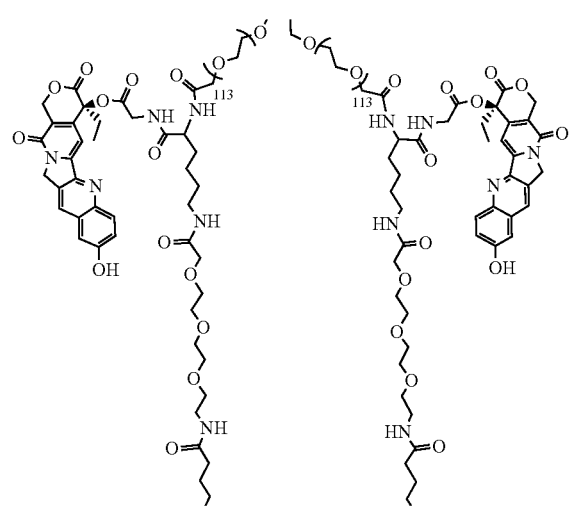
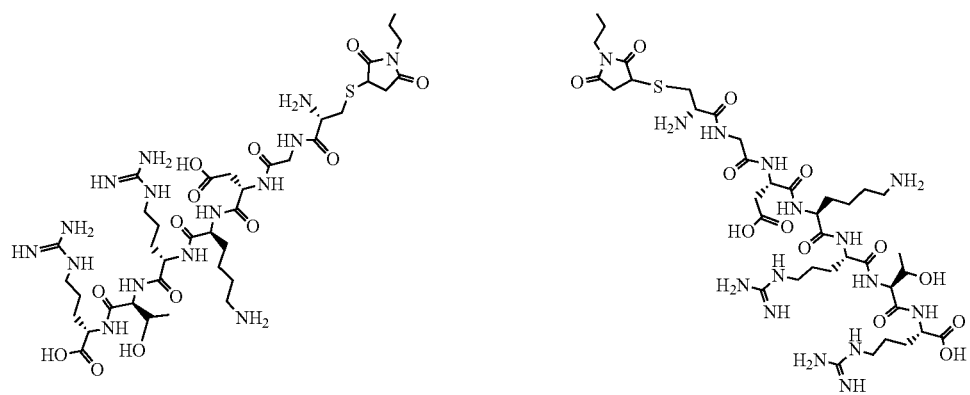

-continued
Compound 13
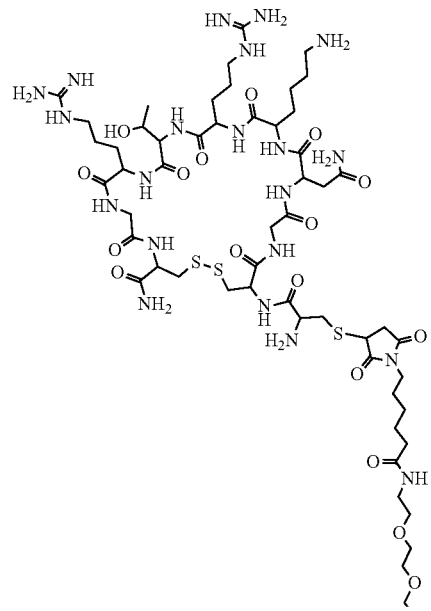
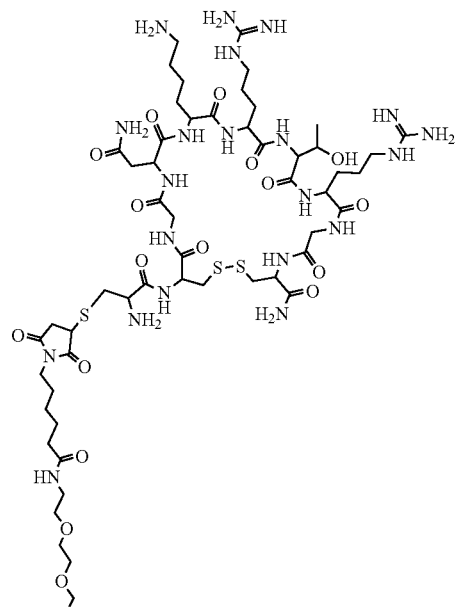
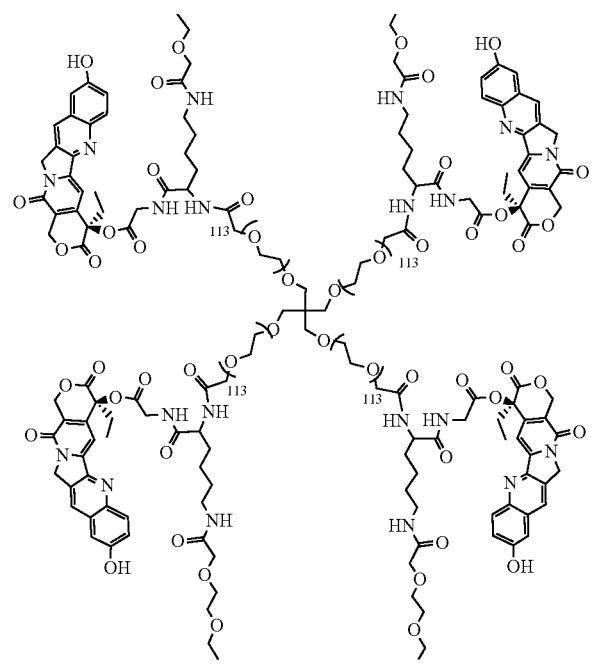

-continued
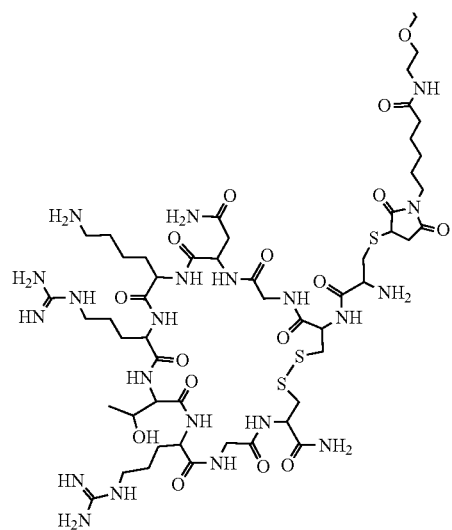
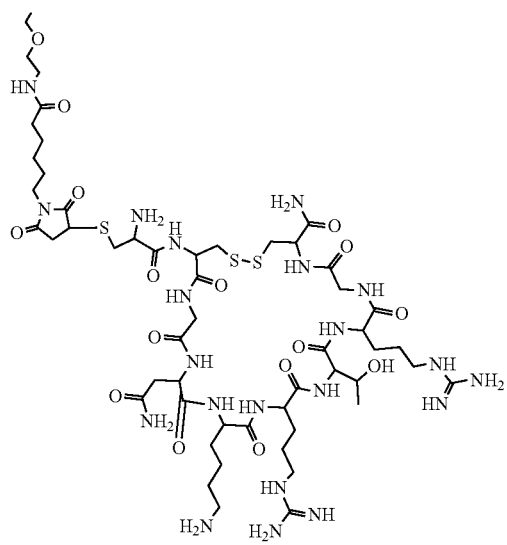
Compound 14
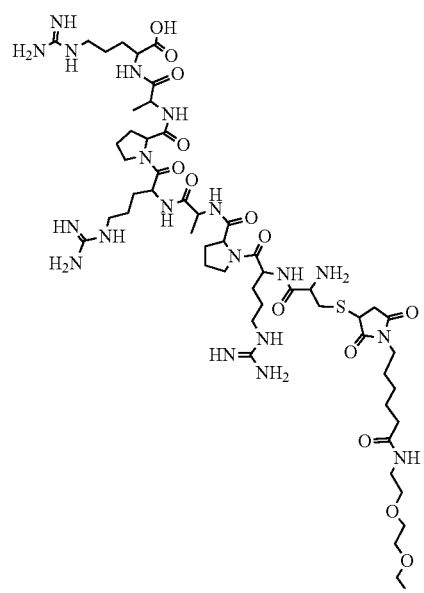
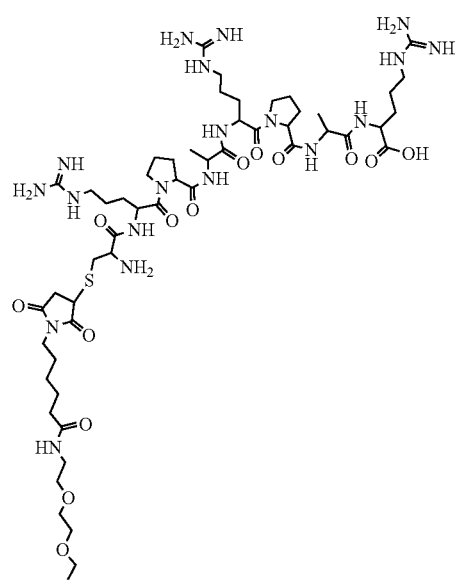

-continued
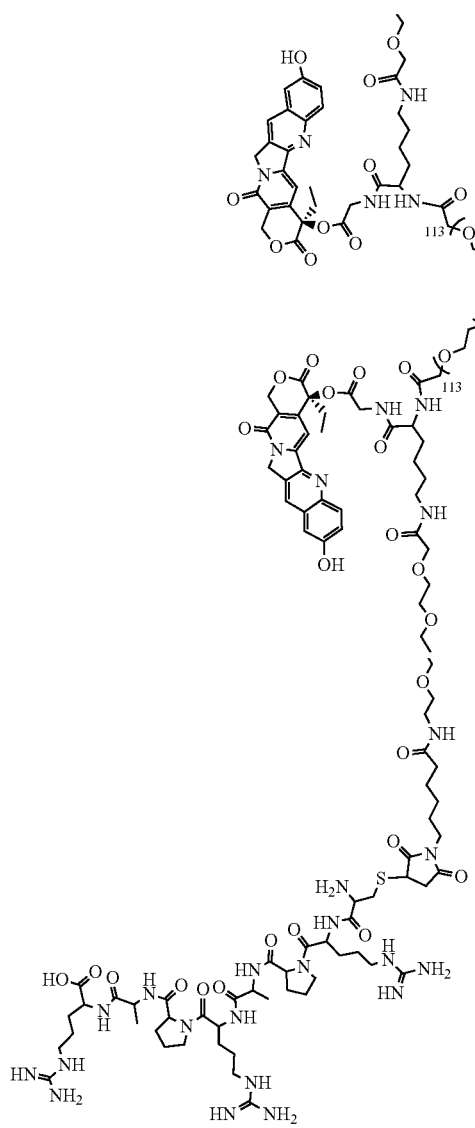
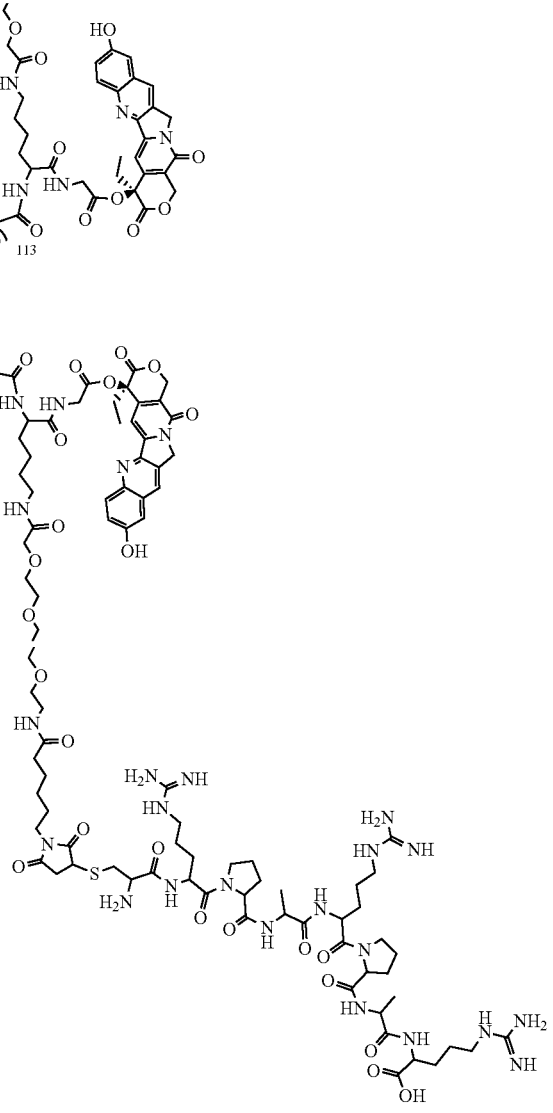
Compound 15
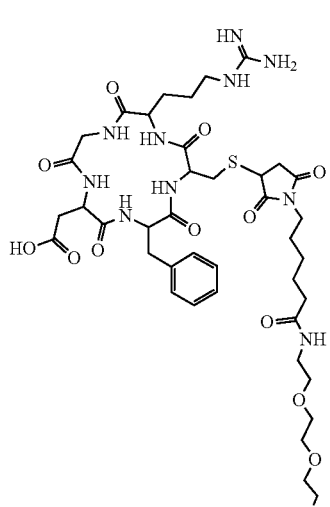
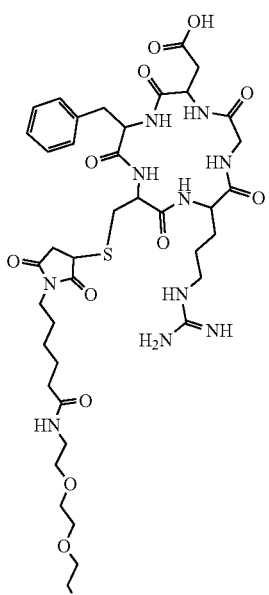

-continued
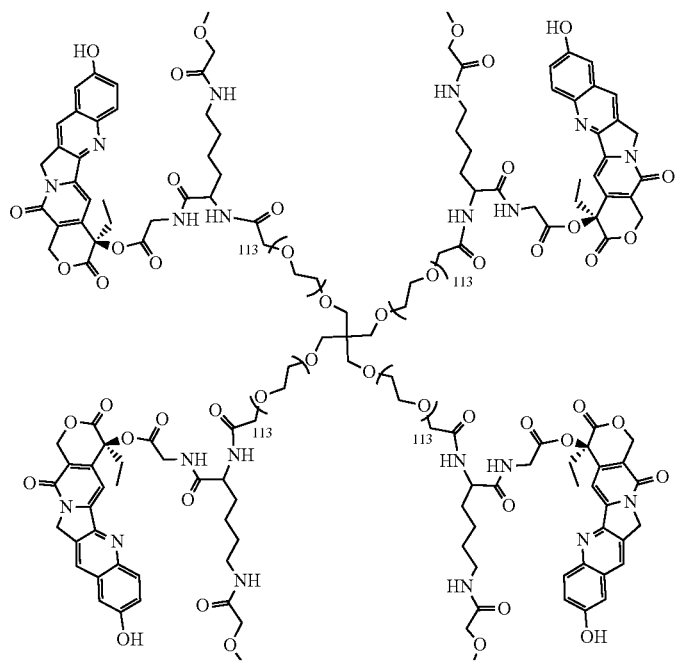
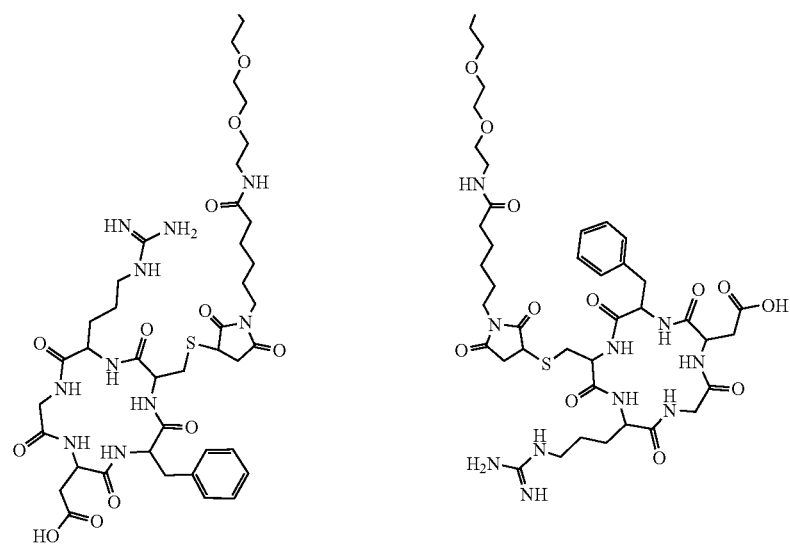

-continued
Compound 16
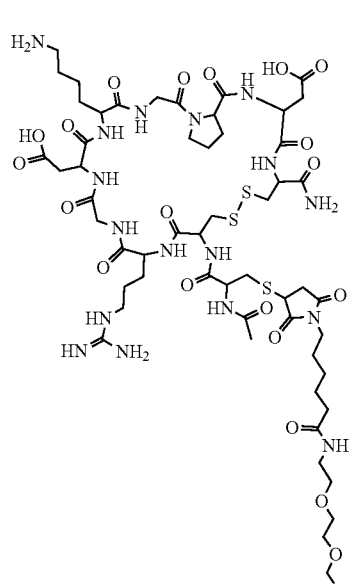
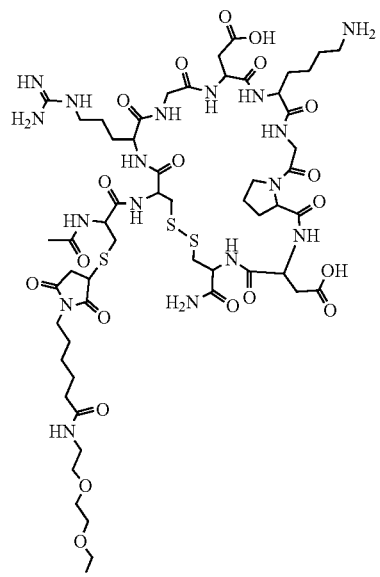
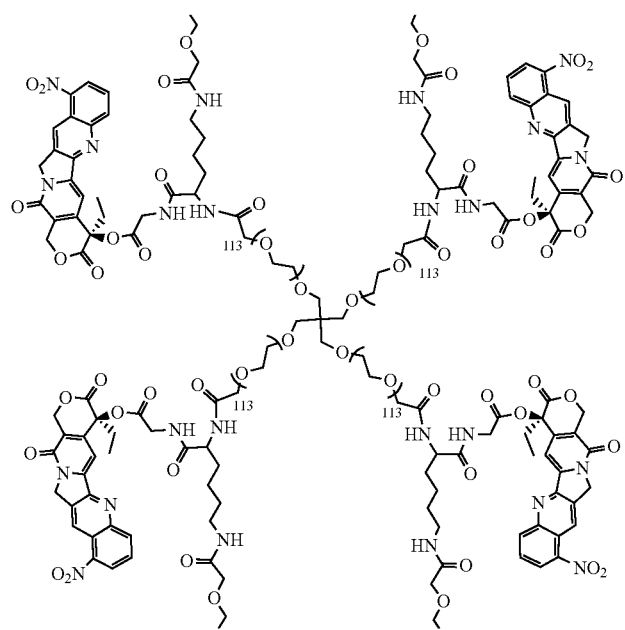

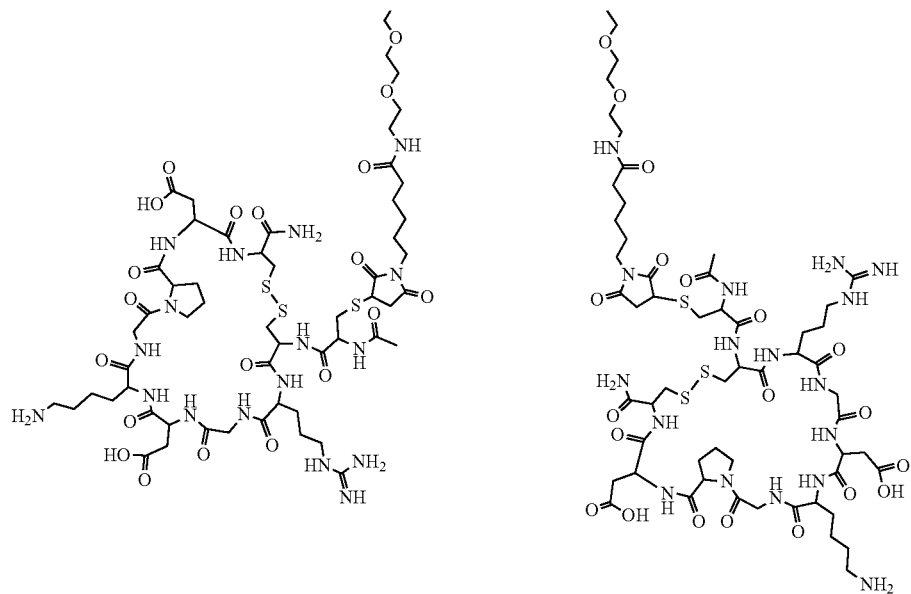
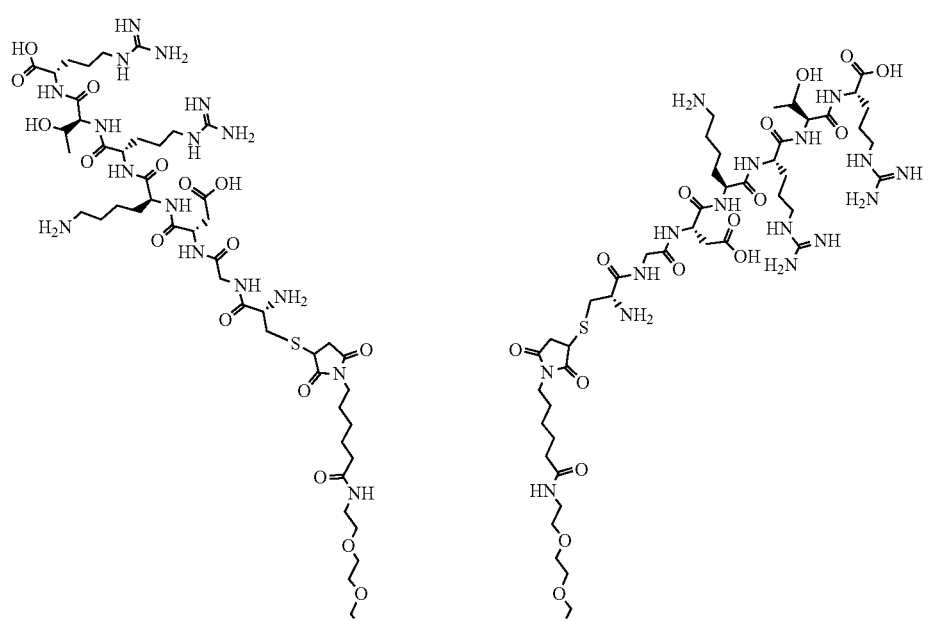
Compound 17

291 292
-continued
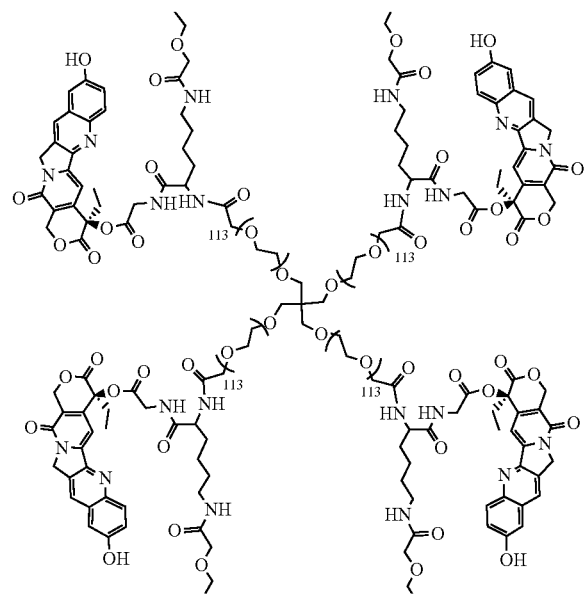
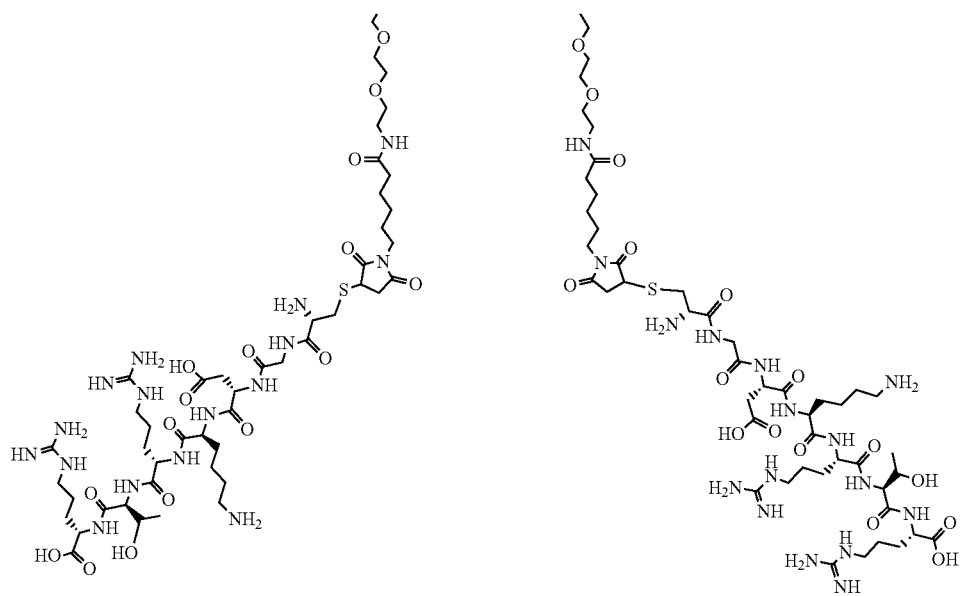

-continued
Compound 18
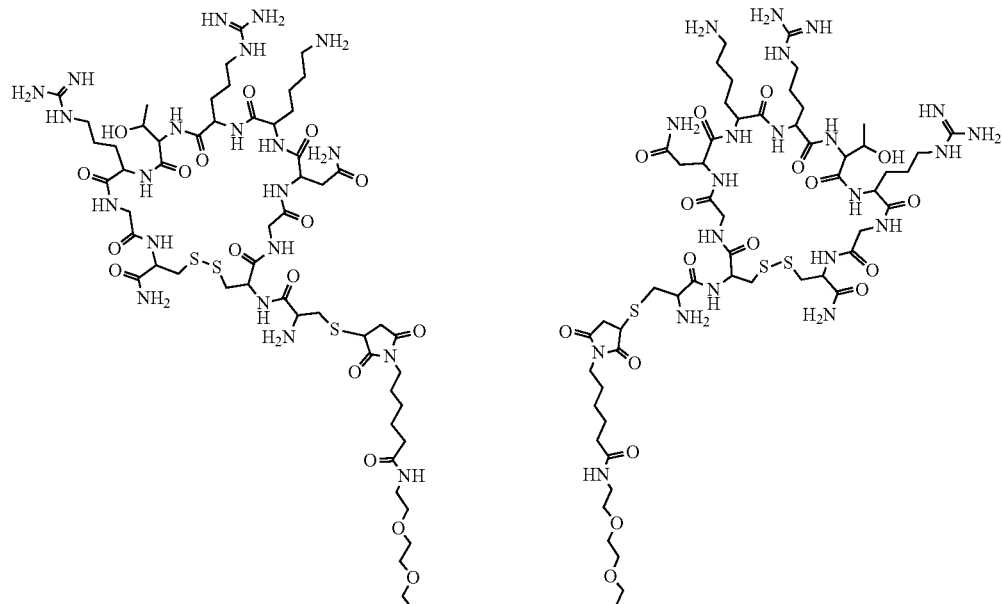
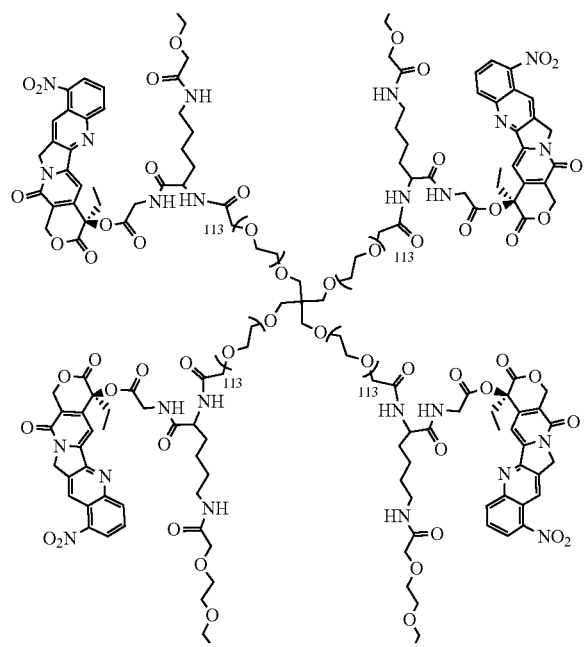

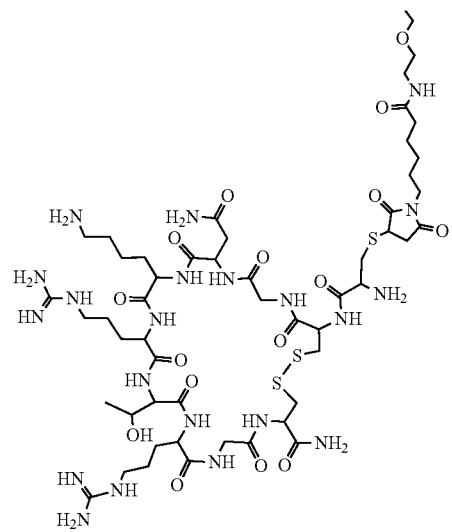
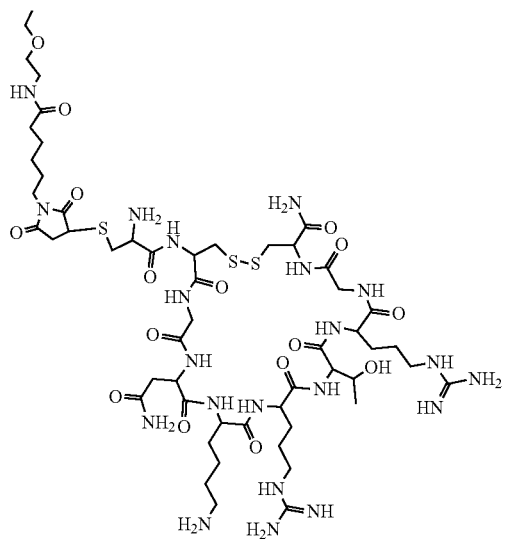
Compound 19
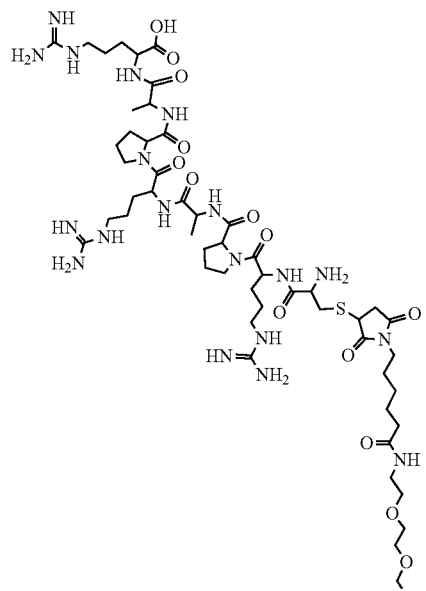
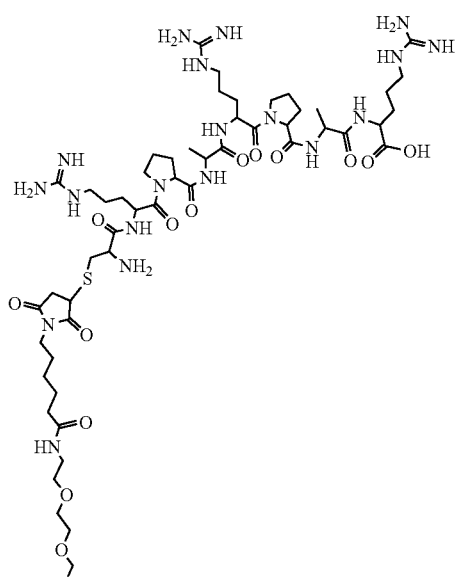

-continued
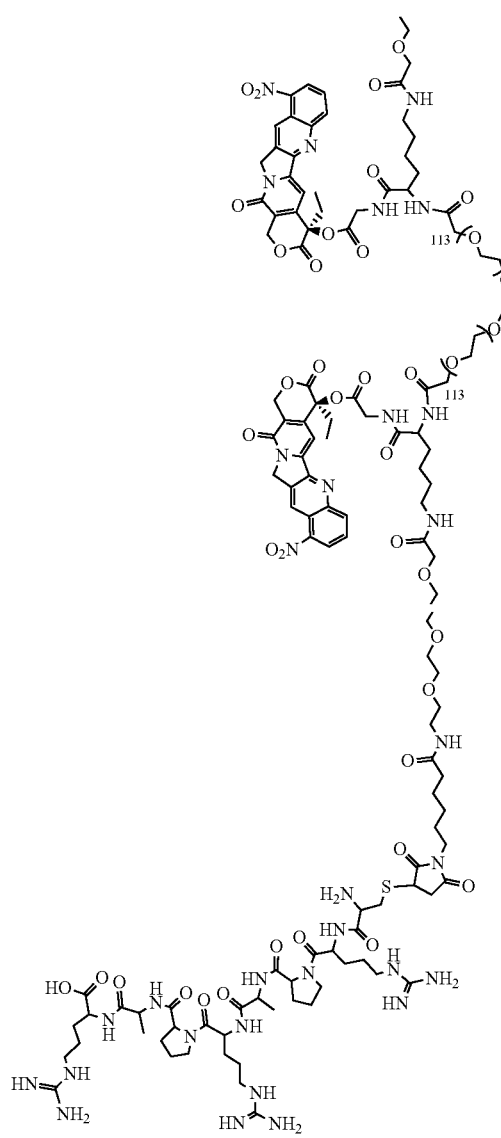
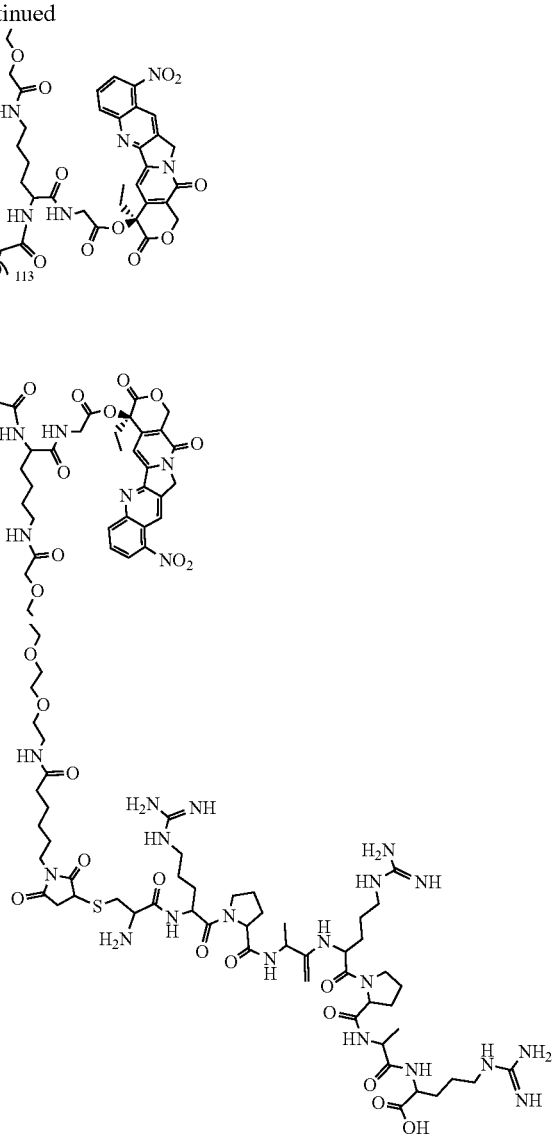
Compound 20
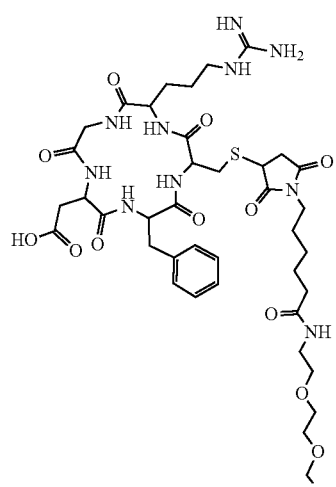
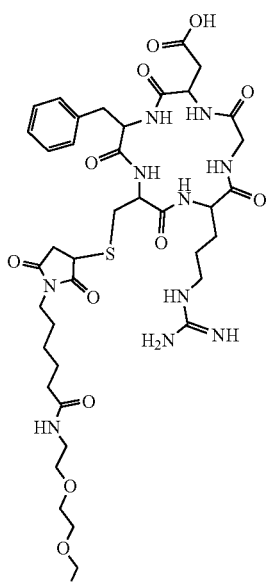

-continued
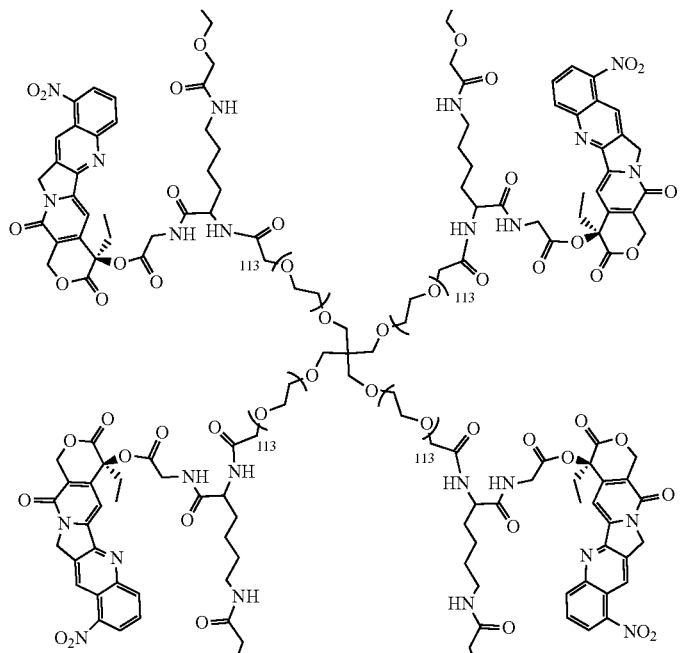
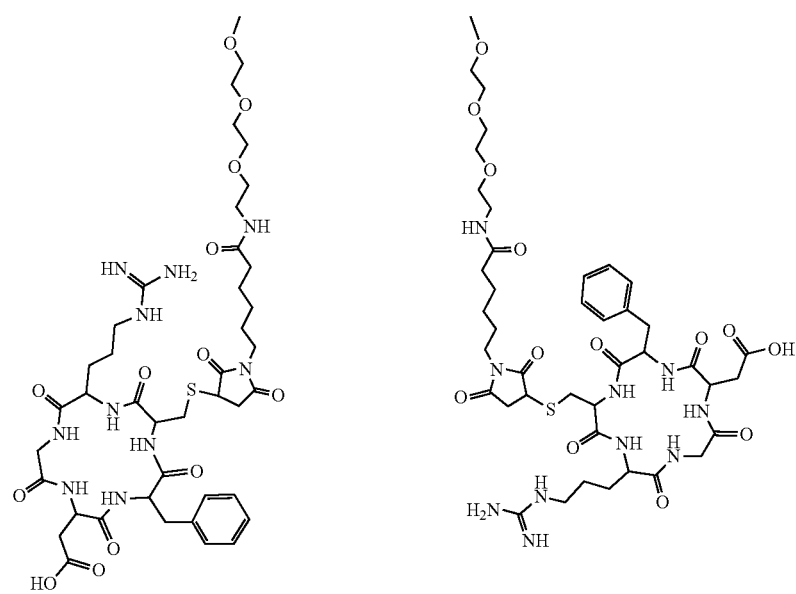

Compound 21
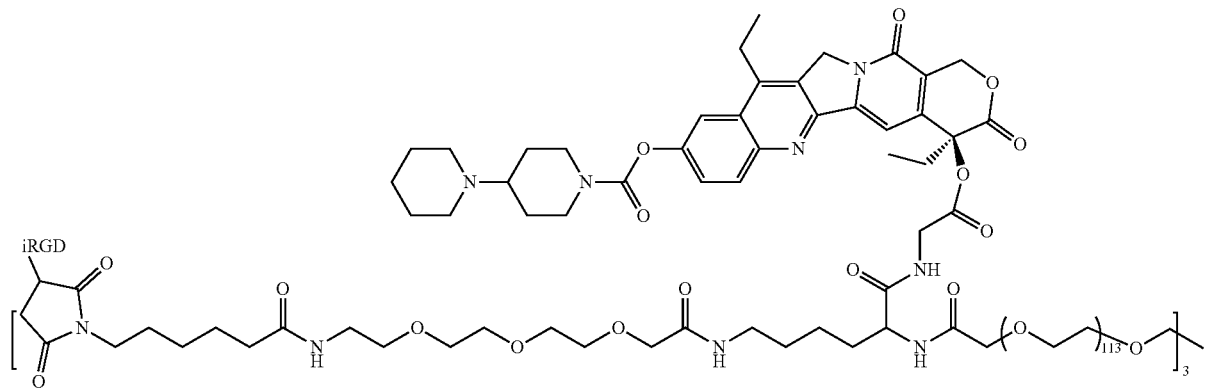
Compound 22
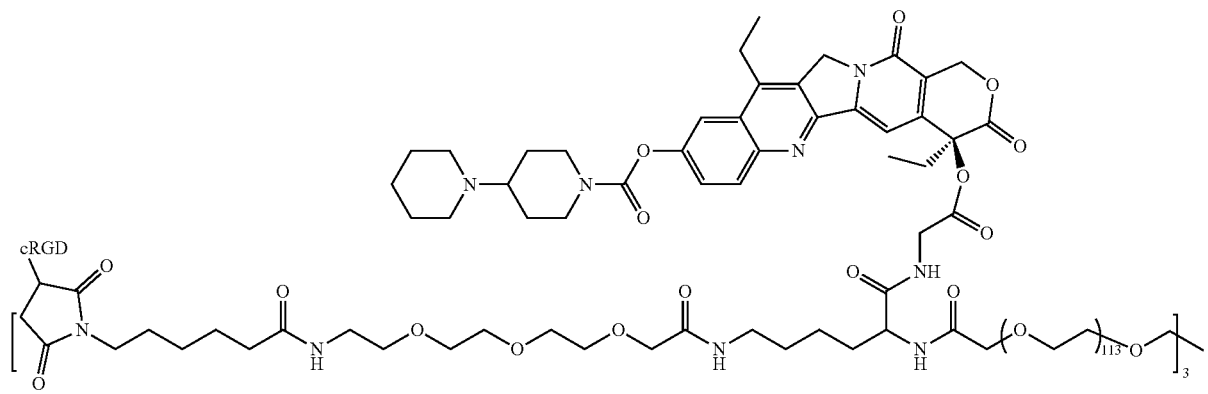
Compound 23
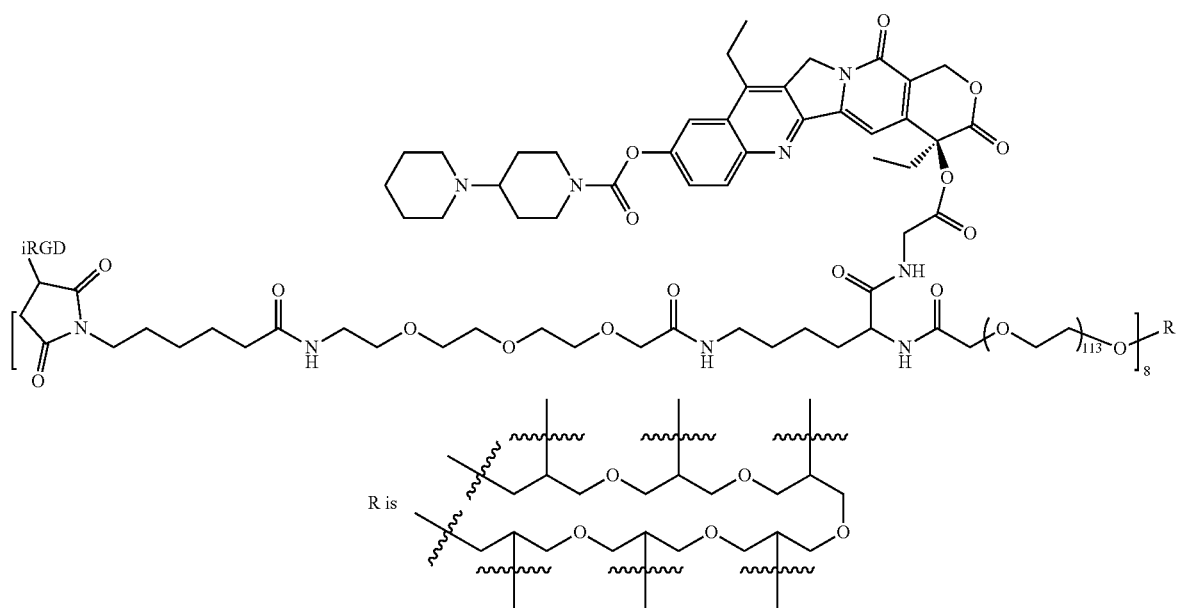

Compound 24
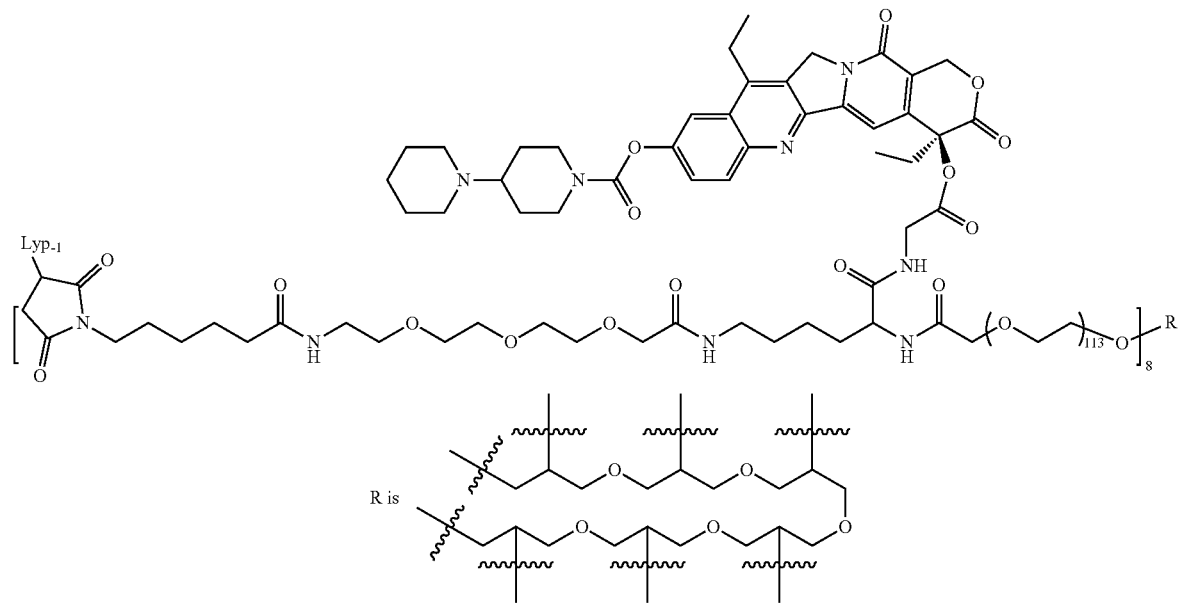
Compound 25
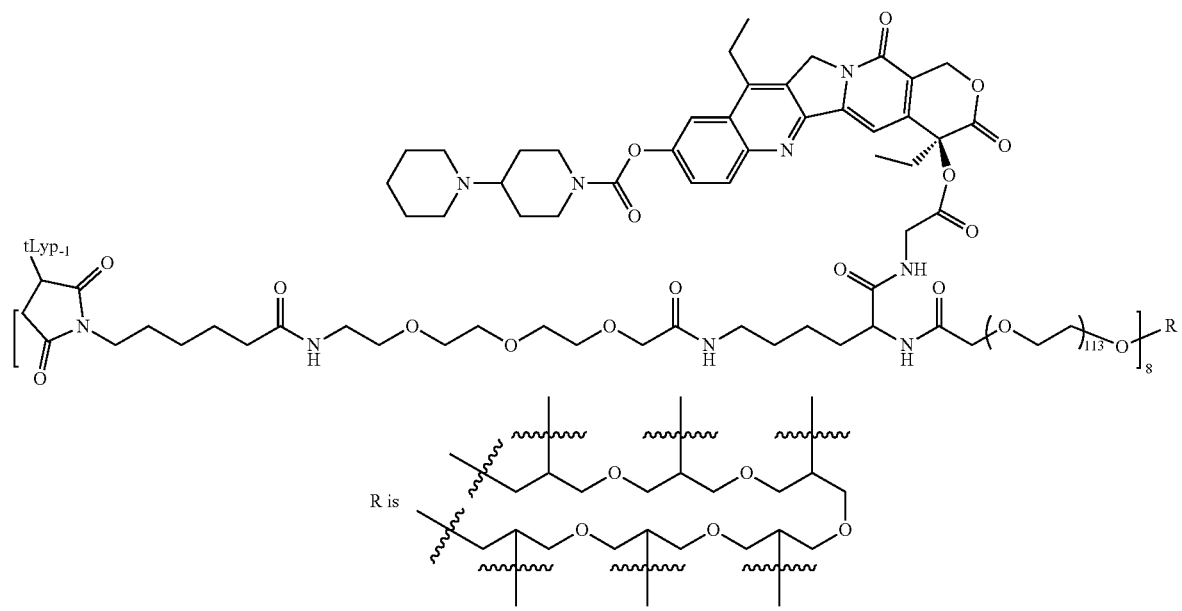

Compound 26
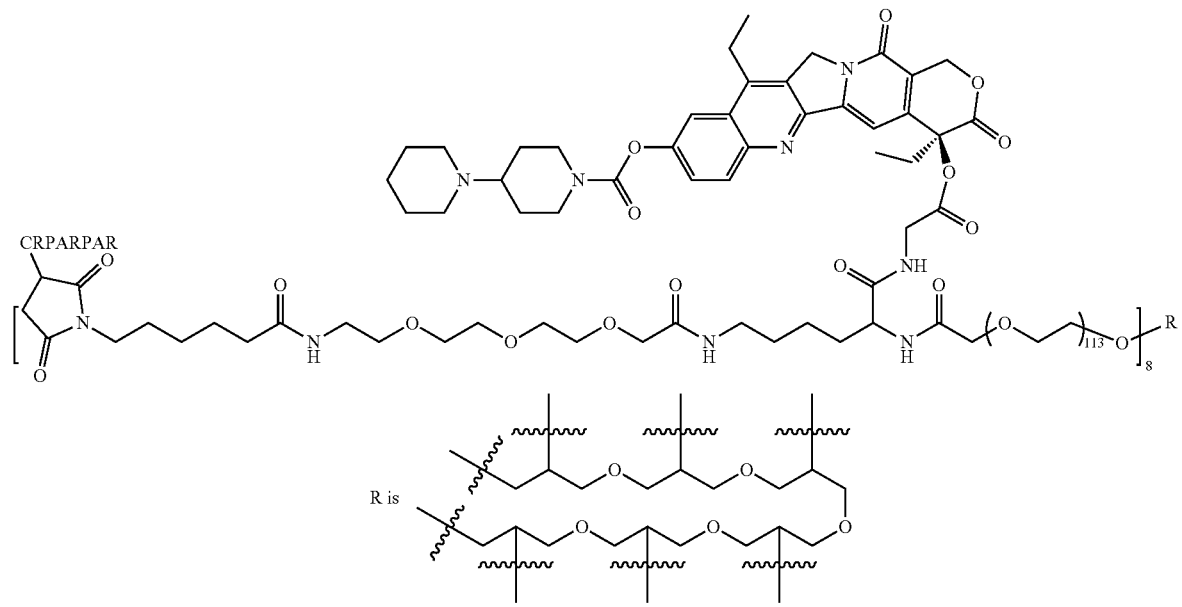
Compound 27
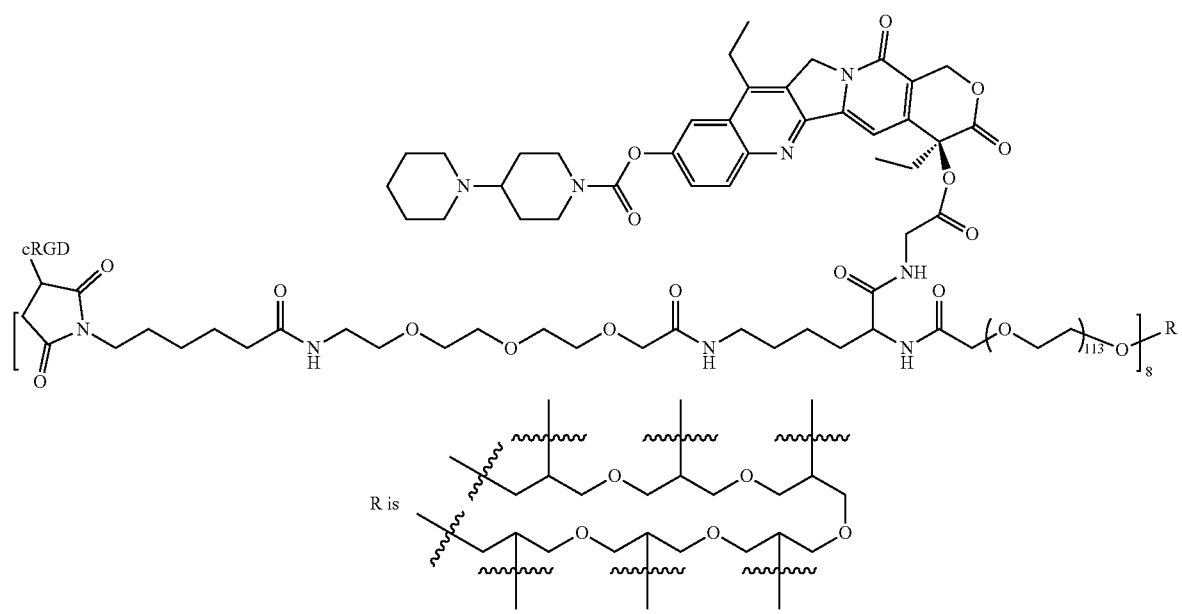

Compound 28
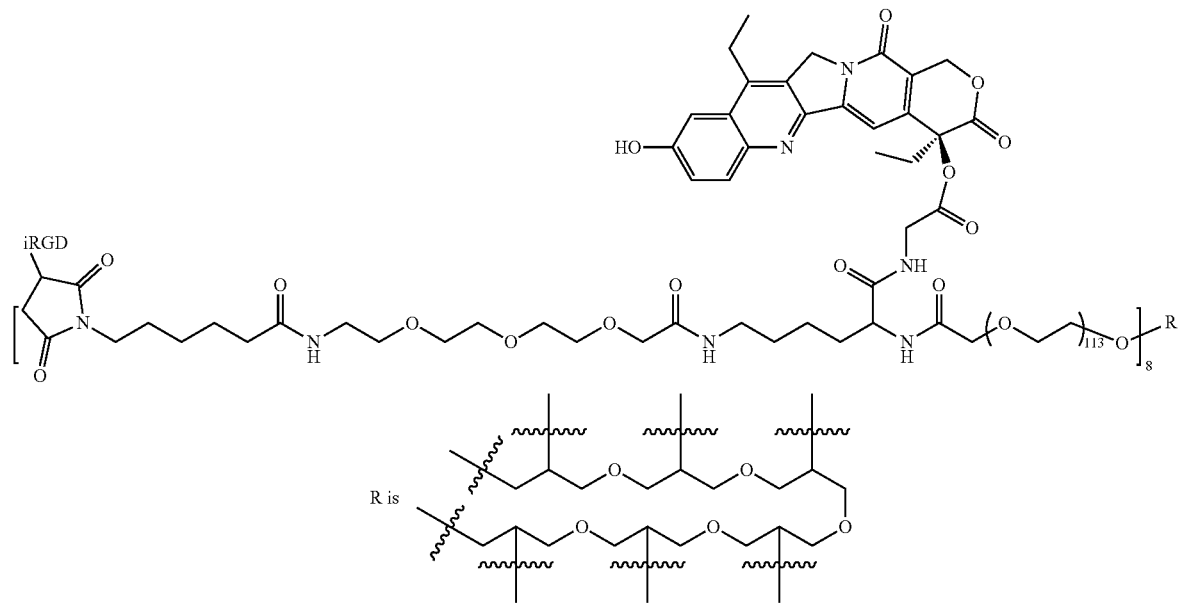
Compound 29
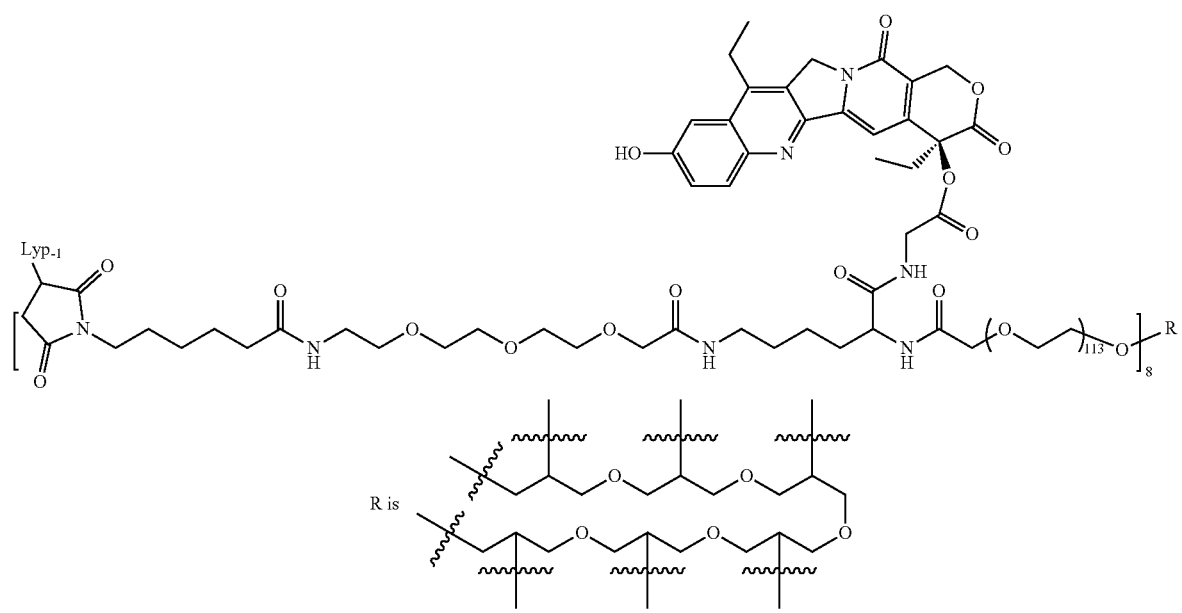

Compound 30
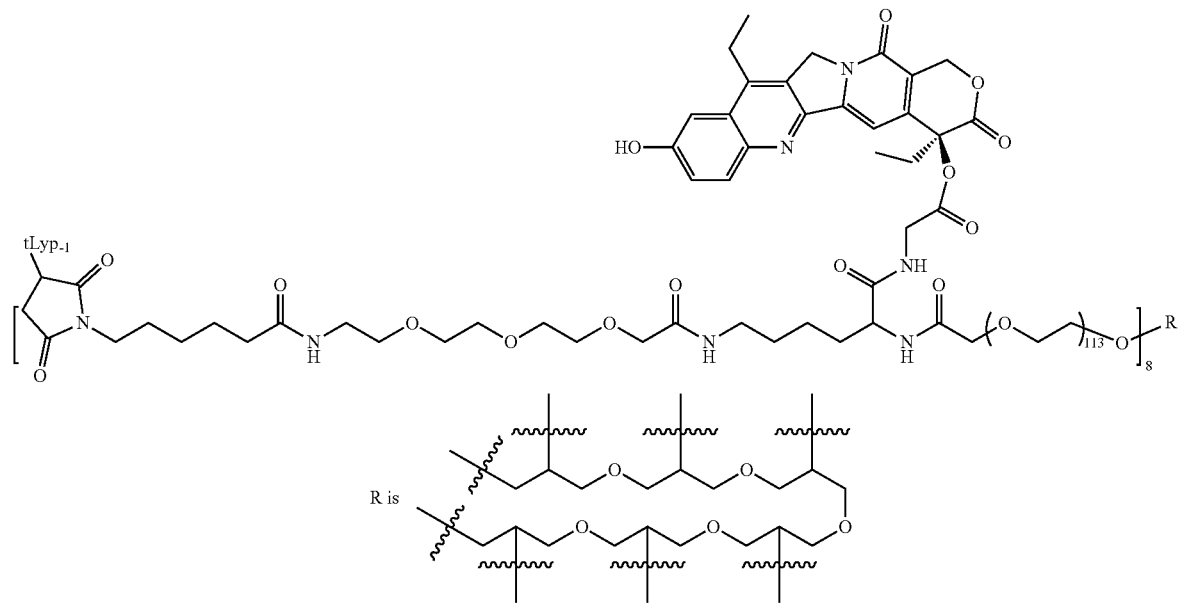
Compound 31
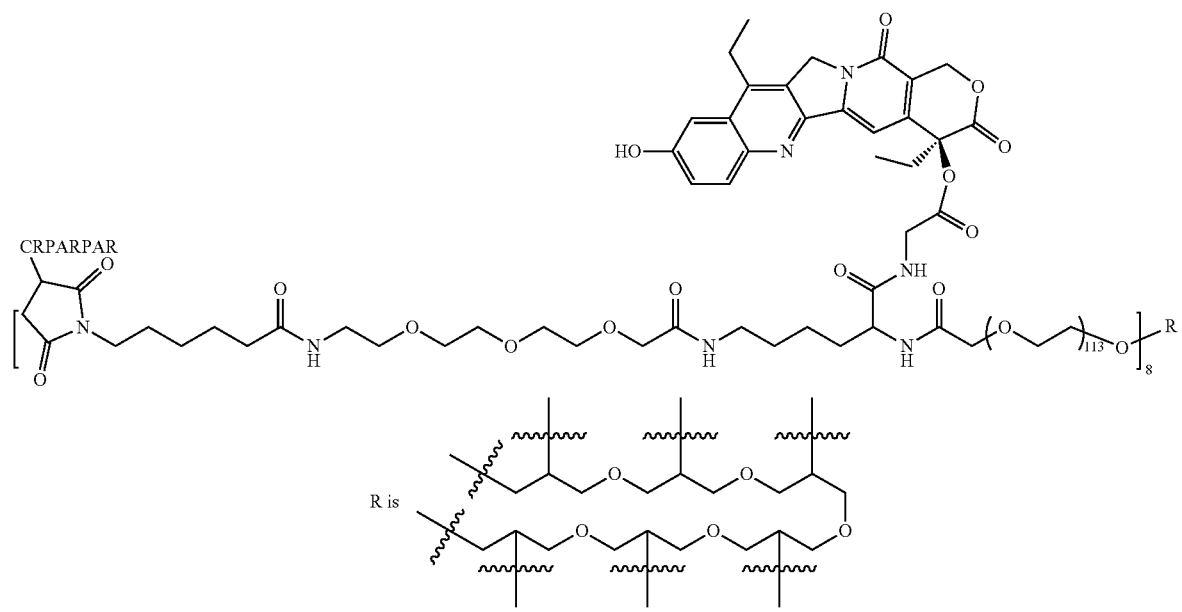

Compound 32
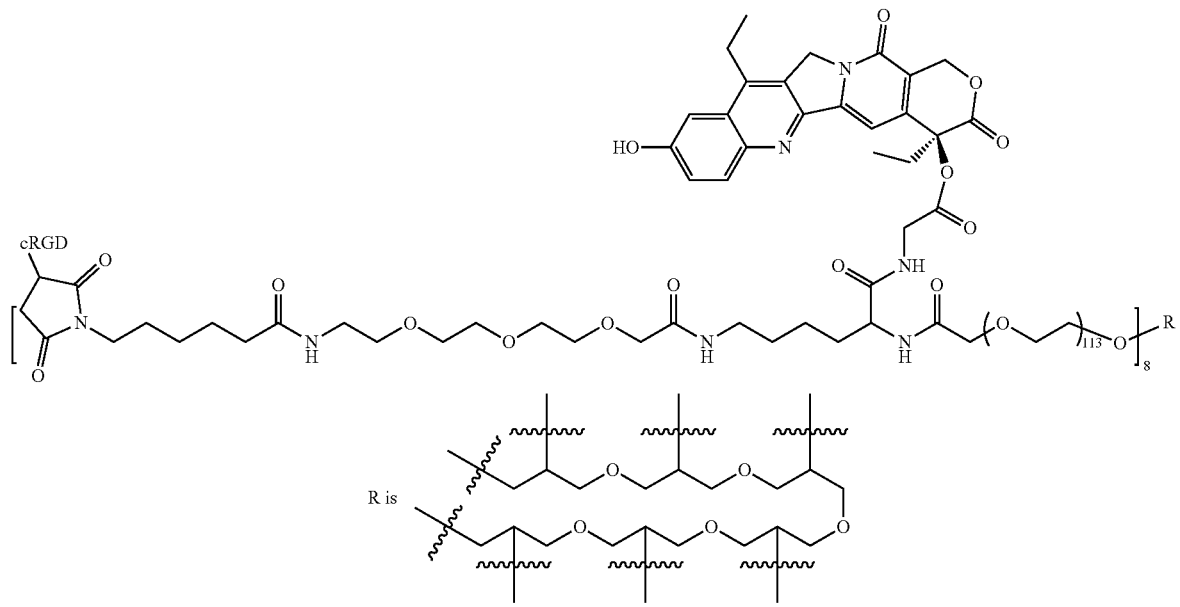
Compound 33
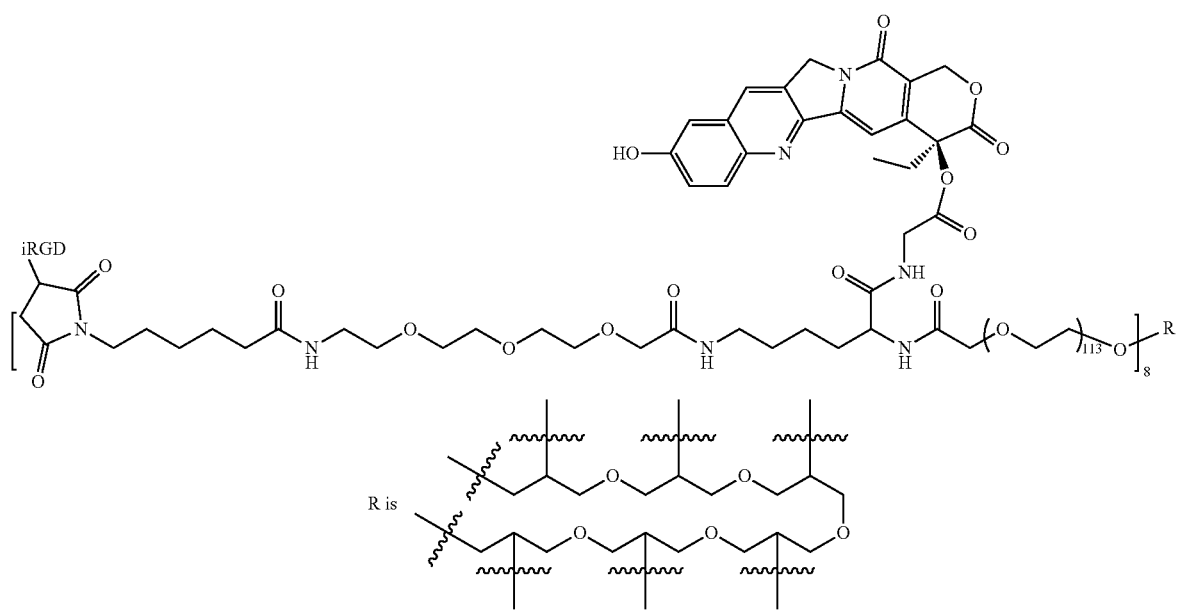

Compound 34
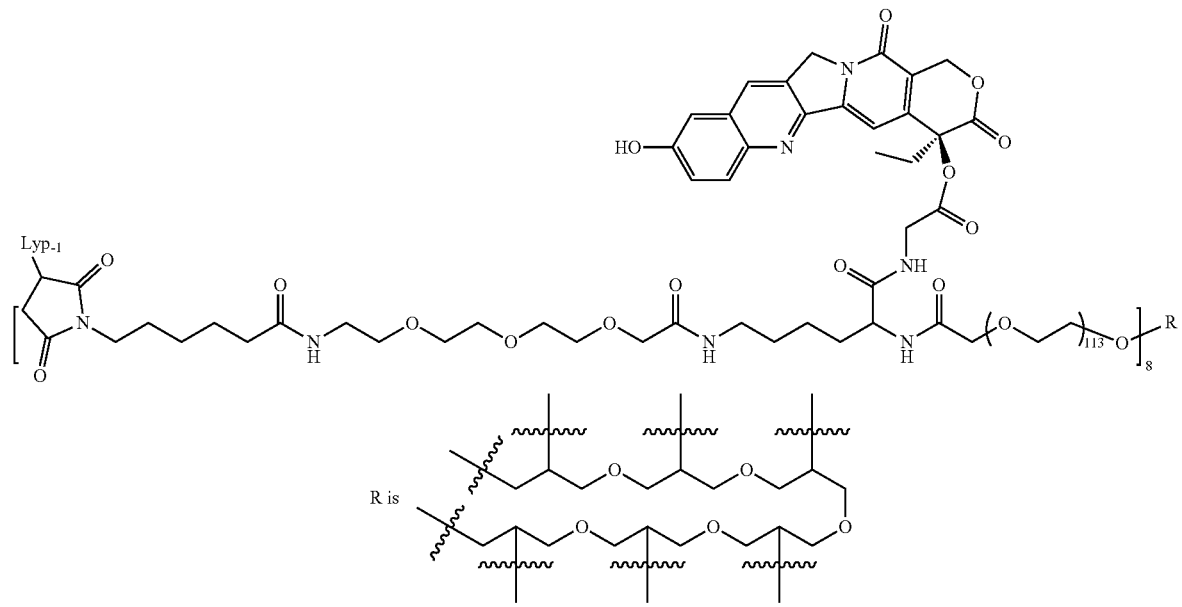
Compound 35
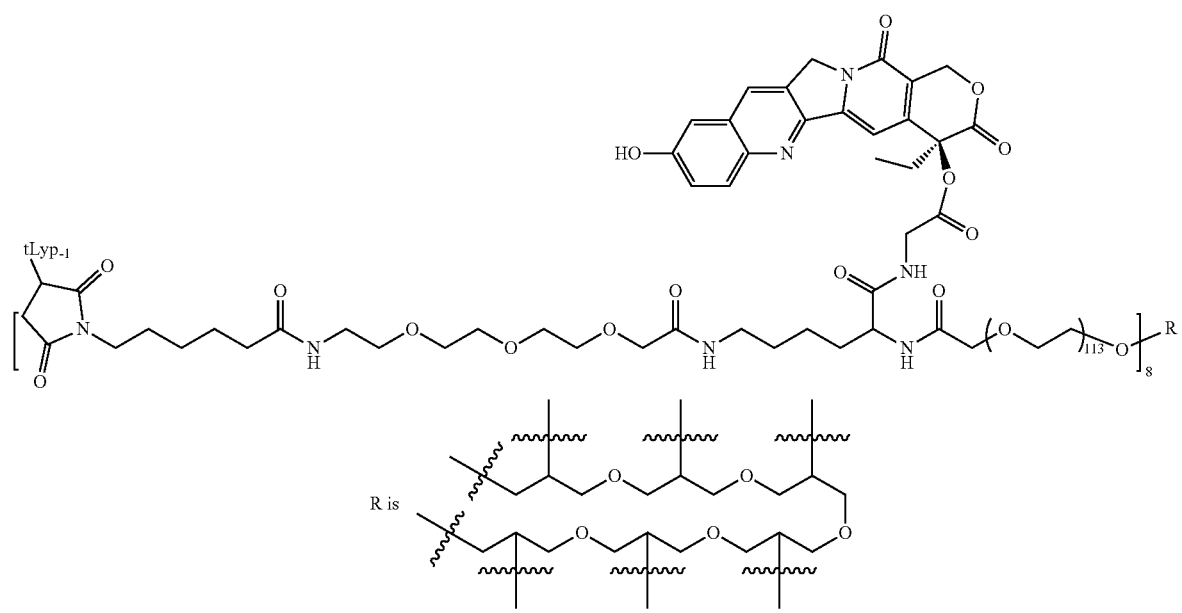

Compound 36
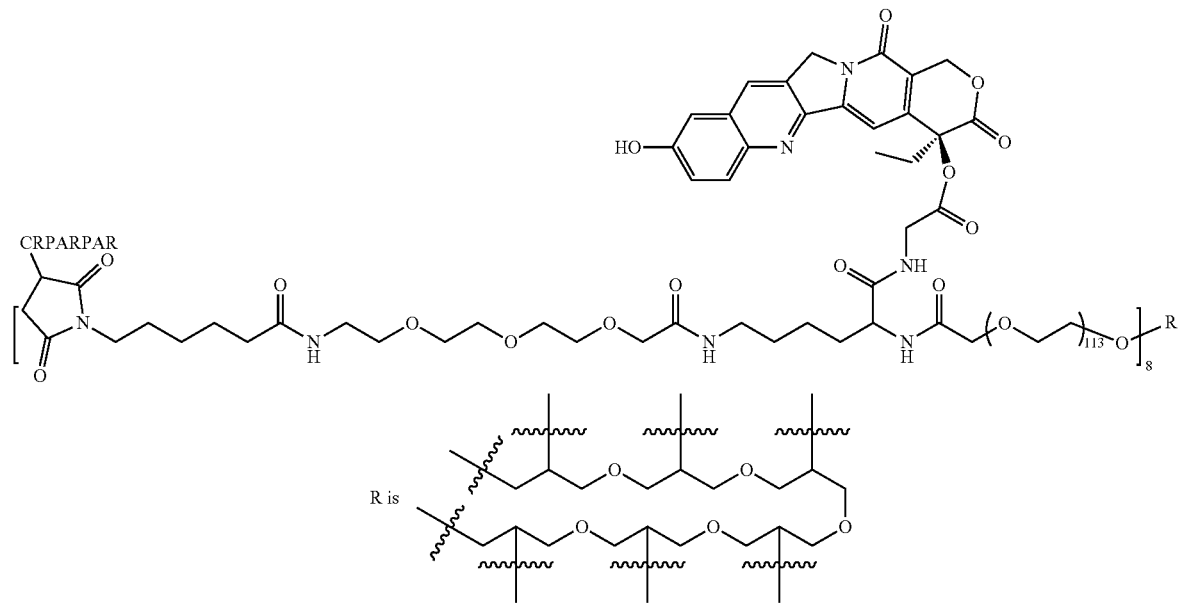
Compound 37
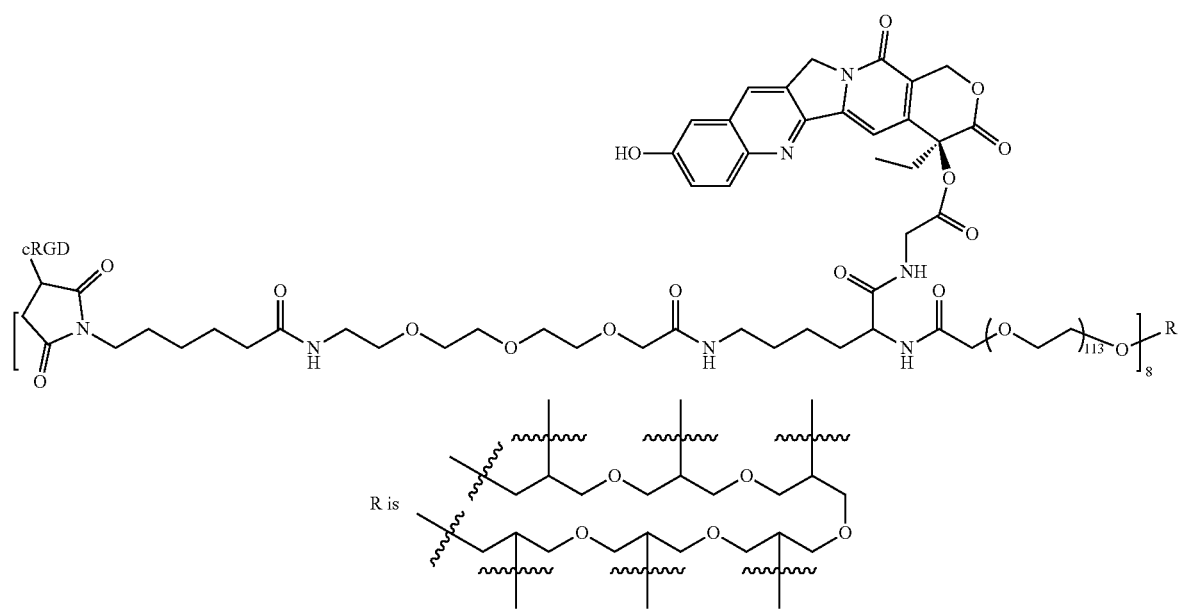

-continued
Compound 38
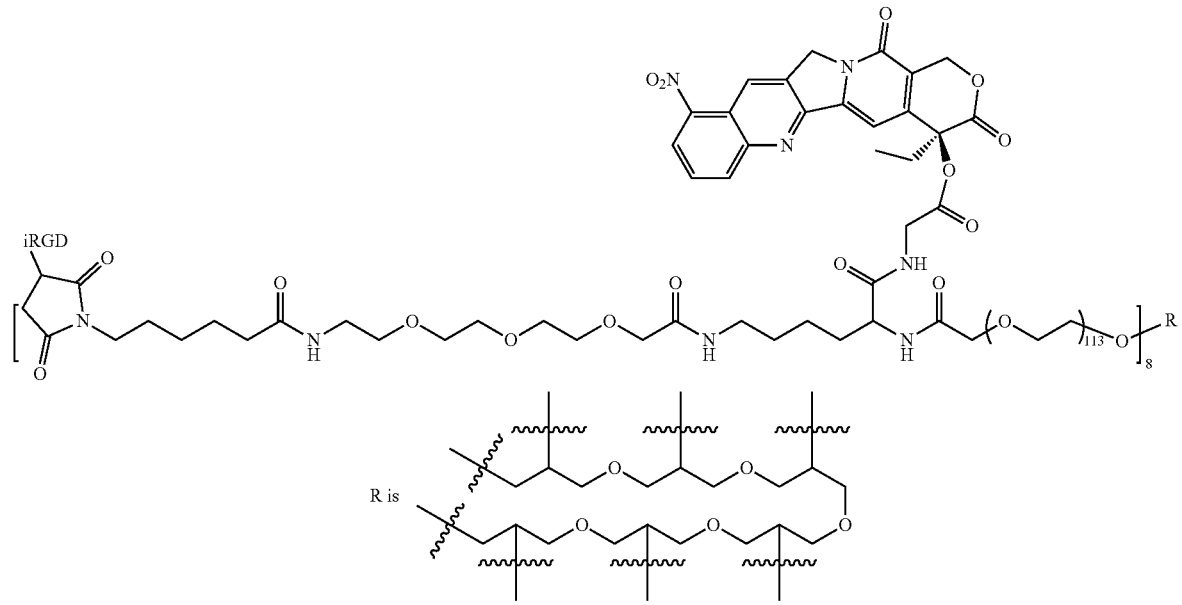
Compound 39
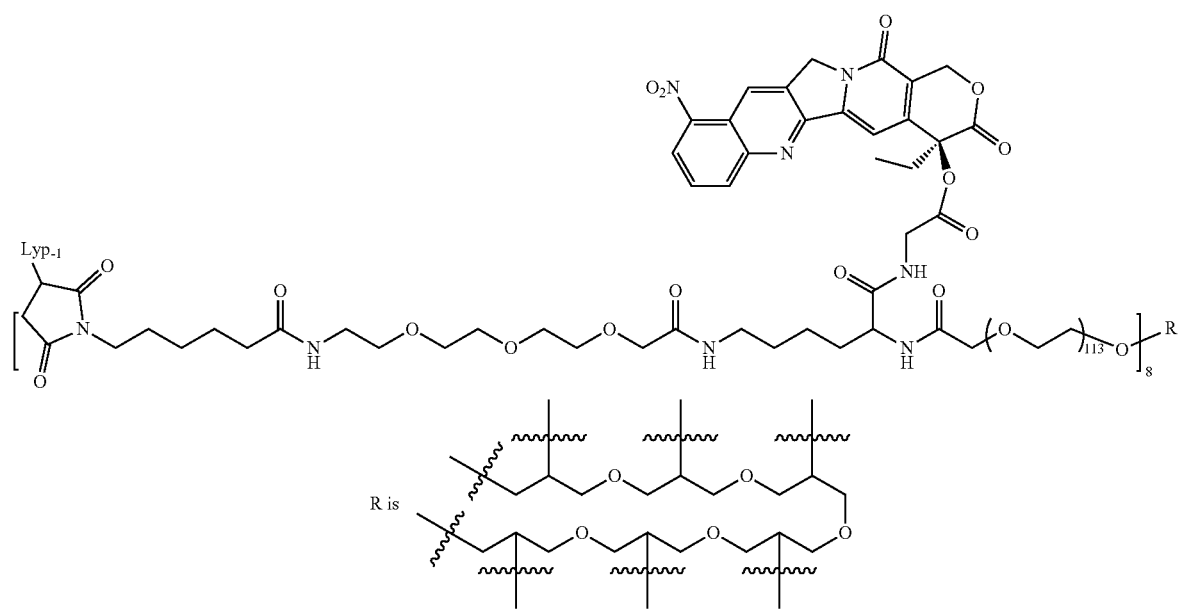

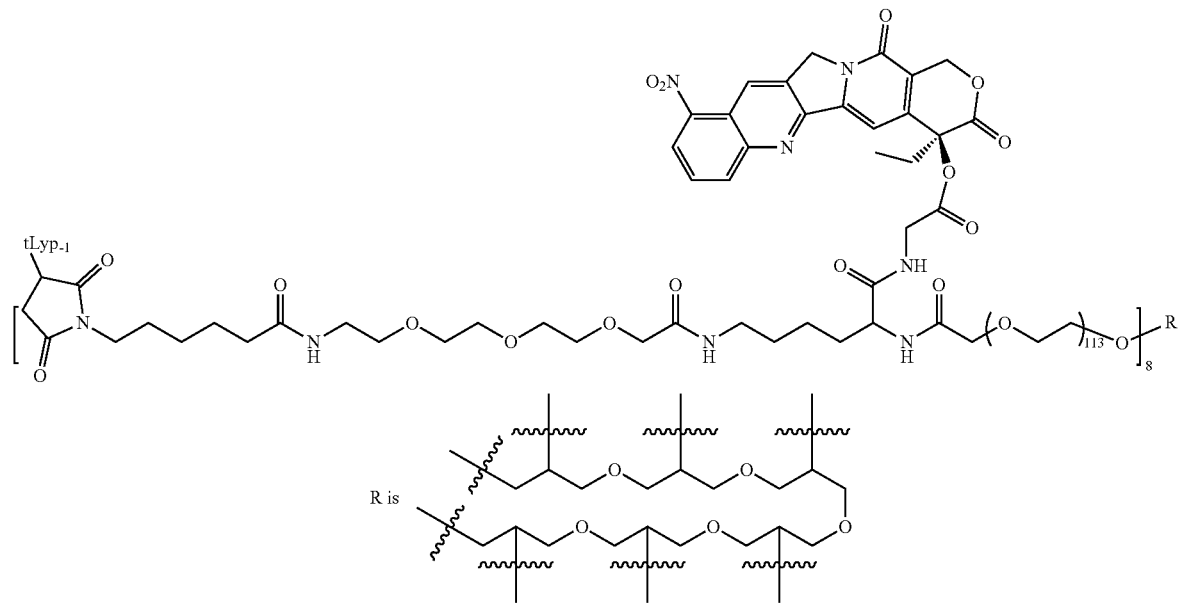
Compound 40
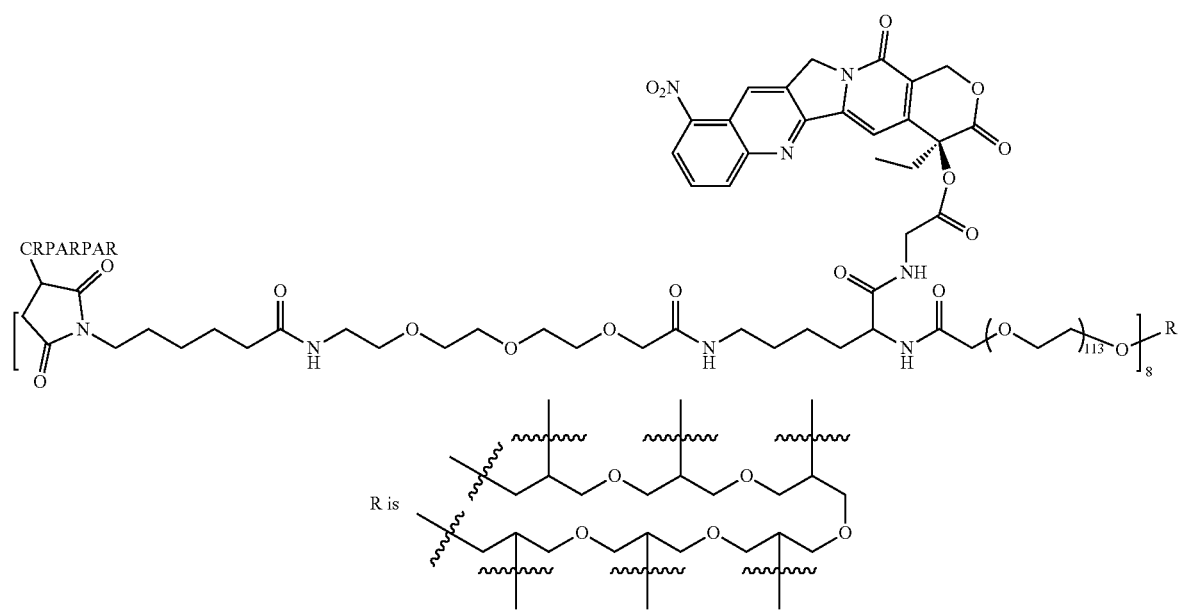
Compound 41

Compound 42

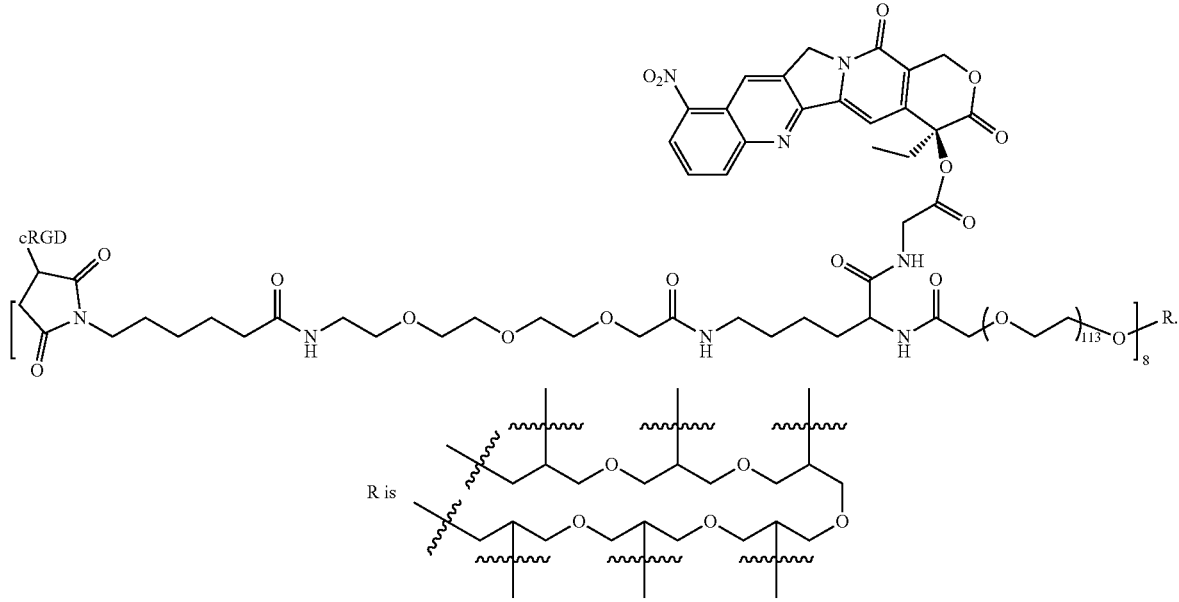

8. A drug composition containing the multi-branched drug conjugate or a pharmaceutically acceptable salt thereof according to claim 1, and a pharmaceutically acceptable excipient.

9. A method for treating colon cancer, lung cancer, breast cancer, ovarian cancer, pancreatic cancer, gastric cancer, brain glioma, and malignant sarcoma, cancer and lymphoma of breast, ovary, colon, kidney, bile duct, lung and brain, comprising administering to a subject in need thereof a therapeutic effective amount of the multi-branched drug conjugate or a pharmaceutically acceptable salt thereof according to claim 1.

10. A preparation method of a multi-branched drug conjugate or a pharmaceutically acceptable salt thereof, comprising:

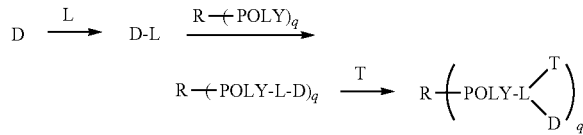

wherein R is an organic core, POLY is polyethylene glycol, L is a multivalent linker, T is a targeting molecule, D is an active agent, q is any integer between 3 and 8, and D is a camptothecin-based drug represented by the following formula:

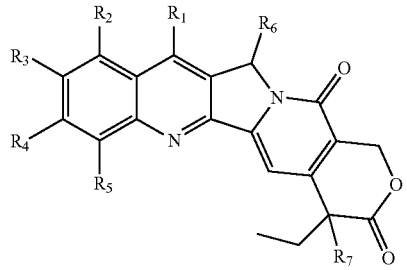

wherein $R_1$ to $R_5$ are selected from the following groups independently from each other: hydrogen, halogen, acyl, alkyl, substituted alkyl, alkoxy, substituted alkoxy, alkenyl, alkynyl, cycloalkyl, hydroxyl, cyano, nitro, azido, amido, hydrazine, amine group, substituted amine group, hydroxycarbonyl, alkoxycarbonyl, alkoxycarbonyloxy, carbamoyloxy, aryl sulfonyloxy, and alkylsulfonyloxy; $R_6$ is H or $OR_8$; $R_8$ is alkyl, alkenyl, cycloalkyl, halogenated alkyl, or hydroxyalkyl; and $R_7$ is hydroxyl;

the multivalent linker L is:

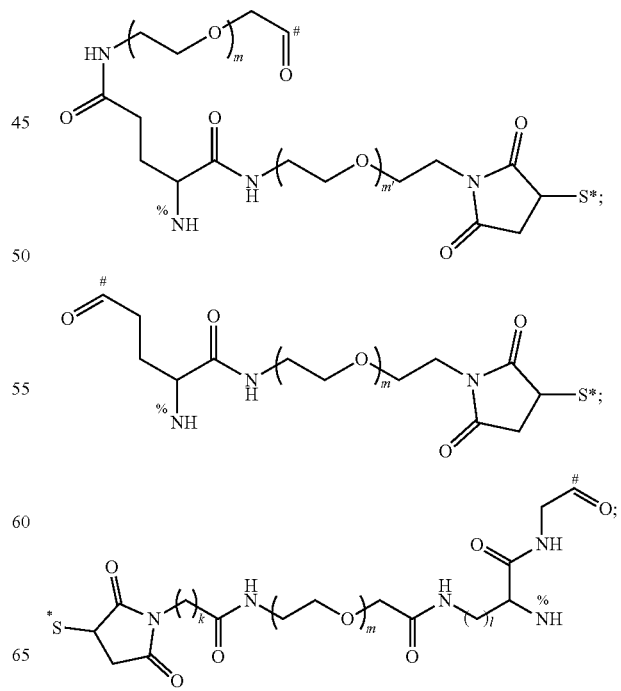

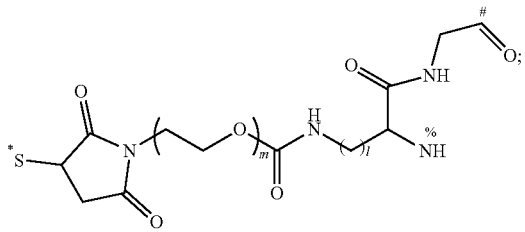

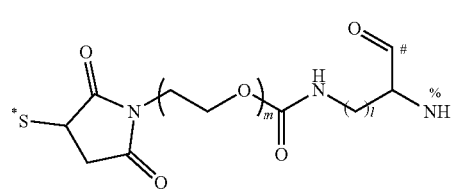

symbol "*" represents an attachment point of the multivalent linker L and the targeting molecule T, "#" represents an attachment point of the multivalent linker L and the active agent D, "%" represents an attachment point of the multivalent linker L and POLY, wherein m and m' are any integer between 1 and 20 respectively, and l and k are any integer between 1 and 10 respectively;

T is an "arginine-glycine-aspartic acid" sequence-containing RGD peptide, tLyp-1, Lyp-1, RPARPAR, Angiopep2, GE11, or folic acid;

(1) the active agent D is attached to the multivalent linker L to obtain a D-L portion;

(2) the D-L portion is attached to a multi-arm polymer R—(POLY)$_q$ to obtain R—(POLY-L-D)$_q$; and (3) R—(POLY-L-D)$_q$ obtained in the previous step is attached to the targeting molecule T.

11. A preparation method of the multi-branched drug conjugate or a pharmaceutically acceptable salt thereof according to claim 10, wherein D is irinotecan, SN-38, 10-hydroxycamptothecin, or rubitecan;

the multi-arm polymer R—(POLY)$_q$ is 3armPEG20K-SCM, 4armPEG20K-SCM, or 8armPEG20K-SCM;
L is

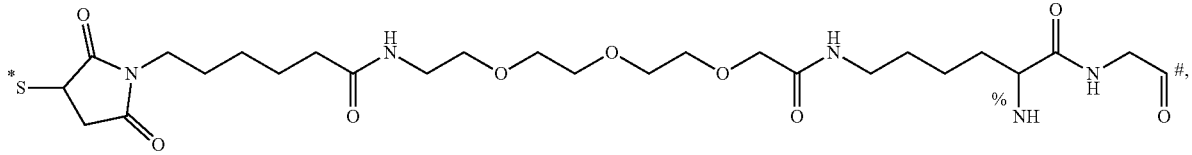

symbol "*" represents an attachment point of the multivalent linker L and the targeting molecule T, "#" represents an attachment point of the multivalent linker L and the active agent D, and "%" represents an attachment point of the multivalent linker L and POLY; and T is iRGD, cRGD, tLyp-1, Lyp-1, RPARPAR, Angiopep2, GE11, or folic acid.

12. The multi-branched drug conjugate or a pharmaceutically acceptable salt thereof according to claim 1, wherein POLY is:

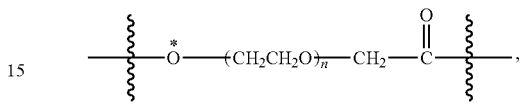

n is 50 to 200.

13. The multi-branched drug conjugate or a pharmaceutically acceptable salt thereof according to claim 1, wherein POLY is:

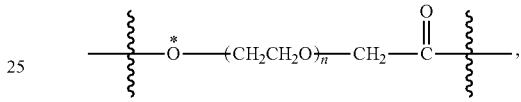

n is 113.

14. The multi-branched drug conjugate or a pharmaceutically acceptable salt thereof according to claim 1, wherein said multi-branched drug conjugate has a structure represented by structural formula (IV), (V), or (VI):

(IV)

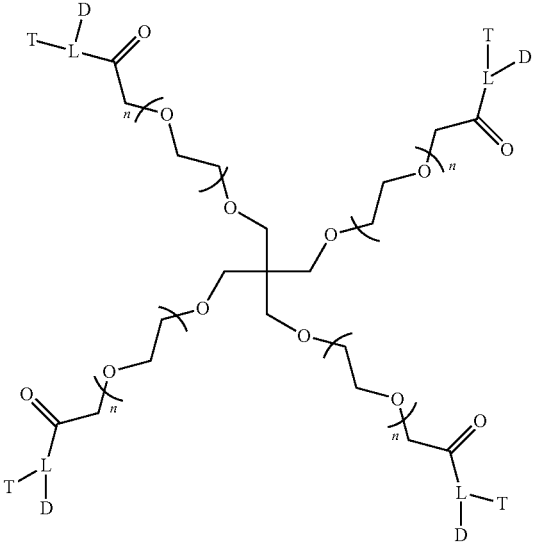

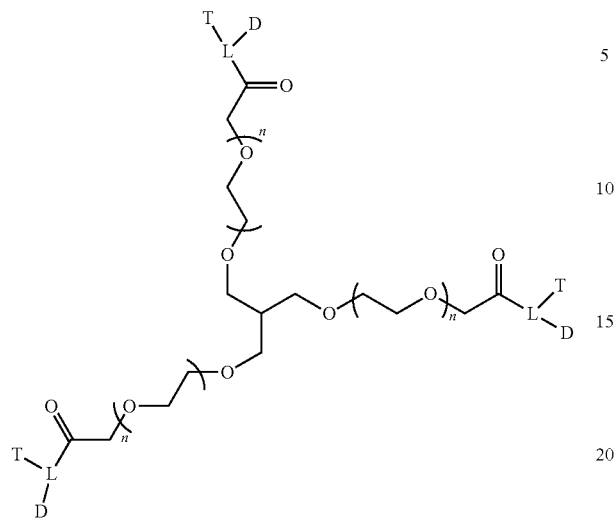
(V)
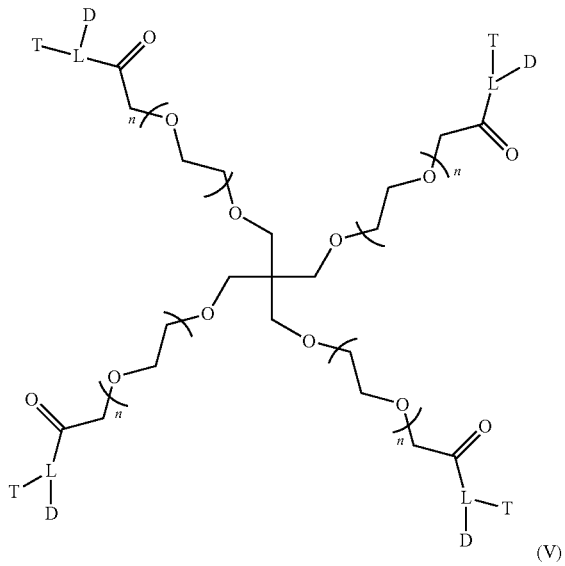
(IV)
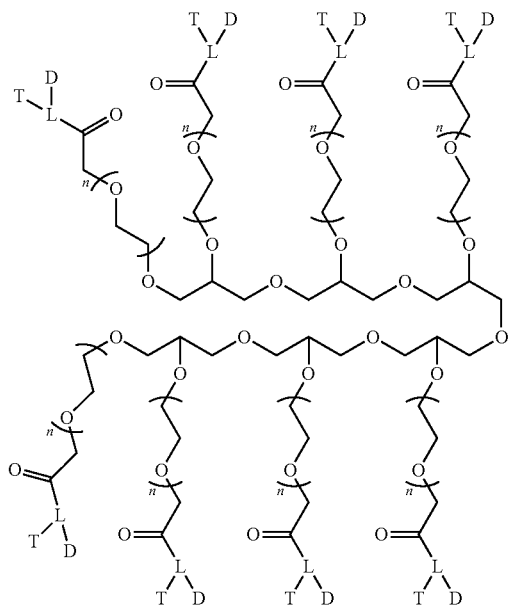
(VI)
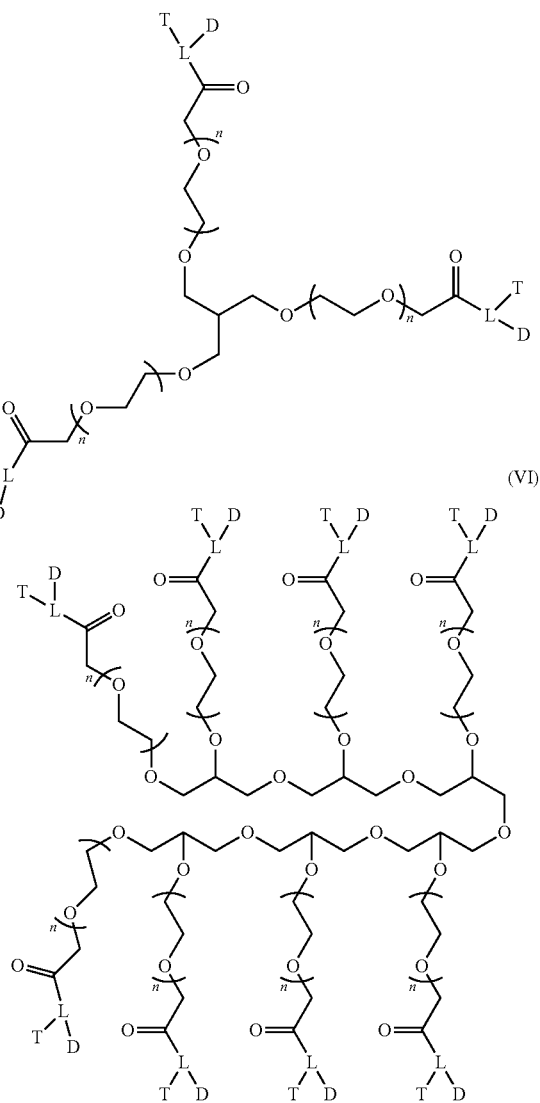
(V)
(VI)
wherein n is 50 to 200.
15. The multi-branched drug conjugate or a pharmaceutically acceptable salt thereof according to claim 1, wherein said multi-branched drug conjugate has a structure represented by structural formula (IV), (V), or (VI):
wherein n is 113.

16. A drug composition containing the multi-branched drug conjugate or a pharmaceutically acceptable salt thereof according to claim 7, and a pharmaceutically acceptable excipient.

17. A method for treating colon cancer, lung cancer, breast cancer, ovarian cancer, pancreatic cancer, gastric cancer, brain glioma, and malignant sarcoma, cancer and lymphoma of breast, ovary, colon, kidney, bile duct, lung and brain, comprising administering to a subject in need thereof a therapeutic effective amount of the multi-branched drug conjugate or a pharmaceutically acceptable salt thereof according to claim 7.

* * * * *

UNITED STATES PATENT AND TRADEMARK OFFICE
CERTIFICATE OF CORRECTION

PATENT NO. : 10,869,863 B2  
APPLICATION NO. : 16/300428  
DATED : December 22, 2020  
INVENTOR(S) : Yuan et al.

Page 1 of 37

It is certified that error appears in the above-identified patent and that said Letters Patent is hereby corrected as shown below:

In the Claims

Column 249, Line 1:

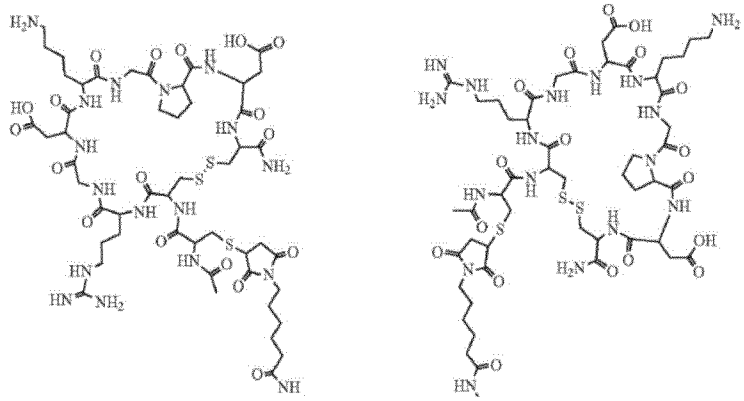

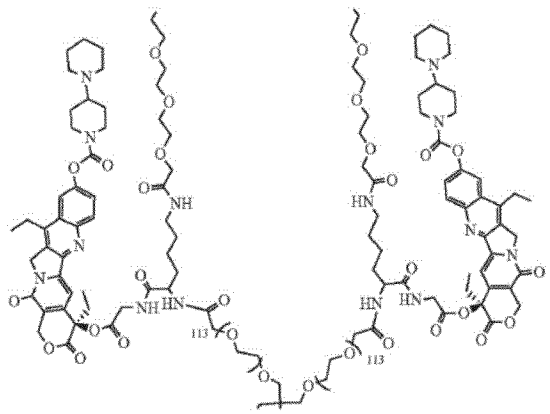

In Claim 7, delete "

Signed and Sealed this  
Eleventh Day of October, 2022

Katherine Kelly Vidal  
*Director of the United States Patent and Trademark Office*

CERTIFICATE OF CORRECTION (continued)
U.S. Pat. No. 10,869,863 B2

Page 2 of 37

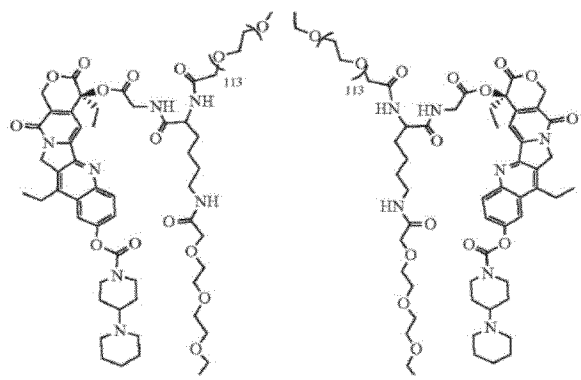

" and insert

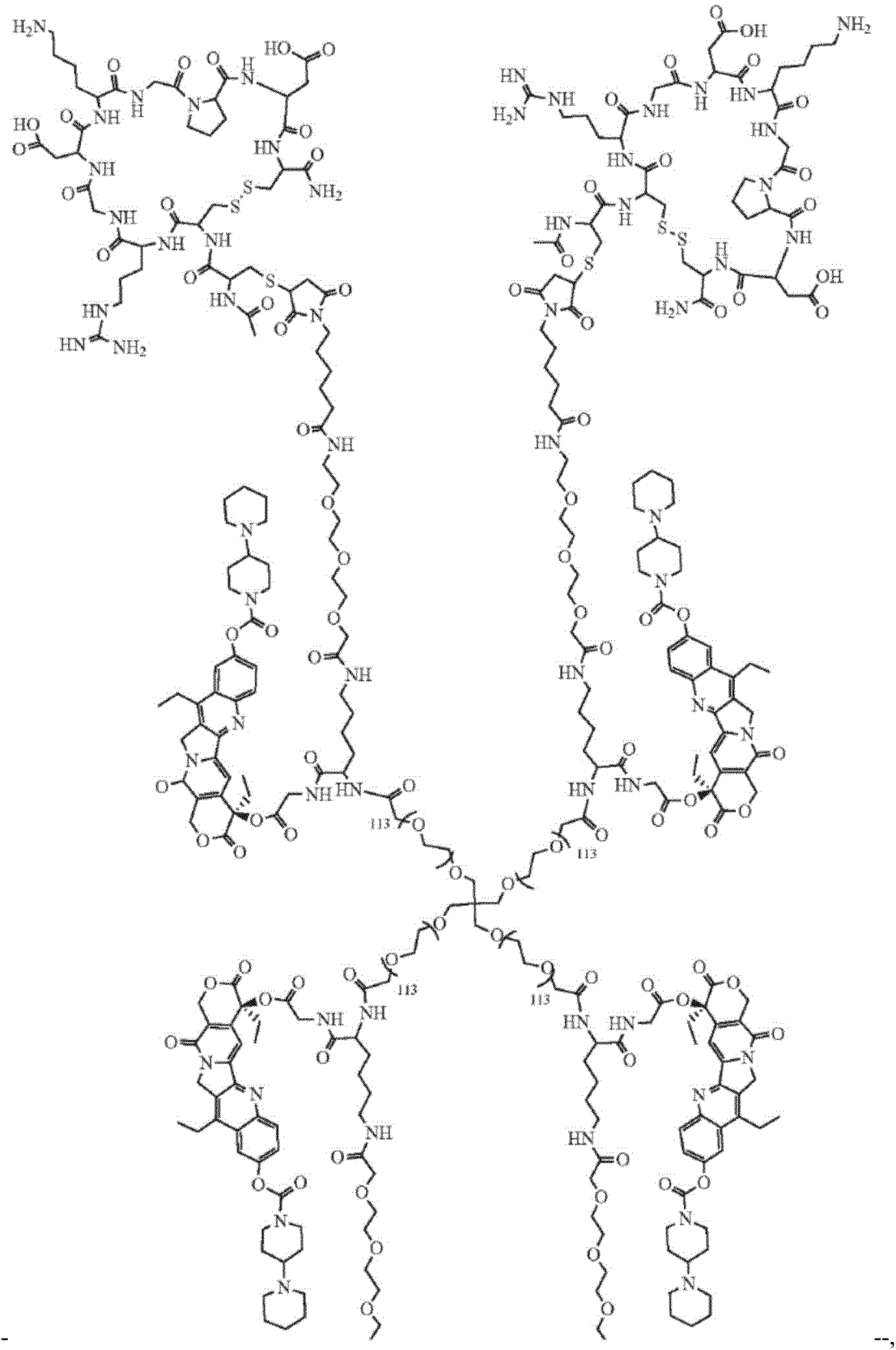
-- therefor.
--,

CERTIFICATE OF CORRECTION (continued)
U.S. Pat. No. 10,869,863 B2

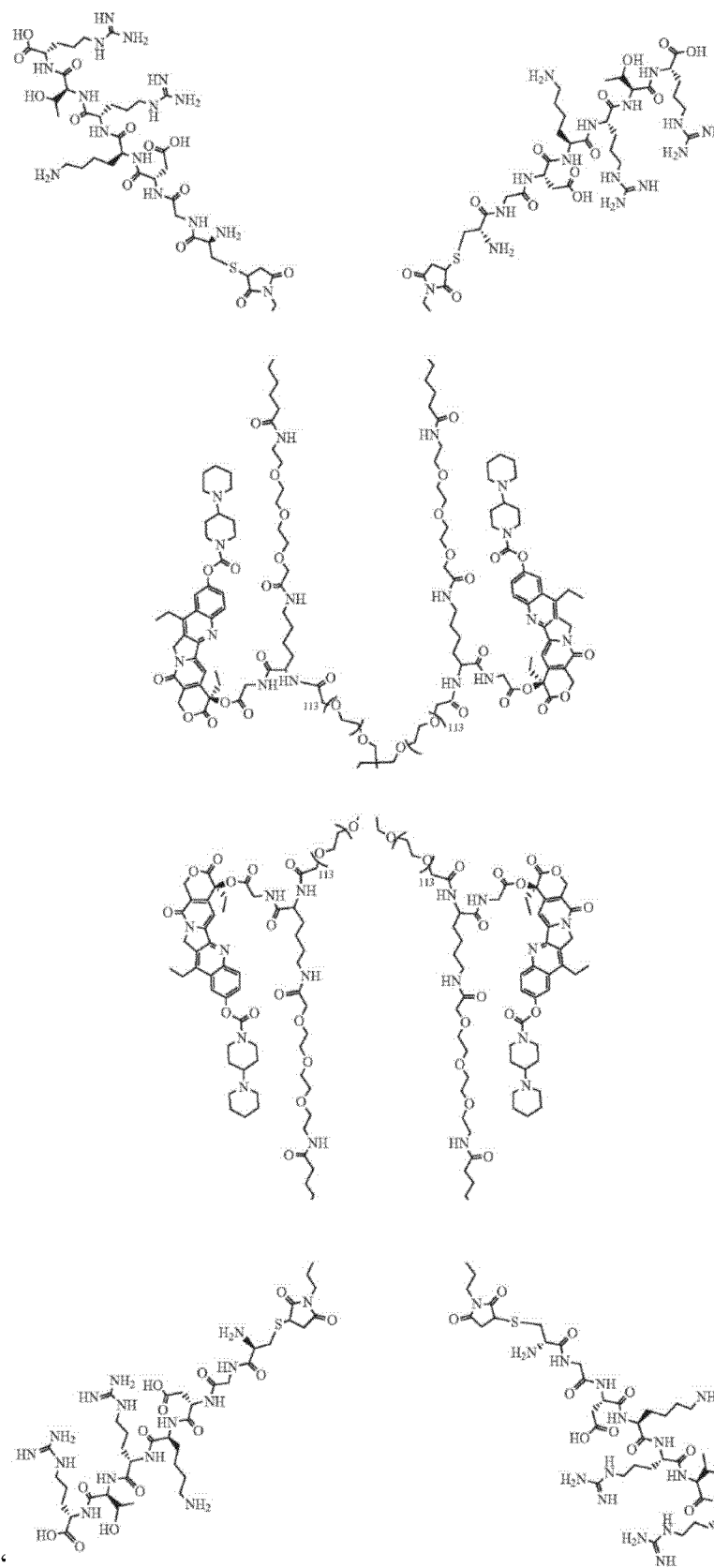

In Claim 7, delete " " and insert

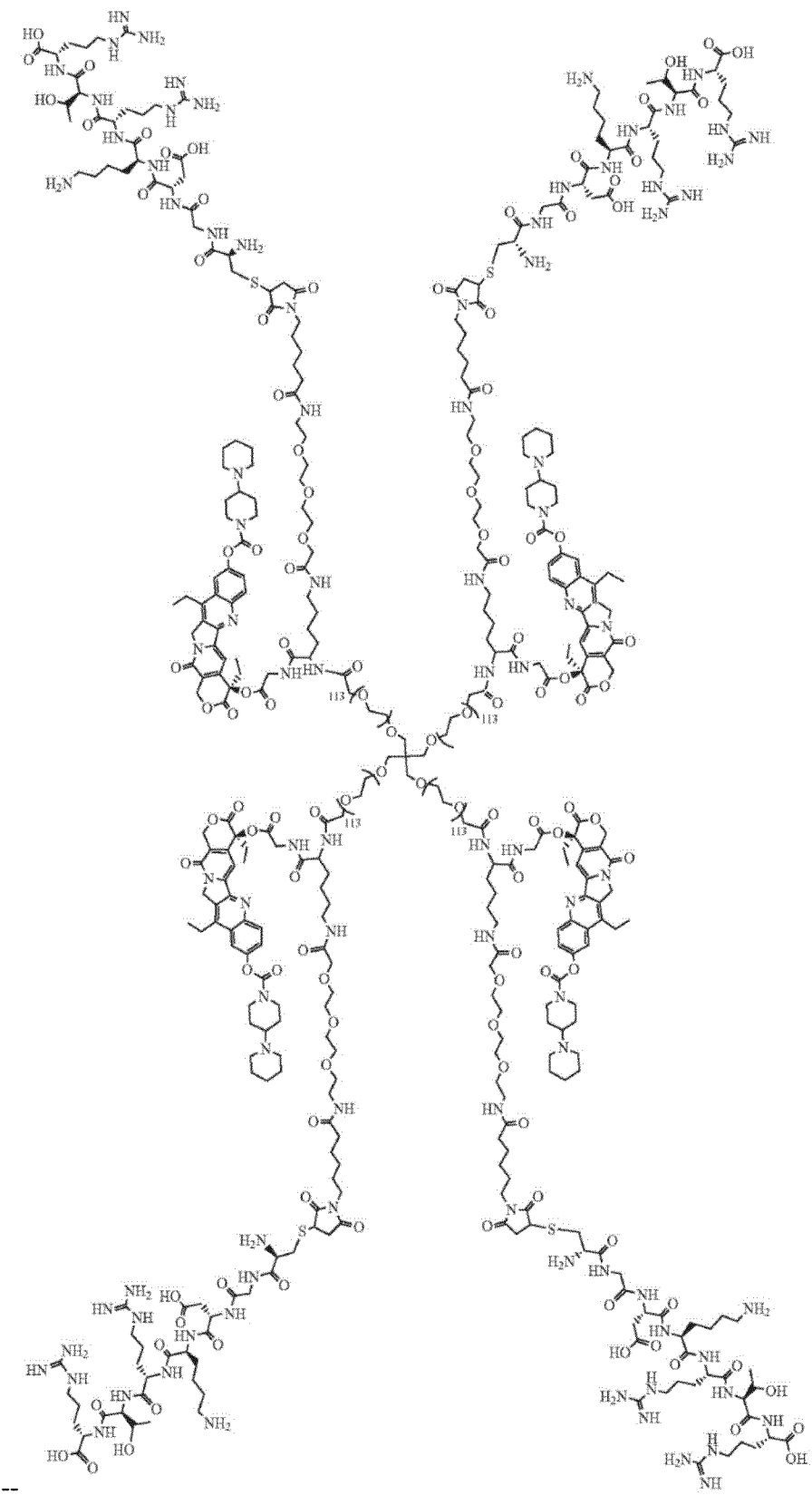
-- --, therefor.

CERTIFICATE OF CORRECTION (continued)
U.S. Pat. No. 10,869,863 B2

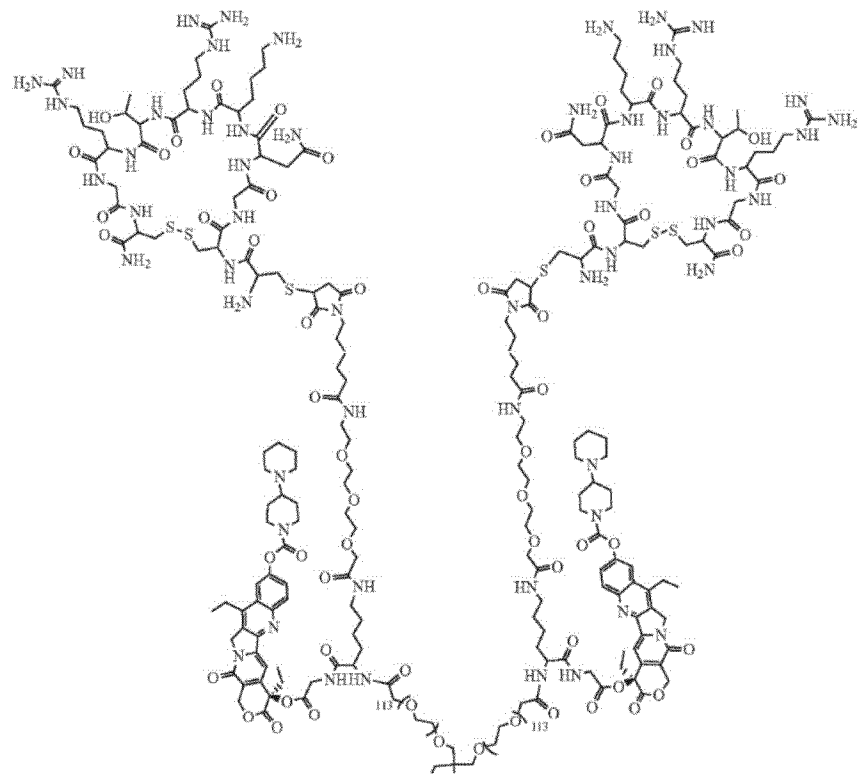

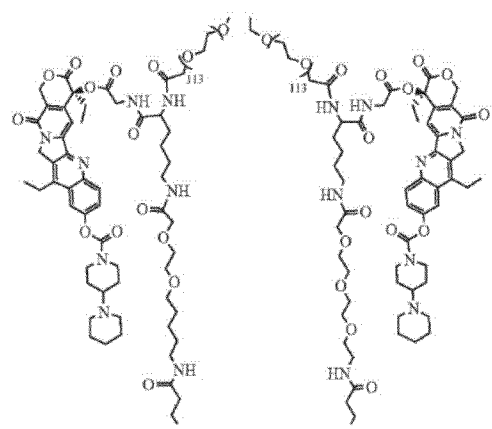

In Claim 7, delete " 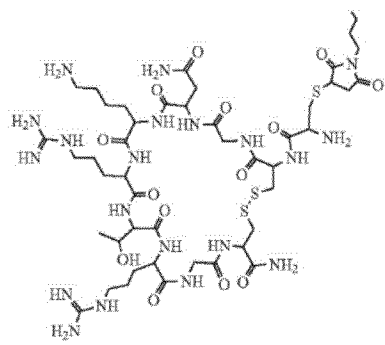 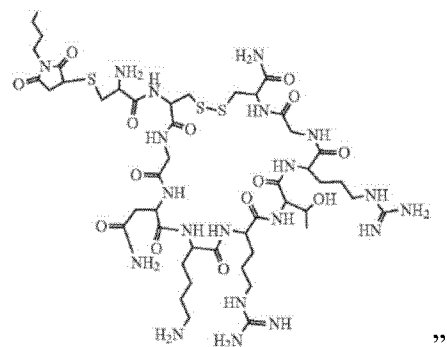 "

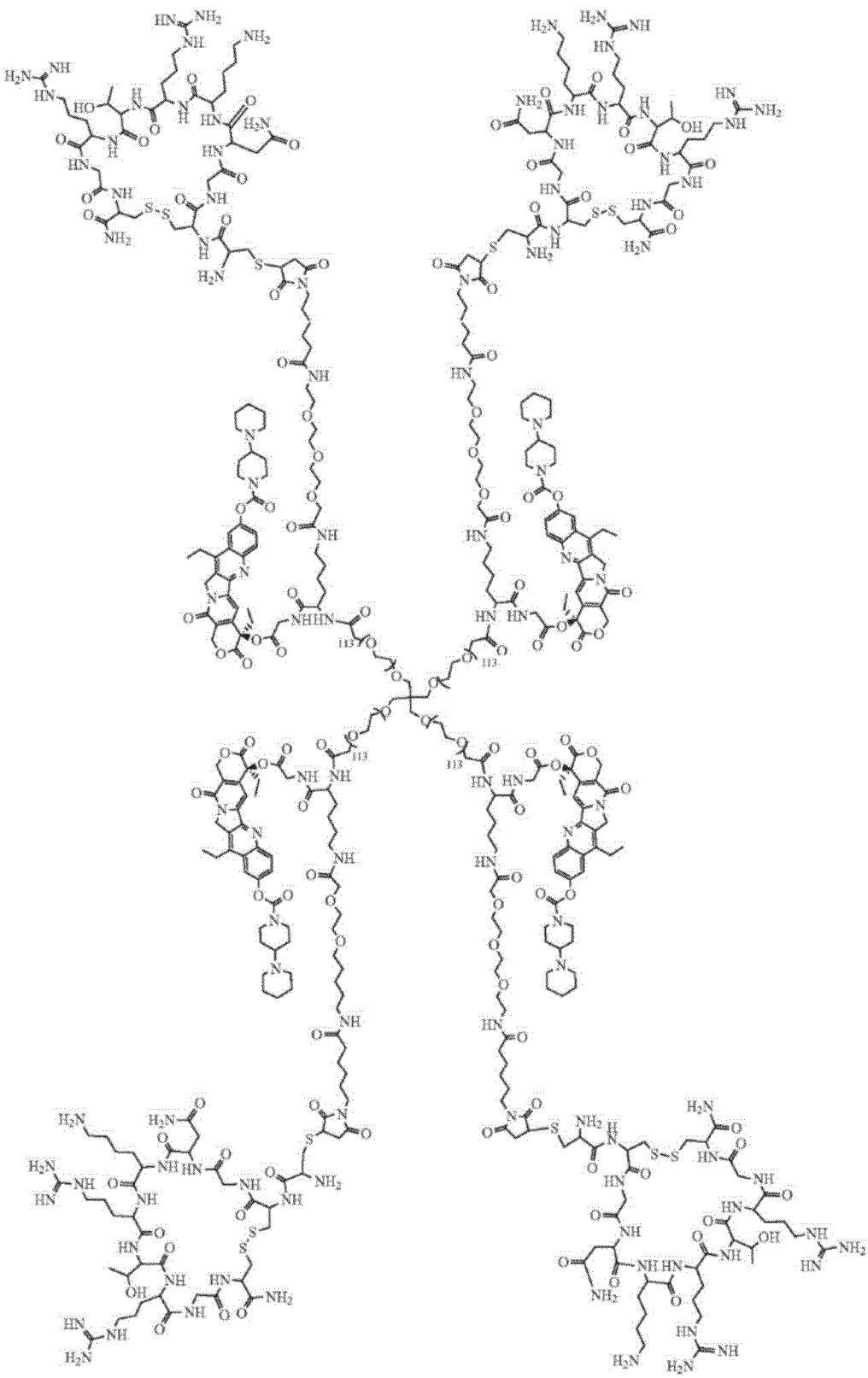
and insert -- therefor.
--,

CERTIFICATE OF CORRECTION (continued)
U.S. Pat. No. 10,869,863 B2

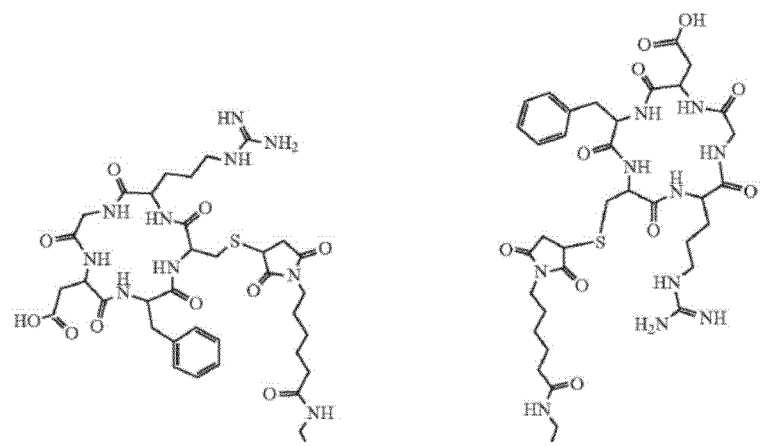

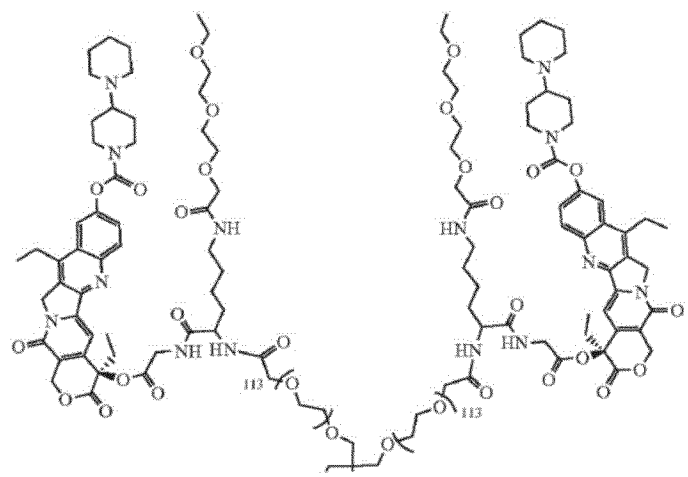

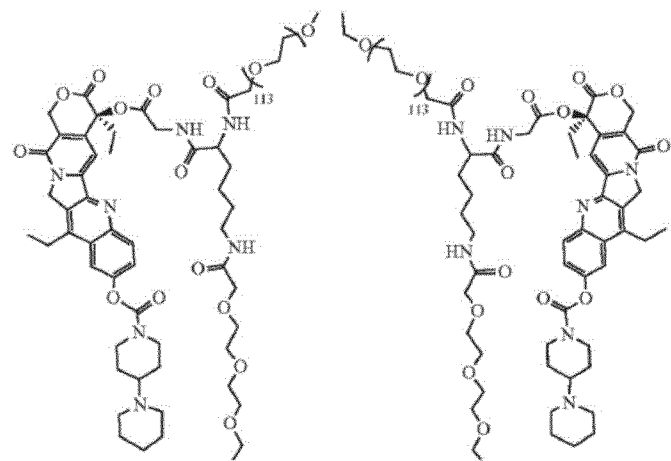

In Claim 7, delete " " and insert

--  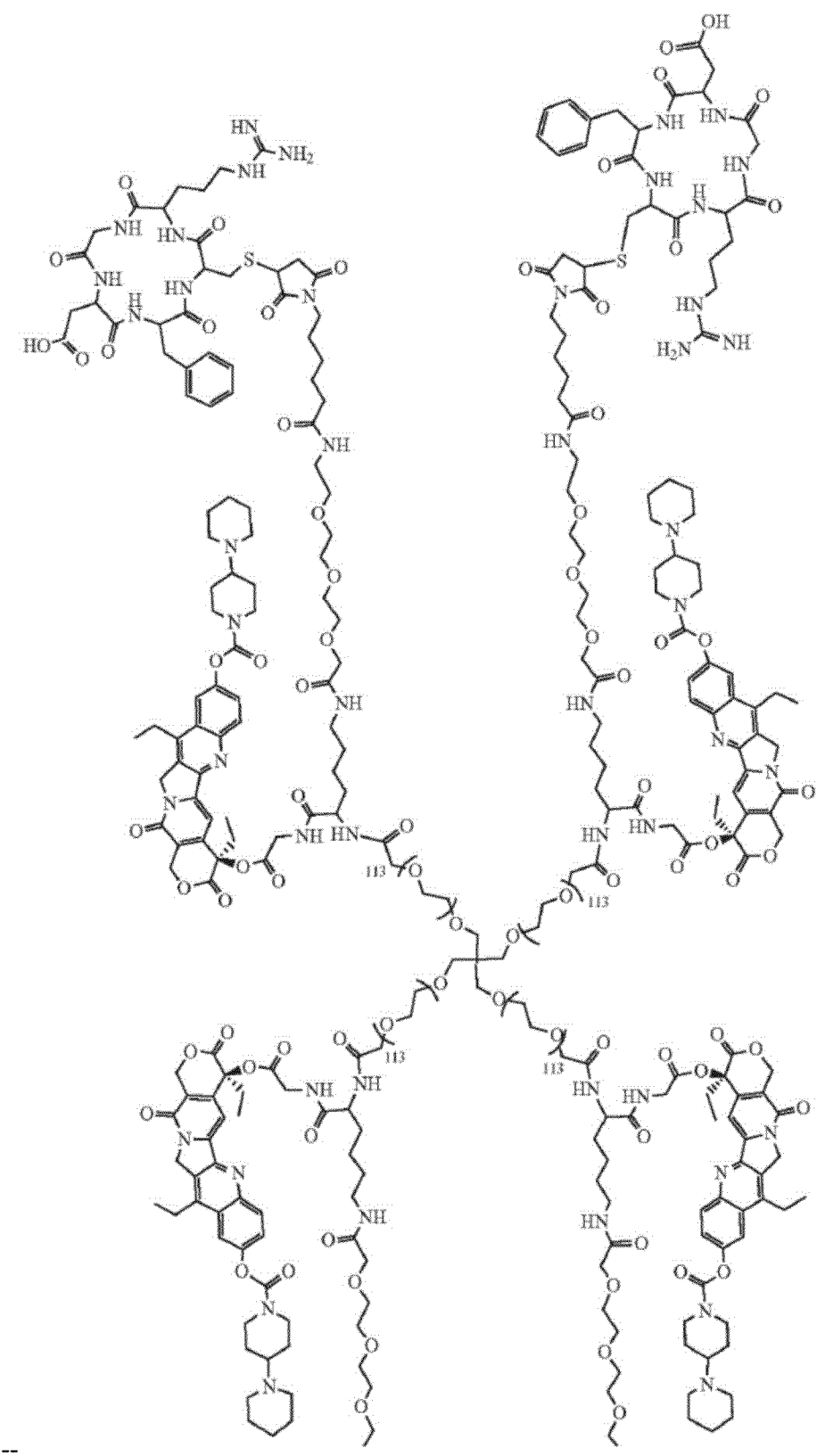  --, therefor.

CERTIFICATE OF CORRECTION (continued)
U.S. Pat. No. 10,869,863 B2

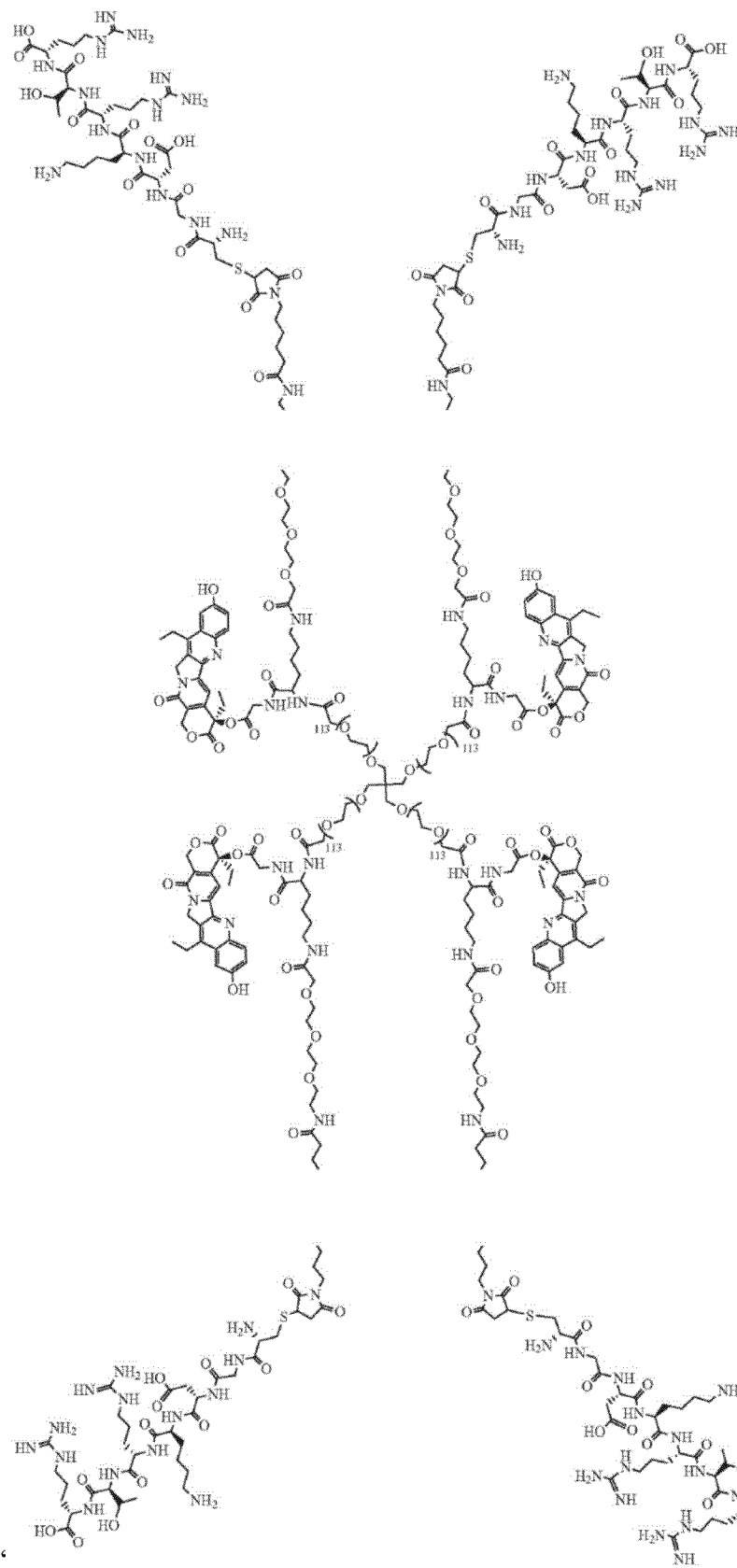

In Claim 7, delete " " and insert

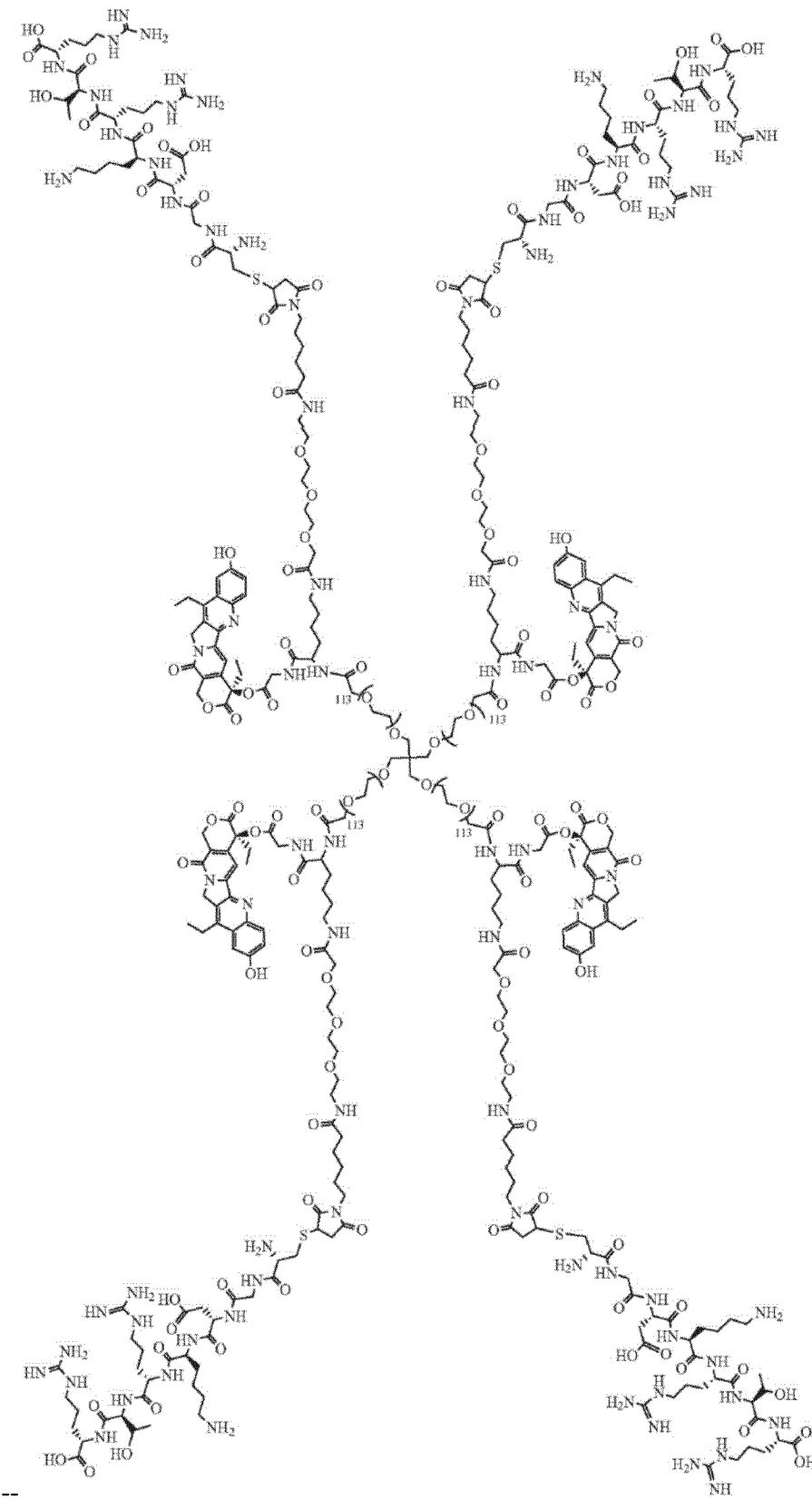
--, therefor.

CERTIFICATE OF CORRECTION (continued)
U.S. Pat. No. 10,869,863 B2

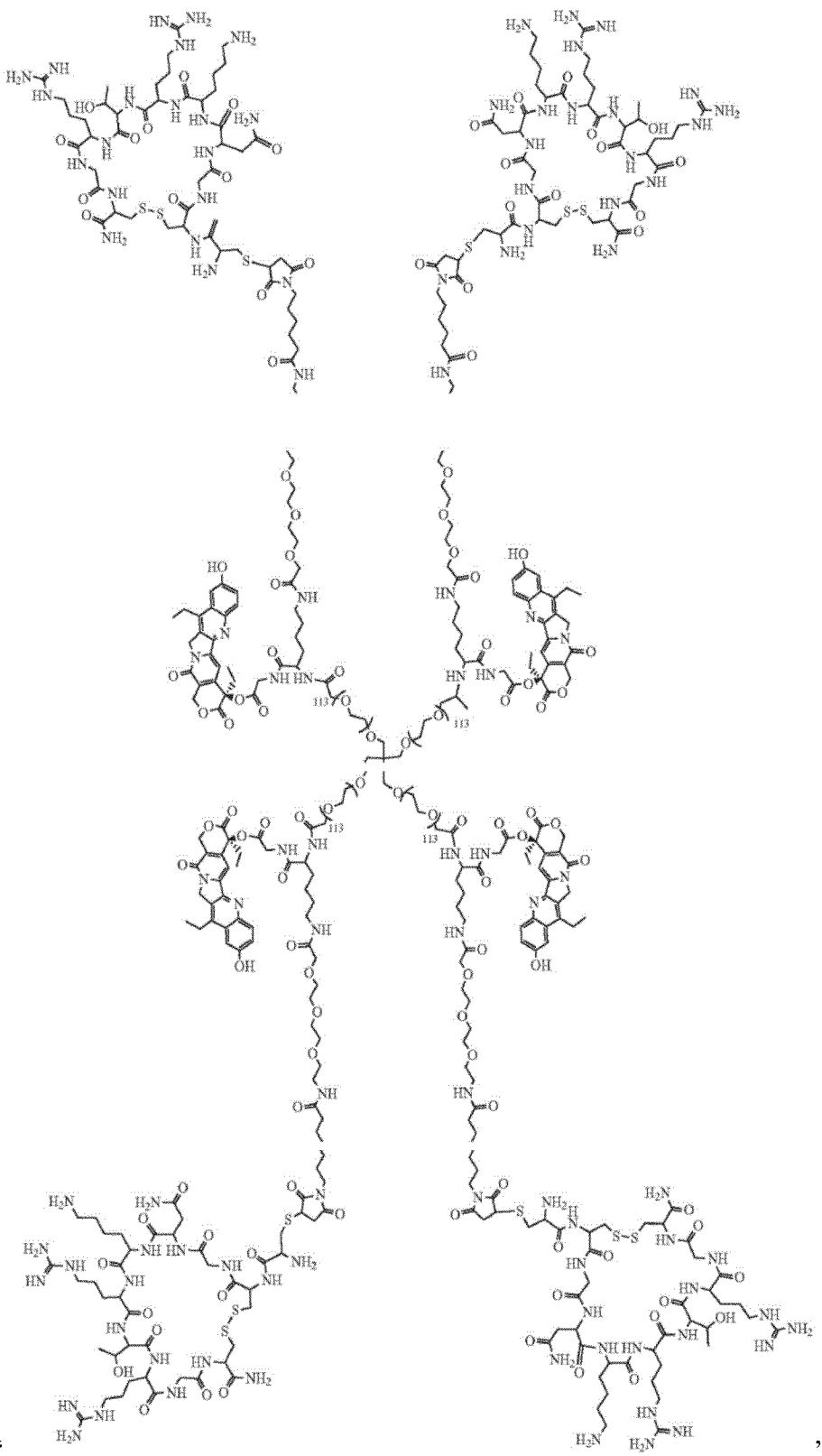

In Claim 7, delete " " and

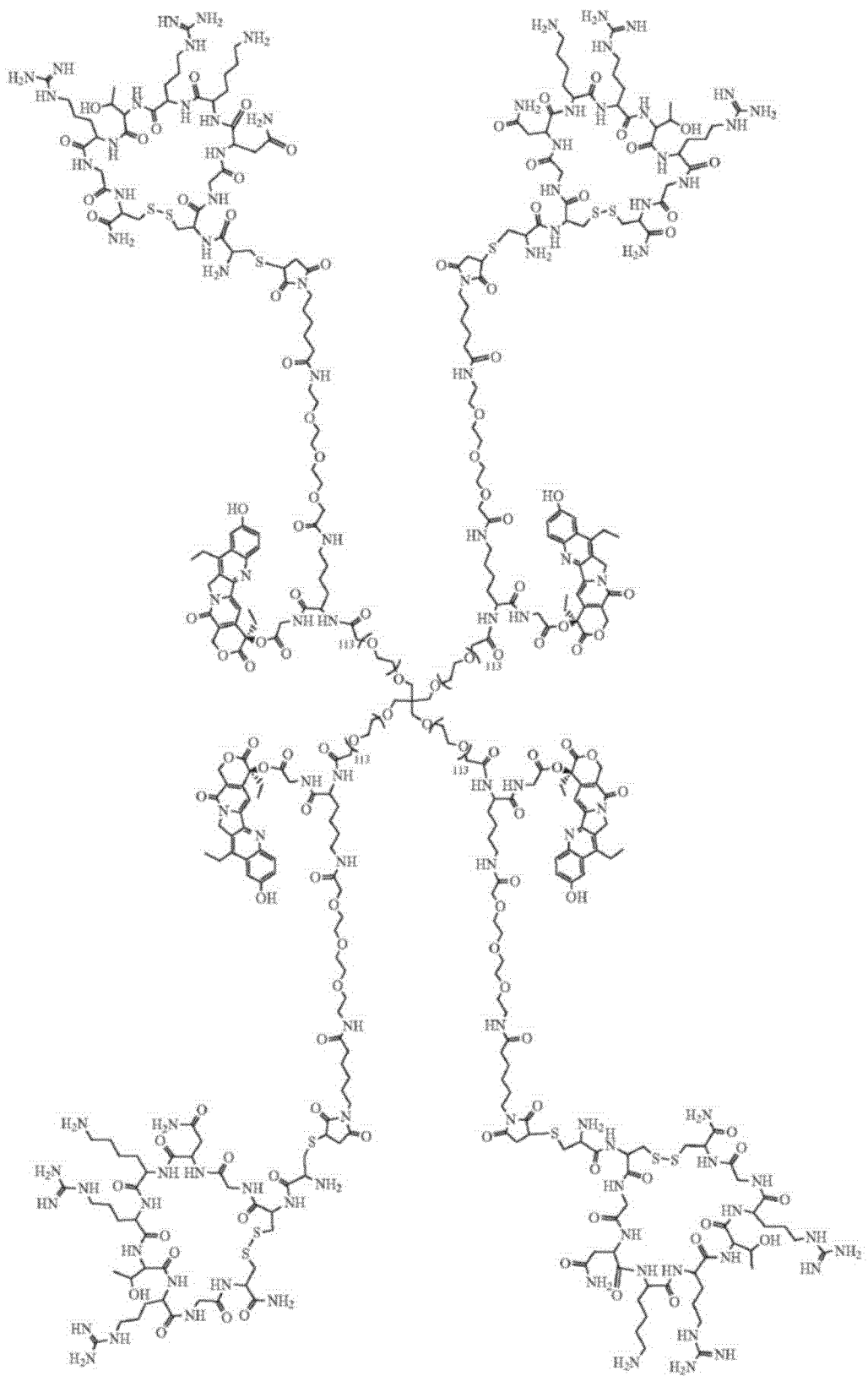
insert -- -- , therefor.

In Claim 7, delete
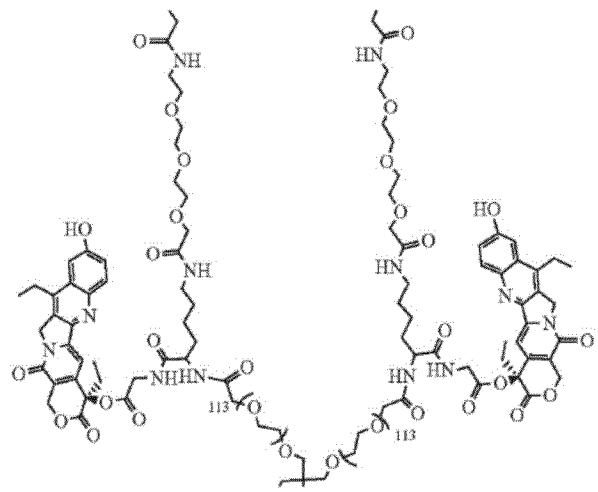
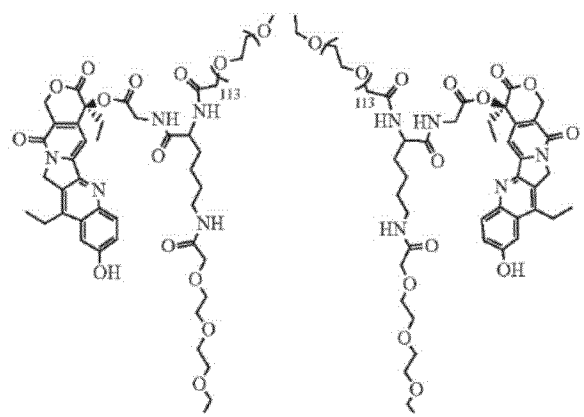
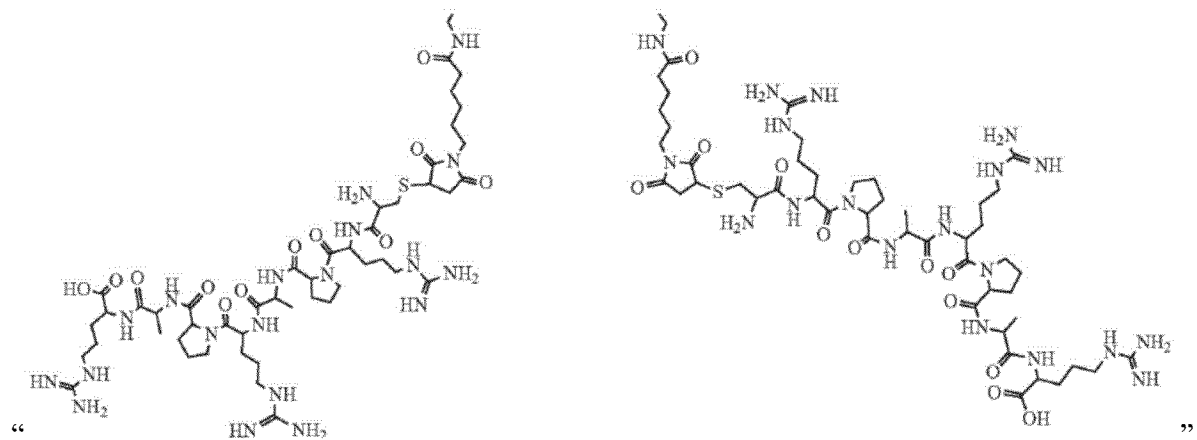
"                                                                    ,"

and insert
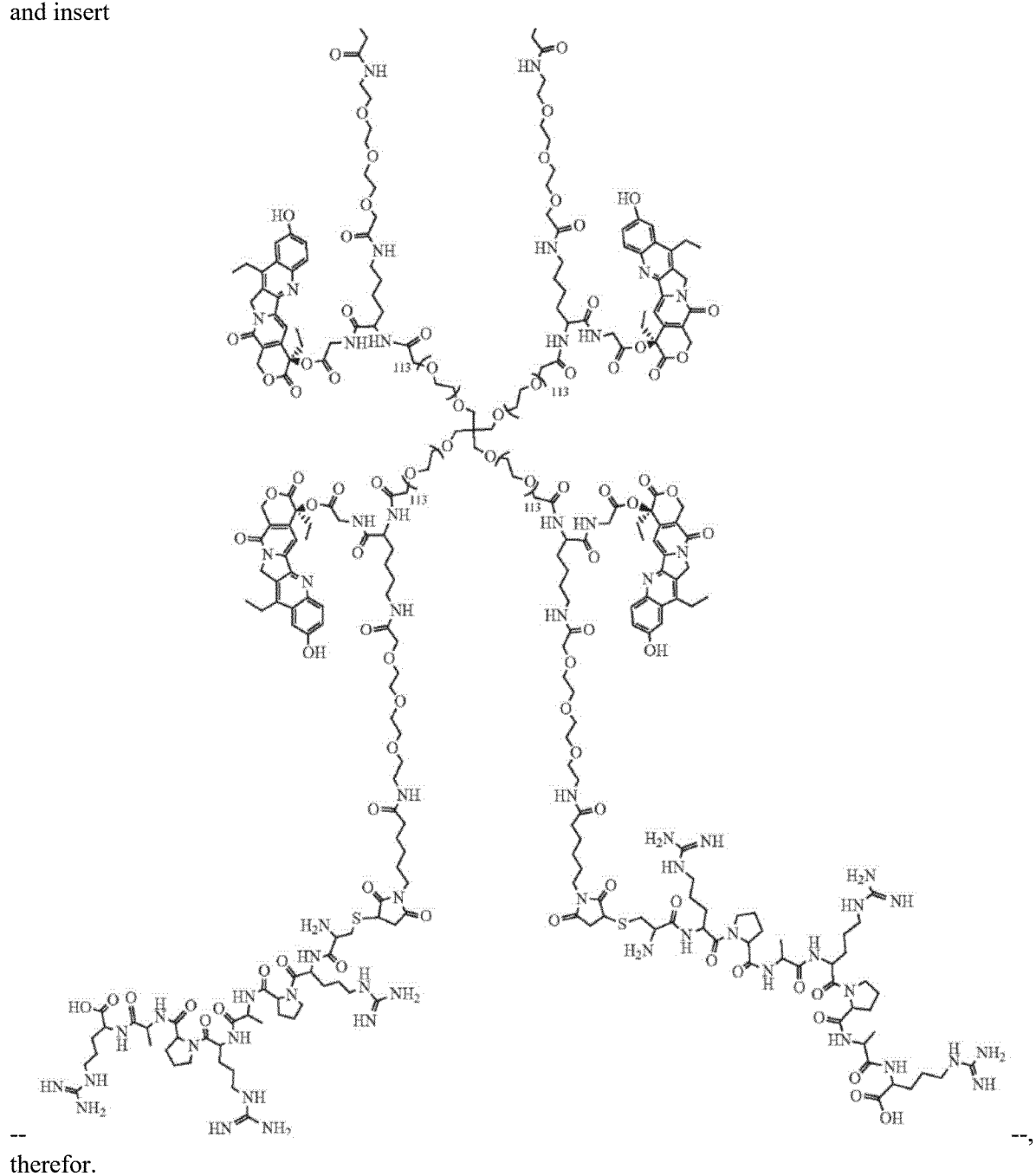
therefor.

CERTIFICATE OF CORRECTION (continued)
U.S. Pat. No. 10,869,863 B2

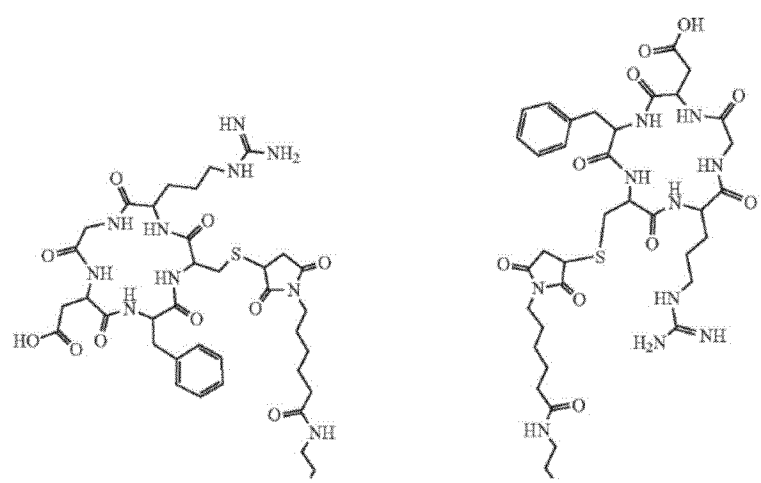

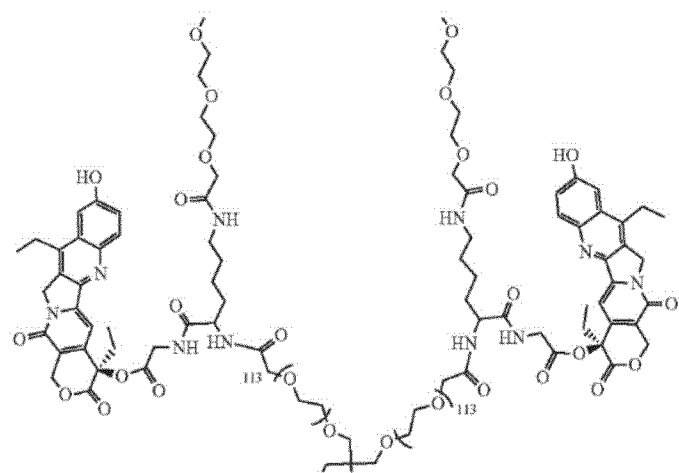

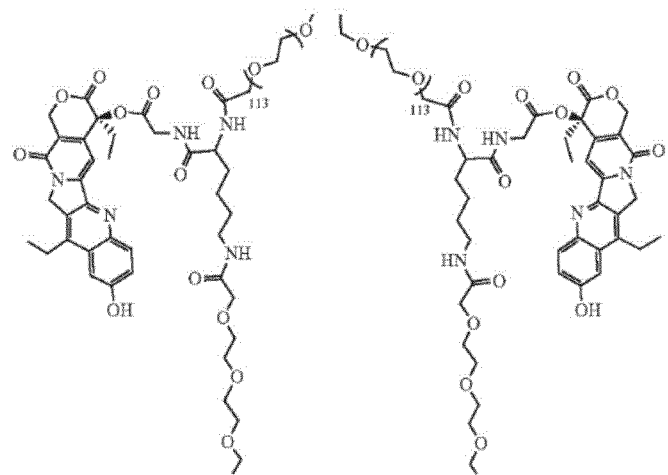

In Claim 7, delete " " and insert -- 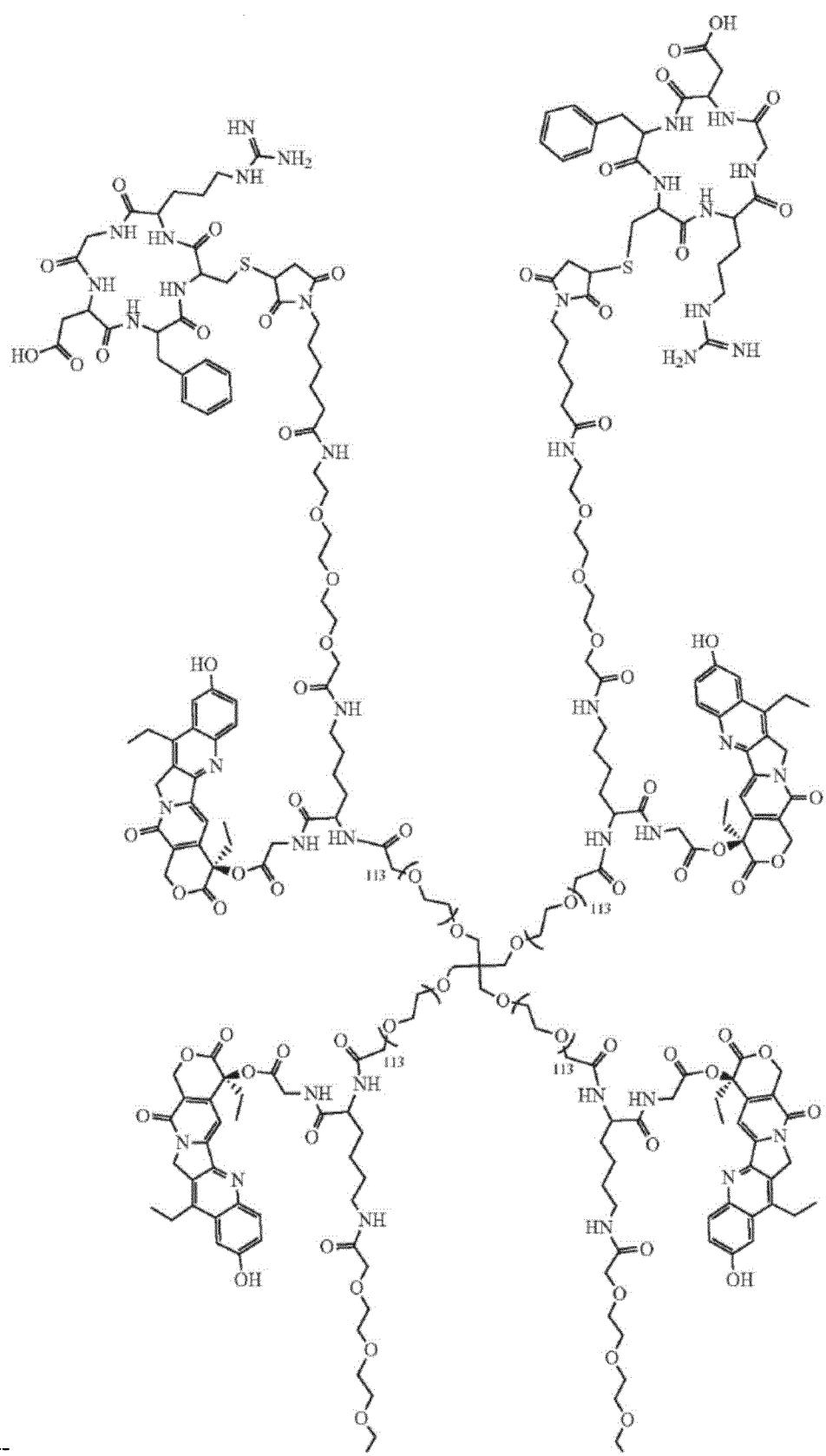 --, therefor.

CERTIFICATE OF CORRECTION (continued)
U.S. Pat. No. 10,869,863 B2

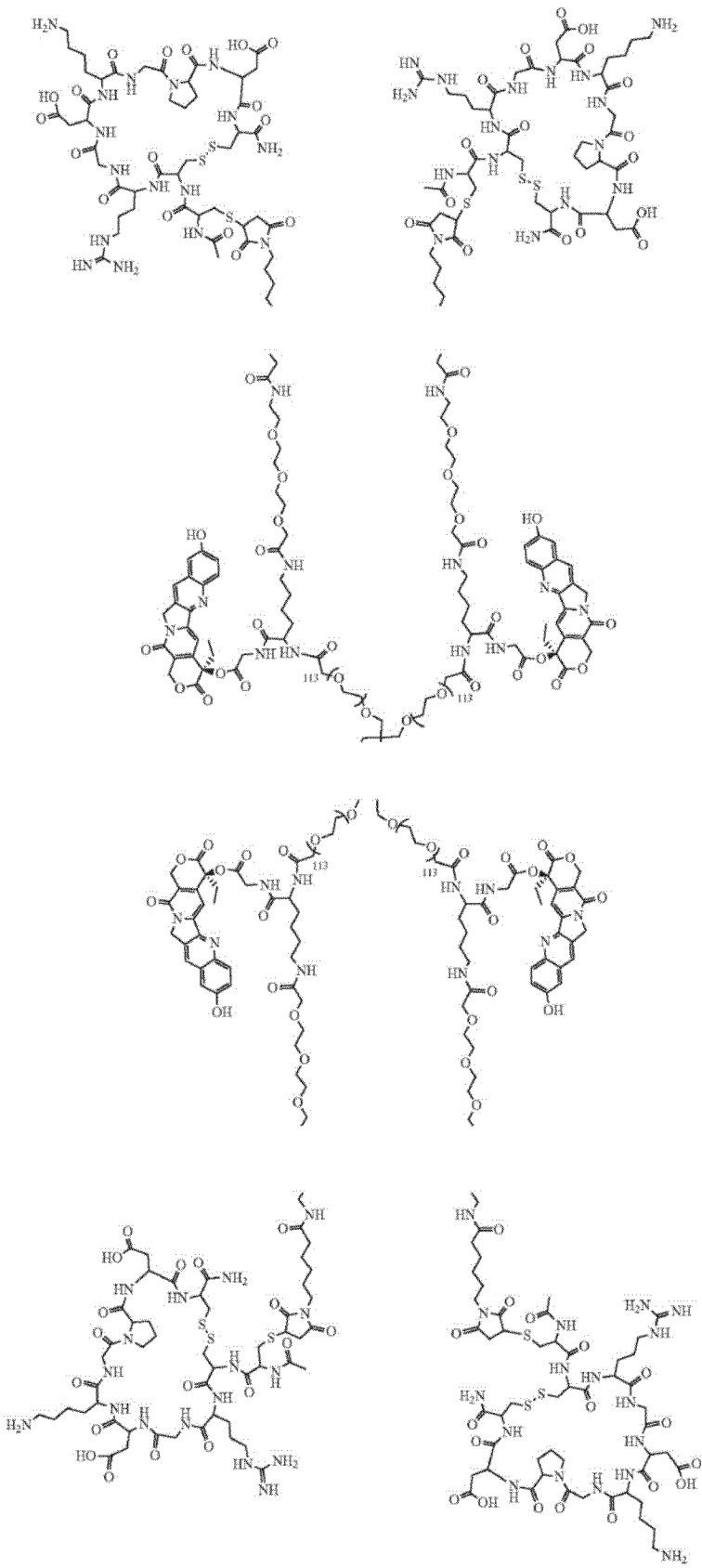

In Claim 7, delete " " and insert

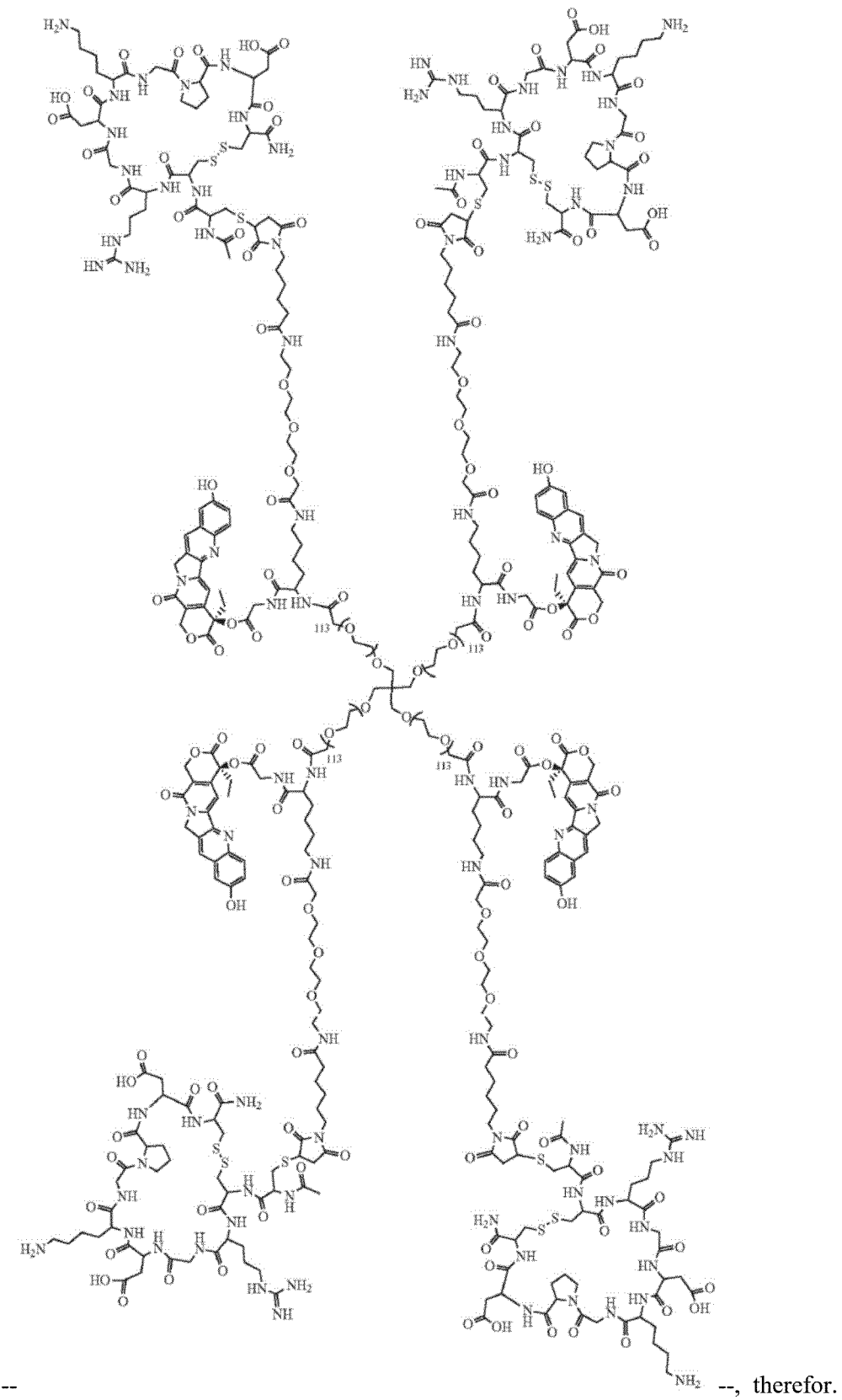
-- --, therefor.

CERTIFICATE OF CORRECTION (continued)
U.S. Pat. No. 10,869,863 B2

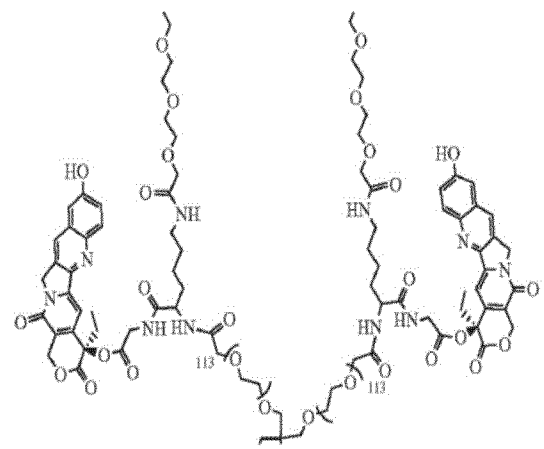

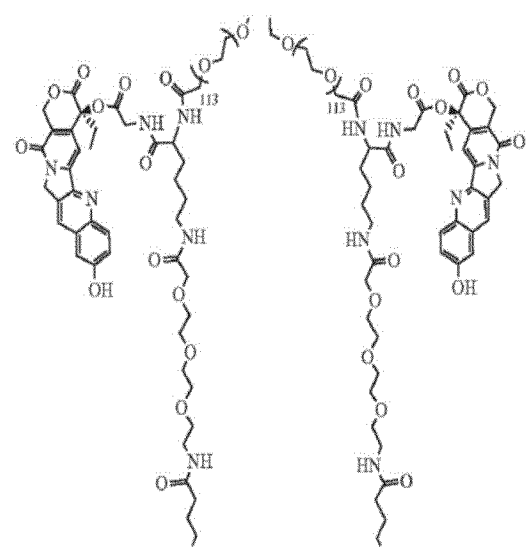

In Claim 7, delete " 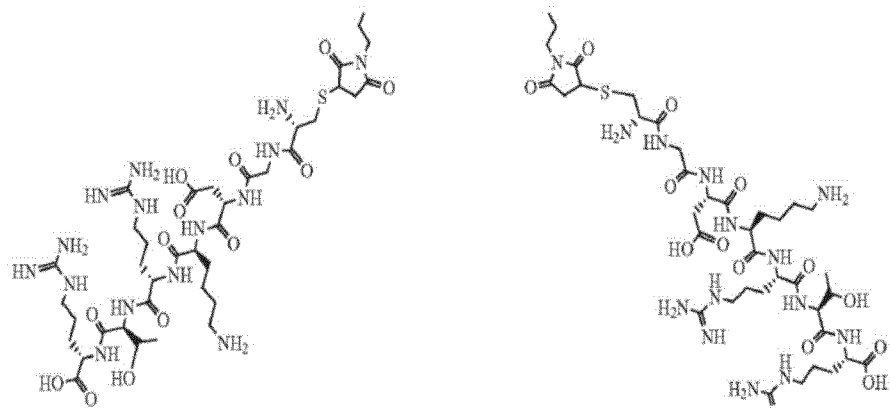 " and

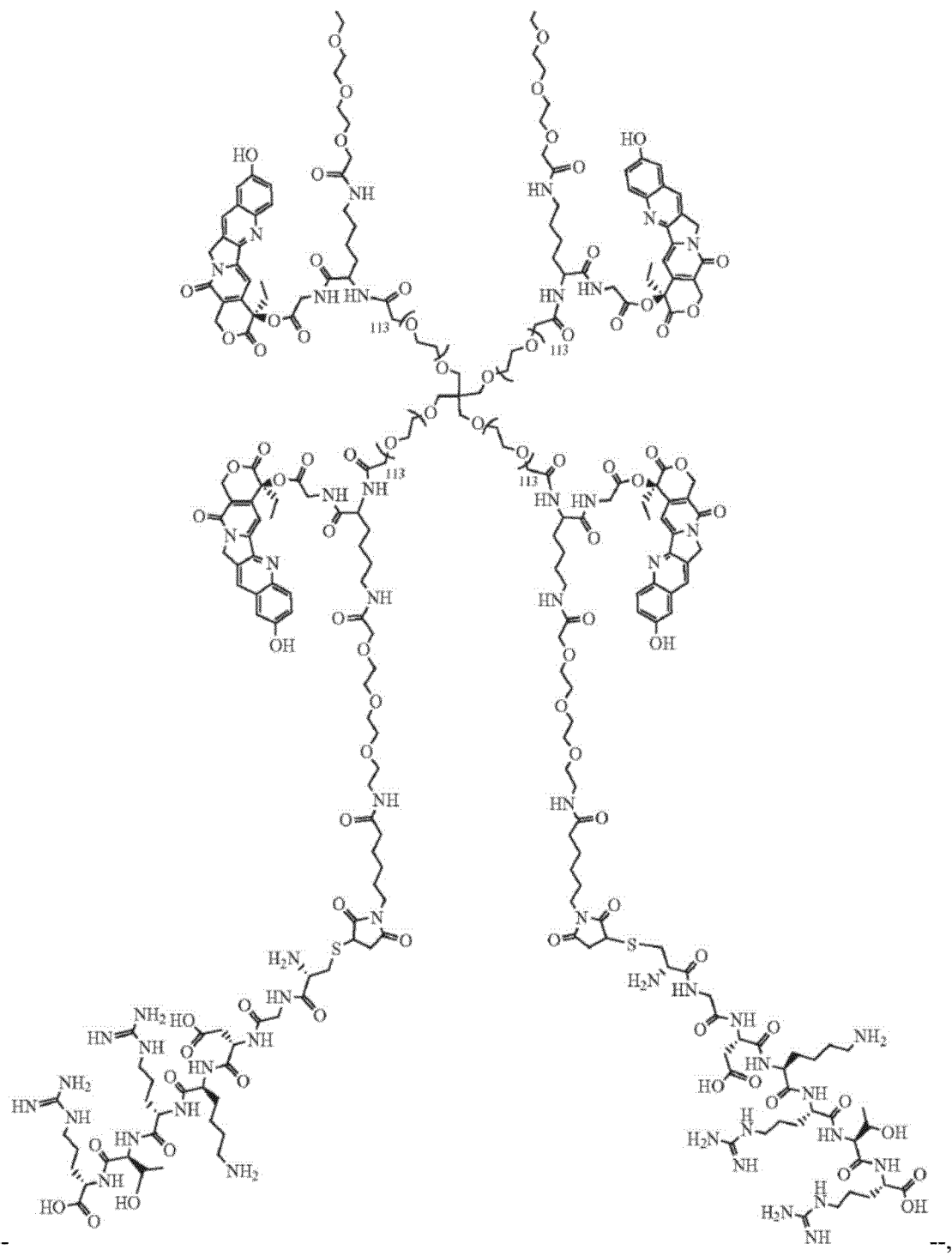
insert -- -- ,
therefor.

CERTIFICATE OF CORRECTION (continued)
U.S. Pat. No. 10,869,863 B2

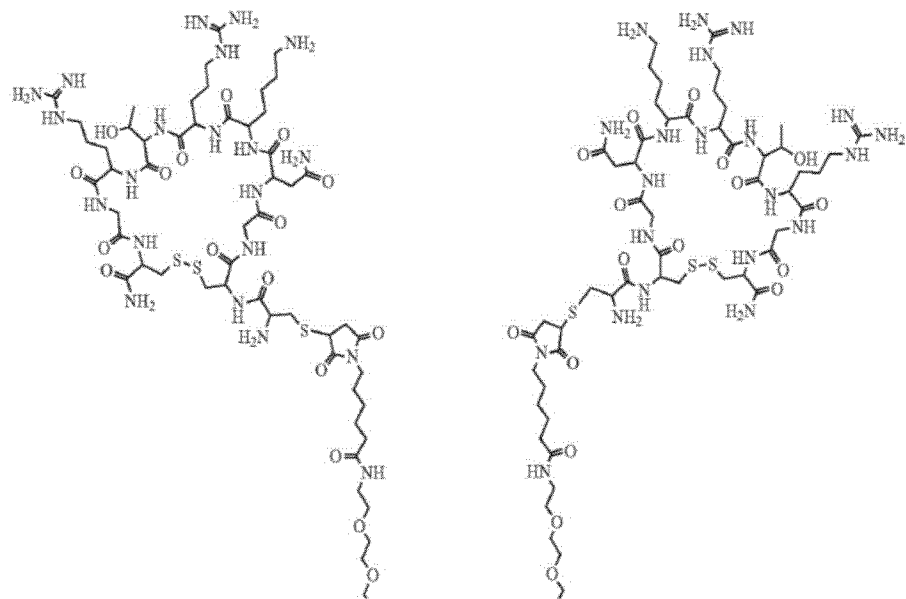

In Claim 7, delete " 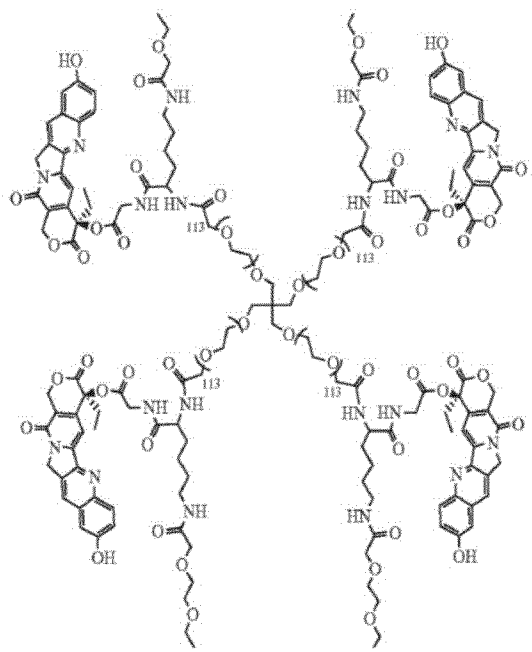 " and

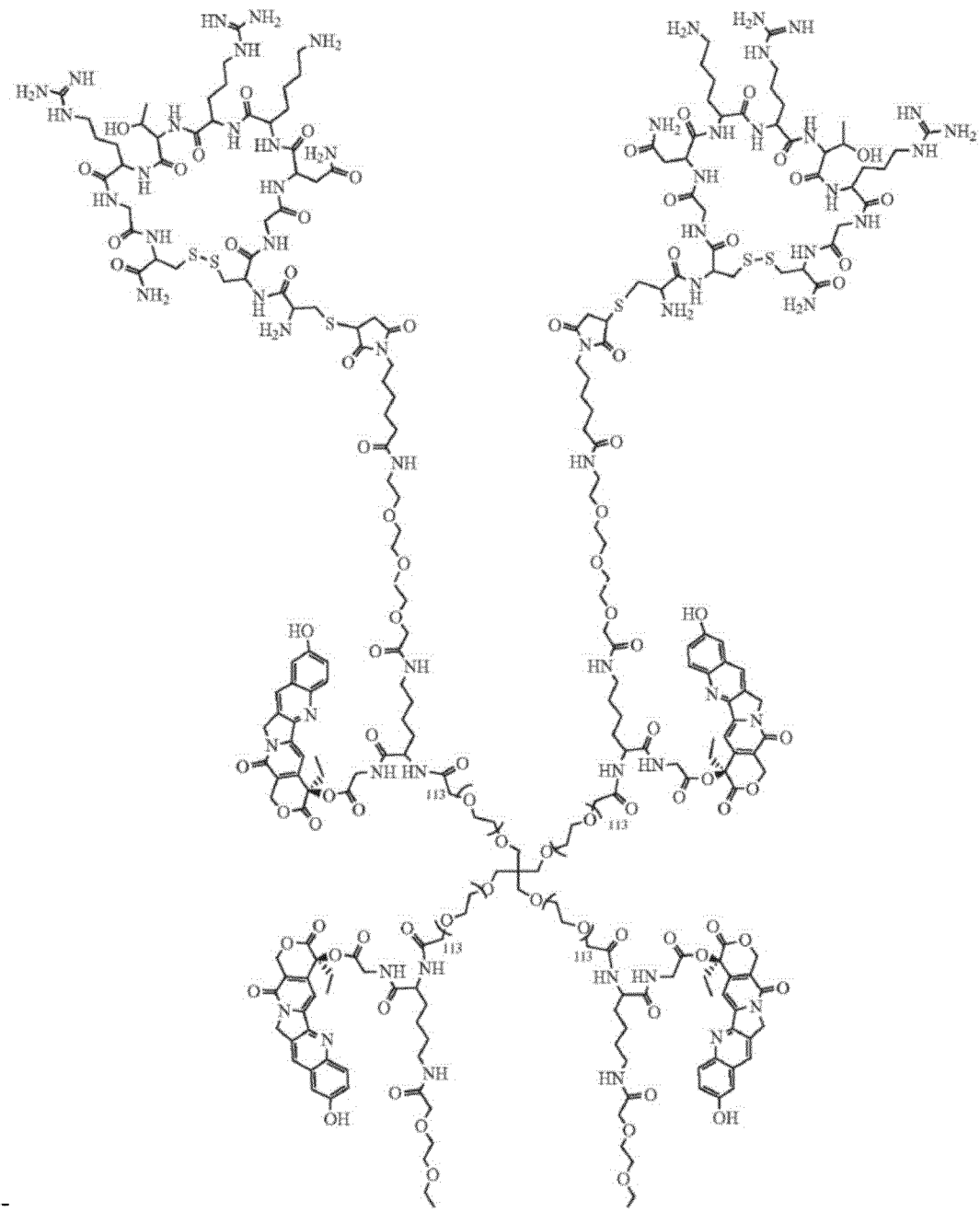
insert -- --,
therefor.

CERTIFICATE OF CORRECTION (continued)
U.S. Pat. No. 10,869,863 B2

In Claim 7, delete

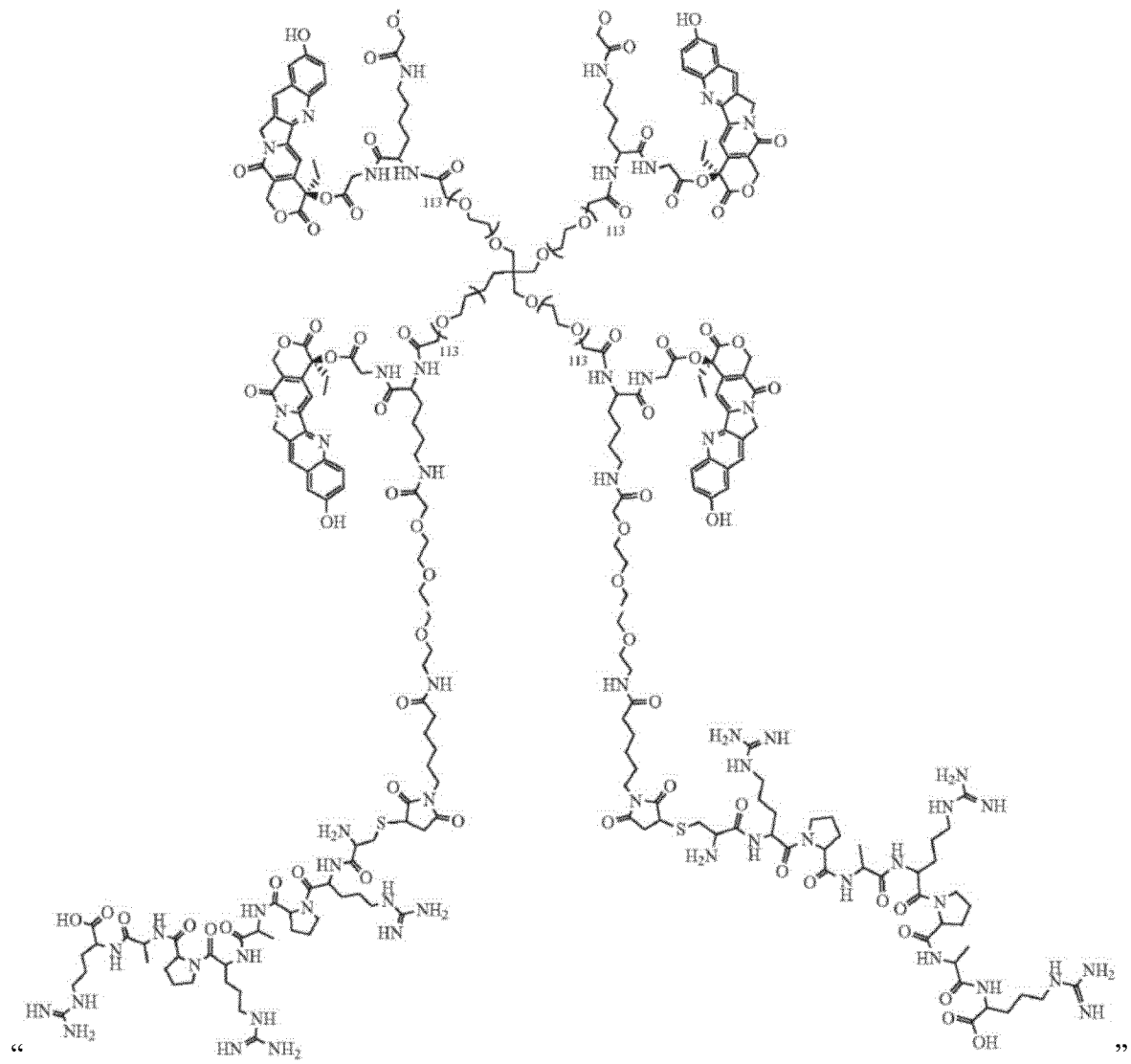

" " and insert

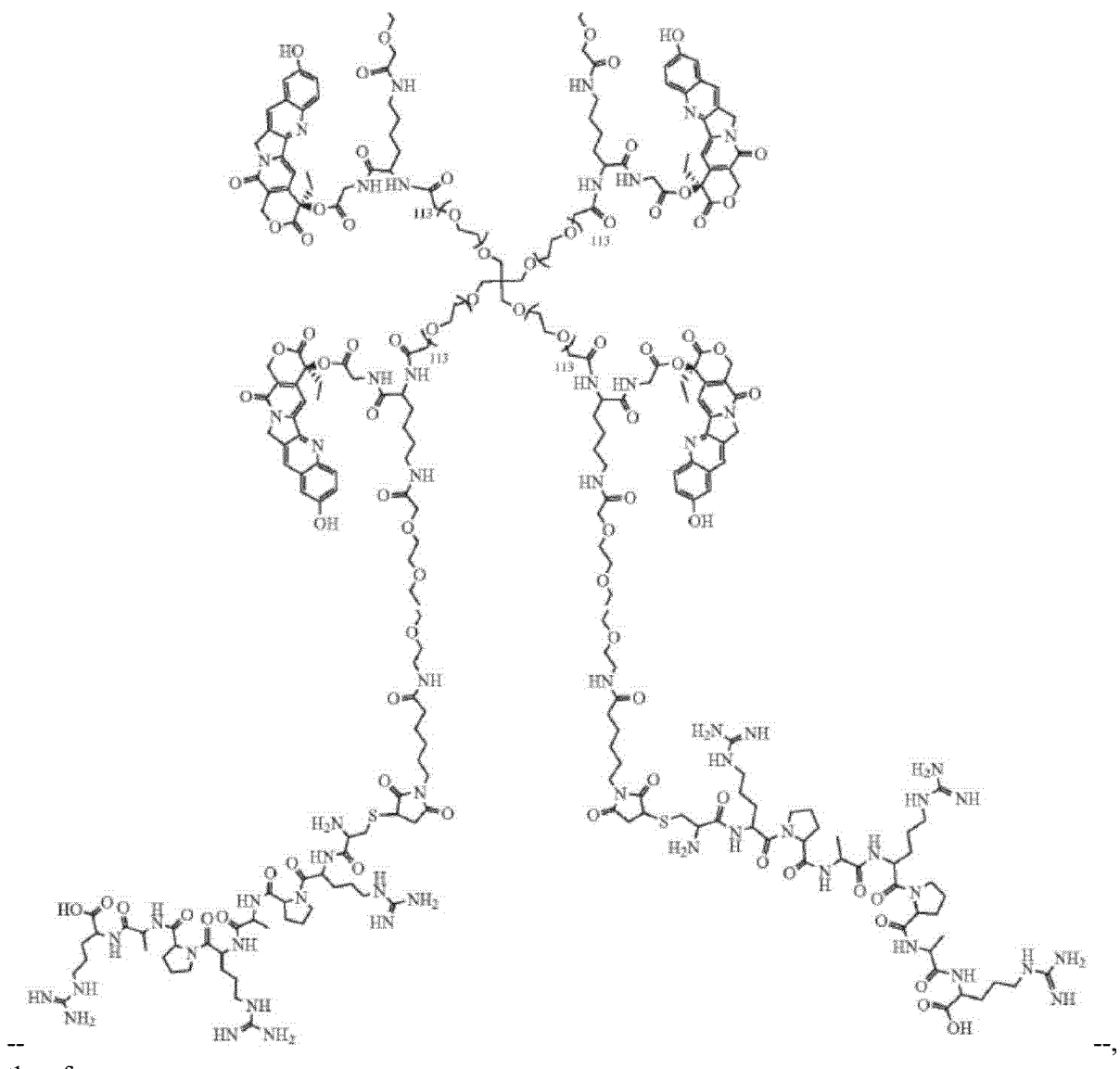
-- therefor.

CERTIFICATE OF CORRECTION (continued)  
U.S. Pat. No. 10,869,863 B2

Page 26 of 37

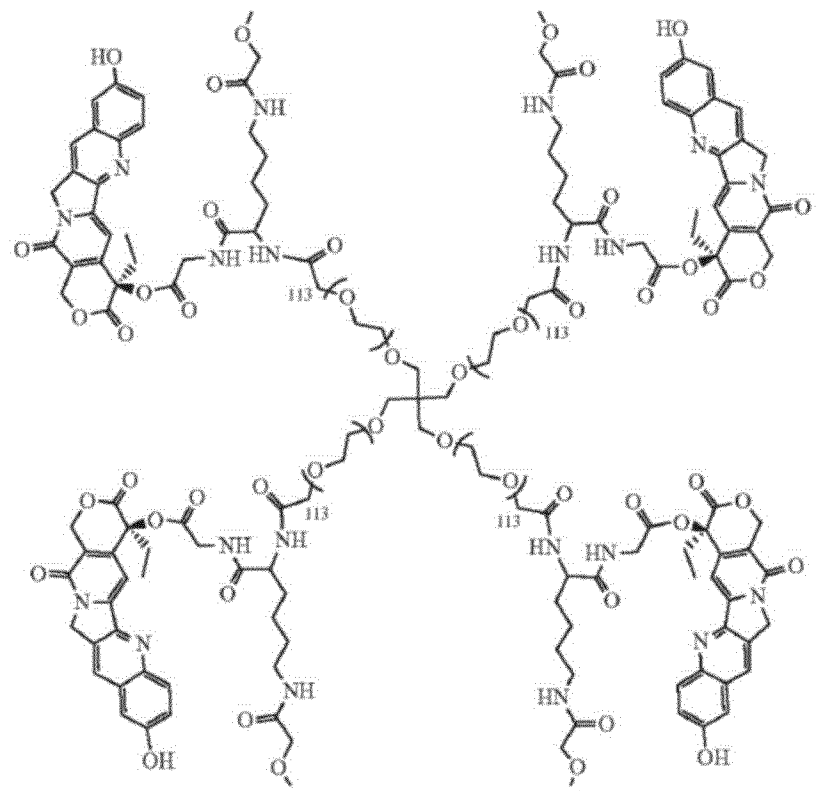

In Claim 7, delete " 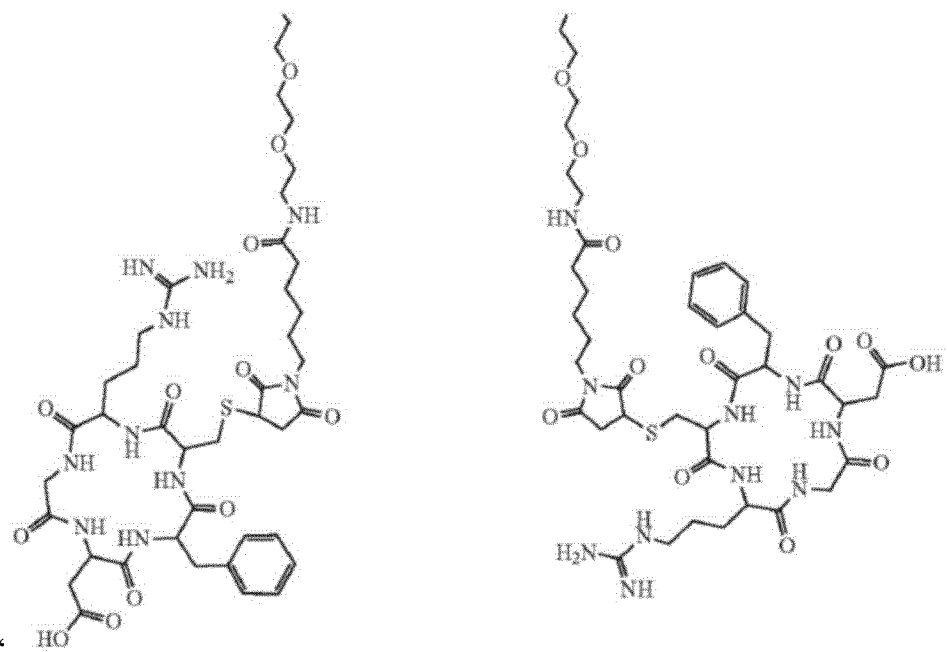 "

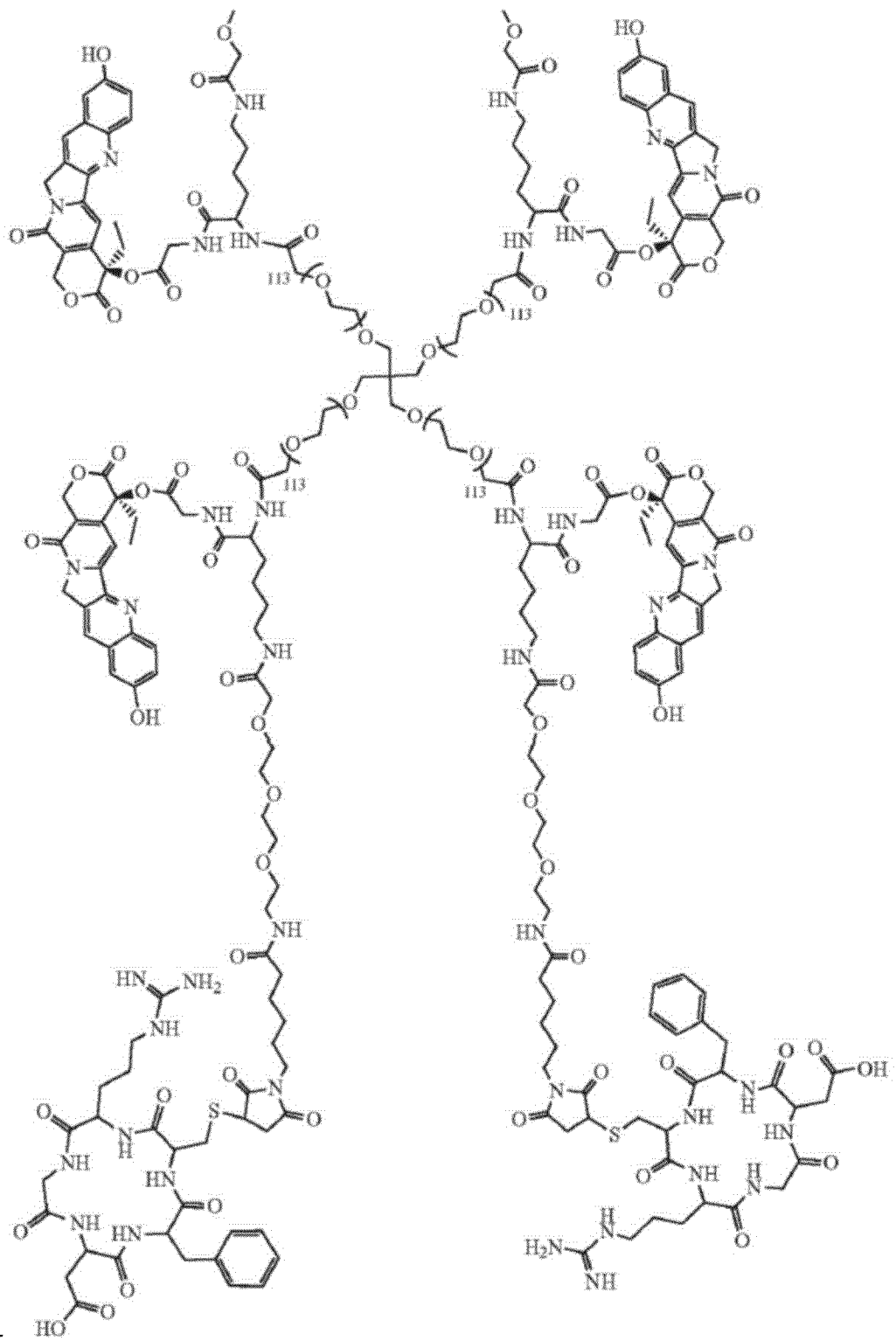
and insert -- therefor.

CERTIFICATE OF CORRECTION (continued)
U.S. Pat. No. 10,869,863 B2

In Claim 7, delete

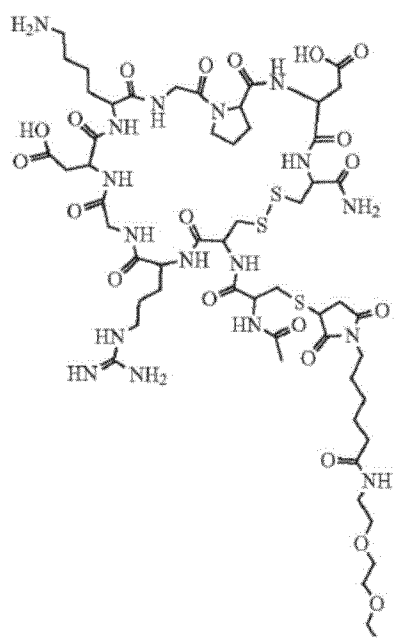
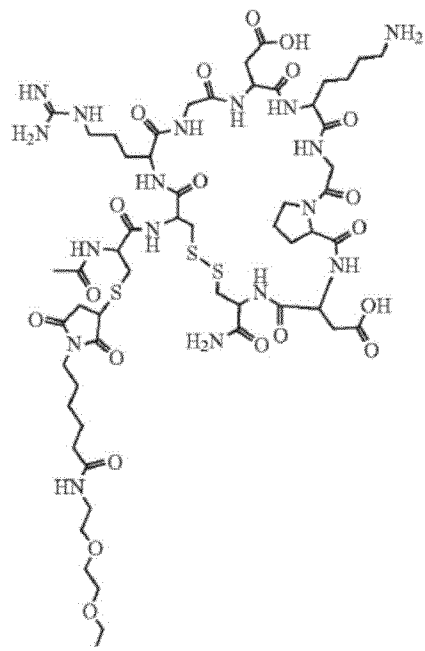

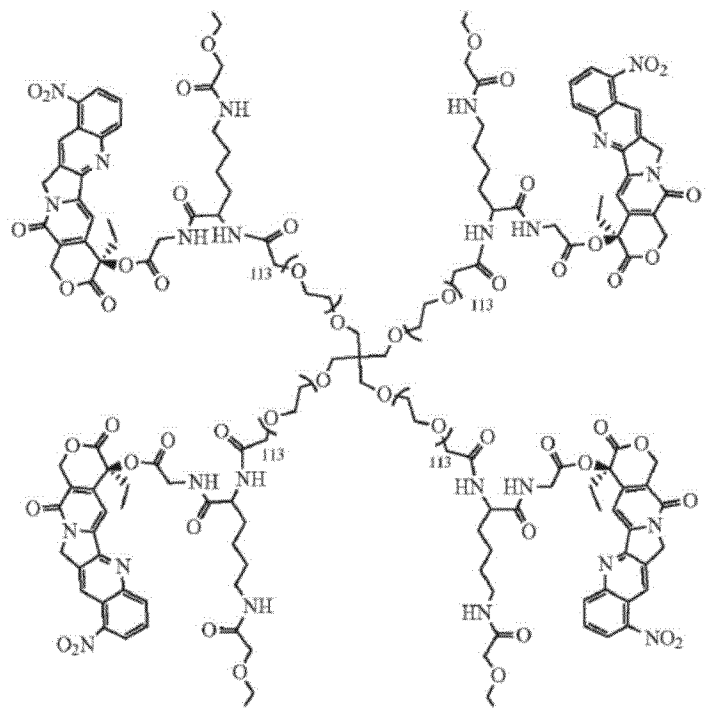

" and insert

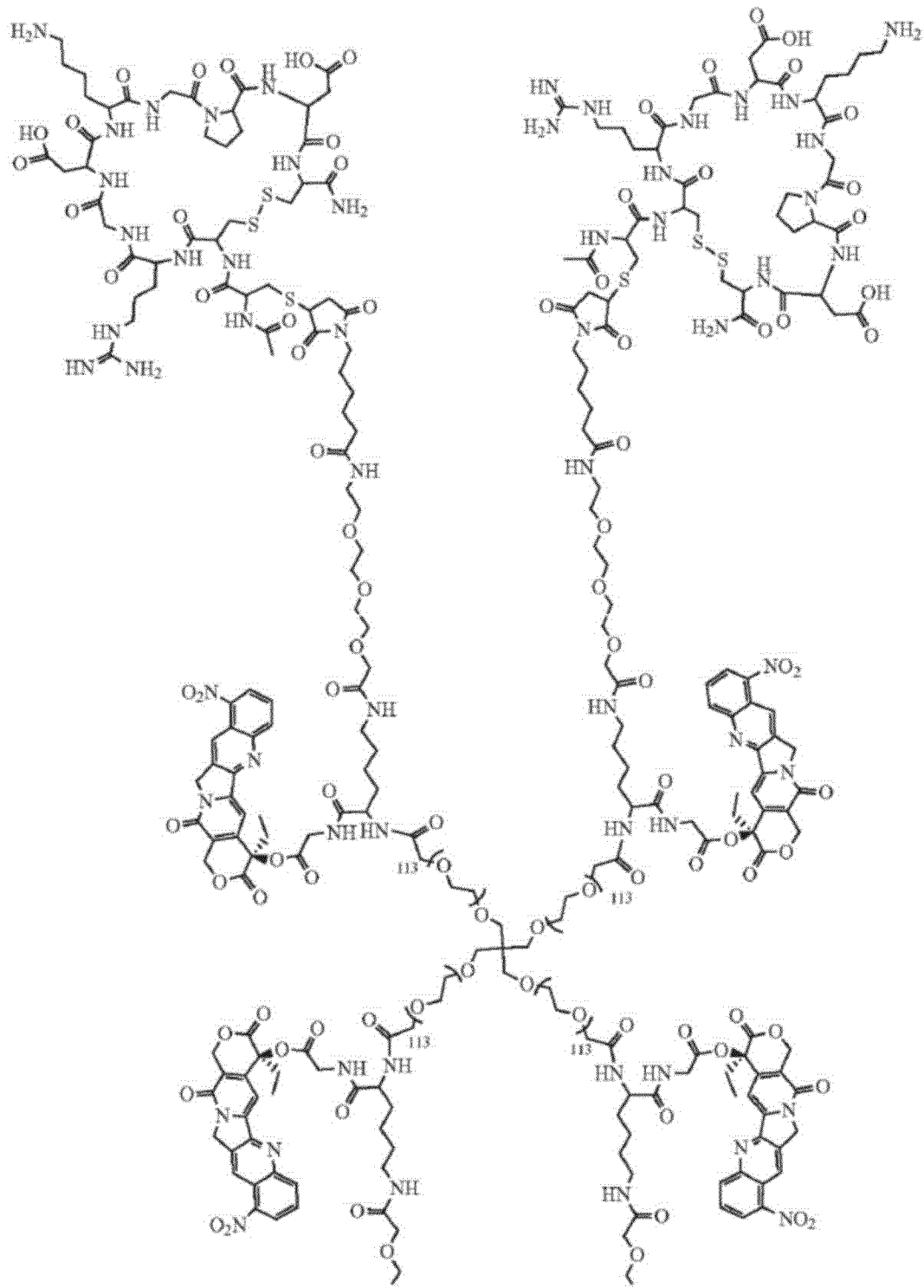
-- therefor. --,

CERTIFICATE OF CORRECTION (continued)
U.S. Pat. No. 10,869,863 B2

In Claim 7, delete

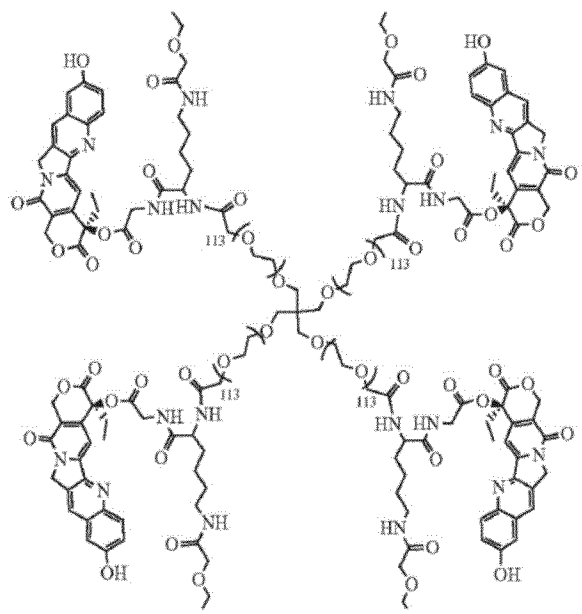

"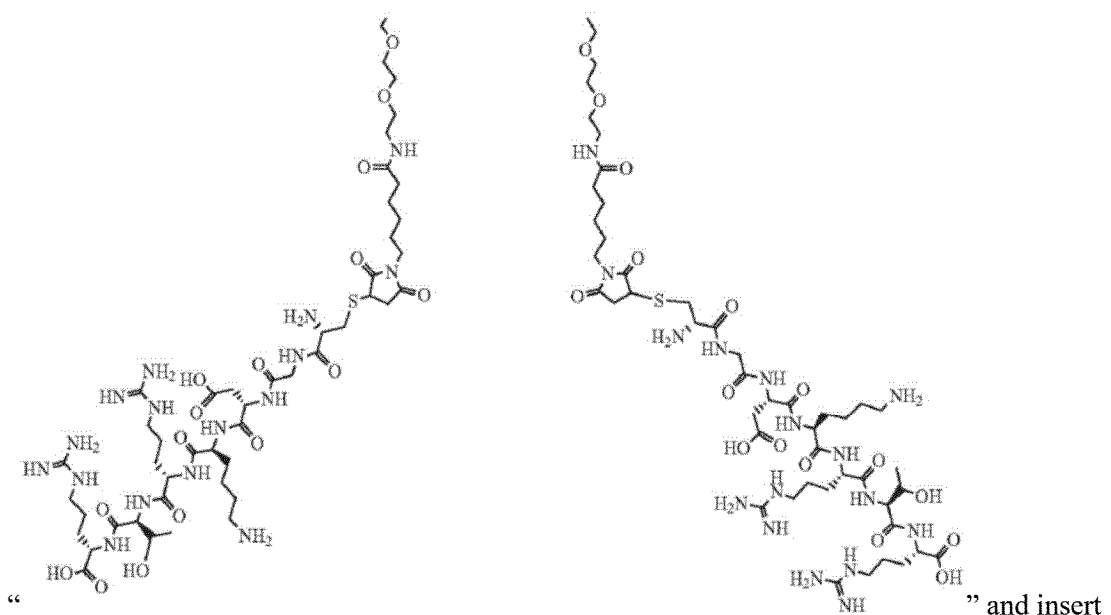" and insert

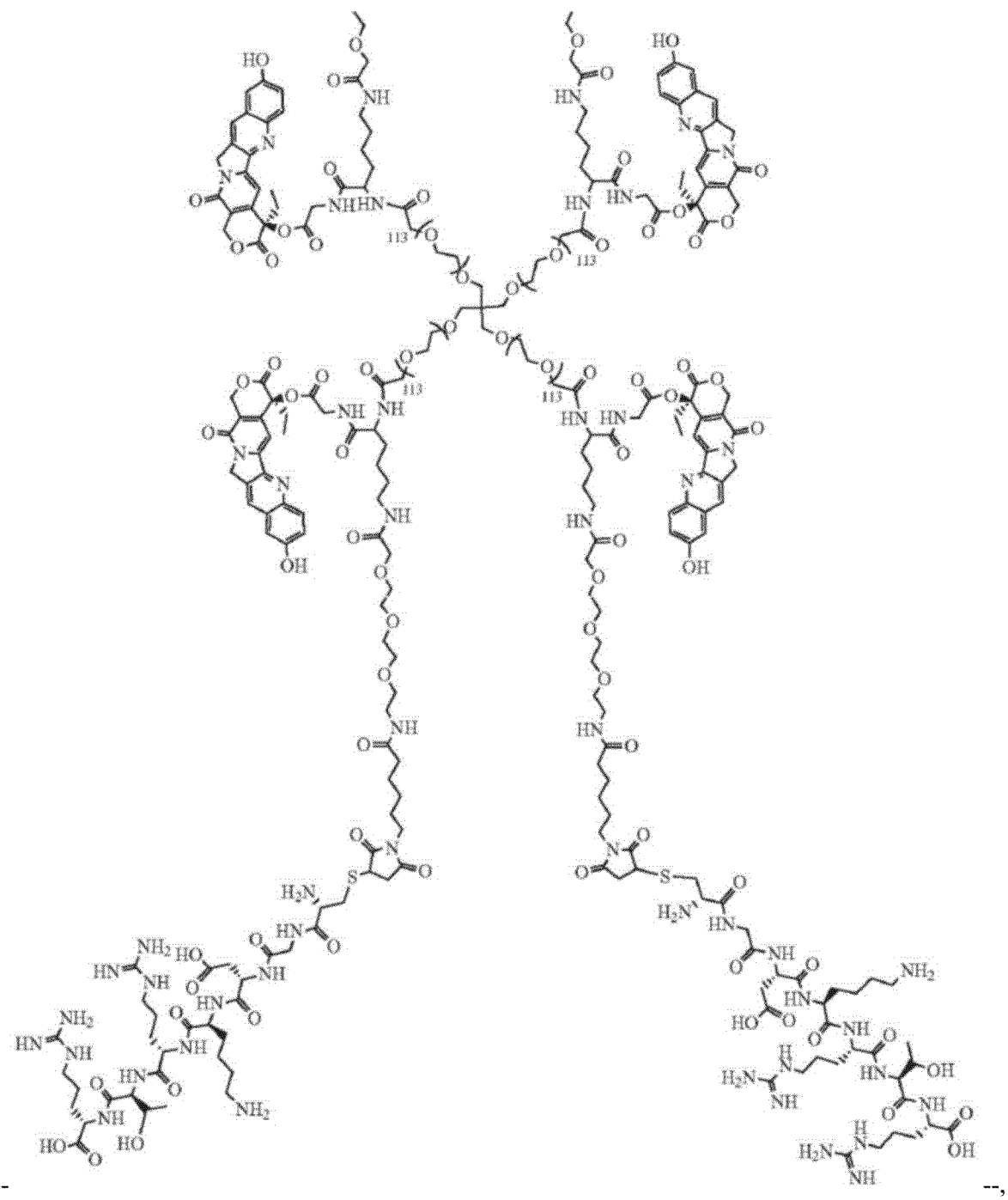
--
therefor.

CERTIFICATE OF CORRECTION (continued)
U.S. Pat. No. 10,869,863 B2

In Claim 7, delete

"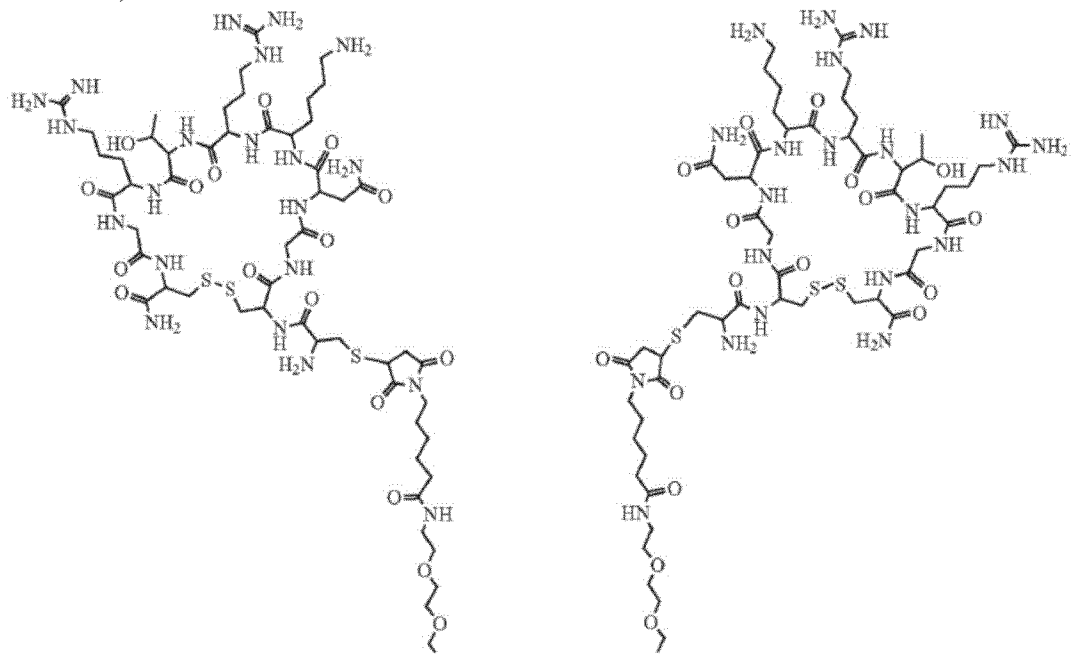

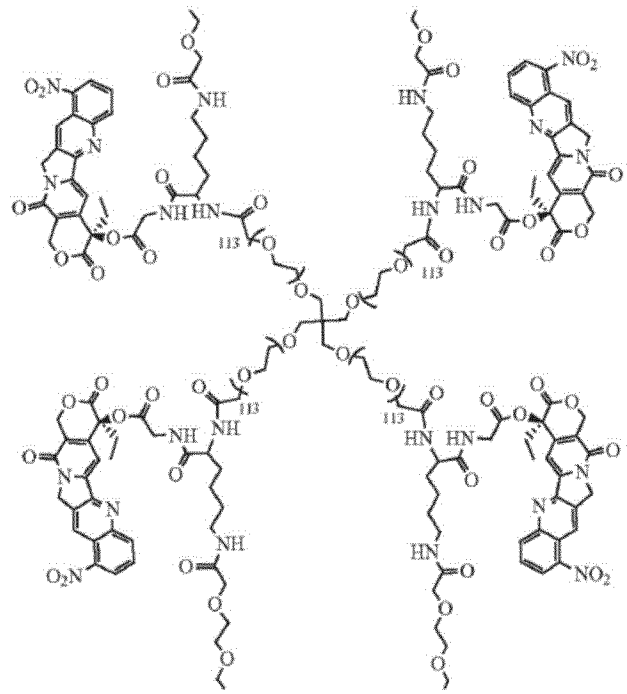

" and

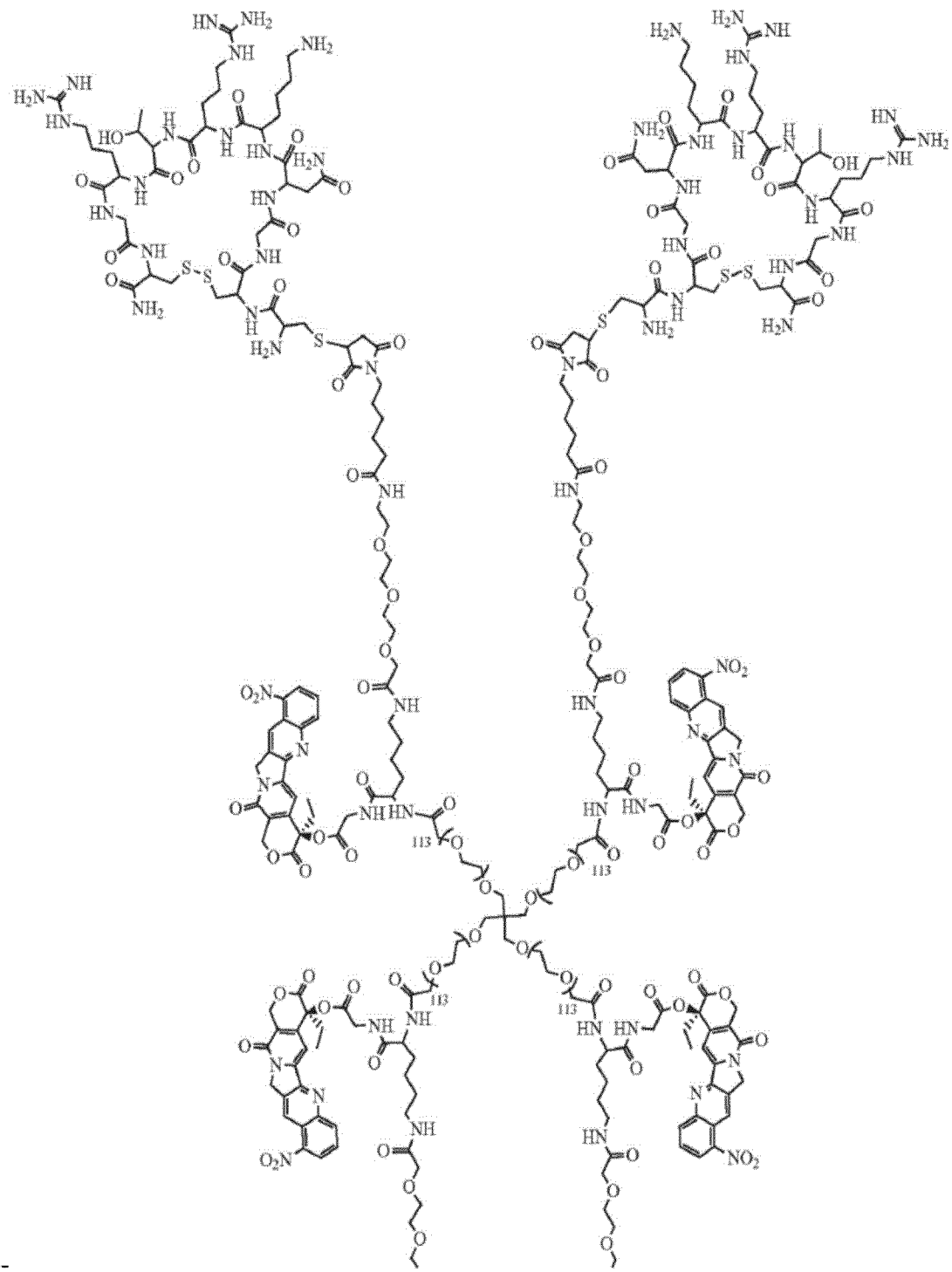
insert --
therefor.
--,

CERTIFICATE OF CORRECTION (continued)
U.S. Pat. No. 10,869,863 B2

In Claim 7, delete "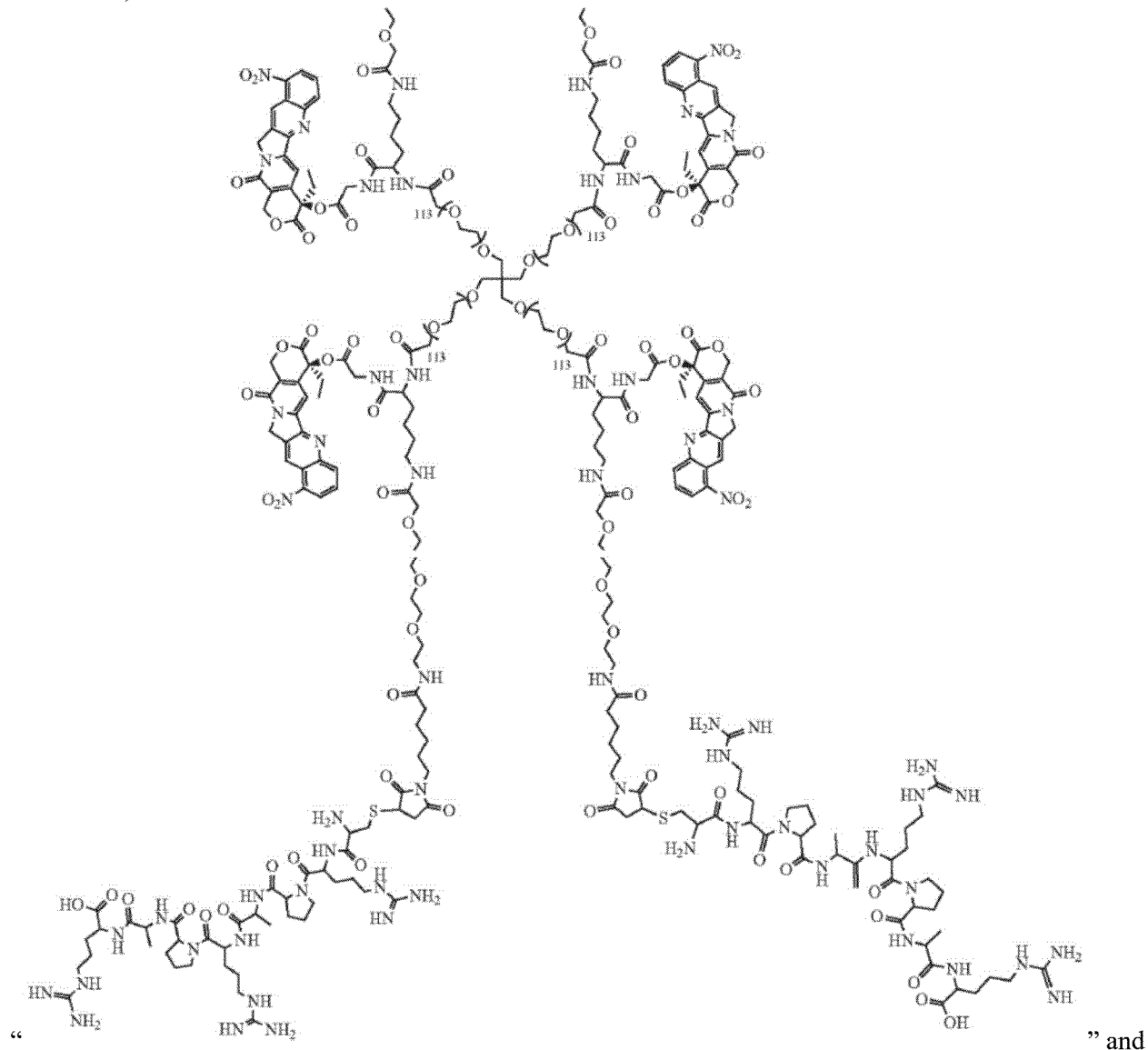" and

CERTIFICATE OF CORRECTION (continued)
U.S. Pat. No. 10,869,863 B2

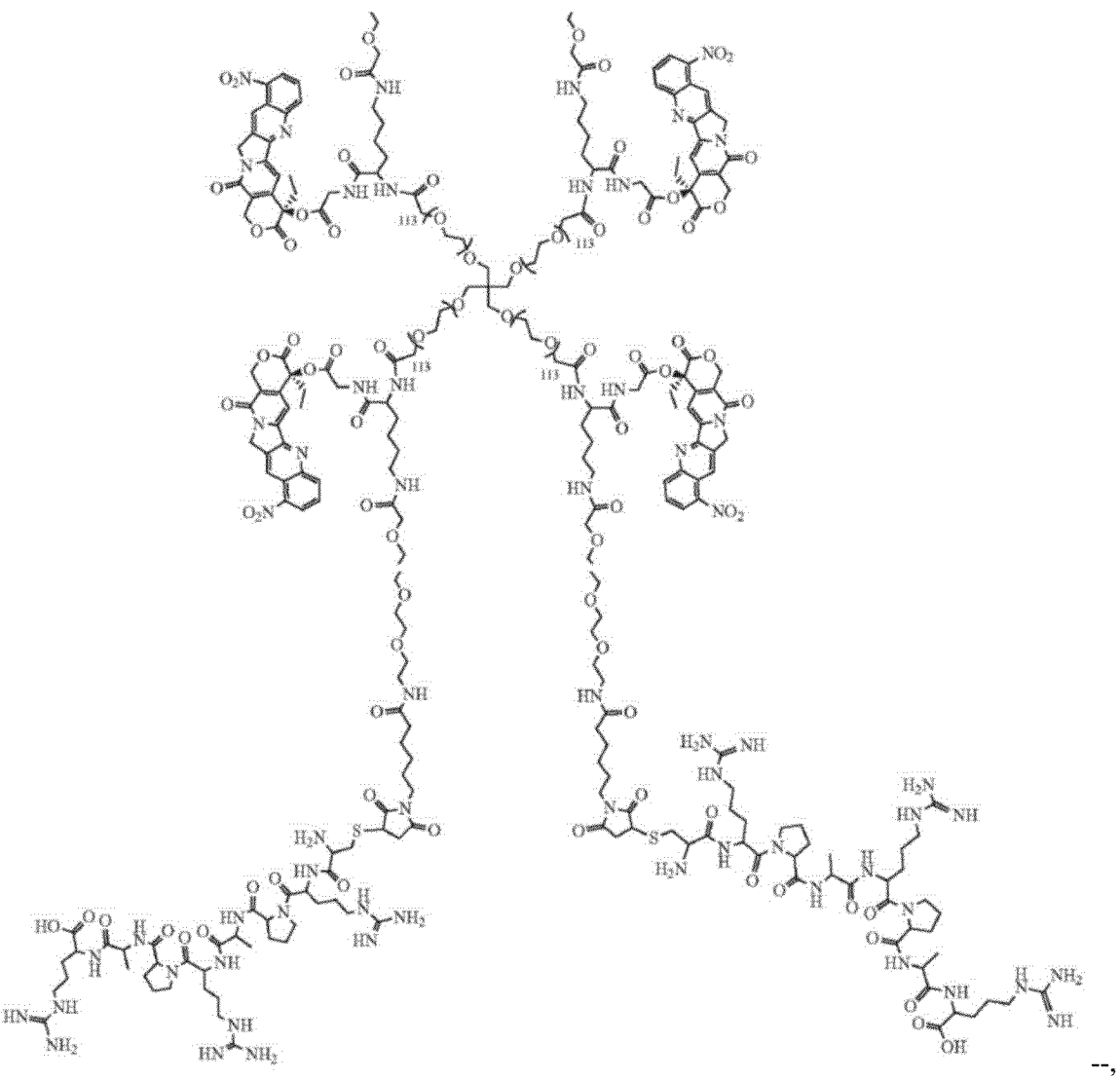

insert -- -- ,
therefor.

CERTIFICATE OF CORRECTION (continued)
U.S. Pat. No. 10,869,863 B2

Page 36 of 37

In Claim 7, delete

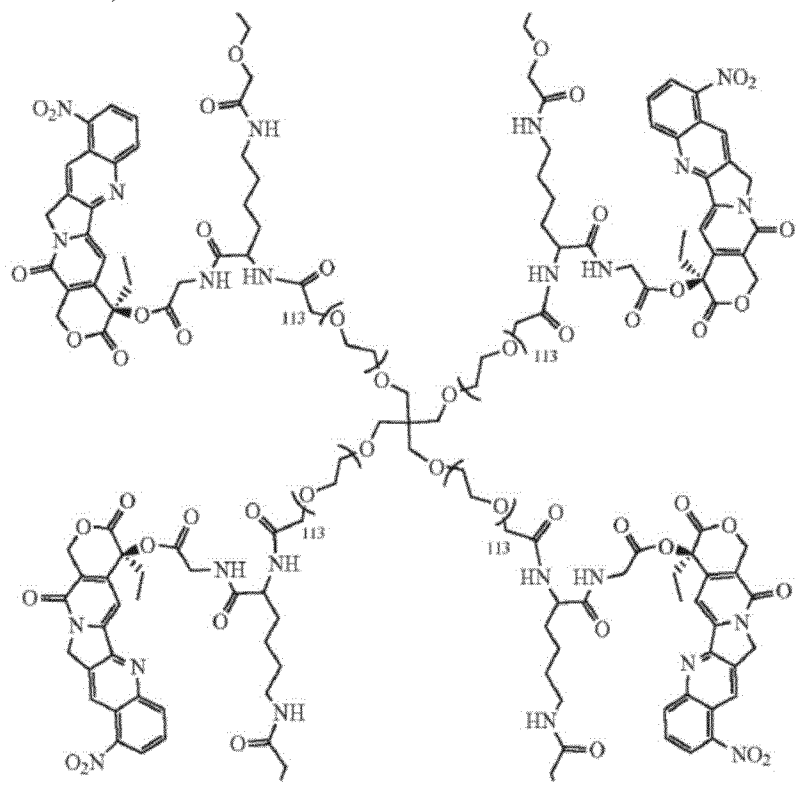

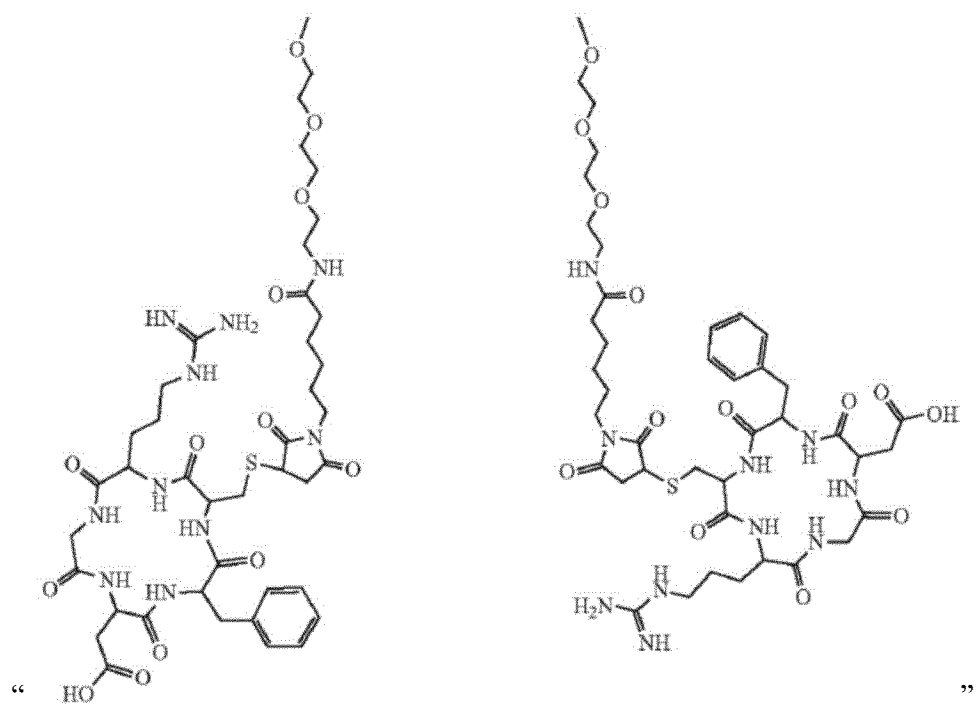

" and insert

CERTIFICATE OF CORRECTION (continued)
U.S. Pat. No. 10,869,863 B2

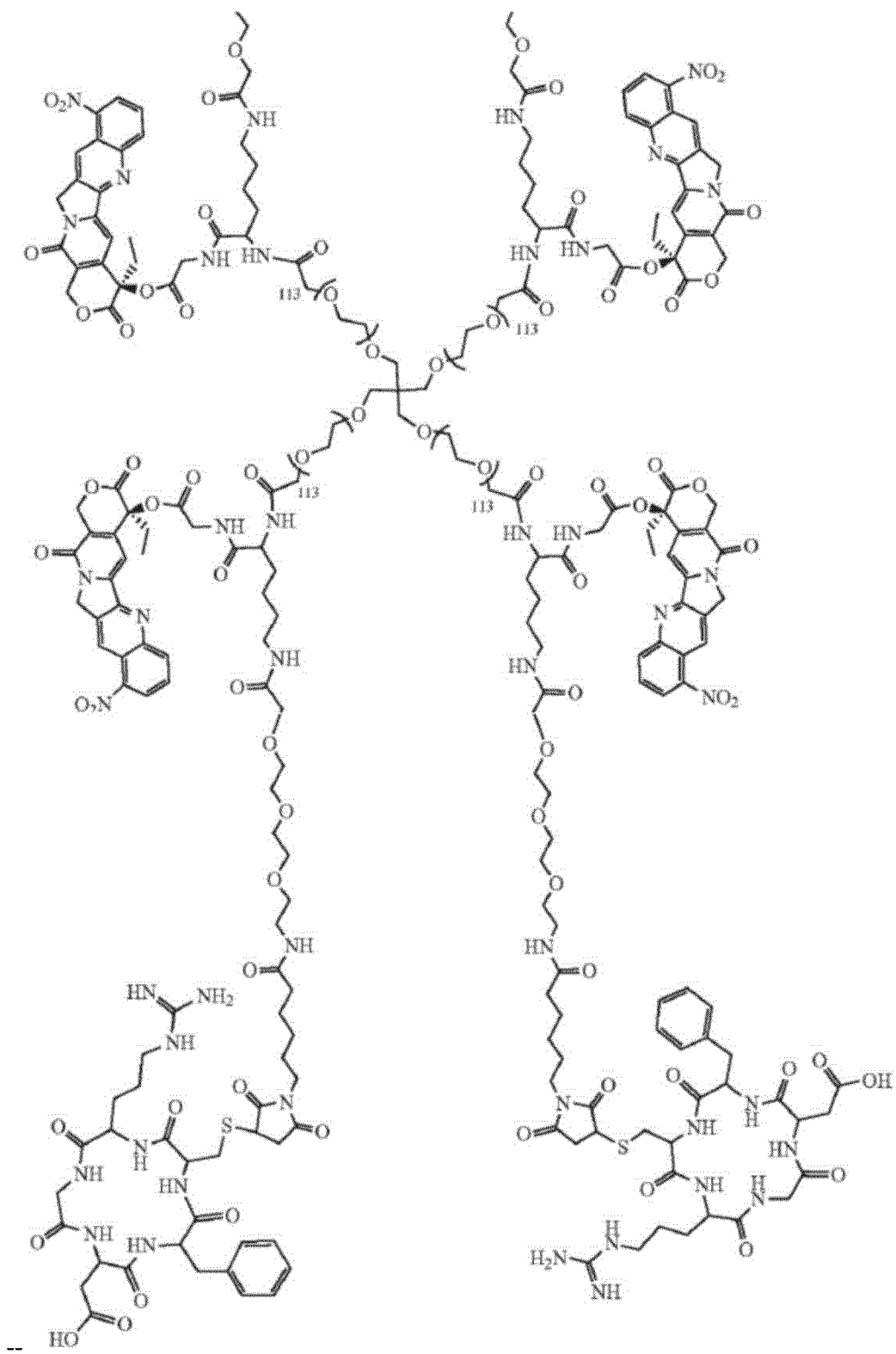

-- , therefor.